(12) United States Patent
Wang et al.

(10) Patent No.: US 10,548,983 B2
(45) Date of Patent: Feb. 4, 2020

(54) METHODS, SYSTEMS AND COMPOSITIONS RELATING TO CELL CONVERSION VIA PROTEIN-INDUCED IN-VIVO CELL REPROGRAMMING

(71) Applicant: Wayne State University, Detroit, MI (US)

(72) Inventors: Jianjun Wang, Troy, MI (US); Qianqian Li, Troy, MI (US); Michael Chopp, Southfield, MI (US); Feng Jiang, Troy, MI (US); Guojun Wu, Northville, MI (US)

(73) Assignee: Wayne State University, Detroit, MI (US)

( * ) Notice: Subject to any disclaimer, the term of this patent is extended or adjusted under 35 U.S.C. 154(b) by 0 days.

(21) Appl. No.: 16/120,829

(22) Filed: Sep. 4, 2018

(65) Prior Publication Data
US 2019/0000982 A1    Jan. 3, 2019

Related U.S. Application Data

(62) Division of application No. 15/031,839, filed as application No. PCT/US2014/062400 on Oct. 27, 2014, now Pat. No. 10,076,574.

(60) Provisional application No. 61/895,562, filed on Oct. 25, 2013.

(51) Int. Cl.
| | | |
|---|---|---|
| A61K 38/17 | (2006.01) | |
| A61K 47/59 | (2017.01) | |
| C12N 5/074 | (2010.01) | |
| A61K 9/00 | (2006.01) | |
| A61K 47/54 | (2017.01) | |
| A61K 48/00 | (2006.01) | |
| A61K 38/00 | (2006.01) | |

(52) U.S. Cl.
CPC ............ A61K 47/59 (2017.08); A61K 9/0019 (2013.01); A61K 38/1709 (2013.01); A61K 47/543 (2017.08); A61K 48/0041 (2013.01); C12N 5/0696 (2013.01); *A61K 38/00* (2013.01); *C12N 2501/602* (2013.01); *C12N 2501/603* (2013.01); *C12N 2501/605* (2013.01); *C12N 2502/30* (2013.01); *C12N 2506/30* (2013.01)

(58) Field of Classification Search
CPC .................. A61K 47/48192; A61K 9/0019
See application file for complete search history.

(56) References Cited

U.S. PATENT DOCUMENTS

| | | |
|---|---|---|
| 4,666,828 A | 5/1987 | Gusella |
| 4,683,202 A | 7/1987 | Mullis |
| 4,801,531 A | 1/1989 | Frossard |
| 5,192,659 A | 3/1993 | Simons |
| 5,272,057 A | 12/1993 | Smulson et al. |
| 5,880,103 A | 3/1999 | Urban et al. |
| 6,407,178 B1 | 6/2002 | Kolbe et al. |
| 6,783,751 B2 | 8/2004 | Heumann |
| 8,722,348 B2 | 5/2014 | Wang et al. |
| 2003/0134352 A1 | 7/2003 | Freimuth et al. |
| 2004/0142474 A1 | 7/2004 | Mahato et al. |
| 2004/0185528 A1 | 9/2004 | Horn et al. |
| 2005/0064545 A1 | 3/2005 | DeMarco et al. |
| 2005/0074840 A1 | 4/2005 | Brondyk et al. |
| 2005/0215474 A1 | 9/2005 | Oaks et al. |
| 2009/0298111 A1 | 12/2009 | Wang et al. |
| 2010/0233804 A1 | 9/2010 | Zhou et al. |
| 2018/0223260 A1* | 8/2018 | Aprikyan ............. C12N 5/0696 |

FOREIGN PATENT DOCUMENTS

| | | |
|---|---|---|
| WO | WO-2002022174 A1 | 3/2002 |
| WO | WO-2005/026196 | 3/2005 |
| WO | WO-2008/050255 | 5/2008 |
| WO | WO-2009/155026 | 12/2009 |
| WO | WO-2010/075575 A1 | 7/2010 |
| WO | WO-2010115052 | 10/2010 |
| WO | WO-2010124143 | 10/2010 |
| WO | WO-2010130446 | 11/2010 |
| WO | WO-2011058064 | 5/2011 |
| WO | WO-2011/097181 | 8/2011 |
| WO | WO-2012/022725 | 2/2012 |
| WO | WO-2012/151234 | 11/2012 |

(Continued)

OTHER PUBLICATIONS

Aridor, Meir et al. Traffic Jam: A Compendium of Human Diseases that Affect Intracellular Transport Processes, Traffic, Toolbox 1:836-851 (2000).

(Continued)

*Primary Examiner* — Karen Cochrane Carlson
(74) *Attorney, Agent, or Firm* — Julie K. Staple; Dinsmore & Shohl LLP

(57) ABSTRACT

Methods for treating a subject in need thereof are provided which include administering a pharmaceutical composition comprising a protein transduction reagent-modified reprogramming protein to the subject, wherein the protein transduction reagent is non-covalently bound to the reprogramming protein and wherein the protein transduction reagent comprises a cation reagent and a lipid. According to aspects, such methods provide delivery of protein-transduction reagent-modified reprogramming proteins to cancer cells, such as tumor cells, as well as diseased cells of diseased tissues and provide in vivo conversion of diseased cells into normal cells via protein-induced in situ cell reprogramming without administration of nucleic acids to the subject.

16 Claims, 25 Drawing Sheets
Specification includes a Sequence Listing.

(56) References Cited

FOREIGN PATENT DOCUMENTS

| WO | WO-2012/151234 A1 | 11/2012 |
|---|---|---|
| WO | WO-2013013105 A2 | 1/2013 |
| WO | WO-2013/033213 | 3/2013 |

OTHER PUBLICATIONS

Ausubel et al. Biology, Green Publishing Associates. Brooklyn, NY, 1988.
Ausubel et al., Current Protocols in Molecular Biology, John Wiley and Sons, Baltimore, Maryland (1989).
Ausubel, et al. (1987 and Supplements) Short Protocols in Molecular Biology, Wiley & Sons Inc., New York.
Birren et al (eds) Genome Analysis: A Laboratory Manual Series, vols. 1-4 Cold Spring Harbor Laboratory-Press, New York (1998).
Brock et al., Biology of Microorganisms, 5.sup.th Edition, Prentice Hall, New Jersey (1988).
Burz, David S. et al., Mapping Structural Interactions Using In-Cell NMR Spectroscopy (STINT-NMR), http://www.nature.com/naturemethods, 2006.
Cai et al. "An efficient and cost-effective isotope labeling protocol for proteins expressed in *Escherichia coli*", J of Biomolecular NMR, 1998, 11:97-102.
Chang et al. "Cellular internalization of fluorescent proteins via arginine-rich intracellular delivery peptide in plant cells", Plant Cell Physiol. 2005, 46(3):482-488.
Crowe et al., (1992) QIAexpress: The High Level Expression & Protein Purification System Quiagen, Inc. Chatsworth, CA.
Demain et al. (Eds), Manual of Industrial Microbiology and Biotechnology, American Society for Microbiology, Washington D.C. (1986).
Deutscher (1990) "Guide to Protein Purification" in Methods in Enzymology, vol. 182.
Dobson, Christopher M. Protein Folding and Misfolding, University of Cambridge, 2003.
Futami et al. "Intracellular delivery of proteins into mammalian living cells by polyethyenimine-cationization", J of Biosci. & bioeng., 2005, 99(2):95-103.
Gerhardt et al. (Eds). Methods for General and Molecular Biology, American Society for Microbiology, Washington D.C. (1994).
Guignet et al. "Reversible site-selective labeling of membrane proteins in live cells", Nature Biotechnology, 2004, 22(4):440-444.
Hochuli (1989) "Guide to Protein Purification" in Methods in Enzymology, vol. 182.
Hochuli (1990) "Purification of Recombinant Proteins with Metal Chelate Absorbent" in Setlow (ed.) Genetic Engineering, Principle and Methods 12:87-98. Plenum Press, N.Y.
Innis, et al. (eds.)(1990) PCR Protocols: A Guide to Methods and Applications Academic Press, N.Y.
Kumagai et al. "Absorptive-mediated endocytosis of cationized albumin and a beta-endorphin-cationized albumin chimeric peptide by isolated brain capillaries", JBC, 1987, 262(31):15214-15219.
Li et al. "Real time investigation of protien folding, structure, and dynamics in living cells", Methods in Cell Biology,2008, 90:287-326.
Maniatis, et al. (1982) Molecular Cloning, A Laboratory Manual, Cold Spring Harbor Laboratory, Cold Spring Harbor Press.
Melamed, et al. (1990) Flow Cytometry and Sorting Wiley-Liss, Inc., New York, N.Y.
Mishell and Shiigi (eds), Selected Methods in Cellular Immunology, W.H. Freeman and Co., New York (1980).
PCR Protocols: A Guide to Methods and Applications, Academic Press, San Diego, CA (1990).
Perbal, A Practical Guide to Molecular Cloning, John Wiley & Sons. New York (1988).
Prochiantz, Alain. For Protein Transduction, Chemistry Can Win Over Biology, Nature Methods, vol. 4, No. 2 (2007).
Robinson, et al. (1993) Handbook of Flow Cytometry Methods Wiley-Liss, New York, N.Y.
Sambrook et al., Molecular Cloning: A Laboratory Manual, Cold Spring Harbor Laboratory Press, New York (1989).
Sambrook, et al. (2001) Molecular Cloning: A Laboratory Manual, (3rd ed.). vols. 1-3, CSH Press, NY.
Shapiro (1988) Practical Flow Cytometry Liss, New York, N.Y.
Stites et al.(eds), Basic and Clinical Immunology (8th Edition), Appleton & Lange, Norwalk, CT (1994).
Wang et al. "Arginine-rich intracellular delivery peptides noncovalently transport protein into living cells", BBRC, 2006. 346:758-767.
Watson et al, Recombinant DNA. Scientific American Books. New York, (1992).
Woodford et al. (Eds), Molecular Bacteriology: Protocols and Clinical Applications, Humana Press, Totowa, N.J. (1998).
Hung, C. et al., Physicochemical characterization and gene transfection efficiency of lipid emulsions with various co-emulsifiers, *International Journal of Pharmaceutics*, 289: 197-208, 2005.
Zelphati, O. et al., Intracellular Delivery of Proteins with a New Lipid-mediated Delivery System, *The Journal of Biological Chemistry*, 276(37): 35103-110, Sep. 14, 2001.
Amabile, G. et al., Induced pluripotent stem cells: current progress and potential for regenerative medicine, *Trends Mol Med.* 15:59-68, 2009.
Amit, M., et al., Feeder layer- and serum-free culture of human embryonic stem cells, Biol Reprod, 70(3):837-45, Mar. 2004.
Carey, B. et al., Reprogramming of murine and human somatic cells using a single polycistronic vector, Proc Natl Acad Sci USA, 106(1):157-62, Jan. 6, 2009.
Chan, E. et al., Live cell imaging distinguishes bona fide human iPS cells from partially reprogrammed cells. Nat Biotechnol, 27(11): 1033-7, 2009.
Cho, H. et al., Induction of pluripotent stem cells from adult somatic cells by protein-based reprogramming without genetic manipulation, Blood, 116, 386-95, 2010.
Feng, B. et al., Reprogramming of fibroblasts into induced pluripotent stem cells with orphan nuclear receptor Esrrb, Nat Cell Biol, 11(2):197-203, 2009.
Gore, A. et al. Somatic coding mutations in human induced pluripotent stem cells, Nature, 471: 63-7, 2011.
Hanna, J. et al., Direct cell reprogramming is a stochastic process amenable to acceleration, Nature, 462:595-601, 2009.
Heng, H. et al., Stochastic cancer progression driven by non-clonal chromosome aberrations, J Cell Physiol, 208: 461-72, 2006.
Heng, H. et al., High-resolution mapping of mammalian genes by in situ hybridization to free chromatin, Proc Natl Acad Sci USA, 89: 9509-13, 1992.
Hussein, S. et al., Genome-wide characterization of the routes to pluripotency, Nature, 516(7530):198-206, Dec. 11, 2014.
Jaenisch, R. et al., Stem cells, the molecular circuitry of pluripotency and nuclear reprogramming, Cell, 132: 567-82, 2008.
Kabouridis, P. et al., Biological applications of protein transduction technology, Trends Biotechnol, 21:498-503, 2003.
Kaji, K. et al., Virus-free induction of pluripotency and subsequent excision of reprogramming factors, Nature, 458: 771-775, 2009.
Kim, K. et al., Epigenetic memory in induced pluripotent stem cells, *Nature*, 467: 285-90, 2010.
Kim D. et al., Generation of human induced pluripotent stem cells by direct delivery of reprogramming proteins, Cell Stem Cell, 4(6):472-6, 2009.
Kiskinis, E. et al., Progress toward the clinical application of patient-specific pluripotent stem cells, *J Clin Invest*, 120:51-9, 2010.
Knoepfler, P. et al., Deconstructing stem cell tumorigenicity: a roadmap to safe regenerative medicine, *Stem Cells*, 27(5):1050-6, 2009.
Lang, J. et al., Reprogramming cancer cells: back to the future, Oncogene, 32(18):2247-8, May 2, 2013.
Lerou, P., et al., Therapeutic potential of embryonic stem cells, Blood Rev., 19(6):321-31, Nov. 2005.
Lim, J. et al., Partial somatic to stem cell transformations induced by cell-permeable reprogramminig factors, Sci Rep, 4:4361, Mar. 12, 2010.
Lin, S. et al., Mir-302 reprograms human skin cancer cells into a pluripotent ES-cell-like state, *RNA*, 14:2115-24, 2008.

(56) References Cited

OTHER PUBLICATIONS

Lister, R. et al., Hotspots of aberrant epigenomic reprogramming in human induced pluripotent stem cells, Nature, 471: 68-73, 2011.
Mahalingam, D. et al., Reversal of aberrant cancer methylome and transcriptome upon direct reprogramming of lung cancer cells, Sci Rep, 2:592, 2012.
Maherali, N. et al., Directly Reprogrammed Fibroblasts Show Global Epigenetic Remodeling and Widespread Tissue Contribution, Cell Stem Cell, 1: 55-70, 2007.
Nakagawa, M. et al., Generation of induced pluripotent stem cells without Myc from mouse and human fibroblasts. Nat. Biotechnol, 26: 101-106, 2008.
Nemes, C. et al., Generation of mouse induced pluripotent stem cells by protein transduction, Tissue Eng Part C Methods, 20(5):383-92, May 2014.
Niwa, H. et al., Quantitative expression of Oct-3/4 defines differentiation, dedifferentiation or self-renewal of ES cells, Nat Genet. 24(4): 372-6, 2000.
Okita, K. et al., Generation of germline-competent induced plutipntent stem cells, Nature, 448:313-7, 2007.
Okita, K. et al., Generation of mouse induced pluripotent stem cells without viral vectors, Science, 322: 949-953, 2008.
Pan, C. et al., Reprogramming human fibroblasts using HIV-1 TAT recombinant proteins OCT4, SOX2, KLF4 and c-MYC, Mol Biol Rep, 37(4):2117-24, Apr. 2010.
Park, I. et al., Reprogramming of human somatic cells to pluripotency with defined factors, Nature, 451: 141-146, 2008.
Polo, J. et al., Cell type of origin influences the molecular and functional properties of mouse induced pluripotent stem cells, Nat Biotechnol, 28: 848-55, 2010.
Raff, M. et al., Two types of astrocytes in cultures of developing rat white matter: differences in morphology, surface gangliosides, and growth characteristics, J Neurosci, 3:1289-1300, 1983.
Robbins, R. et al., Inducible pluripotent stem cells: not quite ready for prime time?, Curr Opin Organ Transplant., 15:61-7, 2010.
Rodin, S. et al., Long-term self-renewal of human pluripotent stem cells on human recombinant laminin-511, Nat Biotechnol, 28: 611-5, 2010.
Rolletschek, A. et al., Induced human pluripotent stem cells: promises and open questions, Biol Chem., 390:845-9, 2009.
Scheper, W. et al., The molecular mechanism of induced pluripotency: a two-stage switch, Stem Cell Rev, 5:204-23, 2009.
Shao, L. et al., Generation of iPS cells using defined factors linked via the self-cleaving 2A sequences in a single open reading frame, Cell Res. 19(3):296-306, Mar. 2009.
Sivashanmugam, A. et al., Practical protocols for production of very high-yield of recombinant proteins in Eschericia coli, Protein Science, 18:936-948, 2009.
Soldner, F. et al., Parkinson's disease patient-derived induced pluripotent stem cells free of viral reprogramming factors, Cell, 136: 964-977, 2009.
Stadtfeld, M. et al., Induced pluripotent stem cells generated without viral integration, Science, 322: 945-949, 2008.
Takahashi, K. et al., Induction of pluripotent stem cells from adult human fibroblasts by defined factors, Cell, 131: 861-872, 2007.
Takahashi, K. et al., Induction of pluripotent stem cells from mouse embryonic and adult fibroblast cultures defined factors, Cell, 126: 663-78, 2006.
Takahashi, K. et al., Induction of pluripotent stem cells from fibroblast cultures, Nat Protoc. 2(12):3081-9, 2007.
Testoni, N. et al., A New Method of "In-Cell Reverse Transcriptase-Polymerase Chain Reaction" for the Detection of BCR/ABL Transcript in Chronic Myeloid Leukemia Patients, Blood, 87(9), 3822-27, 1996.
Tonge, P. et al., Divergent reprogramming routes lead to alternative stem-cell states, Nature, 516(7530):192-7, Dec. 11, 2014.
Trehin, R. et al., Chances and pitfalls of cell penetrating peptides for cellular drug delivery, Eur J Pharm Biopharm, 58:209-23, 2004.
Warren, et al., Highly Efficient Reprogramming to Pluripotency and Directed Differentiation of Human Cells with Synthetic Modified mRNA, Cell Stem Cell, 7: 1-13, 2011.
Wernig, M. et al., In vitro reprogramming of fibroblasts into a pluripotent ES-cell-like state, Nature, 448: 318-324, 2007.
Woltjen, K. et al., piggyBac transposition reprograms fibroblasts to induced pluripotent stem cells, Nature, 458: 766-770, 2009.
Wu, J. et al., Stem cells: A designer's guide to pluripotency, Nature, 516(7530):172-3, Dec. 11, 2014.
Yu, J. et al., Human induced pluripotent stem cells free of vector and transgene sequences, Science, 324: 797-801, 2009.
Yu, J. et al., Induced pluripotent stem cell lines derived from human somatic cells, Science, 318: 1917-1920, 2007.
Zhang, X. et al., Terminal differentiation and loss of tumorigenicity of human cancers via pluripotency-based reprogramming, Oncogene, 32(18):2249-60, 2260.e1-21, May 2, 2013.
Zhou, H. et al., Generation of induced pluripotent stem cells using recombinant proteins, Cell Stem Cell, 4(5):381-4, 2009.
Park, I. et al., Disease-specific induced pluripotent stem (iPS) cells, Cell, 134(5): 877-86, Sep. 5, 2008.
Ebert, A. et al., Induced pluripotent stem cells from a spinal muscular atrophy patient, Nature, 457(7227): 277-80, Jan. 15, 2009.
Dimos, J. et al., Induced pluripotent stem cells generated from patients with ALS can be differentiated into motor neurons, Science, American Association for the Advancement of Science, 321(5893): 1218-1221, Aug. 29, 2008.
Huangpu, D. et al., Induction of pluripotent stem cells from primary human fibroblasts with only Oc4 and Sox2, Nature Biotechnology, 26(11): 1269-75, Nov. 1, 2008.
Kim, J. et al., Direct reprogramming of human neural stem cells by OCT4, Nature, 461(7264): 649-54, Oct. 1, 2009.
Kim, J. et al., Pluripotent stem cells induced from adult neural stem cells by reprogramming with two factors, Nature, 454: 646-50, Jul. 31, 2008.
O'Connor, C., Generation and characterization of the protein-induced pluripotent stem (piPS) cells, M.S. Thesis of Graduate School of Wayne State University, Detroit, MI, 2012.
Lai, Y. et al., SRY (sex determining region Y)-box2 (Sox2)/poly ADP-ribose polymerase 1 (Parp1) complexes regulate pluripotency, PNAS, 109(19): 3772-77, Mar. 6, 2012.
Reijo-Pera, R., et al., Gene expression profiles of human inner cell mass cells and embryonic stem cells, Differentiation, 78: 18-23, 2009.
Reubinoff, B. et al., Embryonic stem cell lines from human blastocysts: somatic differentiation in vitro, Nature Biotechnology, 18: 399-404, Apr. 2000.
Thomson, J. et al., Embryonic Stem Cell Lines Derived from Human Biastocysts, Science, 282: 1145-47, Nov. 6, 1998.
UK House of Parliaments' Select Committee on Science and Technology, Fifth Report of Session Jul. 2006, vol. II, pp. 76-77, Apr. 5, 2007.
Welsch, P. et al., BRCA1 and BRCA2 and the genetics of breast and ovarian cancer, Human Molecular Genetics, 10(7): 705-713, 2001.
Chaves, K. et al., Triple Negative Breast Cancer Cell Lines: One Tool in the Search for Better Treatment of Triple Negative Breast Cancer, Breast Dis., 32(1-2): 35-48, 2010.
Dominiguez-Bendala, J. et al., Islet Cell Therapy and Pancreatic Stem Cells, Handbook of Stem Cells, Chapter 70: Islet Cell Therapy and Pancreatic Stem Cells, pp. 835-853, 2013.
Qian, L. et al., In vivo reprogramming of murine cardiac fibroblasts into induced cardiomyocytes, Nature, 485(7400): 593-598, May 31, 2012.
Hochedlinger, K. et al., Ectopic Expression of Oct-4 Blocks Progenitor-Cell Differentiation and Causes, Dysplasia in Epithelial Tissues, Cell, 121: 465-477, May 6, 2005.
Lotan, R., Differentiation Therapy, The Cancer Handbook 1st Edition, 2002.
Li, M. et al., How far are induced pluripotent stem cells from the clinic?, Ageing Research Reviews, 9: 257-264, 2010.
De Los Angeles, A. et al., Reprogramming in situ, Nature, 502: 309-310, Oct. 17, 2013.
Abad, M. et al., Reprogramming in vivo produces teratomas and iPS cells with totipotency features, Nature, 502: 340-345, Oct. 17, 2013.

(56) References Cited

OTHER PUBLICATIONS

Ohnishi, K. et al., Premature Termination of Reprogramming in vivo Leads to Cancer Development through Altered Epigenetic Regulation, *Cell*, 156: 663-677, Feb. 13, 2014.

* cited by examiner

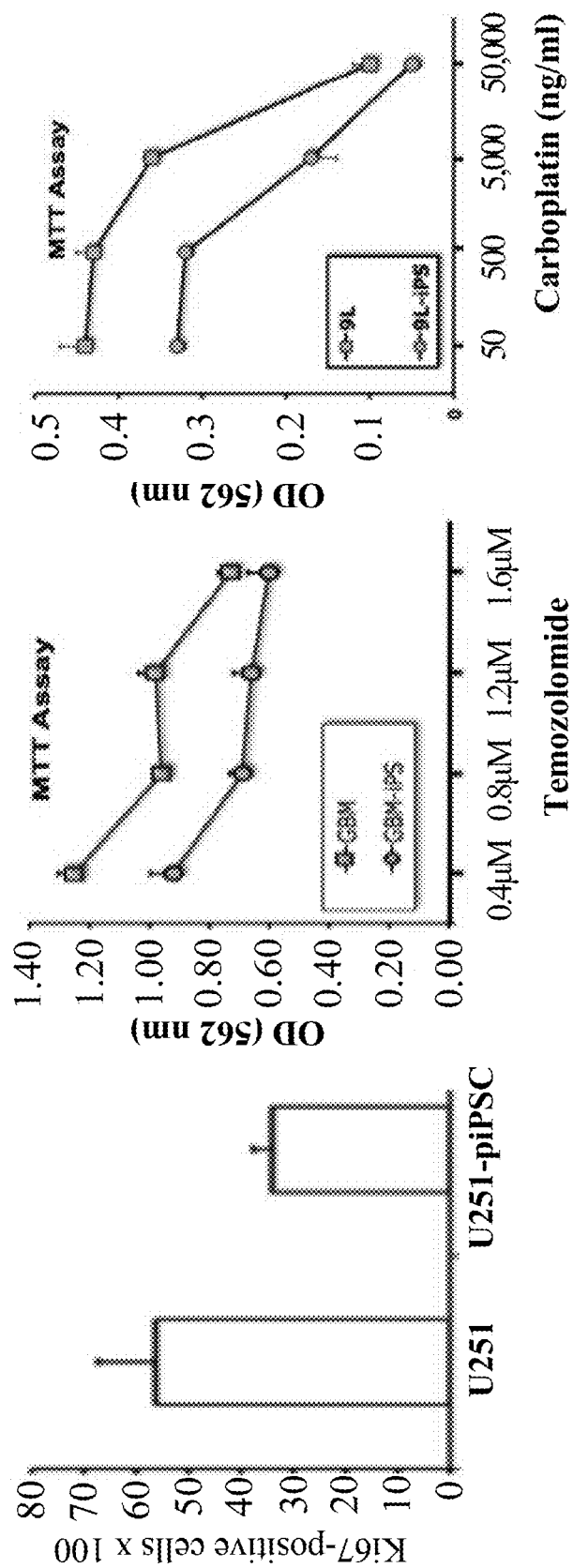

SEQUENCE LISTING

<160> NUMBER OF SEQ ID NOS: 127

<210> SEQ ID NO 1
<211> LENGTH: 317
<212> TYPE: PRT
<213> ORGANISM: Homo sapiens

<400> SEQUENCE: 1

```
Met Tyr Asn Met Met Glu Thr Glu Leu Lys Pro Pro Gly Pro Gln Gln
1               5                   10                  15

Thr Ser Gly Gly Gly Gly Asn Ser Thr Ala Ala Ala Ala Gly Gly
            20                  25                  30

Asn Gln Lys Asn Ser Pro Asp Arg Val Lys Arg Pro Met Asn Ala Phe
        35                  40                  45

Met Val Trp Ser Arg Gly Gln Arg Arg Lys Met Ala Gln Glu Asn Pro
    50                  55                  60

Lys Met His Asn Ser Glu Ile Ser Lys Arg Leu Gly Ala Glu Trp Lys
65                  70                  75                  80

Leu Leu Ser Glu Thr Glu Lys Arg Pro Phe Ile Asp Glu Ala Lys Arg
                85                  90                  95

Leu Arg Ala Leu His Met Lys Glu His Pro Asp Tyr Lys Tyr Arg Pro
```

```
                    100                 105                 110
Arg Arg Lys Thr Lys Thr Leu Met Lys Lys Asp Lys Tyr Thr Leu Pro
            115                 120                 125
Gly Gly Leu Leu Ala Pro Gly Gly Asn Ser Met Ala Ser Gly Val Gly
            130                 135                 140
Val Gly Ala Gly Leu Gly Ala Gly Val Asn Gln Arg Met Asp Ser Tyr
145                 150                 155                 160
Ala His Met Asn Gly Trp Ser Asn Gly Ser Tyr Ser Met Met Gln Asp
                165                 170                 175
Gln Leu Gly Tyr Pro Gln His Pro Gly Leu Asn Ala His Gly Ala Ala
            180                 185                 190
Gln Met Gln Pro Met His Arg Tyr Asp Val Ser Ala Leu Gln Tyr Asn
            195                 200                 205
Ser Met Thr Ser Ser Gln Thr Tyr Met Asn Gly Ser Pro Thr Tyr Ser
            210                 215                 220
Met Ser Tyr Ser Gln Gln Gly Thr Pro Gly Met Ala Leu Gly Ser Met
225                 230                 235                 240
Gly Ser Val Val Lys Ser Glu Ala Ser Ser Ser Pro Pro Val Val Thr
                245                 250                 255
Ser Ser Ser His Ser Arg Ala Pro Cys Gln Ala Gly Asp Leu Arg Asp
                260                 265                 270
Met Ile Ser Met Tyr Leu Pro Gly Ala Glu Val Pro Glu Pro Ala Ala
            275                 280                 285
Pro Ser Arg Leu His Met Ser Gln His Tyr Gln Ser Gly Pro Val Pro
            290                 295                 300
Gly Thr Ala Ile Asn Gly Thr Leu Pro Leu Ser His Met
305                 310                 315

<210> SEQ ID NO 2
<211> LENGTH: 360
<212> TYPE: PRT
<213> ORGANISM: Homo sapiens

<400> SEQUENCE: 2

Met Ala Gly His Leu Ala Ser Asp Phe Ala Phe Ser Pro Pro Pro Gly
1               5                   10                  15
Gly Gly Gly Asp Gly Pro Gly Gly Pro Glu Pro Gly Trp Val Asp Pro
            20                  25                  30
Arg Thr Trp Leu Ser Phe Gln Gly Pro Pro Gly Gly Pro Gly Ile Gly
            35                  40                  45
Pro Gly Val Gly Pro Gly Ser Glu Val Trp Gly Ile Pro Pro Cys Pro
        50                  55                  60
Pro Pro Tyr Glu Phe Cys Gly Gly Met Ala Tyr Cys Gly Pro Gln Val
65                  70                  75                  80
Gly Val Gly Leu Val Pro Gln Gly Gly Leu Glu Thr Ser Gln Pro Glu
                85                  90                  95
Gly Glu Ala Gly Val Gly Val Glu Ser Asn Ser Asp Gly Ala Ser Pro
            100                 105                 110
Glu Pro Cys Thr Val Thr Pro Gly Ala Val Lys Leu Glu Lys Glu Lys
            115                 120                 125
Leu Glu Gln Asn Pro Glu Glu Ser Gln Asp Ile Lys Ala Leu Gln Lys
            130                 135                 140
Glu Leu Glu Gln Phe Ala Lys Leu Leu Lys Gln Lys Arg Ile Thr Leu
145                 150                 155                 160
```

-continued

```
Gly Tyr Thr Gln Ala Asp Val Gly Leu Thr Leu Gly Val Leu Phe Gly
                165                 170                 175
Lys Val Phe Ser Gln Thr Thr Ile Cys Arg Phe Glu Ala Leu Gln Leu
            180                 185                 190
Ser Phe Lys Asn Met Cys Lys Leu Arg Pro Leu Leu Gln Lys Trp Val
        195                 200                 205
Glu Glu Ala Asp Asn Asn Glu Asn Leu Gln Glu Ile Cys Lys Ala Glu
    210                 215                 220
Thr Leu Val Gln Ala Arg Lys Arg Lys Arg Thr Ser Ile Glu Asn Arg
225                 230                 235                 240
Val Arg Gly Asn Leu Glu Asn Leu Phe Leu Gln Cys Pro Lys Pro Thr
                245                 250                 255
Leu Gln Gln Ile Ser His Ile Ala Gln Gln Leu Gly Leu Glu Lys Asp
            260                 265                 270
Val Val Arg Val Trp Phe Cys Asn Arg Arg Gln Lys Gly Lys Arg Ser
        275                 280                 285
Ser Ser Asp Tyr Ala Gln Arg Glu Asp Phe Glu Ala Ala Gly Ser Pro
    290                 295                 300
Phe Ser Gly Gly Pro Val Ser Phe Pro Leu Ala Pro Gly Pro His Phe
305                 310                 315                 320
Gly Thr Pro Gly Tyr Gly Ser Pro His Phe Thr Ala Leu Tyr Ser Ser
                325                 330                 335
Val Pro Phe Pro Glu Gly Glu Ala Phe Pro Pro Val Ser Val Thr Thr
            340                 345                 350
Leu Gly Ser Pro Met His Ser Asn
        355                 360

<210> SEQ ID NO 3
<211> LENGTH: 305
<212> TYPE: PRT
<213> ORGANISM: Homo sapiens

<400> SEQUENCE: 3

Met Ser Val Asp Pro Ala Cys Pro Gln Ser Leu Pro Cys Phe Glu Ala
1               5                   10                  15
Ser Asp Cys Lys Glu Ser Ser Pro Met Pro Val Ile Cys Gly Pro Glu
            20                  25                  30
Glu Asn Tyr Pro Ser Leu Gln Met Ser Ser Ala Glu Met Pro His Thr
        35                  40                  45
Glu Thr Val Ser Pro Leu Pro Ser Ser Met Asp Leu Leu Ile Gln Asp
    50                  55                  60
Ser Pro Asp Ser Ser Thr Ser Pro Lys Gly Lys Gln Pro Thr Ser Ala
65                  70                  75                  80
Glu Lys Ser Val Ala Lys Lys Glu Asp Lys Val Pro Val Lys Lys Gln
                85                  90                  95
Lys Thr Arg Thr Val Phe Ser Ser Thr Gln Leu Cys Val Leu Asn Asp
            100                 105                 110
Arg Phe Gln Arg Gln Lys Tyr Leu Ser Leu Gln Gln Met Gln Glu Leu
        115                 120                 125
Ser Asn Ile Leu Asn Leu Ser Tyr Lys Gln Val Lys Thr Trp Phe Gln
    130                 135                 140
Asn Gln Arg Met Lys Ser Lys Arg Trp Gln Lys Asn Asn Trp Pro Lys
145                 150                 155                 160
Asn Ser Asn Gly Val Thr Gln Lys Ala Ser Ala Pro Thr Tyr Pro Ser
                165                 170                 175
```

```
Leu Tyr Ser Ser Tyr His Gln Gly Cys Leu Val Asn Pro Thr Gly Asn
            180                 185                 190

Leu Pro Met Trp Ser Asn Gln Thr Trp Asn Asn Ser Thr Trp Ser Asn
            195                 200                 205

Gln Thr Gln Asn Ile Gln Ser Trp Ser Asn His Ser Trp Asn Thr Gln
    210                 215                 220

Thr Trp Cys Thr Gln Ser Trp Asn Asn Gln Ala Trp Asn Ser Pro Phe
225                 230                 235                 240

Tyr Asn Cys Gly Glu Glu Ser Leu Gln Ser Cys Met Gln Phe Gln Pro
                245                 250                 255

Asn Ser Pro Ala Ser Asp Leu Glu Ala Ala Leu Glu Ala Ala Gly Glu
            260                 265                 270

Gly Leu Asn Val Ile Gln Gln Thr Thr Arg Tyr Phe Ser Thr Pro Gln
            275                 280                 285

Thr Met Asp Leu Phe Leu Asn Tyr Ser Met Asn Met Gln Pro Glu Asp
    290                 295                 300
Val
305

<210> SEQ ID NO 4
<211> LENGTH: 209
<212> TYPE: PRT
<213> ORGANISM: Homo sapiens

<400> SEQUENCE: 4

Met Gly Ser Val Ser Asn Gln Gln Phe Ala Gly Gly Cys Ala Lys Ala
1               5                   10                  15

Ala Glu Glu Ala Pro Glu Glu Ala Pro Glu Asp Ala Ala Arg Ala Ala
            20                  25                  30

Asp Glu Pro Gln Leu Leu His Gly Ala Gly Ile Cys Lys Trp Phe Asn
        35                  40                  45

Val Arg Met Gly Phe Gly Phe Leu Ser Met Thr Ala Arg Ala Gly Val
    50                  55                  60

Ala Leu Asp Pro Pro Val Asp Val Phe Val His Gln Ser Lys Leu His
65                  70                  75                  80

Met Glu Gly Phe Arg Ser Leu Lys Glu Gly Glu Ala Val Glu Phe Thr
                85                  90                  95

Phe Lys Lys Ser Ala Lys Gly Leu Glu Ser Ile Arg Val Thr Gly Pro
            100                 105                 110

Gly Gly Val Phe Cys Ile Gly Ser Glu Arg Arg Pro Lys Gly Lys Ser
            115                 120                 125

Met Gln Lys Arg Arg Ser Lys Gly Asp Arg Cys Tyr Asn Cys Gly Gly
    130                 135                 140

Leu Asp His His Ala Lys Glu Cys Lys Leu Pro Pro Gln Pro Lys Lys
145                 150                 155                 160

Cys His Phe Cys Gln Ser Ile Ser His Met Val Ala Ser Cys Pro Leu
                165                 170                 175

Lys Ala Gln Gln Gly Pro Ser Ala Gln Gly Lys Pro Thr Tyr Phe Arg
            180                 185                 190

Glu Glu Glu Glu Glu Ile His Ser Pro Thr Leu Leu Pro Glu Ala Gln
        195                 200                 205

Asn

<210> SEQ ID NO 5
```

```
<211> LENGTH: 479
<212> TYPE: PRT
<213> ORGANISM: Homo sapiens

<400> SEQUENCE: 5

Met Arg Gln Pro Pro Gly Glu Ser Asp Met Ala Val Ser Asp Ala Leu
1               5                   10                  15

Leu Pro Ser Phe Ser Thr Phe Ala Ser Gly Pro Ala Gly Arg Glu Lys
            20                  25                  30

Thr Leu Arg Gln Ala Gly Ala Pro Asn Asn Arg Trp Arg Glu Glu Leu
        35                  40                  45

Ser His Met Lys Arg Leu Pro Val Leu Pro Gly Arg Pro Tyr Asp
    50                  55                  60

Leu Ala Ala Ala Thr Val Ala Thr Asp Leu Glu Ser Gly Ala Gly
65              70                  75                  80

Ala Ala Cys Gly Gly Ser Asn Leu Ala Pro Leu Pro Arg Arg Glu Thr
            85                  90                  95

Glu Glu Phe Asn Asp Leu Leu Asp Leu Asp Phe Ile Leu Ser Asn Ser
            100                 105                 110

Leu Thr His Pro Pro Glu Ser Val Ala Ala Thr Val Ser Ser Ser Ala
            115                 120                 125

Ser Ala Ser Ser Ser Ser Ser Pro Ser Ser Ser Gly Pro Ala Ser Ala
    130                 135                 140

Pro Ser Thr Cys Ser Phe Thr Tyr Pro Ile Arg Ala Gly Asn Asp Pro
145                 150                 155                 160

Gly Val Ala Pro Gly Gly Thr Gly Gly Gly Leu Leu Tyr Gly Arg Glu
                165                 170                 175

Ser Ala Pro Pro Pro Thr Ala Pro Phe Asn Leu Ala Asp Ile Asn Asp
            180                 185                 190

Val Ser Pro Ser Gly Gly Phe Val Ala Glu Leu Leu Arg Pro Glu Leu
        195                 200                 205

Asp Pro Val Tyr Ile Pro Pro Gln Gln Pro Gln Pro Pro Gly Gly Gly
    210                 215                 220

Leu Met Gly Lys Phe Val Leu Lys Ala Ser Leu Ser Ala Pro Gly Ser
225                 230                 235                 240

Glu Tyr Gly Ser Pro Ser Val Ile Ser Val Ser Lys Gly Ser Pro Asp
                245                 250                 255

Gly Ser His Pro Val Val Ala Pro Tyr Asn Gly Gly Pro Pro Arg
            260                 265                 270

Thr Cys Pro Lys Ile Lys Gln Glu Ala Val Ser Ser Cys Thr His Leu
            275                 280                 285

Gly Ala Gly Pro Pro Leu Ser Asn Gly His Arg Pro Ala Ala His Asp
    290                 295                 300

Phe Pro Leu Gly Arg Gln Leu Pro Ser Arg Thr Thr Pro Thr Leu Gly
305                 310                 315                 320

Leu Glu Glu Val Leu Ser Ser Arg Asp Cys His Pro Ala Leu Pro Leu
                325                 330                 335

Pro Pro Gly Phe His Pro His Pro Gly Pro Asn Tyr Pro Ser Phe Leu
            340                 345                 350

Pro Asp Gln Met Gln Pro Gln Val Pro Pro Leu His Tyr Gln Glu Leu
        355                 360                 365

Met Pro Pro Gly Ser Cys Met Pro Glu Glu Pro Lys Pro Lys Arg Gly
    370                 375                 380

Arg Arg Ser Trp Pro Arg Lys Arg Thr Ala Thr His Thr Cys Asp Tyr
```

```
                385                 390                 395                 400
Ala Gly Cys Gly Lys Thr Tyr Thr Lys Ser Ser His Leu Lys Ala His
                    405                 410                 415

Leu Arg Thr His Thr Gly Glu Lys Pro Tyr His Cys Asp Trp Asp Gly
                    420                 425                 430

Cys Gly Trp Lys Phe Ala Arg Ser Asp Glu Leu Thr Arg His Tyr Arg
                    435                 440                 445

Lys His Thr Gly His Arg Pro Phe Gln Cys Gln Lys Cys Asp Arg Ala
                    450                 455                 460

Phe Ser Arg Ser Asp His Leu Ala Leu His Met Lys Arg His Phe
465                 470                 475

<210> SEQ ID NO 6
<211> LENGTH: 454
<212> TYPE: PRT
<213> ORGANISM: Homo sapiens

<400> SEQUENCE: 6

Met Asp Phe Phe Arg Val Val Glu Asn Gln Gln Pro Pro Ala Thr Met
1               5                   10                  15

Pro Leu Asn Val Ser Phe Thr Asn Arg Asn Tyr Asp Leu Asp Tyr Asp
                20                  25                  30

Ser Val Gln Pro Tyr Phe Tyr Cys Asp Glu Glu Glu Asn Phe Tyr Gln
            35                  40                  45

Gln Gln Gln Gln Ser Glu Leu Gln Pro Pro Ala Pro Ser Glu Asp Ile
        50                  55                  60

Trp Lys Lys Phe Glu Leu Leu Pro Thr Pro Pro Leu Ser Pro Ser Arg
65                  70                  75                  80

Arg Ser Gly Leu Cys Ser Pro Ser Tyr Val Ala Val Thr Pro Phe Ser
                85                  90                  95

Leu Arg Gly Asp Asn Asp Gly Gly Gly Gly Ser Phe Ser Thr Ala Asp
                100                 105                 110

Gln Leu Glu Met Val Thr Glu Leu Leu Gly Gly Asp Met Val Asn Gln
            115                 120                 125

Ser Phe Ile Cys Asp Pro Asp Asp Glu Thr Phe Ile Lys Asn Ile Ile
        130                 135                 140

Ile Gln Asp Cys Met Trp Ser Gly Phe Ser Ala Ala Ala Lys Leu Val
145                 150                 155                 160

Ser Glu Lys Leu Ala Ser Tyr Gln Ala Ala Arg Lys Asp Ser Gly Ser
                165                 170                 175

Pro Asn Pro Ala Arg Gly His Ser Val Cys Ser Thr Ser Ser Leu Tyr
                180                 185                 190

Leu Gln Asp Leu Ser Ala Ala Ala Ser Glu Cys Ile Asp Pro Ser Val
            195                 200                 205

Val Phe Pro Tyr Pro Leu Asn Asp Ser Ser Ser Pro Lys Ser Cys Ala
        210                 215                 220

Ser Gln Asp Ser Ser Ala Phe Ser Pro Ser Ser Asp Ser Leu Leu Ser
225                 230                 235                 240

Ser Thr Glu Ser Ser Pro Gln Gly Ser Pro Glu Pro Leu Val Leu His
                245                 250                 255

Glu Glu Thr Pro Pro Thr Thr Ser Ser Asp Ser Glu Glu Glu Gln Glu
                260                 265                 270

Asp Glu Glu Glu Ile Asp Val Val Ser Val Glu Lys Arg Gln Ala Pro
            275                 280                 285
```

-continued

```
Gly Lys Arg Ser Glu Ser Gly Ser Pro Ser Ala Gly Gly His Ser Lys
290                 295                 300
Pro Pro His Ser Pro Leu Val Leu Lys Arg Cys His Val Ser Thr His
305                 310                 315                 320
Gln His Asn Tyr Ala Ala Pro Pro Ser Thr Arg Lys Asp Tyr Pro Ala
                325                 330                 335
Ala Lys Arg Val Lys Leu Asp Ser Val Arg Val Leu Arg Gln Ile Ser
                340                 345                 350
Asn Asn Arg Lys Cys Thr Ser Pro Arg Ser Ser Asp Thr Glu Glu Asn
            355                 360                 365
Val Lys Arg Arg Thr His Asn Val Leu Glu Arg Gln Arg Arg Asn Glu
370                 375                 380
Leu Lys Arg Ser Phe Phe Ala Leu Arg Asp Gln Ile Pro Glu Leu Glu
385                 390                 395                 400
Asn Asn Glu Lys Ala Pro Lys Val Val Ile Leu Lys Lys Ala Thr Ala
                405                 410                 415
Tyr Ile Leu Ser Val Gln Ala Glu Glu Gln Lys Leu Ile Ser Glu Glu
                420                 425                 430
Asp Leu Leu Arg Lys Arg Arg Glu Gln Leu Lys His Lys Leu Glu Gln
                435                 440                 445
Leu Arg Asn Ser Cys Ala
450
```

<210> SEQ ID NO 7
<211> LENGTH: 442
<212> TYPE: PRT
<213> ORGANISM: Homo sapiens

<400> SEQUENCE: 7

```
Met Tyr Gln Ser Leu Ala Met Ala Ala Asn His Gly Pro Pro Pro Gly
1               5                   10                  15
Ala Tyr Glu Ala Gly Gly Pro Gly Ala Phe Met His Gly Ala Gly Ala
                20                  25                  30
Ala Ser Ser Pro Val Tyr Val Pro Thr Pro Arg Val Pro Ser Ser Val
            35                  40                  45
Leu Gly Leu Ser Tyr Leu Gln Gly Gly Ala Gly Ser Ala Ser Gly
50                  55                  60
Gly Ala Ser Gly Gly Ser Ser Gly Gly Ala Ala Ser Gly Ala Gly Pro
65                  70                  75                  80
Gly Thr Gln Gln Gly Ser Pro Gly Trp Ser Gln Ala Gly Ala Asp Gly
                85                  90                  95
Ala Ala Tyr Thr Pro Pro Pro Val Ser Pro Arg Phe Ser Phe Pro Gly
                100                 105                 110
Thr Thr Gly Ser Leu Ala Ala Ala Ala Ala Ala Ala Ala Ala Arg Glu
            115                 120                 125
Ala Ala Ala Tyr Ser Ser Gly Gly Gly Ala Ala Gly Ala Gly Leu Ala
            130                 135                 140
Gly Arg Glu Gln Tyr Gly Arg Ala Gly Phe Ala Gly Ser Tyr Ser Ser
145                 150                 155                 160
Pro Tyr Pro Ala Tyr Met Ala Asp Val Gly Ala Ser Trp Ala Ala Ala
                165                 170                 175
Ala Ala Ala Ser Ala Gly Pro Phe Asp Ser Pro Val Leu His Ser Leu
                180                 185                 190
Pro Gly Arg Ala Asn Pro Ala Ala Arg His Pro Asn Leu Asp Met Phe
            195                 200                 205
```

```
Asp Asp Phe Ser Glu Gly Arg Glu Cys Val Asn Cys Gly Ala Met Ser
            210                 215                 220
Thr Pro Leu Trp Arg Arg Asp Gly Thr Gly His Tyr Leu Cys Asn Ala
225                 230                 235                 240
Cys Gly Leu Tyr His Lys Met Asn Gly Ile Asn Arg Pro Leu Ile Lys
                245                 250                 255
Pro Gln Arg Arg Leu Ser Ala Ser Arg Arg Val Gly Leu Ser Cys Ala
            260                 265                 270
Asn Cys Gln Thr Thr Thr Thr Leu Trp Arg Arg Asn Ala Glu Gly
            275                 280                 285
Glu Pro Val Cys Asn Ala Cys Gly Leu Tyr Met Lys Leu His Gly Val
290                 295                 300
Pro Arg Pro Leu Ala Met Arg Lys Glu Gly Ile Gln Thr Arg Lys Arg
305                 310                 315                 320
Lys Pro Lys Asn Leu Asn Lys Ser Lys Thr Pro Ala Ala Pro Ser Gly
                325                 330                 335
Ser Glu Ser Leu Pro Pro Ala Ser Gly Ala Ser Ser Asn Ser Ser Asn
            340                 345                 350
Ala Thr Thr Ser Ser Glu Glu Met Arg Pro Ile Lys Thr Glu Pro
            355                 360                 365
Gly Leu Ser Ser His Tyr Gly His Ser Ser Val Ser Gln Thr Phe
370                 375                 380
Ser Val Ser Ala Met Ser Gly His Gly Pro Ser Ile His Pro Val Leu
385                 390                 395                 400
Ser Ala Leu Lys Leu Ser Pro Gln Gly Tyr Ala Ser Pro Val Ser Gln
                405                 410                 415
Ser Pro Gln Thr Ser Ser Lys Gln Asp Ser Trp Asn Ser Leu Val Leu
            420                 425                 430
Ala Asp Ser His Gly Asp Ile Ile Thr Ala
            435                 440

<210> SEQ ID NO 8
<211> LENGTH: 217
<212> TYPE: PRT
<213> ORGANISM: Homo sapiens

<400> SEQUENCE: 8

Met Ser Leu Val Gly Phe Pro His His Pro Val Val His His Glu
1               5                   10                  15
Gly Tyr Pro Phe Ala Ala Ala Ala Ala Ala Ala Ala Ala
            20                  25                  30
Ser Arg Cys Ser His Glu Glu Asn Pro Tyr Phe His Gly Trp Leu Ile
            35                  40                  45
Gly His Pro Glu Met Ser Pro Pro Asp Tyr Ser Met Ala Leu Ser Tyr
50                  55                  60
Ser Pro Glu Tyr Ala Ser Gly Ala Ala Gly Leu Asp His Ser His Tyr
65                  70                  75                  80
Gly Gly Val Pro Pro Gly Ala Gly Pro Pro Gly Leu Gly Gly Pro Arg
                85                  90                  95
Pro Val Lys Arg Arg Gly Thr Ala Asn Arg Lys Glu Arg Arg Arg Thr
            100                 105                 110
Gln Ser Ile Asn Ser Ala Phe Ala Glu Leu Arg Glu Cys Ile Pro Asn
            115                 120                 125
Val Pro Ala Asp Thr Lys Leu Ser Lys Ile Lys Thr Leu Arg Leu Ala
```

```
                    130                 135                 140
Thr Ser Tyr Ile Ala Tyr Leu Met Asp Leu Leu Ala Lys Asp Asp Gln
145                 150                 155                 160

Asn Gly Glu Ala Glu Ala Phe Lys Ala Glu Ile Lys Lys Thr Asp Val
                165                 170                 175

Lys Glu Glu Lys Arg Lys Lys Glu Leu Asn Glu Ile Leu Lys Ser Thr
            180                 185                 190

Val Ser Ser Asn Asp Lys Lys Thr Lys Gly Arg Thr Gly Trp Pro Gln
            195                 200                 205

His Val Trp Ala Leu Glu Leu Lys Gln
    210                 215

<210> SEQ ID NO 9
<211> LENGTH: 473
<212> TYPE: PRT
<213> ORGANISM: Homo sapiens

<400> SEQUENCE: 9

Met Gly Arg Lys Lys Ile Gln Ile Thr Arg Ile Met Asp Glu Arg Asn
1               5                   10                  15

Arg Gln Val Thr Phe Thr Lys Arg Lys Phe Gly Leu Met Lys Lys Ala
                20                  25                  30

Tyr Glu Leu Ser Val Leu Cys Asp Cys Glu Ile Ala Leu Ile Ile Phe
            35                  40                  45

Asn Ser Thr Asn Lys Leu Phe Gln Tyr Ala Ser Thr Asp Met Asp Lys
        50                  55                  60

Val Leu Leu Lys Tyr Thr Glu Tyr Asn Glu Pro His Glu Ser Arg Thr
65                  70                  75                  80

Asn Ser Asp Ile Val Glu Thr Leu Arg Lys Lys Gly Leu Asn Gly Cys
                85                  90                  95

Asp Ser Pro Asp Pro Asp Ala Asp Asp Ser Val Gly His Ser Pro Glu
            100                 105                 110

Ser Glu Asp Lys Tyr Arg Lys Ile Asn Glu Asp Ile Asp Leu Met Ile
        115                 120                 125

Ser Arg Gln Arg Leu Cys Ala Val Pro Pro Pro Asn Phe Glu Met Pro
    130                 135                 140

Val Ser Ile Pro Val Ser Ser His Asn Ser Leu Val Tyr Ser Asn Pro
145                 150                 155                 160

Val Ser Ser Leu Gly Asn Pro Asn Leu Leu Pro Leu Ala His Pro Ser
                165                 170                 175

Leu Gln Arg Asn Ser Met Ser Pro Gly Val Thr His Arg Pro Pro Ser
            180                 185                 190

Ala Gly Asn Thr Gly Gly Leu Met Gly Gly Asp Leu Thr Ser Gly Ala
        195                 200                 205

Gly Thr Ser Ala Gly Asn Gly Tyr Gly Asn Pro Arg Asn Ser Pro Gly
    210                 215                 220

Leu Leu Val Ser Pro Gly Asn Leu Asn Lys Asn Met Gln Ala Lys Ser
225                 230                 235                 240

Pro Pro Pro Met Asn Leu Gly Met Asn Asn Arg Lys Pro Asp Leu Arg
                245                 250                 255

Val Leu Ile Pro Pro Gly Ser Lys Asn Thr Met Pro Ser Val Ser Glu
            260                 265                 270

Asp Val Asp Leu Leu Leu Asn Gln Arg Ile Asn Asn Ser Gln Ser Ala
        275                 280                 285
```

```
Gln Ser Leu Ala Thr Pro Val Val Ser Val Ala Thr Pro Thr Leu Pro
    290                 295                 300

Gly Gln Gly Met Gly Gly Tyr Pro Ser Ala Ile Ser Thr Thr Tyr Gly
305                 310                 315                 320

Thr Glu Tyr Ser Leu Ser Ser Ala Asp Leu Ser Ser Leu Ser Gly Phe
                325                 330                 335

Asn Thr Ala Ser Ala Leu His Leu Gly Ser Val Thr Gly Trp Gln Gln
            340                 345                 350

Gln His Leu His Asn Met Pro Pro Ser Ala Leu Ser Gln Leu Gly Ala
        355                 360                 365

Cys Thr Ser Thr His Leu Ser Gln Ser Ser Asn Leu Ser Leu Pro Ser
370                 375                 380

Thr Gln Ser Leu Asn Ile Lys Ser Glu Pro Val Ser Pro Pro Arg Asp
385                 390                 395                 400

Arg Thr Thr Thr Pro Ser Arg Tyr Pro Gln His Thr Arg His Glu Ala
                405                 410                 415

Gly Arg Ser Pro Val Asp Ser Leu Ser Ser Cys Ser Ser Ser Tyr Asp
            420                 425                 430

Gly Ser Asp Arg Glu Asp His Arg Asn Glu Phe His Ser Pro Ile Gly
        435                 440                 445

Leu Thr Arg Pro Ser Pro Asp Glu Arg Glu Ser Pro Ser Val Lys Arg
450                 455                 460

Met Arg Leu Ser Glu Gly Trp Ala Thr
465                 470

<210> SEQ ID NO 10
<211> LENGTH: 349
<212> TYPE: PRT
<213> ORGANISM: Homo sapiens

<400> SEQUENCE: 10

Met Ala Asp Ala Asp Glu Gly Phe Gly Leu Ala His Thr Pro Leu Glu
1               5                   10                  15

Pro Asp Ala Lys Asp Leu Pro Cys Asp Ser Lys Pro Glu Ser Ala Leu
            20                  25                  30

Gly Ala Pro Ser Lys Ser Pro Ser Pro Gln Ala Ala Phe Thr Gln Gln
        35                  40                  45

Gln Gly Met Glu Gly Ile Lys Val Phe Leu His Glu Arg Glu Leu Trp
    50                  55                  60

Leu Lys Phe His Glu Val Gly Thr Glu Met Ile Ile Thr Lys Ala Gly
65                  70                  75                  80

Arg Arg Met Phe Pro Ser Tyr Lys Val Lys Val Thr Gly Leu Asn Pro
                85                  90                  95

Lys Thr Lys Tyr Ile Leu Leu Met Asp Ile Val Pro Ala Asp Asp His
            100                 105                 110

Arg Tyr Lys Phe Ala Asp Asn Lys Trp Ser Val Thr Gly Lys Ala Glu
        115                 120                 125

Pro Ala Met Pro Gly Arg Leu Tyr Val His Pro Asp Ser Pro Ala Thr
    130                 135                 140

Gly Ala His Trp Met Arg Gln Leu Val Ser Phe Gln Lys Leu Lys Leu
145                 150                 155                 160

Thr Asn Asn His Leu Asp Pro Phe Gly His Ile Ile Leu Asn Ser Met
                165                 170                 175

His Lys Tyr Gln Pro Arg Leu His Ile Val Lys Ala Asp Glu Asn Asn
            180                 185                 190
```

```
Gly Phe Gly Ser Lys Asn Thr Ala Phe Cys Thr His Val Phe Pro Glu
            195                 200                 205

Thr Ala Phe Ile Ala Val Thr Ser Tyr Gln Asn His Lys Ile Thr Gln
210                 215                 220

Leu Lys Ile Glu Asn Asn Pro Phe Ala Lys Gly Phe Arg Gly Ser Asp
225                 230                 235                 240

Asp Met Glu Leu His Arg Met Ser Arg Met Gln Ser Lys Glu Tyr Pro
            245                 250                 255

Val Val Pro Arg Ser Thr Val Arg Gln Lys Val Ala Ser Asn His Ser
            260                 265                 270

Pro Phe Ser Ser Glu Ser Arg Ala Leu Ser Thr Ser Ser Asn Leu Gly
            275                 280                 285

Ser Gln Tyr Gln Cys Glu Asn Gly Val Ser Gly Pro Ser Gln Asp Leu
            290                 295                 300

Leu Pro Pro Asn Pro Tyr Pro Leu Pro Gln Glu His Ser Gln Ile
305                 310                 315                 320

Tyr His Cys Thr Lys Arg Lys Gly Glu Cys Asp His Pro Trp Ser Ile
            325                 330                 335

Cys Phe Leu Ser Tyr Leu Phe Leu Ser Leu Gly Trp Gly
            340                 345

<210> SEQ ID NO 11
<211> LENGTH: 214
<212> TYPE: PRT
<213> ORGANISM: Homo sapiens

<400> SEQUENCE: 11

Met Thr Pro Gln Pro Ser Gly Ala Pro Thr Val Gln Val Thr Arg Glu
1               5                   10                  15

Thr Glu Arg Ser Phe Pro Arg Ala Ser Glu Asp Val Thr Cys Pro
            20                  25                  30

Thr Ser Ala Pro Pro Ser Pro Thr Arg Thr Arg Gly Asn Cys Ala Glu
        35                  40                  45

Ala Glu Glu Gly Gly Cys Arg Gly Ala Pro Arg Lys Leu Arg Ala Arg
50                  55                  60

Arg Gly Gly Arg Ser Arg Pro Lys Ser Glu Leu Ala Leu Ser Lys Gln
65                  70                  75                  80

Arg Arg Ser Arg Arg Lys Lys Ala Asn Asp Arg Glu Arg Asn Arg Met
            85                  90                  95

His Asn Leu Asn Ser Ala Leu Asp Ala Leu Arg Gly Val Leu Pro Thr
            100                 105                 110

Phe Pro Asp Asp Ala Lys Leu Thr Lys Ile Glu Thr Leu Arg Phe Ala
            115                 120                 125

His Asn Tyr Ile Trp Ala Leu Thr Gln Thr Leu Arg Ile Ala Asp His
            130                 135                 140

Ser Leu Tyr Ala Leu Glu Pro Ala Pro His Cys Gly Glu Leu Gly
145                 150                 155                 160

Ser Pro Gly Gly Ser Pro Gly Asp Trp Gly Ser Leu Tyr Ser Pro Val
            165                 170                 175

Ser Gln Ala Gly Ser Leu Ser Pro Ala Ala Ser Leu Glu Glu Arg Pro
            180                 185                 190

Gly Leu Leu Gly Ala Thr Phe Ser Ala Cys Leu Ser Pro Gly Ser Leu
            195                 200                 205

Ala Phe Ser Asp Phe Leu
```

-continued

<210> SEQ ID NO 12
<211> LENGTH: 343
<212> TYPE: PRT
<213> ORGANISM: Homo sapiens

<400> SEQUENCE: 12

Met Asn Gln Leu Gly Gly Leu Phe Val Asn Gly Arg Pro Leu Pro Leu
1               5                   10                  15

Asp Thr Arg Gln Gln Ile Val Arg Leu Ala Val Ser Gly Met Arg Pro
            20                  25                  30

Cys Asp Ile Ser Arg Ile Leu Lys Val Ser Asn Gly Cys Val Ser Lys
        35                  40                  45

Ile Leu Gly Arg Tyr Tyr Arg Thr Gly Val Leu Glu Pro Lys Gly Ile
    50                  55                  60

Gly Gly Ser Lys Pro Arg Leu Ala Thr Pro Pro Val Val Ala Arg Ile
65                  70                  75                  80

Ala Gln Leu Lys Gly Glu Cys Pro Ala Leu Phe Ala Trp Glu Ile Gln
                85                  90                  95

Arg Gln Leu Cys Ala Glu Gly Leu Cys Thr Gln Asp Lys Thr Pro Ser
            100                 105                 110

Val Ser Ser Ile Asn Arg Val Leu Arg Ala Leu Gln Glu Asp Gln Gly
        115                 120                 125

Leu Pro Cys Thr Arg Leu Arg Ser Pro Ala Val Leu Ala Pro Ala Val
    130                 135                 140

Leu Thr Pro His Ser Gly Ser Glu Thr Pro Arg Gly Thr His Pro Gly
145                 150                 155                 160

Thr Gly His Arg Asn Arg Thr Ile Phe Ser Pro Ser Gln Ala Glu Ala
                165                 170                 175

Leu Glu Lys Glu Phe Gln Arg Gly Gln Tyr Pro Asp Ser Val Ala Arg
            180                 185                 190

Gly Lys Leu Ala Thr Ala Thr Ser Leu Pro Glu Asp Thr Val Arg Val
        195                 200                 205

Trp Phe Ser Asn Arg Arg Ala Lys Trp Arg Arg Gln Glu Lys Leu Lys
    210                 215                 220

Trp Glu Met Gln Leu Pro Gly Ala Ser Gln Gly Leu Thr Val Pro Arg
225                 230                 235                 240

Val Ala Pro Gly Ile Ile Ser Ala Gln Gln Ser Pro Gly Ser Val Pro
                245                 250                 255

Thr Ala Ala Leu Pro Ala Leu Glu Pro Leu Gly Pro Ser Cys Tyr Gln
            260                 265                 270

Leu Cys Trp Ala Thr Ala Pro Glu Arg Cys Leu Ser Asp Thr Pro Pro
        275                 280                 285

Lys Ala Cys Leu Lys Pro Cys Trp Gly His Leu Pro Gln Pro Asn
    290                 295                 300

Ser Leu Asp Ser Gly Leu Leu Cys Leu Pro Cys Pro Ser Ser His Cys
305                 310                 315                 320

His Leu Ala Ser Leu Ser Gly Ser Gln Ala Leu Leu Trp Pro Gly Cys
                325                 330                 335

Pro Leu Leu Tyr Gly Leu Glu
            340

<210> SEQ ID NO 13
<211> LENGTH: 283

```
<212> TYPE: PRT
<213> ORGANISM: Homo sapiens

<400> SEQUENCE: 13

Met Asn Gly Glu Glu Gln Tyr Tyr Ala Ala Thr Gln Leu Tyr Lys Asp
1               5                   10                  15

Pro Cys Ala Phe Gln Arg Gly Pro Ala Pro Glu Phe Ser Ala Ser Pro
            20                  25                  30

Pro Ala Cys Leu Tyr Met Gly Arg Gln Pro Pro Pro Pro Pro His
            35                  40                  45

Pro Phe Pro Gly Ala Leu Gly Ala Leu Glu Gln Gly Ser Pro Pro Asp
    50                  55                  60

Ile Ser Pro Tyr Glu Val Pro Pro Leu Ala Asp Asp Pro Ala Val Ala
65                  70                  75                  80

His Leu His His His Leu Pro Ala Gln Leu Ala Leu Pro His Pro Pro
                85                  90                  95

Ala Gly Pro Phe Pro Glu Gly Ala Glu Pro Gly Val Leu Glu Glu Pro
            100                 105                 110

Asn Arg Val Gln Leu Pro Phe Pro Trp Met Lys Ser Thr Lys Ala His
            115                 120                 125

Ala Trp Lys Gly Gln Trp Ala Gly Gly Ala Tyr Ala Ala Glu Pro Glu
130                 135                 140

Glu Asn Lys Arg Thr Arg Thr Ala Tyr Thr Arg Ala Gln Leu Leu Glu
145                 150                 155                 160

Leu Glu Lys Glu Phe Leu Phe Asn Lys Tyr Ile Ser Arg Pro Arg Arg
                165                 170                 175

Val Glu Leu Ala Val Met Leu Asn Leu Thr Glu Arg His Ile Lys Ile
            180                 185                 190

Trp Phe Gln Asn Arg Arg Met Lys Trp Lys Lys Glu Asp Lys Lys
            195                 200                 205

Arg Gly Gly Gly Thr Ala Val Gly Gly Gly Val Ala Glu Pro Glu
210                 215                 220

Gln Asp Cys Ala Val Thr Ser Gly Glu Glu Leu Leu Ala Leu Pro Pro
225                 230                 235                 240

Pro Pro Pro Pro Gly Gly Ala Val Pro Pro Ala Ala Pro Val Ala Ala
            245                 250                 255

Arg Glu Gly Arg Leu Pro Pro Gly Leu Ser Ala Ser Pro Gln Pro Ser
            260                 265                 270

Ser Val Ala Pro Arg Arg Pro Gln Glu Pro Arg
            275                 280

<210> SEQ ID NO 14
<211> LENGTH: 509
<212> TYPE: PRT
<213> ORGANISM: Homo sapiens

<400> SEQUENCE: 14

Met Asn Leu Leu Asp Pro Phe Met Lys Met Thr Asp Glu Gln Glu Lys
1               5                   10                  15

Gly Leu Ser Gly Ala Pro Ser Pro Thr Met Ser Glu Asp Ser Ala Gly
            20                  25                  30

Ser Pro Cys Pro Ser Gly Ser Gly Ser Asp Thr Glu Asn Thr Arg Pro
            35                  40                  45

Gln Glu Asn Thr Phe Pro Lys Gly Glu Pro Asp Leu Lys Lys Glu Ser
    50                  55                  60
```

-continued

```
Glu Glu Asp Lys Phe Pro Val Cys Ile Arg Glu Ala Val Ser Gln Val
 65                  70                  75                  80

Leu Lys Gly Tyr Asp Trp Thr Leu Val Pro Met Pro Arg Val Asn
                 85                  90                  95

Gly Ser Ser Lys Asn Lys Pro His Val Lys Arg Pro Met Asn Ala Phe
            100                 105                 110

Met Val Trp Ala Gln Ala Ala Arg Arg Lys Leu Ala Asp Gln Tyr Pro
            115                 120                 125

His Leu His Asn Ala Glu Leu Ser Lys Thr Leu Gly Lys Leu Trp Arg
        130                 135                 140

Leu Leu Asn Glu Ser Glu Lys Arg Pro Phe Val Glu Glu Ala Glu Arg
145                 150                 155                 160

Leu Arg Val Gln His Lys Lys Asp His Pro Asp Tyr Lys Tyr Gln Pro
                165                 170                 175

Arg Arg Arg Lys Ser Val Lys Asn Gly Gln Ala Glu Ala Glu Glu Ala
            180                 185                 190

Thr Glu Gln Thr His Ile Ser Pro Asn Ala Ile Phe Lys Ala Leu Gln
        195                 200                 205

Ala Asp Ser Pro His Ser Ser Gly Met Ser Glu Val His Ser Pro
210                 215                 220

Gly Glu His Ser Gly Gln Ser Gln Gly Pro Pro Thr Pro Pro Thr Thr
225                 230                 235                 240

Pro Lys Thr Asp Val Gln Pro Gly Lys Ala Asp Leu Lys Arg Glu Gly
                245                 250                 255

Arg Pro Leu Pro Glu Gly Gly Arg Gln Pro Pro Ile Asp Phe Arg Asp
            260                 265                 270

Val Asp Ile Gly Glu Leu Ser Ser Asp Val Ile Ser Asn Ile Glu Thr
        275                 280                 285

Phe Asp Val Asn Glu Phe Asp Gln Tyr Leu Pro Pro Asn Gly His Pro
290                 295                 300

Gly Val Pro Ala Thr His Gly Gln Val Thr Tyr Thr Gly Ser Tyr Gly
305                 310                 315                 320

Ile Ser Ser Thr Ala Ala Thr Pro Ala Ser Ala Gly His Val Trp Met
                325                 330                 335

Ser Lys Gln Gln Ala Pro Pro Pro Pro Gln Gln Pro Pro Gln Ala
            340                 345                 350

Pro Pro Ala Pro Gln Ala Pro Pro Gln Pro Ala Ala Pro Pro Gln
            355                 360                 365

Gln Pro Ala Ala Pro Pro Gln Gln Pro Gln Ala His Thr Leu Thr Thr
        370                 375                 380

Leu Ser Ser Glu Pro Gly Gln Ser Gln Arg Thr His Ile Lys Thr Glu
385                 390                 395                 400

Gln Leu Ser Pro Ser His Tyr Ser Glu Gln Gln Gln His Ser Pro Gln
                405                 410                 415

Gln Ile Ala Tyr Ser Pro Phe Asn Leu Pro His Tyr Ser Pro Ser Tyr
            420                 425                 430

Pro Pro Ile Thr Arg Ser Gln Tyr Asp Tyr Thr Asp His Gln Asn Ser
        435                 440                 445

Ser Ser Tyr Tyr Ser His Ala Ala Gly Gln Gly Thr Gly Leu Tyr Ser
450                 455                 460

Thr Phe Thr Tyr Met Asn Pro Ala Gln Arg Pro Met Tyr Thr Pro Ile
465                 470                 475                 480

Ala Asp Thr Ser Gly Val Pro Ser Ile Pro Gln Thr His Ser Pro Gln
```

His Trp Glu Gln Pro Val Tyr Thr Gln Leu Thr Arg Pro
            485                 490                 495
            500                     505

<210> SEQ ID NO 15
<211> LENGTH: 268
<212> TYPE: PRT
<213> ORGANISM: Homo sapiens

<400> SEQUENCE: 15

Met Pro Arg Ser Phe Leu Val Lys Lys His Phe Asn Ala Ser Lys Lys
1               5                   10                  15

Pro Asn Tyr Ser Glu Leu Asp Thr His Thr Val Ile Ile Ser Pro Tyr
            20                  25                  30

Leu Tyr Glu Ser Tyr Ser Met Pro Val Ile Pro Gln Pro Glu Ile Leu
        35                  40                  45

Ser Ser Gly Ala Tyr Ser Pro Ile Thr Val Trp Thr Thr Ala Ala Pro
50                  55                  60

Phe His Ala Gln Leu Pro Asn Gly Leu Ser Pro Leu Ser Gly Tyr Ser
65                  70                  75                  80

Ser Ser Leu Gly Arg Val Ser Pro Pro Pro Ser Asp Thr Ser Ser Ser
                85                  90                  95

Lys Asp His Ser Gly Ser Glu Ser Pro Ile Ser Asp Glu Glu Glu Arg
            100                 105                 110

Leu Gln Ser Lys Leu Ser Asp Pro His Ala Ile Glu Ala Glu Lys Phe
        115                 120                 125

Gln Cys Asn Leu Cys Asn Lys Thr Tyr Ser Thr Phe Ser Gly Leu Ala
130                 135                 140

Lys His Lys Gln Leu His Cys Asp Ala Gln Ser Arg Lys Ser Phe Ser
145                 150                 155                 160

Cys Lys Tyr Cys Asp Lys Glu Tyr Val Ser Leu Gly Ala Leu Lys Met
                165                 170                 175

His Ile Arg Thr His Thr Leu Pro Cys Val Cys Lys Ile Cys Gly Lys
            180                 185                 190

Ala Phe Ser Arg Pro Trp Leu Leu Gln Gly His Ile Arg Thr His Thr
        195                 200                 205

Gly Glu Lys Pro Phe Ser Cys Pro His Cys Asn Arg Ala Phe Ala Asp
210                 215                 220

Arg Ser Asn Leu Arg Ala His Leu Gln Thr His Ser Asp Val Lys Lys
225                 230                 235                 240

Tyr Gln Cys Lys Asn Cys Ser Lys Thr Phe Ser Arg Met Ser Leu Leu
                245                 250                 255

His Lys His Glu Glu Ser Gly Cys Cys Val Ala His
            260                 265

<210> SEQ ID NO 16
<211> LENGTH: 353
<212> TYPE: PRT
<213> ORGANISM: Homo sapiens

<400> SEQUENCE: 16

Met Ala Ala Glu Leu Ala Met Gly Ala Glu Leu Pro Ser Ser Pro Leu
1               5                   10                  15

Ala Ile Glu Tyr Val Asn Asp Phe Asp Leu Met Lys Phe Glu Val Lys
            20                  25                  30

Lys Glu Pro Pro Glu Ala Glu Arg Phe Cys His Arg Leu Pro Pro Gly

```
                35                  40                  45
Ser Leu Ser Ser Thr Pro Leu Ser Thr Pro Cys Ser Ser Val Pro Ser
 50                  55                  60

Ser Pro Ser Phe Cys Ala Pro Ser Pro Gly Thr Gly Gly Gly Gly Gly
 65                  70                  75                  80

Ala Gly Gly Gly Gly Ser Ser Gln Ala Gly Gly Ala Pro Gly Pro
                 85                  90                  95

Pro Ser Gly Gly Pro Gly Ala Val Gly Gly Thr Ser Gly Lys Pro Ala
                100                 105                 110

Leu Glu Asp Leu Tyr Trp Met Ser Gly Tyr Gln His His Leu Asn Pro
                115                 120                 125

Glu Ala Leu Asn Leu Thr Pro Glu Asp Ala Val Glu Ala Leu Ile Gly
                130                 135                 140

Ser Gly His His Gly Ala His His Gly Ala His His Pro Ala Ala Ala
145                 150                 155                 160

Ala Ala Tyr Glu Ala Phe Arg Gly Pro Gly Phe Ala Gly Gly Gly Gly
                165                 170                 175

Ala Asp Asp Met Gly Ala Gly His His His Gly Ala His His Ala Ala
                180                 185                 190

His His His His Ala Ala His His His His His His His His His His
                195                 200                 205

Gly Gly Ala Gly His Gly Gly Ala Gly His His Val Arg Leu Glu
210                 215                 220

Glu Arg Phe Ser Asp Asp Gln Leu Val Ser Met Ser Val Arg Glu Leu
225                 230                 235                 240

Asn Arg Gln Leu Arg Gly Phe Ser Lys Glu Glu Val Ile Arg Leu Lys
                245                 250                 255

Gln Lys Arg Arg Thr Leu Lys Asn Arg Gly Tyr Ala Gln Ser Cys Arg
                260                 265                 270

Phe Lys Arg Val Gln Gln Arg His Ile Leu Glu Ser Glu Lys Cys Gln
                275                 280                 285

Leu Gln Ser Gln Val Glu Gln Leu Lys Leu Glu Val Gly Arg Leu Ala
                290                 295                 300

Lys Glu Arg Asp Leu Tyr Lys Glu Lys Tyr Glu Lys Leu Ala Gly Arg
305                 310                 315                 320

Gly Gly Pro Gly Ser Ala Gly Gly Ala Gly Phe Pro Arg Glu Pro Ser
                325                 330                 335

Pro Pro Gln Ala Gly Pro Gly Gly Ala Lys Gly Thr Ala Asp Phe Phe
                340                 345                 350

Leu

<210> SEQ ID NO 17
<211> LENGTH: 356
<212> TYPE: PRT
<213> ORGANISM: Homo sapiens

<400> SEQUENCE: 17

Met Thr Lys Ser Tyr Ser Glu Ser Gly Leu Met Gly Glu Pro Gln Pro
1               5                   10                  15

Gln Gly Pro Pro Ser Trp Thr Asp Glu Cys Leu Ser Ser Gln Asp Glu
                20                  25                  30

Glu His Glu Ala Asp Lys Lys Glu Asp Leu Glu Ala Met Asn Ala
                35                  40                  45

Glu Glu Asp Ser Leu Arg Asn Gly Gly Glu Glu Glu Asp Glu Asp Glu
```

```
                    50                  55                  60

Asp Leu Glu Glu Glu Glu Glu Glu Glu Asp Asp Gln Lys
 65                  70                  75                  80

Pro Lys Arg Arg Gly Pro Lys Lys Lys Met Thr Lys Ala Arg Leu
                 85                  90                  95

Glu Arg Phe Lys Leu Arg Arg Met Lys Ala Asn Ala Arg Glu Arg Asn
            100                 105                 110

Arg Met His Gly Leu Asn Ala Ala Leu Asp Asn Leu Arg Lys Val Val
        115                 120                 125

Pro Cys Tyr Ser Lys Thr Gln Lys Leu Ser Lys Ile Glu Thr Leu Arg
    130                 135                 140

Leu Ala Lys Asn Tyr Ile Trp Ala Leu Ser Glu Ile Leu Arg Ser Gly
145                 150                 155                 160

Lys Ser Pro Asp Leu Val Ser Phe Val Gln Thr Leu Cys Lys Gly Leu
                165                 170                 175

Ser Gln Pro Thr Thr Asn Leu Val Ala Gly Cys Leu Gln Leu Asn Pro
            180                 185                 190

Arg Thr Phe Leu Pro Glu Gln Asn Gln Asp Met Pro Pro His Leu Pro
        195                 200                 205

Thr Ala Ser Ala Ser Phe Pro Val His Pro Tyr Ser Tyr Gln Ser Pro
    210                 215                 220

Gly Leu Pro Ser Pro Pro Tyr Gly Thr Met Asp Ser Ser His Val Phe
225                 230                 235                 240

His Val Lys Pro Pro His Ala Tyr Ser Ala Ala Leu Glu Pro Phe
                245                 250                 255

Phe Glu Ser Pro Leu Thr Asp Cys Thr Ser Pro Ser Phe Asp Gly Pro
            260                 265                 270

Leu Ser Pro Pro Leu Ser Ile Asn Gly Asn Phe Ser Phe Lys His Glu
        275                 280                 285

Pro Ser Ala Glu Phe Glu Lys Asn Tyr Ala Phe Thr Met His Tyr Pro
    290                 295                 300

Ala Ala Thr Leu Ala Gly Ala Gln Ser His Gly Ser Ile Phe Ser Gly
305                 310                 315                 320

Thr Ala Ala Pro Arg Cys Glu Ile Pro Ile Asp Asn Ile Met Ser Phe
                325                 330                 335

Asp Ser His Ser His His Glu Arg Val Met Ser Ala Gln Leu Asn Ala
            340                 345                 350

Ile Phe His Asp
        355

<210> SEQ ID NO 18
<211> LENGTH: 255
<212> TYPE: PRT
<213> ORGANISM: Homo sapiens

<400> SEQUENCE: 18

Met Asp Val Met Asp Gly Cys Gln Phe Ser Pro Ser Glu Tyr Phe Tyr
  1               5                  10                  15

Asp Gly Ser Cys Ile Pro Ser Pro Glu Gly Glu Phe Gly Asp Glu Phe
             20                  25                  30

Val Pro Arg Val Ala Ala Phe Gly Ala His Lys Ala Glu Leu Gln Gly
         35                  40                  45

Ser Asp Glu Asp Glu His Val Arg Ala Pro Thr Gly His His Gln Ala
    50                  55                  60
```

```
Gly His Cys Leu Met Trp Ala Cys Lys Ala Cys Arg Lys Ser Thr
65              70                  75                  80

Thr Met Asp Arg Arg Lys Ala Ala Thr Met Arg Glu Arg Arg Leu
                85                  90                  95

Lys Lys Val Asn Gln Ala Phe Glu Thr Leu Lys Arg Cys Thr Thr Thr
            100                 105                 110

Asn Pro Asn Gln Arg Leu Pro Lys Val Glu Ile Leu Arg Asn Ala Ile
            115                 120                 125

Arg Tyr Ile Glu Ser Leu Gln Glu Leu Leu Arg Glu Gln Val Glu Asn
            130                 135                 140

Tyr Tyr Ser Leu Pro Gly Gln Ser Cys Ser Glu Pro Thr Ser Pro Thr
145             150                 155                 160

Ser Asn Cys Ser Asp Gly Met Pro Glu Cys Asn Ser Pro Val Trp Ser
            165                 170                 175

Arg Lys Ser Ser Thr Phe Asp Ser Ile Tyr Cys Pro Asp Val Ser Asn
            180                 185                 190

Val Tyr Ala Thr Asp Lys Asn Ser Leu Ser Ser Leu Asp Cys Leu Ser
            195                 200                 205

Asn Ile Val Asp Arg Ile Thr Ser Ser Glu Gln Pro Gly Leu Pro Leu
210             215                 220

Gln Asp Leu Ala Ser Leu Ser Pro Val Ala Ser Thr Asp Ser Gln Pro
225             230                 235                 240

Ala Thr Pro Gly Ala Ser Ser Ser Arg Leu Ile Tyr His Val Leu
            245                 250                 255

<210> SEQ ID NO 19
<211> LENGTH: 1276
<212> TYPE: PRT
<213> ORGANISM: Homo sapiens

<400> SEQUENCE: 19

Met Arg Ser Lys Ala Arg Ala Arg Lys Leu Ala Lys Ser Asp Gly Asp
1               5                   10                  15

Val Val Asn Asn Met Tyr Glu Pro Asn Arg Asp Leu Leu Ala Ser His
            20                  25                  30

Ser Ala Glu Asp Glu Ala Glu Asp Ser Ala Met Ser Pro Ile Pro Val
        35                  40                  45

Gly Ser Pro Pro Pro Phe Pro Thr Ser Glu Asp Phe Thr Pro Lys Glu
    50                  55                  60

Gly Ser Pro Tyr Glu Ala Pro Val Tyr Ile Pro Glu Asp Ile Pro Ile
65              70                  75                  80

Pro Ala Asp Phe Glu Leu Arg Glu Ser Ile Pro Gly Ala Gly Leu
                85                  90                  95

Gly Val Trp Ala Lys Arg Lys Met Glu Ala Gly Glu Arg Leu Gly Pro
            100                 105                 110

Cys Val Val Val Pro Arg Ala Ala Ala Lys Glu Thr Asp Phe Gly Trp
            115                 120                 125

Glu Gln Ile Leu Thr Asp Val Glu Val Ser Pro Gln Glu Gly Cys Ile
        130                 135                 140

Thr Lys Ile Ser Glu Asp Leu Gly Ser Glu Lys Phe Cys Val Asp Ala
145             150                 155                 160

Asn Gln Ala Gly Ala Gly Ser Trp Leu Lys Tyr Ile Arg Val Ala Cys
            165                 170                 175

Ser Cys Asp Asp Gln Asn Leu Thr Met Cys Gln Ile Ser Glu Gln Val
            180                 185                 190
```

-continued

Ile Tyr Tyr Lys Val Ile Lys Asp Ile Glu Pro Gly Glu Leu Leu
            195                 200                 205

Val His Val Lys Glu Gly Val Tyr Pro Leu Gly Thr Val Pro Pro Gly
        210                 215                 220

Leu Asp Glu Glu Pro Thr Phe Arg Cys Asp Glu Cys Asp Glu Leu Phe
225                 230                 235                 240

Gln Ser Lys Leu Asp Leu Arg Arg His Lys Lys Tyr Thr Cys Gly Ser
                245                 250                 255

Val Gly Ala Ala Leu Tyr Glu Gly Leu Ala Glu Glu Leu Lys Pro Glu
                260                 265                 270

Gly Leu Gly Gly Gly Ser Gly Gln Ala His Glu Cys Lys Asp Cys Glu
                275                 280                 285

Arg Met Phe Pro Asn Lys Tyr Ser Leu Glu Gln His Met Val Ile His
            290                 295                 300

Thr Glu Glu Arg Glu Tyr Lys Cys Asp Gln Cys Pro Lys Ala Phe Asn
305                 310                 315                 320

Trp Lys Ser Asn Phe Ile Arg His Gln Met Ser His Asp Ser Gly Lys
                325                 330                 335

Arg Phe Glu Cys Glu Asn Cys Val Lys Val Phe Thr Asp Pro Ser Asn
                340                 345                 350

Leu Gln Arg His Ile Arg Ser Gln His Val Gly Ala Arg Ala His Ala
            355                 360                 365

Cys Pro Asp Cys Gly Lys Thr Phe Ala Thr Ser Ser Gly Leu Lys Gln
            370                 375                 380

His Lys His Ile His Ser Thr Val Lys Pro Phe Ile Cys Glu Val Cys
385                 390                 395                 400

His Lys Ser Tyr Thr Gln Phe Ser Asn Leu Cys Arg His Lys Arg Met
                405                 410                 415

His Ala Asp Cys Arg Thr Gln Ile Lys Cys Lys Asp Cys Gly Gln Met
                420                 425                 430

Phe Ser Thr Thr Ser Ser Leu Asn Lys His Arg Arg Phe Cys Glu Gly
            435                 440                 445

Lys Asn His Tyr Thr Pro Gly Gly Ile Phe Ala Pro Gly Leu Pro Leu
            450                 455                 460

Thr Pro Ser Pro Met Met Asp Lys Ala Lys Pro Ser Pro Ser Leu Asn
465                 470                 475                 480

His Ala Ser Leu Gly Phe Asn Glu Tyr Phe Pro Tyr Arg Pro His Pro
                485                 490                 495

Gly Ser Leu Pro Phe Ser Thr Ala Pro Pro Thr Phe Pro Ala Leu Thr
            500                 505                 510

Pro Gly Phe Pro Gly Ile Phe Pro Pro Ser Leu Tyr Pro Arg Pro Pro
            515                 520                 525

Leu Leu Pro Pro Thr Ser Leu Leu Lys Ser Pro Leu Asn His Thr Gln
            530                 535                 540

Asp Ala Lys Leu Pro Ser Pro Leu Gly Asn Pro Ala Leu Pro Leu Val
545                 550                 555                 560

Ser Ala Val Ser Asn Ser Ser Gln Gly Thr Thr Ala Ala Ala Gly Pro
                565                 570                 575

Glu Glu Lys Phe Glu Ser Arg Leu Glu Asp Ser Cys Val Glu Lys Leu
                580                 585                 590

Lys Thr Arg Ser Ser Asp Met Ser Asp Gly Ser Asp Phe Glu Asp Val
            595                 600                 605

-continued

```
Asn Thr Thr Gly Thr Asp Leu Asp Thr Thr Gly Thr Gly Ser
    610                 615                 620

Asp Leu Asp Ser Asp Val Asp Ser Asp Pro Lys Asp Lys Gly Lys
625                 630                 635                 640

Gly Lys Ser Ala Glu Gly Gln Pro Lys Phe Gly Gly Leu Ala Pro
                645                 650                 655

Pro Gly Ala Pro Asn Ser Val Ala Glu Val Pro Val Phe Tyr Ser Gln
                660                 665                 670

His Ser Phe Phe Pro Pro Asp Glu Gln Leu Leu Thr Ala Thr Gly
        675                 680                 685

Ala Ala Gly Asp Ser Ile Lys Ala Ile Ala Ser Ile Ala Glu Lys Tyr
    690                 695                 700

Phe Gly Pro Gly Phe Met Gly Met Gln Glu Lys Lys Leu Gly Ser Leu
705                 710                 715                 720

Pro Tyr His Ser Ala Phe Pro Phe Gln Phe Leu Pro Asn Phe Pro His
                725                 730                 735

Ser Leu Tyr Pro Phe Thr Asp Arg Ala Leu Ala His Asn Leu Leu Val
                740                 745                 750

Lys Ala Glu Pro Lys Ser Pro Arg Asp Ala Leu Lys Val Gly Gly Pro
            755                 760                 765

Ser Ala Glu Cys Pro Phe Asp Leu Thr Thr Lys Pro Lys Asp Val Lys
770                 775                 780

Pro Ile Leu Pro Met Pro Lys Gly Pro Ser Ala Pro Ala Ser Gly Glu
785                 790                 795                 800

Glu Gln Pro Leu Asp Leu Ser Ile Gly Ser Arg Ala Arg Ala Ser Gln
                805                 810                 815

Asn Gly Gly Gly Arg Glu Pro Arg Lys Asn His Val Tyr Gly Glu Arg
                820                 825                 830

Lys Leu Gly Ala Gly Glu Gly Leu Pro Gln Val Cys Pro Ala Arg Met
            835                 840                 845

Pro Gln Gln Pro Pro Leu His Tyr Ala Lys Pro Ser Pro Phe Phe Met
850                 855                 860

Asp Pro Ile Tyr Arg Val Glu Lys Arg Lys Val Thr Asp Pro Val Gly
865                 870                 875                 880

Ala Leu Lys Glu Lys Tyr Leu Arg Pro Ser Pro Leu Leu Phe His Pro
                885                 890                 895

Gln Met Ser Ala Ile Glu Thr Met Thr Glu Lys Leu Glu Ser Phe Ala
            900                 905                 910

Ala Met Lys Ala Asp Ser Gly Ser Ser Leu Gln Pro Leu Pro His His
            915                 920                 925

Pro Phe Asn Phe Arg Ser Pro Pro Thr Leu Ser Asp Pro Ile Leu
930                 935                 940

Arg Lys Gly Lys Glu Arg Tyr Thr Cys Arg Tyr Cys Gly Lys Ile Phe
945                 950                 955                 960

Pro Arg Ser Ala Asn Leu Thr Arg His Leu Arg Thr His Thr Gly Glu
                965                 970                 975

Gln Pro Tyr Arg Cys Lys Tyr Cys Asp Arg Ser Phe Ser Ile Ser Ser
            980                 985                 990

Asn Leu Gln Arg His Val Arg Asn Ile His Asn Lys Glu Lys Pro Phe
            995                 1000                1005

Lys Cys His Leu Cys Asn Arg Cys Phe Gly Gln Gln Thr Asn Leu
    1010                1015                1020

Asp Arg His Leu Lys Lys His Glu His Glu Asn Ala Pro Val Ser
```

```
            1025                1030                1035

Gln His Pro Gly Val Leu Thr Asn His Leu Gly Thr Ser Ala Ser
         1040                1045                1050

Ser Pro Thr Ser Glu Ser Asp Asn His Ala Leu Leu Asp Glu Lys
         1055                1060                1065

Glu Asp Ser Tyr Phe Ser Glu Ile Arg Asn Phe Ile Ala Asn Ser
         1070                1075                1080

Glu Met Asn Gln Ala Ser Thr Arg Thr Glu Lys Arg Ala Asp Met
         1085                1090                1095

Gln Ile Val Asp Gly Ser Ala Gln Cys Pro Gly Leu Ala Ser Glu
         1100                1105                1110

Lys Gln Glu Asp Val Glu Glu Asp Asp Asp Leu Glu Glu
         1115                1120                1125

Asp Asp Glu Asp Ser Leu Ala Gly Lys Ser Gln Asp Asp Thr Val
         1130                1135                1140

Ser Pro Ala Pro Glu Pro Gln Ala Ala Tyr Glu Asp Glu Glu Asp
         1145                1150                1155

Glu Glu Pro Ala Ala Ser Leu Ala Val Gly Phe Asp His Thr Arg
         1160                1165                1170

Arg Cys Ala Glu Asp His Glu Gly Gly Leu Leu Ala Leu Glu Pro
         1175                1180                1185

Met Pro Thr Phe Gly Lys Gly Leu Asp Leu Arg Arg Ala Ala Glu
         1190                1195                1200

Glu Ala Phe Glu Val Lys Asp Val Leu Asn Ser Thr Leu Asp Ser
         1205                1210                1215

Glu Ala Leu Lys His Thr Leu Cys Arg Gln Ala Lys Asn Gln Ala
         1220                1225                1230

Tyr Ala Met Met Leu Ser Leu Ser Glu Asp Thr Pro Leu His Thr
         1235                1240                1245

Pro Ser Gln Gly Ser Leu Asp Ala Trp Leu Lys Val Thr Gly Ala
         1250                1255                1260

Thr Ser Glu Ser Gly Ala Phe His Pro Ile Asn His Leu
         1265                1270                1275

<210> SEQ ID NO 20
<211> LENGTH: 436
<212> TYPE: PRT
<213> ORGANISM: Homo sapiens

<400> SEQUENCE: 20

Met Gln Asn Ser His Ser Gly Val Asn Gln Leu Gly Gly Val Phe Val
1               5                   10                  15

Asn Gly Arg Pro Leu Pro Asp Ser Thr Arg Gln Lys Ile Val Glu Leu
            20                  25                  30

Ala His Ser Gly Ala Arg Pro Cys Asp Ile Ser Arg Ile Leu Gln Thr
        35                  40                  45

His Ala Asp Ala Lys Val Gln Val Leu Asp Asn Gln Asn Val Ser Asn
    50                  55                  60

Gly Cys Val Ser Lys Ile Leu Gly Arg Tyr Tyr Glu Thr Gly Ser Ile
65                  70                  75                  80

Arg Pro Arg Ala Ile Gly Gly Ser Lys Pro Arg Val Ala Thr Pro Glu
                85                  90                  95

Val Val Ser Lys Ile Ala Gln Tyr Lys Arg Glu Cys Pro Ser Ile Phe
            100                 105                 110
```

Ala Trp Glu Ile Arg Asp Arg Leu Ser Gly Val Cys Thr Asn
            115                 120                 125

Asp Asn Ile Pro Ser Val Ser Ser Ile Asn Arg Val Leu Arg Asn Leu
130                 135                 140

Ala Ser Glu Lys Gln Gln Met Gly Ala Asp Gly Met Tyr Asp Lys Leu
145                 150                 155                 160

Arg Met Leu Asn Gly Gln Thr Gly Ser Trp Gly Thr Arg Pro Gly Trp
                165                 170                 175

Tyr Pro Gly Thr Ser Val Pro Gly Gln Pro Thr Gln Asp Gly Cys Gln
            180                 185                 190

Gln Gln Glu Gly Gly Glu Asn Thr Asn Ser Ile Ser Ser Asn Gly
        195                 200                 205

Glu Asp Ser Asp Glu Ala Gln Met Arg Leu Gln Leu Lys Arg Lys Leu
    210                 215                 220

Gln Arg Asn Arg Thr Ser Phe Thr Gln Glu Gln Ile Glu Ala Leu Glu
225                 230                 235                 240

Lys Glu Phe Glu Arg Thr His Tyr Pro Asp Val Phe Ala Arg Glu Arg
                245                 250                 255

Leu Ala Ala Lys Ile Asp Leu Pro Glu Ala Arg Ile Gln Val Trp Phe
            260                 265                 270

Ser Asn Arg Arg Ala Lys Trp Arg Arg Glu Glu Lys Leu Arg Asn Gln
275                 280                 285

Arg Arg Gln Ala Ser Asn Thr Pro Ser His Ile Pro Ile Ser Ser Ser
        290                 295                 300

Phe Ser Thr Ser Val Tyr Gln Pro Ile Pro Gln Pro Thr Thr Pro Val
305                 310                 315                 320

Ser Ser Phe Thr Ser Gly Ser Met Leu Gly Arg Thr Asp Thr Ala Leu
                325                 330                 335

Thr Asn Thr Tyr Ser Ala Leu Pro Pro Met Pro Ser Phe Thr Met Ala
            340                 345                 350

Asn Asn Leu Pro Met Gln Pro Pro Val Pro Ser Gln Thr Ser Ser Tyr
        355                 360                 365

Ser Cys Met Leu Pro Thr Ser Pro Ser Val Asn Gly Arg Ser Tyr Asp
370                 375                 380

Thr Tyr Thr Pro Pro His Met Gln Thr His Met Asn Ser Gln Pro Met
385                 390                 395                 400

Gly Thr Ser Gly Thr Thr Ser Thr Gly Leu Ile Ser Pro Gly Val Ser
                405                 410                 415

Val Pro Val Gln Val Pro Gly Ser Glu Pro Asp Met Ser Gln Tyr Trp
            420                 425                 430

Pro Arg Leu Gln
        435

<210> SEQ ID NO 21
<211> LENGTH: 631
<212> TYPE: PRT
<213> ORGANISM: Homo sapiens

<400> SEQUENCE: 21

Met Val Ser Lys Leu Ser Gln Leu Gln Thr Glu Leu Leu Ala Ala Leu
1               5                   10                  15

Leu Glu Ser Gly Leu Ser Lys Glu Ala Leu Ile Gln Ala Leu Gly Glu
            20                  25                  30

Pro Gly Pro Tyr Leu Leu Ala Gly Glu Gly Pro Leu Asp Lys Gly Glu
        35                  40                  45

```
Ser Cys Gly Gly Gly Arg Gly Glu Leu Ala Glu Leu Pro Asn Gly Leu
    50                  55                  60
Gly Glu Thr Arg Gly Ser Glu Asp Glu Thr Asp Asp Gly Glu Asp
65                  70                  75                  80
Phe Thr Pro Pro Ile Leu Lys Glu Leu Glu Asn Leu Ser Pro Glu Glu
                    85                  90                  95
Ala Ala His Gln Lys Ala Val Val Glu Thr Leu Leu Gln Glu Asp Pro
                100                 105                 110
Trp Arg Val Ala Lys Met Val Lys Ser Tyr Leu Gln Gln His Asn Ile
                115                 120                 125
Pro Gln Arg Glu Val Val Asp Thr Thr Gly Leu Asn Gln Ser His Leu
                130                 135                 140
Ser Gln His Leu Asn Lys Gly Thr Pro Met Lys Thr Gln Lys Arg Ala
145                 150                 155                 160
Ala Leu Tyr Thr Trp Tyr Val Arg Lys Gln Arg Glu Val Ala Gln Gln
                165                 170                 175
Phe Thr His Ala Gly Gln Gly Gly Leu Ile Glu Pro Thr Gly Asp
                180                 185                 190
Glu Leu Pro Thr Lys Lys Gly Arg Arg Asn Arg Phe Lys Trp Gly Pro
                195                 200                 205
Ala Ser Gln Gln Ile Leu Phe Gln Ala Tyr Glu Arg Gln Lys Asn Pro
    210                 215                 220
Ser Lys Glu Glu Arg Glu Thr Leu Val Glu Glu Cys Asn Arg Ala Glu
225                 230                 235                 240
Cys Ile Gln Arg Gly Val Ser Pro Ser Gln Ala Gln Gly Leu Gly Ser
                245                 250                 255
Asn Leu Val Thr Glu Val Arg Val Tyr Asn Trp Phe Ala Asn Arg Arg
                260                 265                 270
Lys Glu Glu Ala Phe Arg His Lys Leu Ala Met Asp Thr Tyr Ser Gly
                275                 280                 285
Pro Pro Pro Gly Pro Gly Pro Gly Pro Ala Leu Pro Ala His Ser Ser
    290                 295                 300
Pro Gly Leu Pro Pro Ala Leu Ser Pro Ser Lys Val His Gly Val
305                 310                 315                 320
Arg Tyr Gly Gln Pro Ala Thr Ser Glu Thr Ala Glu Val Pro Ser Ser
                325                 330                 335
Ser Gly Gly Pro Leu Val Thr Val Ser Thr Pro Leu His Gln Val Ser
                340                 345                 350
Pro Thr Gly Leu Glu Pro Ser His Ser Leu Leu Ser Thr Glu Ala Lys
                355                 360                 365
Leu Val Ser Ala Ala Gly Gly Pro Leu Pro Pro Val Ser Thr Leu Thr
    370                 375                 380
Ala Leu His Ser Leu Glu Gln Thr Ser Pro Gly Leu Asn Gln Gln Pro
385                 390                 395                 400
Gln Asn Leu Ile Met Ala Ser Leu Pro Gly Val Met Thr Ile Gly Pro
                405                 410                 415
Gly Glu Pro Ala Ser Leu Gly Pro Thr Phe Thr Asn Thr Gly Ala Ser
                420                 425                 430
Thr Leu Val Ile Gly Leu Ala Ser Thr Gln Ala Gln Ser Val Pro Val
                435                 440                 445
Ile Asn Ser Met Gly Ser Ser Leu Thr Thr Leu Gln Pro Val Gln Phe
    450                 455                 460
```

```
Ser Gln Pro Leu His Pro Ser Tyr Gln Gln Pro Leu Met Pro Pro Val
465                 470                 475                 480

Gln Ser His Val Thr Gln Ser Pro Phe Met Ala Thr Met Ala Gln Leu
            485                 490                 495

Gln Ser Pro His Ala Leu Tyr Ser His Lys Pro Glu Val Ala Gln Tyr
            500                 505                 510

Thr His Thr Gly Leu Leu Pro Gln Thr Met Leu Ile Thr Asp Thr Thr
            515                 520                 525

Asn Leu Ser Ala Leu Ala Ser Leu Thr Pro Thr Lys Gln Val Phe Thr
            530                 535                 540

Ser Asp Thr Glu Ala Ser Ser Glu Ser Gly Leu His Thr Pro Ala Ser
545                 550                 555                 560

Gln Ala Thr Thr Leu His Val Pro Ser Gln Asp Pro Ala Gly Ile Gln
            565                 570                 575

His Leu Gln Pro Ala His Arg Leu Ser Ala Ser Pro Thr Val Ser Ser
            580                 585                 590

Ser Ser Leu Val Leu Tyr Gln Ser Ser Asp Ser Ser Asn Gly Gln Ser
            595                 600                 605

His Leu Leu Pro Ser Asn His Ser Val Ile Glu Thr Phe Ile Ser Thr
            610                 615                 620

Gln Met Ala Ser Ser Ser Gln
625                 630

<210> SEQ ID NO 22
<211> LENGTH: 350
<212> TYPE: PRT
<213> ORGANISM: Homo sapiens

<400> SEQUENCE: 22

Met Leu Gly Ser Val Lys Met Glu Ala His Asp Leu Ala Glu Trp Ser
1               5                   10                  15

Tyr Tyr Pro Glu Ala Gly Glu Val Tyr Ser Pro Val Thr Pro Val Pro
            20                  25                  30

Thr Met Ala Pro Leu Asn Ser Tyr Met Thr Leu Asn Pro Leu Ser Ser
            35                  40                  45

Pro Tyr Pro Pro Gly Gly Leu Pro Ala Ser Pro Leu Pro Ser Gly Pro
        50                  55                  60

Leu Ala Pro Pro Ala Pro Ala Pro Leu Gly Pro Thr Phe Pro Gly Leu
65                  70                  75                  80

Leu Gly Val Ser Gly Gly Ser Ser Ser Gly Tyr Gly Ala Pro Gly Pro
            85                  90                  95

Pro Gly Leu Val His Gly Lys Glu Met Pro Lys Gly Tyr Arg Arg Pro
            100                 105                 110

Leu Ala His Ala Lys Pro Pro Tyr Ser Tyr Ile Ser Leu Ile Thr Met
            115                 120                 125

Ala Ile Gln Gln Ala Pro Gly Lys Met Leu Thr Leu Ser Glu Ile Tyr
130                 135                 140

Gln Trp Ile Met Asp Leu Phe Pro Tyr Tyr Arg Glu Asn Gln Gln Arg
145                 150                 155                 160

Trp Gln Asn Ser Ile Arg His Ser Leu Ser Phe Asn Asp Cys Phe Val
            165                 170                 175

Lys Val Ala Arg Ser Pro Asp Lys Pro Gly Lys Gly Ser Tyr Trp Ala
            180                 185                 190

Leu His Pro Ser Ser Gly Asn Met Phe Glu Asn Gly Cys Tyr Leu Arg
            195                 200                 205
```

```
Arg Gln Lys Arg Phe Lys Leu Glu Glu Lys Val Lys Lys Gly Gly Ser
            210                 215                 220

Gly Ala Ala Thr Thr Thr Arg Asn Gly Thr Gly Ser Ala Ala Ser Thr
225                 230                 235                 240

Thr Thr Pro Ala Ala Thr Val Thr Ser Pro Pro Gln Pro Pro Pro Pro
            245                 250                 255

Ala Pro Glu Pro Glu Ala Gln Gly Gly Glu Asp Val Gly Ala Leu Asp
            260                 265                 270

Cys Gly Ser Pro Ala Ser Ser Thr Pro Tyr Phe Thr Gly Leu Glu Leu
            275                 280                 285

Pro Gly Glu Leu Lys Leu Asp Ala Pro Tyr Asn Phe Asn His Pro Phe
            290                 295                 300

Ser Ile Asn Asn Leu Met Ser Glu Gln Thr Pro Ala Pro Pro Lys Leu
305                 310                 315                 320

Asp Val Gly Phe Gly Gly Tyr Gly Ala Glu Gly Glu Pro Gly Val
            325                 330                 335

Tyr Tyr Gln Gly Leu Tyr Ser Arg Ser Leu Leu Asn Ala Ser
            340                 345                 350

<210> SEQ ID NO 23
<211> LENGTH: 472
<212> TYPE: PRT
<213> ORGANISM: Homo sapiens

<400> SEQUENCE: 23

Met Leu Gly Thr Val Lys Met Glu Gly His Glu Thr Ser Asp Trp Asn
1               5                   10                  15

Ser Tyr Tyr Ala Asp Thr Gln Glu Ala Tyr Ser Ser Val Pro Val Ser
            20                  25                  30

Asn Met Asn Ser Gly Leu Gly Ser Met Asn Ser Met Asn Thr Tyr Met
        35                  40                  45

Thr Met Asn Thr Met Thr Thr Ser Gly Asn Met Thr Pro Ala Ser Phe
    50                  55                  60

Asn Met Ser Tyr Ala Asn Pro Gly Leu Gly Ala Gly Leu Ser Pro Gly
65                  70                  75                  80

Ala Val Ala Gly Met Pro Gly Gly Ser Ala Gly Ala Met Asn Ser Met
                85                  90                  95

Thr Ala Ala Gly Val Thr Ala Met Gly Thr Ala Leu Ser Pro Ser Gly
            100                 105                 110

Met Gly Ala Met Gly Ala Gln Gln Ala Ala Ser Met Asn Gly Leu Gly
        115                 120                 125

Pro Tyr Ala Ala Ala Met Asn Pro Cys Met Ser Pro Met Ala Tyr Ala
130                 135                 140

Pro Ser Asn Leu Gly Arg Ser Arg Ala Gly Gly Gly Asp Ala Lys
145                 150                 155                 160

Thr Phe Lys Arg Ser Tyr Pro His Ala Lys Pro Pro Tyr Ser Tyr Ile
                165                 170                 175

Ser Leu Ile Thr Met Ala Ile Gln Gln Ala Pro Ser Lys Met Leu Thr
            180                 185                 190

Leu Ser Glu Ile Tyr Gln Trp Ile Met Asp Leu Phe Pro Tyr Tyr Arg
        195                 200                 205

Gln Asn Gln Gln Arg Trp Gln Asn Ser Ile Arg His Ser Leu Ser Phe
    210                 215                 220

Asn Asp Cys Phe Val Lys Val Ala Arg Ser Pro Asp Lys Pro Gly Lys
```

```
                225                 230                 235                 240
Gly Ser Tyr Trp Thr Leu His Pro Asp Ser Gly Asn Met Phe Glu Asn
                    245                 250                 255
Gly Cys Tyr Leu Arg Arg Gln Lys Arg Phe Lys Cys Glu Lys Gln Pro
                260                 265                 270
Gly Ala Gly Gly Gly Gly Ser Gly Gly Ser Gly Ala Lys
                275                 280                 285
Gly Gly Pro Glu Ser Arg Lys Asp Pro Ser Gly Ala Ser Asn Pro Ser
                290                 295                 300
Ala Asp Ser Pro Leu His Arg Gly Val His Gly Lys Thr Gly Gln Leu
305                 310                 315                 320
Glu Gly Ala Pro Ala Pro Gly Pro Ala Ala Ser Pro Gln Thr Leu Asp
                    325                 330                 335
His Ser Gly Ala Thr Ala Thr Gly Gly Ala Ser Glu Leu Lys Thr Pro
                    340                 345                 350
Ala Ser Ser Thr Ala Pro Pro Ile Ser Ser Gly Pro Gly Ala Leu Ala
                    355                 360                 365
Ser Val Pro Ala Ser His Pro Ala His Gly Leu Ala Pro His Glu Ser
            370                 375                 380
Gln Leu His Leu Lys Gly Asp Pro His Tyr Ser Phe Asn His Pro Phe
385                 390                 395                 400
Ser Ile Asn Asn Leu Met Ser Ser Glu Gln Gln His Lys Leu Asp
                    405                 410                 415
Phe Lys Ala Tyr Glu Gln Ala Leu Gln Tyr Ser Pro Tyr Gly Ser Thr
                420                 425                 430
Leu Pro Ala Ser Leu Pro Leu Gly Ser Ala Ser Val Thr Thr Arg Ser
                435                 440                 445
Pro Ile Glu Pro Ser Ala Leu Gly Pro Ala Tyr Tyr Gln Gly Val Tyr
            450                 455                 460
Ser Arg Pro Val Leu Asn Thr Ser
465                 470

<210> SEQ ID NO 24
<211> LENGTH: 463
<212> TYPE: PRT
<213> ORGANISM: Homo sapiens

<400> SEQUENCE: 24

Met His Ser Ala Ser Met Leu Gly Ala Val Lys Met Glu Gly His
1               5                   10                  15
Glu Pro Ser Asp Trp Ser Ser Tyr Tyr Ala Glu Pro Glu Gly Tyr Ser
                20                  25                  30
Ser Val Ser Asn Met Asn Ala Gly Leu Gly Met Asn Gly Met Asn Thr
            35                  40                  45
Tyr Met Ser Met Ser Ala Ala Ala Met Gly Ser Gly Ser Gly Asn Met
        50                  55                  60
Ser Ala Gly Ser Met Asn Met Ser Ser Tyr Val Gly Ala Gly Met Ser
65                  70                  75                  80
Pro Ser Leu Ala Gly Met Ser Pro Gly Ala Gly Ala Met Ala Gly Met
                85                  90                  95
Gly Gly Ser Ala Gly Ala Ala Gly Val Ala Gly Met Gly Pro His Leu
                100                 105                 110
Ser Pro Ser Leu Ser Pro Leu Gly Gly Gln Ala Ala Gly Ala Met Gly
                115                 120                 125
```

```
Gly Leu Ala Pro Tyr Ala Asn Met Asn Ser Met Ser Pro Met Tyr Gly
    130                 135                 140

Gln Ala Gly Leu Ser Arg Ala Arg Asp Pro Lys Thr Tyr Arg Arg Ser
145                 150                 155                 160

Tyr Thr His Ala Lys Pro Pro Tyr Ser Tyr Ile Ser Leu Ile Thr Met
                165                 170                 175

Ala Ile Gln Gln Ser Pro Asn Lys Met Leu Thr Leu Ser Glu Ile Tyr
            180                 185                 190

Gln Trp Ile Met Asp Leu Phe Pro Phe Tyr Arg Gln Asn Gln Gln Arg
        195                 200                 205

Trp Gln Asn Ser Ile Arg His Ser Leu Ser Phe Asn Asp Cys Phe Leu
210                 215                 220

Lys Val Pro Arg Ser Pro Asp Lys Pro Gly Lys Gly Ser Phe Trp Thr
225                 230                 235                 240

Leu His Pro Asp Ser Gly Asn Met Phe Glu Asn Gly Cys Tyr Leu Arg
                245                 250                 255

Arg Gln Lys Arg Phe Lys Cys Glu Lys Gln Leu Ala Leu Lys Glu Ala
            260                 265                 270

Ala Gly Ala Ala Gly Ser Gly Lys Lys Ala Ala Ala Gly Ala Gln Ala
        275                 280                 285

Ser Gln Ala Gln Leu Gly Glu Ala Ala Gly Pro Ala Ser Glu Thr Pro
290                 295                 300

Ala Gly Thr Glu Ser Pro His Ser Ser Ala Ser Pro Cys Gln Glu His
305                 310                 315                 320

Lys Arg Gly Gly Leu Gly Glu Leu Lys Gly Thr Pro Ala Ala Ala Leu
                325                 330                 335

Ser Pro Pro Glu Pro Ala Pro Ser Pro Gly Gln Gln Gln Gln Ala Ala
            340                 345                 350

Ala His Leu Leu Gly Pro Pro His His Pro Gly Leu Pro Pro Glu Ala
        355                 360                 365

His Leu Lys Pro Glu His His Tyr Ala Phe Asn His Pro Phe Ser Ile
370                 375                 380

Asn Asn Leu Met Ser Ser Glu Gln Gln His His His Ser His His His
385                 390                 395                 400

His Gln Pro His Lys Met Asp Leu Lys Ala Tyr Glu Gln Val Met His
                405                 410                 415

Tyr Pro Gly Tyr Gly Ser Pro Met Pro Gly Ser Leu Ala Met Gly Pro
            420                 425                 430

Val Thr Asn Lys Thr Gly Leu Asp Ala Ser Pro Leu Ala Ala Asp Thr
        435                 440                 445

Ser Tyr Tyr Gln Gly Val Tyr Ser Arg Pro Ile Met Asn Ser Ser
    450                 455                 460

<210> SEQ ID NO 25
<211> LENGTH: 344
<212> TYPE: PRT
<213> ORGANISM: Homo sapiens

<400> SEQUENCE: 25

Met Ser Ser His Leu Gln Ser Pro Pro His Ala Pro Ser Ser Ala Ala
1               5                   10                  15

Phe Gly Phe Pro Arg Gly Ala Gly Pro Ala Gln Pro Pro Ala Pro Pro
            20                  25                  30

Ala Ala Pro Glu Pro Leu Gly Gly Ile Cys Glu His Glu Thr Ser Ile
        35                  40                  45
```

```
Asp Ile Ser Ala Tyr Ile Asp Pro Ala Ala Phe Asn Asp Glu Phe Leu
     50                  55                  60

Ala Asp Leu Phe Gln His Ser Arg Gln Gln Glu Lys Ala Lys Ala Ala
 65                  70                  75                  80

Val Gly Pro Thr Gly Gly Gly Gly Asp Phe Asp Tyr Pro Gly
                 85                  90                  95

Ala Pro Ala Gly Pro Gly Gly Ala Val Met Pro Gly Gly Ala His Gly
                100                 105                 110

Pro Pro Pro Gly Tyr Gly Cys Ala Ala Ala Gly Tyr Leu Asp Gly Arg
            115                 120                 125

Leu Glu Pro Leu Tyr Glu Arg Val Gly Ala Pro Ala Leu Arg Pro Leu
        130                 135                 140

Val Ile Lys Gln Glu Pro Arg Glu Glu Asp Glu Ala Lys Gln Leu Ala
145                 150                 155                 160

Leu Ala Gly Leu Phe Pro Tyr Gln Pro Pro Pro Pro Pro Pro Pro Ser
                165                 170                 175

His Pro His Pro His Pro Pro Ala His Leu Ala Ala Pro His Leu
            180                 185                 190

Gln Phe Gln Ile Ala His Cys Gly Gln Thr Thr Met His Leu Gln Pro
        195                 200                 205

Gly His Pro Thr Pro Pro Thr Pro Val Pro Ser Pro His Pro Ala
210                 215                 220

Pro Ala Leu Gly Ala Ala Gly Leu Pro Gly Pro Gly Ser Ala Leu Lys
225                 230                 235                 240

Gly Leu Gly Ala Ala His Pro Asp Leu Arg Ala Ser Gly Gly Ser Gly
                245                 250                 255

Ala Gly Lys Ala Lys Lys Ser Val Asp Lys Asn Ser Asn Glu Tyr Arg
            260                 265                 270

Val Arg Arg Glu Arg Asn Asn Ile Ala Val Arg Lys Ser Arg Asp Lys
        275                 280                 285

Ala Lys Gln Arg Asn Val Glu Thr Gln Gln Lys Val Leu Glu Leu Thr
290                 295                 300

Ser Asp Asn Asp Arg Leu Arg Lys Arg Val Glu Gln Leu Ser Arg Glu
305                 310                 315                 320

Leu Asp Thr Leu Arg Gly Ile Phe Arg Gln Leu Pro Glu Ser Ser Leu
                325                 330                 335

Val Lys Ala Met Gly Asn Cys Ala
            340

<210> SEQ ID NO 26
<211> LENGTH: 271
<212> TYPE: PRT
<213> ORGANISM: Homo sapiens

<400> SEQUENCE: 26

Met Leu Gln Ala Cys Lys Met Glu Gly Phe Pro Leu Val Pro Pro Gln
  1               5                  10                  15

Pro Ser Glu Asp Leu Val Pro Tyr Asp Thr Asp Leu Tyr Gln Arg Gln
                 20                  25                  30

Thr His Glu Tyr Tyr Pro Tyr Leu Ser Ser Asp Gly Glu Ser His Ser
             35                  40                  45

Asp His Tyr Trp Asp Phe His Pro His His Val His Ser Glu Phe Glu
         50                  55                  60

Ser Phe Ala Glu Asn Asn Phe Thr Glu Leu Gln Ser Val Gln Pro Pro
```

```
                65                  70                  75                  80
        Gln Leu Gln Gln Leu Tyr Arg His Met Glu Leu Glu Gln Met His Val
                        85                  90                  95

Leu Asp Thr Pro Met Val Pro Pro His Pro Ser Leu Gly His Gln Val
                        100                 105                 110

Ser Tyr Leu Pro Arg Met Cys Leu Gln Tyr Pro Ser Leu Ser Pro Ala
                        115                 120                 125

Gln Pro Ser Ser Asp Glu Glu Glu Gly Glu Arg Gln Ser Pro Pro Leu
                        130                 135                 140

Glu Val Ser Asp Gly Glu Ala Asp Gly Leu Glu Pro Gly Pro Gly Leu
        145                 150                 155                 160

Leu Pro Gly Glu Thr Gly Ser Lys Lys Lys Ile Arg Leu Tyr Gln Phe
                        165                 170                 175

Leu Leu Asp Leu Leu Arg Ser Gly Asp Met Lys Asp Ser Ile Trp Trp
                        180                 185                 190

Val Asp Lys Asp Lys Gly Thr Phe Gln Phe Ser Ser Lys His Lys Glu
                        195                 200                 205

Ala Leu Ala His Arg Trp Gly Ile Gln Lys Gly Asn Arg Lys Lys Met
                        210                 215                 220

Thr Tyr Gln Lys Met Ala Arg Ala Leu Arg Asn Tyr Gly Lys Thr Gly
        225                 230                 235                 240

Glu Val Lys Lys Val Lys Lys Lys Leu Thr Tyr Gln Phe Ser Gly Glu
                        245                 250                 255

Val Leu Gly Arg Gly Gly Leu Ala Glu Arg Arg His Pro Pro His
                        260                 265                 270

<210> SEQ ID NO 27
<211> LENGTH: 443
<212> TYPE: PRT
<213> ORGANISM: Homo sapiens

<400> SEQUENCE: 27

Met Ala Thr Ala Ala Ser Asn His Tyr Ser Leu Leu Thr Ser Ser Ala
        1               5                   10                  15

Ser Ile Val His Ala Glu Pro Pro Gly Gly Met Gln Gln Gly Ala Gly
                        20                  25                  30

Gly Tyr Arg Glu Ala Gln Ser Leu Val Gln Gly Asp Tyr Gly Ala Leu
                        35                  40                  45

Gln Ser Asn Gly His Pro Leu Ser His Ala His Gln Trp Ile Thr Ala
                50                  55                  60

Leu Ser His Gly Gly Gly Gly Gly Gly Gly Gly Gly Gly Gly Gly Gly
        65                  70                  75                  80

Gly Gly Gly Gly Gly Gly Gly Asp Gly Ser Pro Trp Ser Thr Ser
                        85                  90                  95

Pro Leu Gly Gln Pro Asp Ile Lys Pro Ser Val Val Val Gln Gln Gly
                        100                 105                 110

Gly Arg Gly Asp Glu Leu His Gly Pro Gly Ala Leu Gln Gln Gln His
                        115                 120                 125

Gln Gln Gln Gln Gln Gln Gln Gln Gln Gln Gln Gln Gln Gln Gln Gln
                        130                 135                 140

Gln Gln Gln Gln Gln Arg Pro Pro His Leu Val His His Ala Ala Asn
        145                 150                 155                 160

His His Pro Gly Pro Gly Ala Trp Arg Ser Ala Ala Ala Ala His
                        165                 170                 175
```

```
Leu Pro Pro Ser Met Gly Ala Ser Asn Gly Gly Leu Leu Tyr Ser Gln
            180                 185                 190

Pro Ser Phe Thr Val Asn Gly Met Leu Gly Ala Gly Gly Gln Pro Ala
        195                 200                 205

Gly Leu His His His Gly Leu Arg Asp Ala His Asp Glu Pro His His
        210                 215                 220

Ala Asp His His Pro His Pro His Ser His Pro His Gln Gln Pro Pro
225                 230                 235                 240

Pro Pro Pro Pro Pro Gln Gly Pro Pro Gly His Pro Gly Ala His His
                245                 250                 255

Asp Pro His Ser Asp Glu Asp Thr Pro Thr Ser Asp Asp Leu Glu Gln
            260                 265                 270

Phe Ala Lys Gln Phe Lys Gln Arg Arg Ile Lys Leu Gly Phe Thr Gln
        275                 280                 285

Ala Asp Val Gly Leu Ala Leu Gly Thr Leu Tyr Gly Asn Val Phe Ser
        290                 295                 300

Gln Thr Thr Ile Cys Arg Phe Glu Ala Leu Gln Leu Ser Phe Lys Asn
305                 310                 315                 320

Met Cys Lys Leu Lys Pro Leu Leu Asn Lys Trp Leu Glu Glu Ala Asp
                325                 330                 335

Ser Ser Ser Gly Ser Pro Thr Ser Ile Asp Lys Ile Ala Ala Gln Gly
            340                 345                 350

Arg Lys Arg Lys Lys Arg Thr Ser Ile Glu Val Ser Val Lys Gly Ala
        355                 360                 365

Leu Glu Ser His Phe Leu Lys Cys Pro Lys Pro Ser Ala Gln Glu Ile
        370                 375                 380

Thr Ser Leu Ala Asp Ser Leu Gln Leu Glu Lys Glu Val Val Arg Val
385                 390                 395                 400

Trp Phe Cys Asn Arg Arg Gln Lys Glu Lys Arg Met Thr Pro Pro Gly
                405                 410                 415

Gly Thr Leu Pro Gly Ala Glu Asp Val Tyr Gly Gly Ser Arg Asp Thr
            420                 425                 430

Pro Pro His His Gly Val Gln Thr Pro Val Gln
        435                 440

<210> SEQ ID NO 28
<211> LENGTH: 489
<212> TYPE: PRT
<213> ORGANISM: Homo sapiens

<400> SEQUENCE: 28

Met Leu Asp Met Gly Asp Arg Lys Glu Val Lys Met Ile Pro Lys Ser
1               5                   10                  15

Ser Phe Ser Ile Asn Ser Leu Val Pro Glu Ala Val Gln Asn Asp Asn
            20                  25                  30

His His Ala Ser His Gly His His Asn Ser His Pro Gln His His
        35                  40                  45

His His His His His His His Pro Pro Pro Ala Pro Gln
    50                  55                  60

Pro Pro Pro Pro Gln Gln Gln Gln Pro Pro Pro Pro Pro
65                  70                  75                  80

Ala Pro Gln Pro Pro Gln Thr Arg Gly Ala Pro Ala Ala Asp Asp Asp
            85                  90                  95

Lys Gly Pro Gln Gln Leu Leu Leu Pro Pro Pro Pro Pro Pro Pro Pro
        100                 105                 110
```

```
Ala Ala Ala Leu Asp Gly Ala Lys Ala Asp Gly Leu Gly Gly Lys Gly
            115                 120                 125

Glu Pro Gly Gly Gly Pro Gly Glu Leu Ala Pro Val Gly Pro Asp Glu
        130                 135                 140

Lys Glu Lys Gly Ala Gly Ala Gly Gly Glu Lys Lys Gly Ala Gly
145                 150                 155                 160

Glu Gly Gly Lys Asp Gly Glu Gly Gly Lys Glu Gly Glu Lys Lys Asn
                165                 170                 175

Gly Lys Tyr Glu Lys Pro Pro Phe Ser Tyr Asn Ala Leu Ile Met Met
            180                 185                 190

Ala Ile Arg Gln Ser Pro Glu Lys Arg Leu Thr Leu Asn Gly Ile Tyr
            195                 200                 205

Glu Phe Ile Met Lys Asn Phe Pro Tyr Tyr Arg Glu Asn Lys Gln Gly
            210                 215                 220

Trp Gln Asn Ser Ile Arg His Asn Leu Ser Leu Asn Lys Cys Phe Val
225                 230                 235                 240

Lys Val Pro Arg His Tyr Asp Asp Pro Gly Lys Gly Asn Tyr Trp Met
                245                 250                 255

Leu Asp Pro Ser Ser Asp Asp Val Phe Ile Gly Gly Thr Thr Gly Lys
            260                 265                 270

Leu Arg Arg Arg Ser Thr Thr Ser Arg Ala Lys Leu Ala Phe Lys Arg
            275                 280                 285

Gly Ala Arg Leu Thr Ser Thr Gly Leu Thr Phe Met Asp Arg Ala Gly
            290                 295                 300

Ser Leu Tyr Trp Pro Met Ser Pro Phe Leu Ser Leu His His Pro Arg
305                 310                 315                 320

Ala Ser Ser Thr Leu Ser Tyr Asn Gly Thr Thr Ser Ala Tyr Pro Ser
                325                 330                 335

His Pro Met Pro Tyr Ser Ser Val Leu Thr Gln Asn Ser Leu Gly Asn
            340                 345                 350

Asn His Ser Phe Ser Thr Ala Asn Gly Leu Ser Val Asp Arg Leu Val
            355                 360                 365

Asn Gly Glu Ile Pro Tyr Ala Thr His His Leu Thr Ala Ala Ala Leu
            370                 375                 380

Ala Ala Ser Val Pro Cys Gly Leu Ser Val Pro Cys Ser Gly Thr Tyr
385                 390                 395                 400

Ser Leu Asn Pro Cys Ser Val Asn Leu Leu Ala Gly Gln Thr Ser Tyr
                405                 410                 415

Phe Phe Pro His Val Pro His Pro Ser Met Thr Ser Gln Ser Ser Thr
            420                 425                 430

Ser Met Ser Ala Arg Ala Ala Ser Ser Thr Ser Pro Gln Ala Pro
            435                 440                 445

Ser Thr Leu Pro Cys Glu Ser Leu Arg Pro Ser Leu Pro Ser Phe Thr
450                 455                 460

Thr Gly Leu Ser Gly Gly Leu Ser Asp Tyr Phe Thr His Gln Asn Gln
465                 470                 475                 480

Gly Ser Ser Ser Asn Pro Leu Ile His
                485

<210> SEQ ID NO 29
<211> LENGTH: 523
<212> TYPE: PRT
<213> ORGANISM: Homo sapiens
```

<400> SEQUENCE: 29

```
Met Ala Gly His Thr Gln Gln Pro Ser Gly Arg Gly Asn Pro Arg Pro
1               5                   10                  15

Ala Pro Ser Pro Ser Pro Val Pro Gly Thr Val Pro Gly Ala Ser Glu
            20                  25                  30

Arg Val Ala Leu Lys Lys Glu Ile Gly Leu Leu Ser Ala Cys Thr Ile
        35                  40                  45

Ile Ile Gly Asn Ile Ile Gly Ser Gly Ile Phe Ile Ser Pro Lys Gly
    50                  55                  60

Val Leu Glu His Ser Gly Ser Val Gly Leu Ala Leu Phe Val Trp Val
65                  70                  75                  80

Leu Gly Gly Gly Val Thr Ala Leu Gly Ser Leu Cys Tyr Ala Glu Leu
                85                  90                  95

Gly Val Ala Ile Pro Lys Ser Gly Gly Asp Tyr Ala Tyr Val Thr Glu
            100                 105                 110

Ile Phe Gly Gly Leu Ala Gly Phe Leu Leu Trp Ser Ala Val Leu
    115                 120                 125

Ile Met Tyr Pro Thr Ser Leu Ala Val Ile Ser Met Thr Phe Ser Asn
    130                 135                 140

Tyr Val Leu Gln Pro Val Phe Pro Asn Cys Ile Pro Pro Thr Thr Ala
145                 150                 155                 160

Ser Arg Val Leu Ser Met Ala Cys Leu Met Leu Leu Thr Trp Val Asn
            165                 170                 175

Ser Ser Ser Val Arg Trp Ala Thr Arg Ile Gln Asp Met Phe Thr Gly
            180                 185                 190

Gly Lys Leu Leu Ala Leu Ser Leu Ile Ile Gly Val Gly Leu Leu Gln
        195                 200                 205

Ile Phe Gln Gly His Phe Glu Glu Leu Arg Pro Ser Asn Ala Phe Ala
    210                 215                 220

Phe Trp Met Thr Pro Ser Val Gly His Leu Ala Leu Ala Phe Leu Gln
225                 230                 235                 240

Gly Ser Phe Ala Phe Ser Gly Trp Asn Phe Leu Asn Tyr Val Thr Glu
            245                 250                 255

Glu Met Val Asp Ala Arg Lys Asn Leu Pro Arg Ala Ile Phe Ile Ser
            260                 265                 270

Ile Pro Leu Val Thr Phe Val Tyr Thr Phe Thr Asn Ile Ala Tyr Phe
        275                 280                 285

Thr Ala Met Ser Pro Gln Glu Leu Leu Ser Ser Asn Ala Val Ala Val
    290                 295                 300

Thr Phe Gly Glu Lys Leu Leu Gly Tyr Phe Ser Trp Val Met Pro Val
305                 310                 315                 320

Ser Val Ala Leu Ser Thr Phe Gly Gly Ile Asn Gly Tyr Leu Phe Thr
            325                 330                 335

Tyr Ser Arg Leu Cys Phe Ser Gly Ala Arg Glu Gly His Leu Pro Ser
            340                 345                 350

Leu Leu Ala Met Ile His Val Arg His Cys Thr Pro Ile Pro Ala Leu
        355                 360                 365

Leu Val Cys Cys Gly Ala Thr Ala Val Ile Met Leu Val Gly Asp Thr
    370                 375                 380

Tyr Thr Leu Ile Asn Tyr Val Ser Phe Ile Asn Tyr Leu Cys Tyr Gly
385                 390                 395                 400

Val Thr Ile Leu Gly Leu Leu Leu Leu Arg Trp Arg Arg Pro Ala Leu
            405                 410                 415
```

His Arg Pro Ile Lys Val Asn Leu Leu Ile Pro Val Ala Tyr Leu Val
                420                 425                 430

Phe Trp Ala Phe Leu Leu Val Phe Ser Phe Ile Ser Glu Pro Met Val
            435                 440                 445

Cys Gly Val Gly Val Ile Ile Ile Leu Thr Gly Val Pro Ile Phe Phe
450                 455                 460

Leu Gly Val Phe Trp Arg Ser Lys Pro Lys Cys Val His Arg Leu Thr
465                 470                 475                 480

Glu Ser Met Thr His Trp Gly Gln Leu Cys Phe Val Val Tyr Pro
        485                 490                 495

Gln Asp Ala Pro Glu Glu Glu Asn Gly Pro Cys Pro Pro Ser Leu
        500                 505                 510

Leu Pro Ala Thr Asp Lys Pro Ser Lys Pro Gln
            515                 520

<210> SEQ ID NO 30
<211> LENGTH: 236
<212> TYPE: PRT
<213> ORGANISM: Homo sapiens

<400> SEQUENCE: 30

Met Glu Ser Ser Ala Lys Met Glu Ser Gly Gly Ala Gly Gln Gln Pro
1               5                   10                  15

Gln Pro Gln Pro Gln Gln Pro Phe Leu Pro Pro Ala Ala Cys Phe Phe
            20                  25                  30

Ala Thr Ala Ala Ala Ala Ala Ala Ala Ala Ala Ala Ala Ala Ala Gln
        35                  40                  45

Ser Ala Gln Gln Gln Gln Gln Gln Gln Gln Gln Gln Gln Gln Ala Pro
    50                  55                  60

Gln Leu Arg Pro Ala Ala Asp Gly Gln Pro Ser Gly Gly Gly His Lys
65                  70                  75                  80

Ser Ala Pro Lys Gln Val Lys Arg Gln Arg Ser Ser Pro Glu Leu
                85                  90                  95

Met Arg Cys Lys Arg Arg Leu Asn Phe Ser Gly Phe Gly Tyr Ser Leu
            100                 105                 110

Pro Gln Gln Gln Pro Ala Ala Val Ala Arg Arg Asn Glu Arg Glu Arg
        115                 120                 125

Asn Arg Val Lys Leu Val Asn Leu Gly Phe Ala Thr Leu Arg Glu His
    130                 135                 140

Val Pro Asn Gly Ala Ala Asn Lys Lys Met Ser Lys Val Glu Thr Leu
145                 150                 155                 160

Arg Ser Ala Val Glu Tyr Ile Arg Ala Leu Gln Gln Leu Leu Asp Glu
                165                 170                 175

His Asp Ala Val Ser Ala Ala Phe Gln Ala Gly Val Leu Ser Pro Thr
            180                 185                 190

Ile Ser Pro Asn Tyr Ser Asn Asp Leu Asn Ser Met Ala Gly Ser Pro
        195                 200                 205

Val Ser Ser Tyr Ser Ser Asp Glu Gly Ser Tyr Asp Pro Leu Ser Pro
    210                 215                 220

Glu Glu Gln Glu Leu Leu Asp Phe Thr Asn Trp Phe
225                 230                 235

<210> SEQ ID NO 31
<211> LENGTH: 598
<212> TYPE: PRT

<213> ORGANISM: Homo sapiens

<400> SEQUENCE: 31

```
Met Pro Cys Val Gln Ala Gln Tyr Gly Ser Ser Pro Gln Gly Ala Ser
  1               5                  10                  15
Pro Ala Ser Gln Ser Tyr Ser Tyr His Ser Ser Gly Glu Tyr Ser Ser
             20                  25                  30
Asp Phe Leu Thr Pro Glu Phe Val Lys Phe Ser Met Asp Leu Thr Asn
         35                  40                  45
Thr Glu Ile Thr Ala Thr Thr Ser Leu Pro Ser Phe Ser Thr Phe Met
     50                  55                  60
Asp Asn Tyr Ser Thr Gly Tyr Asp Val Lys Pro Pro Cys Leu Tyr Gln
 65                  70                  75                  80
Met Pro Leu Ser Gly Gln Gln Ser Ser Ile Lys Val Glu Asp Ile Gln
                 85                  90                  95
Met His Asn Tyr Gln Gln His Ser His Leu Pro Pro Gln Ser Glu Glu
            100                 105                 110
Met Met Pro His Ser Gly Ser Val Tyr Tyr Lys Pro Ser Ser Pro Pro
        115                 120                 125
Thr Pro Thr Thr Pro Gly Phe Gln Val Gln His Ser Pro Met Trp Asp
    130                 135                 140
Asp Pro Gly Ser Leu His Asn Phe His Gln Asn Tyr Val Ala Thr Thr
145                 150                 155                 160
His Met Ile Glu Gln Arg Lys Thr Pro Val Ser Arg Leu Ser Leu Phe
                165                 170                 175
Ser Phe Lys Gln Ser Pro Pro Gly Thr Pro Val Ser Ser Cys Gln Met
            180                 185                 190
Arg Phe Asp Gly Pro Leu His Val Pro Met Asn Pro Glu Pro Ala Gly
        195                 200                 205
Ser His His Val Val Asp Gly Gln Thr Phe Ala Val Pro Asn Pro Ile
    210                 215                 220
Arg Lys Pro Ala Ser Met Gly Phe Pro Gly Leu Gln Ile Gly His Ala
225                 230                 235                 240
Ser Gln Leu Leu Asp Thr Gln Val Pro Ser Pro Ser Arg Gly Ser
                245                 250                 255
Pro Ser Asn Glu Gly Leu Cys Ala Val Cys Gly Asp Asn Ala Ala Cys
            260                 265                 270
Gln His Tyr Gly Val Arg Thr Cys Glu Gly Cys Lys Gly Phe Phe Lys
        275                 280                 285
Arg Thr Val Gln Lys Asn Ala Lys Tyr Val Cys Leu Ala Asn Lys Asn
    290                 295                 300
Cys Pro Val Asp Lys Arg Arg Arg Asn Arg Cys Gln Tyr Cys Arg Phe
305                 310                 315                 320
Gln Lys Cys Leu Ala Val Gly Met Val Lys Glu Val Val Arg Thr Asp
                325                 330                 335
Ser Leu Lys Gly Arg Arg Gly Arg Leu Pro Ser Lys Pro Lys Ser Pro
            340                 345                 350
Gln Glu Pro Ser Pro Pro Ser Pro Val Ser Leu Ile Ser Ala Leu
        355                 360                 365
Val Arg Ala His Val Asp Ser Asn Pro Ala Met Thr Ser Leu Asp Tyr
    370                 375                 380
Ser Arg Phe Gln Ala Asn Pro Asp Tyr Gln Met Ser Gly Asp Asp Thr
385                 390                 395                 400
```

```
Gln His Ile Gln Gln Phe Tyr Asp Leu Leu Thr Gly Ser Met Glu Ile
                405                 410                 415

Ile Arg Gly Trp Ala Glu Lys Ile Pro Gly Phe Ala Asp Leu Pro Lys
            420                 425                 430

Ala Asp Gln Asp Leu Leu Phe Glu Ser Ala Phe Leu Glu Leu Phe Val
        435                 440                 445

Leu Arg Leu Ala Tyr Arg Ser Asn Pro Val Glu Gly Lys Leu Ile Phe
    450                 455                 460

Cys Asn Gly Val Val Leu His Arg Leu Gln Cys Val Arg Gly Phe Gly
465                 470                 475                 480

Glu Trp Ile Asp Ser Ile Val Glu Phe Ser Ser Asn Leu Gln Asn Met
                485                 490                 495

Asn Ile Asp Ile Ser Ala Phe Ser Cys Ile Ala Ala Leu Ala Met Val
            500                 505                 510

Thr Glu Arg His Gly Leu Lys Glu Pro Lys Arg Val Glu Glu Leu Gln
        515                 520                 525

Asn Lys Ile Val Asn Cys Leu Lys Asp His Val Thr Phe Asn Asn Gly
    530                 535                 540

Gly Leu Asn Arg Pro Asn Tyr Leu Ser Lys Leu Leu Gly Lys Leu Pro
545                 550                 555                 560

Glu Leu Arg Thr Leu Cys Thr Gln Gly Leu Gln Arg Ile Phe Tyr Leu
                565                 570                 575

Lys Leu Glu Asp Leu Val Pro Pro Ala Ile Ile Asp Lys Leu Phe
            580                 585                 590

Leu Asp Thr Leu Pro Phe
        595

<210> SEQ ID NO 32
<211> LENGTH: 272
<212> TYPE: PRT
<213> ORGANISM: Homo sapiens

<400> SEQUENCE: 32

Met Phe Val Lys Ser Glu Thr Leu Glu Leu Lys Glu Glu Glu Asp Val
1               5                   10                  15

Leu Val Leu Leu Gly Ser Ala Ser Pro Ala Leu Ala Ala Leu Thr Pro
            20                  25                  30

Leu Ser Ser Ala Asp Glu Glu Glu Glu Glu Pro Gly Ala Ser
        35                  40                  45

Gly Gly Ala Arg Arg Gln Arg Gly Ala Glu Ala Gly Gln Gly Ala Arg
    50                  55                  60

Gly Gly Val Ala Ala Gly Ala Glu Gly Cys Arg Pro Ala Arg Leu Leu
65                  70                  75                  80

Gly Leu Val His Asp Cys Lys Arg Arg Pro Ser Arg Ala Arg Ala Val
                85                  90                  95

Ser Arg Gly Ala Lys Thr Ala Thr Val Gln Arg Ile Lys Lys Thr
            100                 105                 110

Arg Arg Leu Lys Ala Asn Asn Arg Glu Arg Asn Arg Met His Asn Leu
        115                 120                 125

Asn Ala Ala Leu Asp Ala Leu Arg Glu Val Leu Pro Thr Phe Pro Glu
    130                 135                 140

Asp Ala Lys Leu Thr Lys Ile Glu Thr Leu Arg Phe Ala His Asn Tyr
145                 150                 155                 160

Ile Trp Ala Leu Thr Glu Thr Leu Arg Leu Ala Asp His Cys Gly Gly
                165                 170                 175
```

```
Gly Gly Gly Gly Leu Pro Gly Ala Leu Phe Ser Glu Ala Val Leu Leu
            180             185                 190

Ser Pro Gly Gly Ala Ser Ala Ala Leu Ser Ser Ser Gly Asp Ser Pro
        195                 200                 205

Ser Pro Ala Ser Thr Trp Ser Cys Thr Asn Ser Pro Ala Pro Ser Ser
210                 215                 220

Ser Val Ser Ser Asn Ser Thr Ser Pro Tyr Ser Cys Thr Leu Ser Pro
225                 230                 235                 240

Ala Ser Pro Ala Gly Ser Asp Met Asp Tyr Trp Gln Pro Pro Pro Pro
                245                 250                 255

Asp Lys His Arg Tyr Ala Pro His Leu Pro Ile Ala Arg Asp Cys Ile
                260                 265                 270

<210> SEQ ID NO 33
<211> LENGTH: 382
<212> TYPE: PRT
<213> ORGANISM: Homo sapiens

<400> SEQUENCE: 33

Met Leu Asp Gly Leu Lys Met Glu Glu Asn Phe Gln Ser Ala Ile Asp
1               5                   10                  15

Thr Ser Ala Ser Phe Ser Ser Leu Leu Gly Arg Ala Val Ser Pro Lys
                20                  25                  30

Ser Val Cys Glu Gly Cys Gln Arg Val Ile Leu Asp Arg Phe Leu Leu
            35                  40                  45

Arg Leu Asn Asp Ser Phe Trp His Glu Gln Cys Val Gln Cys Ala Ser
    50                  55                  60

Cys Lys Glu Pro Leu Glu Thr Thr Cys Phe Tyr Arg Asp Lys Lys Leu
65                  70                  75                  80

Tyr Cys Lys Tyr Asp Tyr Glu Lys Leu Phe Ala Val Lys Cys Gly Gly
                85                  90                  95

Cys Phe Glu Ala Ile Ala Pro Asn Glu Phe Val Met Arg Ala Gln Lys
            100                 105                 110

Ser Val Tyr His Leu Ser Cys Phe Cys Cys Val Cys Glu Arg Gln
            115                 120                 125

Leu Gln Lys Gly Asp Glu Phe Val Leu Lys Glu Gly Gln Leu Leu Cys
    130                 135                 140

Lys Gly Asp Tyr Glu Lys Glu Arg Glu Leu Leu Ser Leu Val Ser Pro
145                 150                 155                 160

Ala Ala Ser Asp Ser Gly Lys Ser Asp Asp Glu Glu Ser Leu Cys Lys
                165                 170                 175

Ser Ala His Gly Ala Gly Lys Gly Thr Ala Glu Glu Gly Lys Asp His
            180                 185                 190

Lys Arg Pro Lys Arg Pro Arg Thr Ile Leu Thr Thr Gln Gln Arg Arg
        195                 200                 205

Ala Phe Lys Ala Ser Phe Glu Val Ser Ser Lys Pro Cys Arg Lys Val
    210                 215                 220

Arg Glu Thr Leu Ala Ala Glu Thr Gly Leu Ser Val Arg Val Val Gln
225                 230                 235                 240

Val Trp Phe Gln Asn Gln Arg Ala Lys Met Lys Lys Leu Ala Arg Arg
                245                 250                 255

Gln Gln Gln Gln Gln Gln Asp Gln Gln Asn Thr Gln Arg Leu Ser Ser
                260                 265                 270

Ala Gln Thr Asn Gly Gly Gly Ser Ala Gly Met Glu Gly Ile Met Asn
```

```
            275                 280                 285
Pro Tyr Thr Ala Leu Pro Thr Pro Gln Gln Leu Leu Ala Ile Glu Gln
290                 295                 300

Ser Val Tyr Ser Ser Asp Pro Phe Arg Gln Gly Leu Thr Pro Pro Gln
305                 310                 315                 320

Met Pro Gly Asp His Met His Pro Tyr Gly Ala Glu Pro Leu Phe His
                325                 330                 335

Asp Leu Asp Ser Asp Asp Thr Ser Leu Ser Asn Leu Gly Asp Cys Phe
                340                 345                 350

Leu Ala Thr Ser Glu Ala Gly Pro Leu Gln Ser Arg Val Gly Asn Pro
                355                 360                 365

Ile Asp His Leu Tyr Ser Met Gln Asn Ser Tyr Phe Thr Ser
370                 375                 380

<210> SEQ ID NO 34
<211> LENGTH: 400
<212> TYPE: PRT
<213> ORGANISM: Homo sapiens

<400> SEQUENCE: 34

Met Glu Lys Ser Lys Asn Phe Arg Ile Glu Pro Cys Trp Arg Trp Thr
1               5                   10                  15

Pro His Glu Pro Pro Leu Ala Glu Arg Ala Leu Ala Lys Val Thr Ser
                20                  25                  30

Pro Pro Val Pro Ala Ser Gly Thr Gly Gly Gly Gly Gly Gly Gly Gly
                35                  40                  45

Ala Ser Gly Gly Thr Ser Gly Ser Cys Ser Pro Ala Ser Ser Glu Pro
        50                  55                  60

Pro Ala Ala Pro Ala Asp Arg Leu Arg Ala Glu Ser Pro Ser Pro Pro
65                  70                  75                  80

Arg Leu Leu Ala Ala His Cys Ala Leu Leu Pro Lys Pro Gly Phe Leu
                85                  90                  95

Gly Ala Gly Gly Gly Gly Gly Thr Gly Gly Gly His Gly Gly Pro
                100                 105                 110

His His His Ala His Pro Gly Ala Ala Ala Ala Ala Ala Ala Ala
                115                 120                 125

Ala Ala Ala Ala Ala Ala Gly Gly Leu Ala Leu Gly Leu His Pro
        130                 135                 140

Gly Gly Ala Gln Gly Gly Ala Gly Leu Pro Ala Gln Ala Ala Leu Tyr
145                 150                 155                 160

Gly His Pro Val Tyr Gly Tyr Ser Ala Ala Ala Ala Ala Ala Ala Leu
                165                 170                 175

Ala Gly Gln His Pro Ala Leu Ser Tyr Ser Tyr Pro Gln Val Gln Gly
                180                 185                 190

Ala His Pro Ala His Pro Ala Asp Pro Ile Lys Leu Gly Ala Gly Thr
                195                 200                 205

Phe Gln Leu Asp Gln Trp Leu Arg Ala Thr Ala Gly Met Ile Leu Pro
210                 215                 220

Lys Met Pro Asp Phe Asn Ser Gln Ala Gln Ser Asn Leu Leu Gly Lys
225                 230                 235                 240

Cys Arg Arg Pro Arg Thr Ala Phe Thr Ser Gln Gln Leu Leu Glu Leu
                245                 250                 255

Glu His Gln Phe Lys Phe Asn Lys Tyr Leu Ser Arg Pro Lys Arg Phe
                260                 265                 270
```

```
Glu Val Ala Thr Ser Leu Met Leu Thr Glu Thr Gln Val Lys Ile Trp
            275                 280                 285
Phe Gln Asn Arg Arg Met Lys Trp Lys Arg Ser Lys Ala Lys Glu
290                 295                 300
Gln Ala Ala Gln Glu Ala Glu Lys Gln Lys Gly Gly Gly Gly Ala
305                 310                 315                 320
Gly Lys Gly Gly Ala Glu Pro Gly Ala Glu Leu Leu Gly Pro
            325                 330                 335
Pro Ala Pro Arg Asp Lys Gly Ser Gly Pro Ala Asp Leu Arg Asp
            340                 345                 350
Ser Asp Pro Glu Glu Asp Glu Asp Asp Glu Asp His Phe Pro
            355                 360                 365
Tyr Ser Asn Gly Ala Ser Val His Ala Ala Ser Ser Asp Cys Ser Ser
            370                 375                 380
Glu Asp Asp Ser Pro Pro Arg Pro Ser His Gln Pro Ala Pro Gln
385                 390                 395                 400
```

<210> SEQ ID NO 35
<211> LENGTH: 397
<212> TYPE: PRT
<213> ORGANISM: Homo sapiens

<400> SEQUENCE: 35

```
Met Leu Leu Glu Thr Gly Leu Glu Arg Asp Arg Ala Arg Pro Gly Ala
1               5                   10                  15
Ala Ala Val Cys Thr Leu Gly Gly Thr Arg Glu Ile Pro Leu Cys Ala
            20                  25                  30
Gly Cys Asp Gln His Ile Leu Asp Arg Phe Ile Leu Lys Ala Leu Asp
        35                  40                  45
Arg His Trp His Ser Lys Cys Leu Lys Cys Ser Asp Cys His Thr Pro
    50                  55                  60
Leu Ala Glu Arg Cys Phe Ser Arg Gly Glu Ser Val Tyr Cys Lys Asp
65                  70                  75                  80
Asp Phe Phe Lys Arg Phe Gly Thr Lys Cys Ala Ala Cys Gln Leu Gly
                85                  90                  95
Ile Pro Pro Thr Gln Val Val Arg Arg Ala Gln Asp Phe Val Tyr His
            100                 105                 110
Leu His Cys Phe Ala Cys Val Val Cys Lys Arg Gln Leu Ala Thr Gly
        115                 120                 125
Asp Glu Phe Tyr Leu Met Glu Asp Ser Arg Leu Val Cys Lys Ala Asp
    130                 135                 140
Tyr Glu Thr Ala Lys Gln Arg Glu Ala Glu Ala Thr Ala Lys Arg Pro
145                 150                 155                 160
Arg Thr Thr Ile Thr Ala Lys Gln Leu Glu Thr Leu Lys Ser Ala Tyr
                165                 170                 175
Asn Thr Ser Pro Lys Pro Ala Arg His Val Arg Glu Gln Leu Ser Ser
            180                 185                 190
Glu Thr Gly Leu Asp Met Arg Val Val Gln Val Trp Phe Gln Asn Arg
        195                 200                 205
Arg Ala Lys Glu Lys Arg Leu Lys Lys Asp Ala Gly Arg Gln Arg Trp
    210                 215                 220
Gly Gln Tyr Phe Arg Asn Met Lys Arg Ser Arg Gly Gly Ser Lys Ser
225                 230                 235                 240
Asp Lys Asp Ser Val Gln Glu Gly Gln Asp Ser Asp Ala Glu Val Ser
                245                 250                 255
```

```
Phe Pro Asp Glu Pro Ser Leu Ala Glu Met Gly Pro Ala Asn Gly Leu
            260                 265                 270

Tyr Gly Ser Leu Gly Glu Pro Thr Gln Ala Leu Gly Arg Pro Ser Gly
        275                 280                 285

Ala Leu Gly Asn Phe Ser Leu Glu His Gly Gly Leu Ala Gly Pro Glu
    290                 295                 300

Gln Tyr Arg Glu Leu Arg Pro Gly Ser Pro Tyr Gly Val Pro Pro Ser
305                 310                 315                 320

Pro Ala Ala Pro Gln Ser Leu Pro Gly Pro Gln Pro Leu Leu Ser Ser
                325                 330                 335

Leu Val Tyr Pro Asp Thr Ser Leu Gly Leu Val Pro Ser Gly Ala Pro
                340                 345                 350

Gly Gly Pro Pro Pro Met Arg Val Leu Ala Gly Asn Gly Pro Ser Ser
            355                 360                 365

Asp Leu Ser Thr Gly Ser Ser Gly Gly Tyr Pro Asp Phe Pro Ala Ser
    370                 375                 380

Pro Ala Ser Trp Leu Asp Glu Val Asp His Ala Gln Phe
385                 390                 395

<210> SEQ ID NO 36
<211> LENGTH: 328
<212> TYPE: PRT
<213> ORGANISM: Homo sapiens

<400> SEQUENCE: 36

Met Thr Gly Val Phe Asp Ser Leu Val Ala Asp Met His Ser Thr Gln
1               5                   10                  15

Ile Ala Ala Ser Ser Thr Tyr His Gln His Gln Pro Pro Ser Gly
            20                  25                  30

Gly Gly Ala Gly Pro Gly Gly Asn Ser Ser Ser Ser Ser Leu His
        35                  40                  45

Lys Pro Gln Glu Ser Pro Thr Leu Pro Val Ser Thr Ala Thr Asp Ser
    50                  55                  60

Ser Tyr Tyr Thr Asn Gln Gln His Pro Ala Gly Gly Gly Gly Gly
65              70                  75                  80

Gly Ser Pro Tyr Ala His Met Gly Ser Tyr Gln Tyr Gln Ala Ser Gly
                85                  90                  95

Leu Asn Asn Val Pro Tyr Ser Ala Lys Ser Ser Tyr Asp Leu Gly Tyr
            100                 105                 110

Thr Ala Ala Tyr Thr Ser Tyr Ala Pro Tyr Gly Thr Ser Ser Ser Pro
        115                 120                 125

Ala Asn Asn Glu Pro Glu Lys Glu Asp Leu Glu Pro Glu Ile Arg Ile
130                 135                 140

Val Asn Gly Lys Pro Lys Lys Val Arg Lys Pro Arg Thr Ile Tyr Ser
145                 150                 155                 160

Ser Phe Gln Leu Ala Ala Leu Gln Arg Arg Phe Gln Lys Thr Gln Tyr
                165                 170                 175

Leu Ala Leu Pro Glu Arg Ala Glu Leu Ala Ala Ser Leu Gly Leu Thr
            180                 185                 190

Gln Thr Gln Val Lys Ile Trp Phe Gln Asn Arg Arg Ser Lys Phe Lys
        195                 200                 205

Lys Met Trp Lys Ser Gly Glu Ile Pro Ser Glu Gln His Pro Gly Ala
210                 215                 220

Ser Ala Ser Pro Pro Cys Ala Ser Pro Pro Val Ser Ala Pro Ala Ser
```

```
225                 230                 235                 240

Trp Asp Phe Gly Val Pro Gln Arg Met Ala Gly Gly Gly Pro Gly
                245                 250                 255

Ser Gly Gly Ser Gly Ala Gly Ser Ser Gly Ser Ser Pro Ser Ala
                260                 265                 270

Ala Ser Ala Phe Leu Gly Asn Tyr Pro Trp Tyr His Gln Thr Ser Gly
                275                 280                 285

Ser Ala Ser His Leu Gln Ala Thr Ala Pro Leu Leu His Pro Thr Gln
                290                 295                 300

Thr Pro Gln Pro His His His His His His Gly Gly Gly Gly Ala
305                 310                 315                 320

Pro Val Ser Ala Gly Thr Ile Phe
                325

<210> SEQ ID NO 37
<211> LENGTH: 521
<212> TYPE: PRT
<213> ORGANISM: Homo sapiens

<400> SEQUENCE: 37

Met Ala Ser Asn Ser Leu Phe Ser Thr Val Thr Pro Cys Gln Gln Asn
1               5                   10                  15

Phe Phe Trp Asp Pro Ser Thr Ser Arg Arg Phe Ser Pro Pro Ser Ser
                20                  25                  30

Ser Leu Gln Pro Gly Lys Met Ser Asp Val Ser Pro Val Val Ala Ala
                35                  40                  45

Gln Gln Gln Gln Gln Gln Gln Gln Gln Gln Gln Gln Gln Gln Gln Gln
        50                  55                  60

Gln Gln Gln Gln Gln Gln Gln Glu Ala Ala Ala Ala Ala Ala Ala Ala
65                  70                  75                  80

Ala Ala Ala Ala Ala Ala Ala Ala Val Pro Arg Leu Arg Pro Pro
                85                  90                  95

His Asp Asn Arg Thr Met Val Glu Ile Ile Ala Asp His Pro Ala Glu
                100                 105                 110

Leu Val Arg Thr Asp Ser Pro Asn Phe Leu Cys Ser Val Leu Pro Ser
        115                 120                 125

His Trp Arg Cys Asn Lys Thr Leu Pro Val Ala Phe Lys Val Val Ala
        130                 135                 140

Leu Gly Glu Val Pro Asp Gly Thr Val Val Thr Val Met Ala Gly Asn
145                 150                 155                 160

Asp Glu Asn Tyr Ser Ala Glu Leu Arg Asn Ala Ser Ala Val Met Lys
                165                 170                 175

Asn Gln Val Ala Arg Phe Asn Asp Leu Arg Phe Val Gly Arg Ser Gly
                180                 185                 190

Arg Gly Lys Ser Phe Thr Leu Thr Ile Thr Val Phe Thr Asn Pro Pro
        195                 200                 205

Gln Val Ala Thr Tyr His Arg Ala Ile Lys Val Thr Val Asp Gly Pro
        210                 215                 220

Arg Glu Pro Arg Arg His Arg Gln Lys Leu Asp Asp Ser Lys Pro Ser
225                 230                 235                 240

Leu Phe Ser Asp Arg Leu Ser Asp Leu Gly Arg Ile Pro His Pro Ser
                245                 250                 255

Met Arg Val Gly Val Pro Pro Gln Asn Pro Arg Pro Ser Leu Asn Ser
                260                 265                 270
```

Ala Pro Ser Pro Phe Asn Pro Gln Gly Gln Ser Gln Ile Thr Asp Pro
275 280 285

Arg Gln Ala Gln Ser Ser Pro Pro Trp Ser Tyr Asp Gln Ser Tyr Pro
290 295 300

Ser Tyr Leu Ser Gln Met Thr Ser Pro Ser Ile His Ser Thr Thr Pro
305 310 315 320

Leu Ser Ser Thr Arg Gly Thr Gly Leu Pro Ala Ile Thr Asp Val Pro
325 330 335

Arg Arg Ile Ser Asp Asp Asp Thr Ala Thr Ser Asp Phe Cys Leu Trp
340 345 350

Pro Ser Thr Leu Ser Lys Lys Ser Gln Ala Gly Ala Ser Glu Leu Gly
355 360 365

Pro Phe Ser Asp Pro Arg Gln Phe Pro Ser Ile Ser Ser Leu Thr Glu
370 375 380

Ser Arg Phe Ser Asn Pro Arg Met His Tyr Pro Ala Thr Phe Thr Tyr
385 390 395 400

Thr Pro Pro Val Thr Ser Gly Met Ser Leu Gly Met Ser Ala Thr Thr
405 410 415

His Tyr His Thr Tyr Leu Pro Pro Pro Tyr Pro Gly Ser Ser Gln Ser
420 425 430

Gln Ser Gly Pro Phe Gln Thr Ser Ser Thr Pro Tyr Leu Tyr Tyr Gly
435 440 445

Thr Ser Ser Gly Ser Tyr Gln Phe Pro Met Val Pro Gly Gly Asp Arg
450 455 460

Ser Pro Ser Arg Met Leu Pro Pro Cys Thr Thr Thr Ser Asn Gly Ser
465 470 475 480

Thr Leu Leu Asn Pro Asn Leu Pro Asn Gln Asn Asp Gly Val Asp Ala
485 490 495

Asp Gly Ser His Ser Ser Ser Pro Thr Val Leu Asn Ser Ser Gly Arg
500 505 510

Met Asp Glu Ser Val Trp Arg Pro Tyr
515 520

<210> SEQ ID NO 38
<211> LENGTH: 763
<212> TYPE: PRT
<213> ORGANISM: Homo sapiens

<400> SEQUENCE: 38

Met Leu Thr Asp Pro Asp Leu Pro Gln Glu Phe Glu Arg Met Ser Ser
1 5 10 15

Lys Arg Pro Ala Ser Pro Tyr Gly Glu Ala Asp Gly Glu Val Ala Met
20 25 30

Val Thr Ser Arg Gln Lys Val Glu Glu Glu Ser Asp Gly Leu Pro
35 40 45

Ala Phe His Leu Pro Leu His Val Ser Phe Pro Asn Lys Pro His Ser
50 55 60

Glu Glu Phe Gln Pro Val Ser Leu Leu Thr Gln Glu Thr Cys Gly His
65 70 75 80

Arg Thr Pro Thr Ser Gln His Asn Thr Met Glu Val Asp Gly Asn Lys
85 90 95

Val Met Ser Ser Phe Ala Pro His Asn Ser Ser Thr Ser Pro Gln Lys
100 105 110

Ala Glu Glu Gly Gly Arg Gln Ser Gly Glu Ser Leu Ser Ser Thr Ala
115 120 125

```
Leu Gly Thr Pro Glu Arg Arg Lys Gly Ser Leu Ala Asp Val Val Asp
            130                 135                 140

Thr Leu Lys Gln Arg Lys Met Glu Glu Leu Ile Lys Asn Glu Pro Glu
145                 150                 155                 160

Glu Thr Pro Ser Ile Glu Lys Leu Leu Ser Lys Asp Trp Lys Asp Lys
                165                 170                 175

Leu Leu Ala Met Gly Ser Gly Asn Phe Gly Glu Ile Lys Gly Thr Pro
            180                 185                 190

Glu Ser Leu Ala Glu Lys Glu Arg Gln Leu Met Gly Met Ile Asn Gln
        195                 200                 205

Leu Thr Ser Leu Arg Glu Gln Leu Leu Ala Ala His Asp Glu Gln Lys
    210                 215                 220

Lys Leu Ala Ala Ser Gln Ile Glu Lys Gln Arg Gln Gln Met Glu Leu
225                 230                 235                 240

Ala Lys Gln Gln Gln Glu Gln Ile Ala Arg Gln Gln Gln Gln Leu Leu
                245                 250                 255

Gln Gln Gln His Lys Ile Asn Leu Leu Gln Gln Gln Ile Gln Val Gln
            260                 265                 270

Gly Gln Leu Pro Pro Leu Met Ile Pro Val Phe Pro Pro Asp Gln Arg
        275                 280                 285

Thr Leu Ala Ala Ala Gln Gln Gly Phe Leu Leu Pro Pro Gly Phe
    290                 295                 300

Ser Tyr Lys Ala Gly Cys Ser Asp Pro Tyr Pro Val Gln Leu Ile Pro
305                 310                 315                 320

Thr Thr Met Ala Ala Ala Ala Ala Thr Pro Gly Leu Gly Pro Leu
                325                 330                 335

Gln Leu Gln Gln Leu Tyr Ala Ala Gln Leu Ala Ala Met Gln Val Ser
            340                 345                 350

Pro Gly Gly Lys Leu Pro Gly Ile Pro Gln Gly Asn Leu Gly Ala Ala
        355                 360                 365

Val Ser Pro Thr Ser Ile His Thr Asp Lys Ser Thr Asn Ser Pro Pro
    370                 375                 380

Pro Lys Ser Lys Asp Glu Val Ala Gln Pro Leu Asn Leu Ser Ala Lys
385                 390                 395                 400

Pro Lys Thr Ser Asp Gly Lys Ser Pro Thr Ser Pro Thr Ser Pro His
                405                 410                 415

Met Pro Ala Leu Arg Ile Asn Ser Gly Ala Gly Pro Leu Lys Ala Ser
            420                 425                 430

Val Pro Ala Ala Leu Ala Ser Pro Ser Ala Arg Val Ser Thr Ile Gly
        435                 440                 445

Tyr Leu Asn Asp His Asp Ala Val Thr Lys Ala Ile Gln Glu Ala Arg
    450                 455                 460

Gln Met Lys Glu Gln Leu Arg Arg Glu Gln Gln Val Leu Asp Gly Lys
465                 470                 475                 480

Val Ala Val Val Asn Ser Leu Gly Leu Asn Asn Cys Arg Thr Glu Lys
                485                 490                 495

Glu Lys Thr Thr Leu Glu Ser Leu Thr Gln Gln Leu Ala Val Lys Gln
            500                 505                 510

Asn Glu Glu Gly Lys Phe Ser His Ala Met Met Asp Phe Asn Leu Ser
        515                 520                 525

Gly Asp Ser Asp Gly Ser Ala Gly Val Ser Glu Ser Arg Ile Tyr Arg
    530                 535                 540
```

Glu Ser Arg Gly Arg Gly Ser Asn Glu Pro His Ile Lys Arg Pro Met
545                 550                 555                 560

Asn Ala Phe Met Val Trp Ala Lys Asp Glu Arg Arg Lys Ile Leu Gln
            565                 570                 575

Ala Phe Pro Asp Met His Asn Ser Asn Ile Ser Lys Ile Leu Gly Ser
        580                 585                 590

Arg Trp Lys Ala Met Thr Asn Leu Glu Lys Gln Pro Tyr Tyr Glu Glu
    595                 600                 605

Gln Ala Arg Leu Ser Lys His Leu Glu Lys Tyr Pro Asp Tyr Lys
610                 615                 620

Tyr Lys Pro Arg Pro Lys Arg Thr Cys Leu Val Asp Gly Lys Lys Leu
625                 630                 635                 640

Arg Ile Gly Glu Tyr Lys Ala Ile Met Arg Asn Arg Arg Gln Glu Met
                645                 650                 655

Arg Gln Tyr Phe Asn Val Gly Gln Gln Ala Gln Ile Pro Ile Ala Thr
            660                 665                 670

Ala Gly Val Val Tyr Pro Gly Ala Ile Ala Met Ala Gly Met Pro Ser
        675                 680                 685

Pro His Leu Pro Ser Glu His Ser Val Ser Ser Pro Glu Pro
    690                 695                 700

Gly Met Pro Val Ile Gln Ser Thr Tyr Gly Val Lys Gly Glu Glu Pro
705                 710                 715                 720

His Ile Lys Glu Glu Ile Gln Ala Glu Asp Ile Asn Gly Glu Ile Tyr
                725                 730                 735

Asp Glu Tyr Asp Glu Glu Glu Asp Asp Pro Asp Val Asp Tyr Gly Ser
            740                 745                 750

Asp Ser Glu Asn His Ile Ala Gly Gln Ala Asn
        755                 760

<210> SEQ ID NO 39
<211> LENGTH: 808
<212> TYPE: PRT
<213> ORGANISM: Homo sapiens

<400> SEQUENCE: 39

Met Ser Ser Lys Gln Ala Thr Ser Pro Phe Ala Cys Ala Ala Asp Gly
1               5                   10                  15

Glu Asp Ala Met Thr Gln Asp Leu Thr Ser Arg Glu Lys Glu Glu Gly
            20                  25                  30

Ser Asp Gln His Val Ala Ser His Leu Pro Leu His Pro Ile Met His
        35                  40                  45

Asn Lys Pro His Ser Glu Glu Leu Pro Thr Leu Val Ser Thr Ile Gln
50                  55                  60

Gln Asp Ala Asp Trp Asp Ser Val Leu Ser Ser Gln Gln Arg Met Glu
65                  70                  75                  80

Ser Glu Asn Asn Lys Leu Cys Ser Leu Tyr Ser Phe Arg Asn Thr Ser
                85                  90                  95

Thr Ser Pro His Lys Pro Asp Glu Gly Ser Arg Asp Arg Glu Ile Met
            100                 105                 110

Thr Ser Val Thr Phe Gly Thr Pro Glu Arg Arg Lys Gly Ser Leu Ala
        115                 120                 125

Asp Val Val Asp Thr Leu Lys Gln Lys Lys Leu Glu Glu Met Thr Arg
130                 135                 140

Thr Glu Gln Glu Asp Ser Ser Cys Met Glu Lys Leu Leu Ser Lys Asp
145                 150                 155                 160

```
Trp Lys Glu Lys Met Glu Arg Leu Asn Thr Ser Glu Leu Leu Gly Glu
                165                 170                 175

Ile Lys Gly Thr Pro Glu Ser Leu Ala Glu Lys Glu Arg Gln Leu Ser
            180                 185                 190

Thr Met Ile Thr Gln Leu Ile Ser Leu Arg Glu Gln Leu Leu Ala Ala
        195                 200                 205

His Asp Glu Gln Lys Lys Leu Ala Ala Ser Gln Ile Glu Lys Gln Arg
    210                 215                 220

Gln Gln Met Asp Leu Ala Arg Gln Gln Glu Gln Ile Ala Arg Gln
225                 230                 235                 240

Gln Gln Gln Leu Leu Gln Gln His Lys Ile Asn Leu Leu Gln Gln
                245                 250                 255

Gln Ile Gln Val Gln Gly His Met Pro Pro Leu Met Ile Pro Ile Phe
                260                 265                 270

Pro His Asp Gln Arg Thr Leu Ala Ala Ala Ala Ala Gln Gln Gly
    275                 280                 285

Phe Leu Phe Pro Pro Gly Ile Thr Tyr Lys Pro Gly Asp Asn Tyr Pro
    290                 295                 300

Val Gln Phe Ile Pro Ser Thr Met Ala Ala Ala Ala Ser Gly Leu
305                 310                 315                 320

Ser Pro Leu Gln Leu Gln Lys Gly His Ala Ser His Pro Gln Ile Asn
                325                 330                 335

Gln Arg Leu Lys Gly Leu Ser Asp Arg Phe Gly Arg Asn Leu Asp Thr
                340                 345                 350

Phe Glu His Gly Gly Gly His Ser Tyr Asn His Lys Gln Ile Glu Gln
        355                 360                 365

Leu Tyr Ala Ala Gln Leu Ala Ser Met Gln Val Ser Pro Gly Ala Lys
    370                 375                 380

Met Pro Ser Thr Pro Gln Pro Pro Asn Thr Ala Gly Thr Val Ser Pro
385                 390                 395                 400

Thr Gly Ile Lys Asn Glu Lys Arg Gly Thr Ser Pro Val Thr Gln Val
                405                 410                 415

Lys Asp Glu Ala Ala Ala Gln Pro Leu Asn Leu Ser Ser Arg Pro Lys
            420                 425                 430

Thr Ala Glu Pro Val Lys Ser Pro Thr Ser Pro Thr Gln Asn Leu Phe
        435                 440                 445

Pro Ala Ser Lys Thr Ser Pro Val Asn Leu Pro Asn Lys Ser Ser Ile
    450                 455                 460

Pro Ser Pro Ile Gly Gly Ser Leu Gly Arg Gly Ser Ser Leu Asp Ile
465                 470                 475                 480

Leu Ser Ser Leu Asn Ser Pro Ala Leu Phe Gly Asp Gln Asp Thr Val
                485                 490                 495

Met Lys Ala Ile Gln Glu Ala Arg Lys Met Arg Glu Gln Ile Gln Arg
            500                 505                 510

Glu Gln Gln Gln Gln Gln Pro His Gly Val Asp Gly Lys Leu Ser Ser
        515                 520                 525

Ile Asn Asn Met Gly Leu Asn Ser Cys Arg Asn Glu Lys Glu Arg Thr
    530                 535                 540

Arg Phe Glu Asn Leu Gly Pro Gln Leu Thr Gly Lys Ser Asn Glu Asp
545                 550                 555                 560

Gly Lys Leu Gly Pro Gly Val Ile Asp Leu Thr Arg Pro Glu Asp Ala
                565                 570                 575
```

Glu Gly Gly Ala Thr Val Ala Glu Ala Arg Val Tyr Arg Asp Ala Arg
              580                 585                 590

Gly Arg Ala Ser Ser Glu Pro His Ile Lys Arg Pro Met Asn Ala Phe
          595                 600                 605

Met Val Trp Ala Lys Asp Glu Arg Arg Lys Ile Leu Gln Ala Phe Pro
      610                 615                 620

Asp Met His Asn Ser Asn Ile Ser Lys Ile Leu Gly Ser Arg Trp Lys
625                 630                 635                 640

Ser Met Ser Asn Gln Glu Lys Gln Pro Tyr Tyr Glu Gln Ala Arg
              645                 650                 655

Leu Ser Lys Ile His Leu Glu Lys Tyr Pro Asn Tyr Lys Tyr Lys Pro
              660                 665                 670

Arg Pro Lys Arg Thr Cys Ile Val Asp Gly Lys Lys Leu Arg Ile Gly
              675                 680                 685

Glu Tyr Lys Gln Leu Met Arg Ser Arg Arg Gln Glu Met Arg Gln Phe
              690                 695                 700

Phe Thr Val Gly Gln Gln Pro Gln Ile Pro Ile Thr Thr Gly Thr Gly
705                 710                 715                 720

Val Val Tyr Pro Gly Ala Ile Thr Met Ala Thr Thr Pro Ser Pro
              725                 730                 735

Gln Met Thr Ser Asp Cys Ser Ser Thr Ser Ala Ser Pro Glu Pro Ser
              740                 745                 750

Leu Pro Val Ile Gln Ser Thr Tyr Gly Met Lys Thr Asp Gly Gly Ser
              755                 760                 765

Leu Ala Gly Asn Glu Met Ile Asn Gly Glu Asp Glu Met Glu Met Tyr
770                 775                 780

Asp Asp Tyr Glu Asp Asp Pro Lys Ser Asp Tyr Ser Ser Glu Asn Glu
785                 790                 795                 800

Ala Pro Glu Ala Val Ser Ala Asn
              805

<210> SEQ ID NO 40
<211> LENGTH: 595
<212> TYPE: PRT
<213> ORGANISM: Homo sapiens

<400> SEQUENCE: 40

Met Ala Leu Thr Asp Gly Gly Trp Cys Leu Pro Lys Arg Phe Gly Ala
1               5                   10                  15

Ala Gly Ala Asp Ala Ser Asp Ser Arg Ala Phe Pro Ala Arg Glu Pro
              20                  25                  30

Ser Thr Pro Pro Ser Pro Ile Ser Ser Ser Ser Ser Cys Ser Arg
              35                  40                  45

Gly Gly Glu Arg Gly Pro Gly Gly Ala Ser Asn Cys Gly Thr Pro Gln
          50                  55                  60

Leu Asp Thr Glu Ala Ala Ala Gly Pro Pro Ala Arg Ser Leu Leu Leu
65                  70                  75                  80

Ser Ser Tyr Ala Ser His Pro Phe Gly Ala Pro His Gly Pro Ser Ala
              85                  90                  95

Pro Gly Val Ala Gly Pro Gly Asn Leu Ser Ser Trp Glu Asp Leu
              100                 105                 110

Leu Leu Phe Thr Asp Leu Asp Gln Ala Ala Thr Ala Ser Lys Leu Leu
          115                 120                 125

Trp Ser Ser Arg Gly Ala Lys Leu Ser Pro Phe Ala Pro Glu Gln Pro
          130                 135                 140

```
Glu Glu Met Tyr Gln Thr Leu Ala Ala Leu Ser Ser Gln Gly Pro Ala
145                 150                 155                 160

Ala Tyr Asp Gly Ala Pro Gly Gly Phe Val His Ser Ala Ala Ala Ala
                165                 170                 175

Ala Ala Ala Ala Ala Ala Ala Ser Ser Pro Val Tyr Val Pro Thr Thr
            180                 185                 190

Arg Val Gly Ser Met Leu Pro Gly Leu Pro Tyr His Leu Gln Gly Ser
            195                 200                 205

Gly Ser Gly Pro Ala Asn His Ala Gly Ala Gly Ala His Pro Gly
            210                 215                 220

Trp Pro Gln Ala Ser Ala Asp Ser Pro Tyr Gly Ser Gly Gly Gly
225                 230                 235                 240

Ala Ala Gly Gly Gly Ala Ala Gly Pro Gly Gly Ala Gly Ser Ala Ala
            245                 250                 255

Ala His Val Ser Ala Arg Phe Pro Tyr Ser Pro Ser Pro Met Ala
            260                 265                 270

Asn Gly Ala Ala Arg Glu Pro Gly Gly Tyr Ala Ala Ala Gly Ser Gly
            275                 280                 285

Gly Ala Gly Gly Val Ser Gly Gly Ser Ser Leu Ala Ala Met Gly
            290                 295                 300

Gly Arg Glu Pro Gln Tyr Ser Ser Leu Ser Ala Ala Arg Pro Leu Asn
305                 310                 315                 320

Gly Thr Tyr His His His His His His His His Pro Ser Pro
                325                 330                 335

Tyr Ser Pro Tyr Val Gly Ala Pro Leu Thr Pro Ala Trp Pro Ala Gly
                340                 345                 350

Pro Phe Glu Thr Pro Val Leu His Ser Leu Gln Ser Arg Ala Gly Ala
            355                 360                 365

Pro Leu Pro Val Pro Arg Gly Pro Ser Ala Asp Leu Leu Glu Asp Leu
            370                 375                 380

Ser Glu Ser Arg Glu Cys Val Asn Cys Gly Ser Ile Gln Thr Pro Leu
385                 390                 395                 400

Trp Arg Arg Asp Gly Thr Gly His Tyr Leu Cys Asn Ala Cys Gly Leu
                405                 410                 415

Tyr Ser Lys Met Asn Gly Leu Ser Arg Pro Leu Ile Lys Pro Gln Lys
                420                 425                 430

Arg Val Pro Ser Ser Arg Arg Leu Gly Leu Ser Cys Ala Asn Cys His
            435                 440                 445

Thr Thr Thr Thr Thr Leu Trp Arg Arg Asn Ala Glu Gly Glu Pro Val
            450                 455                 460

Cys Asn Ala Cys Gly Leu Tyr Met Lys Leu His Gly Val Pro Arg Pro
465                 470                 475                 480

Leu Ala Met Lys Lys Glu Gly Ile Gln Thr Arg Lys Arg Lys Pro Lys
                485                 490                 495

Asn Ile Asn Lys Ser Lys Thr Cys Ser Gly Asn Ser Asn Ser Ile
                500                 505                 510

Pro Met Thr Pro Thr Ser Thr Ser Asn Ser Asp Asp Cys Ser Lys
            515                 520                 525

Asn Thr Ser Pro Thr Thr Gln Pro Thr Ala Ser Gly Ala Gly Ala Pro
            530                 535                 540

Val Met Thr Gly Ala Gly Glu Ser Thr Asn Pro Glu Asn Ser Glu Leu
545                 550                 555                 560
```

```
Lys Tyr Ser Gly Gln Asp Gly Leu Tyr Ile Gly Val Ser Leu Ala Ser
                565                 570                 575

Pro Ala Glu Val Thr Ser Ser Val Arg Pro Asp Ser Trp Cys Ala Leu
            580                 585                 590

Ala Leu Ala
        595

<210> SEQ ID NO 41
<211> LENGTH: 413
<212> TYPE: PRT
<213> ORGANISM: Homo sapiens

<400> SEQUENCE: 41

Met Glu Phe Pro Gly Leu Gly Ser Leu Gly Thr Ser Glu Pro Leu Pro
1               5                   10                  15

Gln Phe Val Asp Pro Ala Leu Val Ser Ser Thr Pro Glu Ser Gly Val
            20                  25                  30

Phe Phe Pro Ser Gly Pro Glu Gly Leu Asp Ala Ala Ala Ser Ser Thr
        35                  40                  45

Ala Pro Ser Thr Ala Thr Ala Ala Ala Ala Leu Ala Tyr Tyr Arg
    50                  55                  60

Asp Ala Glu Ala Tyr Arg His Ser Pro Val Phe Gln Val Tyr Pro Leu
65                  70                  75                  80

Leu Asn Cys Met Glu Gly Ile Pro Gly Gly Ser Pro Tyr Ala Gly Trp
                85                  90                  95

Ala Tyr Gly Lys Thr Gly Leu Tyr Pro Ala Ser Thr Val Cys Pro Thr
            100                 105                 110

Arg Glu Asp Ser Pro Pro Gln Ala Val Glu Asp Leu Asp Gly Lys Gly
            115                 120                 125

Ser Thr Ser Phe Leu Glu Thr Leu Lys Thr Glu Arg Leu Ser Pro Asp
        130                 135                 140

Leu Leu Thr Leu Gly Pro Ala Leu Pro Ser Ser Leu Pro Val Pro Asn
145                 150                 155                 160

Ser Ala Tyr Gly Gly Pro Asp Phe Ser Ser Thr Phe Phe Ser Pro Thr
                165                 170                 175

Gly Ser Pro Leu Asn Ser Ala Ala Tyr Ser Ser Pro Lys Leu Arg Gly
            180                 185                 190

Thr Leu Pro Leu Pro Pro Cys Glu Ala Arg Glu Cys Val Asn Cys Gly
            195                 200                 205

Ala Thr Ala Thr Pro Leu Trp Arg Arg Asp Arg Thr Gly His Tyr Leu
    210                 215                 220

Cys Asn Ala Cys Gly Leu Tyr His Lys Met Asn Gly Gln Asn Arg Pro
225                 230                 235                 240

Leu Ile Arg Pro Lys Lys Arg Leu Ile Val Ser Lys Arg Ala Gly Thr
                245                 250                 255

Gln Cys Thr Asn Cys Gln Thr Thr Thr Thr Thr Leu Trp Arg Arg Asn
            260                 265                 270

Ala Ser Gly Asp Pro Val Cys Asn Ala Cys Gly Leu Tyr Tyr Lys Leu
        275                 280                 285

His Gln Val Asn Arg Pro Leu Thr Met Arg Lys Asp Gly Ile Gln Thr
    290                 295                 300

Arg Asn Arg Lys Ala Ser Gly Lys Gly Lys Lys Arg Gly Ser Ser
305                 310                 315                 320

Leu Gly Gly Thr Gly Ala Ala Glu Gly Pro Ala Gly Gly Phe Met Val
                325                 330                 335
```

-continued

```
Val Ala Gly Gly Ser Gly Ser Gly Asn Cys Gly Glu Val Ala Ser Gly
            340                 345                 350

Leu Thr Leu Gly Pro Pro Gly Thr Ala His Leu Tyr Gln Gly Leu Gly
            355                 360                 365

Pro Val Val Leu Ser Gly Pro Val Ser His Leu Met Pro Phe Pro Gly
            370                 375                 380

Pro Leu Leu Gly Ser Pro Thr Gly Ser Phe Pro Thr Gly Pro Met Pro
385                 390                 395                 400

Pro Thr Thr Ser Thr Thr Val Val Ala Pro Leu Ser Ser
            405                 410

<210> SEQ ID NO 42
<211> LENGTH: 452
<212> TYPE: PRT
<213> ORGANISM: Homo sapiens

<400> SEQUENCE: 42

Met Asp Gly Thr Ile Lys Glu Ala Leu Ser Val Val Ser Asp Asp Gln
1               5                   10                  15

Ser Leu Phe Asp Ser Ala Tyr Gly Ala Ala His Leu Pro Lys Ala
            20                  25                  30

Asp Met Thr Ala Ser Gly Ser Pro Asp Tyr Gly Gln Pro His Lys Ile
            35                  40                  45

Asn Pro Leu Pro Pro Gln Gln Glu Trp Ile Asn Gln Pro Val Arg Val
            50                  55                  60

Asn Val Lys Arg Glu Tyr Asp His Met Asn Gly Ser Arg Glu Ser Pro
65                  70                  75                  80

Val Asp Cys Ser Val Ser Lys Cys Ser Lys Leu Val Gly Gly Gly Glu
            85                  90                  95

Ser Asn Pro Met Asn Tyr Asn Ser Tyr Met Asp Glu Lys Asn Gly Pro
            100                 105                 110

Pro Pro Pro Asn Met Thr Thr Asn Glu Arg Arg Val Ile Val Pro Ala
            115                 120                 125

Asp Pro Thr Leu Trp Thr Gln Glu His Val Arg Gln Trp Leu Glu Trp
            130                 135                 140

Ala Ile Lys Glu Tyr Ser Leu Met Glu Ile Asp Thr Ser Phe Phe Gln
145                 150                 155                 160

Asn Met Asp Gly Lys Glu Leu Cys Lys Met Asn Lys Glu Asp Phe Leu
            165                 170                 175

Arg Ala Thr Thr Leu Tyr Asn Thr Glu Val Leu Leu Ser His Leu Ser
            180                 185                 190

Tyr Leu Arg Glu Ser Ser Leu Leu Ala Tyr Asn Thr Thr Ser His Thr
            195                 200                 205

Asp Gln Ser Ser Arg Leu Ser Val Lys Glu Asp Pro Ser Tyr Asp Ser
            210                 215                 220

Val Arg Arg Gly Ala Trp Gly Asn Asn Met Asn Ser Gly Leu Asn Lys
225                 230                 235                 240

Ser Pro Pro Leu Gly Gly Ala Gln Thr Ile Ser Lys Asn Thr Glu Gln
            245                 250                 255

Arg Pro Gln Pro Asp Pro Tyr Gln Ile Leu Gly Pro Thr Ser Ser Arg
            260                 265                 270

Leu Ala Asn Pro Gly Ser Gly Gln Ile Gln Leu Trp Gln Phe Leu Leu
            275                 280                 285

Glu Leu Leu Ser Asp Ser Ala Asn Ala Ser Cys Ile Thr Trp Glu Gly
```

```
            290                 295                 300
Thr Asn Gly Glu Phe Lys Met Thr Asp Pro Asp Glu Val Ala Arg Arg
305                 310                 315                 320

Trp Gly Glu Arg Lys Ser Lys Pro Asn Met Asn Tyr Asp Lys Leu Ser
            325                 330                 335

Arg Ala Leu Arg Tyr Tyr Tyr Asp Lys Asn Ile Met Thr Lys Val His
                340                 345                 350

Gly Lys Arg Tyr Ala Tyr Lys Phe Asp Phe His Gly Ile Ala Gln Ala
            355                 360                 365

Leu Gln Pro His Pro Thr Glu Ser Ser Met Tyr Lys Tyr Pro Ser Asp
        370                 375                 380

Ile Ser Tyr Met Pro Ser Tyr His Ala His Gln Gln Lys Val Asn Phe
385                 390                 395                 400

Val Pro Pro His Pro Ser Ser Met Pro Val Thr Ser Ser Ser Phe Phe
                405                 410                 415

Gly Ala Ala Ser Gln Tyr Trp Thr Ser Pro Thr Gly Gly Ile Tyr Pro
            420                 425                 430

Asn Pro Asn Val Pro Arg His Pro Asn Thr His Val Pro Ser His Leu
            435                 440                 445

Gly Ser Tyr Tyr
        450
```

<210> SEQ ID NO 43
<211> LENGTH: 362
<212> TYPE: PRT
<213> ORGANISM: Homo sapiens

<400> SEQUENCE: 43

```
Met Ala Thr Ala Glu Thr Ala Leu Pro Ser Ile Ser Thr Leu Thr Ala
1               5                   10                  15

Leu Gly Pro Phe Pro Asp Thr Gln Asp Asp Phe Leu Lys Trp Trp Arg
            20                  25                  30

Ser Glu Glu Ala Gln Asp Met Gly Pro Gly Pro Pro Asp Pro Thr Glu
        35                  40                  45

Pro Pro Leu His Val Lys Ser Glu Asp Gln Pro Gly Glu Glu Glu Asp
    50                  55                  60

Asp Glu Arg Gly Ala Asp Ala Thr Trp Asp Leu Asp Leu Leu Leu Thr
65                  70                  75                  80

Asn Phe Ser Gly Pro Glu Pro Gly Gly Ala Pro Gln Thr Cys Ala Leu
                85                  90                  95

Ala Pro Ser Glu Ala Ser Gly Ala Gln Tyr Pro Pro Pro Pro Glu Thr
            100                 105                 110

Leu Gly Ala Tyr Ala Gly Gly Pro Gly Leu Val Ala Gly Leu Leu Gly
        115                 120                 125

Ser Glu Asp His Ser Gly Trp Val Arg Pro Ala Leu Arg Ala Arg Ala
    130                 135                 140

Pro Asp Ala Phe Val Gly Pro Ala Leu Ala Pro Ala Pro Ala Pro Glu
145                 150                 155                 160

Pro Lys Ala Leu Ala Leu Gln Pro Val Tyr Pro Gly Pro Gly Ala Gly
                165                 170                 175

Ser Ser Gly Gly Tyr Phe Pro Arg Thr Gly Leu Ser Val Pro Ala Ala
            180                 185                 190

Ser Gly Ala Pro Tyr Gly Leu Leu Ser Gly Tyr Pro Ala Met Tyr Pro
        195                 200                 205
```

```
Ala Pro Gln Tyr Gln Gly His Phe Gln Leu Phe Arg Gly Leu Gln Gly
    210                 215                 220

Pro Ala Pro Gly Pro Ala Thr Ser Pro Ser Phe Leu Ser Cys Leu Gly
225                 230                 235                 240

Pro Gly Thr Val Gly Thr Gly Leu Gly Gly Thr Ala Glu Asp Pro Gly
                245                 250                 255

Val Ile Ala Glu Thr Ala Pro Ser Lys Arg Gly Arg Arg Ser Trp Ala
            260                 265                 270

Arg Lys Arg Gln Ala Ala His Thr Cys Ala His Pro Gly Cys Gly Lys
        275                 280                 285

Ser Tyr Thr Lys Ser Ser His Leu Lys Ala His Leu Arg Thr His Thr
    290                 295                 300

Gly Glu Lys Pro Tyr Ala Cys Thr Trp Glu Gly Cys Gly Trp Arg Phe
305                 310                 315                 320

Ala Arg Ser Asp Glu Leu Thr Arg His Tyr Arg Lys His Thr Gly Gln
                325                 330                 335

Arg Pro Phe Arg Cys Gln Leu Cys Pro Arg Ala Phe Ser Arg Ser Asp
            340                 345                 350

His Leu Ala Leu His Met Lys Arg His Leu
        355                 360

<210> SEQ ID NO 44
<211> LENGTH: 319
<212> TYPE: PRT
<213> ORGANISM: Homo sapiens

<400> SEQUENCE: 44

Met Glu Leu Leu Ser Pro Pro Leu Arg Asp Val Asp Leu Thr Ala Pro
1               5                   10                  15

Asp Gly Ser Leu Cys Ser Phe Ala Thr Thr Asp Asp Phe Tyr Asp Asp
                20                  25                  30

Pro Cys Phe Asp Ser Pro Asp Leu Arg Phe Phe Glu Asp Leu Asp Pro
            35                  40                  45

Arg Leu Met His Val Gly Ala Leu Leu Lys Pro Glu Glu His Ser His
50                  55                  60

Phe Pro Ala Ala Val His Pro Ala Pro Gly Ala Arg Glu Asp Glu His
65                  70                  75                  80

Val Arg Ala Pro Ser Gly His His Gln Ala Gly Arg Cys Leu Leu Trp
                85                  90                  95

Ala Cys Lys Ala Cys Lys Arg Lys Thr Thr Asn Ala Asp Arg Arg Lys
            100                 105                 110

Ala Ala Thr Met Arg Glu Arg Arg Arg Leu Ser Lys Val Asn Glu Ala
        115                 120                 125

Phe Glu Thr Leu Lys Arg Cys Thr Ser Ser Asn Pro Asn Gln Arg Leu
130                 135                 140

Pro Lys Val Glu Ile Leu Arg Asn Ala Ile Arg Tyr Ile Glu Gly Leu
145                 150                 155                 160

Gln Ala Leu Leu Arg Asp Gln Asp Ala Ala Pro Pro Gly Ala Ala Ala
                165                 170                 175

Phe Tyr Ala Pro Gly Pro Leu Pro Pro Gly Arg Gly Gly Glu His Tyr
            180                 185                 190

Ser Gly Asp Ser Asp Ala Ser Ser Pro Arg Ser Asn Cys Ser Asp Gly
        195                 200                 205

Met Met Asp Tyr Ser Gly Pro Pro Ser Gly Ala Arg Arg Arg Asn Cys
210                 215                 220
```

```
Tyr Glu Gly Ala Tyr Tyr Asn Glu Ala Pro Ser Glu Pro Arg Pro Gly
225                 230                 235                 240

Lys Ser Ala Ala Val Ser Ser Leu Asp Tyr Leu Ser Ser Ile Val Glu
            245                 250                 255

Arg Ile Ser Thr Glu Ser Pro Ala Ala Pro Ala Leu Leu Leu Ala Asp
            260                 265                 270

Val Pro Ser Glu Ser Pro Arg Arg Gln Glu Ala Ala Pro Ser
        275                 280                 285

Glu Gly Glu Ser Ser Gly Asp Pro Thr Gln Ser Pro Asp Ala Ala Pro
        290                 295                 300

Gln Cys Pro Ala Gly Ala Asn Pro Asn Pro Ile Tyr Gln Val Leu
305                 310                 315

<210> SEQ ID NO 45
<211> LENGTH: 525
<212> TYPE: PRT
<213> ORGANISM: Homo sapiens

<400> SEQUENCE: 45

Met His Arg Ala Pro Ser Pro Thr Ala Glu Gln Pro Pro Gly Gly Gly
1               5                   10                  15

Asp Ser Ala Arg Arg Thr Leu Gln Pro Arg Leu Lys Pro Ser Ala Arg
            20                  25                  30

Ala Met Ala Leu Pro Arg Thr Leu Gly Glu Leu Gln Leu Tyr Arg Val
        35                  40                  45

Leu Gln Arg Ala Asn Leu Leu Ser Tyr Tyr Glu Thr Phe Ile Gln Gln
50                  55                  60

Gly Gly Asp Asp Val Gln Gln Leu Cys Glu Ala Gly Glu Glu Glu Phe
65                  70                  75                  80

Leu Glu Ile Met Ala Leu Val Gly Met Ala Thr Lys Pro Leu His Val
                85                  90                  95

Arg Arg Leu Gln Lys Ala Leu Arg Glu Trp Ala Thr Asn Pro Gly Leu
            100                 105                 110

Phe Ser Gln Pro Val Pro Ala Val Pro Val Ser Ser Ile Pro Leu Phe
        115                 120                 125

Lys Ile Ser Glu Thr Ala Gly Thr Arg Lys Gly Ser Met Ser Asn Gly
130                 135                 140

His Gly Ser Pro Gly Glu Lys Ala Gly Ser Ala Arg Ser Phe Ser Pro
145                 150                 155                 160

Lys Ser Pro Leu Glu Leu Gly Glu Lys Leu Ser Pro Leu Pro Gly Gly
                165                 170                 175

Pro Gly Ala Gly Asp Pro Arg Ile Trp Pro Gly Arg Ser Thr Pro Glu
            180                 185                 190

Ser Asp Val Gly Ala Gly Glu Glu Glu Ala Gly Ser Pro Pro Phe
        195                 200                 205

Ser Pro Pro Ala Gly Gly Val Pro Glu Gly Thr Gly Ala Gly Gly
        210                 215                 220

Leu Ala Ala Gly Gly Thr Gly Gly Pro Asp Arg Leu Glu Pro Glu
225                 230                 235                 240

Met Val Arg Met Val Val Glu Ser Val Glu Arg Ile Phe Arg Ser Phe
                245                 250                 255

Pro Arg Gly Asp Ala Gly Glu Val Thr Ser Leu Leu Lys Leu Asn Lys
            260                 265                 270

Lys Leu Ala Arg Ser Val Gly His Ile Phe Glu Met Asp Asp Asn Asp
```

```
                275                 280                 285
Ser Gln Lys Glu Glu Ile Arg Lys Tyr Ser Ile Ile Tyr Gly Arg
    290                 295                 300

Phe Asp Ser Lys Arg Arg Glu Gly Lys Gln Leu Ser Leu His Glu Leu
305                 310                 315                 320

Thr Ile Asn Glu Ala Ala Gln Phe Cys Met Arg Asp Asn Thr Leu
                325                 330                 335

Leu Leu Arg Arg Val Glu Leu Phe Ser Leu Ser Arg Gln Val Ala Arg
                340                 345                 350

Glu Ser Thr Tyr Leu Ser Ser Leu Lys Gly Ser Arg Leu His Pro Glu
                355                 360                 365

Glu Leu Gly Gly Pro Pro Leu Lys Lys Leu Lys Gln Glu Val Gly Glu
    370                 375                 380

Gln Ser His Pro Glu Ile Gln Gln Pro Pro Gly Pro Glu Ser Tyr
385                 390                 395                 400

Val Pro Pro Tyr Arg Pro Ser Leu Glu Glu Asp Ser Ala Ser Leu Ser
                405                 410                 415

Gly Glu Ser Leu Asp Gly His Leu Gln Ala Val Gly Ser Cys Pro Arg
                420                 425                 430

Leu Thr Pro Pro Pro Ala Asp Leu Pro Leu Ala Leu Pro Ala His Gly
                435                 440                 445

Leu Trp Ser Arg His Ile Leu Gln Gln Thr Leu Met Asp Glu Gly Leu
    450                 455                 460

Arg Leu Ala Arg Leu Val Ser His Asp Arg Val Gly Arg Leu Ser Pro
465                 470                 475                 480

Cys Val Pro Ala Lys Pro Pro Leu Ala Glu Phe Glu Glu Gly Leu Leu
                485                 490                 495

Asp Arg Cys Pro Ala Pro Gly Pro His Pro Ala Leu Val Glu Gly Arg
                500                 505                 510

Arg Ser Ser Val Lys Val Glu Ala Glu Ala Ser Arg Gln
                515                 520                 525

<210> SEQ ID NO 46
<211> LENGTH: 543
<212> TYPE: PRT
<213> ORGANISM: Homo sapiens

<400> SEQUENCE: 46

Met Ala Ala Ala Lys Ala Glu Met Gln Leu Met Ser Pro Leu Gln Ile
1               5                   10                  15

Ser Asp Pro Phe Gly Ser Phe Pro His Ser Pro Thr Met Asp Asn Tyr
                20                  25                  30

Pro Lys Leu Glu Glu Met Met Leu Leu Ser Asn Gly Ala Pro Gln Phe
            35                  40                  45

Leu Gly Ala Ala Gly Ala Pro Glu Gly Ser Gly Ser Asn Ser Ser Ser
    50                  55                  60

Ser Ser Ser Gly Gly Gly Gly Gly Gly Gly Ser Asn Ser Ser
65                  70                  75                  80

Ser Ser Ser Ser Thr Phe Asn Pro Gln Ala Asp Thr Gly Glu Gln Pro
                85                  90                  95

Tyr Glu His Leu Thr Ala Glu Ser Phe Pro Asp Ile Ser Leu Asn Asn
                100                 105                 110

Glu Lys Val Leu Val Glu Thr Ser Tyr Pro Ser Gln Thr Thr Arg Leu
            115                 120                 125
```

```
Pro Pro Ile Thr Tyr Thr Gly Arg Phe Ser Leu Glu Pro Ala Pro Asn
    130                 135                 140

Ser Gly Asn Thr Leu Trp Pro Glu Pro Leu Phe Ser Leu Val Ser Gly
145                 150                 155                 160

Leu Val Ser Met Thr Asn Pro Pro Ala Ser Ser Ser Ala Pro Ser
                165                 170                 175

Pro Ala Ala Ser Ser Ala Ser Ala Ser Gln Ser Pro Pro Leu Ser Cys
                180                 185                 190

Ala Val Pro Ser Asn Asp Ser Pro Ile Tyr Ser Ala Ala Pro Thr
                195                 200                 205

Phe Pro Thr Pro Asn Thr Asp Ile Phe Pro Glu Pro Gln Ser Gln Ala
    210                 215                 220

Phe Pro Gly Ser Ala Gly Thr Ala Leu Gln Tyr Pro Pro Ala Tyr
225                 230                 235                 240

Pro Ala Ala Lys Gly Gly Phe Gln Val Pro Met Ile Pro Asp Tyr Leu
                245                 250                 255

Phe Pro Gln Gln Gln Gly Asp Leu Gly Leu Gly Thr Pro Asp Gln Lys
                260                 265                 270

Pro Phe Gln Gly Leu Glu Ser Arg Thr Gln Gln Pro Ser Leu Thr Pro
    275                 280                 285

Leu Ser Thr Ile Lys Ala Phe Ala Thr Gln Ser Gly Ser Gln Asp Leu
    290                 295                 300

Lys Ala Leu Asn Thr Ser Tyr Gln Ser Gln Leu Ile Lys Pro Ser Arg
305                 310                 315                 320

Met Arg Lys Tyr Pro Asn Arg Pro Ser Lys Thr Pro Pro His Glu Arg
                325                 330                 335

Pro Tyr Ala Cys Pro Val Glu Ser Cys Asp Arg Arg Phe Ser Arg Ser
                340                 345                 350

Asp Glu Leu Thr Arg His Ile Arg Ile His Thr Gly Gln Lys Pro Phe
                355                 360                 365

Gln Cys Arg Ile Cys Met Arg Asn Phe Ser Arg Ser Asp His Leu Thr
    370                 375                 380

Thr His Ile Arg Thr His Thr Gly Glu Lys Pro Phe Ala Cys Asp Ile
385                 390                 395                 400

Cys Gly Arg Lys Phe Ala Arg Ser Asp Glu Arg Lys Arg His Thr Lys
                405                 410                 415

Ile His Leu Arg Gln Lys Asp Lys Lys Ala Asp Lys Ser Val Val Ala
                420                 425                 430

Ser Ser Ala Thr Ser Ser Leu Ser Ser Tyr Pro Ser Pro Val Ala Thr
                435                 440                 445

Ser Tyr Pro Ser Pro Val Thr Thr Ser Tyr Pro Ser Pro Ala Thr Thr
    450                 455                 460

Ser Tyr Pro Ser Pro Val Pro Thr Ser Phe Ser Ser Pro Gly Ser Ser
465                 470                 475                 480

Thr Tyr Pro Ser Pro Val His Ser Gly Phe Pro Ser Pro Ser Val Ala
                485                 490                 495

Thr Thr Tyr Ser Ser Val Pro Pro Ala Phe Pro Ala Gln Val Ser Ser
                500                 505                 510

Phe Pro Ser Ser Ala Val Thr Asn Ser Phe Ser Ala Ser Thr Gly Leu
    515                 520                 525

Ser Asp Met Thr Ala Thr Phe Ser Pro Arg Thr Ile Glu Ile Cys
530                 535                 540
```

<210> SEQ ID NO 47
<211> LENGTH: 422
<212> TYPE: PRT
<213> ORGANISM: Homo sapiens

<400> SEQUENCE: 47

Met Pro Arg Ser Phe Leu Val Lys Ser Lys Ala His Ser Tyr His
1               5                   10                  15

Gln Pro Arg Ser Pro Gly Pro Asp Tyr Ser Leu Arg Leu Glu Asn Val
            20                  25                  30

Pro Ala Pro Ser Arg Ala Asp Ser Thr Ser Asn Ala Gly Gly Ala Lys
        35                  40                  45

Ala Glu Pro Arg Asp Arg Leu Ser Pro Glu Ser Gln Leu Thr Glu Ala
    50                  55                  60

Pro Asp Arg Ala Ser Ala Ser Pro Asp Ser Cys Glu Gly Ser Val Cys
65                  70                  75                  80

Glu Arg Ser Ser Glu Phe Glu Asp Phe Trp Arg Pro Ser Pro Ser
                85                  90                  95

Ala Ser Pro Ala Ser Glu Lys Ser Met Cys Pro Ser Leu Asp Glu Ala
            100                 105                 110

Gln Pro Phe Pro Leu Pro Phe Lys Pro Tyr Ser Trp Ser Gly Leu Ala
        115                 120                 125

Gly Ser Asp Leu Arg His Leu Val Gln Ser Tyr Arg Pro Cys Gly Ala
    130                 135                 140

Leu Glu Arg Gly Ala Gly Leu Gly Leu Phe Cys Glu Pro Ala Pro Glu
145                 150                 155                 160

Pro Gly His Pro Ala Ala Leu Tyr Gly Pro Lys Arg Ala Ala Gly Gly
                165                 170                 175

Ala Gly Ala Gly Ala Pro Gly Ser Cys Ser Ala Gly Ala Gly Ala Thr
            180                 185                 190

Ala Gly Pro Gly Leu Gly Leu Tyr Gly Asp Phe Gly Ser Ala Ala Ala
        195                 200                 205

Gly Leu Tyr Glu Arg Pro Thr Ala Ala Ala Gly Leu Leu Tyr Pro Glu
    210                 215                 220

Arg Gly His Gly Leu His Ala Asp Lys Gly Ala Gly Val Lys Val Glu
225                 230                 235                 240

Ser Glu Leu Leu Cys Thr Arg Leu Leu Leu Gly Gly Gly Ser Tyr Lys
                245                 250                 255

Cys Ile Lys Cys Ser Lys Val Phe Ser Thr Pro His Gly Leu Glu Val
            260                 265                 270

His Val Arg Arg Ser His Ser Gly Thr Arg Pro Phe Ala Cys Glu Met
        275                 280                 285

Cys Gly Lys Thr Phe Gly His Ala Val Ser Leu Glu Gln His Lys Ala
    290                 295                 300

Val His Ser Gln Glu Arg Ser Phe Asp Cys Lys Ile Cys Gly Lys Ser
305                 310                 315                 320

Phe Lys Arg Ser Ser Thr Leu Ser Thr His Leu Leu Ile His Ser Asp
                325                 330                 335

Thr Arg Pro Tyr Pro Cys Gln Tyr Cys Gly Lys Arg Phe His Gln Lys
            340                 345                 350

Ser Asp Met Lys Lys His Thr Phe Ile His Thr Gly Glu Lys Pro His
        355                 360                 365

Lys Cys Gln Val Cys Gly Lys Ala Phe Ser Gln Ser Ser Asn Leu Ile
    370                 375                 380

Thr His Ser Arg Lys His Thr Gly Phe Lys Pro Phe Gly Cys Asp Leu
385                 390                 395                 400

Cys Gly Lys Gly Phe Gln Arg Lys Val Asp Leu Arg Arg His Arg Glu
            405                 410                 415

Thr Gln His Gly Leu Lys
        420

<210> SEQ ID NO 48
<211> LENGTH: 391
<212> TYPE: PRT
<213> ORGANISM: Homo sapiens

<400> SEQUENCE: 48

Met Asp Leu Glu Lys Asn Tyr Pro Thr Pro Arg Thr Ser Arg Thr Gly
1               5                   10                  15

His Gly Gly Val Asn Gln Leu Gly Gly Val Phe Val Asn Gly Arg Pro
            20                  25                  30

Leu Pro Asp Val Val Arg Gln Arg Ile Val Glu Leu Ala His Gln Gly
            35                  40                  45

Val Arg Pro Cys Asp Ile Ser Arg Gln Leu Arg Val Ser His Gly Cys
50                  55                  60

Val Ser Lys Ile Leu Gly Arg Tyr Tyr Glu Thr Gly Ser Ile Lys Pro
65                  70                  75                  80

Gly Val Ile Gly Gly Ser Lys Pro Lys Val Ala Thr Pro Lys Val Val
                85                  90                  95

Glu Lys Ile Ala Glu Tyr Lys Arg Gln Asn Pro Thr Met Phe Ala Trp
            100                 105                 110

Glu Ile Arg Asp Arg Leu Leu Ala Glu Arg Val Cys Asp Asn Asp Thr
        115                 120                 125

Val Pro Ser Val Ser Ser Ile Asn Arg Ile Ile Arg Thr Lys Val Gln
    130                 135                 140

Gln Pro Pro Asn Gln Pro Val Pro Ala Ser Ser His Ser Ile Val Ser
145                 150                 155                 160

Thr Gly Ser Val Thr Gln Val Ser Ser Val Ser Thr Asp Ser Ala Gly
                165                 170                 175

Ser Ser Tyr Ser Ile Ser Gly Ile Leu Gly Ile Thr Ser Pro Ser Ala
            180                 185                 190

Asp Thr Asn Lys Arg Lys Arg Asp Glu Gly Ile Gln Glu Ser Pro Val
        195                 200                 205

Pro Asn Gly His Ser Leu Pro Gly Arg Asp Phe Leu Arg Lys Gln Met
    210                 215                 220

Arg Gly Asp Leu Phe Thr Gln Gln Gln Leu Glu Val Leu Asp Arg Val
225                 230                 235                 240

Phe Glu Arg Gln His Tyr Ser Asp Ile Phe Thr Thr Thr Glu Pro Ile
                245                 250                 255

Lys Pro Glu Gln Thr Thr Glu Tyr Ser Ala Met Ala Ser Leu Ala Gly
            260                 265                 270

Gly Leu Asp Asp Met Lys Ala Asn Leu Ala Ser Pro Thr Pro Ala Asp
        275                 280                 285

Ile Gly Ser Ser Val Pro Gly Pro Gln Ser Tyr Pro Ile Val Thr Gly
    290                 295                 300

Arg Asp Leu Ala Ser Thr Thr Leu Pro Gly Tyr Pro Pro His Val Pro
305                 310                 315                 320

Pro Ala Gly Gln Gly Ser Tyr Ser Ala Pro Thr Leu Thr Gly Met Val
                325                 330                 335

```
Pro Gly Ser Glu Phe Ser Gly Ser Pro Tyr Ser His Pro Gln Tyr Ser
                340                 345                 350

Ser Tyr Asn Asp Ser Trp Arg Phe Pro Asn Pro Gly Leu Leu Gly Ser
            355                 360                 365

Pro Tyr Tyr Tyr Ser Ala Ala Arg Gly Ala Ala Pro Pro Ala Ala
370                 375                 380

Ala Thr Ala Tyr Asp Arg His
385                 390

<210> SEQ ID NO 49
<211> LENGTH: 535
<212> TYPE: PRT
<213> ORGANISM: Homo sapiens

<400> SEQUENCE: 49

Met Gly Ile Val Glu Pro Gly Cys Gly Asp Met Leu Thr Gly Thr Glu
1               5                   10                  15

Pro Met Pro Gly Ser Asp Glu Gly Arg Ala Pro Gly Ala Asp Pro Gln
            20                  25                  30

His Arg Tyr Phe Tyr Pro Glu Pro Gly Ala Gln Asp Ala Asp Glu Arg
        35                  40                  45

Arg Gly Gly Gly Ser Leu Gly Ser Pro Tyr Pro Gly Gly Ala Leu Val
    50                  55                  60

Pro Ala Pro Pro Ser Arg Phe Leu Gly Ala Tyr Ala Tyr Pro Pro Arg
65                  70                  75                  80

Pro Gln Ala Ala Gly Phe Pro Gly Ala Gly Glu Ser Phe Pro Pro Pro
                85                  90                  95

Ala Asp Ala Glu Gly Tyr Gln Pro Gly Glu Gly Tyr Ala Ala Pro Asp
            100                 105                 110

Pro Arg Ala Gly Leu Tyr Pro Gly Pro Arg Glu Asp Tyr Ala Leu Pro
        115                 120                 125

Ala Gly Leu Glu Val Ser Gly Lys Leu Arg Val Ala Leu Asn Asn His
    130                 135                 140

Leu Leu Trp Ser Lys Phe Asn Gln His Gln Thr Glu Met Ile Ile Thr
145                 150                 155                 160

Lys Gln Gly Arg Arg Met Phe Pro Phe Leu Ser Phe Thr Val Ala Gly
                165                 170                 175

Leu Glu Pro Thr Ser His Tyr Arg Met Phe Val Asp Val Val Leu Val
            180                 185                 190

Asp Gln His His Trp Arg Tyr Gln Ser Gly Lys Trp Val Gln Cys Gly
        195                 200                 205

Lys Ala Glu Gly Ser Met Pro Gly Asn Arg Leu Tyr Val His Pro Asp
    210                 215                 220

Ser Pro Asn Thr Gly Ala His Trp Met Arg Gln Glu Val Ser Phe Gly
225                 230                 235                 240

Lys Leu Lys Leu Thr Asn Asn Lys Gly Ala Ser Asn Asn Val Thr Gln
                245                 250                 255

Met Ile Val Leu Gln Ser Leu His Lys Tyr Gln Pro Arg Leu His Ile
            260                 265                 270

Val Glu Val Asn Asp Gly Glu Pro Glu Ala Ala Cys Asn Ala Ser Asn
        275                 280                 285

Thr His Ile Phe Thr Phe Gln Glu Thr Gln Phe Ile Ala Val Thr Ala
    290                 295                 300

Tyr Gln Asn Ala Glu Ile Thr Gln Leu Lys Ile Asp Asn Asn Pro Phe
```

```
              305                 310                 315                 320
Ala Lys Gly Phe Arg Glu Asn Phe Glu Ser Met Tyr Thr Ser Val Asp
                    325                 330                 335

Thr Ser Ile Pro Ser Pro Pro Gly Pro Asn Cys Gln Phe Leu Gly Gly
            340                 345                 350

Asp His Tyr Ser Pro Leu Leu Pro Asn Gln Tyr Pro Val Pro Ser Arg
                355                 360                 365

Phe Tyr Pro Asp Leu Pro Gly Gln Ala Lys Asp Val Pro Gln Ala
    370                 375                 380

Tyr Trp Leu Gly Ala Pro Arg Asp His Ser Tyr Glu Ala Glu Phe Arg
385                 390                 395                 400

Ala Val Ser Met Lys Pro Ala Phe Leu Pro Ser Ala Pro Gly Pro Thr
                405                 410                 415

Met Ser Tyr Tyr Arg Gly Gln Glu Val Leu Ala Pro Gly Ala Gly Trp
            420                 425                 430

Pro Val Ala Pro Gln Tyr Pro Pro Lys Met Gly Pro Ala Ser Trp Phe
                435                 440                 445

Arg Pro Met Arg Thr Leu Pro Met Glu Pro Gly Pro Gly Gly Ser Glu
    450                 455                 460

Gly Arg Gly Pro Glu Asp Gln Gly Pro Pro Leu Val Trp Thr Glu Ile
465                 470                 475                 480

Ala Pro Ile Arg Pro Glu Ser Ser Asp Ser Gly Leu Gly Glu Gly Asp
                485                 490                 495

Ser Lys Arg Arg Arg Val Ser Pro Tyr Pro Ser Ser Gly Asp Ser Ser
                500                 505                 510

Ser Pro Ala Gly Ala Pro Ser Pro Phe Asp Lys Glu Ala Glu Gly Gln
            515                 520                 525

Phe Tyr Asn Tyr Phe Pro Asn
        530                 535

<210> SEQ ID NO 50
<211> LENGTH: 444
<212> TYPE: PRT
<213> ORGANISM: Homo sapiens

<400> SEQUENCE: 50

Met Glu Val Thr Ala Asp Gln Pro Arg Trp Val Ser His His Pro
1               5                   10                  15

Ala Val Leu Asn Gly Gln His Pro Asp Thr His His Pro Gly Leu Ser
                20                  25                  30

His Ser Tyr Met Asp Ala Ala Gln Tyr Pro Leu Pro Glu Glu Val Asp
            35                  40                  45

Val Leu Phe Asn Ile Asp Gly Gln Gly Asn His Val Pro Pro Tyr Tyr
        50                  55                  60

Gly Asn Ser Val Arg Ala Thr Val Gln Arg Tyr Pro Pro Thr His His
65                  70                  75                  80

Gly Ser Gln Val Cys Arg Pro Pro Leu Leu His Gly Ser Leu Pro Trp
                85                  90                  95

Leu Asp Gly Gly Lys Ala Leu Gly Ser His His Thr Ala Ser Pro Trp
                100                 105                 110

Asn Leu Ser Pro Phe Ser Lys Thr Ser Ile His His Gly Ser Pro Gly
            115                 120                 125

Pro Leu Ser Val Tyr Pro Pro Ala Ser Ser Ser Leu Ser Gly Gly
        130                 135                 140
```

```
His Ala Ser Pro His Leu Phe Thr Phe Pro Thr Pro Pro Lys Asp
145                 150                 155                 160

Val Ser Pro Asp Pro Ser Leu Ser Thr Pro Gly Ser Ala Gly Ser Ala
                165                 170                 175

Arg Gln Asp Glu Lys Glu Cys Leu Lys Tyr Gln Val Pro Leu Pro Asp
            180                 185                 190

Ser Met Lys Leu Glu Ser Ser His Ser Arg Gly Ser Met Thr Ala Leu
        195                 200                 205

Gly Gly Ala Ser Ser Ser Thr His His Pro Ile Thr Thr Tyr Pro Pro
    210                 215                 220

Tyr Val Pro Glu Tyr Ser Ser Gly Leu Phe Pro Pro Ser Ser Leu Leu
225                 230                 235                 240

Gly Gly Ser Pro Thr Gly Phe Gly Cys Lys Ser Arg Pro Lys Ala Arg
                245                 250                 255

Ser Ser Thr Glu Gly Arg Glu Cys Val Asn Cys Gly Ala Thr Ser Thr
            260                 265                 270

Pro Leu Trp Arg Arg Asp Gly Thr Gly His Tyr Leu Cys Asn Ala Cys
        275                 280                 285

Gly Leu Tyr His Lys Met Asn Gly Gln Asn Arg Pro Leu Ile Lys Pro
    290                 295                 300

Lys Arg Arg Leu Ser Ala Ala Arg Arg Ala Gly Thr Ser Cys Ala Asn
305                 310                 315                 320

Cys Gln Thr Thr Thr Thr Thr Leu Trp Arg Arg Asn Ala Asn Gly Asp
                325                 330                 335

Pro Val Cys Asn Ala Cys Gly Leu Tyr Tyr Lys Leu His Asn Ile Asn
            340                 345                 350

Arg Pro Leu Thr Met Lys Lys Glu Gly Ile Gln Thr Arg Asn Arg Lys
        355                 360                 365

Met Ser Ser Lys Ser Lys Lys Cys Lys Lys Val His Asp Ser Leu Glu
    370                 375                 380

Asp Phe Pro Lys Asn Ser Ser Phe Asn Pro Ala Ala Leu Ser Arg His
385                 390                 395                 400

Met Ser Ser Leu Ser His Ile Ser Pro Phe Ser His Ser Ser His Met
                405                 410                 415

Leu Thr Thr Pro Thr Pro Met His Pro Pro Ser Ser Leu Ser Phe Gly
            420                 425                 430

Pro His His Pro Ser Ser Met Val Thr Ala Met Gly
        435                 440

<210> SEQ ID NO 51
<211> LENGTH: 431
<212> TYPE: PRT
<213> ORGANISM: Homo sapiens

<400> SEQUENCE: 51

Met Pro Asn Pro Arg Pro Gly Lys Pro Ser Ala Pro Ser Leu Ala Leu
1               5                   10                  15

Gly Pro Ser Pro Gly Ala Ser Pro Ser Trp Arg Ala Ala Pro Lys Ala
            20                  25                  30

Ser Asp Leu Leu Gly Ala Arg Gly Pro Gly Gly Thr Phe Gln Gly Arg
        35                  40                  45

Asp Leu Arg Gly Gly Ala His Ala Ser Ser Ser Leu Asn Pro Met
    50                  55                  60

Pro Pro Ser Gln Leu Gln Leu Pro Thr Leu Pro Leu Val Met Val Ala
65                  70                  75                  80
```

Pro Ser Gly Ala Arg Leu Gly Pro Leu Pro His Leu Gln Ala Leu Leu
            85                  90                  95

Gln Asp Arg Pro His Phe Met His Gln Leu Ser Thr Val Asp Ala His
            100                 105                 110

Ala Arg Thr Pro Val Leu Gln Val His Pro Leu Glu Ser Pro Ala Met
            115                 120                 125

Ile Ser Leu Thr Pro Pro Thr Thr Ala Thr Gly Val Phe Ser Leu Lys
            130                 135                 140

Ala Arg Pro Gly Leu Pro Pro Gly Ile Asn Val Ala Ser Leu Glu Trp
145                 150                 155                 160

Val Ser Arg Glu Pro Ala Leu Leu Cys Thr Phe Pro Asn Pro Ser Ala
            165                 170                 175

Pro Arg Lys Asp Ser Thr Leu Ser Ala Val Pro Gln Ser Ser Tyr Pro
            180                 185                 190

Leu Leu Ala Asn Gly Val Cys Lys Trp Pro Gly Cys Glu Lys Val Phe
            195                 200                 205

Glu Glu Pro Glu Asp Phe Leu Lys His Cys Gln Ala Asp His Leu Leu
            210                 215                 220

Asp Glu Lys Gly Arg Ala Gln Cys Leu Leu Gln Arg Glu Met Val Gln
225                 230                 235                 240

Ser Leu Glu Gln Gln Leu Val Leu Glu Lys Glu Lys Leu Ser Ala Met
            245                 250                 255

Gln Ala His Leu Ala Gly Lys Met Ala Leu Thr Lys Ala Ser Ser Val
            260                 265                 270

Ala Ser Ser Asp Lys Gly Ser Cys Cys Ile Val Ala Ala Gly Ser Gln
            275                 280                 285

Gly Pro Val Val Pro Ala Trp Ser Gly Pro Arg Glu Ala Pro Asp Ser
290                 295                 300

Leu Phe Ala Val Arg Arg His Leu Trp Gly Ser His Gly Asn Ser Thr
305                 310                 315                 320

Phe Pro Glu Phe Leu His Asn Met Asp Tyr Phe Lys Phe His Asn Met
            325                 330                 335

Arg Pro Pro Phe Thr Tyr Ala Thr Leu Ile Arg Trp Ala Ile Leu Glu
            340                 345                 350

Ala Pro Glu Lys Gln Arg Thr Leu Asn Glu Ile Tyr His Trp Phe Thr
            355                 360                 365

Arg Met Phe Ala Phe Phe Arg Asn His Pro Ala Thr Trp Lys Asn Ala
370                 375                 380

Ile Arg His Asn Leu Ser Leu His Lys Cys Phe Val Arg Val Glu Ser
385                 390                 395                 400

Glu Lys Gly Ala Val Trp Thr Val Asp Glu Leu Glu Phe Arg Lys Lys
            405                 410                 415

Arg Ser Gln Arg Pro Ser Arg Cys Ser Asn Pro Thr Pro Gly Pro
            420                 425                 430

<210> SEQ ID NO 52
<211> LENGTH: 560
<212> TYPE: PRT
<213> ORGANISM: Homo sapiens

<400> SEQUENCE: 52

Met Asp Arg Ala Pro Gln Arg Gln His Arg Ala Ser Arg Glu Leu Leu
1               5                   10                  15

Ala Ala Lys Lys Thr His Thr Ser Gln Ile Glu Val Ile Pro Cys Lys

```
                20                  25                  30
Ile Cys Gly Asp Lys Ser Ser Gly Ile His Tyr Gly Val Ile Thr Cys
             35                  40                  45
Glu Gly Cys Lys Gly Phe Phe Arg Arg Ser Gln Arg Cys Asn Ala Ala
         50                  55                  60
Tyr Ser Cys Thr Arg Gln Gln Asn Cys Pro Ile Asp Arg Thr Ser Arg
65                  70                  75                  80
Asn Arg Cys Gln His Cys Arg Leu Gln Lys Cys Leu Ala Leu Gly Met
                 85                  90                  95
Ser Arg Asp Ala Val Lys Phe Gly Arg Met Ser Lys Lys Gln Arg Asp
            100                 105                 110
Ser Leu His Ala Glu Val Gln Lys Gln Leu Gln Gln Arg Gln Gln Gln
             115                 120                 125
Gln Gln Glu Pro Val Val Lys Thr Pro Pro Ala Gly Ala Gln Gly Ala
        130                 135                 140
Asp Thr Leu Thr Tyr Thr Leu Gly Leu Pro Asp Gly Gln Leu Pro Leu
145                 150                 155                 160
Gly Ser Ser Pro Asp Leu Pro Glu Ala Ser Ala Cys Pro Pro Gly Leu
                165                 170                 175
Leu Lys Ala Ser Gly Ser Gly Pro Ser Tyr Ser Asn Asn Leu Ala Lys
            180                 185                 190
Ala Gly Leu Asn Gly Ala Ser Cys His Leu Glu Tyr Ser Pro Glu Arg
         195                 200                 205
Gly Lys Ala Glu Gly Arg Glu Ser Phe Tyr Ser Thr Gly Ser Gln Leu
       210                 215                 220
Thr Pro Asp Arg Cys Gly Leu Arg Phe Glu Glu His Arg His Pro Gly
225                 230                 235                 240
Leu Gly Glu Leu Gly Gln Gly Pro Asp Ser Tyr Gly Ser Pro Ser Phe
                245                 250                 255
Arg Ser Thr Pro Glu Ala Pro Tyr Ala Ser Leu Thr Glu Ile Glu His
            260                 265                 270
Leu Val Gln Ser Val Cys Lys Ser Tyr Arg Glu Thr Cys Gln Leu Arg
         275                 280                 285
Leu Glu Asp Leu Leu Arg Gln Arg Ser Asn Ile Phe Ser Arg Glu Glu
        290                 295                 300
Val Thr Gly Tyr Gln Arg Lys Ser Met Trp Glu Met Trp Glu Arg Cys
305                 310                 315                 320
Ala His His Leu Thr Glu Ala Ile Gln Tyr Val Val Glu Phe Ala Lys
                325                 330                 335
Arg Leu Ser Gly Phe Met Glu Leu Cys Gln Asn Asp Gln Ile Val Leu
            340                 345                 350
Leu Lys Ala Gly Ala Met Glu Val Val Leu Val Arg Met Cys Arg Ala
         355                 360                 365
Tyr Asn Ala Asp Asn Arg Thr Val Phe Phe Glu Gly Lys Tyr Gly Gly
        370                 375                 380
Met Glu Leu Phe Arg Ala Leu Gly Cys Ser Glu Leu Ile Ser Ser Ile
385                 390                 395                 400
Phe Asp Phe Ser His Ser Leu Ser Ala Leu His Phe Ser Glu Asp Glu
                405                 410                 415
Ile Ala Leu Tyr Thr Ala Leu Val Leu Ile Asn Ala His Arg Pro Gly
            420                 425                 430
Leu Gln Glu Lys Arg Lys Val Glu Gln Leu Gln Tyr Asn Leu Glu Leu
         435                 440                 445
```

```
Ala Phe His His His Leu Cys Lys Thr His Arg Gln Ser Ile Leu Ala
        450                 455                 460

Lys Leu Pro Pro Lys Gly Lys Leu Arg Ser Leu Cys Ser Gln His Val
465                 470                 475                 480

Glu Arg Leu Gln Ile Phe Gln His Leu His Pro Ile Val Val Gln Ala
                485                 490                 495

Ala Phe Pro Pro Leu Tyr Lys Glu Leu Phe Ser Thr Glu Thr Glu Ser
            500                 505                 510

Pro Val Gly Cys Pro Ser Asp Leu Glu Glu Gly Leu Leu Ala Ser Pro
        515                 520                 525

Tyr Gly Leu Leu Ala Thr Ser Leu Asp Pro Val Pro Pro Ser Pro Phe
    530                 535                 540

Ser Phe Pro Met Asn Pro Gly Gly Trp Ser Pro Pro Ala Leu Trp Lys
545                 550                 555                 560

<210> SEQ ID NO 53
<211> LENGTH: 464
<212> TYPE: PRT
<213> ORGANISM: Homo sapiens

<400> SEQUENCE: 53

Met Arg Leu Ser Lys Thr Leu Val Asp Met Asp Met Ala Asp Tyr Ser
1               5                   10                  15

Ala Ala Leu Asp Pro Ala Tyr Thr Thr Leu Glu Phe Glu Asn Val Gln
            20                  25                  30

Val Leu Thr Met Gly Asn Asp Thr Ser Pro Ser Glu Gly Thr Asn Leu
        35                  40                  45

Asn Ala Pro Asn Ser Leu Gly Val Ser Ala Leu Cys Ala Ile Cys Gly
    50                  55                  60

Asp Arg Ala Thr Gly Lys His Tyr Gly Ala Ser Ser Cys Asp Gly Cys
65                  70                  75                  80

Lys Gly Phe Phe Arg Arg Ser Val Arg Lys Asn His Met Tyr Ser Cys
                85                  90                  95

Arg Phe Ser Arg Gln Cys Val Val Asp Lys Asp Lys Arg Asn Gln Cys
            100                 105                 110

Arg Tyr Cys Arg Leu Lys Lys Cys Phe Arg Ala Gly Met Lys Lys Glu
        115                 120                 125

Ala Val Gln Asn Glu Arg Asp Arg Ile Ser Thr Arg Arg Ser Ser Tyr
    130                 135                 140

Glu Asp Ser Ser Leu Pro Ser Ile Asn Ala Leu Leu Gln Ala Glu Val
145                 150                 155                 160

Leu Ser Arg Gln Ile Thr Ser Pro Val Ser Gly Ile Asn Gly Asp Ile
                165                 170                 175

Arg Ala Lys Lys Ile Ala Ser Ile Ala Asp Val Cys Glu Ser Met Lys
            180                 185                 190

Glu Gln Leu Leu Val Leu Val Glu Trp Ala Lys Tyr Ile Pro Ala Phe
        195                 200                 205

Cys Glu Leu Pro Leu Asp Asp Gln Val Ala Leu Leu Arg Ala His Ala
    210                 215                 220

Gly Glu His Leu Leu Leu Gly Ala Thr Lys Arg Ser Met Val Phe Lys
225                 230                 235                 240

Asp Val Leu Leu Leu Gly Asn Asp Tyr Ile Val Pro Arg His Cys Pro
                245                 250                 255

Glu Leu Ala Glu Met Ser Arg Val Ser Ile Arg Ile Leu Asp Glu Leu
```

-continued

```
                260                 265                 270
Val Leu Pro Phe Gln Glu Leu Gln Ile Asp Asp Asn Glu Tyr Ala Tyr
            275                 280                 285
Leu Lys Ala Ile Ile Phe Phe Asp Pro Asp Ala Lys Gly Leu Ser Asp
        290                 295                 300
Pro Gly Lys Ile Lys Arg Leu Arg Ser Gln Val Gln Val Ser Leu Glu
305                 310                 315                 320
Asp Tyr Ile Asn Asp Arg Gln Tyr Asp Ser Arg Gly Arg Phe Gly Glu
                325                 330                 335
Leu Leu Leu Leu Leu Pro Thr Leu Gln Ser Ile Thr Trp Gln Met Ile
            340                 345                 350
Glu Gln Ile Gln Phe Ile Lys Leu Phe Gly Met Ala Lys Ile Asp Asn
        355                 360                 365
Leu Leu Gln Glu Met Leu Leu Gly Gly Ser Pro Ser Asp Ala Pro His
    370                 375                 380
Ala His His Pro Leu His Pro His Leu Met Gln Glu His Met Gly Thr
385                 390                 395                 400
Asn Val Ile Val Ala Asn Thr Met Pro Thr His Leu Ser Asn Gly Gln
                405                 410                 415
Met Ser Thr Pro Glu Thr Pro Gln Pro Ser Pro Pro Gly Gly Ser Gly
            420                 425                 430
Ser Glu Pro Tyr Lys Leu Leu Pro Gly Ala Val Ala Thr Ile Val Lys
        435                 440                 445
Pro Leu Ser Ala Ile Pro Gln Pro Thr Ile Thr Lys Gln Glu Val Ile
    450                 455                 460
```

<210> SEQ ID NO 54
<211> LENGTH: 794
<212> TYPE: PRT
<213> ORGANISM: Homo sapiens

<400> SEQUENCE: 54

```
Met Ala Gly Trp Ile Gln Ala Gln Gln Leu Gln Gly Asp Ala Leu Arg
1               5                   10                  15
Gln Met Gln Val Leu Tyr Gly Gln His Phe Pro Ile Glu Val Arg His
            20                  25                  30
Tyr Leu Ala Gln Trp Ile Glu Ser Gln Pro Trp Asp Ala Ile Asp Leu
        35                  40                  45
Asp Asn Pro Gln Asp Arg Ala Gln Ala Thr Gln Leu Leu Glu Gly Leu
    50                  55                  60
Val Gln Glu Leu Gln Lys Lys Ala Glu His Gln Val Gly Glu Asp Gly
65                  70                  75                  80
Phe Leu Leu Lys Ile Lys Leu Arg His Tyr Ala Thr Gln Leu Gln Lys
                85                  90                  95
Thr Tyr Asp Arg Cys Pro Leu Glu Leu Val Arg Cys Ile Arg His Ile
            100                 105                 110
Leu Tyr Asn Glu Gln Arg Leu Val Arg Glu Ala Asn Asn Cys Ser Ser
        115                 120                 125
Pro Ala Gly Ile Leu Val Asp Ala Met Ser Gln Lys His Leu Gln Ile
    130                 135                 140
Asn Gln Thr Phe Glu Glu Leu Arg Leu Val Thr Gln Asp Thr Glu Asn
145                 150                 155                 160
Glu Leu Lys Lys Leu Gln Gln Thr Gln Glu Tyr Phe Ile Ile Gln Tyr
                165                 170                 175
```

-continued

```
Gln Glu Ser Leu Arg Ile Gln Ala Gln Phe Ala Gln Leu
            180                 185                 190

Ser Pro Gln Glu Arg Leu Ser Arg Glu Thr Ala Leu Gln Gln Lys Gln
        195                 200                 205

Val Ser Leu Glu Ala Trp Leu Gln Arg Glu Ala Gln Thr Leu Gln Gln
210                 215                 220

Tyr Arg Val Glu Leu Ala Glu Lys His Gln Lys Thr Leu Gln Leu Leu
225                 230                 235                 240

Arg Lys Gln Gln Thr Ile Ile Leu Asp Asp Glu Leu Ile Gln Trp Lys
                245                 250                 255

Arg Arg Gln Gln Leu Ala Gly Asn Gly Gly Pro Pro Glu Gly Ser Leu
            260                 265                 270

Asp Val Leu Gln Ser Trp Cys Glu Lys Leu Ala Glu Ile Ile Trp Gln
            275                 280                 285

Asn Arg Gln Gln Ile Arg Arg Ala Glu His Leu Cys Gln Gln Leu Pro
290                 295                 300

Ile Pro Gly Pro Val Glu Glu Met Leu Ala Glu Val Asn Ala Thr Ile
305                 310                 315                 320

Thr Asp Ile Ile Ser Ala Leu Val Thr Ser Thr Phe Ile Ile Glu Lys
                325                 330                 335

Gln Pro Pro Gln Val Leu Lys Thr Gln Thr Lys Phe Ala Ala Thr Val
            340                 345                 350

Arg Leu Leu Val Gly Gly Lys Leu Asn Val His Met Asn Pro Pro Gln
            355                 360                 365

Val Lys Ala Thr Ile Ile Ser Glu Gln Gln Ala Lys Ser Leu Leu Lys
370                 375                 380

Asn Glu Asn Thr Arg Asn Glu Cys Ser Gly Glu Ile Leu Asn Asn Cys
385                 390                 395                 400

Cys Val Met Glu Tyr His Gln Ala Thr Gly Thr Leu Ser Ala His Phe
                405                 410                 415

Arg Asn Met Ser Leu Lys Arg Ile Lys Arg Ala Asp Arg Arg Gly Ala
            420                 425                 430

Glu Ser Val Thr Glu Glu Lys Phe Thr Val Leu Phe Glu Ser Gln Phe
            435                 440                 445

Ser Val Gly Ser Asn Glu Leu Val Phe Gln Val Lys Thr Leu Ser Leu
450                 455                 460

Pro Val Val Val Ile Val His Gly Ser Gln Asp His Asn Ala Thr Ala
465                 470                 475                 480

Thr Val Leu Trp Asp Asn Ala Phe Ala Glu Pro Gly Arg Val Pro Phe
                485                 490                 495

Ala Val Pro Asp Lys Val Leu Trp Pro Gln Leu Cys Glu Ala Leu Asn
            500                 505                 510

Met Lys Phe Lys Ala Glu Val Gln Ser Asn Arg Gly Leu Thr Lys Glu
            515                 520                 525

Asn Leu Val Phe Leu Ala Gln Lys Leu Phe Asn Asn Ser Ser Ser His
530                 535                 540

Leu Glu Asp Tyr Ser Gly Leu Ser Val Ser Trp Ser Gln Phe Asn Arg
545                 550                 555                 560

Glu Asn Leu Pro Gly Trp Asn Tyr Thr Phe Trp Gln Trp Phe Asp Gly
                565                 570                 575

Val Met Glu Val Leu Lys Lys His His Lys Pro His Trp Asn Asp Gly
            580                 585                 590

Ala Ile Leu Gly Phe Val Asn Lys Gln Gln Ala His Asp Leu Leu Ile
```

```
                    595                 600                 605
Asn Lys Pro Asp Gly Thr Phe Leu Leu Arg Phe Ser Asp Ser Glu Ile
610                 615                 620

Gly Gly Ile Thr Ile Ala Trp Lys Phe Asp Ser Pro Glu Arg Asn Leu
625                 630                 635                 640

Trp Asn Leu Lys Pro Phe Thr Arg Asp Phe Ser Ile Arg Ser Leu
                645                 650                 655

Ala Asp Arg Leu Gly Asp Leu Ser Tyr Leu Ile Tyr Val Phe Pro Asp
                660                 665                 670

Arg Pro Lys Asp Glu Val Phe Ser Lys Tyr Tyr Thr Pro Val Leu Ala
                675                 680                 685

Lys Ala Val Asp Gly Tyr Val Lys Pro Gln Ile Lys Gln Val Val Pro
690                 695                 700

Glu Phe Val Asn Ala Ser Ala Asp Ala Gly Ser Ser Ala Thr Tyr
705                 710                 715                 720

Met Asp Gln Ala Pro Ser Pro Ala Val Cys Pro Gln Ala Pro Tyr Asn
                725                 730                 735

Met Tyr Pro Gln Asn Pro Asp His Val Leu Asp Gln Asp Gly Glu Phe
                740                 745                 750

Asp Leu Asp Glu Thr Met Asp Val Ala Arg His Val Glu Glu Leu Leu
                755                 760                 765

Arg Arg Pro Met Asp Ser Leu Asp Ser Arg Leu Ser Pro Pro Ala Gly
770                 775                 780

Leu Phe Thr Ser Ala Arg Gly Ser Leu Ser
785                 790

<210> SEQ ID NO 55
<211> LENGTH: 574
<212> TYPE: PRT
<213> ORGANISM: Homo sapiens

<400> SEQUENCE: 55

Met Trp Thr Phe Leu Gly Ile Ala Thr Phe Thr Tyr Phe Tyr Lys Lys
1               5                   10                  15

Phe Gly Asp Phe Ile Thr Leu Ala Asn Arg Glu Val Leu Leu Cys Val
                20                  25                  30

Leu Val Phe Leu Ser Leu Gly Leu Val Leu Ser Tyr Arg Cys Arg His
            35                  40                  45

Arg Asn Gly Gly Leu Leu Gly Arg Gln Gln Ser Gly Ser Gln Phe Ala
        50                  55                  60

Leu Phe Ser Asp Ile Leu Ser Gly Leu Pro Phe Ile Gly Phe Phe Trp
65                  70                  75                  80

Ala Lys Ser Pro Pro Glu Ser Glu Asn Lys Glu Gln Leu Glu Ala Arg
                85                  90                  95

Arg Arg Arg Lys Gly Thr Asn Ile Ser Glu Thr Ser Leu Ile Gly Thr
            100                 105                 110

Ala Ala Cys Thr Ser Thr Ser Ser Gln Asn Asp Pro Glu Val Ile Ile
        115                 120                 125

Val Gly Ala Gly Val Leu Gly Ser Ala Leu Ala Ala Val Leu Ser Arg
    130                 135                 140

Asp Gly Arg Lys Val Thr Val Ile Glu Arg Asp Leu Lys Glu Pro Asp
145                 150                 155                 160

Arg Ile Val Gly Glu Phe Leu Gln Pro Gly Gly Tyr His Val Leu Lys
                165                 170                 175
```

-continued

Asp Leu Gly Leu Gly Asp Thr Val Glu Gly Leu Asp Ala Gln Val Val
            180                 185                 190

Asn Gly Tyr Met Ile His Asp Gln Glu Ser Lys Ser Glu Val Gln Ile
        195                 200                 205

Pro Tyr Pro Leu Ser Glu Asn Asn Gln Val Gln Ser Gly Arg Ala Phe
210                 215                 220

His His Gly Arg Phe Ile Met Ser Leu Arg Lys Ala Ala Met Ala Glu
225                 230                 235                 240

Pro Asn Ala Lys Phe Ile Glu Gly Val Val Leu Gln Leu Leu Glu Glu
                245                 250                 255

Asp Asp Val Val Met Gly Val Gln Tyr Lys Asp Lys Glu Thr Gly Asp
            260                 265                 270

Ile Lys Glu Leu His Ala Pro Leu Thr Val Val Ala Asp Gly Leu Phe
        275                 280                 285

Ser Lys Phe Arg Lys Ser Leu Val Ser Asn Lys Val Ser Val Ser Ser
290                 295                 300

His Phe Val Gly Phe Leu Met Lys Asn Ala Pro Gln Phe Lys Ala Asn
305                 310                 315                 320

His Ala Glu Leu Ile Leu Ala Asn Pro Ser Pro Val Leu Ile Tyr Gln
                325                 330                 335

Ile Ser Ser Ser Glu Thr Arg Val Leu Val Asp Ile Arg Gly Glu Met
            340                 345                 350

Pro Arg Asn Leu Arg Glu Tyr Met Val Glu Lys Ile Tyr Pro Gln Ile
        355                 360                 365

Pro Asp His Leu Lys Glu Pro Phe Leu Glu Ala Thr Asp Asn Ser His
370                 375                 380

Leu Arg Ser Met Pro Ala Ser Phe Leu Pro Pro Ser Ser Val Lys Lys
385                 390                 395                 400

Arg Gly Val Leu Leu Leu Gly Asp Ala Tyr Asn Met Arg His Pro Leu
                405                 410                 415

Thr Gly Gly Gly Met Thr Val Ala Phe Lys Asp Ile Lys Leu Trp Arg
            420                 425                 430

Lys Leu Leu Lys Gly Ile Pro Asp Leu Tyr Asp Asp Ala Ala Ile Phe
        435                 440                 445

Glu Ala Lys Lys Ser Phe Tyr Trp Ala Arg Lys Thr Ser His Ser Phe
450                 455                 460

Val Val Asn Ile Leu Ala Gln Ala Leu Tyr Glu Leu Phe Ser Ala Thr
465                 470                 475                 480

Asp Asp Ser Leu His Gln Leu Arg Lys Ala Cys Phe Leu Tyr Phe Lys
                485                 490                 495

Leu Gly Gly Glu Cys Val Ala Gly Pro Val Gly Leu Leu Ser Val Leu
            500                 505                 510

Ser Pro Asn Pro Leu Val Leu Ile Gly His Phe Phe Ala Val Ala Ile
        515                 520                 525

Tyr Ala Val Tyr Phe Cys Phe Lys Ser Glu Pro Trp Ile Thr Lys Pro
530                 535                 540

Arg Ala Leu Leu Ser Ser Gly Ala Val Leu Tyr Lys Ala Cys Ser Val
545                 550                 555                 560

Ile Phe Pro Leu Ile Tyr Ser Glu Met Lys Tyr Met Val His
                565                 570

<210> SEQ ID NO 56
<211> LENGTH: 342
<212> TYPE: PRT

<213> ORGANISM: Homo sapiens

<400> SEQUENCE: 56

```
Met Asp Leu Trp Asn Trp Asp Glu Ala Ser Pro Gln Glu Val Pro Pro
1               5                   10                  15
Gly Asn Lys Leu Ala Gly Leu Glu Gly Ala Lys Leu Gly Phe Cys Phe
            20                  25                  30
Pro Asp Leu Ala Leu Gln Gly Asp Thr Pro Thr Ala Thr Ala Glu Thr
        35                  40                  45
Cys Trp Lys Gly Thr Ser Ser Leu Ala Ser Phe Pro Gln Leu Asp
    50                  55                  60
Trp Gly Ser Ala Leu Leu His Pro Glu Val Pro Trp Gly Ala Glu Pro
65                  70                  75                  80
Asp Ser Gln Ala Leu Pro Trp Ser Gly Asp Trp Thr Asp Met Ala Cys
                85                  90                  95
Thr Ala Trp Asp Ser Trp Ser Gly Ala Ser Gln Thr Leu Gly Pro Ala
            100                 105                 110
Pro Leu Gly Pro Gly Pro Ile Pro Ala Ala Gly Ser Glu Gly Ala Ala
        115                 120                 125
Gly Gln Asn Cys Val Pro Val Ala Gly Glu Ala Thr Ser Trp Ser Arg
    130                 135                 140
Ala Gln Ala Ala Gly Ser Asn Thr Ser Trp Asp Cys Ser Val Gly Pro
145                 150                 155                 160
Asp Gly Asp Thr Tyr Trp Gly Ser Gly Leu Gly Glu Pro Arg Thr
                165                 170                 175
Asp Cys Thr Ile Ser Trp Gly Pro Ala Gly Pro Asp Cys Thr Thr
            180                 185                 190
Ser Trp Asn Pro Gly Leu His Ala Gly Gly Thr Thr Ser Leu Lys Arg
        195                 200                 205
Tyr Gln Ser Ser Ala Leu Thr Val Cys Ser Glu Pro Ser Pro Gln Ser
    210                 215                 220
Asp Arg Ala Ser Leu Ala Arg Cys Pro Lys Thr Asn His Arg Gly Pro
225                 230                 235                 240
Ile Gln Leu Trp Gln Phe Leu Leu Glu Leu His Asp Gly Ala Arg
                245                 250                 255
Ser Ser Cys Ile Arg Trp Thr Gly Asn Ser Arg Glu Phe Gln Leu Cys
            260                 265                 270
Asp Pro Lys Glu Val Ala Arg Leu Trp Gly Glu Arg Lys Arg Lys Pro
        275                 280                 285
Gly Met Asn Tyr Glu Lys Leu Ser Arg Gly Leu Arg Tyr Tyr Tyr Arg
    290                 295                 300
Arg Asp Ile Val Arg Lys Ser Gly Gly Arg Lys Tyr Thr Tyr Arg Phe
305                 310                 315                 320
Gly Gly Arg Val Pro Ser Leu Ala Tyr Pro Asp Cys Ala Gly Gly Gly
                325                 330                 335
Arg Gly Ala Glu Thr Gln
            340
```

<210> SEQ ID NO 57
<211> LENGTH: 480
<212> TYPE: PRT
<213> ORGANISM: Homo sapiens

<400> SEQUENCE: 57

Met Glu Val Ala Pro Glu Gln Pro Arg Trp Met Ala His Pro Ala Val

-continued

```
1               5                    10                   15
Leu Asn Ala Gln His Pro Asp Ser His His Pro Gly Leu Ala His Asn
            20                  25                  30
Tyr Met Glu Pro Ala Gln Leu Leu Pro Pro Asp Glu Val Asp Val Phe
            35                  40                  45
Phe Asn His Leu Asp Ser Gln Gly Asn Pro Tyr Tyr Ala Asn Pro Ala
 50                  55                  60
His Ala Arg Ala Arg Val Ser Tyr Ser Pro Ala His Ala Arg Leu Thr
 65                  70                  75                  80
Gly Gly Gln Met Cys Arg Pro His Leu Leu His Ser Pro Gly Leu Pro
                85                  90                  95
Trp Leu Asp Gly Gly Lys Ala Ala Leu Ser Ala Ala Ala His His
            100                 105                 110
His Asn Pro Trp Thr Val Ser Pro Phe Ser Lys Thr Pro Leu His Pro
            115                 120                 125
Ser Ala Ala Gly Gly Pro Gly Gly Pro Leu Ser Val Tyr Pro Gly Ala
130                 135                 140
Gly Gly Gly Ser Gly Gly Ser Gly Ser Ser Val Ala Ser Leu Thr
145                 150                 155                 160
Pro Thr Ala Ala His Ser Gly Ser His Leu Phe Gly Phe Pro Pro Thr
                165                 170                 175
Pro Pro Lys Glu Val Ser Pro Asp Pro Ser Thr Thr Gly Ala Ala Ser
            180                 185                 190
Pro Ala Ser Ser Ser Ala Gly Gly Ser Ala Ala Arg Gly Glu Asp Lys
            195                 200                 205
Asp Gly Val Lys Tyr Gln Val Ser Leu Thr Glu Ser Met Lys Met Glu
            210                 215                 220
Ser Gly Ser Pro Leu Arg Pro Gly Leu Ala Thr Met Gly Thr Gln Pro
225                 230                 235                 240
Ala Thr His His Pro Ile Pro Thr Tyr Pro Ser Tyr Val Pro Ala Ala
                245                 250                 255
Ala His Asp Tyr Ser Ser Gly Leu Phe His Pro Gly Gly Phe Leu Gly
            260                 265                 270
Gly Pro Ala Ser Ser Phe Thr Pro Lys Gln Arg Ser Lys Ala Arg Ser
            275                 280                 285
Cys Ser Glu Gly Arg Glu Cys Val Asn Cys Gly Ala Thr Ala Thr Pro
            290                 295                 300
Leu Trp Arg Arg Asp Gly Thr Gly His Tyr Leu Cys Asn Ala Cys Gly
305                 310                 315                 320
Leu Tyr His Lys Met Asn Gly Gln Asn Arg Pro Leu Ile Lys Pro Lys
            325                 330                 335
Arg Arg Leu Ser Ala Ala Arg Arg Ala Gly Thr Cys Cys Ala Asn Cys
            340                 345                 350
Gln Thr Thr Thr Thr Thr Leu Trp Arg Arg Asn Ala Asn Gly Asp Pro
            355                 360                 365
Val Cys Asn Ala Cys Gly Leu Tyr Tyr Lys Leu His Asn Val Asn Arg
            370                 375                 380
Pro Leu Thr Met Lys Lys Glu Gly Ile Gln Thr Arg Asn Arg Lys Met
385                 390                 395                 400
Ser Asn Lys Ser Lys Lys Ser Lys Lys Gly Ala Glu Cys Phe Glu Glu
                405                 410                 415
Leu Ser Lys Cys Met Gln Glu Lys Ser Ser Pro Phe Ser Ala Ala Ala
            420                 425                 430
```

```
Leu Ala Gly His Met Ala Pro Val Gly His Leu Pro Pro Phe Ser His
        435                 440                 445

Ser Gly His Ile Leu Pro Thr Pro Thr Pro Ile His Pro Ser Ser Ser
450                 455                 460

Leu Ser Phe Gly His Pro His Pro Ser Ser Met Val Thr Ala Met Gly
465                 470                 475                 480

<210> SEQ ID NO 58
<211> LENGTH: 304
<212> TYPE: PRT
<213> ORGANISM: Homo sapiens

<400> SEQUENCE: 58

Met Lys Arg Ala His Pro Glu Tyr Ser Ser Asp Ser Glu Leu Asp
1               5                   10                  15

Glu Thr Ile Glu Val Glu Lys Glu Ser Ala Asp Glu Asn Gly Asn Leu
                20                  25                  30

Ser Ser Ala Leu Gly Ser Met Ser Pro Thr Thr Ser Ser Gln Ile Leu
            35                  40                  45

Ala Arg Lys Arg Arg Arg Gly Ile Ile Glu Lys Arg Arg Arg Asp Arg
        50                  55                  60

Ile Asn Asn Ser Leu Ser Glu Leu Arg Arg Leu Val Pro Ser Ala Phe
65                  70                  75                  80

Glu Lys Gln Gly Ser Ala Lys Leu Glu Lys Ala Glu Ile Leu Gln Met
                85                  90                  95

Thr Val Asp His Leu Lys Met Leu His Thr Ala Gly Gly Lys Gly Tyr
                100                 105                 110

Phe Asp Ala His Ala Leu Ala Met Asp Tyr Arg Ser Leu Gly Phe Arg
            115                 120                 125

Glu Cys Leu Ala Glu Val Ala Arg Tyr Leu Ser Ile Ile Glu Gly Leu
        130                 135                 140

Asp Ala Ser Asp Pro Leu Arg Val Arg Leu Val Ser His Leu Asn Asn
145                 150                 155                 160

Tyr Ala Ser Gln Arg Glu Ala Ala Ser Gly Ala His Ala Gly Leu Gly
                165                 170                 175

His Ile Pro Trp Gly Thr Val Phe Gly His His Pro His Ile Ala His
            180                 185                 190

Pro Leu Leu Leu Pro Gln Asn Gly His Gly Asn Ala Gly Thr Thr Ala
        195                 200                 205

Ser Pro Thr Glu Pro His His Gln Gly Arg Leu Gly Ser Ala His Pro
210                 215                 220

Glu Ala Pro Ala Leu Arg Ala Pro Pro Ser Gly Ser Leu Gly Pro Val
225                 230                 235                 240

Leu Pro Val Val Thr Ser Ala Ser Lys Leu Ser Pro Pro Leu Leu Ser
                245                 250                 255

Ser Val Ala Ser Leu Ser Ala Phe Pro Phe Ser Phe Gly Ser Phe His
            260                 265                 270

Leu Leu Ser Pro Asn Ala Leu Ser Pro Ser Ala Pro Thr Gln Ala Ala
        275                 280                 285

Asn Leu Gly Lys Pro Tyr Arg Pro Trp Gly Thr Glu Ile Gly Ala Phe
        290                 295                 300

<210> SEQ ID NO 59
<211> LENGTH: 337
<212> TYPE: PRT
```

<213> ORGANISM: Homo sapiens

<400> SEQUENCE: 59

```
Met Lys Arg Pro Cys Glu Glu Thr Thr Ser Glu Ser Asp Met Asp Glu
1               5                   10                  15

Thr Ile Asp Val Gly Ser Glu Asn Asn Tyr Ser Gly Gln Ser Thr Ser
            20                  25                  30

Ser Val Ile Arg Leu Asn Ser Pro Thr Thr Thr Ser Gln Ile Met Ala
        35                  40                  45

Arg Lys Lys Arg Arg Gly Ile Ile Glu Lys Arg Arg Arg Asp Arg Ile
    50                  55                  60

Asn Asn Ser Leu Ser Glu Leu Arg Arg Leu Val Pro Thr Ala Phe Glu
65                  70                  75                  80

Lys Gln Gly Ser Ala Lys Leu Glu Lys Ala Glu Ile Leu Gln Met Thr
                85                  90                  95

Val Asp His Leu Lys Met Leu Gln Ala Thr Gly Gly Lys Gly Tyr Phe
            100                 105                 110

Asp Ala His Ala Leu Ala Met Asp Phe Met Ser Ile Gly Phe Arg Glu
        115                 120                 125

Cys Leu Thr Glu Val Ala Arg Tyr Leu Ser Ser Val Glu Gly Leu Asp
130                 135                 140

Ser Ser Asp Pro Leu Arg Val Arg Leu Val Ser His Leu Ser Thr Cys
145                 150                 155                 160

Ala Thr Gln Arg Glu Ala Ala Ala Met Thr Ser Ser Met Ala His His
                165                 170                 175

His His Pro Leu His Pro His His Trp Ala Ala Phe His His Leu
            180                 185                 190

Pro Ala Ala Leu Leu Gln Pro Asn Gly Leu His Ala Ser Glu Ser Thr
        195                 200                 205

Pro Cys Arg Leu Ser Thr Thr Ser Glu Val Pro Pro Ala His Gly Ser
    210                 215                 220

Ala Leu Leu Thr Ala Thr Phe Ala His Ala Asp Ser Ala Leu Arg Met
225                 230                 235                 240

Pro Ser Thr Gly Ser Val Ala Pro Cys Val Pro Pro Leu Ser Thr Ser
                245                 250                 255

Leu Leu Ser Leu Ser Ala Thr Val His Ala Ala Ala Ala Ala Ala Thr
            260                 265                 270

Ala Ala Ala His Ser Phe Pro Leu Ser Phe Ala Gly Ala Phe Pro Met
        275                 280                 285

Leu Pro Pro Asn Ala Ala Ala Ala Val Ala Ala Thr Ala Ile Ser
    290                 295                 300

Pro Pro Leu Ser Val Ser Ala Thr Ser Ser Pro Gln Gln Thr Ser Ser
305                 310                 315                 320

Gly Thr Asn Asn Lys Pro Tyr Arg Pro Trp Gly Thr Glu Val Gly Ala
                325                 330                 335

Phe
```

<210> SEQ ID NO 60
<211> LENGTH: 553
<212> TYPE: PRT
<213> ORGANISM: Homo sapiens

<400> SEQUENCE: 60

```
Met Gln Ala Arg Tyr Ser Val Ser Pro Asn Ser Leu Gly Val Val
1               5                   10                  15
```

```
Pro Tyr Leu Gly Gly Glu Gln Ser Tyr Tyr Arg Ala Ala Ala Ala
             20                  25                  30
Ala Gly Gly Gly Tyr Thr Ala Met Pro Ala Pro Met Ser Val Tyr Ser
         35                  40                  45
His Pro Ala His Ala Glu Gln Tyr Pro Gly Met Ala Arg Ala Tyr
 50                  55                  60
Gly Pro Tyr Thr Pro Gln Pro Gln Pro Lys Asp Met Val Lys Pro Pro
 65                  70                  75                  80
Tyr Ser Tyr Ile Ala Leu Ile Thr Met Ala Ile Gln Asn Ala Pro Asp
                 85                  90                  95
Lys Lys Ile Thr Leu Asn Gly Ile Tyr Gln Phe Ile Met Asp Arg Phe
                100                 105                 110
Pro Phe Tyr Arg Asp Asn Lys Gln Gly Trp Gln Asn Ser Ile Arg His
            115                 120                 125
Asn Leu Ser Leu Asn Glu Cys Phe Val Lys Val Pro Arg Asp Asp Lys
130                 135                 140
Lys Pro Gly Lys Gly Ser Tyr Trp Thr Leu Asp Pro Asp Ser Tyr Asn
145                 150                 155                 160
Met Phe Glu Asn Gly Ser Phe Leu Arg Arg Arg Arg Phe Lys Lys
                165                 170                 175
Lys Asp Ala Val Lys Asp Lys Glu Lys Asp Arg Leu His Leu Lys
            180                 185                 190
Glu Pro Pro Pro Gly Arg Gln Pro Pro Ala Pro Pro Glu Gln
            195                 200                 205
Ala Asp Gly Asn Ala Pro Gly Pro Gln Pro Pro Val Arg Ile Gln
            210                 215                 220
Asp Ile Lys Thr Glu Asn Gly Thr Cys Pro Ser Pro Pro Gln Pro Leu
225                 230                 235                 240
Ser Pro Ala Ala Ala Leu Gly Ser Gly Ser Ala Ala Ala Val Pro Lys
                245                 250                 255
Ile Glu Ser Pro Asp Ser Ser Ser Ser Leu Ser Ser Gly Ser Ser
            260                 265                 270
Pro Pro Gly Ser Leu Pro Ser Ala Arg Pro Leu Ser Leu Asp Gly Ala
            275                 280                 285
Asp Ser Ala Pro Pro Pro Ala Pro Ser Ala Pro Pro His His
            290                 295                 300
Ser Gln Gly Phe Ser Val Asp Asn Ile Met Thr Ser Leu Arg Gly Ser
305                 310                 315                 320
Pro Gln Ser Ala Ala Ala Glu Leu Ser Ser Gly Leu Leu Ala Ser Ala
                325                 330                 335
Ala Ala Ser Ser Arg Ala Gly Ile Ala Pro Pro Leu Ala Leu Gly Ala
                340                 345                 350
Tyr Ser Pro Gly Gln Ser Ser Leu Tyr Ser Ser Pro Cys Ser Gln Thr
                355                 360                 365
Ser Ser Ala Gly Ser Ser Gly Gly Gly Gly Ala Gly Ala Ala
            370                 375                 380
Gly Gly Ala Gly Gly Ala Gly Thr Tyr His Cys Asn Leu Gln Ala Met
385                 390                 395                 400
Ser Leu Tyr Ala Ala Gly Glu Arg Gly Gly His Leu Gln Gly Ala Pro
                405                 410                 415
Gly Gly Ala Gly Gly Ser Ala Val Asp Asp Pro Leu Pro Asp Tyr Ser
                420                 425                 430
```

```
Leu Pro Pro Val Thr Ser Ser Ser Ser Leu Ser His Gly Gly
        435                 440                 445

Gly Gly Gly Gly Gly Gly Gly Gln Glu Ala Gly His His Pro Ala
450                 455                 460

Ala His Gln Gly Arg Leu Thr Ser Trp Tyr Leu Asn Gln Ala Gly Gly
465                 470                 475                 480

Asp Leu Gly His Leu Ala Ser Ala Ala Ala Ala Ala Ala Ala Gly
                485                 490                 495

Tyr Pro Gly Gln Gln Asn Phe His Ser Val Arg Glu Met Phe Glu
            500                 505                 510

Ser Gln Arg Ile Gly Leu Asn Asn Ser Pro Val Asn Gly Asn Ser Ser
        515                 520                 525

Cys Gln Met Ala Phe Pro Ser Ser Gln Ser Leu Tyr Arg Thr Ser Gly
530                 535                 540

Ala Phe Val Tyr Asp Cys Ser Lys Phe
545                 550

<210> SEQ ID NO 61
<211> LENGTH: 501
<212> TYPE: PRT
<213> ORGANISM: Homo sapiens

<400> SEQUENCE: 61

Met Gln Ala Arg Tyr Ser Val Ser Asp Pro Asn Ala Leu Gly Val Val
1               5                   10                  15

Pro Tyr Leu Ser Glu Gln Asn Tyr Tyr Arg Ala Ala Gly Ser Tyr Gly
            20                  25                  30

Gly Met Ala Ser Pro Met Gly Val Tyr Ser Gly His Pro Glu Gln Tyr
        35                  40                  45

Ser Ala Gly Met Gly Arg Ser Tyr Ala Pro Tyr His His His Gln Pro
    50                  55                  60

Ala Ala Pro Lys Asp Leu Val Lys Pro Pro Tyr Ser Tyr Ile Ala Leu
65                  70                  75                  80

Ile Thr Met Ala Ile Gln Asn Ala Pro Glu Lys Lys Ile Thr Leu Asn
                85                  90                  95

Gly Ile Tyr Gln Phe Ile Met Asp Arg Phe Pro Phe Tyr Arg Glu Asn
            100                 105                 110

Lys Gln Gly Trp Gln Asn Ser Ile Arg His Asn Leu Ser Leu Asn Glu
        115                 120                 125

Cys Phe Val Lys Val Pro Arg Asp Asp Lys Lys Pro Gly Lys Gly Ser
    130                 135                 140

Tyr Trp Thr Leu Asp Pro Asp Ser Tyr Asn Met Phe Glu Asn Gly Ser
145                 150                 155                 160

Phe Leu Arg Arg Arg Arg Arg Phe Lys Lys Lys Asp Val Ser Lys Glu
                165                 170                 175

Lys Glu Glu Arg Ala His Leu Lys Glu Pro Pro Ala Ala Ser Lys
            180                 185                 190

Gly Ala Pro Ala Thr Pro His Leu Ala Asp Ala Pro Lys Glu Ala Glu
        195                 200                 205

Lys Lys Val Val Ile Lys Ser Glu Ala Ala Ser Pro Ala Leu Pro Val
    210                 215                 220

Ile Thr Lys Val Glu Thr Leu Ser Pro Glu Ser Ala Leu Gln Gly Ser
225                 230                 235                 240

Pro Arg Ser Ala Ala Ser Thr Pro Ala Gly Ser Pro Asp Gly Ser Leu
                245                 250                 255
```

Pro Glu His His Ala Ala Pro Asn Gly Leu Pro Gly Phe Ser Val
          260                 265                 270

Glu Asn Ile Met Thr Leu Arg Thr Ser Pro Pro Gly Glu Leu Ser
              275                 280                 285

Pro Gly Ala Gly Arg Ala Gly Leu Val Val Pro Pro Leu Ala Leu Pro
290                 295                 300

Tyr Ala Ala Ala Pro Pro Ala Ala Tyr Gly Gln Pro Cys Ala Gln Gly
305                 310                 315                 320

Leu Glu Ala Gly Ala Ala Gly Gly Tyr Gln Cys Ser Met Arg Ala Met
              325                 330                 335

Ser Leu Tyr Thr Gly Ala Glu Arg Pro Ala His Met Cys Val Pro Pro
              340                 345                 350

Ala Leu Asp Glu Ala Leu Ser Asp His Pro Ser Gly Pro Thr Ser Pro
              355                 360                 365

Leu Ser Ala Leu Asn Leu Ala Ala Gly Gln Glu Gly Ala Leu Ala Ala
370                 375                 380

Thr Gly His His His Gln His His Gly His His His Pro Gln Ala Pro
385                 390                 395                 400

Pro Pro Pro Pro Ala Pro Gln Pro Gln Pro Thr Pro Gln Pro Gly Ala
              405                 410                 415

Ala Ala Ala Gln Ala Ala Ser Trp Tyr Leu Asn His Ser Gly Asp Leu
              420                 425                 430

Asn His Leu Pro Gly His Thr Phe Ala Ala Gln Gln Gln Thr Phe Pro
              435                 440                 445

Asn Val Arg Glu Met Phe Asn Ser His Arg Leu Gly Ile Glu Asn Ser
              450                 455                 460

Thr Leu Gly Glu Ser Gln Val Ser Gly Asn Ala Ser Cys Gln Leu Pro
465                 470                 475                 480

Tyr Arg Ser Thr Pro Pro Leu Tyr Arg His Ala Ala Pro Tyr Ser Tyr
              485                 490                 495

Asp Cys Thr Lys Tyr
              500

<210> SEQ ID NO 62
<211> LENGTH: 388
<212> TYPE: PRT
<213> ORGANISM: Homo sapiens

<400> SEQUENCE: 62

Met Ala Ser Leu Leu Gly Ala Tyr Pro Trp Pro Glu Gly Leu Glu Cys
1               5                   10                  15

Pro Ala Leu Asp Ala Glu Leu Ser Asp Gly Gln Ser Pro Pro Ala Val
              20                  25                  30

Pro Arg Pro Pro Gly Asp Lys Gly Ser Glu Ser Arg Ile Arg Arg Pro
              35                  40                  45

Met Asn Ala Phe Met Val Trp Ala Lys Asp Glu Arg Lys Arg Leu Ala
              50                  55                  60

Val Gln Asn Pro Asp Leu His Asn Ala Glu Leu Ser Lys Met Leu Gly
65                  70                  75                  80

Lys Ser Trp Lys Ala Leu Thr Leu Ser Gln Lys Arg Pro Tyr Val Asp
              85                  90                  95

Glu Ala Glu Arg Leu Arg Leu Gln His Met Gln Asp Tyr Pro Asn Tyr
              100                 105                 110

Lys Tyr Arg Pro Arg Arg Lys Lys Gln Ala Lys Arg Leu Cys Lys Arg

```
            115                 120                 125
Val Asp Pro Gly Phe Leu Leu Ser Ser Leu Ser Arg Asp Gln Asn Ala
130                 135                 140

Leu Pro Glu Lys Arg Ser Gly Ser Arg Gly Ala Leu Gly Lys Glu
145                 150                 155                 160

Asp Arg Gly Glu Tyr Ser Pro Gly Thr Ala Leu Pro Ser Leu Arg Gly
                165                 170                 175

Cys Tyr His Glu Gly Pro Ala Gly Gly Gly Gly Thr Pro Ser
            180                 185                 190

Ser Val Asp Thr Tyr Pro Tyr Gly Leu Pro Thr Pro Glu Met Ser
                195                 200                 205

Pro Leu Asp Val Leu Glu Pro Glu Gln Thr Phe Phe Ser Ser Pro Cys
210                 215                 220

Gln Glu Glu His Gly His Pro Arg Arg Ile Pro His Leu Pro Gly His
225                 230                 235                 240

Pro Tyr Ser Pro Glu Tyr Ala Pro Ser Pro Leu His Cys Ser His Pro
                245                 250                 255

Leu Gly Ser Leu Ala Leu Gly Gln Ser Pro Gly Val Ser Met Met Ser
                260                 265                 270

Pro Val Pro Gly Cys Pro Pro Ser Pro Ala Tyr Tyr Ser Pro Ala Thr
                275                 280                 285

Tyr His Pro Leu His Ser Asn Leu Gln Ala His Leu Gly Gln Leu Ser
                290                 295                 300

Pro Pro Pro Glu His Pro Gly Phe Asp Ala Leu Asp Gln Leu Ser Gln
305                 310                 315                 320

Val Glu Leu Leu Gly Asp Met Asp Arg Asn Glu Phe Asp Gln Tyr Leu
                325                 330                 335

Asn Thr Pro Gly His Pro Asp Ser Ala Thr Gly Ala Met Ala Leu Ser
                340                 345                 350

Gly His Val Pro Val Ser Gln Val Thr Pro Thr Gly Pro Thr Glu Thr
                355                 360                 365

Ser Leu Ile Ser Val Leu Ala Asp Ala Thr Ala Thr Tyr Tyr Asn Ser
                370                 375                 380

Tyr Ser Val Ser
385

<210> SEQ ID NO 63
<211> LENGTH: 384
<212> TYPE: PRT
<213> ORGANISM: Homo sapiens

<400> SEQUENCE: 63

Met Gln Arg Ser Pro Gly Tyr Gly Ala Gln Asp Asp Pro Pro Ala
1               5                   10                  15

Arg Arg Asp Cys Ala Trp Ala Pro Gly His Gly Ala Ala Ala Asp Thr
                20                  25                  30

Arg Gly Leu Ala Ala Gly Pro Ala Ala Leu Ala Ala Pro Ala Ala Pro
            35                  40                  45

Ala Ser Pro Pro Ser Pro Gln Arg Ser Pro Arg Ser Pro Glu Pro
        50                  55                  60

Gly Arg Tyr Gly Leu Ser Pro Ala Gly Arg Gly Glu Arg Gln Ala Ala
65                  70                  75                  80

Asp Glu Ser Arg Ile Arg Arg Pro Met Asn Ala Phe Met Val Trp Ala
                85                  90                  95
```

```
Lys Asp Glu Arg Lys Arg Leu Ala Gln Gln Asn Pro Asp Leu His Asn
                100                 105                 110

Ala Val Leu Ser Lys Met Leu Gly Lys Ala Trp Lys Glu Leu Asn Ala
            115                 120                 125

Ala Glu Lys Arg Pro Phe Val Glu Glu Ala Glu Arg Leu Arg Val Gln
        130                 135                 140

His Leu Arg Asp His Pro Asn Tyr Lys Tyr Arg Pro Arg Arg Lys Lys
145                 150                 155                 160

Gln Ala Arg Lys Ala Arg Arg Leu Glu Pro Gly Leu Leu Leu Pro Gly
                165                 170                 175

Leu Ala Pro Pro Gln Pro Pro Glu Pro Phe Pro Ala Ala Ser Gly
            180                 185                 190

Ser Ala Arg Ala Phe Arg Glu Leu Pro Pro Leu Gly Ala Glu Phe Asp
        195                 200                 205

Gly Leu Gly Leu Pro Thr Pro Glu Arg Ser Pro Leu Asp Gly Leu Glu
210                 215                 220

Pro Gly Glu Ala Ala Phe Phe Pro Pro Ala Ala Pro Glu Asp Cys
225                 230                 235                 240

Ala Leu Arg Pro Phe Arg Ala Pro Tyr Ala Pro Thr Glu Leu Ser Arg
            245                 250                 255

Asp Pro Gly Gly Cys Tyr Gly Ala Pro Leu Ala Glu Ala Leu Arg Thr
        260                 265                 270

Ala Pro Pro Ala Ala Pro Leu Ala Gly Leu Tyr Tyr Gly Thr Leu Gly
            275                 280                 285

Thr Pro Gly Pro Tyr Pro Gly Pro Leu Ser Pro Pro Glu Ala Pro
    290                 295                 300

Pro Leu Glu Ser Ala Glu Pro Leu Gly Pro Ala Ala Asp Leu Trp Ala
305                 310                 315                 320

Asp Val Asp Leu Thr Glu Phe Asp Gln Tyr Leu Asn Cys Ser Arg Thr
                325                 330                 335

Arg Pro Asp Ala Pro Gly Leu Pro Tyr His Val Ala Leu Ala Lys Leu
            340                 345                 350

Gly Pro Arg Ala Met Ser Cys Pro Glu Glu Ser Ser Leu Ile Ser Ala
        355                 360                 365

Leu Ser Asp Ala Ser Ser Ala Val Tyr Tyr Ser Ala Cys Ile Ser Gly
    370                 375                 380

<210> SEQ ID NO 64
<211> LENGTH: 8
<212> TYPE: PRT
<213> ORGANISM: Artificial Sequence
<220> FEATURE:
<223> OTHER INFORMATION: his tag

<400> SEQUENCE: 64

His His His His His His Ser Ser
1               5

<210> SEQ ID NO 65
<211> LENGTH: 954
<212> TYPE: DNA
<213> ORGANISM: Homo sapiens

<400> SEQUENCE: 65
atgtacaaca tgatggagac ggagctgaag ccgccgggcc cgcagcaaac ttcgggggc      60 ggcggcggca actccaccgc ggcggcggcc ggcggcaacc agaaaaacag cccggaccgc    120
```

| | |
|---|---|
| gtcaagcggc ccatgaatgc cttcatggtg tggtcccgcg ggcagcggcg caagatggcc | 180 |
| caggagaacc ccaagatgca caactcggag atcagcaagc gcctgggcgc cgagtggaaa | 240 |
| cttttgtcgg agacggagaa gcggccgttc atcgacgagg ctaagcggct gcgagcgctg | 300 |
| cacatgaagg agcacccgga ttataaatac cggccccggc ggaaaaccaa gacgctcatg | 360 |
| aagaaggata agtacacgct gcccggcggg ctgctggccc ccggcggcaa tagcatggcg | 420 |
| agcggggtcg gggtgggcgc cggcctgggc gcgggcgtga accagcgcat ggacagttac | 480 |
| gcgcacatga acggctggag caacggcagc tacagcatga tgcaggacca gctgggctac | 540 |
| ccgcagcacc cgggcctcaa tgcgcacggc gcagcgcaga tgcagcccat gcaccgctac | 600 |
| gacgtgagcg ccctgcagta caactccatg accagctcgc agacctacat gaacggctcg | 660 |
| cccacctaca gcatgtccta ctcgcagcag ggcaccctg gcatggctct ggctccatg | 720 |
| ggttcggtgg tcaagtccga ggccagctcc agccccctg tggttacctc ttcctcccac | 780 |
| tccagggcgc cctgccaggc cggggacctc cgggacatga tcagcatgta tctccccggc | 840 |
| gccgaggtgc cggaacccgc cgccccccagc agacttcaca tgtcccagca ctaccagagc | 900 |
| ggcccggtgc ccggcacggc cattaacggc acactgcccc tctcacacat gtga | 954 |

<210> SEQ ID NO 66
<211> LENGTH: 1083
<212> TYPE: DNA
<213> ORGANISM: Homo sapiens

<400> SEQUENCE: 66

| | |
|---|---|
| atggcgggac acctggcttc ggatttcgcc ttctcgcccc ctccaggtgg tggaggtgat | 60 |
| gggccagggg ggccggagcc gggctgggtt gatcctcgga cctggctaag cttccaaggc | 120 |
| cctcctggag ggcaggaat cgggccgggg gttgggccag gctctgaggt gtgggggatt | 180 |
| cccccatgcc ccccgccgta tgagttctgt gggggatgg cgtactgtgg gccccaggtt | 240 |
| ggagtggggc tagtgcccca aggcggcttg gagacctctc agcctgaggg cgaagcagga | 300 |
| gtcggggtgg agagcaactc cgatggggcc tccccggagc cctgcaccgt caccccctggt | 360 |
| gccgtgaagc tggagaagga gaagctggag caaaacccgg aggagtccca ggacatcaaa | 420 |
| gctctgcaga aagaactcga gcaatttgcc aagctcctga gcagaagag gatcacccctg | 480 |
| ggatatacac aggccgatgt ggggctcacc ctgggggttc tatttgggaa ggtattcagc | 540 |
| caaacgacca tctgccgctt tgaggctctg cagcttagct tcaagaacat gtgtaagctg | 600 |
| cggcccttgc tgcagaagtg ggtggaggaa gctgacaaca atgaaaatct tcaggagata | 660 |
| tgcaaagcag aaaccctcgt gcaggcccga agagaaagc gaaccagtat cgagaaccga | 720 |
| gtgagaggca acctggagaa tttgttcctg cagtgcccga aacccacact gcagcagatc | 780 |
| agccacatcg cccagcagct tgggctcgag aaggatgtgg tccgagtgtg gttctgtaac | 840 |
| cggcgccaga agggcaagcg atcaagcagc gactatgcac aacgagagga ttttgaggct | 900 |
| gctgggtctc ctttctcagg gggaccagtg tcctttcctc tggccccagg gccccatttt | 960 |
| ggtaccccag gctatgggag ccctcacttc actgcactgt actcctcggt cccttttccct | 1020 |
| gaggggggaag cctttccccc tgtctccgtc accactctgg gctctcccat gcattcaaac | 1080 |
| tga | 1083 |

<210> SEQ ID NO 67
<211> LENGTH: 918
<212> TYPE: DNA
<213> ORGANISM: Homo sapiens

<400> SEQUENCE: 67

```
atgagtgtgg atccagcttg tccccaaagc ttgccttgct ttgaagcatc cgactgtaaa      60
gaatcttcac ctatgcctgt gatttgtggg cctgaagaaa actatccatc cttgcaaatg     120
tcttctgctg agatgcctca cacggagact gtctctcctc ttccttcctc catggatctg     180
cttattcagg acagccctga ttcttccacc agtcccaaag caaacaacc cacttctgca      240
gagaagagtg tcgcaaaaaa ggaagacaag gtcccggtca agaaacagaa gaccagaact     300
gtgttctctt ccacccagct gtgtgtactc aatgatagat tcagagaca gaaatacctc      360
agcctccagc agatgcaaga actctccaac atcctgaacc tcagctacaa acaggtgaag     420
acctggttcc agaaccagag aatgaaatct aagaggtggc agaaaaacaa ctggccgaag     480
aatagcaatg gtgtgacgca agaggcctca gcacctacct accccagcct ttactcttcc     540
taccaccagg gatgcctggt gaacccgact gggaaccttc aatgtggag caaccagacc      600
tggaacaatt caacctggag caaccagacc cagaacatcc agtcctggag caaccactcc     660
tggaacactc agacctggtg cacccaatcc tggaacaatc aggcctggaa cagtcccttc     720
tataactgtg gagaggaatc tctgcagtcc tgcatgcagt tccagccaaa ttctcctgcc     780
agtgacttgg aggctgcctt ggaagctgct ggggaaggcc ttaatgtaat acagcagacc     840
actaggtatt ttagtactcc acaaaccatg gatttattcc taaactactc catgaacatg     900
caacctgaag acgtgtga                                                    918
```

<210> SEQ ID NO 68
<211> LENGTH: 630
<212> TYPE: DNA
<213> ORGANISM: Homo sapiens

<400> SEQUENCE: 68

```
atgggctccg tgtccaacca gcagtttgca ggtggctgcg ccaaggcggc agaagaggcg      60
cccgaggagg cgccggagga cgcggcccgg gcggcggacg agcctcagct gctgcacggt     120
gcgggcatct gtaagtggtt caacgtgcgc atggggttcg gcttcctgtc catgaccgcc     180
cgcgccgggg tcgcgctcga ccccccagtg gatgtctttg tgcaccagag taagctgcac     240
atggaagggt tccggagctt gaaggagggt gaggcagtgg agttcacctt taagaagtca     300
gccaagggtc tggaatccat ccgtgtcacc ggacctggtg gagtattctg tattgggagt     360
gagaggcggc caaaaggaaa gagcatgcag aagcgcagat caaaaggaga caggtgctac     420
aactgtggag tctagatca tcatgccaag gaatgcaagc tgccacccca gcccaagaag     480
tgccacttct gccagagcat cagccatatg gtagcctcat gtccgctgaa ggcccagcag     540
ggccctagtg cacagggaaa gccaacctac tttcgagagg aagaagaaga atccacagc      600
cctaccctgc tcccggaggc acagaattga                                       630
```

<210> SEQ ID NO 69
<211> LENGTH: 1440
<212> TYPE: DNA
<213> ORGANISM: Homo sapiens

<400> SEQUENCE: 69

```
atgaggcagc cacctggcga gtctgacatg gctgtcagcg acgcgctgct cccatctttc      60
tccacgttcg cgtctggccc ggcgggaagg gagaagacac tgcgtcaagc aggtgccccg     120
aataaccgct ggcgggagga gctctcccac atgaagcgac ttccccagt gcttcccggc     180
```

| | |
|---|---|
| cgcccctatg acctggcggc ggcgaccgtg gccacagacc tggagagcgg cggagccggt | 240 |
| gcggcttgcg gcggtagcaa cctggcgccc ctacctcgga gagagaccga ggagttcaac | 300 |
| gatctcctgg acctggactt tattctctcc aattcgctga cccatcctcc ggagtcagtg | 360 |
| gccgccaccg tgtcctcgtc agcgtcagcc tcctcttcgt cgtcgccgtc gagcagcggc | 420 |
| cctgccagcg cgccctccac ctgcagcttc acctatccga tccgggccgg gaacgacccg | 480 |
| ggcgtggcgc cgggcggcac gggcggaggc ctcctctatg cagggagtc cgctccccct | 540 |
| ccgacggctc ccttcaacct ggcggacatc aacgacgtga gccctcgggg cggcttcgtg | 600 |
| gccgagctcc tgcggccaga attggacccg gtgtacattc gccgcagca gccgcagccg | 660 |
| ccaggtggcg ggctgatggg caagttcgtg ctgaaggcgt cgctgagcgc ccctggcagc | 720 |
| gagtacggca gcccgtcggt catcagcgtc agcaaaggca gccctgacgg cagccacccg | 780 |
| gtggtggtgg cgccctacaa cggcgggccg ccgcgcacgt gccccaagat caagcaggag | 840 |
| gcggtctctt cgtgcaccca cttgggcgct ggaccccctc tcagcaatgg ccaccggccg | 900 |
| gctgcacacg acttcccct ggggcggcag ctccccagca ggactacccc gaccctgggt | 960 |
| cttgaggaag tgctgagcag cagggactgt caccctgccc tgccgcttcc tcccggcttc | 1020 |
| catccccacc cggggcccaa ttacccatcc ttcctgcccg atcagatgca gccgcaagtc | 1080 |
| ccgccgctcc attaccaaga gctcatgcca cccggttcct gcatgccaga ggagcccaag | 1140 |
| ccaaagaggg gaagacgatc gtggcccgg aaaaggaccg ccacccacac ttgtgattac | 1200 |
| gcgggctgcg gcaaaaccta cacaaagagt tcccatctca aggcacacct gcgaacccac | 1260 |
| acaggtgaga aaccttacca ctgtgactgg gacggctgtg gatggaaatt cgcccgctca | 1320 |
| gatgaactga ccaggcacta ccgtaaacac acggggcacc gcccgttcca gtgccaaaaa | 1380 |
| tgcgaccgag cattttccag gtcggaccac ctcgccttac acatgaagag gcatttttaa | 1440 |

<210> SEQ ID NO 70
<211> LENGTH: 1365
<212> TYPE: DNA
<213> ORGANISM: Homo sapiens

<400> SEQUENCE: 70

| | |
|---|---|
| ctggattttt ttcgggtagt ggaaaaccag cagcctcccg cgacgatgcc cctcaacgtt | 60 |
| agcttcacca acaggaacta tgacctcgac tacgactcgg tgcagccgta tttctactgc | 120 |
| gacgaggagg agaacttcta ccagcagcag cagcagagcg agctgcagcc cccggcgccc | 180 |
| agcgaggata tctggaagaa attcgagctg ctgcccaccc cgcccctgtc ccctagccgc | 240 |
| cgctccgggc tctgctcgcc ctcctacgtt gcggtcacac ccttctccct tcggggagac | 300 |
| aacgacggcg gtggcgggag cttctccacg gccgaccagc tggagatggt gaccgagctg | 360 |
| ctgggaggag acatggtgaa ccagagtttc atctgcgacc cggacgacga gaccttcatc | 420 |
| aaaaacatca tcatccagga ctgtatgtgg agcggcttct cggccgccgc caagctcgtc | 480 |
| tcagagaagc tggcctccta ccaggctgcg cgcaaagaca gcggcagccc gaaccccgcc | 540 |
| cgcggccaca gcgtctgctc cacctccagc ttgtacctgc aggatctgag cgccgccgcc | 600 |
| tcagagtgca tcgaccccctc ggtggtcttc ccctaccctc tcaacgacag cagctcgccc | 660 |
| aagtcctgcg cctcgcaaga ctccagcgcc ttctctccgt cctcggattc tctgctctcc | 720 |
| tcgacggagt cctccccgca gggcagcccc gagcccctgg tgctccatga ggagacaccg | 780 |
| cccaccacca gcagcgactc tgaggaggaa caagaagatg aggaagaaat cgatgttgtt | 840 |
| tctgtggaaa agaggcaggc tcctggcaaa aggtcagagt ctggatcacc ttctgctgga | 900 |

| | |
|---|---|
| ggccacagca aacctcctca cagcccactg gtcctcaaga ggtgccacgt ctccacacat | 960 |
| cagcacaact acgcagcgcc tccctccact cggaaggact atcctgctgc caagagggtc | 1020 |
| aagttggaca gtgtcagagt cctgagacag atcagcaaca accgaaaatg caccagcccc | 1080 |
| aggtcctcgg acaccgagga gaatgtcaag aggcgaacac acaacgtctt ggagcgccag | 1140 |
| aggaggaacg agctaaaacg gagcttttt gccctgcgtg accagatccc ggagttggaa | 1200 |
| aacaatgaaa aggcccccaa ggtagttatc cttaaaaaag ccacagcata catcctgtcc | 1260 |
| gtccaagcag aggagcaaaa gctcatttct gaagaggact tgttgcggaa acgacgagaa | 1320 |
| cagttgaaac acaaacttga acagctacgg aactcttgtg cgtaa | 1365 |

<210> SEQ ID NO 71
<211> LENGTH: 1329
<212> TYPE: DNA
<213> ORGANISM: Homo sapiens

<400> SEQUENCE: 71

| | |
|---|---|
| atgtatcaga gcttggccat ggccgccaac cacgggccgc ccccggtgc ctacgaggcg | 60 |
| ggcggcccg cgccttcat gcacggcgcg ggcgccgcgt cctcgccagt ctacgtgccc | 120 |
| acaccgcggg tgcctcctc cgtgctgggc ctgtcctacc tccagggcgg aggcgcgggc | 180 |
| tctgcgtccg gaggcgcctc gggcggcagc tccggtgggg ccgcgtctgg tgcggggccc | 240 |
| gggacccagc agggcagccc gggatggagc caggcgggag ccgacggagc cgcttacacc | 300 |
| ccgccgccgt tgtcgccgcg cttctccttc ccggggacca ccgggtccct ggcggccgcc | 360 |
| gccgccgctg ccgcggcccg ggaagctgcg gcctacagca gtggcggcgg agcggcgggt | 420 |
| gcgggcctgg cgggccgcga gcagtacggg cgcgccggct tcgcgggctc ctactccagc | 480 |
| ccctacccgg cttacatggc cgacgtgggc gcgtcctggg ccgcagccgc cgccgcctcc | 540 |
| gccggccct tcgacagccc ggtcctgcac agcctgcccg gccgggccaa ccgcccgcc | 600 |
| cgacacccca atctcgatat gttgacgac ttctcagaag gcagagagtg tgtcaactgt | 660 |
| ggggctatgt ccaccccgct ctggaggcga gatgggacgg gtcactatct gtgcaacgcc | 720 |
| tgcggcctct accacaagat gaacggcatc aaccggccgc tcatcaagcc tcagcgccgg | 780 |
| ctgtccgcct cccgccgagt gggcctctcc tgtgccaact gccagaccac caccaccacg | 840 |
| ctgtggcgcc gcaatgcgga gggcgagcct gtgtgcaatg cctgcggcct ctacatgaag | 900 |
| ctccacgggg tccccaggcc tcttgcaatg cggaaagagg ggatccaaac cagaaaacgg | 960 |
| aagcccaaga acctgaataa atctaagaca ccagcagctc cttcaggcag tgagagcctt | 1020 |
| cctcccgcca gcggtgcttc cagcaactcc agcaacgcca ccaccagcag cagcgaggag | 1080 |
| atgcgtccca tcaagacgga gcctggcctg tcatctcact acgggcacag cagctccgtg | 1140 |
| tcccagacgt tctcagtcag tgcgatgtct ggccatgggc cctccatcca ccctgtcctc | 1200 |
| tcggccctga gctctccccc acaaggctat gcgtctcccg tcagccagtc tccacagacc | 1260 |
| agctccaagc aggactcttg gaacagcctg gtcttggccg acagtcacgg ggacataatc | 1320 |
| actgcgtaa | 1329 |

<210> SEQ ID NO 72
<211> LENGTH: 654
<212> TYPE: DNA
<213> ORGANISM: Homo sapiens

<400> SEQUENCE: 72

```
atgagtctgg taggtggttt tccccaccac ccggtggtgc accacgaggg ctacccgttt      60
gccgccgccg ccgccgcagc tgccgccgcc gccgccagcc gctgcagcca tgaggagaac     120
ccctacttcc atggctggct catcggccac cccgagatgt cgccccccga ctacagcatg     180
gccctgtcct acagcccga gtatgccagc ggcgccgccg gcctggacca ctcccattac      240
ggggggggtgc cgccgggcgc cgggcccccg gcctggggg ggccgcgccc ggtgaagcgc     300
cgaggcaccg ccaaccgcaa ggagcggcgc aggactcaga gcatcaacag cgccttcgcc     360
gaactgcgcg agtgcatccc caacgtaccc gccgacacca aactctccaa aatcaagacc     420
ctgcgcctgg ccaccagcta catcgcctac ctcatggacc tgctggccaa ggacgaccag     480
aatggcgagg cggaggcctt caaggcagag atcaagaaga ccgacgtgaa agaggagaag     540
aggaagaagg agctgaacga aatcttgaaa agcacagtga gcagcaacga caagaaaacc     600
aaaggccgga cgggctggcc gcagcacgtc tgggccctgg agctcaagca gtga           654

<210> SEQ ID NO 73
<211> LENGTH: 1422
<212> TYPE: DNA
<213> ORGANISM: Homo sapiens

<400> SEQUENCE: 73
atggggagaa aaaagattca gattacgagg attatggatg aacgtaacag acaggtgaca     60
tttacaaaga ggaaatttgg gttgatgaag aaggcttatg agctgagcgt gctgtgtgac    120
tgtgagattg cgctgatcat cttcaacagc accaacaagc tgttccagta tgccagcacc    180
gacatggaca aagtgcttct caagtacacg gagtacaacg agccgcatga gagccggaca   240
aactcagaca tcgtggagac gttgagaaag aagggcctta atggctgtga cagcccagac   300
cccgatgcgg acgattccgt aggtcacagc cctgagtctg aggacaagta caggaaaatt   360
aacgaagata ttgatctaat gatcagcagg caaagattgt gtgctgttcc acctcccaac   420
ttcgagatgc cagtctccat cccagtgtcc agcacaacaa gtttggtgta cagcaaccct   480
gtcagctcac tgggaaaccc caacctattg ccactggctc accttctct gcagaggaat   540
agtatgtctc ctggtgtaac acatcgacct ccaagtgcag gtaacacagg tggtctgatg   600
ggtggagacc tcacgtctgg tgcaggcacc agtgcaggga cgggtatgg caatccccga   660
aactcaccag gtctgctggt ctcacctggt aacttgaaca agaatatgca agcaaaatct   720
cctcccccaa tgaatttagg aatgaataac cgtaaaccag atctccgagt tcttattcca   780
ccaggcagca gaatacgat gccatcagtg tctgaggatg tcgacctgct tttgaatcaa   840
aggataaaata actcccagtc ggctcagtca ttggctaccc cagtggtttc cgtagcaact   900
cctactttac caggacaagg aatgggagga tatccatcag ccatttcaac aacatatggt   960
accgagtact ctctgagtag tgcagacctg tcatctctgt ctgggtttaa caccgccagc  1020
gctcttcacc ttggttcagt aactggctgg caacagcaac acctacataa catgccacca  1080
tctgccctca gtcagttggg agcttgcact agcactcatt tatctcagag ttcaaatctc  1140
tccctgcctt ctactcaaag cctcaacatc aagtcagaac ctgtttctcc tcctagagac  1200
cgtaccacca cccttcgag ataccacaa cacacgcgcc acgaggcggg agatctcct   1260
gttgacagct tgagcagctg tagcagttcg tacgacggga gcgaccgaga ggatcaccgg  1320
aacgaattcc actcccccat ggactcacc agaccttcgc cggacgaaag ggaaagtccc  1380
tcagtcaagc gcatgcgact ttctgaagga tgggcaacat ga                    1422
```

-continued

<210> SEQ ID NO 74
<211> LENGTH: 1050
<212> TYPE: DNA
<213> ORGANISM: Homo sapiens

<400> SEQUENCE: 74

| atggccgacg | cagacgaggg | ctttggcctg | gcgcacacgc | tctggagcc | tgacgcaaaa | 60 |
| gacctgccct | gcgattcgaa | acccgagagc | gcgctcgggg | ccccagcaa | gtccccgtcg | 120 |
| tccccgcagg | ccgccttcac | ccagcagggc | atggagggaa | tcaaagtgtt | tctccatgaa | 180 |
| agagaactgt | ggctaaaatt | ccacgaagtg | ggcacggaaa | tgatcataac | caaggctgga | 240 |
| aggcggatgt | tcccagtta | caaagtgaag | gtgacgggcc | ttaatcccaa | aacgaagtac | 300 |
| attcttctca | tggacattgt | acctgccgac | gatcacagat | acaaattcgc | agataataaa | 360 |
| tggtctgtga | cgggcaaagc | tgagcccgcc | atgcctggcc | gcctgtacgt | gcacccagac | 420 |
| tcccccgcca | ccggggcgca | ttggatgagg | cagctcgtct | ccttccagaa | actcaagctc | 480 |
| accaacaacc | acctggaccc | atttgggcat | attattctaa | attccatgca | caaataccag | 540 |
| cctagattac | acatcgtgaa | agcggatgaa | aataatggat | ttggctcaaa | aaatacagcg | 600 |
| ttctgcactc | acgtcttttcc | tgagactgcg | tttatagcag | tgacttccta | ccagaaccac | 660 |
| aagatcacgc | aattaaagat | tgagaataat | ccctttgcca | aaggatttcg | ggcagtgat | 720 |
| gacatggagc | tgcacagaat | gtcaagaatg | caaagtaaag | aatatcccgt | ggtccccagg | 780 |
| agcaccgtga | ggcaaaaagt | ggcctccaac | cacagtcctt | tcagcagcga | gtctcgagct | 840 |
| ctctccacct | catccaattt | ggggtcccaa | taccagtgtg | agaatggtgt | ttccggcccc | 900 |
| tcccaggacc | tcctgcctcc | acccaaccca | tacccactgc | cccaggagca | tagccaaatt | 960 |
| taccattgta | ccaagaggaa | aggtgagtgt | gatcaccct | ggtcaatttg | ctttctttct | 1020 |
| tacctttttcc | tttccttggg | ttgggggtga | | | | 1050 |

<210> SEQ ID NO 75
<211> LENGTH: 645
<212> TYPE: DNA
<213> ORGANISM: Homo sapiens

<400> SEQUENCE: 75

| atgacgcctc | aaccctcggg | tgcgcccact | gtccaagtga | cccgtgagac | ggagcggtcc | 60 |
| ttccccagag | cctcggaaga | cgaagtgacc | tgccccacgt | ccgccccgcc | cagccccact | 120 |
| cgcacacggg | ggaactgcgc | agaggcggaa | gagggaggct | gccgaggggc | cccgaggaag | 180 |
| ctccgggcac | ggcgcgggg | acgcagccgg | cctaagagcg | agttggcact | gagcaagcag | 240 |
| cgacggagtc | ggcgaaagaa | ggccaacgac | cgcgagcgca | atcgaatgca | caacctcaac | 300 |
| tcggcactgg | acgccctgcg | cggtgtcctg | cccaccttcc | cagacgacgc | gaagctcacc | 360 |
| aagatcgaga | cgctgcgctt | cgcccacaac | tacatctggg | cgctgactca | aacgctgcgc | 420 |
| atagcggacc | acagcttgta | cgcgctggag | ccgccggcgc | cgcactgcgg | ggagctgggc | 480 |
| agcccaggcg | gttccccgg | ggactggggg | tccctctact | cccagtctc | ccaggctggc | 540 |
| agcctgagtc | ccgccgcgtc | gctggaggag | cgacccgggc | tgctgggggc | cacctttttcc | 600 |
| gcctgcttga | gccaggcag | tctggctttc | tcagattttc | tgtga | | 645 |

<210> SEQ ID NO 76
<211> LENGTH: 1032
<212> TYPE: DNA
<213> ORGANISM: Homo sapiens

<400> SEQUENCE: 76

```
atgaaccagc ttgggggct ctttgtgaat ggccggcccc tgcctctgga tacccggcag      60
cagattgtgc ggctagcagt cagtggaatg cggccctgtg acatctcacg gatccttaag    120
gtatctaatg gctgtgtgag caagatccta gggcgttact accgcacagg tgtcttggag    180
ccaaagggca ttgggggaag caagccacgg ctggctacac cccctgtggt ggctcgaatt    240
gcccagctga aggtgagtg tccagccctc tttgcctggg aaatccaacg ccagctttgt    300
gctgaagggc tttgcaccca ggacaagact cccagtgtct cctccatcaa ccgagtcctg    360
cgggcattac aggaggacca gggactaccg tgcacacggc tcaggtcacc agctgttttg    420
gctccagctg tcctcactcc ccatagtggc tctgagactc cccggggtac ccacccaggg    480
accggccacc ggaatcggac tatcttctcc ccaagccaag cagaggcact ggagaaagag    540
ttccagcgtg ggcagtatcc tgattcagtg gcccgtggaa agctggctac tgccacctct    600
ctgcctgagg acacggtgag ggtctggttt ccaacagaa gagccaaatg gcgtcggcaa    660
gagaagctca gtgggaaat gcagctgcca ggtgcttccc aggggctgac tgtaccaagg    720
gttgccccag gaatcatctc tgcacagcag tcccctggca gtgtgccac agcagccctg    780
cctgccctgg aaccactggg tccctcctgc tatcagctgt gctgggcaac agcaccagaa    840
aggtgtctga gtgacacccc acctaaagcc tgtctcaagc cctgctgggg ccacttgccc    900
ccacagccga attccctgga ctcaggactg ctttgccttc cttgcccttc ctcccactgt    960
cacctggcca gtcttagtgg ctctcaggcc ctgctctggc ctggctgccc actactgtat   1020
ggcttggaat ga                                                       1032
```

<210> SEQ ID NO 77
<211> LENGTH: 852
<212> TYPE: DNA
<213> ORGANISM: Homo sapiens

<400> SEQUENCE: 77

```
atgaacggcg aggagcagta ctacgcggcc acgcagcttt acaaggaccc atgcgcgttc     60
cagcgaggcc cggcgccgga gttcagcgcc agccccctg cgtgcctgta catgggccgc    120
cagccccgc cgccgccgcc gcacccgttc cctggcgccc tgggcgcgct ggagcagggc    180
agccccccgg acatctcccc gtacgaggtg ccccccctcg ccgacgaccc cgcggtggcg    240
caccttcacc accacctccc ggctcagctc gcgctccccc acccgcccgc cgggcccttc    300
ccggagggag ccgagccggg cgtcctggag gagcccaacc gcgtccagct gccttcccca    360
tggatgaagt ctaccaaagc tcacgcgtgg aaaggccagt gggcaggcgg cgcctacgct    420
gcggagccgg aggagaacaa gcggacgcgc acggcctaca gcgcgcacac gctgctagag    480
ctggagaagg agttcctatt caacaagtac atctcacggc cgcgccgggt ggagctggct    540
gtcatgttga acttgaccga gagacacatc aagatctggt tccaaaaccg ccgcatgaag    600
tggaaaaagg aggaggacaa gaagcgcggc ggcgggacag ctgtcggggg tggcgggtc    660
gcggagcctg agcaggactg cgccgtgacc tccggcgagg agcttctggc gctgccgccg    720
ccgccgcccc ccgaggtgc tgtgccgccc gctgccccg ttgccgcccg agagggccgc    780
ctgccgcctg gccttagcgc gtcgccacag ccctccagcg tcgcgcctcg gcggccgcag    840
gaaccacgat ga                                                       852
```

<210> SEQ ID NO 78
<211> LENGTH: 1530

```
<212> TYPE: DNA
<213> ORGANISM: Homo sapiens

<400> SEQUENCE: 78
atgaatctcc tggaccccctt catgaagatg accgacgagc aggagaaggg cctgtccggc      60
gcccccagcc ccaccatgtc cgaggactcc gcgggctcgc cctgcccgtc gggctccggc     120
tcggacaccg agaacacgcg gccccaggag aacacgttcc ccaagggcga gcccgatctg     180
aagaaggaga gcgaggagga caagttcccc gtgtgcatcc gcgaggcggt cagccaggtg     240
ctcaaaggct acgactggac gctggtgccc atgccggtgc gcgtcaacgg ctccagcaag     300
aacaagccgc acgtcaagcg gcccatgaac gccttcatgg tgtgggcgca ggcggcgcgc     360
aggaagctcg cggaccagta cccgcacttg cacaacgccg agctcagcaa gacgctgggc     420
aagctctgga gacttctgaa cgagagcgag aagcggccct cgtggagga ggcggagcgg      480
ctgcgcgtgc agcacaagaa ggaccacccg gattacaagt accagccgcg gcggaggaag     540
tcggtgaaga cgggcaggc ggaggcagag gaggccacgg agcagacgca catctccccc      600
aacgccatct tcaaggcgct gcaggccgac tcgccacact cctcctccgg catgagcgag     660
gtgcactccc ccggcgagca ctcgggggcaa tcccagggcc caccgacccc acccaccacc     720
cccaaaaccg acgtgcagcc gggcaaggct gacctgaagc gagaggggcg cccccttgcca    780
gaggggggca gacagccccc tatcgacttc cgcgacgtgg acatcggcga gctgagcagc     840
gacgtcatct ccaacatcga gaccttcgat gtcaacgagt ttgaccagta cctgccgccc     900
aacggccacc ggggggtgcc ggccacgcac ggccaggtca cctacacggg cagctacggc     960
atcagcagca ccgcggccac cccggcgagc gcgggccacg tgtggatgtc caagcagcag    1020
gcgccgccgc caccccgca gcagcccca caggccccgc cggccccgca ggcgcccccg       1080
cagccgcagg cggcgccccc acagcagccg gcggcacccc cgcagcagcc acaggcgcac    1140
acgctgacca cgctgagcag cgagccgggc cagtcccagc gaacgcacat caagacggag    1200
cagctgagcc ccagccacta cagcgagcag cagcagcact cgccccaaca gatcgcctac    1260
agccccttca acctcccaca ctacagcccc tcctacccgc ccatcacccg ctcacagtac    1320
gactacaccg accaccagaa ctccagctcc tactacagcc acgcgggcagg ccagggcacc    1380
ggcctctact ccaccttcac ctacatgaac cccgctcagc gccccatgta caccccccatc    1440
gccgacacct ctgggtccc ttccatcccg cagacccaca gcccccagca ctgggaacaa     1500
cccgtctaca cacagctcac tcgaccttga                                      1530

<210> SEQ ID NO 79
<211> LENGTH: 807
<212> TYPE: DNA
<213> ORGANISM: Homo sapiens

<400> SEQUENCE: 79
atgccgcgct ccttcctggt caagaagcat ttcaacgcct ccaaaaagcc aaactacagc       60
gaactggaca cacatacagt gattatttcc ccgtatctct atgagagtta ctccatgcct     120
gtcataccac aaccagagat cctcagctca ggagcataca gccccatcac tgtgtggact     180
accgctgctc cattccacgc ccagctaccc aatggcctct ctcctctttc cggatactcc     240
tcatctttgg ggcgagtgag tcccccctcct ccatctgaca cctcctccaa ggaccacagt    300
ggctcagaaa gccccattag tgatgaagag gaaagactac agtccaagct ttcagacccc    360
catgccattg aagctgaaaa gtttcagtgc aatttatgca ataagacctta ttcaactttt   420
```

| | |
|---|---|
| tctgggctgg ccaaacataa gcagctgcac tgcgatgccc agtctagaaa atctttcagc | 480 |
| tgtaaatact gtgacaagga atatgtgagc ctgggcgccc tgaagatgca tattcggacc | 540 |
| cacacattac cttgtgtttg caagatctgc ggcaaggcgt tttccagacc ctggttgctt | 600 |
| caaggacaca ttagaactca cacggggag aagccttttt cttgccctca ctgcaacaga | 660 |
| gcatttgcag acaggtcaaa tctgagggct catctgcaga cccattctga tgtaaagaaa | 720 |
| taccagtgca aaaactgctc caaaaccttc tccagaatgt ctctcctgca caaacatgag | 780 |
| gaatctggct gctgtgtagc acactga | 807 |

<210> SEQ ID NO 80
<211> LENGTH: 1062
<212> TYPE: DNA
<213> ORGANISM: Homo sapiens

<400> SEQUENCE: 80

| | |
|---|---|
| atggccgcgg agctggcgat gggcgccgag ctgcccagca gcccgctggc catcgagtac | 60 |
| gtcaacgact tcgacctgat gaagttcgag gtgaagaagg agcctcccga ggccgagcgc | 120 |
| ttctgccacc gcctgccgcc aggctcgctg tcctcgacgc cgctcagcac gccctgctcc | 180 |
| tccgtgccct cctcgcccag cttctgcgcg cccagcccgg caccggcgg cggcggcggc | 240 |
| gcggggggcg gcggcggctc gtctcaggcc ggggcgccc ccgggccgcc gagcgggggc | 300 |
| cccggcgccg tcgggggcac ctcggggaag ccggcgctgg aggatctgta ctggatgagc | 360 |
| ggctaccagc atcacctcaa ccccgaggcg ctcaacctga cgcccgagga cgcggtggag | 420 |
| gcgctcatcg cagcggcca ccacggcgcg caccacggcg cgcaccaccc ggcggccgcc | 480 |
| gcagcctacg aggctttccg cggcccgggc ttcgcgggcg cggcggagc ggacgacatg | 540 |
| ggcgccggcc accaccacgg cgcgcaccac gccgcccacc atcaccacgc cgcccaccac | 600 |
| caccaccacc accaccacca ccatggcggc gcgggacacg gcggtggcgc gggccaccac | 660 |
| gtgcgcctgg aggagcgctt ctccgacgac cagctggtgt ccatgtcggt gcgcgagctg | 720 |
| aaccggcagc tccgcggctt cagcaaggag gaggtcatcc ggctcaagca gaagcggcgc | 780 |
| acgctcaaga accgcggcta cgcgcagtcc tgccgcttca gcgggtgca gcagcggcac | 840 |
| attctggaga gcgagaagtg ccaactccag agccaggtgg agcagctgaa gctggaggtg | 900 |
| gggcgcctgg ccaaagagcg ggacctgtac aaggagaaat acgagaagct ggcgggccgg | 960 |
| ggcggccccg ggagcgcggg cggggccggt tcccgcgggg agccttcgcc gccgcaggcc | 1020 |
| ggtcccggcg ggccaagggg cacggccgac ttcttcctgt ag | 1062 |

<210> SEQ ID NO 81
<211> LENGTH: 1071
<212> TYPE: DNA
<213> ORGANISM: Homo sapiens

<400> SEQUENCE: 81

| | |
|---|---|
| atgaccaaat cgtacagcga gagtgggctg atgggcgagc ctcagcccca aggtcctcca | 60 |
| agctggacag acgagtgtct cagttctcag gacgaggagc acgaggcaga caagaaggag | 120 |
| gacgacctcg aagccatgaa cgcagaggag gactcactga ggaacggggg agaggaggag | 180 |
| gacgaagatg aggacctgga agaggaggaa gaagaggaag aggaggatga cgatcaaaag | 240 |
| cccaagagac gcggccccaa aaagaagaag atgactaagg ctcgcctgga gcgttttaaa | 300 |
| ttgagacgca tgaaggctaa cgcccgggag cggaaccgca tgcacggact gaacgcggcg | 360 |
| ctagacaacc tgcgcaaggt ggtgccttgc tattctaaga cgcagaagct gtccaaaatc | 420 |

| | |
|---|---|
| gagactctgc gcttggccaa gaactacatc tgggctctgt cggagatcct gcgctcaggc | 480 |
| aaaagcccag acctggtctc cttcgttcag acgctttgca agggcttatc ccaacccacc | 540 |
| accaacctgg ttgcgggctg cctgcaactc aatcctcgga cttttctgcc tgagcagaac | 600 |
| caggacatgc cccccacct gccgacggcc agcgcttcct tccctgtaca cccctactcc | 660 |
| taccagtcgc ctgggctgcc cagtccgcct tacggtacca tggacagctc ccatgtcttc | 720 |
| cacgttaagc ctccgccgca cgcctacagc gcagcgctgg agcccttctt tgaaagccct | 780 |
| ctgactgatt gcaccagccc ttcctttgat ggacccctca gcccgccgct cagcatcaat | 840 |
| ggcaacttct ctttcaaaca cgaaccgtcc gccgagtttg agaaaaatta tgcctttacc | 900 |
| atgcactatc ctgcagcgac actggcaggg gcccaaagcc acggatcaat cttctcaggc | 960 |
| accgctgccc ctcgctgcga gatccccata gacaatatta tgtccttcga tagccattca | 1020 |
| catcatgagc gagtcatgag tgcccagctc aatgccatat ttcatgatta g | 1071 |

<210> SEQ ID NO 82
<211> LENGTH: 768
<212> TYPE: DNA
<213> ORGANISM: Homo sapiens

<400> SEQUENCE: 82

| | |
|---|---|
| atggacgtga tggatggctg ccagttctca ccttctgagt acttctacga cggctcctgc | 60 |
| ataccgtccc ccgagggtga atttggggac gagtttgtgc cgcgagtggc tgccttcgga | 120 |
| gcgcacaaag cagagctgca gggctcgat gaggacgagc acgtgcgagc gcctaccggc | 180 |
| caccaccagg ctggtcactg cctcatgtgg gcctgcaaag cctgcaagag gaagtccacc | 240 |
| accatggatc ggcggaaggc agccactatg cgcgagcgga ggcgcctgaa gaaggtcaac | 300 |
| caggctttcg aaaccctcaa gaggtgtacc acgaccaacc caaccagag gctgcccaag | 360 |
| gtggagatcc tcaggaatgc catccgctac atcgagagcc tgcaggagtt gctgagagag | 420 |
| caggtggaga actactatag cctgccggga cagagctgct cggagcccac cagccccacc | 480 |
| tccaactgct ctgatggcat gcccgaatgt aacagtcctg tctggtccag aaagagcagt | 540 |
| acttttgaca gcatctactg tcctgatgta tcaaatgtat atgccacaga taaaaactcc | 600 |
| ttatccagct tggattgctt atccaacata gtggaccgga tcacctcctc agagcaacct | 660 |
| gggttgcctc tccaggatct ggcttctctc tctccagttg ccagcaccga ttcacagcct | 720 |
| gcaactccag gggcttctag ttccaggctt atctatcatg tgctatga | 768 |

<210> SEQ ID NO 83
<211> LENGTH: 3831
<212> TYPE: DNA
<213> ORGANISM: Homo sapiens

<400> SEQUENCE: 83

| | |
|---|---|
| atgcgatcca aggcgagggc gaggaagcta gccaaaagtg acggtgacgt tgtaaataat | 60 |
| atgtatgagc ccaaccggga cctgctggcc agccacagcg cggaggacga ggccgaggac | 120 |
| agtgccatgt cgcccatccc cgtggggtca ccgcccccct tccccaccag cgaggacttc | 180 |
| acccccaagg agggctcgcc gtacgaggcc ctgtctacaa ttcctgaaga cattccgatc | 240 |
| ccagcagact tcgagctccg agagtcctcc atcccagggg ctggcctggg ggtctgggcc | 300 |
| aagaggaaga tggaagccgg ggagaggctg gggccctgcg tggtggtgcc ccgggcggcg | 360 |
| gcaaaggaga cagacttcgg atgggagcaa atactgacgg acgtggaagt gtcgcccag | 420 |

-continued

```
gaaggctgca tcacaaagat ctccgaagac ctgggcagtg agaagttctg cgtggatgca    480
aatcaggcgg gggctggcag ctggctcaag tacatccgtg tggcgtgctc ctgcgatgac    540
cagaacctca ccatgtgtca gatcagtgag caggtaattt actataaagt cattaaggac    600
attgagccag gtgaggagct gctggtgcac gtgaaggaag cgtctaccc cctgggcaca     660 gtgccgcccg gcctggacga ggagcccacg ttccgctgtg acgagtgtga cgaactcttc    720
cagtccaagc tggacctgcg cgcgccataag aagtacacgt gtggctcagt ggggctgcg    780 ctctacgagg gcctggctga ggagctcaag cccgagggcc ttggcggtgg cagcggccaa    840
gcccacgagt gcaaggactg cgagcggatg ttccccaaca agtacagcct ggagcagcac    900
atggtcatcc acacggagga gcgcgagtac aaatgcgacc agtgtcccaa ggccttcaac    960
tggaagtcca acttcatccg ccaccagatg tcccacgaca gcggcaaacg cttcgaatgt    1020
gaaaactgcg tgaaggtgtt cacggacccc agcaaccttc agcggcacat ccgctcgcag    1080
cacgtgggcg ctcgggccca cgcctgcccc gactgcggga agaccttcgc cacgtcctcc    1140
ggcctcaagc agcacaagca tatccacagc acggtgaagc cttttcatatg tgaggtctgc    1200 cacaagtcct acacgcagtt ctccaacctg tgccggcaca agcggatgca cgccgactgc    1260
cgcacgcaga tcaagtgcaa ggactgtggc cagatgttca gcactacctc ctccctcaac    1320
aagcaccggc gcttctgcga gggcaagaac cattacacgc cgggcggcat ctttgccccg    1380
ggcctgccct tgaccccag ccccatgatg acaaggcaa aaccctcccc cagcctcaat     1440
cacgccagcc tgggcttcaa cgagtacttt ccctacaggc cgcacccggg gagcctgccc    1500
ttctccacgg cgcctccac gttccccgca ctcaccccccg gcttcccggg catcttccct    1560
ccatccttgt accccccggcc gcctctgcta cctcccacat cgctgctcaa gagccccctg    1620
aaccacaccc aggacgccaa gctccccagt cccctgggga cccagccct gcccctggtc    1680 tccgccgtca gcaacagcag ccagggcacg acggcagctg cggggcccga ggagaagttc    1740
gagagccgcc tggaggactc ctgtgtggag aagctgaaga ccaggagcag cgacatgtcg    1800
gacggcagtg actttgagga cgtcaacacc accacggggga ccgacctgga cacgaccacg    1860
gggacgggct cggacctgga cagcgacgtg gacagcgacc ctgacaagga caagggcaag    1920
ggcaagtccg ccgagggcca gcccaagttt gggggcggct tggcgccccc ggggggccccg   1980 aacagcgtgg ccgaggtgcc tgtcttctat tcccagcact cattcttccc gccacccgac    2040
gagcagctgc tgactgcaac gggcgccgcc ggggactcca tcaaggccat cgcatccatt    2100
gccgagaagt actttggccc cggcttcatg gggatgcagg agaagaagct gggctcgctc    2160
ccctaccact cggcgttccc cttccagttc ctgcccaact tccccccactc cctttacccc    2220 ttcacggacc gagccctcgc ccacaacttg ctggtcaagg ccgagccaaa gtcacccccgg   2280 gacgccctca aggtgggcgg ccccagtgcc gagtgccccct tgatctcac caccaagccc    2340 aaagacgtga agcccatcct gcccatgccc aagggcccct cggccccccgc atccggcgag    2400 gagcagccgc tggacctgag catcggcagc cgggcccgtg ccagccaaaa cggcggcggg    2460
cgggagcccc gcaagaacca cgtctatggg gaacgcaagc tgggcgccgg cgaggggctg    2520
ccccaggtgt gccggcgcg gatgcccag cagccccgc tccactacgc caagccctcg      2580
cccttcttca tggaccccat ctacagggta gaaaagcgga aggtcacaga ccccgtggga    2640
gccctgaagg agaagtacct gcggccgtcc ccgctgctct ccaccccca gatgtcagcc    2700 atagagacca tgacagagaa gctggagagc tttgcagcca tgaaggcgga ctcgggcagc    2760
tccctgcagc cctccccca ccacccttc aacttccggt cccacccccc aacgctctcc      2820
```

```
gacccccatcc tcaggaaggg caaggagcga tacacgtgca ggtactgtgg aagatcttc    2880 cccagatcag ccaatctcac cagacacctg aggacgcaca ctggggagca gccgtacagg    2940
tgtaagtact gcgaccgctc cttcagcatc tcttcgaacc tccagcggca cgtccggaac    3000
atccacaaca aggagaagcc tttcaagtgc cacctgtgca accgctgctt cgggcagcag    3060
accaacctgg accggcacct caagaagcac gagcacgaga acgcaccagt gagccagcac    3120
cccggggtcc tcacgaacca cctggggacc agcgcgtcct ctcccacctc agagtcggac    3180
aaccacgcac ttttagacga gaaagaagac tcttatttct cggaaatcag aaactttatt    3240
gccaatagtg agatgaacca agcatcaacg cgaacagaga acgggcggga catgcagatc    3300
gtggacggca gtgcccagtg tccaggccta gccagtgaga agcaggagga cgtggaggag    3360
gaggacgacg atgacctgga ggaggacgat gaggacagcc tggccgggaa gtcgcaggat    3420
gacaccgtgt cccccgcacc cgagcccag gccgcctacg aggatgagga ggatgaggag    3480
ccagccgcct ccctggccgt gggctttgac cacacccgaa ggtgtgctga ggaccacgaa    3540
ggcggtctgt tagctttgga gccgatgccg acttttggga aggggctgga cctccgcaga    3600
gcagctgagg aagcatttga agttaaagat gtgcttaatt ccaccttaga ttctgaggct    3660
ttaaaacata cactgtgcag gcaggctaag aaccaggcat atgcaatgat gctgtccctt    3720
tccgaagaca ctcctctcca caccccctcc cagggttctc tggacgcttg gttgaaggtc    3780
actggagcca cgtcggagtc tggagcattt caccccatca accacctctg a            3831

<210> SEQ ID NO 84
<211> LENGTH: 1311
<212> TYPE: DNA
<213> ORGANISM: Homo sapiens

<400> SEQUENCE: 84
atgcagaaca gtcacagcgg agtgaatcag ctcggtggtg tctttgtcaa cgggcggcca      60
ctgccggact ccacccggca gaagattgta gagctagctc acagcggggc ccggccgtgc     120
gacatttccc gaattctgca gacccatgca gatgcaaaag tccaagtgct ggacaatcaa     180
aacgtgtcca acggatgtgt gagtaaaatt ctgggcaggt attacgagac tggctccatc     240
agacccaggg caatcggtgg tagtaaaccg agagtagcga ctccagaagt tgtaagcaaa     300
atagcccagt ataagcggga gtgcccgtcc atctttgctt gggaaatccg agacagatta     360
ctgtccgagg gggtctgtac caacgataac ataccaagcg tgtcatcaat aaacagagtt     420
cttcgcaacc tggctagcga aaagcaacag atgggcgcag acggcatgta tgataaacta     480
aggatgttga acgggcagac cggaagctgg ggcacccgcc ctggttggta tccggggact     540
tcggtgccag gcaacctac gcaagatggc tgccagcaac aggaaggagg gggagagaat     600
accaactcca tcagttccaa cggagaagat tcagatgagg ctcaaatgcg acttcagctg     660
aagcggaagc tgcaaagaaa tagaacatcc tttacccaag agcaaattga ggccctggag     720
aaagagtttg agagaaccca ttatccagat gtgtttgccc gagaaagact agcagccaaa     780
atagatctac ctgaagcaag aatacaggta tggttttcta atcgaaggc caaatggaga     840 agagaagaaa aactgaggaa tcagagaaga caggccagca acacacctag tcatattcct     900
atcagcagta gtttcagcac cagtgtctac caaccaattc cacaacccac cacaccggtt     960
tcctccttca catctggctc catgttgggc cgaacagaca cagccctcac aaacacctac    1020
agcgctctgc cgcctatgcc cagcttcacc atggcaaata acctgcctat gcaaccccca    1080
```

```
gtccccagcc agacctcctc atactcctgc atgctgccca ccagcccttc ggtgaatggg    1140
cggagttatg atacctacac ccccccacat atgcagacac acatgaacag tcagccaatg    1200
ggcacctcgg gcaccacttc aacaggactc atttcccctg tgtgtcagt tccagttcaa     1260 gttcccggaa gtgaacctga tatgtctcaa tactggccaa gattacagta a             1311
```

<210> SEQ ID NO 85
<211> LENGTH: 1896
<212> TYPE: DNA
<213> ORGANISM: Homo sapiens

<400> SEQUENCE: 85

```
atggtttcta aactgagcca gctgcagacg gagctcctgg cggccctgct cgagtcaggg    60
ctgagcaaag aggcactgat ccaggcactg ggtgagccgg ggccctacct cctggctgga    120
gaaggccccc tggacaaggg ggagtcctgc ggcggcggtc gaggggagct ggctgagctg    180
cccaatgggc tggggagac tcggggctcc gaggacgaga cggacgacga tggggaagac    240
ttcacgccac ccatcctcaa agagctggag aacctcagcc ctgaggaggc ggcccaccag    300
aaagccgtgg tggagaccct tctgcaggag gacccgtggc gtgtggcgaa gatggtcaag    360
tcctacctgc agcagcacaa catcccacag cgggaggtgg tcgataccac tggcctcaac    420
cagtcccacc tgtcccaaca cctcaacaag ggcactccca tgaagacgca gaagcgggcc    480
gccctgtaca cctggtacgt ccgcaagcag cgagaggtgg cgcagcagtt cacccatgca    540
gggcagggag ggctgattga agagcccaca ggtgatgagc taccaaccaa gaaggggcgg    600
aggaaccgtt tcaagtgggg cccagcatcc cagcagatcc tgttccaggc ctatgagagg    660
cagaagaacc ctagcaagga ggagcgagag acgctagtgg aggagtgcaa tagggcggaa    720
tgcatccaga gaggggtgtc cccatcacag gcacaggggc tgggctccaa cctcgtcacg    780
gaggtgcgtg tctacaactg gtttgccaac cggcgcaaag aagaagcctt ccggcacaag    840
ctggccatgg acacgtacag cgggcccccc caggggccag gcccgggacc tgcgctgccc    900
gctcacagct cccctggcct gcctccacct gccctctccc ccagtaaggt ccacggtgtg    960
cgctatggac agcctgcgac cagtgagact gcagaagtac cctcaagcag cggcggtccc    1020
ttagtgacag tgtctacacc cctccaccaa gtgtccccca cgggcctgga gcccagccac    1080
agcctgctga gtacagaagc caagctggtc tcagcagctg ggggcccct cccccctgtc    1140 agcaccctga cagcactgca cagcttggag cagacatccc caggcctcaa ccagcagccc    1200
cagaacctca tcatggcctc acttcctggg gtcatgacca tcgggcctgg tgagcctgcc    1260
tccctgggtc ctacgttcac caacacaggt gcctccaccc tggtcatcgg cctggcctcc    1320
acgcaggcac agagtgtgcc ggtcatcaac agcatgggca gcagcctgac cacccctgcag   1380 cccgtccagt tctcccagcc gctgcacccc tcctaccagc agccgctcat gcacctgtg     1440 cagagccatg tgacccagag ccccttcatg gccaccatgg ctcagctgca gagccccac     1500 gccctctaca gccacaagcc cgaggtggcc cagtacaccc acgggcct gctcccgcag      1560 actatgctca tcaccgacac caccaacctg agcgccctgg ccagcctcac gccaccaag     1620 caggtcttca cctcagacac tgaggcctcc agtgagtccg gcttcacac gccggcatct    1680 caggccacca ccctccacgt ccccagccag gaccctgccg gcatccagca cctgcagccg   1740
gcccaccggc tcagcgccag ccccacagtg tcctccagca gctggtgct gtaccagagc   1800 tcagactcca gcaatggcca gagccacctg ctgcctcag accacagcgt catcgagacc    1860
ttcatctcca cccagatggc ctcttcctcc cagtaa                              1896
```

<210> SEQ ID NO 86
<211> LENGTH: 1053
<212> TYPE: DNA
<213> ORGANISM: Homo sapiens

<400> SEQUENCE: 86

| | | | | | |
|---|---|---|---|---|---|
| atgctgggct | cagtgaagat | ggaggcccat | gacctggccg | agtggagcta | ctacccggag | 60 |
| gcgggcgagg | tctactcgcc | ggtgacccca | gtgcccacca | tggccccct | caactcctac | 120 |
| atgaccctga | atcctctaag | ctctccctat | cccctgggg | gctccctgc | ctccccactg | 180 |
| ccctcaggac | ccctggcacc | cccagcacct | gcagcccccc | tggggcccac | tttcccaggc | 240 |
| ctgggtgtca | gcggtggcag | cagcagctcc | gggtacgggg | cccgggtcc | tgggctggtg | 300 |
| cacgggaagg | agatgccgaa | ggggtatcgg | cggccctgg | cacacgccaa | gccaccgtat | 360 |
| tcctatatct | cactcatcac | catggccatc | agcaggcgc | cgggcaagat | gctgaccttg | 420 |
| agtgaaatct | accagtggat | catggacctc | ttcccttact | accgggagaa | tcagcagcgc | 480 |
| tggcagaact | ccattcgcca | ctcgctgtct | ttcaacgact | gcttcgtcaa | ggtggcgcgt | 540 |
| tccccagaca | agcctggcaa | gggctcctac | tgggccctac | accccagctc | aggaacatg | 600 |
| tttgagaatg | gctgctacct | gcgccgccag | aaacgcttca | agctggagga | gaaggtgaaa | 660 |
| aaagggggca | gcggggctgc | caccaccacc | aggaacggga | cagggtctgc | tgcctcgacc | 720 |
| accaccccg | cggccacagt | cacctcccg | cccagcccc | cgcctccagc | ccctgagcct | 780 |
| gaggcccagg | gcggggaaga | tgtggggggct | ctggactgtg | gctcacccgc | ttcctccaca | 840 |
| ccctatttca | ctggcctgga | gctcccaggg | gagctgaagc | tggacgcgcc | ctacaacttc | 900 |
| aaccaccctt | tctccatcaa | caacctaatg | tcagaacaga | caccagcacc | tcccaaactg | 960 |
| gacgtggggt | ttgggggcta | cggggctgaa | ggtggggagc | ctggagtcta | ctaccagggc | 1020 |
| ctctattccc | gctctttgct | taatgcatcc | tag | | | 1053 |

<210> SEQ ID NO 87
<211> LENGTH: 1053
<212> TYPE: DNA
<213> ORGANISM: Homo sapiens

<400> SEQUENCE: 87

| | | | | | |
|---|---|---|---|---|---|
| atgctgggct | cagtgaagat | ggaggcccat | gacctggccg | agtggagcta | ctacccggag | 60 |
| gcgggcgagg | tctactcgcc | ggtgacccca | gtgcccacca | tggccccct | caactcctac | 120 |
| atgaccctga | atcctctaag | ctctccctat | cccctgggg | gctccctgc | ctccccactg | 180 |
| ccctcaggac | ccctggcacc | cccagcacct | gcagcccccc | tggggcccac | tttcccaggc | 240 |
| ctgggtgtca | gcggtggcag | cagcagctcc | gggtacgggg | cccgggtcc | tgggctggtg | 300 |
| cacgggaagg | agatgccgaa | ggggtatcgg | cggccctgg | cacacgccaa | gccaccgtat | 360 |
| tcctatatct | cactcatcac | catggccatc | agcaggcgc | cgggcaagat | gctgaccttg | 420 |
| agtgaaatct | accagtggat | catggacctc | ttcccttact | accgggagaa | tcagcagcgc | 480 |
| tggcagaact | ccattcgcca | ctcgctgtct | ttcaacgact | gcttcgtcaa | ggtggcgcgt | 540 |
| tccccagaca | agcctggcaa | gggctcctac | tgggccctac | accccagctc | aggaacatg | 600 |
| tttgagaatg | gctgctacct | gcgccgccag | aaacgcttca | agctggagga | gaaggtgaaa | 660 |
| aaagggggca | gcggggctgc | caccaccacc | aggaacggga | cagggtctgc | tgcctcgacc | 720 |
| accaccccg | cggccacagt | cacctcccg | cccagcccc | cgcctccagc | ccctgagcct | 780 |

```
gaggcccagg gcggggaaga tgtgggggct ctggactgtg gctcacccgc ttcctccaca    840
ccctatttca ctggcctgga gctcccaggg gagctgaagc tggacgcgcc ctacaacttc    900
aaccacccct tctccatcaa caacctaatg tcagaacaga caccagcacc tcccaaactg    960
gacgtggggt ttgggggcta cggggctgaa ggtggggagc ctggagtcta ctaccagggc   1020
ctctattccc gctctttgct taatgcatcc tag                                1053

<210> SEQ ID NO 88
<211> LENGTH: 1392
<212> TYPE: DNA
<213> ORGANISM: Homo sapiens

<400> SEQUENCE: 88
atgcactcgg cttccagtat gctgggagcg gtgaagatgg aagggcacga gccgtccgac     60
tggagcagct actatgcaga gcccgagggc tactcctccg tgagcaacat gaacgccggc    120
ctggggatga acggcatgaa cacgtacatg agcatgtcgg cggccgccat gggcagcggc    180
tcgggcaaca tgagcgcggg ctccatgaac atgtcgtcgt acgtgggcgc tggcatgagc    240
ccgtccctgg cggggatgtc ccccggcgcg gcgccatgg cgggcatggg cggctcggcc    300 gggcggccg gcgtggcggg catggggccg cacttgagtc ccagcctgag cccgctcggg    360 ggcaggcgg ccggggccat gggcggcctg gcccctacg ccaacatgaa ctccatgagc    420
cccatgtacg gcaggcggg cctgagccgc gcccgcgacc ccaagaccta caggcgcagc    480
tacacgcacg caaagccgcc ctactcgtac atctcgctca tcaccatggc catccagcag    540
agccccaaca gatgctgac gctgagcgag atctaccagt ggatcatgga cctcttcccc    600
ttctaccggc agaaccagca gcgctggcag aactccatcc gccactcgct ctccttcaac    660
gactgtttcc tgaaggtgcc ccgctcgccc gacaagcccg gcaagggctc cttctggacc    720
ctgcaccctg actcgggcaa catgttcgag aacggctgct acctgcgccg ccagaagcgc    780
ttcaagtgcg agaagcagct ggcgctgaag gaggccgcag gcgccgccgg cagcggcaag    840
aaggcggccg ccggagccca ggcctcacag gctcaactcg gggaggccgc cgggccggcc    900
tccgagactc cggcgggcac cgagtcgcct cactcgagcg cctccccgtg ccaggagcac    960
aagcgagggg gcctgggaga gctgaagggg acgccggctg cggcgctgag cccccagag   1020 ccggcgccct ctcccgggca gcagcagcag gccgcggccc acctgctggg cccgccccac   1080
cacccgggcc tgccgcctga ggcccacctg aagccggaac accactacgc cttcaaccac   1140
ccgttctcca tcaacaacct catgtcctcg gagcagcagc accaccacag ccaccaccac   1200
caccaacccc acaaaatgga cctcaaggcc tacgaacagg tgatgcacta ccccggctac   1260
ggttccccca tgcctggcag cttggccatg ggccgggtca cgaacaaaac gggcctggac   1320
gcctcgcccc tggccgcaga tacctcctac taccaggggg tgtactcccg gcccattatg   1380
aactcctctt aa                                                       1392

<210> SEQ ID NO 89
<211> LENGTH: 1035
<212> TYPE: DNA
<213> ORGANISM: Homo sapiens

<400> SEQUENCE: 89
atgagcagcc acctgcagag ccccccgcac gcgcccagca gcgccgcctt cggctttccc     60
cggggcgcgg gccccgcgca gcctcccgcc ccacctgccg ccccggagcc gctgggcggc    120
atctgcgagc acgagacgtc catcgacatc agcgcctaca tcgacccggc cgccttcaac    180
```

```
gacgagttcc tggccgacct gttccagcac agccggcagc aggagaaggc caaggcggcc      240
gtgggcccca cgggcggcgg cggcggcggc gactttgact acccgggcgc gcccgcgggc      300
cccggcggcg ccgtcatgcc cggggagcg cacgggcccc cgcccggcta cggctgcgcg       360
gccgccggct acctgacgg caggctggag ccctgtacg agcgcgtcgg ggcgccggcg        420
ctgcggccgc tggtgatcaa gcaggagccc cgcgaggagg atgaagccaa gcagctggcg      480
ctggccggcc tcttccctta ccagccgccg ccgccgccgc cgcctcgca cccgcacccg       540 cacccgccgc ccgcgcacct ggccgccccg cacctgcagt ccagatcgc gcactgcggc      600 cagaccacca tgcacctgca gcccggtcac cccacgccgc cgcccacgcc cgtgcccagc     660
ccgcaccccg cgcccgcgct cggtgccgcc ggcctgccgg gcctggcag cgcgctcaag      720 gggctgggcg ccgcgcaccc cgacctccgc gcgagtggcg gcagcggcgc gggcaaggcc     780
aagaagtcgg tggacaagaa cagcaacgag taccgggtgc ggcgcgagcg caacaacatc     840
gcggtgcgca agagccgcga caaggccaag cagcgcaacg tggagacgca gcagaaggtg     900
ctggagctga ccagtgacaa tgaccgcctg cgcaagcggg tggaacagct gagccgcgaa     960
ctggacacgc tgcgggggcat cttccgccag ctgccagaga gctccttggt caaggccatg    1020
ggcaactgcg cgtga                                                      1035

<210> SEQ ID NO 90
<211> LENGTH: 816
<212> TYPE: DNA
<213> ORGANISM: Homo sapiens

<400> SEQUENCE: 90
atgttacagg cgtgcaaaat ggaagggttt cccctcgtcc ccctcagcc atcagaagac       60 ctggtgccct atgacacgga tctataccaa cgccaaacgc acgagtatta cccctatctc     120
agcagtgatg gggagagcca tagcgaccat tactgggact ccacccccca ccacgtgcac    180
agcgagttcg agagcttcgc cgagaacaac ttcacggagc tccagagcgt gcagccccg    240 cagctgcagc agctctaccg ccacatggag ctggagcaga tgcacgtcct cgataccccc   300
atggtgccac cccatcccag tcttggccac caggtctcct acctgccccg gatgtgcctc   360
cagtacccat ccctgtcccc agcccagccc agctcagatg aggaggaggg cgagcggcag   420
agccccccac tggaggtgtc tgacggcgag gcggatggcc tggagcccgg gcctgggctc   480
ctgcctgggg agacaggcag caagaagaag atccgcctgt accagttcct gttggacctg    540
ctccgcagcg gcgacatgaa ggacagcatc tggtgggtgg acaaggacaa gggcaccttc     600
cagttctcgt ccaagcacaa ggaggcgctg cgcaccgct ggggcatcca gaagggcaac    660
cgcaagaaga tgacctacca gaagatggcg cgcgcgctgc gcaactacgg caagacgggc    720
gaggtcaaga aggtgaagaa gaagctcacc taccagttca gcggcgaagt gctgggccgc    780
ggggggctgg ccgagcggcg ccacccgccc cactga                              816

<210> SEQ ID NO 91
<211> LENGTH: 1332
<212> TYPE: DNA
<213> ORGANISM: Homo sapiens

<400> SEQUENCE: 91
atggcgaccg cagcgtctaa ccactacagc ctgctcacct ccagcgcctc catcgtgcac       60
gccgagccgc ccggcggcat gcagcagggc gcggggggct accgcgaagc gcagagcctg     120
```

| | |
|---|---:|
| gtgcagggcg actacggcgc tctgcagagc aacggacacc cgctcagcca cgctcaccag | 180 |
| tggatcaccg cgctgtccca cggcggcggc ggcggggggcg gtggcggcgg cggggggggc | 240 |
| ggggcggcg gcggggcgg cggcgacggc tccccgtggt ccaccagccc cctgggccag | 300 |
| ccggacatca agccctcggt ggtggtgcag cagggcggcc gcggagacga gctgcacggg | 360 |
| ccaggcgccc tgcagcagca gcatcagcag cagcaacagc aacagcagca gcaacagcag | 420 |
| caacagcagc agcagcagca gcaacagcgg ccgccgcatc tggtgcacca cgccgctaac | 480 |
| caccacccgg gacccggggc atggcggagc gcggcggctg cagcgcacct cccaccctcc | 540 |
| atgggagcgt ccaacggcgg cttgctctac tcgcagccca gcttcacggt gaacggcatg | 600 |
| ctgggcgccg gcgggcagcc ggccggtctg caccaccacg gcctgcggga cgcgcacgac | 660 |
| gagccacacc atgccgacca ccacccgcac ccgcactcgc acccacacca gcagccgccg | 720 |
| cccccgccgc ccccgcaggg tccgcctggc cacccaggcg cgcaccacga cccgcactcg | 780 |
| gacgaggaca cgccgacctc ggacgacctg gagcagttcg ccaagcagtt caagcagcgg | 840 |
| cggatcaaac tgggatttac ccaagcggac gtggggctgg ctctgggcac cctgtatggc | 900 |
| aacgtgttct cgcagaccac catctgcagg tttgaggccc tgcagctgag cttcaagaac | 960 |
| atgtgcaagc tgaagccttt gttgaacaag tggttggagg aggcggactc gtcctcgggc | 1020 |
| agccccacga gcatagacaa gatcgcagcg caagggcgca agcggaaaaa gcggacctcc | 1080 |
| atcgaggtga gcgtcaaggg ggctctggag agccatttcc tcaaatgccc caagccctcg | 1140 |
| gcccaggaga tcacctcccct cgcggacagc ttacagctgg agaaggaggt ggtgagagtt | 1200 |
| tggttttgta acaggagaca gaaagagaaa aggatgaccc ctcccggagg gactctgccg | 1260 |
| ggcgccgagg atgtgtacgg ggggagtagg gacactccac cacaccacgg ggtgcagacg | 1320 |
| cccgtccagt ga | 1332 |

<210> SEQ ID NO 92
<211> LENGTH: 1470
<212> TYPE: DNA
<213> ORGANISM: Homo sapiens

<400> SEQUENCE: 92

| | |
|---|---:|
| atgctggaca tgggagatag gaaagaggtg aaaatgatcc ccaagtcctc gttcagcatc | 60 |
| aacagcctgg tgcccgaggc ggtccagaac gacaaccacc acgcgagcca cggccaccac | 120 |
| aacagccacc accccagca ccaccaccac caccaccacc atcaccacca cccgccgccg | 180 |
| cccgccccgc aaccgccgcc gccgccgcag cagcagcagc cgccgccgcc gccgcccccg | 240 |
| gcaccgcagc cccccagac gcggggcgcc ccggccgccg acgacgacaa gggcccccag | 300 |
| cagctgctgc tcccgccgcc gccaccgcca ccaccggccg ccgccctgga cggggctaaa | 360 |
| gcggacgggc tgggcggcaa gggcgagccg ggcggcgggc cggggagct ggcgcccgtc | 420 |
| gggccggacg agaaggagaa gggcgccggc gccgggggg aggagaagaa ggggcgggc | 480 |
| gagggcggca aggacgggga ggggggcaag gagggcgaga agaagaacgg caagtacgag | 540 |
| aagccgccgt tcagctacaa cgcgctcatc atgatggcca tccggcagag ccccgagaag | 600 |
| cggctcacgc tcaacggcat ctacgagttc atcatgaaga acttcccctta ctaccgcgag | 660 |
| aacaagcagg gctggcagaa ctccatccgc cacaatctgt ccctcaacaa gtgcttcgtg | 720 |
| aaggtgccgc gccactacga cgacccgggc aagggcaact actggatgct ggacccgtcg | 780 |
| agcgacgacg tgttcatcgg cggcaccacg ggcaagctgc ggcgccgctc caccacctcg | 840 |
| cgggccaagc tggccttcaa gcgcggtgcg cgcctcacct ccaccggcct caccttcatg | 900 |

```
gaccgcgccg gctccctcta ctggcccatg tcgcccttcc tgtccctgca ccaccccgc      960 gccagcagca ctttgagtta caacggcacc acgtcggcct accccagcca ccccatgcc     1020 tacagctccg tgttgactca gaactcgctg ggcaacaacc actccttctc caccgccaac    1080
ggcctgagcg tggaccggct ggtcaacggg gagatcccgt acgccacgca ccacctcacg    1140
gccgccgcgc tagccgcctc ggtgccctgc ggcctgtcgg tgccctgctc tgggacctac    1200
tccctcaacc cctgctccgt caacctgctc gcgggccaga ccagttactt tttcccccac    1260
gtcccgcacc cgtcaatgac ttcgcagagc agcacgtcca tgagcgccag gccgcgtcc     1320 tcctccacgt cgccgcaggc cccctcgacc ctgccctgtg agtctttaag accctctttg    1380 ccaagttttta cgacgggact gtctggggga ctgtctgatt atttcacaca tcaaaatcag   1440
gggtcttctt ccaacccttt aatacattaa                                    1470

<210> SEQ ID NO 93
<211> LENGTH: 1572
<212> TYPE: DNA
<213> ORGANISM: Homo sapiens

<400> SEQUENCE: 93
atggccggcc acacgcagca gccgagcggg cgcgggaacc ccaggcctgc gccctcgccc      60
tccccagtcc cagggaccgt ccccggcgcc tcggagcggg tggcgctcaa gaaggagatc     120
gggctgctga gcgcctgcac catcatcatc gggaacatca tcggctcggg catcttcatc     180
tcgcccaagg gggtcctgga gcactcaggc tccgtgggtc tggccctgtt cgtctgggtc     240
ctgggtgggg gcgtgacggc tctgggctcc ctctgctatg cagagctggg agtcgccatc     300
cccaagtctg gcggggacta cgcctacgtc acagagatct tcgggggcct ggctggcttt     360
ctgctgctct ggagcgccgt cctcatcatg taccccacca gccttgctgt catctccatg     420
accttctcca actacgtgct gcagcccgtg ttccccaact gcatccccc  caccacagcc     480 tcccgggtgc tgtccatggc ctgcctgatg ctcctgacat gggtgaacag ctccagtgtg    540
cgctgggcca cgcgcatcca ggacatgttc acaggcggga agctgctggc cttgtccctc    600
atcatcggcg tgggccttct ccagatcttc caaggacact tcgaggagct gaggcccagc    660
aatgcctttg ctttctggat gacgccctcc gtgggacacc tggccctggc cttcctccag    720
ggctccttcg ccttcagtgg ctggaacttc ctcaactatg tcaccgagga gatggttgac    780
gcccgaaaga acctacctcg cgccatcttc atctccatcc cactggtgac cttcgtgtac    840
acgttcacca acattgccta cttcacggcc atgtcccccc aggagctgct ctcctccaat    900
gcggtggctg tgaccttcgg ggagaagctg ctgggctact tttcttgggt catgcctgtc    960
tccgtggctc tgtcaacctt cggagggatc aatggttacc tgttcaccta ctccaggctg   1020
tgcttctctg gagcccgcga ggggcacctg cccagcctgc tggccatgat ccacgtcaga   1080
cactgcaccc ccatcccgc cctcctcgtc tgttgcgggg ccacagccgt catcatgctc    1140
gtgggcgaca cgtacacgct catcaactat gtgtccttca tcaactacct ctgctacggc    1200
gtcaccatcc tgggcctgct gctgctgcgc tggaggcggc ctgcactcca caggcccatc    1260
aaggtgaacc ttctcatccc cgtggcgtac ttggtcttct gggccttcct gctggtcttc    1320
agcttcatct cagagcctat ggtctgtggg gtcggcgtca tcatcatcct tacggggtg    1380 cccattttct ttctgggagt gttctggaga agcaaaccaa agtgtgtgca cagactcaca   1440
gagtccatga cacactgggg ccaggagctg tgtttcgtgg tctaccccca ggacgccccc   1500
```

```
gaagaggagg agaatggccc ctgcccaccc tccctgctgc ctgccacaga caagccctcg    1560
aagccacaat ga                                                        1572
```

<210> SEQ ID NO 94
<211> LENGTH: 711
<212> TYPE: DNA
<213> ORGANISM: Homo sapiens

<400> SEQUENCE: 94

```
atggaaagct ctgccaagat ggagagcggc ggcgccggcc agcagcccca gccgcagccc      60
cagcagccct tcctgccgcc cgcagcctgt ttctttgcca cggccgcagc cgcggcggcc     120
gcagccgccg cagcggcagc gcagagcgcg cagcagcaga gcagcagca gcagcagcag      180 cagcaggcgc cgcagctgag accggcggcc gacggccagc cctcaggggg cggtcacaag     240
tcagcgccca gcaagtcaa gcgacagcgc tcgtcttcgc ccgaactgat gcgctgcaaa      300
cgccggctca acttcagcgg ctttggctac agcctgccgc agcagcagcc ggccgccgtg     360
gcgcgccgca acgagcgcga gcgcaaccgc gtcaagttgg tcaacctggg ctttgccacc     420
cttcgggagc acgtccccaa cggcgcggcc aacaagaaga tgagtaaggt ggagacactg     480
cgctcggcgg tcgagtacat ccgcgcgctg cagcagctgc tggacgagca tgacgcggtg     540
agcgccgcct ccaggcagg cgtcctgtcg cccaccatct cccccaacta ctccaacgac      600
ttgaactcca tggccggctc gccggtctca tcctactcgt cggacgaggg ctcttacgac     660
ccgctcagcc ccgaggagca ggagcttctc gacttcacca actggttctg a              711
```

<210> SEQ ID NO 95
<211> LENGTH: 1797
<212> TYPE: DNA
<213> ORGANISM: Homo sapiens

<400> SEQUENCE: 95

```
atgccttgtg ttcaggcgca gtatgggtcc tcgcctcaag gagccagccc cgcttctcag      60
agctacagtt accactcttc gggagaatac agctccgatt tcttaactcc agagtttgtc     120
aagtttagca tggacctcac caacactgaa atcactgcca ccacttctct ccccagcttc     180 agtacccttta tggacaacta cagcacaggc tacgacgtca agccaccttg cttgtaccaa    240
atgcccctgt ccggacagca gtcctccatt aaggtagaag acattcagat gcacaactac     300
cagcaacaca gccacctgcc ccccagtct gaggagatga tgccgcactc cgggtcggtt     360
tactacaagc cctcctcgcc cccgacgccc accaccccgg gcttccaggt gcagcacagc     420
cccatgtggg acgacccggg atctctccac aacttccacc agaactacgt ggccactacg     480
cacatgatcg agcagaggaa aacgccagtc tcccgcctct ccctcttctc ctttaagcaa     540
tcgccccctg gcaccccggt gtctagttgc cagatgcgct tcgacgggcc cctgcacgtc     600
cccatgaacc cggagcccgc cggcagccac acgtggtgg acgggcagac cttcgctgtg     660
cccaacccca ttcgcaagcc cgcgtccatg ggcttcccgg gctgcagat cggccacgcg      720 tctcagctgc tcgacacgca ggtgccctca ccgccgtcgc ggggctcccc ctccaacgag     780
gggctgtgcg ctgtgtgtgg ggacaacgcg gcctgccaac actacggcgt gcgcacctgt     840
gagggctgca aaggcttctt taagcgcaca gtgcaaaaaa atgcaaaata cgtgtgttta     900
gcaaataaaa actgcccagt ggacaagcgt cgccggaatc gctgtcagta ctgccgattt     960
cagaagtgcc tggctgttgg gatggtcaaa gaagtggttc gcacagacag tttaaaaggc    1020
cggagaggtc gtttgccctc gaaaccgaag agcccacagg agccctctcc cccttcgccc    1080
```

-continued

```
ccggtgagtc tgatcagtgc cctcgtcagg gcccatgtcg actccaaccc ggctatgacc    1140
agcctggact attccaggtt ccaggcgaac cctgactatc aaatgagtgg agatgacacc    1200
cagcatatcc agcaattcta tgatctcctg actggctcca tggagatcat ccggggctgg    1260
gcagagaaga tccctggctt cgcagacctg cccaaagccg accaagacct gcttttgaa     1320 tcagctttct tagaactgtt tgtccttcga ttagcataca ggtccaaccc agtggagggt    1380
aaactcatct tttgcaatgg ggtggtcttg cacaggttgc aatgcgttcg tggctttggg    1440
gaatggattg attccattgt tgaattctcc tccaacttgc agaatatgaa catcgacatt    1500
tctgccttct cctgcattgc tgccctggct atggtcacag agagacacgg gctcaaggaa    1560
cccaagagag tggaagaact gcaaaacaag attgtaaatt gtctcaaaga ccacgtgact    1620
ttcaacaatg gggggttgaa ccgccccaat tatttgtcca aactgttggg gaagctccca    1680
gaacttcgta ccctttgcac acaggggcta cagcgcattt tctacctgaa attggaagac    1740
ttggtgccac cgccagcaat aattgacaaa cttttcctgg acactttacc tttctaa      1797
```

<210> SEQ ID NO 96
<211> LENGTH: 819
<212> TYPE: DNA
<213> ORGANISM: Homo sapiens

<400> SEQUENCE: 96

```
atgttcgtca atccgagac cttggagttg aaggaggaag aggacgtgtt agtgctgctc     60
ggatcggcct ccccgcctt ggcggccctg accccgctgt catccagcgc cgacgaagaa    120
gaggaggagg agccgggcgc gtcaggcggg gcgcgtcggc agcgcggggc tgaggccggg    180 caggggcgc ggggcggcgt ggctgcgggt gcggagggct gccggcccgc acggctgctg    240
ggtctggtac acgattgcaa acggcgccct tcccgggcgc gggccgtctc ccgaggcgcc    300
aagacggccg agacggtgca gcgcatcaag aagacccgta gactgaaggc caacaaccgc    360
gagcgaaacc gcatgcacaa cctcaacgcg gcactggacg cgctgcgcga ggtgctcccc    420
acgttccccg aggacgccaa gctcaccaag atcgagaccc tgcgcttcgc ccacaactac    480
atctgggcac tcaccgagac cctgcgcctg gcggatcact gcggggcgg cggcgggggc    540 ctgccggggg cgctcttctc cgaggcagtg ttgctgagcc cgggaggagc cagcgccgcc    600
ctgagcagca gcggagacag ccccctcgccc gcctccacgt ggagttgcac caacagcccc    660
gcgccgtcct cctccgtgtc ctccaattcc acctccccct acagctgcac tttatcgccc    720
gccagcccgg ccgggtcaga catggactat tggcagcccc cacctcccga caagcaccgc    780
tatgcacctc acctccccat agccagggat tgtatctag                          819
```

<210> SEQ ID NO 97
<211> LENGTH: 1149
<212> TYPE: DNA
<213> ORGANISM: Homo sapiens

<400> SEQUENCE: 97

```
atgctggacg gcctaaagat ggaggagaac ttccaaagcg cgatcgacac ctcggcctcc     60
ttctcctcgc tgctgggcag agcggtgagc cccaagtctg tctgcgaggg ctgtcagcgg    120
gtcatcttgg acaggtttct gctgcggctc aacgacagct tctggcatga gcagtgcgtg    180
cagtgcgcct cctgcaaaga gcccctggag accacctgct ctaccgggga caagaagctg    240
tactgcaagt atgactacga gaagctgttt gctgttaaat gtggggctg cttcgaggcc    300
```

| | |
|---|---|
| atcgctccca atgagtttgt tatgcgggcc cagaagagtg tataccacct gagctgcttc | 360 |
| tgctgctgtg tctgcgagcg acagcttcag aagggtgatg agtttgtcct gaaggagggg | 420 |
| cagctgctct gcaaagggga ctatgagaag gagcgggagc tgctcagcct ggtgagccca | 480 |
| gcagcctcag actcaggtaa aagtgatgat gaagaaagtc tctgcaagtc agcccatggg | 540 |
| gcagggaaag gaactgctga ggaaggcaag gaccataagc gccccaaacg tccgagaacc | 600 |
| atcttgacaa ctcaacagag gcgagcattc aaggcctcat ttgaagtatc ctccaagccc | 660 |
| tgcaggaagg tgagagagac tctggctgca gagacagggc tgagtgtccg tgtcgtccag | 720 |
| gtgtggttcc aaaaccagag agcgaagatg aagaagctgg ccaggcgaca gcagcagcag | 780 |
| cagcaagatc agcagaacac ccagaggctg agctctgctc agacaaacgg tggtgggagt | 840 |
| gctgggatgg aaggaatcat gaaccctac acggctctgc ccaccccaca gcagctcctg | 900 |
| gccatcgagc agagtgtcta cagctcagat cccttccgac agggtctcac cccacccag | 960 |
| atgcctggag accacatgca cccttatggt gccgagcccc ttttccatga cctggatagc | 1020 |
| gacgacacct ccctcagtaa cctgggtgat tgtttcctag caacctcaga agctgggcct | 1080 |
| ctgcagtcca gagtgggaaa ccccattgac catctgtact ccatgcagaa ttcttacttc | 1140 |
| acatcttga | 1149 |

<210> SEQ ID NO 98
<211> LENGTH: 694
<212> TYPE: DNA
<213> ORGANISM: Homo sapiens

<400> SEQUENCE: 98

| | |
|---|---|
| atggaaaaat ccaaaaattt ccgcatcgag ccctgctggc ggtggacccc ccacgagccg | 60 |
| cctctcgcag agcgcgcgct ggccaaggtc acgtcgccgc ccgtgcccgc atctggcacc | 120 |
| ggaggtggcg gcggcggcgg cggggcgagc ggcgggacta gcggcagctg cagccccgcg | 180 |
| tcctcggagc cgccggctgc gcccgccgac cgcctgcgcg ccgagagccc gtcgccgccg | 240 |
| cgcctgctgg ccgcgcactg cgcgctgctg cccaagccgg gcttcctggg cgcgggcggc | 300 |
| ggcggcggcg gcacgggcgg cgggcacggg gggccccacc accacgcgca tccgggcgca | 360 |
| gcggccgctg ccgccgccgc cgccgccgcc gccgccgccg ccgctggggg cctggcgctg | 420 |
| gggctgcacc ctgggggcgc gcagggcggc gcgggcctcc cggcgcaggc ggcgctctac | 480 |
| ggccacccgg tctacggcta ctccgcggcg gcggcggcgg ctgcgctggc gggccagcac | 540 |
| ccggcgctct cctactcgta cccgcaggtg caaggcgcgc accccgcgca ccccgccgac | 600 |
| cccatcaagc tgggcgccgg caccttccag ctggaccagt ggctgcgcgc gtccaccgcg | 660 |
| ggcatgatcc tgcctaagat gcccgacttc aact | 694 |

<210> SEQ ID NO 99
<211> LENGTH: 1194
<212> TYPE: DNA
<213> ORGANISM: Homo sapiens

<400> SEQUENCE: 99

| | |
|---|---|
| atgctgctgg aaacggggct cgagcgcgac cgagcgaggc ccggggccgc cgccgtctgc | 60 |
| accttgggcg ggactcggga gatcccgctg tgcgctggct gtgaccagca catcctggac | 120 |
| cgcttcatcc tcaaggctct ggaccgccac tggcacagca agtgtctcaa gtgcagcgac | 180 |
| tgccacacgc cactggccga gcgctgcttc agcgaggggg agagcgttta ctgcaaggac | 240 |
| gactttttca agcgcttcgg gaccaagtgc gccgcgtgcc agctgggcat cccgcccacg | 300 |

```
caggtggtgc gccgcgccca ggacttcgtg taccacctgc actgctttgc ctgcgtcgtg    360
tgcaagcgga agctggccac gggcgacgag ttctacctca tggaggacag ccggctcgtg    420
tgcaaggcgg actacgaaac cgccaagcag cgagaggccg aggccacggc caagcggccg    480
cgcacgacca tcaccgccaa gcagctggag acgctgaaga gcgcttacaa cacctcgccc    540
aagccggcgc gccacgtgcg cgagcagctc tcgtccgaga cgggcctgga catgcgcgtg    600
gtgcaggttt ggttccagaa ccgccgggcc aaggagaaga ggctgaagaa ggacgccggc    660
cggcagcgct gggggcagta tttccgcaac atgaagcgct cccgcggcgg ctccaagtcg    720
gacaaggaca cgttcagga ggggcaggac agcgacgctg aggtctcctt ccccgatgag    780
ccttccttgg cggaaatggg cccggccaat ggcctctacg ggagcttggg ggaacccacc    840
caggccttgg gccggccctc gggagccctg ggcaacttct ccctggagca tggaggcctg    900
gcaggcccag agcagtaccg agagctgcgt cccggcagcc cctacggtgt ccccccatcc    960
cccgccgccc cgcagagcct ccctggcccc cagcccctcc tctccagcct ggtgtaccca   1020
gacaccagct tgggccttgt gccctcggga gccccggcg ggccccccacc catgagggtg   1080 ctggcaggga acggacccag ttctgaccta tccacgggga gcagcggggg ttaccccgac   1140
ttccctgcca gccccgcctc ctggctggat gaggtagacc acgctcagtt ctga         1194
```

<210> SEQ ID NO 100
<211> LENGTH: 987
<212> TYPE: DNA
<213> ORGANISM: Homo sapiens

<400> SEQUENCE: 100

```
atgactggag tctttgacag tctagtggct gatatgcact cgacccagat cgccgcctcc     60
agcacgtacc accagcacca gcagccccg agcggcggcg gcgccggccc gggtggcaac    120
agcagcagca gcagcagcct ccacaagccc caggagtcgc ccaccttcc ggtgtccacc    180 gccaccgaca gcagctacta caccaaccag cagcaccgg cggcggcgg cggcggcggg    240 ggctcgccct acgcgcacat gggttcctac cagtaccaag ccagcggcct caacaacgtc    300
ccttactccg ccaagagcag ctatgacctg ggctacaccg ccgcctacac ctcctacgct    360
ccctatggaa ccagttcgtc cccagccaac aacgagcctg agaaggagga ccttgagcct    420
gaaattcgga tagtgaacgg gaagccaaag aaagtccgga acccccgcac catctactcc    480
agtttccagc tggcggctct tcagcggcgt ttccaaaaga ctcaatactt ggccttgccg    540
gagcgagccg agctggcggc ctctctgggc ctcacccaga ctcaggtcaa aatctggttc    600
cagaaccgcc ggtccaagtt caagaagatg tggaaaagtg gtgagatccc ctcggagcag    660
caccctgggg ccagcgcttc tccaccttgt gcttcgccgc cagtctcagc gccggcctcc    720
tgggactttg gtgtgccgca gcggatggcg ggcggcggtg gtccgggcag tggcggcagc    780
ggcgccggca gctcgggctc cagcccgagc agcgcggcct cggcttttct gggcaactac    840
ccctggtacc accagaccctc gggatccgcc tcacacctgc aggccacggc gccgctgctg    900
caccccactc agaccccgca gccgcatcac caccaccacc atcacggcgg cggggggcgcc    960 ccggtgagcg cggggacgat tttctaa                                        987
```

<210> SEQ ID NO 101
<211> LENGTH: 1566
<212> TYPE: DNA
<213> ORGANISM: Homo sapiens

<400> SEQUENCE: 101

```
atggcatcaa acagcctctt cagcacagtg acaccatgtc agcaaaactt cttttgggat     60
ccgagcacca gccggcgctt cagcccccc tccagcagcc tgcagcccgg caaaatgagc    120
gacgtgagcc cggtggtggc tgcgcaacag cagcagcaac agcagcagca gcaacagcag    180
cagcagcagc agcaacagca gcagcagcag caggaggcgg cggcggcggc tgcggcggcg    240
gcggcggctg cggcggcggc agctgcagtg ccccggttgc ggccgcccca cgacaaccgc    300
accatggtgg agatcatcgc cgaccacccg gccgaactcg tccgcaccga cagccccaac    360
ttcctgtgct cggtgctgcc ctcgcactgg cgctgcaaca agaccctgcc cgtggccttc    420
aaggtggtag ccctcggaga ggtaccagat gggactgtgg ttactgtcat ggcgggtaac    480
gatgaaaatt attctgctga gctccggaat gcctctgctg ttatgaaaaa ccaagtagca    540
aggttcaacg atctgagatt tgtgggccgg agtggacgag gcaagagttt caccttgacc    600
ataaccgtct tcacaaatcc tcccaagta gctacctatc acagagcaat taaagttaca    660
gtagatggac ctcgggaacc cagaaggcac agacagaagc ttgatgactc taaacctagt    720
ttgttctctg accgcctcag tgatttaggg cgcattcctc atcccagtat gagagtaggt    780
gtcccgcctc agaacccacg gcctcctg aactctgcac caagtccttt taatccacaa    840
ggacagagtc agattacaga ccccaggcag gcacagtctt ccccgccgtg gtcctatgac    900
cagtcttacc cctcctacct gagccagatg acgtccccgt ccatccactc taccaccccg    960
ctgtcttcca cacggggcac tgggcttcct gccatcaccg atgtgcctag gcgcatttca   1020
gatgatgaca ctgccaccctc tgacttctgc ctctggcctt ccactctcag taagaagagc   1080
caggcaggtg cttcagaact gggcccttt tcagacccca ggcagttccc aagcatttca   1140
tccctcactg agagccgctt ctccaaccca cgaatgcact atccagccac ctttacttac   1200
accccgccag tcacctcagg catgtccctc ggtatgtccg ccaccactca ctaccacacc   1260
tacctgccac caccctaccc cggctcttcc caaagccaga gtggaccctt ccagaccagc   1320
agcactccat atctctacta tggcacttcg tcaggatcct atcagtttcc catggtgccg   1380
gggggagacc ggtctccttc cagaatgctt ccgccatgca ccaccacctc gaatggcagc   1440
acgctattaa atccaaattt gcctaaccag aatgatggtg ttgacgctga tggaagccac   1500
agcagttccc caactgtttt gaattctagt ggcagaatgg atgaatctgt ttggcgacca   1560
tattga                                                               1566
```

<210> SEQ ID NO 102
<211> LENGTH: 2292
<212> TYPE: DNA
<213> ORGANISM: Homo sapiens

<400> SEQUENCE: 102

```
atgcttactg accctgattt acctcaggag tttgaaagga tgtcttccaa gcgaccagcc     60
tctccgtatg gggaagcaga tggagaggta gccatggtga caagcagaca gaaagtggaa    120
gaagaggaga gtgacgggct cccagccttt caccttccct gcatgtgag ttttcccaac     180
aagcctcact ctgaggaatt tcagccagtt tctctgctga cgcaagagac ttgtggccat    240
aggactccca cttctcagca caatacaatg gaagttgatg gcaataaagt tatgtcttca    300
tttgccccac acaactcatc tacctcacct cagaaggcag aagaaggtgg gcgacagagt    360
ggcgagtcct tgtctagtac agccctggga actcctgaac ggcgcaaggg cagtttagct    420
gatgttgttg acaccttgaa gcagaggaaa atggaagagc tcatcaaaaa cgagccggaa    480
```

```
gaaaccccca gtattgaaaa actactctca aaggactgga aagacaagct tcttgcaatg      540
ggatcgggga actttggcga aataaaaggg actcccgaga gcttagctga aaagaaagg      600 caactcatgg gtatgatcaa ccagctgacc agcctccgag agcagctgtt ggctgcccac      660
gatgagcaga agaaactagc tgcctctcag attgagaaac agcgtcagca aatggagctg      720
gccaagcagc aacaagaaca aattgcaaga cagcagcagc agcttctaca gcaacaacac      780
aaaatcaatt tgctccagca acagatccag gttcaaggtc agctgccgcc attaatgatt      840
cccgtattcc ctcctgatca acggacactg gctgcagctg cccagcaagg attcctcctc      900
cctccaggct tcagctataa ggctggatgt agtgacccct accctgttca gctgatccca      960
actaccatgg cagctgctgc cgcagcaaca ccaggcttag cccactccaa actgcagcag     1020
ttatatgctg cccagctagc tgcaatgcag gtatctccag agggaagct gccaggcata      1080 ccccaaggca accttggtgc tgctgtatct cctaccagca ttcacacaga caagagcaca     1140
aacagcccac cacccaaaag caaggatgaa gtggcacagc cactgaacct atcagctaaa     1200
cccaagacct ctgatggcaa atcacccaca tcacccacct ctccccatat gccagctctg     1260
agaataaaca gtggggcagg cccctcaaa gcctctgtcc cagcagcgtt agctagtcct      1320
tcagccagag ttagcacaat aggttactta aatgaccatg atgctgtcac caaggcaatc     1380
caagaagctc ggcaaatgaa ggagcaactc cgacgggaac aacaggtgct tgatgggaag     1440
gtggctgttg tgaatagtct gggtctcaat aactgccgaa cagaaaagga aaaacaaca      1500 ctggagagtc tgactcagca actggcagtt aaacagaatg aagaaggaaa atttagccat     1560
gcaatgatgg atttcaatct gagtggagat tctgatggaa gtgctggagt ctcagagtca     1620
agaatttata gggaatcccg agggcgtggt agcaatgaac cccacataaa gcgtccaatg     1680
aatgccttca tggtgtgggc taaagatgaa cggagaaaga tccttcaagc ctttcctgac     1740
atgcacaact ccaacatcag caagatattg ggatctcgct ggaaagctat gacaaaccta     1800
gagaaacagc catattatga ggagcaagcc cgtctcagca gcagcacct ggagaagtac      1860 cctgactata gtacaagcc caggccaaag cgcacctgcc tggtggatgg caaaaagctg      1920
cgcattggtg aatacaaggc aatcatgcgc aacaggcggc aggaaatgcg gcagtacttc     1980
aatgttgggc aacaagcaca gatccccatt gccactgctg gtgttgtgta ccctggagcc     2040
atcgccatgg ctgggatgcc ctcccctcac ctgccctcgg agcactcaag cgtgtctagc     2100
agcccagagc ctgggatgcc tgttatccag agcacttacg gtgtgaaagg agaggagcca     2160
catatcaaag aagagataca ggccgaggac atcaatggag aaatttatga tgagtacgac     2220
gaggaagagg atgatccaga tgtagattat gggagtgaca gtgaaaacca tattgcagga     2280
caagccaact ga                                                         2292

<210> SEQ ID NO 103
<211> LENGTH: 2427
<212> TYPE: DNA
<213> ORGANISM: Homo sapiens

<400> SEQUENCE: 103
atgtcttcca agcaagccac ctctccattt gcctgtgcag ctgatggaga ggatgcaatg       60
acccaggatt taacctcaag ggaaaaggaa gagggcagtg atcaacatgt ggcctcccat      120
ctgcctctgc accccataat gcacaacaaa cctcactctg aggagctacc aacacttgtc      180
agtaccattc aacaagatgc tgactgggac agcgttctgt catctcagca aagaatggaa      240
```

```
tcagagaata ataagttatg ttccctatat tccttccgaa atacctctac ctcaccacat      300
aagcctgacg aagggagtcg ggaccgtgag ataatgacca gtgttacttt tggaacccca      360
gagcgccgca aagggagtct tgccgatgtg gtggacacac tgaaacagaa gaagcttgag      420
gaaatgactc ggactgaaca agaggattcc tcctgcatgg aaaaactact ttcaaaagat      480
tggaaggaaa aaatggaaag actaaatacc agtgaacttc ttggagaaat taaaggtaca      540
cctgagagcc tggcagaaaa agaacggcag ctctccacca tgattaccca gctgatcagt      600
ttacgggagc agctactggc agcgcatgat gaacagaaaa aactggcagc gtcacaaatt      660
gagaaacaac ggcagcaaat ggaccttgct cgccaacagc aagaacagat tgcgagacaa      720
cagcagcaac ttctgcaaca gcagcacaaa attaatctcc tgcagcaaca gatccaggtt      780
cagggtcaca tgcctccgct catgatccca attttccac atgaccagcg gactctggca       840
gcagctgctg ctgcccaaca gggattcctc ttcccccctg gaataacata caaaccaggt      900
gataactacc ccgtacagtt cattccatca acaatggcag ctgctgctgc ttctggactc      960 agcccttac agctccagaa gggtcatgcc tcccacccac aaattaacca aaggctaaag     1020
ggcctaagtg accgttttgg caggaatttg gacacctttg aacatggtgg tggccactct     1080
tacaaccaca aacagattga gcagctctat gccgctcagc tggccagcat gcaggtgtca     1140
cctggagcaa agatgccatc aactccacag ccaccaaaca cagcagggac ggtctcacct     1200
actgggataa aaatgaaaa gagagggacc agccctgtaa ctcaagttaa ggatgaagca     1260
gcagcacagc ctctgaatct ctcatcccga cccaagacag cagagcctgt aaagtcccca     1320
acgtctccca cccagaacct cttcccagcc agcaaaacca gccctgtcaa tctgccaaac     1380
aaaagcagca tccctagccc cattggagga agcctgggaa gaggatcctc tttagatatc     1440
ctatctagtc tcaactcccc tgccctttt ggggatcagg atacagtgat gaaagccatt      1500
caggaggcgc ggaagatgcg agagcagatc cagcgggagc aacagcagca acagccacat     1560
ggtgttgacg ggaaactgtc ctccataaat aatatgggc tgaacagctg caggaatgaa      1620
aaggaaagaa cgcgctttga gaatttgggg ccccagttaa cgggaaagtc aaatgaagat     1680
ggaaaactgg gcccaggtgt catcgacctt actcggccag aagatgcaga gggaggtgcc     1740
actgtggctg aagcacgagt ctacagggac gcccgcggcc gtgccagcag cgagccacac     1800
attaagcgac caatgaatgc attcatggtt tgggcaaagg atgagaggag aaaaatcctt     1860
caggccttcc ccgacatgca taactccaac attagcaaaa tcttaggatc tcgctggaaa     1920
tcaatgtcca accaggagaa gcaaccttat tatgaagagc aggcccggct aagcaagatc     1980
cacttagaga agtacccaaa ctataaatac aaaccccgac cgaaacgcac ctgcattgtt     2040
gatggcaaaa agcttcggat tgggagtat aagcaactga tgaggtctcg gagacaggag      2100
atgaggcagt tctttactgt ggggcaacag cctcagattc caatcaccac aggaacaggt     2160
gttgtgtatc ctggtgctat cactatggca actaccacac catcgcctca gatgacatct     2220
gactgctcta gcacctcggc cagcccggag cccagcctcc cggtcatcca gagcacttat     2280
ggtatgaaga cagatggcgg aagcctagct ggaaatgaaa tgatcaatgg agaggatgaa     2340
atggaaatgt atgatgacta tgaagatgac cccaaatcag actatagcag tgaaaatgaa     2400
gccccggagg ctgtcagtgc caactga                                         2427
```

<210> SEQ ID NO 104
<211> LENGTH: 1788
<212> TYPE: DNA
<213> ORGANISM: Homo sapiens

<400> SEQUENCE: 104

```
atggccttga ctgacggcgg ctggtgcttg ccgaagcgct tcggggccgc gggtgcggac    60
gccagcgact ccagagcctt tccagcgcgg gagccctcca cgccgccttc ccccatctct   120
tcctcgtcct cctcctgctc ccggggcgga gagcggggcc ccggcggcgc cagcaactgc   180
gggacgcctc agctcgacac ggaggcggcg gccggacccc cggcccgctc gctgctgctc   240
agttcctacg cttcgcatcc cttcggggct ccccacggac cttcggcgcc tggggtcgcg   300
ggccccgggg gcaacctgtc gagctggag gacttgctgc tgttcactga cctcgaccaa   360
gccgcgaccg ccagcaagct gctgtggtcc agccgcggcg ccaagctgag ccccttcgca   420
cccgagcagc cggaggagat gtaccagacc ctcgccgctc tctccagcca gggtccggcc   480
gcctacgacg cgcgcccgg cggcttcgtg cactctgcgg ccgcggcggc agcagccgcg   540
gcggcggcca gctccccggt ctacgtgccc accaccgcg tgggttccat gctgcccggc   600
ctaccgtacc acctgcaggg gtcgggcagt gggccagcca accacgcggg cggcgcgggc   660
gcgcaccccg gctggcctca ggcctcggcc gacagccctc catacggcag cggaggcggc   720
gcggctggcg gcggggccgc ggggcctggc ggcgctggct cagccgcggc gcacgtctcg   780
gcgcgcttcc cctactctcc cagcccgccc atggccaacg gcgccgcgcg ggagccggga   840
ggctacgcgg cggcgggcag tggggcgcg ggaggcgtga gcggcggcgg cagtagcctg   900
gcggccatgg gcggccgcga gccccagtac agctcgctgt cggccgcgcg ccgctgaac   960
gggacgtacc accaccacca ccaccaccac caccaccatc cgagcccta ctcgccctac  1020
gtggggcgc cactgacgcc tgcctggccc gccggaccct cgagaccccc ggtgctgcac  1080
agcctgcaga gccgcgccgg agcccgctc ccggtgcccc ggggtcccag tgcagacctg  1140
ctggaggacc tgtccgagag ccgcgagtgc gtgaactgcg gctccatcca gacgccgctg  1200
tggcggcggg acggcaccgg ccactacctg tgcaacgcct gcgggctcta cagcaagatg  1260
aacggcctca gccggcccct catcaagccg cagaagcgcg tgccttcatc acggcggctt  1320
ggattgtcct gtgccaactg tcacaccaca ctaccacct tatggcgcag aaacgccgag  1380
ggtgaacccg tgtgcaatgc ttgtggactc tacatgaaac tccatggggt gcccagacca  1440
cttgctatga aaaagaggg aattcaaacc aggaaacgaa aacctaagaa cataaataaa  1500
tcaaagactt gctctggtaa tagcaataat tccattccca tgactccaac ttccacctct  1560
tctaactcag atgattgcag caaaaatact tcccccacaa cacaacctac agcctcaggg  1620
gcgggtgccc cggtgatgac tggtgcggga gagagcacca atcccgagaa cagcgagctc  1680
aagtattcgg gtcaagatgg gctctacata ggcgtcagtc tcgcctcgcc ggccgaagtc  1740
acgtcctccg tgcgaccgga ttcctggtgc gccctggccc tggcctga                1788
```

<210> SEQ ID NO 105
<211> LENGTH: 1242
<212> TYPE: DNA
<213> ORGANISM: Homo sapiens

<400> SEQUENCE: 105

```
atggagttcc ctggcctggg gtccctgggg acctcagagc cctcccca gtttgtggat    60
cctgctctgg tgtcctccac accagaatca ggggttttct tcccctctgg gcctgagggc   120
ttggatgcag cagcttcctc cactgccccg agcacagcca ccgctgcagc tgcggcactg   180
gcctactaca gggacgctga ggcctacaga cactccccag tctttcaggt gtacccattg   240
```

| | |
|---|---|
| ctcaactgta tggaggggat cccagggggc tcaccatatg ccggctgggc ctacggcaag | 300 |
| acggggctct accctgcctc aactgtgtgt cccacccgcg aggactctcc tccccaggcc | 360 |
| gtggaagatc tggatggaaa aggcagcacc agcttcctgg agactttgaa gacagagcgg | 420 |
| ctgagcccag acctcctgac cctgggacct gcactgcctt catcactccc tgtccccaat | 480 |
| agtgcttatg ggggccctga cttttccagt accttctttt ctcccaccgg agccccctc | 540 |
| aattcagcag cctattcctc tcccaagctt cgtggaactc tcccccctgcc tcctgtgag | 600 |
| gccagggagt gtgtgaactg cggagcaaca gccactccac tgtggcggag ggacaggaca | 660 |
| ggccactacc tatgcaacgc ctgcggcctc tatcacaaga tgaatgggca gaacaggccc | 720 |
| ctcatccggc caagaagcg cctgattgtc agtaaacggg caggtactca gtgcaccaac | 780 |
| tgccagacga ccaccacgac actgtggcgg agaaatgcca gtggggatcc cgtgtgcaat | 840 |
| gcctgcggcc tctactacaa gctacaccag gtgaaccggc cactgaccat gcggaaggat | 900 |
| ggtattcaga ctcgaaaccg caaggcatct ggaaaaggga aaagaaacg gggctccagt | 960 |
| ctgggaggca caggagcagc cgaaggacca gctggtggct tatggtggt ggctggggc | 1020 |
| agcggtagcg ggaattgtgg ggaggtggct tcaggcctga cactgggccc ccaggtact | 1080 |
| gcccatctct accaaggcct gggccctgtg gtgctgtcag gcctgttag ccacctcatg | 1140 |
| cctttccctg gaccctact gggctcaccc acgggctcct tccccacagg ccccatgccc | 1200 |
| cccaccacca gcactactgt ggtggctccg ctcagctcat ga | 1242 |

<210> SEQ ID NO 106
<211> LENGTH: 1359
<212> TYPE: DNA
<213> ORGANISM: Homo sapiens

<400> SEQUENCE: 106

| | |
|---|---|
| atggacggga ctattaagga ggctctgtcg gtggtgagcg acgaccagtc cctctttgac | 60 |
| tcagcgtacg gagcggcagc ccatctcccc aaggccgaca tgactgcctc ggggagtcct | 120 |
| gactacgggc agccccacaa gatcaacccc ctcccaccac agcaggagtg gatcaatcag | 180 |
| ccagtgaggg tcaacgtcaa gcgggagtat gaccacatga atggatccag ggagtctccg | 240 |
| gtggactgca gcgttagcaa atgcagcaag ctggtgggcg gaggcgagtc caaccccatg | 300 |
| aactacaaca gctatatgga cgagaagaat ggcccccctc ctcccaacat gaccaccaac | 360 |
| gagaggagag tcatcgtccc cgcagacccc acactgtgga cacaggagca tgtgaggcaa | 420 |
| tggctggagt gggccataaa ggagtacagc ttgatggaga tcgacacatc ctttttccag | 480 |
| aacatggatg gcaaggaact tgtgtaaaatg aacaaggagg acttcctccg cgccaccacc | 540 |
| ctctacaaca cggaagtgct gttgtcacac ctcagttacc tcagggaaag ttcactgctg | 600 |
| gcctataata caacctccca caccgaccaa tcctcacgat tgagtgtcaa agaagaccct | 660 |
| tcttatgact cagtcagaag aggagcttgg ggcaataaca tgaattctgg cctcaacaaa | 720 |
| agtcctcccc ttggaggggc acaaacgatc agtaagaata cagagcaacg gccccagcca | 780 |
| gatccgtatc agatcctggg cccgaccagc agtcgcctag ccaaccctgg aagcgggcag | 840 |
| atccagctgt ggcaattcct cctggagctg ctctccgaca cgccaacgc cagctgtatc | 900 |
| acctgggagg ggaccaacgg ggagttcaaa atgacggacc ccgatgaggt ggccaggcgc | 960 |
| tggggcgagc ggaaaagcaa gcccaacatg aattacgaca agctgagccg ggcccctccgt | 1020 |
| tattactatg ataaaaacat tatgaccaaa gtgcacggca aagatatgc ttacaaattt | 1080 |
| gacttccacg gcattgccca ggctctgcag ccacatccga ccgagtcgtc catgtacaag | 1140 |

| taccccttctg | acatctccta | catgccttcc | taccatgccc | accagcagaa | ggtgaacttt | 1200 |
| gtccctcccc | atccatcctc | catgcctgtc | acttcctcca | gcttctttgg | agccgcatca | 1260 |
| caatactgga | cctccccac | gggggaatc | taccccaacc | ccaacgtccc | ccgccatcct | 1320 |
| aacacccacg | tgccttcaca | cttaggcagc | tactactag | | | 1359 |

<210> SEQ ID NO 107
<211> LENGTH: 1089
<212> TYPE: DNA
<213> ORGANISM: Homo sapiens

<400> SEQUENCE: 107

| atggccacag | ccgagaccgc | cttgccctcc | atcagcacac | tgaccgccct | gggcccttc | 60 |
| ccggacacac | aggatgactt | cctcaagtgg | tggcgctccg | aagaggcgca | ggacatgggc | 120 |
| ccgggtcctc | ctgaccccac | ggagccgccc | ctccacgtga | agtctgagga | ccagcccggg | 180 |
| gaggaagagg | acgatgagag | gggcgcggac | gccacctggg | acctggatct | cctcctcacc | 240 |
| aacttctcgg | gcccggagcc | cggtggcgcg | cccagacct | gcgctctggc | gcccagcgag | 300 |
| gcctccgggg | cgcaatatcc | gccgccgccc | gagactctgg | gcgcatatgc | tggcggcccg | 360 |
| gggctggtgg | ctgggctttt | gggttcggag | gatcactcgg | gttgggtgcg | ccctgccctg | 420 |
| cgagcccggg | ctcccgacgc | cttcgtgggc | ccagccctgg | ctccagcccc | ggcccccgag | 480 |
| cccaaggcgc | tggcgctgca | accggtgtac | ccggggcccg | gcgccggctc | ctcgggtggc | 540 |
| tacttcccgc | ggaccgggct | ttcagtgcct | gcggcgtcgg | gcgccccta | cgggctactg | 600 |
| tccgggtacc | ccgcgatgta | cccggcgcct | cagtaccaag | gcacttcca | gctcttccgc | 660 |
| gggctccagg | gacccgcgcc | cggtcccgcc | acgtccccct | ccttcctgag | ttgtttggga | 720 |
| cccgggacgg | tgggcactgg | actcgggggg | actgcagagg | atccaggtgt | gatagccgag | 780 |
| accgcgccat | ccaagcgagg | ccgacgttcg | tgggcgcgca | agaggcaggc | agcgcacacg | 840 |
| tgcgcgcacc | cggggttgcgg | caagagctac | accaagagct | cccacctgaa | ggcgcatctg | 900 |
| cgcacgcaca | caggggagaa | gccatacgcc | tgcacgtggg | aaggctgcgg | ctggagattc | 960 |
| gcgcgctcgg | acgagctgac | ccgccactac | cggaaacaca | cggggcagcg | cccccttccgc | 1020 |
| tgccagctct | gcccacgtgc | tttttcgcgc | tctgaccacc | tggccttgca | catgaagcgc | 1080 |
| cacctttga | | | | | | 1089 |

<210> SEQ ID NO 108
<211> LENGTH: 960
<212> TYPE: DNA
<213> ORGANISM: Homo sapiens

<400> SEQUENCE: 108

| atggagctac | tgtcgccacc | gctccgcgac | gtagacctga | cggcccccga | cggctctctc | 60 |
| tgctcctttg | ccacaacgga | cgacttctat | gacgacccgt | gtttcgactc | cccggacctg | 120 |
| cgcttcttcg | aagacctgga | cccgcgcctg | atgcacgtgg | gcgcgctcct | gaaacccgaa | 180 |
| gagcactcgc | acttcccgc | ggcggtgcac | ccggccccgg | gcgcacgtga | ggacgagcat | 240 |
| gtgcgcgcgc | ccagcgggca | ccaccaggcg | ggccgctgcc | tactgtgggc | ctgcaaggcg | 300 |
| tgcaagcgca | agaccaccaa | cgccgaccgc | gcaaggccg | ccaccatgcg | cgagcggcgc | 360 |
| cgcctgagca | aagtaaatga | ggcctttgag | acactcaagc | gctgcacgtc | gagcaatcca | 420 |
| aaccagcggt | tgcccaaggt | ggagatcctg | cgcaacgcca | tccgctatat | cgagggcctg | 480 |

| | |
|---|---|
| caggctctgc tgcgcgacca ggacgccgcg ccccctggcg cagccgcctt ctatgcgccg | 540 |
| ggcccgctgc ccccgggccg cggcggcgag cactacagcg gcgactccga cgcgtccagc | 600 |
| ccgcgctcca actgctccga cggcatgatg gactacagcg gcccccgag cggcgcccgg | 660 |
| cggcggaact gctacgaagg cgcctactac aacgaggcgc ccagcgaacc caggcccggg | 720 |
| aagagtgcgg cggtgtcgag cctagactac ctgtccagca tcgtggagcg catctccacc | 780 |
| gagagccctg cggcgcccgc cctcctgctg gcggacgtgc cttctgagtc gcctccgcgc | 840 |
| aggcaagagg ctgccgcccc cagcgaggga gagagcagcg gcgaccccac ccagtcaccg | 900 |
| gacgccgccc cgcagtgccc tgcgggtgcg aaccccaacc cgatatacca ggtgctctga | 960 |

<210> SEQ ID NO 109
<211> LENGTH: 1578
<212> TYPE: DNA
<213> ORGANISM: Homo sapiens

<400> SEQUENCE: 109

| | |
|---|---|
| atgcacagag cgccttcccc cacagccgag cagccgccgg gcggagggga cagcgcccgc | 60 |
| cggaccctgc agcccagact caagcccagt gcccgagcca tggcactgcc tcggacgctg | 120 |
| ggggagctgc agctgtaccg ggtcctgcag cgcgccaacc tcctttccta ctatgagacc | 180 |
| ttcatccagc agggagggga cgacgtgcag cagctgtgtg aggcgggtga ggaggagttt | 240 |
| ctggagatca tggcacttgt gggcatggcc accaagcccc tccatgtccg cgcctgcag | 300 |
| aaggcactga gagagtgggc caccaatcca gggctcttca gtcaaccagt gcctgctgtt | 360 |
| cccgtctcca gcatcccgct cttcaagatc tctgagactg cgggtacccg gaaagggagc | 420 |
| atgagcaatg gcatggcag cccaggggaa aaggcaggca gtgcccgcag ttttagcccc | 480 |
| aagagccccc ttgaacttgg agagaagcta tcaccactgc ctgggggacc tggggcaggg | 540 |
| gaccccccgga tctggccagg ccggagcact ccagagtcgg acgttggggc aggaggagaa | 600 |
| gaggaggctg gctcgccccc cttctccccc cctgcagggg gaggagtccc tgaggggact | 660 |
| ggggctgggg ggctggcagc aggtgggact gggggtggtc cagaccgact ggagccagag | 720 |
| atggtacgca tggtggtgga aagtgtggag aggatcttcc ggagcttccc aagggggat | 780 |
| gctggggagg tcacatccct gctaaagctg aataagaagc tggcacggag cgttgggcac | 840 |
| atctttgaga tggatgataa tgacagccag aaggaagagg agatccgcaa atacagcatc | 900 |
| atctatggcc gtttcgactc taagcggcgg gagggcaagc agctcagcct gcacgagctc | 960 |
| accatcaacg aggctgctgc ccagttctgc atgagggaca cacgctctct attacggaga | 1020 |
| gtggagctct tctctttgtc ccgccaagta gcccgagaga gcacctactt gtcctccttg | 1080 |
| aagggctcca ggcttcaccc tgaagaactg ggaggccctc cactgaagaa gctgaaacaa | 1140 |
| gaggttggag aacagagtca ccctgaaatc cagcagcctc cccaggccc tgagtcctat | 1200 |
| gtaccccat accgcccag cctggaggag gacagcgcca gcctgtctgg ggagagtctg | 1260 |
| gatggacatt tgcaggctgt ggggtcatgt ccaaggctga cgccgccccc tgctgacctg | 1320 |
| cctctggcat tgccagccca tgggctatgg agccgacaca tcctgcagca gacactgatg | 1380 |
| gacgaggggc tgcggctcgc ccgcctcgtc tcccacgacc gcgtgggccg cctcagcccc | 1440 |
| tgtgtgcctg cgaagccacc tctcgcagag ttcgaggaag gctgctgga cagatgtcct | 1500 |
| gccccaggac ccatcccgc gctggtggag ggtcgcagga gcagcgtgaa agtggaggct | 1560 |
| gaggccagcc ggcagtga | 1578 |

```
<210> SEQ ID NO 110
<211> LENGTH: 1632
<212> TYPE: DNA
<213> ORGANISM: Homo sapiens

<400> SEQUENCE: 110
atggccgcgg ccaaggccga gatgcagctg atgtccccgc tgcagatctc tgacccgttc      60
ggatcctttc ctcactcgcc caccatggac aactacccta agctggagga gatgatgctg     120
ctgagcaacg gggctcccca gttcctcggc gccgccgggg ccccagaggg cagcggcagc     180
aacagcagca gcagcagcag cgggggcggt ggaggcggcg ggggcggcag caacagcagc     240
agcagcagca gcaccttcaa ccctcaggcg gacacgggcg agcagcccta cgagcacctg     300
accgcagagt cttttcctga catctctctg aacaacgaga aggtgctggt ggagaccagt     360
taccccagcc aaaccactcg actgcccccc atcacctata ctggccgctt ttccctggag     420
cctgcaccca acagtggcaa caccttgtgg cccgagcccc tcttcagctt ggtcagtggc     480
ctagtgagca tgaccaaccc accggcctcc tcgtcctcag caccatctcc agcggcctcc     540
tccgcctccg cctcccagag cccaccctg agctgcgcag tgccatccaa cgacagcagt     600
cccatttact cagcggcacc caccttcccc acgccgaaca ctgacatttt ccctgagcca     660
caaagccagg ccttcccggg ctcggcaggg acagcgctcc agtacccgcc tctgcctac     720 cctgccgcca agggtggctt ccaggttccc atgatcccg actacctgtt tccacacag     780 cagggggatc tgggcctggg caccccagac agaagccct tccagggcct ggagagccgc     840
acccagcagc cttcgctaac ccctctgtct actattaagg cctttgccac tcagtcgggc     900
tcccaggacc tgaaggccct caataccagc taccagtccc agctcatcaa acccagccgc     960
atgcgcaagt accccaaccg gcccagcaag acgccccccc acgaacgccc ttacgcttgc    1020
ccagtggagt cctgtgatcg ccgcttctcc cgctccgacg agctcacccg ccacatccgc    1080
atccacacag gccagaagcc cttccagtgc cgcatctgca tgcgcaactt cagccgcagc    1140
gaccacctca ccacccacat ccgcacccac acaggcgaaa agcccttcgc ctgcgacatc    1200
tgtggaagaa agtttgccag gagcgatgaa cgcaagaggc ataccaagat ccacttgcgg    1260
cagaaggaca agaaagcaga caaaagtgtt gtggcctctt cggccacctc ctctctctct    1320
tcctacccgt ccccggttgc tacctcttac ccgtccccgg ttactacctc ttatccatcc    1380
ccggccacca cctcataccc atcccctgtg cccacctcct ctcctctccc ggctcctcg    1440 acctacccat cccctgtgca cagtggcttc ccctccccgt cggtggccac cacgtactcc    1500
tctgttcccc ctgctttccc ggcccaggtc agcagcttcc cttcctcagc tgtcaccaac    1560
tccttcagcg cctccacagg gctttcggac atgacagcaa ccttttctcc caggacaatt    1620
gaaatttgct aa                                                        1632

<210> SEQ ID NO 111
<211> LENGTH: 1269
<212> TYPE: DNA
<213> ORGANISM: Homo sapiens

<400> SEQUENCE: 111
atgccgcgct catttctcgt caaaagcaag aaggctcaca gctaccacca gccgcgctcc     60
ccaggaccag actattccct ccgtttagag aatgtaccgg cgcctagccg agcagacagc    120
acttcaaatg caggcgggc gaaggcgag ccccgggacc gtttgtcccc cgaatcgcag    180
ctgaccgaag ccccagacag agcctccgca tccccagaca gctgcgaagg cagcgtctgc    240
```

-continued

| | |
|---|---|
| gaacggagct cggagtttga ggacttctgg aggcccccgt caccctccgc gtctccagcc | 300 |
| tcggagaagt caatgtgccc atcgctggac gaagcccagc ccttcccct gcctttcaaa | 360 |
| ccgtactcat ggagcggcct ggcgggttct gacctgcggc acctggtgca gagctaccga | 420 |
| ccgtgtgggg ccctggagcg tggcgctggc ctgggcctct tctgcgaacc cgccccggag | 480 |
| cctggccacc cggccgcgct gtacggcccg aagcgggctg ccggcggcgc ggggggccggg | 540 |
| gcgccaggga gctgcagcgc aggggccggt gccaccgctg gccctggcct agggctctac | 600 |
| ggcgacttcg ggtctgcggc agccgggctg tatgagaggc ccacggcagc ggcgggcttg | 660 |
| ctgtaccccg agcgtggcca cgggctgcac gcagacaagg gcgctggcgt caaggtggag | 720 |
| tcggagctgc tgtgcacccg cctgctgctg ggcggcggct cctacaagtg catcaagtgc | 780 |
| agcaaggtgt tctccacgcc gcacgggctc gaggtgcacg tgcgcaggtc ccacagcggt | 840 |
| accagaccct ttgcctgcga gatgtgcggc aagaccttcg ggcacgcggt gagcctggag | 900 |
| cagcacaaag ccgtgcactc gcaggaacgg agctttgact gtaagatctg tgggaagagc | 960 |
| ttcaagaggt catccacact gtccacacac ctgcttatcc actcagacac tcggccctac | 1020 |
| ccctgtcagt actgtggcaa gaggttccac cagaagtcag acatgaagaa acacactttc | 1080 |
| atccacactg gtgagaagcc tcacaagtgc caggtgtgcg gcaaggcatt cagccagagc | 1140 |
| tccaacctca tcacccacag ccgcaaacac acaggcttca agcccttcgg ctgcgacctc | 1200 |
| tgtgggaagg gtttccagag gaaggtggac ctccgaaggc accgggagac gcagcatggg | 1260 |
| ctcaaatga | 1269 |

<210> SEQ ID NO 112
<211> LENGTH: 1176
<212> TYPE: DNA
<213> ORGANISM: Homo sapiens

<400> SEQUENCE: 112

| | |
|---|---|
| atggatttag agaaaaatta tccgactcct cggaccagca ggacaggaca tggaggagtg | 60 |
| aatcagcttg gggggtttt tgtgaatgga cggccactcc cggatgtagt ccgccagagg | 120 |
| atagtggaac ttgctcatca aggtgtcagg ccctgcgaca tctccaggca gcttcgggtc | 180 |
| agccatggtt gtgtcagcaa aattcttggc aggtattatg agacaggaag catcaagcct | 240 |
| ggggtaattg gaggatccaa accaaaggtc gccacaccca agtggtggaa aaaaatcgct | 300 |
| gaatataaac gccaaaatcc caccatgttt gcctgggaga tcagggaccg gctgctggca | 360 |
| gagcgggtgt gtgacaatga caccgtgcct agcgtcagtt ccatcaacag gatcatccgg | 420 |
| acaaaagtac agcagccacc caaccaacca gtcccagctt ccagtcacag catagtgtcc | 480 |
| actggctccg tgacgcaggt gtcctcggtg agcacggatt cggccggctc gtcgtactcc | 540 |
| atcagcggca tcctgggcat cacgtccccc agcgccgaca ccaacaagcg caagagagac | 600 |
| gaaggtattc aggagtctcc ggtgccgaac ggccactcgc ttccgggcag agacttcctc | 660 |
| cggaagcaga tgcggggaga cttgttcaca cagcagcagc tggaggtgct ggaccgcgtg | 720 |
| tttgagaggc agcactactc agacatcttc accaccacag agcccatcaa gcccgagcag | 780 |
| accacagagt attcagccat ggcctcgctg gctggtgggc tggacgacat gaaggccaat | 840 |
| ctggccagcc ccaccctgc tgacatcggg agcagtgtgc caggcccgca gtcctacccc | 900 |
| attgtgacag gccgtgactt ggcgagcacg accctccccg ggtaccctcc acacgtcccc | 960 |
| cccgctggac agggcagcta ctcagcaccg acgctgacga ggatggtgcc tgggagtgag | 1020 |
| ttttccggga gtccctacag ccaccctcag tattcctcgt acaacgactc ctggaggttc | 1080 |

```
cccaacccgg ggctgcttgg ctcccccta c tattatagcg ctgccgcccg aggagccgcc    1140
ccacctgcag ccgccactgc ctatgaccgt cactga                               1176

<210> SEQ ID NO 113
<211> LENGTH: 1608
<212> TYPE: DNA
<213> ORGANISM: Homo sapiens

<400> SEQUENCE: 113
atgggcatcg tggagccggg ttgcggagac atgctgacgg gcaccgagcc gatgccgggg      60
agcgacgagg gccgggcgcc tggcgccgac ccgcagcacc gctacttcta cccggagccg     120
ggcgcgcagg acgcggacga gcgtcgcggg ggcggcagcc tggggtctcc ctacccgggg     180
ggcgccttgg tgcccgcccc gccgagccgc ttccttggag cctacgccta cccgccgcga     240
ccccaggcgg ccggcttccc cggcgcgggc gagtccttcc cgccgcccgc ggacgccgag     300
ggctaccagc cgggcgaggg ctacgccgcc ccggacccgc gcgccgggct ctacccgggg     360
ccgcgtgagg actacgcgct acccgcggga ctggaggtgt cggggaaact gagggtcgcg     420
ctcaacaacc acctgttgtg gtccaagttt aatcagcacc agacagagat gatcatcacc     480
aagcagggac ggcggatgtt cccattcctg tcatttactg tggccgggct ggagcccacc     540
agccactaca ggatgtttgt ggacgtggtc ttggtggacc agcaccactg gcggtaccag     600
agcggcaagt gggtgcagtg tggaaaggcc gagggcagca tgccaggaaa ccgcctgtac     660
gtccacccgg actcccccaa cacaggagcg cactggatgc gccaggaagt ttcatttggg     720
aaactaaagc tcacaaacaa caaggggggcg tccaacaatg tgacccagat gattgtgctc     780
cagtccctcc ataagtacca gccccggctg catatcgttg aggtgaacga cggagagcca     840
gaggcagcct gcaacgcttc caacacgcat atctttactt tccaagaaac ccagttcatt     900
gccgtgactg cctaccagaa tgccgagatt actcagctga aaattgataa taacccctt     960 gccaaaggat tccgggagaa cttttgagtcc atgtacacat ctgttgacac cagcatcccc    1020
tccccgcctg gacccaactg tcaattcctt gggggagatc actactctcc tctcctaccc    1080
aaccagtatc ctgttcccag ccgcttctac cccgaccttc ctggccaggc gaaggatgtg    1140
gttccccagg cttactggct gggggccccc cgggaccaca gctatgaggc tgagtttcga    1200
gcagtcagca tgaagcctgc attcttgccc tctgcccctg gcccaccat gtcctactac      1260 cgaggccagg aggtcctggc acctggagct ggctggcctg tggcacccca gtaccctccc    1320
aagatgggcc cggccagctg gttccgccct atgcggactc tgcccatgga cccggcccct    1380
ggaggctcag agggacgggg accagaggac cagggtcccc ccttggtgtg gactgagatt    1440 gccccccatcc ggccggaatc cagtgattca ggactgggcg aaggagactc taagaggagg    1500
cgcgtgtccc cctatccttc cagtggtgac agctcctccc ctgctggggc cccttctcct    1560
tttgataagg aagctgaagg acagttttat aactattttc ccaactga                 1608

<210> SEQ ID NO 114
<211> LENGTH: 1335
<212> TYPE: DNA
<213> ORGANISM: Homo sapiens

<400> SEQUENCE: 114
atggaggtga cggcggacca gccgcgctgg gtgagccacc accaccccgc cgtgctcaac      60
gggcagcacc cggacacgca cacccgggc ctcagccact cctacatgga cgcggcgcag     120
```

| | | |
|---|---|---|
| tacccgctgc cggaggaggt ggatgtgctt tttaacatcg acggtcaagg caaccacgtc | 180 | |
| ccgccctact acggaaactc ggtcagggcc acggtgcaga ggtaccctcc gacccaccac | 240 | |
| gggagccagg tgtgccgccc gcctctgctt catggatccc taccctggct ggacggcggc | 300 | |
| aaagccctgg gcagccacca caccgcctcc ccctggaatc tcagccccct ctccaagacg | 360 | |
| tccatccacc acggctcccc ggggcccctc tccgtctacc cccggcctc gtcctcctcc | 420 | |
| ttgtcggggg gccacgccag cccgcacctc ttcaccttcc cgccaccc gccgaaggac | 480 | |
| gtctccccgg acccatcgct gtccaccca ggctcggccg gctcggcccg gcaggacgag | 540 | |
| aaagagtgcc tcaagtacca ggtgcccctg ccgacagca tgaagctgga gtcgtcccac | 600 | |
| tcccgtggca gcatgaccgc cctgggtgga gcctcctcgt cgacccacca ccccatcacc | 660 | |
| acctacccgc cctacgtgcc cgagtacagc tccggactct ccccccccag cagcctgctg | 720 | |
| ggcggctccc ccaccggctt cggatgcaag tccaggccca aggcccggtc cagcacagaa | 780 | |
| ggcagggagt gtgtgaactg tggggcaacc tcgaccccac tgtggcggcg agatggcacg | 840 | |
| ggacactacc tgtgcaacgc ctgcgggctc tatcacaaaa tgaacggaca gaaccggccc | 900 | |
| ctcattaagc ccaagcgaag gctgtctgca gccaggagag cagggacgtc ctgtgcgaac | 960 | |
| tgtcagacca ccacaaccac actctggagg aggaatgcca atggggaccc tgtctgcaat | 1020 | |
| gcctgtgggc tctactacaa gcttcacaat attaacagac ccctgactat gaagaaggaa | 1080 | |
| ggcatccaga ccagaaaccg aaaaatgtct agcaaatcca aaaagtgcaa aaaagtgcat | 1140 | |
| gactcactgg aggacttccc caagaacagc tcgtttaacc cggccgccct ctccagacac | 1200 | |
| atgtcctccc tgagccacat ctcgcccttc agccactcca gccacatgct gaccacgccc | 1260 | |
| acgccgatgc acccgccatc cagcctgtcc tttggaccac accacccctc cagcatggtc | 1320 | |
| accgccatgg gttag | 1335 | |

<210> SEQ ID NO 115
<211> LENGTH: 1296
<212> TYPE: DNA
<213> ORGANISM: Homo sapiens

<400> SEQUENCE: 115

| | | |
|---|---|---|
| atgcccaacc ccaggcctgg caagccctcg gccccttcct ggcccttgg cccatcccca | 60 | |
| ggagcctcgc ccagctggag ggctgcaccc aaagcctcag acctgctggg ggccggggc | 120 | |
| ccaggggaa ccttccaggg ccgagatctt cgaggcgggg cccatgcctc ctcttcttcc | 180 | |
| ttgaacccca tgccaccatc gcagctgcag ctgcccacac tgcccctagt catggtggca | 240 | |
| ccctccgggg cacggctggg ccccttgccc cacttacagg cactcctcca ggacaggcca | 300 | |
| catttcatgc accagctctc aacggtggat gcccacgccc ggacccctgt gctgcaggtg | 360 | |
| caccccctgg agagcccagc catgatcagc ctcacaccac ccaccaccgc cactgggtc | 420 | |
| ttctccctca aggcccggcc tggcctccca cctgggatca acgtggccag cctggaatgg | 480 | |
| gtgtccaggg agcggcact gctctgcacc ttccaaatc ccagtgcacc caggaaggac | 540 | |
| agcacccttt cggctgtgcc ccagagctcc tacccactgc tggcaaatgg tgtctgcaag | 600 | |
| tggcccggat gtgagaaggt cttcgaagag ccagaggact tcctcaagca ctgccaggcg | 660 | |
| gaccatcttc tggatgagaa gggcagggca caatgtctcc tccagagaga gatggtacag | 720 | |
| tctctggagc agcagctggt gctgagaaag gagaagctga gtgccatgca ggcccacctg | 780 | |
| gctgggaaaa tggcactgac caaggcttca tctgtggcat catccgacaa gggctcctgc | 840 | |
| tgcatcgtag ctgctggcag ccaaggccct gtcgtcccag cctggtctgg ccccgggag | 900 | |

```
gcccctgaca gcctgtttgc tgtccggagg cacctgtggg gtagccatgg aaacagcaca    960
ttcccagagt tcctccacaa catggactac ttcaagttcc acaacatgcg accccctttc   1020
acctacgcca cgctcatccg ctgggccatc ctggaggctc agagaagca gcggacactc    1080
aatgagatct accactggtt cacacgcatg tttgccttct tcagaaacca tcctgccacc   1140
tggaagaacg ccatccgcca aacctgagt ctgcacaagt gctttgtgcg ggtggagagc    1200
gagaagggg ctgtgtggac cgtggatgag ctggagttcc gcaagaaacg gagccagagg    1260
cccagcaggt gttccaaccc tacacctggc ccctga                             1296
```

<210> SEQ ID NO 116  
<211> LENGTH: 1683  
<212> TYPE: DNA  
<213> ORGANISM: Homo sapiens

<400> SEQUENCE: 116

```
atggacaggg ccccacagag acagcaccga gcctcacggg agctgctggc tgcaaagaag     60
acccacacct cacaaattga agtgatccct tgcaaaatct gtggggacaa gtcgtctggg    120
atccactacg gggttatcac ctgtgagggg tgcaagggc tcttccgccg gagccagcgc    180
tgtaacgcgg cctactcctg cacccgtcag cagaactgcc ccatcgaccg caccagccga    240
aaccgatgcc agcactgccg cctgcagaaa tgcctggcgc tggggatgtc ccgagatgct    300
gtcaagttcg gccgcatgtc caagaagcag agggacagcc tgcatgcaga agtgcagaaa    360
cagctgcagc agcggcaaca gcagcaacag gaaccagtgg tcaagacccc tccagcaggg    420
gcccaaggag cagataccct cacctacacc ttggggctcc agacgggca gctgcccctg     480
ggctcctcgc ctgacctgcc tgaggcttct gcctgtcccc ctggcctcct gaaagcctca    540
ggctctgggc cctcatattc caacaacttg gccaaggcag ggctcaatgg ggcctcatgc    600
cacctgaat acagccctga gcggggcaag gctgagggca gagagagctt ctatagcaca    660
ggcagccagc tgaccctga ccgatgtgga cttcgttttg aggaacacag gcatcctggg    720
cttggggaac tgggacaggg cccagacagc tacggcagcc ccagtttccg cagcacaccg    780
gaggcaccct atgcctccct gacagagata gagcacctgg tgcagagcgt ctgcaagtcc    840
tacagggaga catgccagct gcggctggag gacctgctgc ggcagcgctc caacatcttc    900
tcccgggagg aagtgactgg ctaccagagg aagtccatgt gggagatgtg ggaacggtgt    960
gcccaccacc tcaccgaggc cattcagtac gtggtggagt cgccaagag gctctcaggc    1020
tttatggagc tctgccagaa tgaccagatt gtgcttctca agcaggagc aatggaagtg    1080
gtgctggtta ggatgtgccg ggcctacaat gctgacaacc gcacggtctt ttttgaaggc    1140
aaatacggtg gcatggagct gttccgagcc ttgggctgca gcgagctcat cagctccatc    1200
tttgacttct cccactccct aagtgccttg cacttttccg aggatgagat tgccctctac    1260
acagcccttg ttctcatcaa tgcccatcgg ccagggctcc aagagaaaag gaaagtagaa    1320
cagctgcagt acaatctgga gctggccttt catcatcatc tctgcaagac tcatcgccaa    1380
agcatcctgg caaagctgcc acccaagggg aagcttcgga gcctgtgtag ccagcatgtg    1440
gaaaggctgc agatcttcca gcacctccac cccatcgtgg tccaagccgc tttccctcca    1500
ctctacaagg agctcttcag cactgaaacc gagtcacctg tgggctgtcc aagtgacctg    1560
gaagagggac tccttgcctc tccctatggc ctgctggcca cctccctgga ccccgttcca    1620
ccctcaccct tttcctttcc catgaaccct ggagggtggt ccccaccagc tctttggaag    1680
``` tga                                                                      1683

<210> SEQ ID NO 117
<211> LENGTH: 1395
<212> TYPE: DNA
<213> ORGANISM: Homo sapiens

<400> SEQUENCE: 117

| | | | | | |
|---|---|---|---|---|---|
| atgcgactct | ccaaaaccct | cgtcgacatg | gacatggccg | actacagtgc | tgcactggac | 60 |
| ccagcctaca | ccaccctgga | atttgagaat | gtgcaggtgt | tgacgatggg | caatgacacg | 120 |
| tccccatcag | aaggcaccaa | cctcaacgcg | cccaacagcc | tgggtgtcag | cgccctgtgt | 180 |
| gccatctgcg | gggaccgggc | cacgggcaaa | cactacggtg | cctcgagctg | tgacggctgc | 240 |
| aagggcttct | tccggaggag | cgtgcggaag | aaccacatgt | actcctgcag | atttagccgg | 300 |
| cagtgcgtgg | tggacaaaga | caagaggaac | cagtgccgct | actgcaggct | caagaaatgc | 360 |
| ttccgggctg | gcatgaagaa | ggaagccgtc | cagaatgagc | gggaccggat | cagcactcga | 420 |
| aggtcaagct | atgaggacag | cagcctgccc | tccatcaatg | cgctcctgca | ggcggaggtc | 480 |
| ctgtcccgac | agatcaccct | ccccgtctcc | gggatcaacg | cgacattcg | ggcgaagaag | 540 |
| attgccagca | tcgcagatgt | gtgtgagtcc | atgaaggagc | agctgctggt | tctcgttgag | 600 |
| tgggccaagt | acatcccagc | tttctgcgag | ctccccctgg | acgaccaggt | ggccctgctc | 660 |
| agagcccatg | ctggcgagca | cctgctgctc | ggagccacca | gagatccat | ggtgttcaag | 720 |
| gacgtgctgc | tcctaggcaa | tgactacatt | gtccctcggc | actgcccgga | gctggcggag | 780 |
| atgagccggg | tgtccatacg | catccttgac | gagctggtgc | tgcccttcca | ggagctgcag | 840 |
| atcgatgaca | atgagtatgc | ctacctcaaa | gccatcatct | tctttgaccc | agatgccaag | 900 |
| gggctgagcg | atccagggaa | gatcaagcgg | ctgcgttccc | aggtgcaggt | gagcttggag | 960 |
| gactacatca | acgaccgcca | gtatgactcg | cgtggccgct | ttggagagct | gctgctgctg | 1020 |
| ctgcccacct | tgcagagcat | cacctggcag | atgatcgagc | agatccagtt | catcaagctc | 1080 |
| ttcggcatgg | ccaagattga | caacctgttg | caggagatgc | tgctgggagg | gtcccccagc | 1140 |
| gatgcacccc | atgcccacca | ccccctgcac | cctcacctga | tgcaggaaca | tatgggaacc | 1200 |
| aacgtcatcg | ttgccaacac | aatgcccact | cacctcagca | acggacagat | gtccacccct | 1260 |
| gagaccccac | agccctcacc | gccaggtggc | tcagggtctg | agccctataa | gctcctgccg | 1320 |
| ggagccgtcg | ccacaatcgt | caagcccctc | tctgccatcc | cccagccgac | catcaccaag | 1380 |
| caggaagtta | tctag      |            |            |            |            | 1395 |

<210> SEQ ID NO 118
<211> LENGTH: 2385
<212> TYPE: DNA
<213> ORGANISM: Homo sapiens

<400> SEQUENCE: 118

| | | | | | |
|---|---|---|---|---|---|
| atggcgggct | ggatccaggc | ccagcagctg | cagggagacg | cgctgcgcca | gatgcaggtg | 60 |
| ctgtacggcc | agcacttccc | catcgaggtc | cggcactact | ggcccagtg | gattgagagc | 120 |
| cagccatggg | atgccattga | cttggacaat | ccccaggaca | gagcccaagc | cacccagctc | 180 |
| ctggagggcc | tggtgcagga | gctgcagaag | aaggcggagc | accaggtggg | ggaagatggg | 240 |
| ttttttactga | agatcaagct | gaggcactac | gccacgcagc | tccagaaaaac | atatgaccgc | 300 |
| tgccccctgg | agctggtccg | ctgcatccgg | cacattctgt | acaatgaaca | gaggctggtc | 360 |
| cgagaagcca | acaattgcag | ctctccggct | gggatcctgg | ttgacgccat | gtcccagaag | 420 |

```
caccttcaga tcaaccagac atttgaggag ctgcgactgg tcacgcagga cacagagaat      480
gagctgaaga aactgcagca gactcaggag tacttcatca tccagtacca ggagagcctg      540
aggatccaag ctcagtttgc ccagctggcc cagctgagcc cccaggagcg tctgagccgg      600
gagacggccc tccagcagaa gcaggtgtct ctggaggcct ggttgcagcg tgaggcacag      660
acactgcagc agtaccgcgt ggagctggcc gagaagcacc agaagaccct gcagctgctg      720
cggaagcagc agaccatcat cctggatgac gagctgatcc agtggaagcg gcggcagcag      780
ctggccggga acggcgggcc ccccgagggc agcctggacg tgctacagtc ctggtgtgag      840
aagttggccg agatcatctg gcagaaccgg cagcagatcc gcagggctga gcacctctgc      900
cagcagctgc ccatccccgg cccagtggag gagatgctgg ccgaggtcaa cgccaccatc      960
acggacatta tctcagccct ggtgaccagc acattcatca ttgagaagca gcctcctcag     1020
gtcctgaaga cccagaccaa gtttgcagcc accgtacgcc tgctggtggg cgggaagctg     1080
aacgtgcaca tgaatccccc ccaggtgaag gccaccatca tcagtgagca gcaggccaag     1140
tctctgctta aaaatgagaa cacccgcaac gagtgcagtg gtgagatcct gaacaactgc     1200
tgcgtgatgg agtaccacca agccacgggc accctcagtg cccacttcag gaacatgtca     1260
ctgaagagga tcaagcgtgc tgaccggcgg ggtgcagagt ccgtgacaga ggagaagttc     1320
acagtcctgt ttgagtctca gttcagtgtt ggcagcaatg agcttgtgtt ccaggtgaag     1380
actctgtccc tacctgtggt tgtcatcgtc cacggcagcc aggaccacaa tgccacggct     1440
actgtgctgt gggacaatgc ctttgctgag ccgggcaggg tgccatttgc cgtgcctgac     1500
aaagtgctgt ggccgcagct gtgtgaggcg ctcaacatga aattcaaggc cgaagtgcag     1560
agcaaccggg gcctgaccaa ggagaacctc gtgttcctgg cgcagaaact gttcaacaac     1620
agcagcagcc acctggagga ctacagtggc ctgtccgtgt cctggtccca gttcaacagg     1680
gagaacttgc cgggctggaa ctacaccttc tggcagtggt ttgacggggt gatggaggtg     1740
ttgaagaagc accacaagcc ccactggaat gatggggcca tcctaggttt tgtgaataag     1800
caacaggccc acgacctgct catcaacaag cccgacggga ccttcttgtt gcgctttagt     1860
gactcagaaa tcggggcat caccatcgcc tggaagtttg attccccgga acgcaacctg      1920
tggaacctga aaccattcac cacgcgggat ttctccatca ggtccctggc tgaccggctg     1980
ggggacctga gctatctcat ctatgtgttt cctgaccgcc ccaaggatga ggtcttctcc     2040
aagtactaca ctcctgtgct ggctaaagct gttgatggat atgtgaaacc acagatcaag     2100
caagtggtcc ctgagtttgt gaatgcatct gcagatgctg ggggcagcag cgccacgtac     2160
atggaccagg cccccctccc agctgtgtgc ccccaggctc cctataacat gtacccacag     2220
aaccctgacc atgtactcga tcaggatgga gaattcgacc tggatgagac catggatgtg     2280
gccaggcacg tggaggaact cttacgccga ccaatggaca gtcttgactc ccgcctctcg     2340 cccectgccg gtcttttcac ctctgccaga ggctccctct catga                     2385
```

<210> SEQ ID NO 119
<211> LENGTH: 1725
<212> TYPE: DNA
<213> ORGANISM: Homo sapiens

<400> SEQUENCE: 119

```
atgtggactt ttctgggcat tgccactttc acctattttt ataagaagtt cggggacttc       60
atcactttgg ccaacaggga ggtcctgttg tgcgtgctgg tgttcctctc gctgggcctg      120
```

| | |
|---|---|
| gtgctctcct accgctgtcg ccaccgaaac gggggtctcc tcgggcgcca gcagagcggc | 180 |
| tcccagttcg ccctcttctc ggatattctc tcaggcctgc cttteattgg cttcttctgg | 240 |
| gccaaatccc ccctgaatc agaaaataag gagcagctcg aggccaggag gcgcagaaaa | 300 |
| ggaaccaata tttcagaaac aagcttaata ggaacagctg cctgtacatc aacatcttct | 360 |
| cagaatgacc cagaagttat catcgtggga gctggcgtgc ttggctctgc tttggcagct | 420 |
| gtgctttcca gagatggaag aaaggtgaca gtcattgaga gagacttaaa agagcctgac | 480 |
| agaatagttg gagaattcct gcagccgggt ggttatcatg ttctcaaaga ccttggtctt | 540 |
| ggagatacag tggaaggtct tgatgcccag gttgtaaatg ttacatgat tcatgatcag | 600 |
| gaaagcaaat cagaggttca gattccttac cctctgtcag aaaacaatca agtgcagagt | 660 |
| ggaagagctt ccatcacgg aagattcatc atgagtctcc ggaaagcagc tatggcagag | 720 |
| cccaatgcaa agtttattga aggtgttgtg ttacagttat tagaggaaga tgatgttgtg | 780 |
| atgggagttc agtacaagga taaagagact ggagatatca aggaactcca tgctccactg | 840 |
| actgttgttg cagatgggct tttctccaag ttcaggaaaa gcctggtctc caataaagtt | 900 |
| tctgtatcat ctcattttgt tggctttctt atgaagaatg caccacagtt taaagcaaat | 960 |
| catgctgaac ttattttagc taacccgagt ccagttctca tctaccagat ttcatccagt | 1020 |
| gaaactcgag tacttgttga cattagagga gaaatgccaa ggaatttaag agaatacatg | 1080 |
| gttgaaaaaa tttacccaca aatacctgat cacctgaaag aaccattctt agaagccact | 1140 |
| gacaattctc atctgaggtc catgccagca agcttccttc ctccttcatc agtgaagaaa | 1200 |
| cgaggtgttc ttcttttggg agacgcatat aatatgaggc atccacttac tggtggagga | 1260 |
| atgactgttg cttttaaaga tataaaacta tggagaaaac tgctaaaggg tatccctgac | 1320 |
| ctttatgatg atgcagctat tttcgaggcc aaaaaatcat tttactgggc aagaaaaaca | 1380 |
| tctcattcct ttgtcgtgaa tatccttgct caggctcttt atgaattatt ttctgccaca | 1440 |
| gatgattccc tgcatcaact aagaaaagcc tgttttcttt atttcaaact tggtggcgaa | 1500 |
| tgtgttgcgg gtcctgttgg gctgctttct gtattgtctc ctaaccctct agttttaatt | 1560 |
| ggacacttct ttgctgttgc aatctatgcc gtgtattttt gctttaagtc agaaccttgg | 1620 |
| attacaaaac ctcgagccct tctcagtagt ggtgctgtat tgtacaaagc gtgttctgta | 1680 |
| atatttcctc taatttactc agaaatgaag tatatggttc attaa | 1725 |

<210> SEQ ID NO 120
<211> LENGTH: 1029
<212> TYPE: DNA
<213> ORGANISM: Homo sapiens

<400> SEQUENCE: 120

| | |
|---|---|
| atggacctgt ggaactggga tgaggcatcc ccacaggaag tgcctccagg gaacaagctg | 60 |
| gcagggcttg aaggagccaa attaggcttc tgtttccctg atctggcact ccaaggggac | 120 |
| acgccgacag cgacagcaga gacatgctgg aaaggtacaa gctcatccct ggcaagcttc | 180 |
| ccacagctgg actggggctc cgcgttactg cacccagaag ttccatgggg ggcggagccc | 240 |
| gactctcagg ctcttccgtg gtccggggac tggacagaca tggcgtgcac agcctgggac | 300 |
| tcttggagcg gcgcctcgca gaccctgggc ccgcccctc tcggcccggg ccccatcccc | 360 |
| gccgccggct ccgaaggcgc cgcgggccag aactgcgtcc cgtggcggg agaggccacc | 420 |
| tcgtggtcgc gcgcccaggc cgccgggagc aacaccagct gggactgttc tgtgggccc | 480 |
| gacggcgata cctactgggg cagtggcctg gcggggagc cgcgcacgga ctgtaccatt | 540 |

| | |
|---|---|
| tcgtggggcg ggcccgcggg cccggactgt accacctcct ggaacccggg gctgcatgcg | 600 |
| ggtggcacca cctctttgaa gcggtaccag agctcagctc tcaccgtttg ctccgaaccg | 660 |
| agcccgcagt cggaccgtgc cagtttggct cgatgcccca aaactaacca ccgaggtccc | 720 |
| attcagctgt ggcagttcct cctggagctg ctccacgacg gggcgcgtag cagctgcatc | 780 |
| cgttggactg gcaacagccg cgagttccag ctgtgcgacc ccaaagaggt ggctcggctg | 840 |
| tggggcgagc gcaagagaaa gccgggcatg aattacgaga agctgagccg gggccttcgc | 900 |
| tactactatc gccgcgacat cgtgcgcaag agcgggggc gaaagtacac gtaccgcttc | 960 |
| gggggccgcg tgcccagcct agcctatccg gactgtgcgg gaggcggacg gggagcagag | 1020 |
| acacaataa | 1029 |

```
<210> SEQ ID NO 121
<211> LENGTH: 1443
<212> TYPE: DNA
<213> ORGANISM: Homo sapiens

<400> SEQUENCE: 121
```

| | |
|---|---|
| atggaggtgg cgcccgagca gccgcgctgg atggcgcacc cggccgtgct gaatgcgcag | 60 |
| caccccgact cacaccaccc gggcctggcg cacaactaca tggaacccgc gcagctgctg | 120 |
| cctccagacg aggtggacgt cttcttcaat cacctcgact cgcagggcaa ccctactat | 180 |
| gccaaccccg ctcacgcgcg ggcgcgcgtc tcctacagcc ccgcgcacgc ccgcctgacc | 240 |
| ggaggccaga tgtgccgccc acacttgttg cacagcccgg gtttgccctg gctggacggg | 300 |
| ggcaaagcag ccctctctgc cgctgcggcc caccaccaca cccctggac cgtgagcccc | 360 |
| ttctccaaga cgccactgca cccctcagct gctggaggcc ctggaggccc actctctgtg | 420 |
| tacccagggg ctgggggtgg gagcggggga ggcagcggga gctcagtggc ctccctcacc | 480 |
| cctacagcag cccactctgg ctcccaccct ttcggcttcc cacccacgcc acccaaagaa | 540 |
| gtgtctcctg accctagcac cacggggct gcgtctccag cctcatcttc gcgggggt | 600 |
| agtgcagccc gaggagagga caaggacggc gtcaagtacc aggtgtcact gacggagagc | 660 |
| atgaagatgg aaagtggcag tccctgcgc ccaggcctag ctactatggg cacccagcct | 720 |
| gctacacacc accccatccc cacctacccc tcctatgtgc cggcggctgc ccacgactac | 780 |
| agcagcggac tcttccaccc cggaggcttc ctgggggac cggcctccag cttcacccct | 840 |
| aagcagcgca gcaaggctcg ttcctgttca gaaggccggg agtgtgtcaa ctgtggggcc | 900 |
| acagccaccc ctctctggcg gcgggacggc accggccact acctgtgcaa tgcctgtggc | 960 |
| ctctaccaca gatgaatgg gcagaaccga ccactcatca gcccaagcg aagactgtcg | 1020 |
| gccgccagaa gagccggcac ctgttgtgca aattgtcaga cgacaaccac caccttatgg | 1080 |
| cgccgaaacg ccaacgggga ccctgtctgc aacgcctgtg gcctctacta caagctgcac | 1140 |
| aatgttaaca ggccactgac catgaagaag gaagggatcc agactcggaa ccggaagatg | 1200 |
| tccaacaagt ccaagaagag caagaaaggg gcggagtgct tcgaggagct gtcaaagtgc | 1260 |
| atgcaggaga agtcatcccc cttcagtgca gctgccctgg ctggacacat ggcacctgtg | 1320 |
| ggccacctcc cgcccttcag ccactccgga cacatcctgc ccactccgac gcccatccac | 1380 |
| ccctcctcca gcctctcctt cggccacccc caccgtcca gcatggtgac cgccatgggc | 1440 |
| tag | 1443 |

```
<210> SEQ ID NO 122
```

```
<211> LENGTH: 915
<212> TYPE: DNA
<213> ORGANISM: Homo sapiens

<400> SEQUENCE: 122
atgaagcgag ctcaccccga gtacagctcc tcggacagcg agctggacga gaccatcgag      60
gtggagaagg agagtgcgga cgagaatgga aacttgagtt cggctctagg ttccatgtcc     120
ccaactacat cttcccagat tttggccaga aaaagacgga gaggaataat tgagaagcgc     180
cgacgagacc ggatcaataa cagtttgtct gagctgagaa ggctggtacc cagtgctttt     240
gagaagcagg gatctgctaa gctagaaaaa gccgagatcc tgcagatgac cgtggatcac     300
ctgaaaatgc tgcatacggc aggagggaaa ggttactttg acgcgcacgc ccttgctatg     360
gactatcgga gtttgggatt cgggaatgc ctggcagaag ttgcgcgtta tctgagcatc      420
attgaaggac tagatgcctc tgacccgctt cgagttcgac tggtttcgca tctcaacaac     480
tacgcttccc agcgggaagc cgcgagcggc gccacgcgg gcctcggaca cattccctgg      540
gggaccgtct tcggacatca cccgcacatc gcgcacccgt gttgctgcc ccagaacggc      600 cacgggaacg cgggcaccac ggcctcaccc acggaaccgc accaccaggg caggctgggc     660
tcggcacatc cggaggcgcc tgctttgcga gcgcccccta gcggcagcct cggaccggtg     720
ctccctgtgg tcacctccgc ctccaaactg tcgccgcctc tgctctcctc agtggcctcc     780
ctgtcggcct tcccttctc tttcggctcc ttccacttac tgtctcccaa tgcactgagc      840
ccttcagcac ccacgcaggc tgcaaacctt ggcaagccct atagaccttg ggggacggag     900
atcggagctt tttaa                                                     915

<210> SEQ ID NO 123
<211> LENGTH: 1014
<212> TYPE: DNA
<213> ORGANISM: Homo sapiens

<400> SEQUENCE: 123
atgaagcgcc cctgcgagga cgcgacctcc gagagcgaca tggacgagac catcgacgtg      60
gggagcgaga acaattactc ggggcaaagt actagctctg tgattagatt gaattctcca     120
acaacaacat ctcagattat ggcaagaaag aaaaggagag ggattataga gaaaaggcgt     180
cgggatcgga taataacag tttatctgag ttgagaagac ttgtgccaac tgcttttgaa      240
aaacaaggat ctgcaaagtt agaaaaagct gaaatattgc aaatgacagt ggatcatttg     300
aagatgcttc aggcaacagg gggtaaaggc tactttgacg cacacgctct tgccatggac     360
ttcatgagca taggattccg agagtgccta acagaagttg cgcggtacct gagctccgtg     420
gaaggcctgg actcctcgga tccgctgcgg gtgcggcttg tgtctcatct cagcacttgc     480
gccacccagc gggaggcggc ggccatgaca tcctccatgg cccaccacca tcatccgctc     540
cacccgcatc actgggccgc cgccttccac cacctgcccg cagccctgct ccagcccaac     600
ggcctccatg cctcagagtc aaccccttgt cgcctctcca caacttcaga agtgcctcct     660
gcccacggct ctgctctcct cacggccacg tttgcccatg cggattcagc cctccgaatg     720
ccatccacgg gcagcgtcgc ccctgcgtg ccacctctct ccacctctct cttgtccctc      780
tctgccaccg tccacgccgc agccgcagca gccaccgcgg ctgcacacag cttccctctg     840
tccttcgcgg ggcattccc catgcttccc ccaaacgcag cagcagcagt ggccgcggcc      900
acagccatca gcccgccctt gtcagtatca gccacgtcca gtcctcagca gaccagcagt     960
ggaacaaaca ataaacctta ccgaccctgg gggacagaag ttggagcttt ttaa           1014
```

<210> SEQ ID NO 124
<211> LENGTH: 1662
<212> TYPE: DNA
<213> ORGANISM: Homo sapiens

<400> SEQUENCE: 124

```
atgcaggcgc gctactccgt gtccagcccc aactccctgg gagtggtgcc ctacctcggc      60
ggcgagcaga gctactaccg cgcggcggcc gcggcggccg ggggcggcta caccgccatg     120
ccggccccca tgagcgtgta ctcgcaccct gcgcacgccg agcagtaccc gggcggcatg     180
gcccgcgcct acgggcccta cacgccgcag ccgcagccca aggacatggt gaagccgccc     240
tatagctaca tcgcgctcat caccatggcc atccagaacg ccccggacaa gaagatcacc     300
ctgaacggca tctaccagtt catcatggac cgcttcccct tctaccggga caacaagcag     360
ggctggcaga acagcatccg ccacaacctc tcgctcaacg agtgcttcgt caaggtgccg     420
cgcgacgaca gaagccgggc aagggcagc tactggacgc tggacccgga ctcctacaac     480
atgttcgaga cggcagctt cctgcggcgg cggcggcgct tcaagaagaa ggacgcggtg     540
aaggacaagg aggagaagga caggctgcac ctcaaggagc cgcccccgcc cggccgccag     600
ccccccgcccg cgccgccgga gcaggccgac ggcaacgcgc ccggtccgca gccgccgccc     660
gtgcgcatcc aggacatcaa gaccgagaac ggtacgtgcc cctcgccgcc ccagcccctg     720
tccccggccg ccgccctggg cagcggcagc gccgccgcgg tgcccaagat cgagagcccc     780
gacagcagca gcagcagcct gtccagcggg agcagccccc cgggcagcct gccgtcggcg     840
cggccgctca gcctggacgg tgcggattcc gcgccgccgc cgcccgcgcc ctccgccccg     900
ccgccgcacc atagccaggg cttcagcgtg acaacatca tgacgtcgct gcggggggtcg     960
ccgcagagcg cggccgcgga gctcagctcc ggccttctgg cctcggcggc cgcgtcctcg    1020
cgcgcgggga tcgcaccccc gctggcgctc ggcgcctact cgcccggcca gagctccctc    1080
tacagctccc cctgcagcca gacctccagc gcgggcagct cggcgcggcgg cggcggcggc    1140
gcggggcccg cgggggcgc gggcggcgcc gggacctacc actgcaacct gcaagccatg    1200
agcctgtacg cggccggcga gcgcggggc cacttgcagg gcgcgcccgg gggcgcgggc    1260
ggctcggccg tggacgaccc cctgcccgac tactctctgc ctccggtcac cagcagcagc    1320
tcgtcgtccc tgagtcacgg cggcggcggc ggcggcggcg gggaggcca ggaggccggc    1380
caccaccctg cggcccacca aggccgcctc acctcgtggt acctgaacca ggcgggcgga    1440
gacctgggcc acttggcgag cgcggcggcg cggcggcgg ccgcaggcta cccgggccag    1500
cagcagaact tccactcggt gcgggagatg ttcgagtcac agaggatcgg cttgaacaac    1560
tctccagtga acgggaatag tagctgtcaa atggccttcc cttccagcca gtctctgtac    1620
cgcacgtccg gagctttcgt ctacgactgt agcaagtttt ga                       1662
```

<210> SEQ ID NO 125
<211> LENGTH: 1506
<212> TYPE: DNA
<213> ORGANISM: Homo sapiens

<400> SEQUENCE: 125

```
atgcaggcgc gctactccgt gtccgacccc aacgccctgg gagtggtgcc ctacctgagc      60
gagcagaatt actaccgggc tgcggcagc tacggcggca tggccagccc catgggcgtc     120
tattccggcc acccggagca gtacagcgcg gggatgggcc gctcctacgc gccctaccac     180
```

| | |
|---|---|
| caccaccagc cgcggcgcc taaggacctg gtgaagccgc cctacagcta catcgcgctc | 240 |
| atcaccatgg ccatccagaa cgcgcccgag aagaagatca ccttgaacgg catctaccag | 300 |
| ttcatcatgg accgcttccc cttctaccgg gagaacaagc agggctggca gaacagcatc | 360 |
| cgccacaacc tctcgctcaa cgagtgcttc gtcaaggtgc cccgcgacga caagaagccc | 420 |
| ggcaagggca gttactggac cctggacccg gactcctaca acatgttcga gaacggcagc | 480 |
| ttcctgcggc gccggcggcg cttcaaaaag aaggacgtgt ccaaggagaa ggaggagcgg | 540 |
| gcccacctca aggagccgcc cccggcggcg tccaagggcg ccccggccac cccccaccta | 600 |
| gcggacgccc ccaaggaggc cgagaagaag gtggtgatca agagcgaggc ggcgtccccg | 660 |
| gcgctgccgg tcatcaccaa ggtggagacg ctgagccccg agcgcgcgct gcagggcagc | 720 |
| ccgcgcagcg cggcctccac gcccgccggc tcccccgacg gctcgctgcc ggagcaccac | 780 |
| gccgcggcgc ccaacgggct gcctggcttc agcgtggaga acatcatgac cctgcgaacg | 840 |
| tcgccgccgg gcggagagct gagcccgggg gccggacgcg cgggcctggt ggtgccgccg | 900 |
| ctggcgctgc cctacgccgc cgcgccgccc gccgcctacg ccagccgtg cgctcagggc | 960 |
| ctggaggccg gggccgccgg gggctaccag tgcagcatgc gagcgatgag cctgtacacc | 1020 |
| ggggccgagc ggccggcgca catgtgcgtc ccgcccgccc tggacgaggc cctctcggac | 1080 |
| cacccgagcg gccccacgtc gcccctgagc gctctcaacc tcgccgccgg ccaggagggc | 1140 |
| gcgctcgccg ccacgggcca ccaccaccag caccacggcc accaccaccc gcaggcgccg | 1200 |
| ccgcccccgc cggctcccca gccccagccg acgccgcagc ccggggccgc cgcggcgcag | 1260 |
| gcggcctcct ggtatctcaa ccacagcggg gacctgaacc acctccccgg ccacacgttc | 1320 |
| gcggcccagc agcaaacttt ccccaacgtg cgggagatgt tcaactccca ccggctgggg | 1380 |
| attgagaact cgaccctcgg ggagtccag gtgagtggca atgccagctg ccagctgccc | 1440 |
| tacagatcca cgccgcctct ctatcgccac gcagccccct actcctacga ctgcacgaaa | 1500 |
| tactga | 1506 |

<210> SEQ ID NO 126
<211> LENGTH: 1167
<212> TYPE: DNA
<213> ORGANISM: Homo sapiens

<400> SEQUENCE: 126

| | |
|---|---|
| atggcttcgc tgctgggagc ctacccttgg cccgagggtc tcgagtgccc ggccctggac | 60 |
| gccgagctgt cggatggaca atcgccgccg ccgtccccc ggcccccggg ggacaagggc | 120 |
| tccgagagcc gtatccggcg gcccatgaac gccttcatgg tttgggccaa ggacgagagg | 180 |
| aaacggctgg cagtgcagaa cccggacctg cacaacgccg agctcagcaa gatgctggga | 240 |
| aagtcgtgga aggcgctgac gctgtcccag aagaggccgt acgtggacga ggcggagcgg | 300 |
| ctgcgcctgc agcacatgca ggactacccc aactacaagt accggccgcg caggaagaag | 360 |
| caggccaagc ggctgtgcaa gcgcgtggac ccgggcttcc ttctgagctc cctctcccgg | 420 |
| gaccagaacg ccctgccgga aagagaagc ggcagccggg gggcgctggg ggagaaggag | 480 |
| gacaggggtg agtactcccc cggcactgcc ctgccagcc tccggggctg ctaccacgag | 540 |
| gggccggctg gtggtggcgg cggcggcacc ccgagcagtg tggacacgta cccgtacggg | 600 |
| ctgcccacac ctcctgaaat gtctcccctg gacgtgctgg agccggagca gaccttcttc | 660 |
| tcctcccccct gccaggagga gcatggccat ccccgccgca tccccacct gccagggcac | 720 |
| ccgtactcac cggagtacgc cccaagccct ctccactgta gccacccccct gggctccctg | 780 |

-continued

```
gcccttggcc agtccccgg cgtctccatg atgtcccctg tacccggctg tcccccatct      840
cctgcctatt actcccggc cacctaccac ccactccact ccaacctcca agcccacctg      900
ggccagcttt ccccgcctcc tgagcaccct ggcttcgacg ccctggatca actgagccag    960
gtggaactcc tggggacat ggatcgcaat gaattcgacc agtatttgaa cactcctggc    1020
cacccagact ccgccacagg ggccatggcc ctcagtgggc atgttccggt ctcccaggtg   1080
acaccaacgg gtcccacaga gaccagcctc atctccgtcc tggctgatgc cacggccacg   1140
tactacaaca gctacagtgt gtcatag                                        1167
```

<210> SEQ ID NO 127
<211> LENGTH: 1155
<212> TYPE: DNA
<213> ORGANISM: Homo sapiens

<400> SEQUENCE: 127

```
atgcagagat cgccgcccgg ctacggcgca caggacgacc cgcccgcccg ccgcgactgt     60
gcatgggccc cgggacacgg ggccgccgct gacacgcgcg gcctcgccgc cggccccgcc    120
gccctcgccg cgcccgccgc gcccgcctcg ccgcccagcc cgcagcgcag tcccccgcgc    180
agccccgagc cggggcgcta tggcctcagc ccggccggcc gcggggaacg ccaggcggca    240
gacgagtcgc gcatccggcg gcccatgaac gccttcatgg tgtgggcaaa ggacgagcgc    300
aagcggctgg ctcagcagaa cccggacctg cacaacgcgg tgctcagcaa gatgctgggc    360
aaagcgtgga aggagctgaa cgcggcggag aagcggccct tcgtggagga agccgaacgg    420
ctgcgcgtgc agcacttgcg cgaccacccc aactacaagt accggccgcg ccgcaagaag    480
caggcgcgca aggcccggcg gctggagccc ggcctcctgc tcccgggatt agcgcccccg    540
cagccaccgc ccgagccttt ccccgcggcg tctggctcgg ctcgcgcctt ccgcgagctg    600
cccccgctgg gcgccgagtt cgacggcctg gggctgccca cgcccgagcg ctcgcctctg    660
gacggcctgg agcccggcga ggctgccttc ttcccaccgc ccgcggcgcc cgaggactgc    720
gcgctgcggc ccttccgcgc gccctacgcg cccaccgagt tgtcgcggga ccccggcggt    780
tgctacgggg ctcccctggc ggaggcgctc aggaccgcgc cccccgcggc gccgctcgct    840
ggcctgtact acggcaccct gggcacgccc ggcccgtacc ccggcccgct gtcgccgccg    900
cccgaggccc cgccgctgga gagcgccgag ccgctgggc ccgccgccga tctgtgggcc    960
gacgtggacc tcaccgagtt cgaccagtac ctcaactgca gccggactcg gcccgacgcc   1020
cccgggctcc cgtaccacgt ggcactggcc aaactgggcc cgcgcgccat gtcctgccca   1080
gaggagagca gcctgatctc cgcgctgtcg gacgccagca gcgcggtcta ttacagcgcg   1140
tgcatctccg gctag                                                    1155
```

METHODS, SYSTEMS AND COMPOSITIONS RELATING TO CELL CONVERSION VIA PROTEIN-INDUCED IN-VIVO CELL REPROGRAMMING

REFERENCE TO RELATED APPLICATIONS

This application is a divisional of U.S. patent application Ser. No. 15/031,839, filed Apr. 25, 2016, which is a U.S. national phase application of PCT/US2014/062400, filed Oct. 27, 2014, which claims priority from U.S. provisional Patent Application Ser. No. 61/895,562, filed Oct. 25, 2013. The entire content of each application is incorporated herein by reference.

GRANT REFERENCE

This invention was made with government support under Grant No. 1 R01 CA172480-01A1, awarded by the National Institutes of Health/National Cancer Institute. The Government has certain rights in the invention.

FIELD OF THE INVENTION

The present invention relates generally to methods, systems and compositions for treatment of a pathological condition in a subject in need thereof. In specific aspects, the present invention relates to methods, systems and compositions for protein-induction of cell conversion in vivo for treatment of a pathological condition in a subject in need thereof.

BACKGROUND OF THE INVENTION

Despite recent medical progress, there is a continuing need for methods and compositions for treatment of disease and injury.

SUMMARY OF THE INVENTION

Methods of treating a subject in need thereof are provided according to aspects of the present invention which include administering a pharmaceutical composition comprising a protein transduction reagent-modified reprogramming protein to the subject, wherein the protein transduction reagent is non-covalently bound to the reprogramming protein and wherein the protein transduction reagent comprises a cation reagent and a lipid.

Methods of treating a subject in need thereof are provided according to aspects of the present invention which include administering a pharmaceutical composition comprising a protein transduction reagent-modified reprogramming protein to the subject, wherein the protein transduction reagent is non-covalently bound to the reprogramming protein and wherein the protein transduction reagent comprises a cation reagent and a lipid, wherein the subject has a disease selected from the group consisting of: cancer; pancreatic disease or injury; heart disease or heart injury such as acute myocardial infarction, chronic myocardial infarction and heart failure; liver injury or liver disease such as familial hyper-cholesterolaemia (FH), Crigler-Najjar syndrome and hereditary tryosinemia I; atherosclerosis; neurological disease or injury such as spinal cord injury, traumatic brain injury, amyotrophic lateral sclerosis, spinal muscular atrophy and Parkinson's disease; arthritis; joint disease or injury; blood disease; diabetes; obesity; muscle disease or injury; cartilage disease or injury; breast disease or injury; and vascular disease or injury.

Methods of treating a subject having a condition characterized by damaged and/or defective cells are provided according to aspects of the present invention including: administering a pharmaceutical composition including a protein transduction reagent-modified reprogramming protein to the subject, wherein the protein transduction reagent is non-covalently bound to the reprogramming protein and wherein the protein transduction reagent comprises a cation reagent and a lipid.

Methods of treating a subject having cancer including: administering a pharmaceutical composition including a protein transduction reagent-modified reprogramming protein to the subject, wherein the protein transduction reagent is non-covalently bound to the reprogramming protein and wherein the protein transduction reagent comprises a cation reagent and a lipid.

Methods of treating a subject having cancer are provided according to aspects of the present invention which include administering a pharmaceutical composition including a protein transduction reagent-modified reprogramming protein selected from the group consisting of: protein transduction reagent-modified Sox2, protein transduction reagent-modified Oct4 and protein transduction reagent-modified Nanog.

Methods of treating a subject having cancer are provided according to aspects of the present invention which include administering a pharmaceutical composition including protein transduction reagent-modified Sox2, protein transduction reagent-modified Oct4 and protein transduction reagent-modified Nanog.

Methods of treating a subject having a brain tumor or breast cancer and are provided according to aspects of the present invention which include administering a pharmaceutical composition including a protein transduction reagent-modified reprogramming protein selected from the group consisting of: protein transduction reagent-modified Sox2, protein transduction reagent-modified Oct4 and protein transduction reagent-modified Nanog.

Methods of treating a subject having a brain tumor or breast cancer and are provided according to aspects of the present invention which include administering a pharmaceutical composition including protein transduction reagent-modified Sox2, protein transduction reagent-modified Oct4 and protein transduction reagent-modified Nanog.

Methods of treating a subject having a condition characterized by damaged and/or defective cells are provided according to aspects of the present invention including: administering a pharmaceutical composition including a protein transduction reagent-modified reprogramming protein to the subject, wherein the protein transduction reagent is non-covalently bound to the reprogramming protein and wherein the protein transduction reagent comprises a cation reagent and a lipid, wherein the condition is a heart disease or heart damage and the pharmaceutical composition comprises one or more of: protein transduction reagent-modified Gata4, protein transduction reagent-modified Hand2, protein transduction reagent-modified MEF2c and protein transduction reagent-modified Tbox5; wherein the condition is a liver disease or liver damage and the pharmaceutical composition comprises one or more of: protein transduction reagent-modified Hnf1a, protein transduction reagent-modified Foxa1, protein transduction reagent-modified Foxa2 and protein transduction reagent-modified Foxa3; wherein the condition is a liver disease or liver damage and the pharmaceutical composition comprises one or more of: protein transduction reagent-modified Gata4, protein transduction reagent-modified Hnf1a and protein transduction reagent-modified Foxa3; wherein the condition is atherosclerosis and the pharmaceutical composition comprises one or more of: protein transduction reagent-modified CEBPα, protein transduction reagent-modified CEBPβ and protein transduction reagent-modified PU.1; wherein the condition is a neurodegenerative disease or neuronal tissue damage and the pharmaceutical composition comprises one or more of: protein transduction reagent-modified Brn2, protein transduction reagent-modified Sox2 and protein transduction reagent-modified Foxg1; one or more of: protein transduction reagent-modified Asc1, protein transduction reagent-modified Lmx1a, protein transduction reagent-modified Nurr1, protein transduction reagent-modified Brn2 and protein transduction reagent-modified Mytl1; one or more of: protein transduction reagent-modified Asc1, protein transduction reagent-modified Brn2, protein transduction reagent-modified Mytl1 and protein transduction reagent-modified NeuroD1; protein transduction reagent-modified Ngn2; one or both of: protein transduction reagent-modified Sox2 and protein transduction reagent-modified NeuroD1; one or more of: protein transduction reagent-modified Brn2; protein transduction reagent-modified Ascl1, protein transduction reagent-modified Mytl1, protein transduction reagent-modified Lhx3 and protein transduction reagent-modified Hb9; one or more of: protein transduction reagent-modified Brn2, protein transduction reagent-modified Ascl1, protein transduction reagent-modified Mytl1, protein transduction reagent-modified Lhx3, protein transduction reagent-modified Hb9, protein transduction reagent-modified Lsl1 and protein transduction reagent-modified Ngn2; protein transduction reagent-modified Dlx2; protein transduction reagent-modified Dlx2 and protein transduction reagent-modified Ascl1; one or more of: protein transduction reagent-modified Asc1, protein transduction reagent-modified Brn2, protein transduction reagent-modified Mytl1, protein transduction reagent-modified Lmx1a and protein transduction reagent-modified Foxa2; or one or more of: protein transduction reagent-modified Asc1, protein transduction reagent-modified Lmx1a and protein transduction reagent-modified Nurr1; wherein the condition is a disease or disorder of the blood and the pharmaceutical composition comprises: protein transduction reagent-modified Oct4; wherein the condition is diabetes, a pancreatic disease or pancreatic tissue damage and the pharmaceutical composition comprises one or more of: protein transduction reagent-modified Ngn3, protein transduction reagent-modified Pdx1 and protein transduction reagent-modified Pax4 or one or more of: protein transduction reagent-modified Ngn3, protein transduction reagent-modified Pdx1 and protein transduction reagent-modified MafA; wherein the condition is obesity and the pharmaceutical composition comprises one or more of: protein transduction reagent-modified Prdm16 and protein transduction reagent-modified C/EBPb; wherein the condition is a muscle disease or muscle damage and the pharmaceutical composition comprises protein transduction reagent-modified MyoD; wherein the condition is arthritis or joint disease or injury and the pharmaceutical composition comprises or one or more of: protein transduction reagent-modified Sox9, protein transduction reagent-modified Runx2, protein transduction reagent-modified Sox5 and protein transduction reagent-modified Sox6; wherein the condition is a breast disease or breast tissue damage and the pharmaceutical composition comprises one or more of: protein transduction reagent-modified Sox9, protein transduction reagent-modified Slug, protein transduction reagent-modified Stat5a, protein transduction reagent-modified Gata3 and protein transduction reagent-modified Brca-1l; wherein the condition is a vascular disease or blood vessel damage and the pharmaceutical composition comprises one or more of: protein transduction reagent-modified Erg1, protein transduction reagent-modified Er71, protein transduction reagent-modified Fli1 and protein transduction reagent-modified Gata2 or one or more of: protein transduction reagent-modified Hey1, protein transduction reagent-modified Hey2, protein transduction reagent-modified FoxC1 and protein transduction reagent-modified FoxC2 or one or both of: protein transduction reagent-modified Sox7 and protein transduction reagent-modified Sox18.

Pharmaceutical compositions are provided according to aspects of the present invention which include one or more protein transduction reagent-reprogramming proteins selected from the group consisting of: protein transduction reagent-modified Gata4, protein transduction reagent-modified Hand2, protein transduction reagent-modified MEF2c, protein transduction reagent-modified Tbox, protein transduction reagent-modified Hnf1a, protein transduction reagent-modified Foxa1, protein transduction reagent-modified Foxa2 and protein transduction reagent-modified Foxa3, protein transduction reagent-modified Hnf1a, protein transduction reagent-modified CEBPα, protein transduction reagent-modified CEBPβ, protein transduction reagent-modified PU.1, protein transduction reagent-modified Brn2, protein transduction reagent-modified Sox2 and protein transduction reagent-modified Foxg1, protein transduction reagent-modified Asc1, protein transduction reagent-modified Lmx1a, protein transduction reagent-modified Nurr1, protein transduction reagent-modified Mytl1, protein transduction reagent-modified NeuroD1, protein transduction reagent-modified Ngn2, protein transduction reagent-modified Lhx3, protein transduction reagent-modified Hb9, protein transduction reagent-modified Lsl1, protein transduction reagent-modified Dlx2, protein transduction reagent-modified Asc1, protein transduction reagent-modified Oct4, protein transduction reagent-modified Ngn3, protein transduction reagent-modified Pdx1, protein transduction reagent-modified Pax4, protein transduction reagent-modified MafA, protein transduction reagent-modified Prdm16, protein transduction reagent-modified MyoD, protein transduction reagent-modified Sox9, protein transduction reagent-modified Runx2, protein transduction reagent-modified Sox5 and protein transduction reagent-modified Sox6, protein transduction reagent-modified Slug, protein transduction reagent-modified Stat5a, protein transduction reagent-modified Gata3, protein transduction reagent-modified Brca-1l, protein transduction reagent-modified Erg1, protein transduction reagent-modified Er71, protein transduction reagent-modified Fli1, protein transduction reagent-modified Gata2, protein transduction reagent-modified Hey1, protein transduction reagent-modified Hey2, protein transduction reagent-modified FoxC1 and protein transduction reagent-modified FoxC2, protein transduction reagent-modified Sox7 and protein transduction reagent-modified Sox18.

Pharmaceutical compositions are provided according to aspects of the present invention which include two or more protein transduction reagent-modified reprogramming proteins selected from the group consisting of: protein transduction reagent-modified Gata4, protein transduction reagent-modified Hand2, protein transduction reagent-modified MEF2c and protein transduction reagent-modified Tbox5; two or more of: protein transduction reagent-modified Hnf1a, protein transduction reagent-modified Foxa1, protein transduction reagent-modified Foxa2 and protein transduction reagent-modified Foxa3; two or more of: protein transduction reagent-modified Gata4, protein transduction reagent-modified Hnf1a and protein transduction reagent-modified Foxa3; protein transduction reagent-modified CEBPα, protein transduction reagent-modified CEBPβ, and protein transduction reagent-modified PU.1; two or more of: protein transduction reagent-modified Brn2, protein transduction reagent-modified Sox2 and protein transduction reagent-modified Foxg1; two or more of: protein transduction reagent-modified Ascl, protein transduction reagent-modified Lmx1a, protein transduction reagent-modified Nurr1, protein transduction reagent-modified Brn2 and protein transduction reagent-modified Mytl1; two or more of: protein transduction reagent-modified Ascl, protein transduction reagent-modified Brn2, protein transduction reagent-modified Mytl1 and protein transduction reagent-modified NeuroD1; protein transduction reagent-modified Ngn2; protein transduction reagent-modified Sox2 and protein transduction reagent-modified NeuroD1; two or more of: protein transduction reagent-modified Brn2, protein transduction reagent-modified Ascl1, protein transduction reagent-modified Mytl1, protein transduction reagent-modified Lhx3 and protein transduction reagent-modified Hb9; two or more of: protein transduction reagent-modified Brn2, protein transduction reagent-modified Ascl1, protein transduction reagent-modified Mytl1, protein transduction reagent-modified Lhx3, protein transduction reagent-modified Hb9, protein transduction reagent-modified Lsl1 and protein transduction reagent-modified Ngn2; protein transduction reagent-modified Dlx2; protein transduction reagent-modified Dlx2 and protein transduction reagent-modified Ascl1; two or more of: protein transduction reagent-modified Ascl, protein transduction reagent-modified Brn2, protein transduction reagent-modified Mytl1, protein transduction reagent-modified Lmx1a and protein transduction reagent-modified Foxa2; two or more of: protein transduction reagent-modified Ascl, protein transduction reagent-modified Lmx1a and protein transduction reagent-modified Nurr1; protein transduction reagent-modified Ngn3, protein transduction reagent-modified Pdx1 and protein transduction reagent-modified Pax4; two or more of: protein transduction reagent-modified Ngn3, protein transduction reagent-modified Pdx1 and protein transduction reagent-modified MafA; protein transduction reagent-modified Prdm16 and protein transduction reagent-modified C/EBPβ; two or more of: protein transduction reagent-modified Sox9, protein transduction reagent-modified Runx2, protein transduction reagent-modified Sox5 and protein transduction reagent-modified Sox6; two or more of: protein transduction reagent-modified Sox9, protein transduction reagent-modified Slug, protein transduction reagent-modified Stat5a, protein transduction reagent-modified Gata3 and protein transduction reagent-modified Brca-1l; two or more of: protein transduction reagent-modified Erg1, protein transduction reagent-modified Er71 protein transduction reagent-modified Fli1 and protein transduction reagent-modified Gata2; two or more of: protein transduction reagent-modified Hey1, protein transduction reagent-modified Hey2, protein transduction reagent-modified FoxC1 and protein transduction reagent-modified FoxC2; or protein transduction reagent-modified Sox7 and protein transduction reagent-modified Sox18.

Methods according to the present invention allow of delivery of protein-transduction reagent-modified reprogramming proteins to cancer cells, such as tumor cells, as well as diseased cells of diseased tissues.

Methods according to aspects of the present invention provide in vivo conversion of diseased cells into normal cells via protein-induced in situ cell reprogramming. Methods according to aspects of the present invention provide in vivo conversion of cancer cells into normal cells via protein-induced in situ cell reprogramming.

Use of protein-transduction reagent-modified reprogramming proteins to reprogram cancer cells or diseased cells in situ into stem cells or transient protein-induced multipotent stem cells that are then induced to differentiate into normal cells in the tissue where the cancer cells or diseased cells were located is provided according to aspects of the present invention.

Methods of treating cancer are provided according to aspects of the present invention which treat the cancer in vivo not by killing the cancer cells but instead by converting the cancer cells into non-cancerous cells by administration, such as systemic or local administration, of one or more protein transduction reagent-modified reprogramming proteins.

BRIEF DESCRIPTION OF THE DRAWINGS

FIG. 3A is a graph showing proliferation of U251 cells and U251-piPSCs monitored by Ki67 assay;

FIG. 3B is a graph showing dose-dependent chemotherapeutic drug sensitivity of patient-derived primary human GBM (12-14) cells (squares) and GBM (12-14)-piPSCs (circles) against the alkylating agent temozolomide;

FIG. 3C is a graph showing dose-dependent chemotherapeutic drug sensitivity of 9L-cells (squares) and 9L-piPSCs (circles) against carboplatin;

DETAILED DESCRIPTION

Figures 1A, 1B:
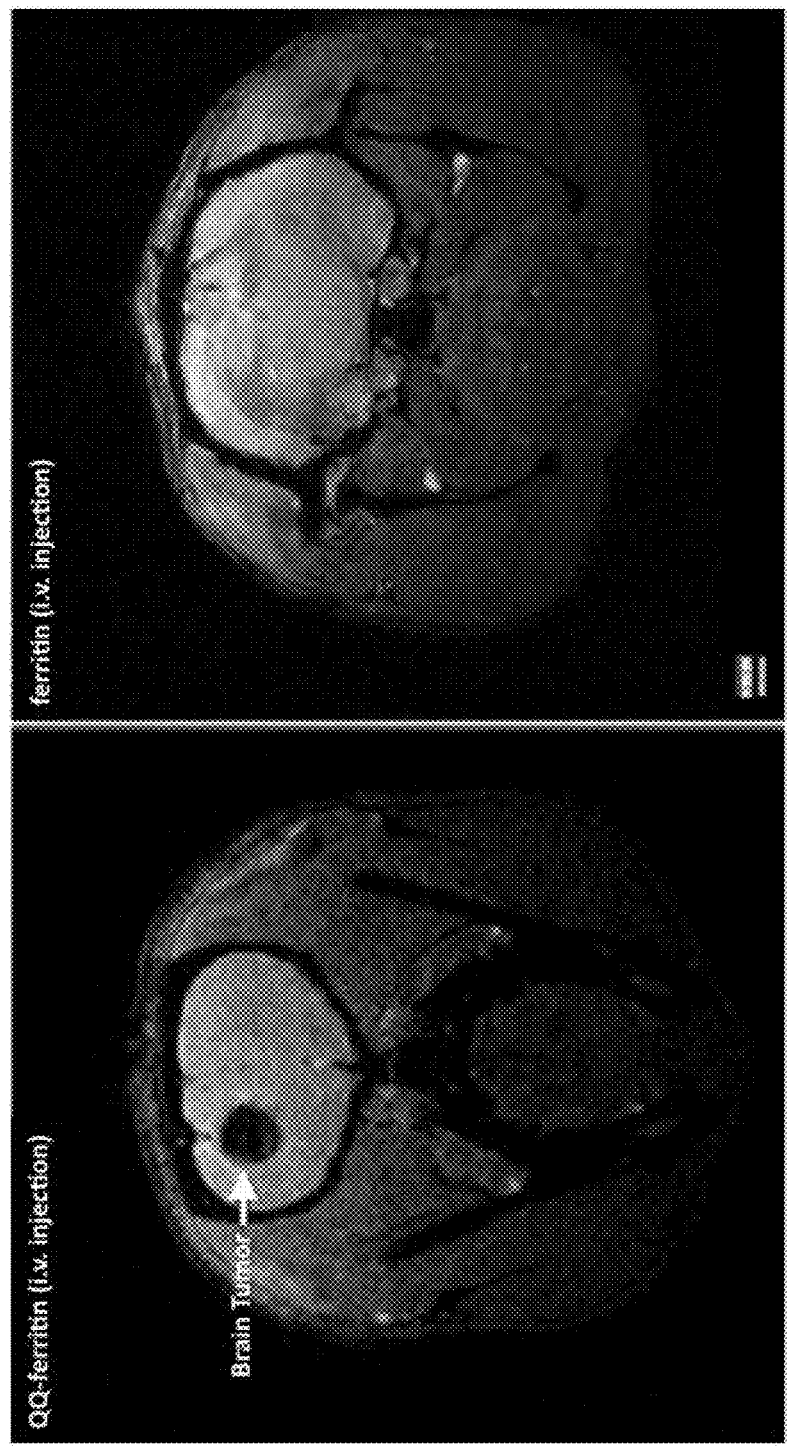
FIG. 1A is a representative MRI image of a 9L-intracranial tumor bearing rat brain showing enhanced permeability and retention effect in a 9L brain tumor for QQ-ferritin showing that the intravenous (i.v.) injected QQ-ferritin was delivered into 9L brain tumor via enhanced permeability and retention effect, causing an enhanced negative MRI image of brain tumor in the 9L-brain tumor bearing rat.
FIG. 1B is a representative MRI image of a 9L-intracranial tumor bearing rat brain showing no enhanced permeability and retention effect in a 9L brain tumor for ferritin without QQ modification showing that the i.v. injected ferritin did not reach into 9L brain tumor and no enhanced negative MRI image of brain tumor was observed in the 9L-brain tumor bearing rat.
Figures 2A, 2B, 2C:
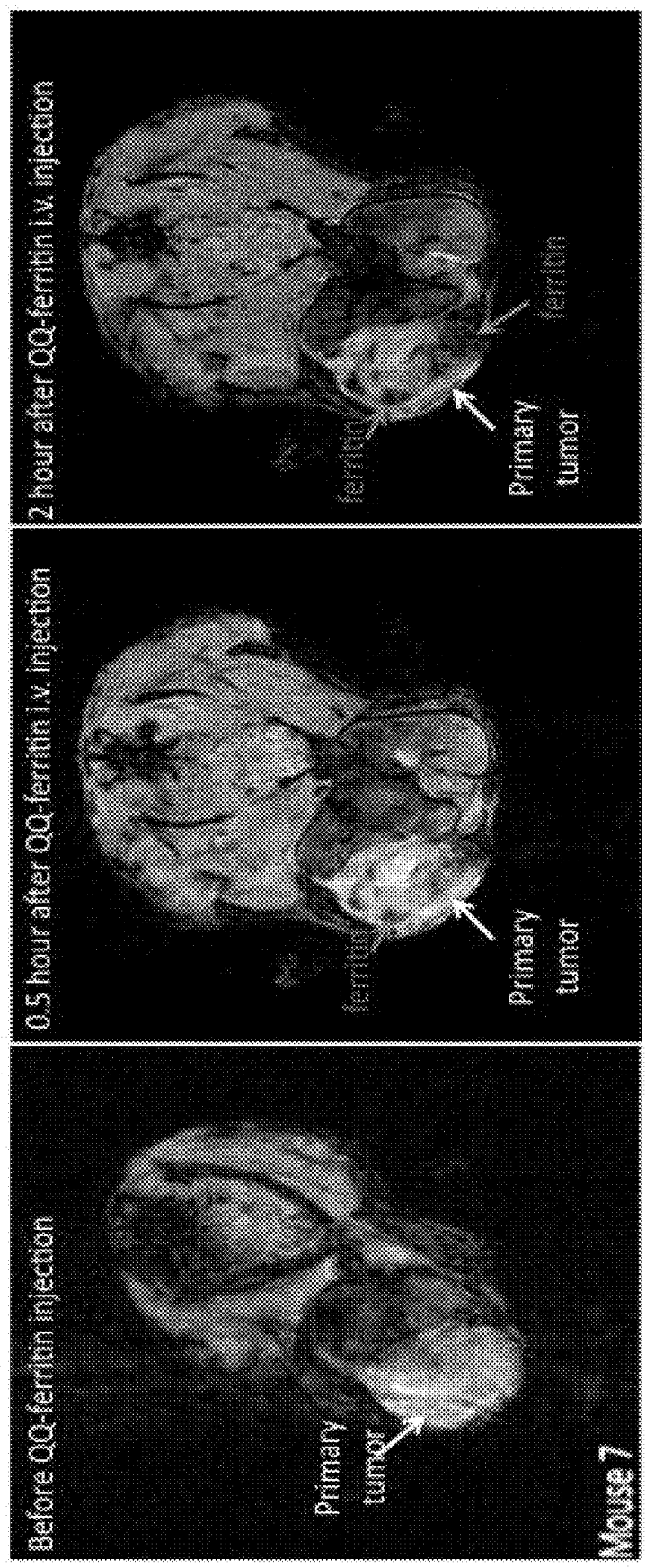
FIG. 2A is a representative MRI image of a mouse bearing a 4T1 breast tumor prior to a tail-vein injection of QQ-ferritin.
FIG. 2B is a representative MRI image of a mouse bearing a 4T1 breast tumor 0.5 hours after a tail-vein injection of QQ-ferritin.
FIG. 2C is a representative MRI image of a mouse bearing a 4T1 breast tumor 2 hours after a tail-vein injection of QQ-ferritin.
Figures 2D, 2E, 2F:
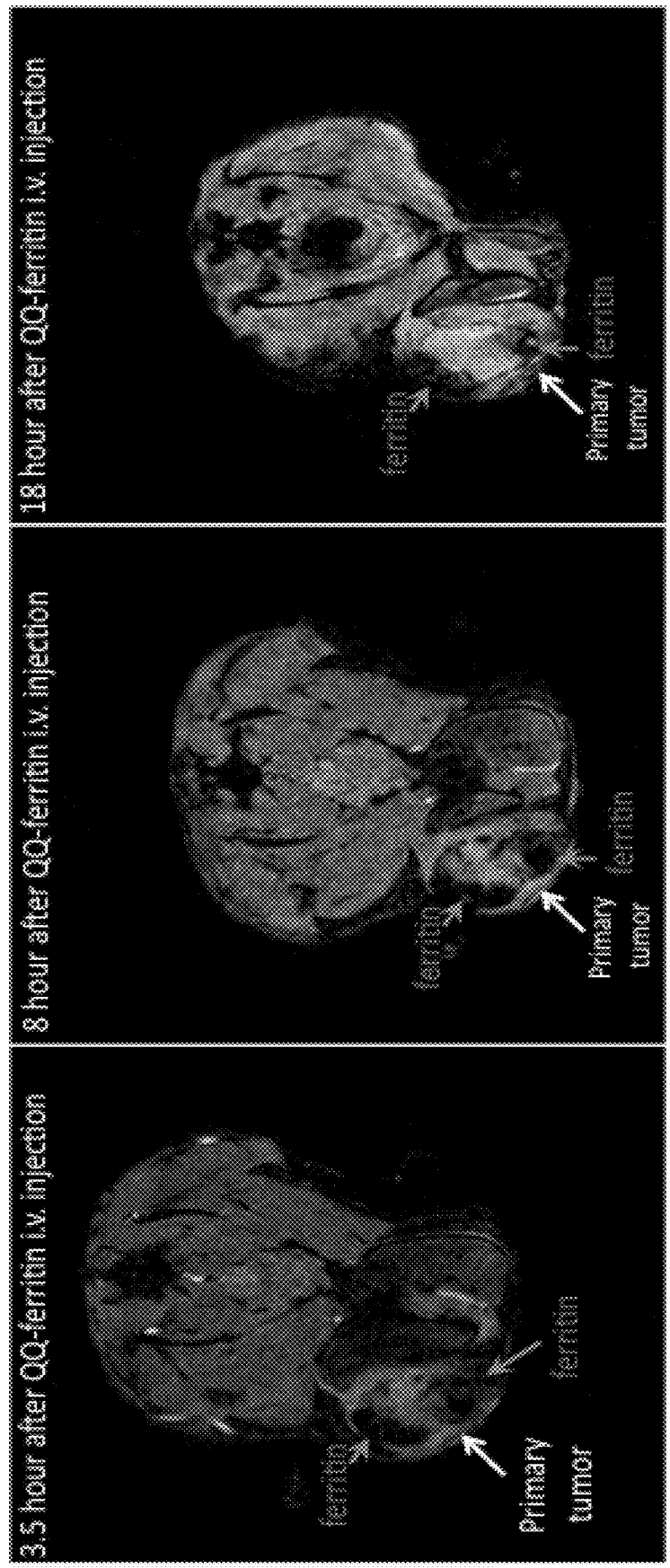
FIG. 2D is a representative MRI image of a mouse bearing a 4T1 breast tumor 3.5 hours after a tail-vein injection of QQ-ferritin.
FIG. 2E is a representative MRI image of a mouse bearing a 4T1 breast tumor 8 hours after a tail-vein injection of QQ-ferritin.
FIG. 2F is a representative MRI image of a mouse bearing a 4T1 breast tumor 18 hours after a tail-vein injection of QQ-ferritin.

Scientific and technical terms used herein are intended to have the meanings commonly understood by those of ordinary skill in the art. Such terms are found defined and used in context in various standard references illustratively including J. Sambrook and D. W. Russell, Molecular Cloning: A Laboratory Manual. Cold Spring Harbor Laboratory Press; 3rd Ed., 2001; F. M. Ausubel, Ed., Short Protocols in Molecular Biology, Current Protocols; 5th Ed., 2002; B. Alberts et al., Molecular Biology of the Cell, 4th Ed., Garland, 2002; D. L. Nelson and M. M. Cox, Lehninger Principles of Biochemistry, 4th Ed., W.H. Freeman & Company, 2004; Engelke, D. R., RNA Interference (RNAi): Nuts and Bolts of RNAi Technology, DNA Press LLC, Eagleville, Pa., 2003; Herdewijn, P. (Ed.), Oligonucleotide Synthesis: Methods and Applications, Methods in Molecular Biology, Humana Press, 2004; A. Nagy, M. Gertsenstein, K. Vintersten, R. Behringer, Manipulating the Mouse Embryo: A Laboratory Manual, 3rd edition, Cold Spring Harbor Laboratory Press; Dec. 15, 2002, ISBN-10: 0879695919; Kursad Turksen (Ed.), Embryonic stem cells: methods and protocols in Methods Mol Biol. 2002; 185, Humana Press; Current Protocols in Stem Cell Biology, ISBN: 9780470151808.

The singular terms "a," "an," and "the" are not intended to be limiting and include plural referents unless explicitly stated otherwise or the context clearly indicates otherwise.

Methods, systems and compositions according to aspects of the present invention provide protein-induced cell reprogramming in vivo to treat a subject in need thereof.

Methods, systems and compositions according to aspects of the present invention provide for conversion of diseased or injured cells into normal cells by introducing one or more QQ-modified reprogramming proteins into the diseased or injured cells in vivo without introduction of nucleic acids encoding the one or more reprogramming proteins.

Methods, systems and compositions according to aspects of the present invention provide for conversion of cancer cells into non-cancerous cells by introducing one or more QQ-modified reprogramming proteins into the cancer cells in vivo without introduction of nucleic acids encoding the one or more reprogramming proteins.

Methods of treating a subject in need thereof are provided according to aspects of the present invention which include systemically and/or locally administering a pharmaceutical composition comprising a protein transduction reagent-modified reprogramming protein to the subject, wherein the protein transduction reagent is non-covalently bound to the reprogramming protein and wherein the protein transduction reagent comprises a cation reagent and a lipid.

Pharmaceutical compositions which include a protein transduction reagent-modified reprogramming protein are provided according to aspects of the present invention.

A "protein transduction reagent-modified reprogramming protein" is a reprogramming protein that has been treated with the protein transduction reagent, also termed a "QQ reagent" herein. The term "protein transduction reagent" refers to a composition effective to enable a protein non-covalently bound to the protein transduction reagent to be delivered into mammalian cells and once present in mammalian cells, to dissociate from the protein to allow proper delivery of the protein to its proper subcellular location. The protein transduction reagent, also termed a "QQ reagent" herein, includes at least one cation reagent, at least one lipid, and optionally an enhancer. The term "QQ modified reprogramming protein" and grammatical variants thereof as used herein is equivalent to "protein transduction reagent-modified reprogramming protein" and grammatical variants thereof as used herein. Similarly, one or more proteins termed "QQ" protein signifies that the proteins is modified by treatment with a protein transduction reagent and is a "protein transduction reagent-modified reprogramming protein. For example, the term "QQ-SON" refers to a mixture of Sox2, Oct4 and Nanog proteins modified by treatment with a protein transduction reagent as described herein to produce protein transduction reagent-modified reprogramming Sox2, Oct4 and Nanog proteins.

One example of an appropriate cation reagent is polyethylenimine (PEI), such as, but not limited to, PEI Mw 1,200 (PEI 1.2K), PEI Mw 2000 (PEI 2K), PEI Mw 4000 (PEI 4K) and PEI Mw 8000 (PEI 8K). The lipid can be any lipid known to those of skill in the art to have the same general properties as those listed herein. Examples of such lipids include, but are not limited to, DOTMA (N-1(-(2,3-dioleyloxy)propyl-N,N,N-trimethyl-ammonium chloride; DOGS (dioctadecylamido-glycylspermine); DOTAP, 1,2-dioleoyl-3-trimethylammonium-propane; DOPE, 1,2-dioleoyl-sn-glycero-3-phosphoethanolamine POPC, 1-palmitoyl-2-oleoyl-sn-glycero-3-phosphocholine, and DMPE 1,2-dimyristoyl-sn-glycero-3-phosphocholine.

Optionally, the protein transduction reagent includes polyethylenimine as a cation reagent and the lipid is DOTAP or DOTMA and DOPE or DOGS; POPC and DMPE; or DOTAP or DOTMA, DOPE or DOGS, POPC and DMPE. Optionally, the protein transduction reagent is QQ1a, QQ2a, QQ3a, QQ4a, QQ5a, QQ6a, QQ7a, QQ8a, QQ9a as described in Table 1.

The optional enhancer can be any enhancer that significantly enhances cell loading of cationized proteins. Examples of such enhancers in cell cultures include, but are not limited to MG132, protease inhibitor, $CaCl_2$, DMSO and growth factors. Other enhancers can also be used, including, but not limited to, cell membrane surfactants. The reagent can also include stabilizers and other inert carriers that do not affect the function of the reagent. As shown in Table 1, the concentrations and specific compounds utilized can vary.

The term "reprogramming protein" as used herein refers to a DNA binding transcription factor protein, or effective portion thereof, which affects transcription of a gene and which induces a change from a first differentiated cell type to a second, different, differentiated cell type. The change from a first differentiated cell type to a second, different, differentiated cell type typically proceeds through an intermediate, less differentiated, cell type, such as a transient stem cell including protein-induced pluripotent stem cells. Reprogramming proteins and nucleic acids that encode them have been isolated from humans and other species. Reprogramming proteins include, but are not limited to, Asc1, Ascl1, Brca-1l, Brn2, C/EBPα, CEBPβ, c-MYC, Dlx2, EKLF, Erg1, Er71, Fli1, Foxa1, Foxa2, Foxa3, FoxC1, FoxC2, FOXG1, FOXP3, Gata1, Gata2, Gata3, Gata4, Gata6, GEL Hand2, Hb9, Hey1, Hey2, HNF4A, Hnf1a, Klf4, Lhx3, LIN28A, Lmx1a, Lsl1, MafA, MEF2c, Mytl1, MYF5, MyoD, NAB2, Nanog, NeuroD1, NEUROG2, NEUROG3, Nurr1, Oct4, Pdx1, Pax4, PAX5, Pax6, Prdm16, PU.1, ROR gamma. Runx2, SLC7A10, Slug, Sox2, Sox5, Sox6, Sox7, Sox9, Sox18, Stat5a, T-bet and Tbox5 Amino acid sequences for such reprogramming proteins are known, as exemplified by the sequences shown herein as SEQ ID NOs:1-63, along with nucleic acids encoding them shown herein as SEQ ID NOs: 65-127.

A reprogramming protein to be QQ-modified is obtained by methods such as isolation, synthesis, or recombinant expression of a nucleic acid encoding the reprogramming protein. Such proteins may also be obtained commercially.

The term "nucleic acid" refers to RNA or DNA molecules having more than one nucleotide in any form including single-stranded, double-stranded, oligonucleotide or polynucleotide. The term "nucleotide sequence" refers to the ordering of nucleotides in an oligonucleotide or polynucleotide in a single-stranded form of nucleic acid.

Recombinant expression of a reprogramming protein to be QQ-modified includes expression of a nucleic acid encoding the protein wherein the nucleic acid is included in an expression construct.

A host cell may be transfected with the expression construct encoding the desired reprogramming protein such that the reprogramming protein is expressed in the cell.

The terms "expression construct" and "expression cassette" are used herein to refer to a double-stranded recombinant DNA molecule containing a desired nucleic acid coding sequence for a reprogramming factor to be expressed and containing one or more regulatory elements necessary or desirable for the expression of the operably linked coding sequence.

Expression constructs operable to express a desired protein include, for example, in operable linkage: a promoter, a DNA sequence encoding a desired protein and a transcription termination site.

The term "regulatory element" as used herein refers to a nucleotide sequence which controls some aspect of the expression of nucleic acid sequences. Exemplary regulatory elements illustratively include an enhancer, an internal ribosome entry site (IRES), an intron; an origin of replication, a polyadenylation signal (polyA), a promoter, a transcription termination sequence, and an upstream regulatory domain, which contribute to the replication, transcription, post-transcriptional processing of a nucleic acid sequence. Those of ordinary skill in the art are capable of selecting and using these and other regulatory elements in an expression construct with no more than routine experimentation. Expression constructs can be generated recombinantly or synthetically using well-known methodology.

The term "operably linked" as used herein refers to a nucleic acid in functional relationship with a second nucleic acid.

A regulatory element included in an expression cassette is a promoter in particular aspects.

The term "promoter" is well-known in the art and refers to one or more DNA sequences operably linked to a nucleic acid sequence to be transcribed and which bind an RNA polymerase and allow for initiation of transcription. A promoter is typically positioned upstream (5') of a nucleic acid encoding a peptide or protein to be expressed.

An included promoter can be a constitutive promoter or can provide inducible expression. One of skill in the art is familiar with various well-known promoters and is able to select a promoter suitable for use in expressing a peptide or protein in a particular environment, such as in a specified cell type.

For expression in a yeast host cell, suitable promoters include, but are not limited to, an ADH1 promoter, a PGK1 promoter, an ENO promoter, a PYK1 promoter and the like; or a regulatable promoter such as a GAL1 promoter, a GAL10 promoter, an ADH2 promoter, a PH05 promoter, a CUP1 promoter, a GAL7 promoter, a MET25 promoter, a MET3 promoter, a CYC1 promoter, a HIS 3 promoter, an ADH1 promoter, a PGK promoter, a GAPDH promoter, an ADC1 promoter, a TRP1 promoter, a URA3 promoter, a LEU2 promoter, an ENO promoter, a TP1 promoter, and AOX1.

For expression in a prokaryotic host cell include, suitable promoters include, but are not limited to, a bacteriophage T7 RNA polymerase promoter; a trp promoter; a lac operon promoter; a trc promoter; a tac promoter; an araBAD promoter; an ssaG promoter; a pagC promoter; a sigma70 promoter, a dps promoter, an spv promoter, an SPI-2 promoter; an actA promoter, an rps M promoter; a tetracycline promoter, an SP6 promoter, a bacteriophage T3 promoter, a gpt promoter and a bacteriophage lambda P promoter.

Additional suitable bacterial and eukaryotic promoters are well-known, for example as described in Sambrook et al., Molecular Cloning, A Laboratory Manual, 2nd ed. 1989; and 3rd ed., 2001; Kriegler, Gene Transfer and Expression: A Laboratory Manual (1990); and Ausubel et al., Current Protocols in Molecular Biology, 2014.

For expression in an eukaryotic cell, promoters that can be included in an expression construct include, but are not limited to, cytomegalovirus immediate early promoter; herpes simplex virus thymidine kinase promoter; early and late SV40 promoters; a phosphoglycerate kinase (PGK) promoter; a promoter present in long terminal repeats from a retrovirus; and a mouse metallothionein-I promoter, a beta-actin promoter, a ROSA26 promoter, a heat shock protein 70 (Hsp70) promoter, an EF-1 alpha gene encoding elongation factor 1 alpha (EE1) promoter, an eukaryotic initiation factor 4A (eIF-4A1) promoter, a chloramphenicol acetyltransferase (CAT) promoter and the long terminal repeat region of Rous Sarcoma virus (RSV promoter).

In addition to a promoter, one or more enhancer sequences may be included such as, but not limited to, cytomegalovirus (CMV) early enhancer element and an SV40 enhancer element.

Additional included sequences include an intron sequence such as the beta globin intron or a generic intron, a transcription termination sequence, and an mRNA polyadenylation (pA) sequence such as, but not limited to SV40-pA, beta-globin-pA and SCF-pA.

An expression construct may include sequences necessary for amplification in bacterial cells, such as a selection marker (e g kanamycin or ampicillin resistance gene) and a replicon.

An internal ribosome entry site (IRES) is an optionally included nucleic acid sequence that permits translation initiation at an internal site in an mRNA. IRES are well-known in the art, for example as described in Pelletier, J. et al., Nature, 334:320-325, 1988; Vagner, S. et al., EMBO Rep., 2:893-898, 2001; and Hellen, C. U. et al, Genes Dev. 15:1593-1612, 2001.

The term "transcription termination site" refers to a DNA sequence operable to terminate transcription by an RNA polymerase. A transcription termination site is generally positioned downstream (3') of a nucleic acid encoding a peptide or protein to be expressed.

A leader sequence is optionally included in an expression construct.

Codon optimization of a nucleic acid encoding a desired protein may be used to improve expression in a particular expression system, for example by improving the efficiency of translation. A selected nucleic acid encoding a desired protein may be codon optimized for expression in any designated host cell, prokaryotic or eukaryotic, such as, but not limited to, bacteria, insect cells, yeast, fungus, bird eggs and mammalian cells.

An expressed protein optionally includes an N-terminal element such as a leader sequence and/or N-terminal methionine.

In addition to one or more nucleic acids encoding a desired reprogramming protein, one or more nucleic acid sequences encoding additional proteins can be included in an expression vector. For example, a nucleic acid sequence encoding a reporter, including, but not limited to, beta-galactosidase, green fluorescent protein and antibiotic resistance reporters is optionally included. In a further example, a his-tag, UST-tag or MBP-tag is optionally included.

A nucleic acid encoding a reprogramming protein can be cloned into an expression vector for transformation into prokaryotic or eukaryotic cells and expression of the encoded peptides and/or protein(s). As used herein, "expression vectors" are defined as polynucleotides which, when introduced into an appropriate host cell, an expression system, can be transcribed and translated, producing the encoded polypeptide(s).

Expression vectors are known in the art and include plasmids, cosmids, viruses and bacteriophages, for example. Expression vectors can be prokaryotic vectors, insect vectors, or eukaryotic vectors, for example.

For example, an expression construct including, in operable linkage: a promoter, a DNA sequence encoding a desired protein and a transcription termination site, is included in a plasmid, cosmid, virus or bacteriophage expression vector.

Particular vectors are known in the art and one of skill in the art will recognize an appropriate vector for a specific purpose.

Any suitable expression vector/host cell system can be used for expression of a transcription factor for administration to a subject according to aspects of the present invention.

Expression of a reprogramming protein using a recombinant expression vector is accomplished by introduction of the expression vector into an eukaryotic or prokaryotic host cell expression system such as an insect cell, mammalian cell, yeast cell, fungus, bird egg, bacterial cell or any other single or multicellular organism recognized in the art.

Host cells containing the recombinant expression vector are maintained under conditions wherein the desired protein is produced. Host cells may be cultured and maintained using known cell culture techniques such as described in Celis, Julio, ed., 1994, Cell Biology Laboratory Handbook, Academic Press, N.Y. Various culturing conditions for these cells, including media formulations with regard to specific nutrients, oxygen, tension, carbon dioxide and reduced serum levels, can be selected and optimized by one of skill in the art.

Bacterial cells can be used as the host cells to produce reprogramming proteins. Recombinant protein expression in bacterial cells and purification of the produced protein may be performed using known protocols, such as described in Paulina Balbás, Argelia Lorence ed., 2004, Recombinant Gene Expression: Reviews and Protocols. Humana Press, New Jersey; Peter E. Vaillancourt, 2003, *E. Coli* Gene Expression Protocols, Springer Science & Business Media.

Optionally, recombinantly produced reprogramming proteins are purified to remove endotoxin when an endotoxin producing host cell type is used. For example, an additional washing step can be added during protein purification stage using 10 column volume of 0.2% of Triton X114 to remove endotoxin from bacterially expressed recombinant reprogramming proteins.

Alternatively, in order to produce recombinant reprogramming proteins which do not trigger endotoxic response in human cells, a genetically modified bacterial strain, ClearColi™ BL21(DE3) can be used as host cells such that no endotoxin removal is required.

For expression in a host cell, any of the well-known procedures for introducing recombinant nucleic acids into host cells may be used, such as calcium phosphate transfection, polybrene, protoplast fusion, electroporation, sonoporation, liposomes and microinjection, examples of which are described in Sambrook et al., Molecular Cloning: A Laboratory Manual, Cold Spring Harbor Laboratory Press, 2001; and Ausubel, F. et al., (Eds.), Current Protocols in Molecular Biology, 2014.

Cell free expression systems is optionally used to express a reprogramming protein, such as described in Ausubel, F. et al., (Eds.), Current Protocols in Molecular Biology, 2014.

Human reprogramming proteins shown herein as SEQ ID NOs: 1-63, and encoded by the nucleic acid sequences of SEQ ID NOs:65-127, and variants thereof, can be used in methods according to aspects described herein.

As used herein, the term "variant" refers to a variation of a nucleic acid sequence encoding a reprogramming protein or a variation of a reprogramming protein in which one or more nucleotides or amino acid residues have been modified by nucleotide or amino acid substitution, addition, or deletion while retaining the function of the reference nucleic acid sequence or reprogramming protein. Variants of a nucleic acid sequence or reprogramming protein described herein are characterized by conserved functional properties compared to the corresponding nucleic acid sequence or reprogramming protein.

Mutations can be introduced using standard molecular biology techniques, such as chemical synthesis, site-directed mutagenesis and PCR-mediated mutagenesis.

One of skill in the art will recognize that one or more amino acid mutations can be introduced without altering the functional properties of a desired reprogramming protein. For example, one or more amino acid substitutions, additions, or deletions can be made without altering the functional properties of a desired reprogramming protein.

Biological activity of a reprogramming protein variant is readily determined by one of skill in the art, for instance using any of the functional assays described herein or other functional assays known in the art.

Variants of a reprogramming protein described herein are characterized by conserved functional properties compared to the corresponding reprogramming protein and have 75%, 80%, 85%, 90%, 95%, 96%, 97%, 98%, 99% or greater identity to the amino acid sequence of a reference reprogramming protein.

When comparing a reference reprogramming protein to a variant, amino acid similarity may be considered in addition to identity of amino acids at corresponding positions in an amino acid sequence. "Amino acid similarity" refers to amino acid identity and conservative amino acid substitutions in a putative homologue compared to the corresponding amino acid positions in a reference protein.

Variants of a reprogramming protein described herein are characterized by conserved functional properties compared to the corresponding reprogramming protein and have 75%, 80%, 85%, 90%, 95%, 96%, 97%, 98%, 99% or greater similarity to the amino acid sequence of a reference reprogramming protein.

Conservative amino acid substitutions can be made in reference proteins to produce variants.

Conservative amino acid substitutions are art recognized substitutions of one amino acid for another amino acid having similar characteristics. For example, each amino acid may be described as having one or more of the following characteristics: electropositive, electronegative, aliphatic, aromatic, polar, hydrophobic and hydrophilic. A conservative substitution is a substitution of one amino acid having a specified structural or functional characteristic for another amino acid having the same characteristic. Acidic amino acids include aspartate, glutamate; basic amino acids include histidine, lysine, arginine; aliphatic amino acids include isoleucine, leucine and valine; aromatic amino acids include phenylalanine, glycine, tyrosine and tryptophan; polar amino acids include aspartate, glutamate, histidine, lysine, asparagine, glutamine, arginine, serine, threonine and tyrosine; and hydrophobic amino acids include alanine, cysteine, phenylalanine, glycine, isoleucine, leucine, methionine, proline, valine and tryptophan; and conservative substitutions include substitution among amino acids within each group. Amino acids may also be described in terms of relative size, alanine, cysteine, aspartate, glycine, asparagine, proline, threonine, serine, valine, all typically considered to be small.

A variant can include synthetic amino acid analogs, amino acid derivatives and/or non-standard amino acids, illustratively including, without limitation, alpha-aminobutyric acid, citrulline, canavanine, cyanoalanine, diaminobutyric acid, diaminopimelic acid, dihydroxy-phenylalanine, djenkolic acid, homoarginine, hydroxyproline, norleucine, norvaline, 3-phosphoserine, homoserine, 5-hydroxytryptophan, 1-methylhistidine, 3-methylhistidine, and ornithine.

Percent identity is determined by comparison of amino acid or nucleic acid sequences, including a reference amino acid or nucleic acid sequence and a putative homologue amino acid or nucleic acid sequence. To determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/total number of positions X 100%). The two sequences compared are generally the same length or nearly the same length.

The determination of percent identity between two sequences can also be accomplished using a mathematical algorithm. Algorithms used for determination of percent identity illustratively include the algorithms of S. Karlin and S. Altshul, PNAS, 90:5873-5877, 1993; T. Smith and M. Waterman, Adv. Appl. Math. 2:482-489, 1981, S. Needleman and C. Wunsch, J. Mol. Biol., 48:443-453, 1970, W. Pearson and D. Lipman, PNAS, 85:2444-2448, 1988 and others incorporated into computerized implementations such as, but not limited to, GAP, BESTFIT, FASTA, TFASTA; and BLAST, for example incorporated in the Wisconsin Genetics Software Package, Genetics Computer Group, 575 Science Drive, Madison, Wis.) and publicly available from the National Center for Biotechnology Information.

A non-limiting example of a mathematical algorithm utilized for the comparison of two sequences is the algorithm of Karlin and Altschul, 1990, PNAS 87:2264-2268, modified as in Karlin and Altschul, 1993, PNAS. 90:5873-5877. Such an algorithm is incorporated into the NBLAST and XBLAST programs of Altschul et al., 1990, J. Mol. Biol. 215:403. BLAST nucleotide searches are performed with the NBLAST nucleotide program parameters set, e.g., for score=100, word length=12 to obtain nucleotide sequences homologous to a nucleic acid molecules of the present invention. BLAST protein searches are performed with the XBLAST program parameters set, e.g., to score 50, word length=3 to obtain amino acid sequences homologous to a protein molecule of the present invention. To obtain gapped alignments for comparison purposes, Gapped BLAST are utilized as described in Altschul et al., 1997, Nucleic Acids Res. 25:3389-3402. Alternatively, PSI BLAST is used to perform an iterated search which detects distant relationships between molecules. When utilizing BLAST, Gapped BLAST, and PSI Blast programs, the default parameters of the respective programs (e.g., of XBLAST and NBLAST) are used. Another preferred, non-limiting example of a mathematical algorithm utilized for the comparison of sequences is the algorithm of Myers and Miller, 1988, CABIOS 4:11-17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 is used.

The percent identity between two sequences is determined using techniques similar to those described above, with or without allowing gaps. In calculating percent identity, typically only exact matches are counted.

One of skill in the art will recognize that one or more nucleic acid or amino acid mutations can be introduced without altering the functional properties of a given nucleic acid or protein, respectively.

As noted, human reprogramming proteins shown herein as SEQ ID NOs: 1-63, are encoded by the nucleic acid sequences of SEQ ID NOs:65-127. It is appreciated that due to the degenerate nature of the genetic code, alternate nucleic acid sequences encode a particular reprogramming protein, and that such alternate nucleic acids may be expressed to produce the desired reprogramming protein.

The term "complementary" refers to Watson-Crick base pairing between nucleotides and specifically refers to nucleotides hydrogen bonded to one another with thymine or uracil residues linked to adenine residues by two hydrogen bonds and cytosine and guanine residues linked by three hydrogen bonds. In general, a nucleic acid includes a nucleotide sequence described as having a "percent complementarity" to a specified second nucleotide sequence. For example, a nucleotide sequence may have 80%, 90%, or 100% complementarity to a specified second nucleotide sequence, indicating that 8 of 10, 9 of 10 or 10 of 10 nucleotides of a sequence are complementary to the specified second nucleotide sequence. For instance, the nucleotide sequence 3'-TCGA-5' is 100% complementary to the nucleotide sequence 5'-AGCT-3'. Further, the nucleotide sequence 3'-TCGA-5' is 100% complementary to a region of the nucleotide sequence 5'-TTAGCTGG-3'.

The terms "hybridization" and "hybridizes" refer to pairing and binding of complementary nucleic acids. Hybridization occurs to varying extents between two nucleic acids depending on factors such as the degree of complementarity of the nucleic acids, the melting temperature, Tm, of the nucleic acids and the stringency of hybridization conditions, as is well known in the art. The term "stringency of hybridization conditions" refers to conditions of temperature, ionic strength, and composition of a hybridization medium with respect to particular common additives such as formamide and Denhardt's solution. Determination of particular hybridization conditions relating to a specified nucleic acid is routine and is well known in the art, for instance, as described in J. Sambrook and D. W. Russell, Molecular Cloning: A Laboratory Manual, Cold Spring Harbor Laboratory Press; 3rd Ed., 2001; and F. M. Ausubel, Ed., Short Protocols in Molecular Biology, Current Protocols; 5th Ed., 2002. High stringency hybridization conditions are those which only allow hybridization of substantially complementary nucleic acids. Typically, nucleic acids having about 85-100% complementarity are considered highly complementary and hybridize under high stringency conditions. Intermediate stringency conditions are exemplified by conditions under which nucleic acids having intermediate complementarity, about 50-84% complementarity, as well as those having a high degree of complementarity, hybridize. In contrast, low stringency hybridization conditions are those in which nucleic acids having a low degree of complementarity hybridize.

The terms "specific hybridization" and "specifically hybridizes" refer to hybridization of a particular nucleic acid to a target nucleic acid without substantial hybridization to nucleic acids other than the target nucleic acid in a sample.

Stringency of hybridization and washing conditions depends on several factors, including the Tm of the probe and target and ionic strength of the hybridization and wash conditions, as is well-known to the skilled artisan. Hybridization and conditions to achieve a desired hybridization stringency are described, for example, in Sambrook et al., Molecular Cloning: A Laboratory Manual, Cold Spring Harbor Laboratory Press, 2001; and Ausubel, F. et al., (Eds.), Short Protocols in Molecular Biology, Wiley, 2002.

An example of high stringency hybridization conditions is hybridization of nucleic acids over about 100 nucleotides in length in a solution containing 6×SSC, 5×Denhardt's solution, 30% formamide, and 100 micrograms/ml denatured salmon sperm at 37° C. overnight followed by washing in a solution of 0.1×SSC and 0.1% SDS at 60° C. for 15 minutes. SSC is 0.15M NaCl/0.015M Na citrate. Denhardt's solution is 0.02% bovine serum albumin/0.02% FICOLL/0.02% polyvinylpyrrolidone.

A reprogramming protein modified by QQ is an isolated protein according to aspects of the present invention. The term "isolated protein" indicates that the protein has been separated from biological materials, such as cells, cellular debris and other proteins, which may be present in the system in which the protein is produced. The term "isolated protein" may, but does not necessarily, indicate that the protein is purified. Purified protein included in methods and compositions of the present invention contains least about 1-100% of the mass, by weight, such as about 25%, 50%, 75%, 85%, 95%, 99% or greater than about 99% of the mass, by weight, of the protein included.

The term "subject" refers to an individual in need of treatment for a disease or injury responsive to the beneficial effects of cell reprogramming, and generally includes mammals and birds, such as, but not limited to, humans, other primates, cats, dogs, sheep, cows, goats, horses, pigs, poultry, rabbits and rodents, such as rats, mice and guinea pigs. According to aspects of the present invention, the subject is human.

Condition Characterized by Damaged, and/or Defective Cells.

The terms "treating" and "treatment" used to refer to treatment of a condition characterized by damaged, and/or defective cells such as a disease or injury of a subject include: inhibiting or ameliorating the disease or injury in the subject, such as slowing progression of the disease and/or reducing or ameliorating a sign or symptom of the disease or injury.

Conditions characterized by angiogenesis are treated according to aspects of methods of the present invention and are characterized by effective delivery of QQ-modified reprogramming proteins via the enhanced permeability and retention effect (EPR effect) of the angiogenic blood vessels.

Conditions characterized by damaged, and/or defective cells treated according to aspects of the present invention are various human conditions, including, but not limited to, cancer; cardiovascular disease or injury such as acute and chronic myocardial infarction, ischemia, heart injury, coronary artery disease, congenital heart disease, cardiomyopathies such as alcoholic cardiomyopathy, arrhythmogenic right ventricular cardiomyopathy, hypertensive cardiomyopathy, dilated cardiomyopathy, hypertrophic cardiomyopathy, inflammatory cardiomyopathy, ischemic cardiomyopathy, cardiomyopathy secondary to a systemic metabolic disease, myocardiodystrophy, noncompaction cardiomyopathy, restrictive cardiomyopathy, and valvular cardiomyopathy; vascular disease or blood vessel damage; anemias; ischemic and hemorrhagic stroke; metabolic diseases or conditions, such as diabetes, type I and type II, and obesity; neurological diseases and injuries such as spinal cord injury, traumatic brain injury, Huntington's disease, schizophrenia, Alzheimer's disease, amyotrophic lateral sclerosis, ataxias, autism, Lyme disease, meningitis, migraine, motor neuron diseases, movement disorders such as Parkinson's disease, neuropathy, pain, neuropathic pain, spinal cord disorders, peripheral and central nerve disorders, autonomic nervous system disorders, seizure disorders such as epilepsy, sleep disorders, dementias such as Alzheimer's disease, muscular dystrophy, Charcot-Marie-Tooth Neuropathy Type 1A and demyelinating diseases such as acute disseminated encephalomyelitis, adrenoleukodystrophy, adrenomyeloneuropathy, multiple sclerosis, neuromyelitis optica, optic neuritis, and transverse myelitis; wounds; inflammatory conditions; liver diseases and injuries such as liver disease such as familial hyper-cholesterolaemia (FH), Crigler-Najjar syndrome, hereditary tryosinemia I, fulminant hepatic failure, viral hepatitis, drug-induced liver injury, cirrhosis, inherited hepatic insufficiency such as due to Wilson's disease, Gilbert's syndrome, or al-antitrypsin deficiency, hepatobiliary carcinoma, autoimmune liver disease, such as autoimmune chronic hepatitis or primary biliary cirrhosis; autoimmune diseases; osteoarthritis; rheumatoid arthritis; cartilage disease or injury such as due to joint disorder, osteoarthritis, cartilage injury, traumatic rupture or detachment, achondroplasia, costochondritis, spinal disc herniation, relapsing polychonritis, tumor, chondroma, chondrosarcoma, and pleomorphic adenoma; Crohn's disease and genetic abnormalities.

Particular cancers treated using methods and compositions described herein are characterized by abnormal cell proliferation including, but not limited to, pre-neoplastic hyperproliferation, cancer in-situ, neoplasms and metastasis.

The terms "treating" and "treatment" used to refer to treatment of a cancer in a subject include: inhibiting or ameliorating the cancer in the subject, such as slowing progression of the cancer and/or reducing or ameliorating a sign or symptom of the cancer.

A therapeutically effective amount of a composition including an anti-cancer composition of the present invention is an amount which has a beneficial effect in a subject being treated. In subjects having cancer, such as a condition characterized by abnormal cell proliferation including, but not limited to, pre-neoplastic hyperproliferation, cancer in-situ, neoplasms, metastasis, a tumor, a benign growth or other condition responsive to an inventive composition, a therapeutically effective amount of a QQ-modified protein is effective to ameliorate one or more signs and/or symptoms of the cancer. For example, a therapeutically effective amount of a composition is effective to detectably decrease proliferation of cells of a cancer characterized by abnormal cell proliferation including, but not limited to, pre-neoplastic hyperproliferation, cancer in-situ, neoplasms, metastasis, a tumor, a benign growth or other condition responsive to an administered QQ-modified protein.

Such cancers include solid and non-solid cancers such as cancer of the bladder; breast; colorectal; cervical; esophagus; head and neck; kidney; lung; cancers of the nervous system such as glioblastoma, astrocytoma, ependymoma, neuroblastoma, retinoblastoma, meningiomas, granular cell tumors and nerve sheath tumors; ovary; pancreas; prostate; skin; stomach; testicle; throat cancer; urachus; or vagina.

A pharmaceutical composition according to aspects of the present invention includes a QQ-modified reprogramming protein and a pharmaceutically acceptable carrier.

The term "pharmaceutically acceptable carrier" as used herein refers to a carrier or diluent that is generally non-toxic to an intended recipient and which does not significantly inhibit activity of a QQ-modified protein or other active agent included in the composition.

A composition according to the present invention generally includes about 0.1-99% of a QQ-modified reprogramming protein.

Pharmaceutical compositions suitable for delivery to a subject may be prepared in various forms illustratively including physiologically acceptable sterile aqueous or non-aqueous solutions, dispersions, suspensions or emulsions, and sterile powders for reconstitution into sterile injectable solutions or dispersions.

Pharmaceutical compositions optionally include a buffer, a solvent, or a diluent.

Examples of suitable aqueous and nonaqueous carriers include water, ethanol, polyols such as propylene glycol, polyethylene glycol and glycerol; vegetable oils such as olive oil; and injectable organic esters such as ethyloleate; and suitable mixtures of any two or more thereof.

Such formulations are administered by a suitable route including parenteral administration. Optionally, administration includes systemic or local administration.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. One or more isotonic agents is optionally included, for example, sugars and or salts such as sodium chloride.

In particular aspects, QQ-modified proteins are administered by topical application.

A topical formulation can be an ointment, lotion, cream or gel in particular aspects. Topical dosage forms such as ointment, lotion, cream or gel bases are described in Remington: The Science and Practice of Pharmacy, 21$^{st}$ Ed., Lippincott Williams & Wilkins, 2006, p. 880-882 and p. 886-888; and in Allen, L. V. et al., Ansel's Pharmaceutical Dosage Forms and Drug Delivery Systems, 8$^{th}$ Ed., Lippincott Williams & Wilkins, 2005, p. 277-297.

Pharmaceutically acceptable carriers and formulation of pharmaceutical compositions are known in the art, illustratively including, but not limited to, as described in Remington: The Science and Practice of Pharmacy, 21$^{st}$ Ed Lippincott, Williams & Wilkins, Philadelphia, Pa., 2006; and Allen, L. V. et al., Ansel's Pharmaceutical Dosage Forms and Drug Delivery Systems, 8$^{th}$ Ed., Lippincott, Williams & Wilkins, Philadelphia, Pa., 2005.

A pharmaceutical composition including a QQ-modified protein is suitable for administration to a subject by a variety of systemic and/or local routes including, but not limited to, parenteral, oral, rectal, nasal, pulmonary, epidural, ocular, otic, intraarterial, intracardiac, intracerebroventricular, intracranial, intradermal, intravenous, intramuscular, intraperitoneal, intraosseous, intrathecal, intratumoral, intravesical, subcutaneous, topical, transdermal, and transmucosal, such as by sublingual, buccal, vaginal, and inhalational routes of administration.

Administration of Pharmaceutical Composition

An inventive composition may be administered acutely or chronically. For example, a composition as described herein may be administered as a unitary dose or in multiple doses over a relatively limited period of time, such as seconds-hours. In a further embodiment, administration may include multiple doses administered over a period of days-years, such as for chronic treatment of cancer.

A therapeutically effective amount of a QQ-modified protein will vary depending on the route of administration and form of the composition being administered and the particular composition administered, the severity and type of condition being treated in the subject, the species of the subject, the age and sex of the subject and the general physical characteristics of the subject to be treated. One of skill in the art could determine a therapeutically effective amount in view of these and other considerations typical in medical practice without undue experimentation in view of the present disclosure and what is known in the art. In general it is contemplated that a therapeutically effective amount would be in the range of about 0.001 ng/kg-100 mg/kg body weight, optionally in the range of about 0.01 ng/kg-1 mg/kg, and further optionally in the range of about 0.1 ng/kg-0.1 mg/kg. Further, dosage may be adjusted depending on whether treatment is to be acute or continuing.

Usually between 1 and 100 doses of a QQ-modified protein are administered to treat a subject in need thereof, although more doses can be given. A QQ-modified protein can be administered twice a day, daily, biweekly, weekly, every other week, monthly or at some other interval, for a treatment course extending one day, 1 week, 2 weeks, 4 weeks, 1 month, 2 months, 3-6 months or longer. A course of treatment is optionally repeated and may extend to chronic treatment if necessary.

Administration of a QQ-modified protein according to aspects of a method of the present invention includes administration according to a dosage regimen to produce a desired response. A suitable schedule for administration of doses depends on several factors including age, weight, gender, medical history and health status of the subject, type of composition used and route of administration, for example. One of skill in the art is able to readily determine a dose and schedule of administration for a particular subject.

Methods according to embodiments of the present invention include administration of a QQ-modified protein as a pharmaceutical formulation, such as by systemic or local administration. Exemplary routes of administration include, but are not limited to, parenteral, oral, rectal, nasal, pulmonary, epidural, ocular, otic, intraarterial, intracardiac, intracerebroventricular, intracranial, intradermal, intravenous, intramuscular, intraperitoneal, intraosseous, intrathecal, intratumoral, intravesical, subcutaneous, topical, transdermal, and transmucosal, such as by sublingual, buccal, vaginal, and inhalational routes of administration.

The QQ-modified protein may be administered parenterally, for example, by injection such as intravenous injection, intramuscular injection, intraperitoneal injection, subcutaneous injection, transdermal injection, intrathecal injection, intracranial injection, intracerobrospinal injection, and/or continuous infusion such as by an intravenous or intracerobrospinal continuous infusion device.

According to aspects, a protein transduction reagent-modified reprogramming protein is a DNA binding transcription factor. Administration of a protein transduction reagent-modified reprogramming protein is effective to reprogram one or more cell types in situ at the site of disease or damage to treat the disease or damage in vivo according to aspects described herein. Administration of a protein transduction reagent-modified reprogramming protein is effective to reprogram one or more cell types in situ at the site of disease or damage, generating transient stem cells which then differentiate into normal cells in situ at the site of disease or damage in vivo to treat the disease or damage according to aspects described herein.

Methods of treating cancer according to aspects of the present invention include administering one or more of: protein transduction reagent-modified Sox2, protein transduction reagent-modified Oct4 and protein transduction reagent-modified Nanog. Methods of treating cancer according to aspects of the present invention include administering two or more of: protein transduction reagent-modified Sox2, protein transduction reagent-modified Oct4 and protein transduction reagent-modified Nanog. Methods of treating cancer according to aspects of the present invention include administering: protein transduction reagent-modified Sox2, protein transduction reagent-modified Oct4 and protein transduction reagent-modified Nanog. Such methods produce new normal cells at the site of the cancer by reprogramming cancer cells at the site.

Methods of treating brain tumor according to aspects of the present invention include administering one or more of: protein transduction reagent-modified Sox2, protein transduction reagent-modified Oct4 and protein transduction reagent-modified Nanog. Methods of treating brain tumor according to aspects of the present invention include administering two or more of: protein transduction reagent-modified Sox2, protein transduction reagent-modified Oct4 and protein transduction reagent-modified Nanog. Methods of treating brain tumor according to aspects of the present invention include administering: protein transduction reagent-modified Sox2, protein transduction reagent-modified Oct4 and protein transduction reagent-modified Nanog. Such methods produce new normal cells at the site of the brain tumor by reprogramming brain tumor cells at the site.

Methods of treating brain tumor according to aspects of the present invention including administrating one or more of: protein transduction reagent-modified Sox2 and protein transduction reagent-modified NeuroD. Methods of treating pancreatic cancer according to aspects of the present invention including administrating: protein transduction reagent-modified Sox2 and protein transduction reagent-modified NeuroD. Such methods produce new normal cells at the site of pancreatic cancer by reprogramming brain tumor cells at the site.

Methods of treating breast cancer according to aspects of the present invention include administering one or more of: protein transduction reagent-modified Sox2, protein transduction reagent-modified Oct4 and protein transduction reagent-modified Nanog. Methods of treating breast cancer according to aspects of the present invention include administering two or more of: protein transduction reagent-modified Sox2, protein transduction reagent-modified Oct4 and protein transduction reagent-modified Nanog. Methods of treating breast cancer according to aspects of the present invention include administering: protein transduction reagent-modified Sox2, protein transduction reagent-modified Oct4 and protein transduction reagent-modified Nanog. Such methods produce new normal cells at the site of the breast cancer by reprogramming breast cancer cells at the site.

Methods of treating breast cancer according to aspects of the present invention including administrating one or more of: protein transduction reagent-modified Sox9, protein transduction reagent-modified Slug, protein transduction reagent-modified Gata3, protein transduction reagent-modified Brca-1 and protein transduction reagent-modified State5a. Methods of treating breast cancer according to aspects of the present invention including administrating two or more of: protein transduction reagent-modified Sox9, protein transduction reagent-modified Slug, protein transduction reagent-modified Gata3, protein transduction reagent-modified Brca-1 and protein transduction reagent-modified State5a. Methods of treating breast cancer according to aspects of the present invention including administrating three or more of: protein transduction reagent-modified Sox9, protein transduction reagent-modified Slug, protein transduction reagent-modified Gata3, protein transduction reagent-modified Brca-1 and protein transduction reagent-modified State5a. Methods of treating breast cancer according to aspects of the present invention including administrating four or more of: protein transduction reagent-modified Sox9, protein transduction reagent-modified Slug, protein transduction reagent-modified Gata3, protein transduction reagent-modified Brca-1 and protein transduction reagent-modified State5a. Methods of treating breast cancer according to aspects of the present invention including administrating: protein transduction reagent-modified Sox9, protein transduction reagent-modified Slug, protein transduction reagent-modified Gata3, protein transduction reagent-modified Brca-1 and protein transduction reagent-modified State5a. Such methods produce new normal cells at the site of breast cancer by reprogramming breast cancer cells at the site.

Methods of treating pancreatic cancer according to aspects of the present invention including administrating one or more of: protein transduction reagent-modified Sox2, protein transduction reagent-modified Oct4 and protein transduction reagent-modified Nanog. Methods of treating pancreatic cancer according to aspects of the present invention including administrating two or more of: protein transduction reagent-modified Sox2, protein transduction reagent-modified Oct4 and protein transduction reagent-modified Nanog. Methods of treating pancreatic cancer according to aspects of the present invention including administrating: protein transduction reagent-modified Sox2, protein transduction reagent-modified Oct4 and protein transduction reagent-modified Nanog. Such methods produce new normal cells at the site of pancreatic cancer by reprogramming pancreatic cancer cells at the site.

Methods of treating pancreatic cancer according to aspects of the present invention including administrating one or more of: protein transduction reagent-modified PDX1, protein transduction reagent-modified PAX4, protein transduction reagent-modified MafA and protein transduction reagent-modified Ngn3. Methods of treating pancreatic cancer according to aspects of the present invention including administrating two or more of: protein transduction reagent-modified PDX1, protein transduction reagent-modified PAX4, protein transduction reagent-modified MafA and protein transduction reagent-modified Ngn3. Methods of treating pancreatic cancer according to aspects of the present invention including administrating three or more of: protein transduction reagent-modified PDX1, protein transduction reagent-modified PAX4, protein transduction reagent-modified MafA and protein transduction reagent-modified Ngn3. Methods of treating pancreatic cancer according to aspects of the present invention including administrating: protein transduction reagent-modified PDX1, protein transduction reagent-modified PAX4, protein transduction reagent-modified MafA and protein transduction reagent-modified Ngn3. Such methods produce new normal cells at the site of pancreatic cancer by reprogramming pancreatic cancer cells at the site.

Methods of treating a heart disease or heart damage, such as damage due to acute or chronic myocardial infarction, according to aspects of the present invention include administering one or more of: protein transduction reagent-modified Gata4, protein transduction reagent-modified Hand2, protein transduction reagent-modified MEF2c and protein transduction reagent-modified Tbox5. Methods of treating a heart disease or heart damage according to aspects of the present invention include administering two or more of: protein transduction reagent-modified Gata4, protein transduction reagent-modified Hand2, protein transduction reagent-modified MEF2c and protein transduction reagent-modified Tbox5. Methods of treating a heart disease or heart damage according to aspects of the present invention include administering three or more of: protein transduction reagent-modified Gata4, protein transduction reagent-modified Hand2, protein transduction reagent-modified MEF2c and protein transduction reagent-modified Tbox5. Methods of treating a heart disease or heart damage according to aspects of the present invention include administering: protein transduction reagent-modified Gata4, protein transduction reagent-modified Hand2, protein transduction reagent-modified MEF2c and protein transduction reagent-modified Tbox5. Such methods produce new cardiomyocytes, smooth muscle cells and endothelial cells at the site of the disease or damage by reprogramming fibroblasts at the site.

Methods of treating a liver disease or liver damage according to aspects of the present invention include administering one or more of: protein transduction reagent-modified Gata4, protein transduction reagent-modified Hnf1a and protein transduction reagent-modified Foxa3. Methods of treating a liver disease or liver damage according to aspects of the present invention include administering two or more of: protein transduction reagent-modified Gata4, protein transduction reagent-modified Hnf1a and protein transduction reagent-modified Foxa3. Methods of treating a liver disease or liver damage according to aspects of the present invention include administering: protein transduction reagent-modified Gata4, protein transduction reagent-modified Hnf1a and protein transduction reagent-modified Foxa3. Such methods produce new hepatocytes at the site of the disease or damage by reprogramming fibroblasts at the site. Examples of such liver disease or liver damage include familial hyper-cholesterolaemia (FH), Crigler-Najjar syndrome and hereditary tryosinaemica I.

Methods of treating a liver disease or liver damage according to aspects of the present invention include administering one or more of: protein transduction reagent-modified Hnf1a, protein transduction reagent-modified Foxa1, protein transduction reagent-modified Foxa2 and protein transduction reagent-modified Foxa3. Methods of treating a liver disease or liver damage according to aspects of the present invention include administering two or more of: protein transduction reagent-modified Hnf1a, protein transduction reagent-modified Foxa1, protein transduction reagent-modified Foxa2 and protein transduction reagent-modified Foxa3. Methods of treating a liver disease or liver damage according to aspects of the present invention include administering: protein transduction reagent-modified Hnf1a, protein transduction reagent-modified Foxa1, protein transduction reagent-modified Foxa2 and protein transduction reagent-modified Foxa3. Such methods produce new hepatocytes at the site of the disease or damage by reprogramming fibroblasts at the site. Examples of such liver disease or liver damage include familial hyper-cholesterolaemia (FH), Crigler-Najjar syndrome and hereditary tryosinaemica I.

Methods of treating atherosclerosis according to aspects of the present invention include administering one or more of: protein transduction reagent-modified CEBP/$\alpha$/$\beta$ and protein transduction reagent-modified PU.1. Methods of treating atherosclerosis according to aspects of the present invention include administering both of: CEBP/$\alpha$/$\beta$ and protein transduction reagent-modified PU.1. Such methods produce new foam cells and macrophages at the site of the atherosclosis by reprogramming fibroblasts at the site.

Methods of treating a neurodegenerative disease or neuronal tissue damage according to aspects of the present invention include administering one or more of: protein transduction reagent-modified Brn2, protein transduction reagent-modified Sox2 and protein transduction reagent-modified Foxg1. Methods of treating a neurodegenerative disease or neuronal tissue damage according to aspects of the present invention include administering two or more of: protein transduction reagent-modified Brn2, protein transduction reagent-modified Sox2 and protein transduction reagent-modified Foxg1. Methods of treating neurodegenerative disease or neuronal tissue damage according to aspects of the present invention include administering: protein transduction reagent-modified Brn2, protein transduction reagent-modified Sox2 and protein transduction reagent-modified Foxg1. Such methods produce new neurons at the site of the disease or damage by reprogramming fibroblasts at the site.

Methods of treating a neurodegenerative disease or neuronal tissue damage according to aspects of the present invention include administering one or more of: protein transduction reagent-modified Asc1, protein transduction reagent-modified Lmx1a, protein transduction reagent-modified Nurr1, protein transduction reagent-modified Brn2 and protein transduction reagent-modified Mytl1. Methods of treating neurodegenerative disease or neuronal tissue damage according to aspects of the present invention include administering two or more of: protein transduction reagent-modified Asc1, protein transduction reagent-modified Lmx1a, protein transduction reagent-modified Nurr1, protein transduction reagent-modified Brn2 and protein transduction reagent-modified Mytl1. Methods of treating neurodegenerative disease or neuronal tissue damage according to aspects of the present invention include administering three or more of: protein transduction reagent-modified Asc1, protein transduction reagent-modified Lmx1a, protein transduction reagent-modified Nurr1, protein transduction reagent-modified Brn2 and protein transduction reagent-modified Mytl1. Methods of treating neurodegenerative disease or neuronal tissue damage according to aspects of the present invention include administering four or more of: protein transduction reagent-modified Asc1, protein transduction reagent-modified Lmx1a, protein transduction reagent-modified Nurr1, protein transduction reagent-modified Brn2 and protein transduction reagent-modified Mytl1. Methods of treating neurodegenerative disease or neuronal tissue damage according to aspects of the present invention include administering: protein transduction reagent-modified Asc1, protein transduction reagent-modified Lmx1a, protein transduction reagent-modified Nurr1, protein transduction reagent-modified Brn2 and protein transduction reagent-modified Mytl1. Such methods produce new glutamatergic neurons at the site of the disease or damage by reprogramming fibroblasts at the site.

Methods of treating a neurodegenerative disease or neuronal tissue damage according to aspects of the present invention include administering one or more of: protein transduction reagent-modified Asc1, protein transduction reagent-modified Brn2, protein transduction reagent-modified Mytl1 and protein transduction reagent-modified NeuroD1. Methods of treating neurodegenerative disease or neuronal tissue damage according to aspects of the present invention include administering two or more of: protein transduction reagent-modified Asc1, protein transduction reagent-modified Brn2, protein transduction reagent-modified Mytl1 and protein transduction reagent-modified NeuroD1. Methods of treating neurodegenerative disease or neuronal tissue damage according to aspects of the present invention include administering three or more of: protein transduction reagent-modified Asc1, protein transduction reagent-modified Brn2, protein transduction reagent-modified Mytl1 and protein transduction reagent-modified NeuroD1. Methods of treating neurodegenerative disease or neuronal tissue damage according to aspects of the present invention include administering: protein transduction reagent-modified Asc1, protein transduction reagent-modified Brn2, protein transduction reagent-modified Mytl1 and protein transduction reagent-modified NeuroD1. Such methods produce new glutamatergic neurons at the site of the disease or damage by reprogramming fibroblasts at the site.

Methods of treating a neurodegenerative disease or neuronal tissue damage according to aspects of the present invention include administering: protein transduction reagent-modified Ngn2. Such methods produce new glutamatergic neurons at the site of the disease or damage by reprogramming astrocytes at the site.

Methods of treating a neurodegenerative disease or neuronal tissue damage according to aspects of the present invention include administering one or more of: protein transduction reagent-modified Sox2 and protein transduction reagent-modified NeuroD1. Methods of treating neurodegenerative disease or neuronal tissue damage according to aspects of the present invention include administering: protein transduction reagent-modified Sox2 and protein transduction reagent-modified NeuroD1. Such methods produce new neural stem cells at the site of the disease or damage.

Methods of treating a neurological disease or neuronal tissue damage according to aspects of the present invention include administering one or more of: protein transduction reagent-modified Brn2, protein transduction reagent-modified Ascl1, protein transduction reagent-modified Mytl1, protein transduction reagent-modified Lhx3 and protein transduction reagent-modified Hb9. Methods of treating neurological disease or neuronal tissue damage according to aspects of the present invention include administering two or more of: protein transduction reagent-modified Brn2, protein transduction reagent-modified Ascl1, protein transduction reagent-modified Mytl1, protein transduction reagent-modified Lhx3 and protein transduction reagent-modified Hb9. Methods of treating neurological disease or neuronal tissue damage according to aspects of the present invention include administering three or more of: protein transduction reagent-modified Brn2, protein transduction reagent-modified Ascl1, protein transduction reagent-modified Mytl1, protein transduction reagent-modified Lhx3 and protein transduction reagent-modified Hb9. Methods of treating neurological disease or neuronal tissue damage according to aspects of the present invention include administering four or more of: protein transduction reagent-modified Brn2, protein transduction reagent-modified Ascl1, protein transduction reagent-modified Mytl1, protein transduction reagent-modified Lhx3 and protein transduction reagent-modified Hb9. Methods of treating neurological disease or neuronal tissue damage according to aspects of the present invention include administering: protein transduction reagent-modified Brn2, protein transduction reagent-modified Ascl1, protein transduction reagent-modified Mytl1, protein transduction reagent-modified Lhx3 and protein transduction reagent-modified Hb9. Such methods produce new motor neurons at the site of the disease or damage by reprogramming fibroblasts at the site. Examples of such neurological diseases include amyotrophic lateral sclerosis (ALS).

Methods of treating a neurological disease or neuronal tissue damage according to aspects of the present invention include administering one or more of: protein transduction reagent-modified Brn2, protein transduction reagent-modified Ascl1, protein transduction reagent-modified Mytl1, protein transduction reagent-modified Lhx3, protein transduction reagent-modified Hb9, protein transduction reagent-modified Lsl1 and protein transduction reagent-modified Ngn2. Methods of treating neurological disease or neuronal tissue damage according to aspects of the present invention include administering two or more of: protein transduction reagent-modified Brn2, protein transduction reagent-modified Ascl1, protein transduction reagent-modified Mytl1, protein transduction reagent-modified Lhx3, protein transduction reagent-modified Hb9, protein transduction reagent-modified Lsl1 and protein transduction reagent-modified Ngn2 Methods of treating neurological disease or neuronal tissue damage according to aspects of the present invention include administering three or more of: protein transduction reagent-modified Brn2, protein transduction reagent-modified Ascl1, protein transduction reagent-modified Mytl1, protein transduction reagent-modified Lhx3, protein transduction reagent-modified Hb9, protein transduction reagent-modified Lsl1 and protein transduction reagent-modified Ngn2. Methods of treating neurological disease or neuronal tissue damage according to aspects of the present invention include administering four or more of: protein transduction reagent-modified Brn2, protein transduction reagent-modified Ascl1, protein transduction reagent-modified Mytl1, protein transduction reagent-modified Lhx3, protein transduction reagent-modified Hb9, protein transduction reagent-modified Lsl1 and protein transduction reagent-modified Ngn2 Methods of treating neurological disease or neuronal tissue damage according to aspects of the present invention include administering five or more of: protein transduction reagent-modified Brn2, protein transduction reagent-modified Ascl1, protein transduction reagent-modified Mytl1, protein transduction reagent-modified Lhx3, protein transduction reagent-modified Hb9, protein transduction reagent-modified Lsl1 and protein transduction reagent-modified Ngn2. Methods of treating neurological disease or neuronal tissue damage according to aspects of the present invention include administering six or more of: protein transduction reagent-modified Brn2, protein transduction reagent-modified Ascl1, protein transduction reagent-modified Mytl1, protein transduction reagent-modified Lhx3, protein transduction reagent-modified Hb9, protein transduction reagent-modified Lsl1 and protein transduction reagent-modified Ngn2 Methods of treating neurological disease or neuronal tissue damage according to aspects of the present invention include administering: protein transduction reagent-modified Brn2, protein transduction reagent-modified Ascl1, protein transduction reagent-modified Mytl1, protein transduction reagent-modified Lhx3, protein transduction reagent-modified Hb9, protein transduction reagent-modified Lsl1 and protein transduction reagent-modified Ngn2. Such methods produce new motor neurons at the site of the disease or damage by reprogramming fibroblasts at the site. Examples of such neurological diseases include amyotrophic lateral sclerosis (ALS).

Methods of treating a neurological disease or neuronal tissue damage according to aspects of the present invention include administering: protein transduction reagent-modified. Such methods produce new GABA neurons at the site of the disease or damage by reprogramming fibroblasts at the site. Examples of such neurological diseases include spinal muscular atrophy (SMA).

Methods of treating a neurological disease or neuronal tissue damage according to aspects of the present invention include administering: protein transduction reagent-modified Dlx2. Such methods produce new GABA neurons at the site of the disease or damage by reprogramming fibroblasts at the site. Examples of such neurological diseases include amyotrophic lateral sclerosis (ALS), spinal muscular atrophy (SMA) and Parkinson's disease.

Methods of treating a neurological disease or neuronal tissue damage according to aspects of the present invention include administering: protein transduction reagent-modified Dlx2 and protein transduction reagent-modified Ascl1. Such methods produce new GABA neurons at the site of the disease or damage by reprogramming astrocytes at the site. Examples of such neurological diseases include spinal muscular atrophy (SMA).

Methods of treating a neurological disease or neuronal tissue damage according to aspects of the present invention include administering one or more of: protein transduction reagent-modified Asc1, protein transduction reagent-modified Brn2, protein transduction reagent-modified Mytl1, protein transduction reagent-modified Lmx1a and protein transduction reagent-modified Foxa2. Methods of treating neurological disease or neuronal tissue damage according to aspects of the present invention include administering two or more of: protein transduction reagent-modified Asc1, protein transduction reagent-modified Brn2, protein transduction reagent-modified Mytl1, protein transduction reagent-modified Lmx1a and protein transduction reagent-modified Foxa2. Methods of treating neurological disease or neuronal tissue damage according to aspects of the present invention include administering three or more of: protein transduction reagent-modified Asc1, protein transduction reagent-modified Brn2, protein transduction reagent-modified Mytl1, protein transduction reagent-modified Lmx1a and protein transduction reagent-modified Foxa2. Methods of treating neurological disease or neuronal tissue damage according to aspects of the present invention include administering four or more of: protein transduction reagent-modified Asc1, protein transduction reagent-modified Brn2, protein transduction reagent-modified Mytl1, protein transduction reagent-modified Lmx1a and protein transduction reagent-modified Foxa2. Methods of treating neurological disease or neuronal tissue damage according to aspects of the present invention include administering: protein transduction reagent-modified Asc1, protein transduction reagent-modified Brn2, protein transduction reagent-modified Mytl1, protein transduction reagent-modified Lmx1a and protein transduction reagent-modified Foxa2. Such methods produce new dopamine neurons at the site of the disease or damage by reprogramming fibroblasts at the site. Examples of such neurological diseases include Parkinson's disease.

Methods of treating a neurological disease or neuronal tissue damage according to aspects of the present invention include administering one or more of: protein transduction reagent-modified Asc1, protein transduction reagent-modified Lmx1a and protein transduction reagent-modified Nurr1 Methods of treating a neurological disease or neuronal tissue damage according to aspects of the present invention include administering two or more of: protein transduction reagent-modified Asc1, protein transduction reagent-modified Lmx1a and protein transduction reagent-modified Nurr1. Methods of treating neurological disease or neuronal tissue damage according to aspects of the present invention include administering: protein transduction reagent-modified Asc1, protein transduction reagent-modified Lmx1a and protein transduction reagent-modified Nurr1. Such methods produce new neurons at the site of the disease or damage by reprogramming fibroblasts at the site. Examples of such neurological diseases include Parkinson's disease.

Methods of treating a disease or disorder of the blood according to aspects of the present invention include administering: protein transduction reagent-modified Oct4. Such methods produce new hematopoietic cells at the site of the disease or damage by reprogramming fibroblasts at the site.

Methods of treating diabetes, a pancreatic disease or pancreatic tissue damage according to aspects of the present invention include administering one or more of: protein transduction reagent-modified Ngn3, protein transduction reagent-modified Pdx1 and protein transduction reagent-modified Pax4. Methods of treating diabetes, a pancreatic disease or pancreatic tissue damage according to aspects of the present invention include administering two or more of: protein transduction reagent-modified Ngn3, protein transduction reagent-modified Pdx1 and protein transduction reagent-modified Pax4. Methods of treating diabetes, a pancreatic disease or pancreatic tissue damage according to aspects of the present invention include administering: protein transduction reagent-modified Ngn3, protein transduction reagent-modified Pdx1 and protein transduction reagent-modified Pax4. Such methods produce new pancreatic beta-cells at the site of the disease or damage by reprogramming fibroblasts at the site.

Methods of treating diabetes, a pancreatic disease or pancreatic tissue damage according to aspects of the present invention include administering one or more of: protein transduction reagent-modified Ngn3, protein transduction reagent-modified Pdx1 and protein transduction reagent-modified MafA. Methods of treating diabetes, a pancreatic disease or pancreatic tissue damage according to aspects of the present invention include administering two or more of: protein transduction reagent-modified Ngn3, protein transduction reagent-modified Pdx1 and protein transduction reagent-modified MafA. Methods of treating diabetes, a pancreatic disease or pancreatic tissue damage according to aspects of the present invention include administering: protein transduction reagent-modified Ngn3, protein transduction reagent-modified Pdx1 and protein transduction reagent-modified MafA. Such methods produce new pancreatic beta-cells at the site of the disease or damage by reprogramming pancreatic exocrine cells at the site.

Methods of treating obesity according to aspects of the present invention include administering one or both of: protein transduction reagent-modified Prdm16 and protein transduction reagent-modified C/EBPb. Methods of treating obesity according to aspects of the present invention include administering both: protein transduction reagent-modified Prdm16 and protein transduction reagent-modified C/EBPb. Such methods produce new brown adipocytes at the site of the disease or damage by reprogramming white adipocytes at the site.

Methods of treating a muscle disease or muscle damage according to aspects of the present invention include administering: protein transduction reagent-modified MyoD. Such methods produce new muscle cells at the site of the disease or damage by reprogramming fibroblasts at the site.

Methods of treating arthritis, osteoarthritis, cartilage degeneration and/or cartilage injury according to aspects of the present invention include administering one or more of: protein transduction reagent-modified Sox9, protein transduction reagent-modified Runx2, protein transduction reagent-modified Sox5 and protein transduction reagent-modified Sox6. Methods of treating arthritis, osteoarthritis, cartilage degeneration and/or cartilage injury according to aspects of the present invention include administering two or more of: protein transduction reagent-modified Sox9, protein transduction reagent-modified Runx2, protein transduction reagent-modified Sox5 and protein transduction reagent-modified Sox6. Methods of treating arthritis, osteoarthritis, cartilage degeneration and/or cartilage injury according to aspects of the present invention include administering three or more of: protein transduction reagent-modified Sox9, protein transduction reagent-modified Runx2, protein transduction reagent-modified Sox5 and protein transduction reagent-modified Sox6. Methods of treating arthritis, osteoarthritis, cartilage degeneration and/or cartilage injury according to aspects of the present invention include administering: protein transduction reagent-modified Sox9, protein transduction reagent-modified Runx2, protein transduction reagent-modified Sox5 and protein transduction reagent-modified Sox6. Such methods produce new chondrocytes at the site of the disease or damage by reprogramming fibroblasts at the site.

Methods of treating a breast disease or breast tissue damage according to aspects of the present invention include administering one or more of: protein transduction reagent-modified Sox9, protein transduction reagent-modified Slug, protein transduction reagent-modified Stat5a, protein transduction reagent-modified Gata3 and protein transduction reagent-modified Brca-1. Methods of treating a breast disease or breast tissue damage according to aspects of the present invention include administering protein transduction reagent-modified Brca-1. Methods of treating a breast disease or breast tissue damage according to aspects of the present invention include administering two or more of: protein transduction reagent-modified Sox9, protein transduction reagent-modified Slug, protein transduction reagent-modified Stat5a, protein transduction reagent-modified Gata3 and protein transduction reagent-modified Brca-1. Methods of treating a breast disease or breast tissue damage according to aspects of the present invention include administering both: protein transduction reagent-modified Sox9 and protein transduction reagent-modified Slug. Methods of treating a breast disease or breast tissue damage according to aspects of the present invention include administering both: protein transduction reagent-modified Stat5a and protein transduction reagent-modified Gata3. Methods of treating a breast disease or breast tissue damage according to aspects of the present invention include administering three or more of: protein transduction reagent-modified Sox9, protein transduction reagent-modified Slug, protein transduction reagent-modified Stat5a, protein transduction reagent-modified Gata3 and protein transduction reagent-modified Brca-1. Methods of treating a breast disease or breast tissue damage according to aspects of the present invention include administering four or more of: protein transduction reagent-modified Sox9, protein transduction reagent-modified Slug, protein transduction reagent-modified Stat5a, protein transduction reagent-modified Gata3 and protein transduction reagent-modified Brca-1. Methods of treating a breast disease or breast tissue damage according to aspects of the present invention include administering: protein transduction reagent-modified Sox9, protein transduction reagent-modified Slug, protein transduction reagent-modified Stat5a, protein transduction reagent-modified Gata3 and protein transduction reagent-modified Brca-1. Such methods produce new mammary duct cells at the site of the disease or damage by reprogramming fibroblasts at the site.

Methods of treating a vascular disease or blood vessel damage according to aspects of the present invention include administering one or more of: protein transduction reagent-modified Erg1, protein transduction reagent-modified Er71, protein transduction reagent-modified Fli1 and protein transduction reagent-modified Gata2. Methods of treating a vascular disease or blood vessel damage according to aspects of the present invention include administering two or more of: protein transduction reagent-modified Erg1, protein transduction reagent-modified Er71, protein transduction reagent-modified Fli1 and protein transduction reagent-modified Gata2. Methods of treating a vascular disease or blood vessel damage according to aspects of the present invention include administering three or more of: protein transduction reagent-modified Erg1, protein transduction reagent-modified Er71, protein transduction reagent-modified Fli1 and protein transduction reagent-modified Gata2. Methods of treating a vascular disease or blood vessel damage according to aspects of the present invention include administering: protein transduction reagent-modified Erg1, protein transduction reagent-modified Er71, protein transduction reagent-modified Fli1 and protein transduction reagent-modified Gata2. Such methods produce new endothelial cells at the site of the disease or damage by reprogramming cells at the site.

Methods of treating a vascular disease or blood vessel damage according to aspects of the present invention include administering one or more of: protein transduction reagent-modified Hey1, protein transduction reagent-modified Hey2, protein transduction reagent-modified FoxC1 and protein transduction reagent-modified FoxC2. Methods of treating a vascular disease or blood vessel damage according to aspects of the present invention include administering two or more of: protein transduction reagent-modified Hey1, protein transduction reagent-modified Hey2, protein transduction reagent-modified FoxC1 and protein transduction reagent-modified FoxC2. Methods of treating a vascular disease or blood vessel damage according to aspects of the present invention include administering three or more of: protein transduction reagent-modified Hey1, protein transduction reagent-modified Hey2, protein transduction reagent-modified FoxC1 and protein transduction reagent-modified FoxC2. Methods of treating a vascular disease or blood vessel damage according to aspects of the present invention include administering: protein transduction reagent-modified Hey1, protein transduction reagent-modified Hey2, protein transduction reagent-modified FoxC1 and protein transduction reagent-modified FoxC2. Such methods produce new arterial endothelial cells at the site of the disease or damage by reprogramming cells at the site.

Methods of treating a vascular disease or blood vessel damage according to aspects of the present invention include administering one or both of: protein transduction reagent-modified Sox7 and protein transduction reagent-modified Sox18. Methods of treating a vascular disease or blood vessel damage according to aspects of the present invention include administering both: protein transduction reagent-modified Sox7 and protein transduction reagent-modified Sox18. Such methods produce new venous endothelial cells at the site of the disease or damage by reprogramming cells at the site.

Combination Treatments

Combinations of therapeutic agents are administered according to aspects of the present invention.

In some aspects, two or more QQ-modified proteins are administered to a subject to treat a disorder in a subject in need thereof.

In further aspects, at least one QQ-modified protein and at least one additional therapeutic agent are administered to a subject to treat a disorder in a subject in need thereof.

In still further aspects, at least one QQ-modified protein and at least two additional therapeutic agents are administered to a subject to treat a disorder in a subject in need thereof.

In some aspects, two or more QQ-modified proteins are administered to a subject to treat cancer in a subject in need thereof. In further aspects, at least one QQ-modified protein and at least one additional therapeutic agent are administered to a subject to treat cancer in a subject in need thereof. In still further aspects, at least one QQ-modified protein and at least two additional therapeutic agents are administered to a subject to treat cancer in a subject in need thereof.

The term "additional therapeutic agent" is used herein to denote a chemical compound, a mixture of chemical compounds, a biological macromolecule (such as a nucleic acid, an antibody, a protein or portion thereof, e.g., a peptide), or an extract made from biological materials such as bacteria, plants, fungi, or animal (particularly mammalian) cells or tissues which is a biologically, physiologically, or pharmacologically active substance (or substances) that acts locally or systemically in a subject.

Additional therapeutic agents included in aspects of methods and compositions of the present invention include, but are not limited to, antibiotics, antivirals, antineoplastic agents, analgesics, antipyretics, antidepressants, antipsychotics, anti-cancer agents, antihistamines, anti-osteoporosis agents, anti-osteonecrosis agents, antiinflammatory agents, anxiolytics, chemotherapeutic agents, diuretics, growth factors, hormones, non-steroidal anti-inflammatory agents, steroids and vasoactive agents.

Combination therapies utilizing one or more QQ-modified proteins and one or more additional therapeutic agents may show synergistic effects, e.g., a greater therapeutic effect than would be observed using either the one or more QQ-modified proteins or one or more additional therapeutic agents alone as a monotherapy.

According to aspects, combination therapies include: (1) pharmaceutical compositions that include one or more QQ-modified proteins in combination with one or more additional therapeutic agents; and (2) co-administration of one or more QQ-modified proteins with one or more additional therapeutic agents wherein the one or more QQ-modified proteins and the one or more additional therapeutic agents have not been formulated in the same composition. When using separate formulations, the one or more QQ-modified proteins may be administered at the same time, intermittent times, staggered times, prior to, subsequent to, or combinations thereof, with reference to the administration of the one or more additional therapeutic agents.

Combination treatments can allow for reduced effective dosage and increased therapeutic index of the one or more QQ-modified proteins and the one or more additional therapeutic agents used in methods of the present invention.

Optionally, a method of treating a subject having cancer or at risk of having cancer further includes an adjunct anti-cancer treatment. An adjunct anti-cancer treatment can be administration of an anti-cancer agent.

Anti-cancer agents are described, for example, in Goodman et al., Goodman and Gilman's The Pharmacological Basis of Therapeutics, 8th Ed., Macmillan Publishing Co., 1990.

Anti-cancer agents illustratively include acivicin, aclarubicin, acodazole, acronine, adozelesin, aldesleukin, alitretinoin, allopurinol, altretamine, ambomycin, ametantrone, amifostine, aminoglutethimide, amsacrine, anastrozole, anthramycin, arsenic trioxide, asparaginase, asperlin, azacitidine, azetepa, azotomycin, batimastat, benzodepa, bicalutamide, bisantrene, bisnafide dimesylate, bizelesin, bleomycin, brequinar, bropirimine, busulfan, cactinomycin, calusterone, capecitabine, caracemide, carbetimer, carboplatin, carmustine, carubicin, carzelesin, cedefingol, celecoxib, chlorambucil, cirolemycin, cisplatin, cladribine, crisnatol mesylate, cyclophosphamide, cytarabine, dacarbazine, dactinomycin, daunorubicin, decitabine, dexormaplatin, dezaguanine, dezaguanine mesylate, diaziquone, docetaxel, doxorubicin, droloxifene, dromostanolone, duazomycin, edatrexate, eflomithine, elsamitrucin, enloplatin, enpromate, epipropidine, epirubicin, erbulozole, esorubicin, estramustine, etanidazole, etoposide, etoprine, fadrozole, fazarabine, fenretinide, floxuridine, fludarabine, fluorouracil, flurocitabine, fosquidone, fostriecin, fulvestrant, gemcitabine, hydroxyurea, idarubicin, ifosfamide, ilmofosine, interleukin II (IL-2, including recombinant interleukin II or rIL2), interferon alfa-2a, interferon alfa-2b, interferon alfa-n1, interferon alfa-n3, interferon beta-Ia, interferon gamma-Ib, iproplatin, irinotecan, lanreotide, letrozole, leuprolide, liarozole, lometrexol, lomustine, losoxantrone, masoprocol, maytansine, mechlorethamine hydrochlride, megestrol, melengestrol acetate, melphalan, menogaril, mercaptopurine, methotrexate, metoprine, meturedepa, mitindomide, mitocarcin, mitocromin, mitogillin, mitomalcin, mitomycin, mitosper, mitotane, mitoxantrone, mycophenolic acid, nelarabine, nocodazole, nogalamycin, ormnaplatin, oxisuran, paclitaxel, pegaspargase, peliomycin, pentamustine, peplomycin, perfosfamide, pipobroman, piposulfan, piroxantrone hydrochloride, plicamycin, plomestane, porfimer, porfiromycin, prednimustine, procarbazine, puromycin, pyrazofurin, riboprine, rogletimide, safingol, semustine, simtrazene, sparfosate, sparsomycin, spirogermanium, spiromustine, spiroplatin, streptonigrin, streptozocin, sulofenur, talisomycin, tamoxifen, tecogalan, tegafur, teloxantrone, temoporfin, teniposide, teroxirone, testolactone, thiamiprine, thioguanine, thiotepa, tiazofurin, tirapazamine, topotecan, toremifene, trestolone, triciribine, trimetrexate, triptorelin, tubulozole, uracil mustard, uredepa, vapreotide, verteporfin, vinblastine, vincristine sulfate, vindesine, vinepidine, vinglycinate, vinleurosine, vinorelbine, vinrosidine, vinzolidine, vorozole, zeniplatin, zinostatin, zoledronate, and zorubicin.

An adjunct anti-cancer treatment can be a radiation treatment of a subject or an affected area of a subject's body.

Embodiments of inventive compositions and methods are illustrated in the following examples. These examples are provided for illustrative purposes and are not considered limitations on the scope of inventive compositions and methods.

EXAMPLES

Example 1

Reprogramming Protein Expression and Preparation

Plasmid Construction

DNA encoding each of Oct4, Sox2, Klf4, and c-Myc, Nanog, GATA4, Hand2, Mef2c and Tbox5 reprogramming proteins were separately subcloned into an sHT-pET30a bacterial expression vector, in which a short his-tag: 'HHH-HHHSS' (SEQ ID NO:64) replaced the long his-tag in the pET30a expression vector from Novagen. A factor Xa (IEGR) cleavage site is placed between the short his-tag and the coding genes. The sequences of the bacterial expression vectors were confirmed by DNA sequencing.

Protein Expression and Purification

The DNA constructs of reprogramming proteins were transformed into *E. Coli* strain BL-21(DE3) or ClearColi™ BL21(DE3) bacterial cells individually. The ClearColi™ BL21(DE3) bacterial cells were used for production of recombinant reprogramming proteins which are endotoxin-free. A single colony was selected for bacterial protein expression. After brief optimization, protein expression was induced by 0.5-1.2 mM IPTG depending on different proteins and continued to culture at 18 C.° for 12-16 hours. The cells were harvested in the binding buffer containing 6M urea and sonicated several times to extract proteins. The recombinant reprogramming proteins were purified using a His-Bind Resin column (Novagen) according to the manual with modifications. Usually the protein extraction supernatant was loaded on the column twice, washed with 5× column volume of the binding buffers. When using regular bacterial strain, BL21(DE3) to produce recombinant reprogramming proteins, an additional washing step can be added during protein purification stage using 10 column volume of 0.2% of Triton X-114 to remove endotoxin from bacterially expressed recombinant reprogramming proteins. The column loaded with recombinant proteins is washed again using 10× column volume washing buffer containing 15-50 mM imidazole. The purified proteins were eluted from the column using elusion buffer containing 500 mM imidazole. The purified proteins were dialyzed extensively against water and lyophilized into protein powders.

Example 2

QQ-Modification: Modification of Expressed Reprogramming Proteins with Protein Transduction Reagent to Produce Protein Transduction Reagent-Modified Reprogramming Proteins The protein transduction reagent (QQ reagent) can be adjusted by altering the composition to include reagents as shown in Table 1 to obtain the best protein transduction efficiency for the particular reprogramming protein and cell type.

For in vivo applications, to make total volume 1 ml:

TABLE 1

| Protein transduction reagent (QQ reagent) | PEI 1.2K | PEI 2K | PEI 4K | PEI 8K | DOTAP or DOTMA | DOPE or DOGS | POPC | DMPE |
|---|---|---|---|---|---|---|---|---|
| QQ1a | 10-200 µl | — | — | — | 25-100 µl | 25-100 µl | — | — |
| QQ2a | 10-200 µl | — | 10-100 µl | — | 25-100 µl | 25-100 µl | — | — |
| QQ3a | 10-200 µl | — | 10-100 µl | 10-100 µl | 25-100 µl | 25-100 µl | — | — |
| QQ4a | 10-200 µl | 10-100 µl | — | 10-100 µl | 25-100 µl | 25-100 µl | — | — |
| QQ5a | 10-200 µl | 10-100 µl | 10-100 µl | 10-100 µl | 25-100 µl | 25-100 µl | — | — |
| QQ6a | 10-200 µl | 10-100 µl | 10-100 µl | 10-100 µl | — | — | 25-100 µl | 25-100 µl |
| QQ7a | 10-200 µl | 10-100 µl | 10-100 µl | 10-100 µl | 25-100 µl | 25-100 µl | 25-100 µl | 25-100 µl |
| QQ8a | 10-200 µl | — | — | 10-100 µl | 25-100 µl | 25-100 µl | 25-100 µl | 25-100 µl |
| QQ9a | 10-200 µl | — | 10-100 µl | 10-100 µl | — | — | 25-100 µl | 25-100 µl |

The polyethylenimine (PEI) concentration for the stock solution:

| 1.2K | 2K | 4K | 8K |
|---|---|---|---|
| 5 mg/ml | 2 mg/ml | 2 mg/ml | 2 mg/ml |

Lipid concentration for the stock solution:

| DOTAP | DOTMA | DOPE | DOGS | POPC | DMPE |
|---|---|---|---|---|---|
| 1 mg/ml | 1 mg/ml | 1 mg/ml | 1 mg/ml | 1 mg/ml | 1 mg/ml |

PBS buffer containing reprogramming proteins in 1-6 M urea and specified PEI, lipids is used to make 1 ml total volume.

The reprogramming protein(s) is first dissolved in sodium phosphate buffer (pH7.0, NaCl 50 mM) at concentrations of 0.5-10 mg/ml, depending on protein solubility. Protein solubility was found to influence cationization efficiency. To completely dissolve proteins, an overnight stir of the protein solution is performed at room temperature (with or without DTT at 3 mM for overnight, depending on if the reprogramming protein has cysteine residues). Proteins can also be dissolved in 1-6 M urea to improve protein solubility.

A lipid DOTAP/DOPE (1:1) emulsion was prepared using a method as the following: 1 mg of DOTAP/DOPE (0.5 mg:0.5 mg=1:1) mixture was dissolved in chloroform and dried under N2 gas. The dried lipid film was then dissolved in PBS buffer, pH7.0 and the lipid solution was sonicated for 3×30 seconds using a power of 7-8 on a sonicator from Fisher Scientific (Sonic Dismembrator, Model 100) with micro probe. The lipid solution was further incubated at 37° C. for 2 hours until the suspension becomes semi-clear. The prepared emulsion was stored at 4° C. and is stable for one month.

The other ingredients of the QQ reagents (not including the lipid emulsion or the optional Ca or DMSO) were mixed in a tube, according to the recipe described above. The QQ reagent is then titrated into the protein solution very slowly, drop by drop, while stirring and then add the lipid emulsion. Once this is completed, the resulting protein solution is left at room temperature for 4 hours before use. During this period, gentle stirring is necessary to mix the QQ reagent with protein solution and also to allow the protein modification reaction to complete. If precipitation is observed, the protein solution can be centrifuged at 14,000 rpm for 15 minutes to remove the precipitate. If the precipitate occurs, a BCA protein assay will be carried out using the supernatant to check the amount of protein remaining in solution. To ensure the efficiency of protein transfer into the cells, the concentration of modified protein has to be high enough at >0.1 mg/ml.

Typically, QQ-modified proteins are prepared at 0.5-1.5 mg/ml concentration, depending on protein solubility, for in vivo administration.

QQ modification may be performed on each protein individually or on a mixture of proteins to be administered together to a subject.

Optionally, the QQ modification is performed on each protein individually, the QQ-modified proteins mixed together for several hours and then aliquoted into small tubes at 1 ml/tube and stored at −20° C. where they are stable for several months.

If the majority of the reprogramming protein is precipitated, another QQ reagent can be used for protein modification. The QQ series reagents cover a wide range of cationization reagents along with different lipids and enhancers, thus any precipitation problem is solved. The above procedure can be repeated to prepare higher concentrations of protein transduction reagent-modified reprogramming protein.

The protein transduction reagent-modified reprogramming protein is passed through a desalting column to separate the protein transduction reagent-modified reprogramming protein from remaining unreacted materials. The purified proteins are passed through a filter (0.22 µm cutoff, for sterilization before in vivo administration. The purified protein fractions can be concentrated before or after sterilization, such as by using a spin column, and are stable and can be stored at −20° C. for between a few weeks to a few months.

Different QQ reagents can also be used for the best efficiency of protein transfer as well as the least cell toxicity. In addition, different proteins are modified with different QQ reagents for best efficiency of protein transfer into cells. In general, for better in vivo delivery efficiency, QQ5a-QQ9a are used. However, this may cause larger in vivo toxicity. When using QQ5a-QQ9a, use of lower concentrations of larger PEI and lipids is emphasized.

For good in vivo delivery efficiency, QQ1a-QQ4a is used with less in vivo toxicity. QQ1-QQ4 can be used with higher lipid concentrations.

Example 3

The reprogramming proteins were dissolved in 50 mM sodium phosphate pH 7.4 with 2 M urea. Protein transduction reagents (QQ-reagents) were freshly prepared based on the recipe. QQ-reagent used in this example is a cocktail of polyethylenimine (PEI) 1,200 (1.2K, 0.05-1.0 mg/ml) and DOTAP/DOPE (25-100 µg/ml). The QQ-modification of reprogramming proteins was performed by mixing the QQ-reagent with one or more reprogramming proteins, such as Oct4/Sox2/Nanog: 1 mg/ml, for 4-hours at room temperature or overnight in a cold room.

Example 4

QQ-Protein Delivery into Brain Tumors in Rats by an Intravenous Injection

Ferritin is a ubiquitous iron-containing protein useful as a negative contrast reagent for magnetic resonance imaging (MRI).

In this example, ferritin or ferritin treated with QQ reagent to produce QQ-ferritin is intravenously injected into rats having brain tumors generated by implantation of rat gliosarcoma cell line 9L cells.

Cells of a rat gliosarcoma cell line 9L were freshly prepared and adjusted to $1 \times 10^6$ cells/ml before implantation. The intracranial xenografts were performed according to standard protocols. Fisher rats were anesthetized and placed in a stereotactic frame, and the skull was exposed. A hole was made 3 mm to the right and 1 mm anterior of the bregma, and 9L cells ($5 \times 10^4$ cells in 5 µl) were injected using a 10-µl Hamilton syringe with a 26s-gauge needle mounted in a stereotactic holder (Bonaduz, GR, Switzerland). The syringe was lowered to a depth of 3.5 mm and then raised to a depth of 3.0 mm. The tumor cells were injected at a rate of 0.5 µl/10 s, and the craniotomy covered with Horsley's bone wax. 12-days after 9L-cell implantation, QQ-modified ferritin or ferritin alone, 100 µg/100 µl/rat, was injected via the rat tail vein. Four hours after injection, the rats were anesthetized and the rat brains were imaged by MRI. After MRI, the animals were sacrificed. The extracted brains were fixed in 4% paraformaldehyde overnight and then embedded in paraffin for further analysis. Six micrometer thin sections were cut from each of the blocks and were stained with hematoxylin and eosin. The sizes of brain tumors were microscopically determined.

FIGS. 1A and 1B show MRI evidence of targeted delivery of QQ-ferritin into 9L-brain tumor in rats and no detectable ferritin in 9L-brain tumor of rats injected with ferritin alone. FIG. 1A is a representative MRI image of a rat with 9L-brain tumor injected with QQ-ferritin via tail-vein. The arrow points to a 9L-brain tumor and the black color is indicative of ferritin delivered to the tumor. FIG. 1B: A representative MRI image of a rat with 9L-brain tumor injected with ferritin without QQ modification. No ferritin is observed in the brain tumor in this case although the rat was sacrificed and confirmed to have a large 9L-brain tumor.

Double immunostains of the QQ-ferritin injected 9L-brain tumor tissue sections were performed using an antibody for a blood vessel marker, CD31, and an antibody for ferritin. The nuclei of the 9L-cancer cells in the sections were stained with DAPI. Overlapping immunostaining for the CD31 and ferritin were observed in blood vessels of the brain tumors, indicating that QQ-ferritin leaked out from the blood vessels by the enhanced permeability and retention effect (EPR effect) of the angiogenic blood vessels associated with brain tumor. In the QQ-ferritin treated animal, immunostaining for ferritin was observed inside the cytosol of the tumor cells near or next to the blood vessels, indicating that the QQ-ferritin penetrated into tumor cells. In contrast, ferritin immunostaining in the 9L-tumor sections treated with ferritin without QQ-modification showed that the ferritin without QQ modification did not penetrate into tumor cells, although immunostaining indicated that this unmodified ferritin also leaked out of the tumor-associated angiogenic blood vessels. These unmodified ferritin nanoparticles were observed between cells and likely did not accumulate due to the fluid between cells inside the tissues so that no tumor was observed by MRI without QQ-modification of the ferritin.

These data provide MRI evidence of the targeted delivery of ferritin to brain tumor in rats by the QQ-protein delivery technology, which is confirmed by histology analysis and immunostaining of the brain tissue sections.

Example 5

QQ-Protein Delivery into Breast Cancer in Mice by an Intravenous Injection.

In this example, ferritin or ferritin treated with QQ reagent to produce QQ-ferritin is intravenously injected into mice having orthotopic breast tumors generated by implantation of mouse metastatic breast cancer cell line 4T1 cells. Implantation of mouse metastatic breast cancer cell line 4T1 cells in mice is a mouse model for spontaneous metastatic breast cancer.

4T1 cells were implanted into the breast (#4 fat pad) of 2 month old female BALB/c mice (20,000 4T1 cells in 50 µl/mouse). At day 18 after 4T1 cell implantation, 4T1 tumors had grown in the mouse breast to a size of ~1.0-1.5 cm in diameter. QQ-modified ferritin (100 µg/50 µl/mouse) was injected via tail-vein. The mice were anesthetized and subjected to MRI imaging before injection of the QQ-modified ferritin and at 0.5 hours, 2 hours, 3.5 hours, 8 hours and 18 hours following the injection.

FIGS. 2A-F are representative MRI images from this time course showing QQ-delivered ferritin in the primary tumor of breast cancer bearing mouse as darkened areas in the primary tumor. This primary tumor darkness was time-dependent and reached a maximum at 8-hours, then started to decrease in intensity.

MRI results were confirmed by histology analysis using Prussian blue stain and ferritin immunostaining Immunohistochemical stain and Prussian blue stain of the primary tumor tissue sections of 4T1-breast cancer bearing mouse at 18-hour after QQ-ferritin injection showed positive ferritin and Prussian blue stains inside the primary tumor. This histological result confirmed the MRI observation of QQ-delivered ferritin inside the primary tumor of 4T1-tumor bearing mice.

Example 6

QQ-Protein Delivery of Oct4 and Klf4 Protein into the Nuclei of 4T1-Breast Cancer Cells of the Primary Tumor of 4T1 Breast Cancer Bearing Mice 4T1 cells ($2 \times 10^4$ cells/50 µl/mouse) were implanted into female BALB/c mice. 15-days after tumor cell implantation Alexa Fluor594 labeled Klf4 was prepared. QQ-modified unlabeled Oct4 (QQ-Oct4) and QQ-modified Alexa Fluor594 labeled Klf4 were then prepared. Intra-tumoral injection of 50 µg QQ-Oct4 and QQ-Alexa Fluor594 labeled Klf4 proteins was performed. The mice were sacrificed 5 hours after injection and tumor tissue sections were prepared for immunostaining and fluorescence microscopy. Immunostaining for Oct4 in the primary 4T1-breast cancer tissue sections demonstrated nuclear localization of Oct4 in the 4T1-cancer cells and co-localization with DAPI. Fluorescence microscopic imaging also showed nuclear localization of Klf4 in the primary 4T1-breast cancer tissue sections and co-localization with DAPI.

Example 7

QQ-Protein Delivery of GATA4, OCT4 and SOX2 to the Injured Hearts of Rats after Acute Myocardial Infarction QQ-modified and fluorescence labeled GATA4, Sox2 and Oct4 are administered by an intraperitoneal injection to rats after myocardial infarction and the QQ-modified proteins and fluorescence labeled were delivered to injured heart tissues in the animals.

GATA4, Sox2 and Oct4 are each labeled with Alexa Fluor488 according to methods specified by the manufacturer. The labeled GATA4, Sox2 and Oct4 proteins were purified with small spin columns. The Alexa Fluor488-GATA4, Alexa Fluor488-Sox2 and Alexa Fluor488-Oct4 are then QQ-modified to generate QQ-modified Alexa Fluor488-GATA4, QQ-modified Alexa Fluor488-Sox2 and QQ-modified Alexa Fluor488-Oct4.

Lewis rats were anesthetized and coronary artery ligation surgery was performed to create myocardial infarction in the Lewis rats. 24-hours after coronary artery ligation surgery, QQ-modified Alexa Fluor488-labeled GATA4, QQ-modified Alexa Fluor488-labeled Sox2 and QQ-modified Alexa Fluor488-labeled Oct4 (200 µg/100 µl/rat) were intraperitoneally injected into Lewis rats. 7-hours after fluorescence labeled protein injections, the rats were sacrificed and heart tissue sections were prepared for either Trichrome staining for infarction sizes or for immunostaining with an α-actinin antibody, which is a heart muscle marker indicative of mature cardiomyocytes.

Fluorescence microscopic analysis showed colocalization of Alexa. Fluor488-GATA4 protein with α-actinin immunofluorescence, indicating that intraperitoneal injection of QQ-fluorescence labeled GATA4 resulted in delivery of the GATA4 protein into the scar zone of the injured heart tissue after coronary artery ligation. Similarly, fluorescence microscopic analysis of Alexa Fluor488-Sox2 and α-actinin immunofluorescence indicated that intraperitoneal injection of QQ-modified Alexa Fluor488 labeled-Sox2 resulted in location of the Sox2 protein in the border zone of the injured heart tissue after coronary artery ligation. Finally, fluorescence images of Alexa Fluor488-Oct4 showed localization of injected QQ-modified Alexa Fluor488-Oct4 in the remote normal heart tissue zone. These results indicate that fluorescence labeled and QQ-modified GATA4, Sox2 and Oct4 administered by intraperitoneal injection reached injured heart tissues in the scar zone, the border zone and the normal heart tissue zones. These data demonstrate that QQ-protein delivery targeted deliver these proteins into the injured heart tissues.

Example 8

Malignant glioma cells including 9L-, U251-, U87- and a primary GBM cell line from a patient were reprogrammed into protein induced pluripotent stem cells (piPSCs) using QQ-modified Sox2, Oct4 and Nanog (SON) proteins as follows: At day 0, glioma cells were seeded for 24-hours to allow them to grow in a 50 mm petri dish. At day 2, QQ-SON proteins were added to the culture medium at 0.5-2.0 µg/ml and cultured for 24 hours. Next day, fresh QQ-SON proteins were added into new culture medium and cultured for 24 hours. Such cycles were repeated for 5-7 cycles depending on glioma cells used for cell reprogramming. At the end of cell reprogramming, the culture media were changed to maintaining medium for 2 days. During cell reprogramming, piPSC colonies appeared. At day 8, whole dish passage was performed to expand the generated piPSCs Immunostaining of the whole dish passaged glioma-piPSCs including both monolayer and colony of the 9L-piPSCs using pluripotency markers including nuclear markers Oct4, Nanog, Rex-1 and surface markers ALP, Tra1-60, and Tra1-81 showed nearly all cells were positive for these pluripotency markers. In contrast, immunostains of 9L-cells showed negative stains for these markers. These data indicate high conversion efficiency of cell reprogramming of 9L-cells into 9L-piPSCs using the QQ-SON proteins.

This is confirmed by immunostaining of whole well (96-well) of 9L-piPSCs using Nanog and Oct4. When counting positive 9L-piPSC clones compared with negative clones, an average of 96±2% conversion efficiency is found, see Table 2. A control immunostaining of 9L cells showed negative stains for these two pluripotency markers Nanog and Oct4. The conversion efficiency of 9L-piPSCs from 9L cells was calculated by positively stained colonies and monolayer 9L-piPSCs versus total colonies and monolayer cells as stained with DAPI using the software provided by EVOS Auto fluorescence microscope. Immunostaining of the 9L-piPSCs of duplicated 96-wells were used to calculate average conversion efficiency and standard deviation.

TABLE 2

Conversion efficiency of QQ-SON protein-induced cell reprogramming of 9L-gliosacoma cells

| Marker | Oct4 | Nanog | Average |
| --- | --- | --- | --- |
| Whole Wells Counted | 2 | 2 | 2 |
| Conversion Efficiency (%) | 94.0 ± 1.0 | 98.0 ± 0.1 | 96.0 ± 2.0 |

Cell reprogramming of 9L cells to generate 9L-piPSCs using the QQ-SON proteins (0.5 ug/ml. Sox2:Oct4:Nanog = 1:1:1, 5 continue cycles).

Using a similar cell reprogramming protocol, 4T1-piPSCs were generated from 4T1 mouse breast cancer cells. The reprogramming conversion efficiency of 4T1 cells into 4T1-piPSCs is 96±1.3% using the same whole well counting method (96-wells), see Table 3.

TABLE 3

Conversion efficiency of QQ-SON protein-induced cell reprogramming of 4T1-breast cancer cells

| Pluripotent Marker | Number of Wells | Number of Colonies/Well | Conversion Efficiency (%) |
| --- | --- | --- | --- |
| Nanog | 2 | 1344 ± 200 | 98 ± 1 |
| Rex 1 | 2 | 1943 ± 234 | 96 ± 1 |
| Sox 2 | 2 | 1862 ± 198 | 94 ± 2 |
| Average | | | 96 ± 1.3 |

Example 9

Cells of human glioblastoma cell line U251 are reprogrammed into U251-piPSCs using QQ-modified Sox2, Oct4 and Nanog (SON) proteins as follows: At day 0, U251glioblastoma cells were seeded for 24-hours to allow them to grow in a 50 mm petri dish. At day 2, QQ-SON proteins were added to the culture medium at 0.5-2.0 µg/ml and cultured for 24 hours. Next day, fresh QQ-SON proteins were added into new culture medium and cultured for 24 hours. Such cycles were repeated for 5-7 cycles. At the end of cell reprogramming, the culture media were changed to maintaining medium for 2 days. During cell reprogramming, U251-piPSCs colonies appeared. At day 8, whole dish passage was performed to expand the generated U251-piPSCs.

Proliferative activity of U251 and U251-piPSCs was assayed by determining the number of Ki67-positive cells. FIG. 3A is a graph showing results of this assay indicating that cell reprogramming of glioma cells into piPSCs significantly reduces their proliferation, error Bar represents standard error of three independent experiments.

Example 10

Cells of a patient-derived primary human glioblastoma multiforme (GBM) cell line, GBM (12-14), is reprogrammed into GBM-piPSCs using QQ-modified Sox2, Oct4 and Nanog (SON) proteins as follows: At day 0, GBM cells were seeded for 24-hours to allow them to grow in a 50 mm petri dish. At day 2, QQ-SON proteins were added to the culture medium at 0.5-2.0 µg/ml and cultured for 24 hours. Next day, fresh QQ-SON proteins were added into new culture medium and cultured for 24 hours. Such cycles were repeated for 5-7 cycles. At the end of cell reprogramming, the culture media were changed to maintaining medium for 2 days. During cell reprogramming, GBM1-piPSCs colonies appeared. At day 8, whole dish passage was performed to expand the generated GBM-piPSCs.

Dose-dependent chemotherapeutic drug sensitivity of patient-derived primary human GBM (12-14) cells (squares) and GBM (12-14)-piPSCs (circles) against the alkylating agent temozolomide was determined and results are shown in FIG. 3B. Experiments were done in triplicate, mean±SD, p<0.01. Drug sensitivity of the GBM-piPSCs was significantly enhanced to temozolomide as compared with the parental glioblastoma cells.

Example 11

Cells of rat gliosarcoma cell line 9L are reprogrammed into 9L-piPSCs using QQ-modified Sox2, Oct4 and Nanog (SON) proteins as follows: At day 0, 9L glioma cells were seeded for 24-hours to allow them to grow in a 50 mm petri dish. At day 2, QQ-SON proteins were added to the culture medium at 0.5-2.0 µg/ml and cultured for 24 hours. Next day, fresh QQ-SON proteins were added into new culture medium and cultured for 24 hours. Such cycles were repeated for 5-7 cycles. At the end of cell reprogramming, the culture media were changed to maintaining medium for 2 days. During cell reprogramming, 9L-piPSCs colonies appeared. At day 8, whole dish passage was performed to expand the generated 9L-piPSCs.

Dose-dependent chemotherapeutic drug sensitivity of 9L-cells (squares) and 9L-piPSCs (circles) against carboplatin was determined by an MTT assay and results are shown in FIG. 3C. Experiments were done in triplicate, mean±SD, p<0.01. Drug sensitivity of the 9L-piPSCs was significantly enhanced to carboplatin as compared with the parental 9L cells.

Example 12

Cells of mouse mammary tumor cell line 4T1 are reprogrammed into 4T1-piPSCs using QQ-modified Sox2, Oct4 and Nanog (SON) proteins as follows: At day 0, 4T1 cells were seeded for 24-hours to allow them to grow in a 50 mm petri dish. At day 2, QQ-SON proteins were added to the culture medium at 0.5-2.0 µg/ml and cultured for 24 hours. Next day, fresh QQ-SON proteins were added into new culture medium and cultured for 24 hours. Such cycles were repeated for 5-7 cycles. At the end of cell reprogramming, the culture media were changed to maintaining medium for 2 days. During cell reprogramming, 4T1-piPSCs colonies appeared. At day 8, whole dish passage was performed to expand the generated 4T1-piPSCs.

Proliferative activity of 4T1-cells and 4T1-piPSCs was assayed by determining the number of Ki67-positive cells and it was found that cell reprogramming of 4T1 mammary tumor cells into 4T1-piPSCs significantly reduces their proliferation.

Mammary sphere formation of 4T1-piPSCs was reduced as compared with that of 4T1-cells.

Dose-dependent chemotherapeutic drug sensitivity of 4T1-cells and 4T1-piPSCs against doxorubicin and paclitaxel was determined using an MTT assay. Drug sensitivity of the 4T1-piPSCs was significantly enhanced to doxorubicin and paclitaxel as compared with the parental 4T1 cells.

Example 13

Glioma Cell-Derived piPSC Differentiation into Three Germ Layers In Vitro

Embryonic bodies (EBs) were prepared for glioma-piPSCs using the hanging-drop method. The glioma-piPSCs EBs were placed into a spontaneous differentiation medium for 10-days, followed by immunostaining with markers of ectoderm, mesoderm and endoderm, showing positive immunostains of PAX6 for ectoderm, positive immunostains of desmin for mesoderm and positive immunostains of α-fetoprotein (AFP) for endoderm. Immunostaining of control 9L cells was negative for these markers. Similar results have been also obtained for 4T1-piPSCs, indicating that the 4T1-piPSCs also differentiated into three germ layers.

Example 14

Glioma Cell-Derived piPSC Differentiation into Neural-Lineage In Vitro

Glioma-piPSCs EBs were placed into a specific neural-lineage inducing differentiation medium for 14-days, followed by immunostaining with neural lineage markers, showing positive immunostains of Tuj I for neurons, positive immunostains of GFAP for astrocytes and positive immunostains of nestin for neural stem cells. These neural-specifically differentiated cells also displayed neural cell morphology. Immunostaining of control 9L cells was negative for these markers.

Example 15

Cell Reprogramming Causes a Mesenchymal-to-Epithelial Transition (MET) and Reduction of Tumorigenicity In Vitro.

Figures 4A, 4B, 4C:
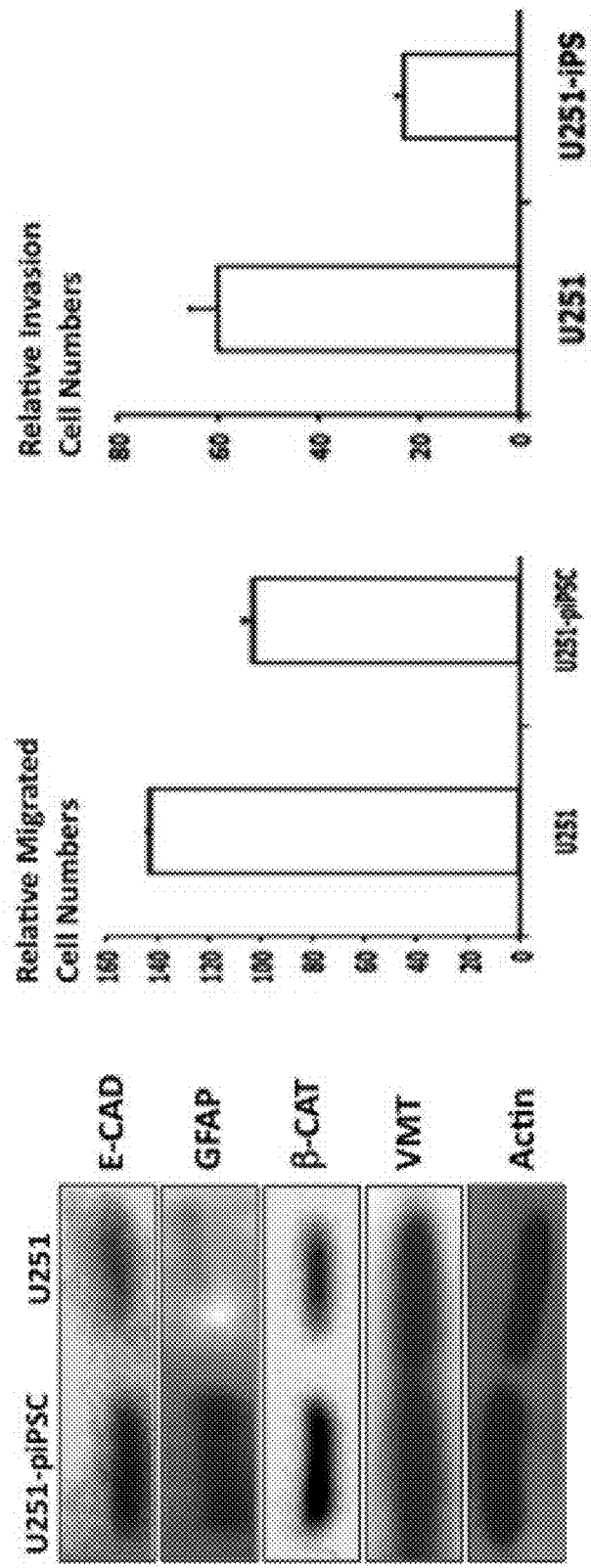
FIG. 4A is an image showing Western blots of several epithelial and mesenchymal markers of U251 cells and U251-piPSCs, including E-cadherin (E-cad), β-catenin (β-cat), vimentin (VMT), indicating a mesenchymal-to-epithelial transition (MET) during cell reprogramming. In addition, cell reprogramming of 9L-cells into 9L-piPSCs also caused an enhanced expression of glial fibrillary acidic protein (GFAP), a marker for astrocytes.
FIG. 4B is a graph showing that the tumorigenicity reduction of U251 cells after cell reprogramming according to aspects of the present invention is continued by in vitro assays for cell migration of U251-cells and U251-piPSCs, indicating significantly reduced migration of U251-piPSCs ($p<0.01$) in vitro.
FIG. 4C is a graph showing that the tumorigenicity reduction of U251 cells after cell reprogramming according to aspects of the present invention is confirmed by in vitro assays for invasion of U251-cells and U251-piPSCs, indicating significantly reduced invasion by U251-piPSCs ($p<0.01$) in vitro.

Results of Western blot analysis of several epithelial and mesenchymal markers of U251 cells and U251-piPSCs, including E-cadherin (E-cad), β-catenin (β-cat), vimentin (VMT), see FIG. 4A, indicate an MET during cell reprogramming which is confirmed by cell morphology changes and qRT-PCR results. GFAP protein level is also significantly enhanced after cell reprogramming into U251-piPSCs from U251 cells, indicating that cell reprogramming caused a significant reduction of tumorigenicity of U251 cells in vitro during cell reprogramming. Actin protein expression was used as an internal control. Immunostaining of U251 cells and U251-piPSCs using an anti-GFAP antibody, confirmed up-regulated protein expression of GFAP in U251-piPSCs as shown in Western blot. In addition, the GFAP-expressing cells displayed morphologies of neural cells.

The tumorigenicity reduction of U251 cells after cell reprogramming has been confirmed by in vitro assays for cell migration, FIG. 4B, and invasion, FIG. 4C, of U251-cells and U251-piPSCs, indicating significantly reduced migration and invasion of U251-piPSCs ($p<0.01$).

Figures 4D, 4E:
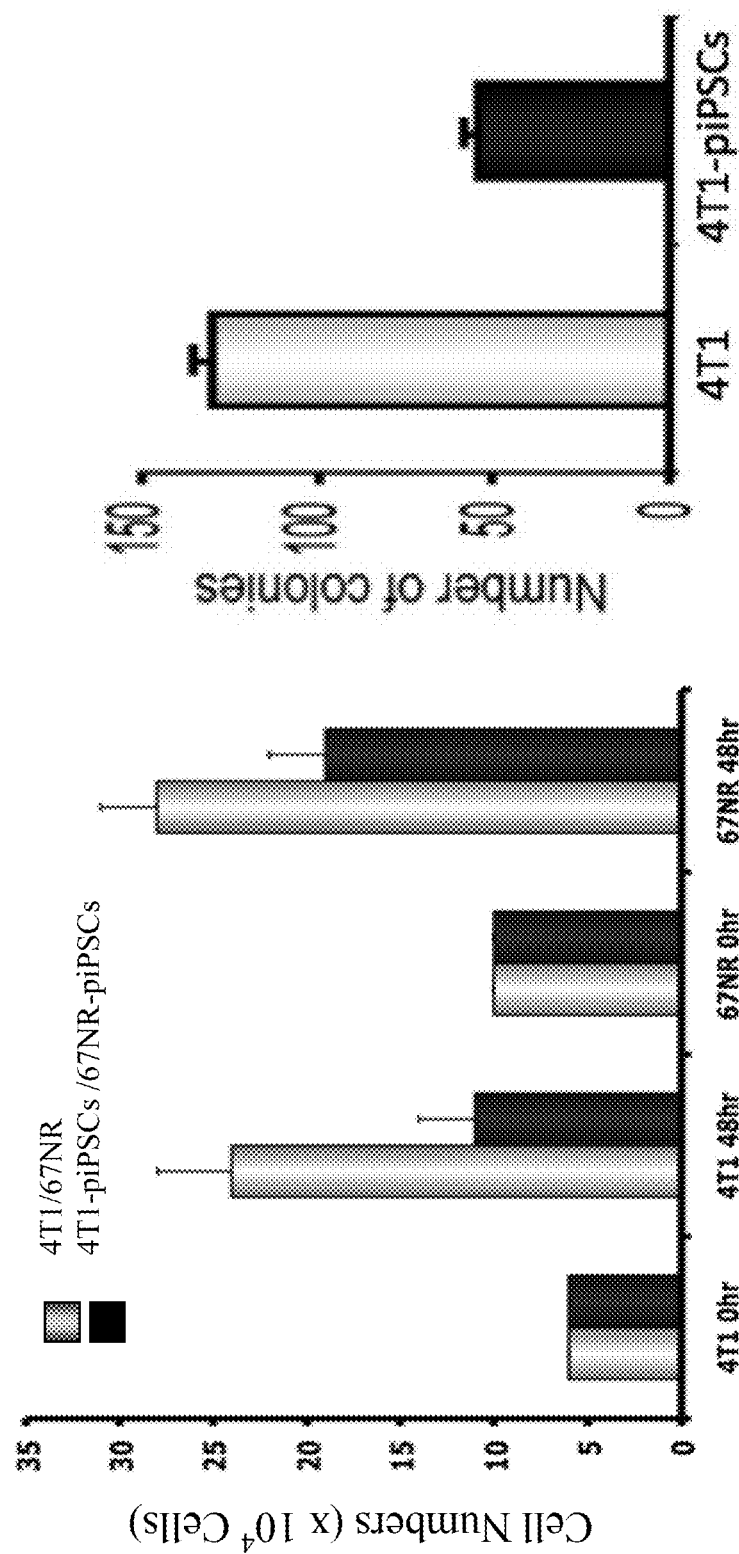
FIG. 4D is a graph showing reduced proliferation of 4T1-piPSCs and 67NR-piPSCs as compared to those properties of the parental 4T1 cells and 67NR cells, indicating a significantly reduced tumorigenicity of 4T1 cells and 67NR cells after cell reprogramming into 4T1-piPSCs and 67NR-piPSCs in vitro.
FIG. 4E is a graph showing reduced mammary sphere formation of 4T1-piPSCs as compared to those properties of the parental 4T1 cells, indicating a significantly reduced tumorigenicity of 4T1 cells after cell reprogramming into 4T1-piPSCs in vitro.
Figures 4F, 4G:
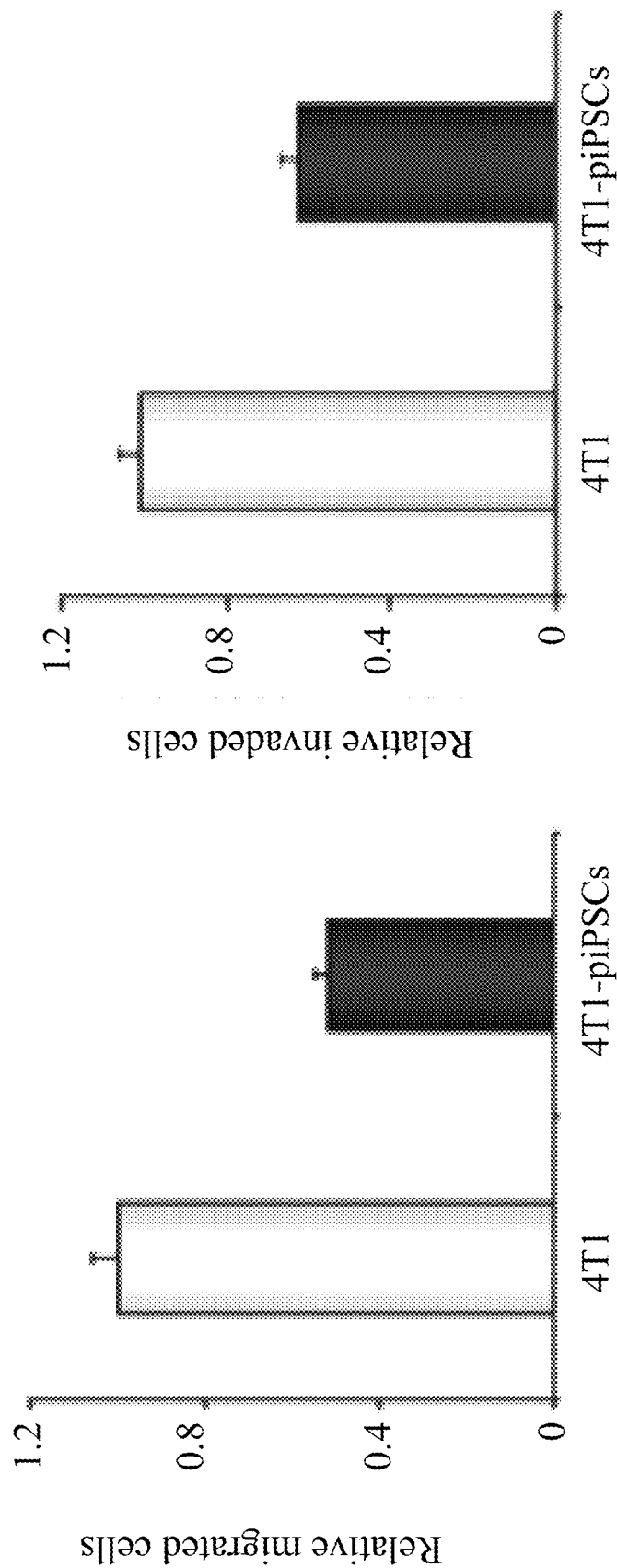
FIG. 4F is a graph showing reduced migration of 4T1-piPSCs as compared to those properties of the parental 4T1 cells, indicating a significantly reduced tumorigenicity of 4T1 cells after cell reprogramming into 4T1-piPSCs in vitro.
FIG. 4G is a graph showing reduced invasion of 4T1-piPSCs as compared to those properties of the parental 4T1 cells, indicating a significantly reduced tumorigenicity of 4T1 cells after cell reprogramming into 4T1-piPSCs in vitro.

Similarly, immunostainings of 41-piPSCs and 4T1 cells using an epithelial marker: E-cadherin and a mesenchymal marker fibronectin were compared and showed that while 4T1 cells display positive E-cadherin immunostaining, 4T1-piPSCs showed much stronger E-cadherin immunostaining. In contrast, 4T1 cells displayed stronger fibronectin immunostaining and 4T1-piPSCs exhibited nearly negative fibronectin immunostaining. This results confirm a MET of 4T1 cells during cell reprogramming into 4T1-piPSCs. In addition, 4T1-piPSCs also exhibited reduced proliferation, FIG. 4D, reduced mammary sphere formation, FIG. 4E, reduced migration, FIG. 4F, and reduced invasion, FIG. 4G, as compared to those properties of the parental 4T1 cells, indicating a significantly reduced tumorigenicity of 4T1 cells after cell reprogramming into 4T1-piPSCs in vitro.

Example 16

Co-culture between glioma cells and glioma-piPSCs indicated that glioma-piPSCs displayed a bystander effect to change the phenotypes of their surrounding glioma cells and reduced tumorigenicity in vitro.

Cell morphology changes of U251 cells indirectly co-cultured with U251-piPSCs for 40-64 hours are observed indicating a mesenchymal-to-epithelial transition (MET) of the co-cultured glioma cells. FIG. 5A is an image showing cell morphology of U251 cells and FIG. 5B is an image showing changes in cell morphology of U251 cells indirectly co-cultured with U251-piPSCs for 40-64 hours.

This MET was confirmed by immunostaining of U251 cells, U251-piPSCs, first ($1^{st}$) co-cultured U251 cells and second ($2^{nd}$) co-cultured U251 cells using an anti-pan-cadherin antibody, showing cytosol/nuclear localization of pan-cadherin in U251 cells and membrane/nuclear localization of U251-piPSCs and $1^{st}/2^{nd}$ co-cultured U251 cells, suggesting a major enhancement of cell-cell adhesion among U251-piPSCs as well as among the $1^{st}/2^{nd}$ co-cultured U251 cells. This is an indication of MET during cell reprogramming and the $1^{st}/2^{nd}$ co-cultured U251 cells. A $2^{nd}$ co-culture is the indirect co-culture experiment that places the $1^{st}$ co-cultured cells into the transwell insert and fresh U251 cells in the basolateral chamber. Double immunostains of the U251 cells and indirectly co-cultured U251 cells using distinctly labeled anti-GFAP and anti-Tuj1 antibodies, showing significant GFAP protein expression in the co-cultured U251 cells with neural morphology whereas U251 cells (spindle morphology) do not express GFAP.

Figure 5C:
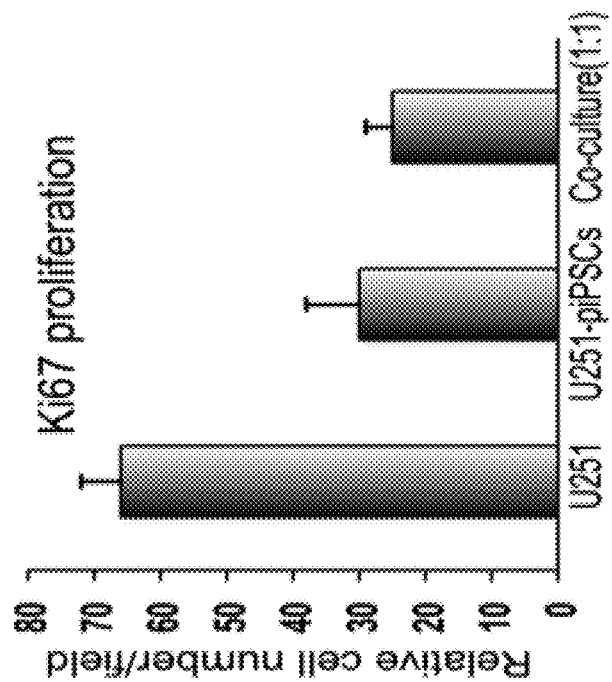
FIG. 5C is a graph showing significantly reduced proliferation of U251-piPSCs and U251 cells indirectly co-cultured with U251-piPSCs at a 1:1 ratio of the U251-piPSCs and U251 cells, indicating a significantly reduced tumorigenicity of the co-cultured U251 cells and supporting the observation of a bystander effect.
Figure 5A:
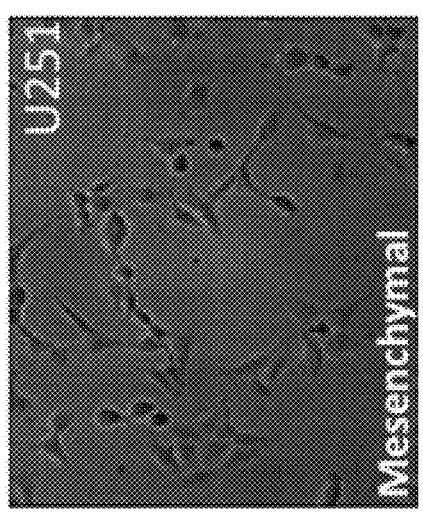
FIG. 5A is an image showing cell morphology of U251 cells.
Figure 5B:
FIG. 5B is an image showing changes in cell morphology of U251 cells indirectly co-cultured with U251-piPSCs for 40-64 hours, indicative of mesenchymal-to-epithelial transition and demonstrating a bystander effect of the U251-piPSCs on U251 cells.
Figures 5D, 5E:
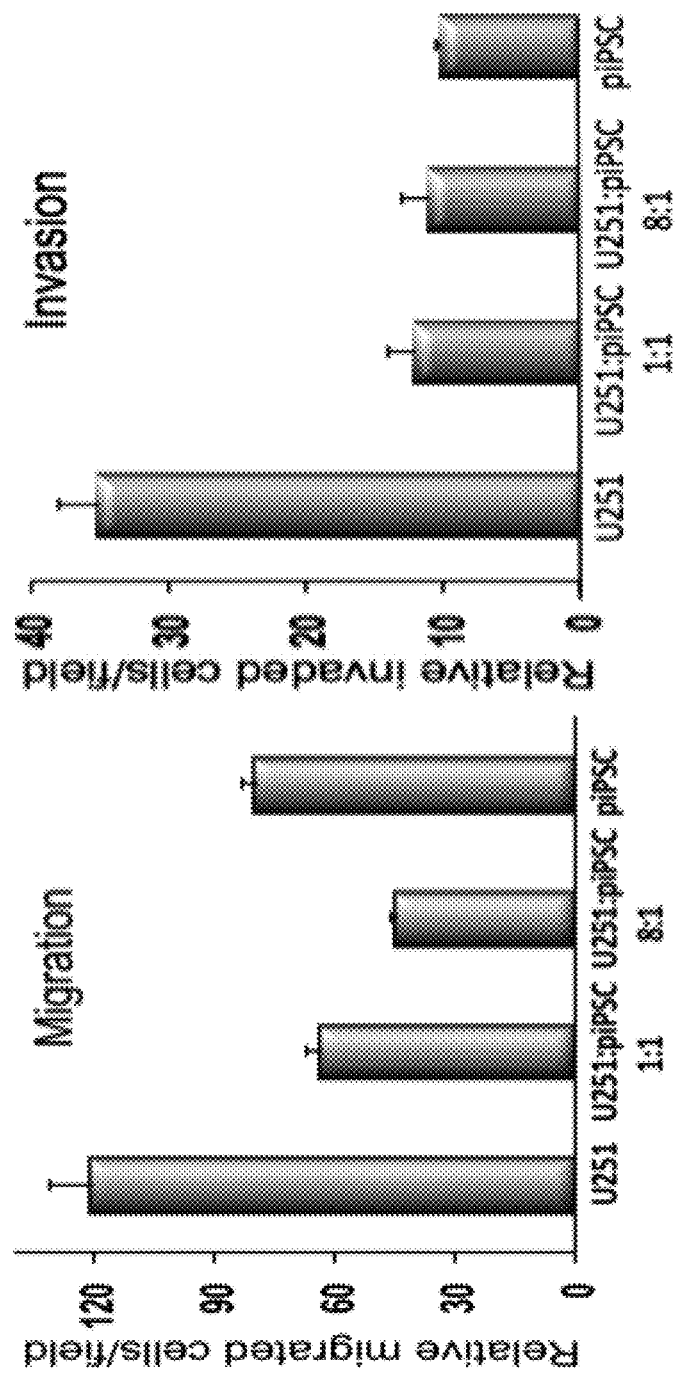
FIG. 5D is a graph showing significantly reduced migration of U251-piPSCs and U251 cells indirectly co-cultured with U251-piPSCs at 1:1 and 8:1 ratios (U251:U251-piPSCs), ($p<0.005$), indicating a significantly reduced tumorigenicity of the co-cultured U251 cells and supporting the observation of a bystander effect.
FIG. 5E is a graph showing significantly reduced invasion of U251-piPSCs and U251 cells indirectly co-cultured with U251-piPSCs at 1:1 and 8:1 ratios (U251:U251-piPSCs), ($p<0.005$), indicating a significantly reduced tumorigenicity of the co-cultured U251 cells and supporting the observation of a bystander effect.

Results of proliferation assay of U251 cells, U251-piPSCs and indirectly co-cultured U251 cells by Ki-67 immunostaining show significantly reduced proliferation of U251-piPSCs and the co-cultured U251 cells, FIG. 5C. Results of migration assays, FIG. 5D, and invasion assays, FIG. 5E, of U251 cells, U251-piPSCs, directly co-cultured U251 cells at 1:1 and 8:1 ratios (U251:U251-piPSCs), show significantly reduced migration and invasion of the U251 cells after co-cultures with U251-piPSCs ($p<0.005$).

Figures 5F, 5G, 5H:
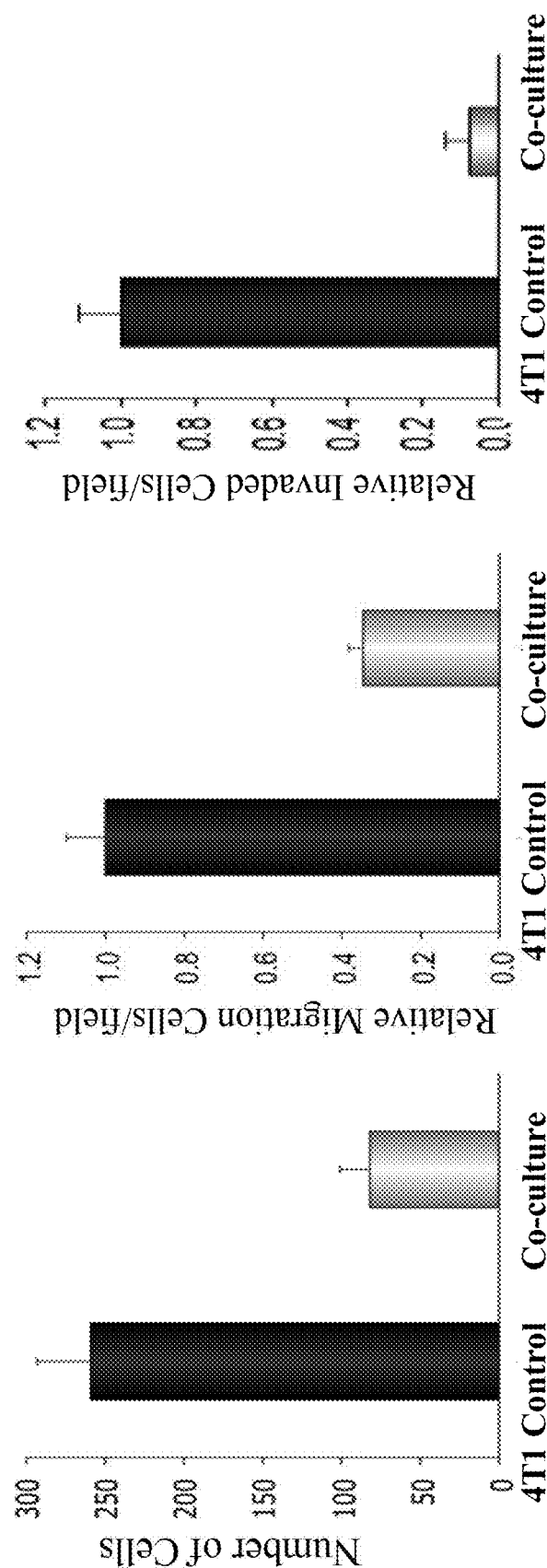
FIG. 5F is a graph showing significantly reduced proliferation of 4T1 cells co-cultured with 4T1-piPSCs for 40 hours, indicating a significantly reduced tumorigenicity of the co-cultured 4T1 cells and supporting the observation of a bystander effect.
FIG. 5G is a graph showing significantly reduced migration of 4T1 cells co-cultured with 4T1-piPSCs for 40 hours, indicating a significantly reduced tumorigenicity of the co-cultured 4T1 cells and supporting the observation of a bystander effect.
FIG. 5H is a graph showing significantly reduced invasion of 4T1 cells co-cultured with 4T1-piPSCs for 40 hours, indicating a significantly reduced tumorigenicity of the co-cultured 4T1 cells and supporting the observation of a bystander effect.

Following a similar co-culture experiment, MET of co-cultured 4T1 cells with 4T1-piPSCs was observed. Immunostains of co-cultured 4T1 cells and 4T1-piPSCs showed that both cells had high protein expression of E-cadherin and lower protein expression of fibronectin, confirming a MET of the co-cultured 4T1 cells. In addition, the co-cultured 4T1 cells also displayed a significantly reduced proliferation, FIG. 5F, migration, FIG. 5G, and invasion, FIG. 5H, indicating a significantly reduced tumorigenicity of the 4T1 cells after co-cultured with 4T1-piPSCs for 40-hours.

Co-culture of patient-derived primary brain tumor cells, GBM (12-14), with U251-piPSCs also causes a mesenchymal-to-epithelial transition and reduced tumorigenicity of the co-cultured patient-derived primary brain tumor cells—a bystander effect of U251-piPSCs.

These results indicate that a bystander effect of piPSCs changes the phenotypes of surrounding cancer cells for tumorigenicity and malignancy reduction. This bystander effect indicates that a smaller number of piPSCs can change malignant phenotype of a large numbers of surrounding tumor cells via this bystander effect, serving a cellular mechanism of a cell-converting cancer therapy.

Example 17

Significantly Reduced Tumorigenicity and Metastasis/Infiltration Inhibition In Vivo of piPSCs Generated from Malignant Cancer Cells.

In a first set of animals, equal numbers of 9L cells or 9L-piPSCs ($5\times10^4$ cells/5 µl) were implanted into Fisher rats intracranially. In a second set of animals, equal numbers of 9L cells or 9L-piPSCs ($1\times10^6$ cells/100 ml) were implanted into Fisher rats subcutaneously.

Figures 6A, 6B:
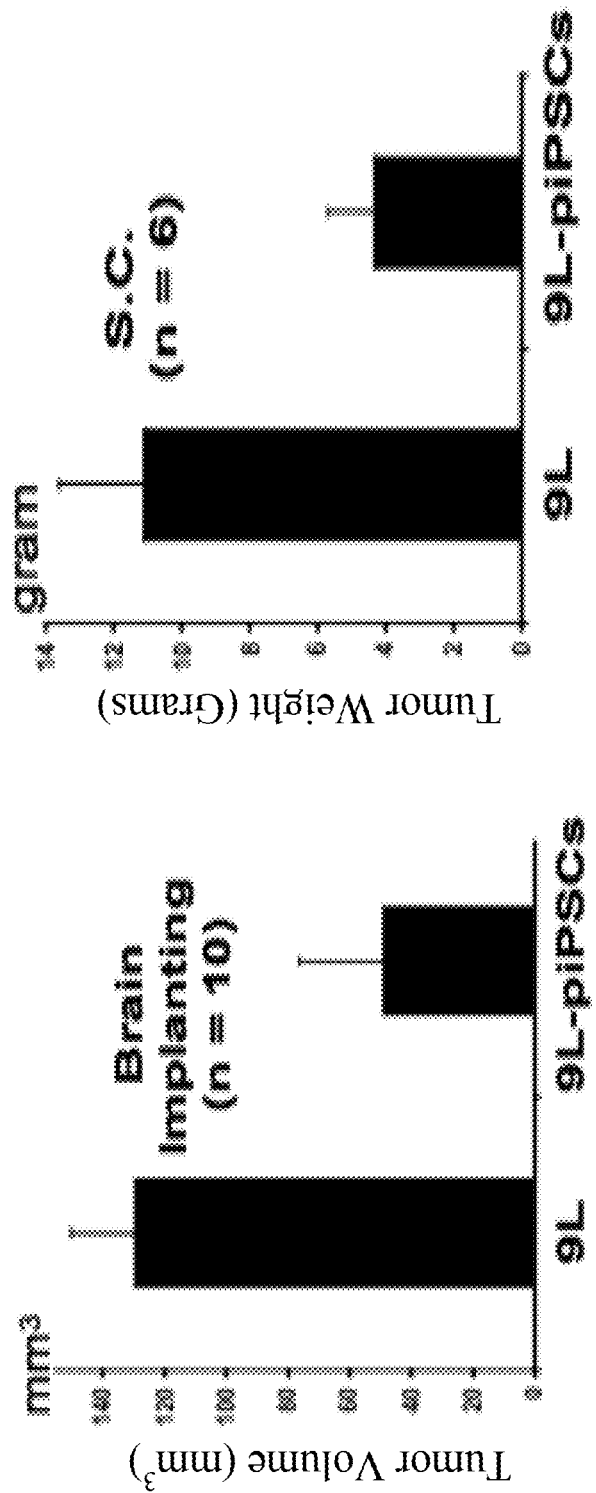
FIG. 6A is a graph showing tumor volume (mm3) in rats intracranially-implanted with either 9L cells or 9L-piPSCs (n=10) at day 14 and showing significantly reduced volume of the intracranial 9L-piPSC tumors as compared with those of 9L-tumors, indicating a significantly reduced tumorigenicity of 9L-cells after cell reprogramming into 9L-piPSCs in vivo.
FIG. 6B is a graph showing tumor weight (grams) in rats subcutaneously-implanted with 9L cells and 9L-piPSCs at day 25 after implantation (n=6) and showing significantly reduced weight of the subcutaneous 9L-piPSC tumors as compared with those of 9L-tumors, indicating a significantly reduced in vivo tumorigenicity of 9L-cells after cell reprogramming into 9L-piPSCs in vivo.

Tumor volume (mm$^3$) of intracranial-implanted rats with either 9L cells or 9L-piPSCs, n=10 was measured at day 14, see FIG. 6A. Tumor weight in grams of subcutaneously-implanted rats with 9L cells and 9L-piPSCs was measured at day 25 after 4T1-cell implantation, n=6, see FIG. 6B. Results showed a significantly reduced volume of the intracranial 9L-piPSC tumors and a significantly reduced weight of the subcutaneous 9L-piPSC tumors as compared with those of 9L-tumors, indicating a significantly reduced tumorigenicity of 9L-cells after cell reprogramming into 9L-piPSCs. This result is also confirmed by hematoxylin and eosin (H&E) staining of the tumors from 9L-cell and 9L-piPSC implanted animals, indicating a major inhibition of 9L-cell infiltration, since the 9L-piPSC intracranial tumor showed a clear intact border, whereas 9L-intracranial tumor showed a broken border with a major infiltration of the 9L-tumor cells into normal brain tissues.

Example 18

Significantly Reduced Tumorigenicity and Metastasis/Infiltration Inhibition In Vivo of piPSCs Generated from Malignant Breast Cancer Cells.

Equal numbers of 4T1 cells and 4T1-piPSCs ($2\times10^4$ cells/50 µl) were implanted into the #4 fat pads of 2-3 month old female BALB/c mice (20 grams). 4T1 breast tumors were observed at day 5-7 after cell implantation. The tumor volume and body weight of the mice were monitored every day. At day 25, the mice were sacrificed and the tumors were weighed. For the survival experiment, animals were sacrificed once they reached tumor burden.

Figure 6D:
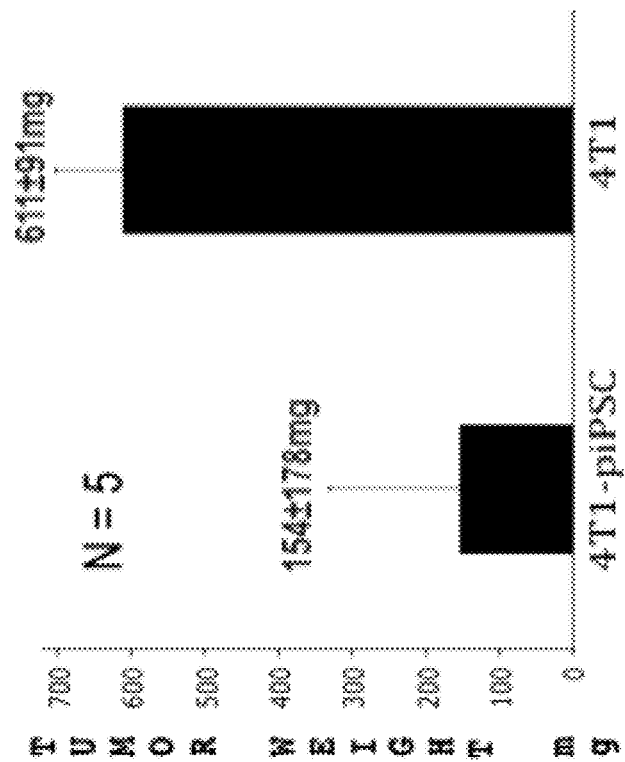
FIG. 6D is a graph showing 4T1- and 4T1-piPSC tumor growth curve as measured using tumor weight at day 25 after 4T1- and 4T1-piPSC implantation, indicating a significant in vivo tumor stasis of 4T1 cells after cell reprogrammed into 4T1-piPSCs in vivo.
Figure 6C:
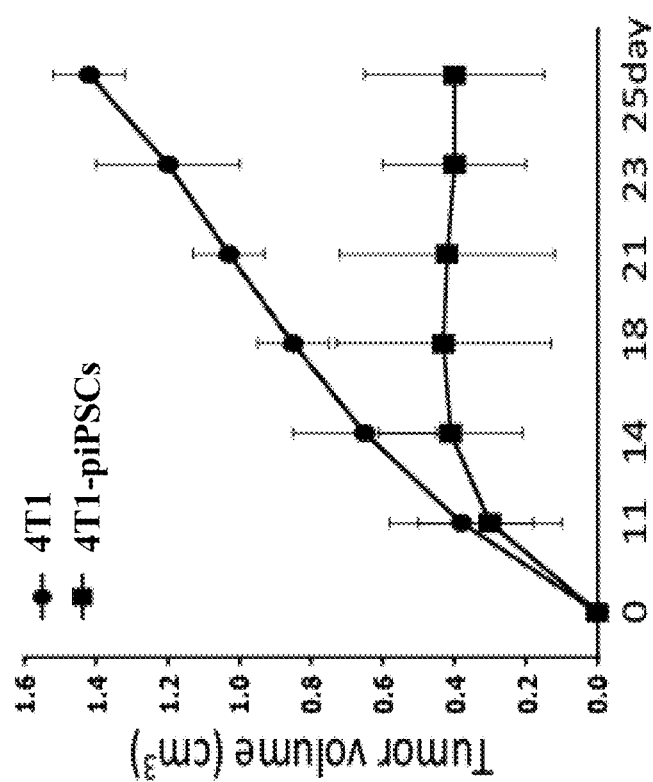
FIG. 6C is a graph showing 4T1- and 4T1-piPSC tumor growth curve as measured using tumor volume over 25 days after 4T1- and 4T1-piPSC implantation, indicating a significant in vivo tumor stasis of 4T1 cells after cell reprogrammed into 4T1-piPSCs in vivo.

4T1 and 4T1-piPSC tumor growth were measured by tumor volume, FIG. 6C, and tumor weight, FIG. 6D, at day 25 after 4T1- and 4T1-piPSC implantation, indicating a significant tumor stasis of 4T1 cells after cell reprogrammed into 4T1-piPSCs.

Figure 6E:
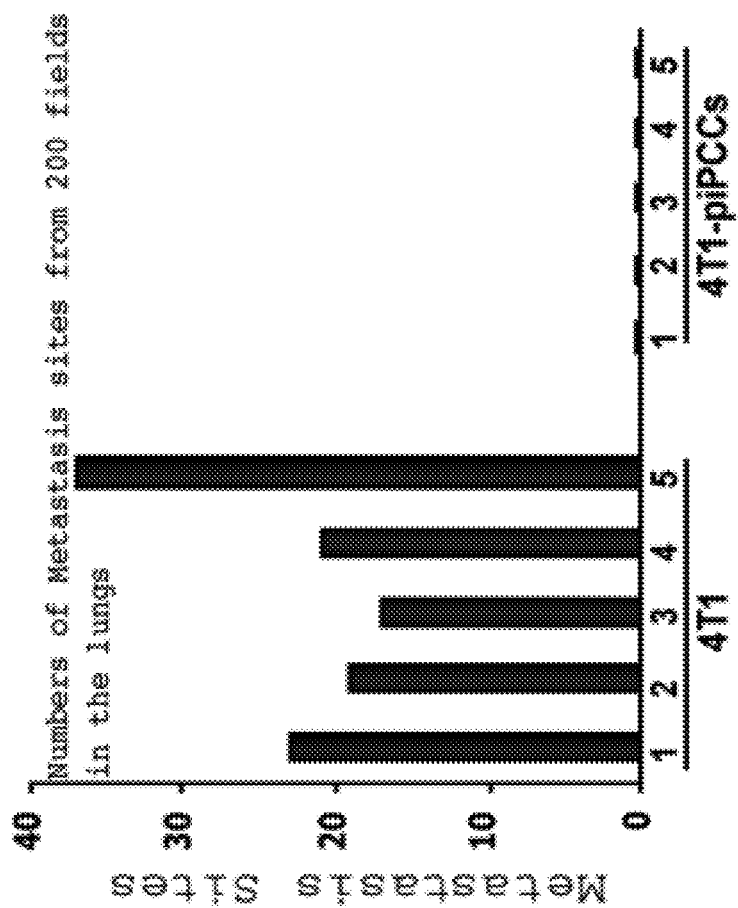
FIG. 6E is a graph showing lung metastases in mice implanted with 4T1 cells or 4T1-piPSCs at day 25 after cell implantation, indicating a major in vivo metastasis inhibition caused by cell reprogramming of 4T1 cells into 4T1-piPSCs in vivo; the lung was divided into 200 fields and number of metastases was counted and reported in the y-axis.

Lung metastases of the mice that were implanted with 4T1 cells and 4T1-piPSCs were analyzed at day 25 after cell implantation. While all the mice implanted with 4T1 cells displayed many metastatic lesions, no lung metastases were observed in the mice implanted with 4T1-piPSCs at day 25 after cell implantation, FIG. 6E, indicating a major metastasis inhibition caused by cell reprogramming of 4T1 cells into 4T1-piPSCs. This result was confirmed by H&E stain of the lung tissue sections of 4T1-bearing mice and 4T1-piPSC bearing mice, showing no lung metastasis in the mice implanted with 4T1-piPSCs.

Figure 6F:
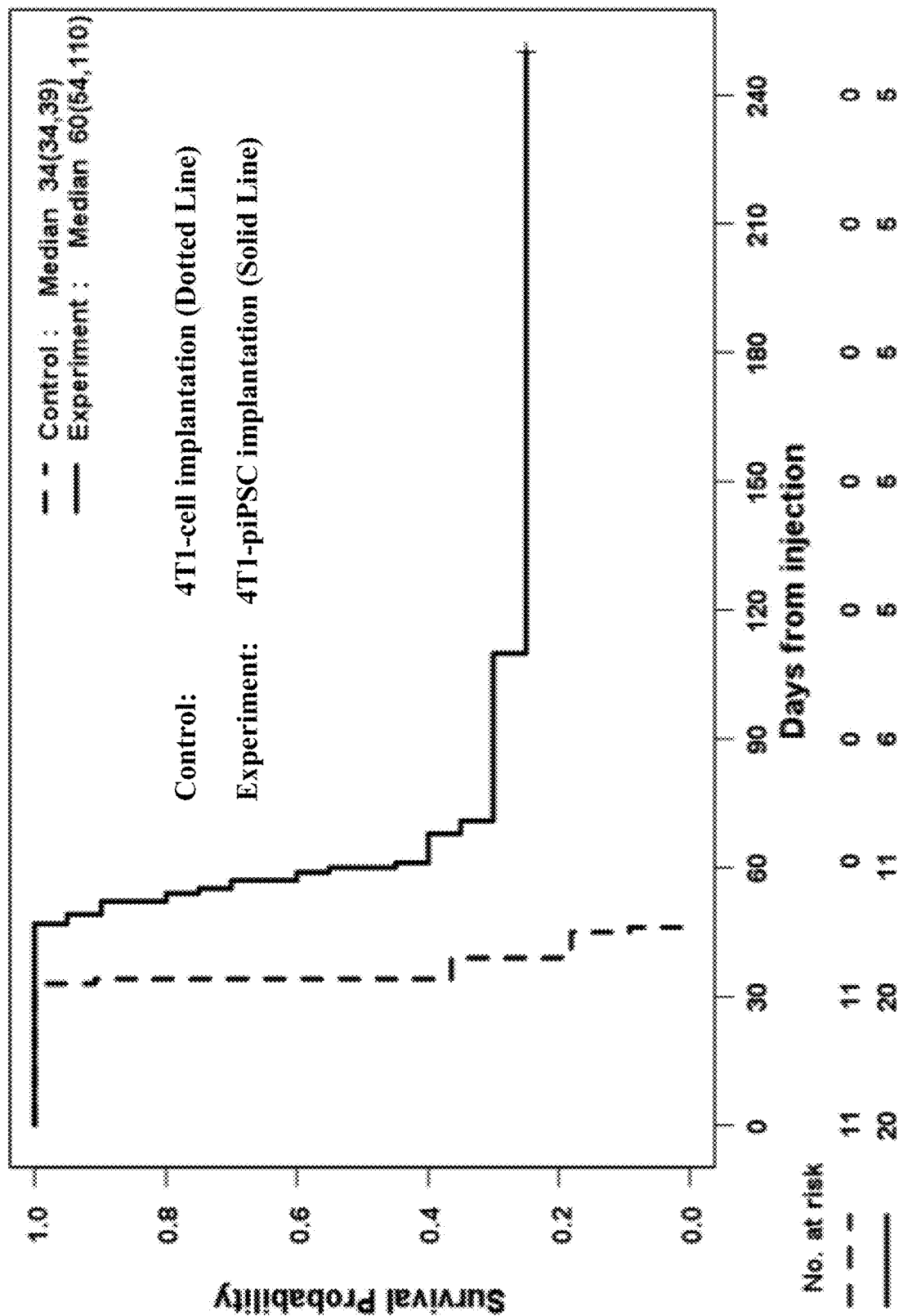
FIG. 6F is a Kaplan-Meier survival curve of mice implanted with 4T1 cells and 4T1-piPSCs in the #4 fat pads, demonstrating a significantly prolonged survival of the 4T1-piPSCs during this 250-day survival experiment, indicating that cell reprogramming of malignant cancer cells into piPSCs significantly reduces tumorigenicity and metastatic properties of the parental cancer cells.

A Kaplan-Meier survival curve of the mice implanted with 4T1 cells and 4T1-piPSCs in the #4 fat pads, FIG. 6F, demonstrates a significantly prolonged survival of the 4T1-piPSC bearing mice during this 250-day survival experiment. These results demonstrate that cell preprogramming of malignant cancer cells into piPSCs significantly reduces tumorigenicity and metastatic property of the parental cancer cells, thus significantly prolonging the survival of the mice implanted with 4T1-piPSCs.

Example 19

Tumor Cell Derived piPSCs Differentiate into Different Normal Tissues In Vivo Depending on Different Differentiating Tissue Environments.

H&E stains of the brain tissue sections of 9L-intracranial implanted rats showed major glioma angiogenesis into normal brain tissues and severe bleeding inside brain tumors, whereas much less angiogenesis and bleeding were observed in the 9L-piPSC-intracranial implanted rats. In addition, 9L-piPSC-intracranial implanted rats also showed newly differentiated neural rosettes near the tumors in the brain. Further, H&E stain of the tumor tissue slides of subcutaneously-implanted rats with 9L-piPSCs, showed immature sweat glands with cuboidal and low columnar epithelial cells and melanocytes with brown color of melanin within the tumors. H&E stains of tumor tissue slides of rats subcutaneously implanted with 9L-piPSCs also showed skin epithelium with two layers of epidermis and early simple columnar epithelial cells with longer shape and nuclei in the base of the cells.

Similarly, H&E staining of the tumor masses of the 4T1-piPSC-bearing mice showed in vivo differentiation of the implanted 4T1-piPSCs into normal breast tissues including adipocytes including both brown and white adipocytes and mature and immature mammary ducts.

These results indicate that tumor cell derived-piPSCs differentiate into different normal tissue cells in vivo depending on different differentiating tissue environments.

Example 20

Lineage Tracing Shows Tumor Cell Derived piPSCs Differentiate into Normal Tissues.

To ensure that tumor cell derived piPSCs differentiate into normal tissues, GFP-expressing 9L- and 4T1-cells were prepared.

GFP-9L-piPSCs and GFP-4T1-piPSCs were prepared.

Lineage-tracing experiments were performed using both cell types. For GFP-9L-piPSCs, the cells were subcutaneously implanted into left flanks of Fisher rats. For GFP-4T1-piPSCs, the cells were implanted into the #4 fat pad of female BALB/c mice. Small tumor mass were observed at day 10-15 for GFP-9L-piPSC-implanted rats and at day 20-25 days for GFP-4T1-piPSC-implanted mice. The animals were sacrificed at different days after cell implantation and tumor masses were collected and used to make tissue sections for H&E stains and immunostaining. Immunostaining with Tuj I and Nestin neural marker antibodies, adiponectin (an adipocytes marker), cytokeratin 8, 14, 18 (CK8, 14, 18) or cytokeratin 5,8 (CK5,8) (mammary duct markers) were performed using differentially detectable labels.

H&E stain of both the center and edges of tumor mass of the 4T1-piPSC-bearing mice showed appearance of potential adipocytes and immature mammary ducts in the tumor mass.

Immunostains of the tissue section of the GFP-9L-piPSCs tumor mass obtained from the lineage tracing experiment using an anti-Tuj I antibody showed positive Tuj I immunostaining that overlapped with GFP fluorescence of GFP-expressing cells of the same tissue sections. Only overlapping Tuj I and GFP fluorescence images were observed in the tissue sections, indicating that these Tuj I-positive cells originated from the GFP-expressing 9L-piPSCs. The Tuj I/GFP-positive cells displayed neuronal cell morphology. This data demonstrates that the GFP-expressing 9L-piPSCs differentiated in vivo into Tuj I-positive neuronal lineage cells.

Immunostains of the tissue section of the GFP-9L-piPSCs tumor mass obtained from the lineage tracing experiment using an anti-nestin antibody showed positive nestin immunostaining that overlapped with GFP fluorescence of GFP-expressing cells of the same tissue sections. Only overlapping nestin and GFP fluorescence images were observed in the tissue sections, indicating that these nestin-positive cells originated from the GFP-expressing 9L-piPSCs. This data demonstrates that the GFP-expressing 9L-piPSCs differentiated in vivo into nestin-positive neural lineage cells.

Immunostains of the tumor tissue sections of the 4T1-piPSC-bearing mice with an anti-adiponectin antibody showed adiponectin-positive immunostaining that overlapped with green fluorescence from the GFP-expressing cells. Only overlapping adiponectin and GFP fluorescence were observed in the tissue sections in cells with adipocyte morphology, indicating presence of adipocytes in the middle of the tumor mass of the 4T1-piPSC-bearing mice and these adipocytes originated from differentiation of the implanted GFP-4T1-piPSCs, since these adipocytes expressed GFP.

Immunostains of the tumor tissue sections of the 4T1-piPSC-bearing mice with anti-CK8,18,14 and anti-CK5,8 antibodies showed CK8,18,14- and anti-CK5,8-positive immunostaining that overlapped with green fluorescence from the GFP-expressing cells. Only overlapping CK8,18, 14- or anti-CK5,8-positive and GFP fluorescence were observed in the tissue sections in cells with morphology of mammary ducts, indicating presence of immature mammary ducts that originated from differentiation of the implanted GFP-4T1-piPSCs, since these mammary ducts expressed GFP.

Example 21

QQ-SON Protein-Induced Cell Reprogramming Treatment of Tumors In Vivo

To generate 9L-tumor bearing rats, 9L cells ($1 \times 10^6$ cells/100 µl) were implanted into Fisher rats subcutaneously. 5-days after 9L-implantation, QQ-SON protein was administered by intra-tumor injection every day at 1 µg/day (n=5), 5 µg/day (n=5), or 10 µg/day (n=10) for 18 daily treatments. QQ-reagent in PBS buffer was administered by intra-tumor injection to control rats (n=10). The tumor volume and body weight of the rats were monitored every day. At day 23, the rats were sacrificed and the tumors were weighed.

Figure 7A:
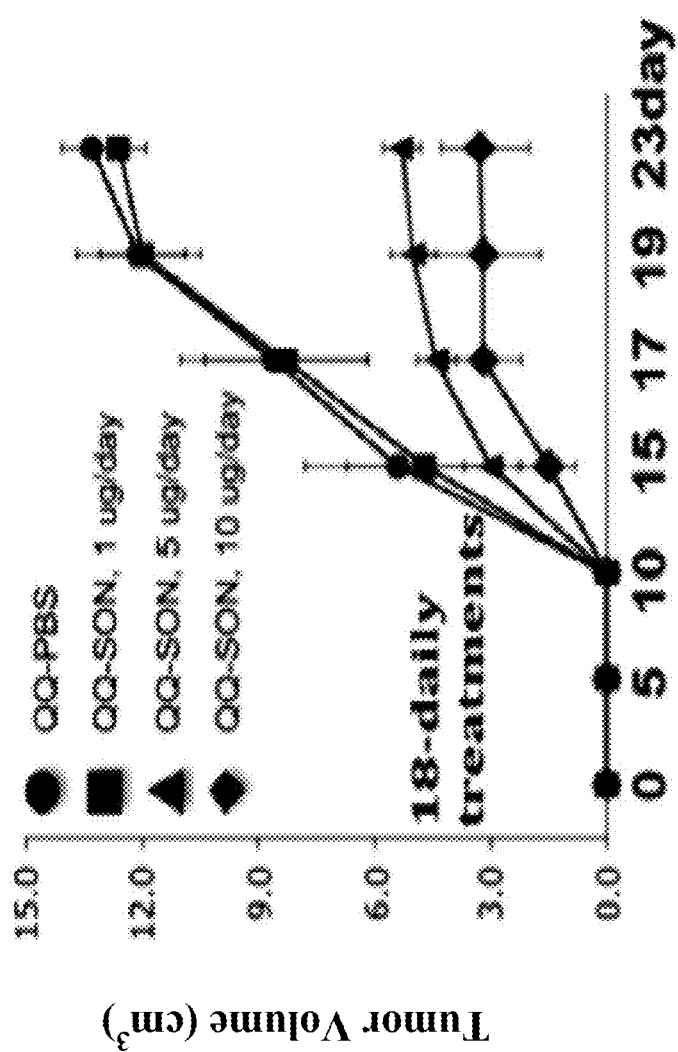
FIG. 7A is a graph showing dose-dependent 9L tumor growth curves measured by tumor volume in rats treated with QQ-reagent in PBS buffer (n=10), QQ-SON proteins 1 μg/day (n=5), QQ-SON proteins 5 μg/day (n=5), and QQ-SON proteins 10 μg/day=10) for 18 daily treatments where the treatment started at day 5 after 9L cell implantation and the rats were sacrificed at day 23.
Figure 7B:
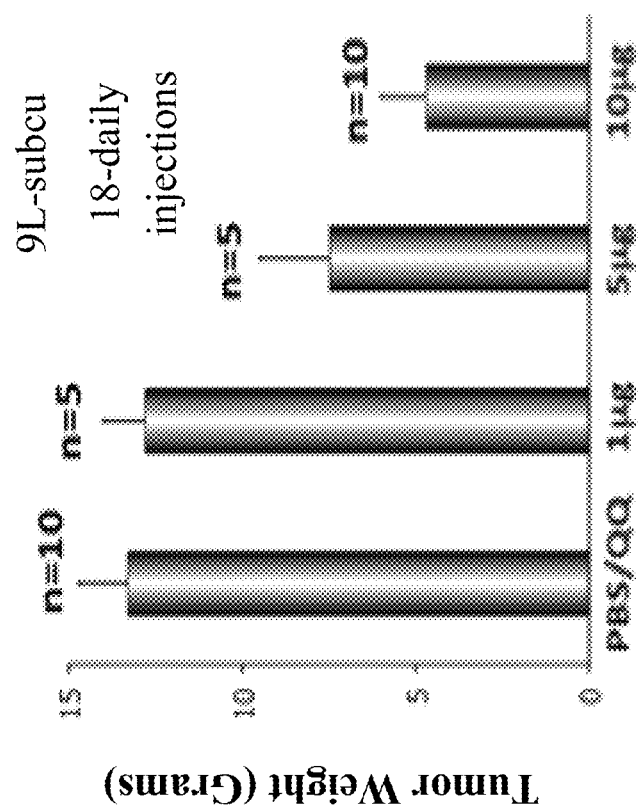
FIG. 7B is a graph showing 9L tumor weight in rats treated with QQ-reagent in PBS buffer (n=10), QQ-SON proteins 1 μg/day (n=5), QQ-SON proteins 5 μg/day (n=5), and QQ-SON proteins 10 μg/day (n=10) for 18 daily treatments where the treatment started at day 5 after 9L cell implantation and the rats were sacrificed at day 23.

Tumor growth was measured by volume, see FIG. 7A and tumor weight in grains, see FIG. 7B. The rats were sacrificed at day 23 and tumors were weighed. This data indicates that QQ-SON treatment induced in situ cell reprogramming that results in tumor stasis.

Figure 7C:
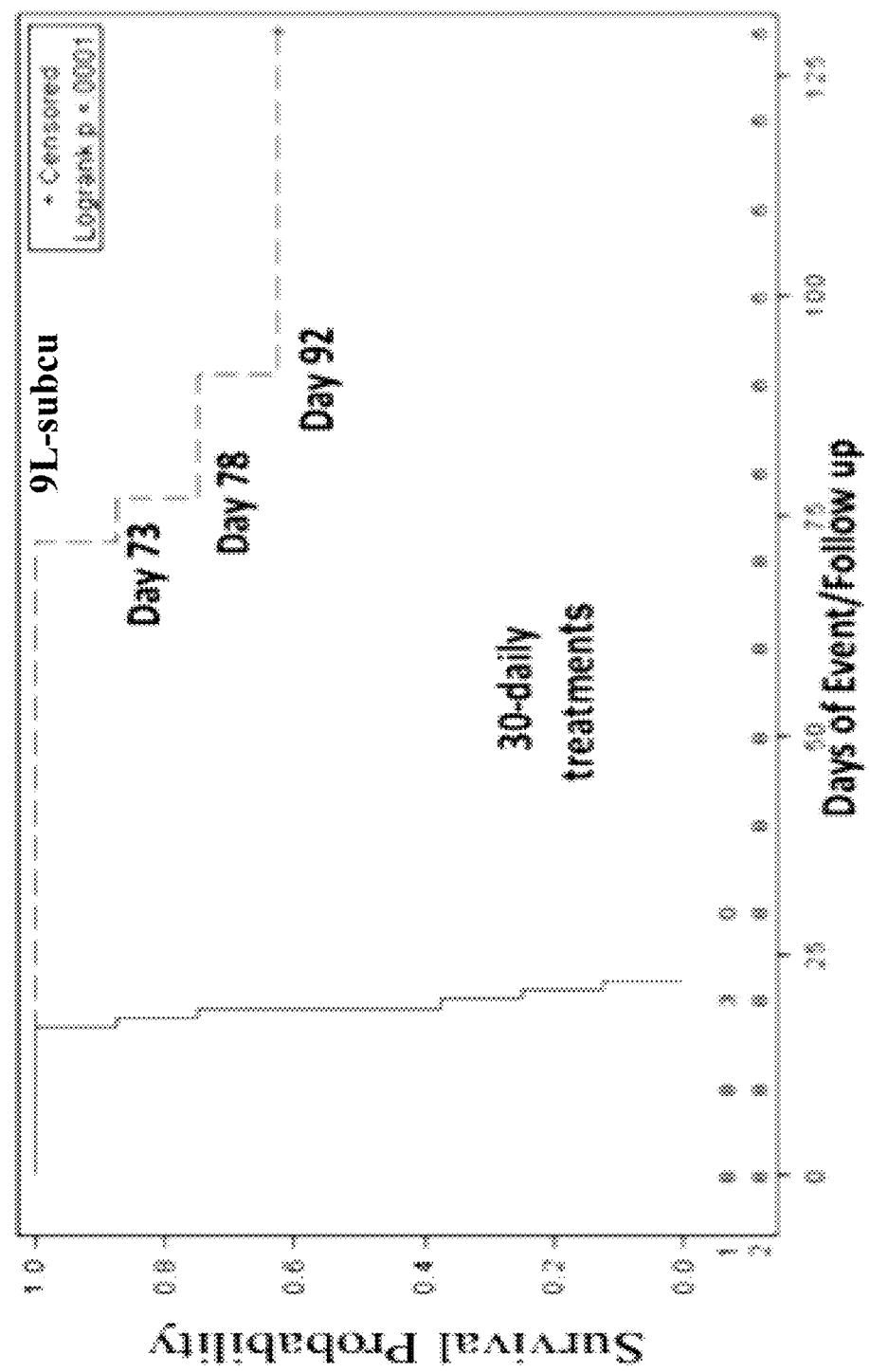
FIG. 7C is a Kaplan-Meier survival curve (130-days) of rats having subcutaneous 9L tumors treated with QQ-reagents in PBS (solid line, n=6; median survival=21 days) or QQ-SON proteins (dashed line, 10 μg/day, n=8; median survival=127 days) for 30 daily treatments, the endpoint is when tumor volume reaches 12 cm$^3$.

To determine the effect of QQ-SON protein treatment on the survival of the rats subcutaneously implanted with 9L-cells, at day 5 after 9L cell implantation rats were treated with QQ-reagents in PBS (n=8; median survival=21 days) or QQ-SON proteins (10 µg/day, n=8; median survival=127 days) for 30 daily treatments. Animals were sacrificed once they reached tumor burden (<12 cm$^3$). Kaplan-Meier survival curve (130-days) is shown in FIG. 7C. This data indicated that QQ-SON protein treatment significantly prolonged the survival of 9L-tumor bearing rats.

Example 22

QQ-SON Protein-Induced Cell Reprogramming Treatment of Tumors In Vivo

To generate orthotopic 4T1 breast cancer-bearing mice, 4T1 cells (2×10$^4$ cells/50 ml) were implanted into the #4 fat pads of 2-3 month old female BALB/c mice (20 grams). 4T1 breast tumors were observed at day 5-7 after cell implantation. The tumor volume and body weight of the mice were monitored every day. At day 25, the mice were sacrificed and the tumors were weighed. For the survival experiment, animals were sacrificed once they reached endpoints including tumor burden (<2 gram), metastasis causing labored breath, uncontrollable pain, etc.

Figures 7D, 7E:
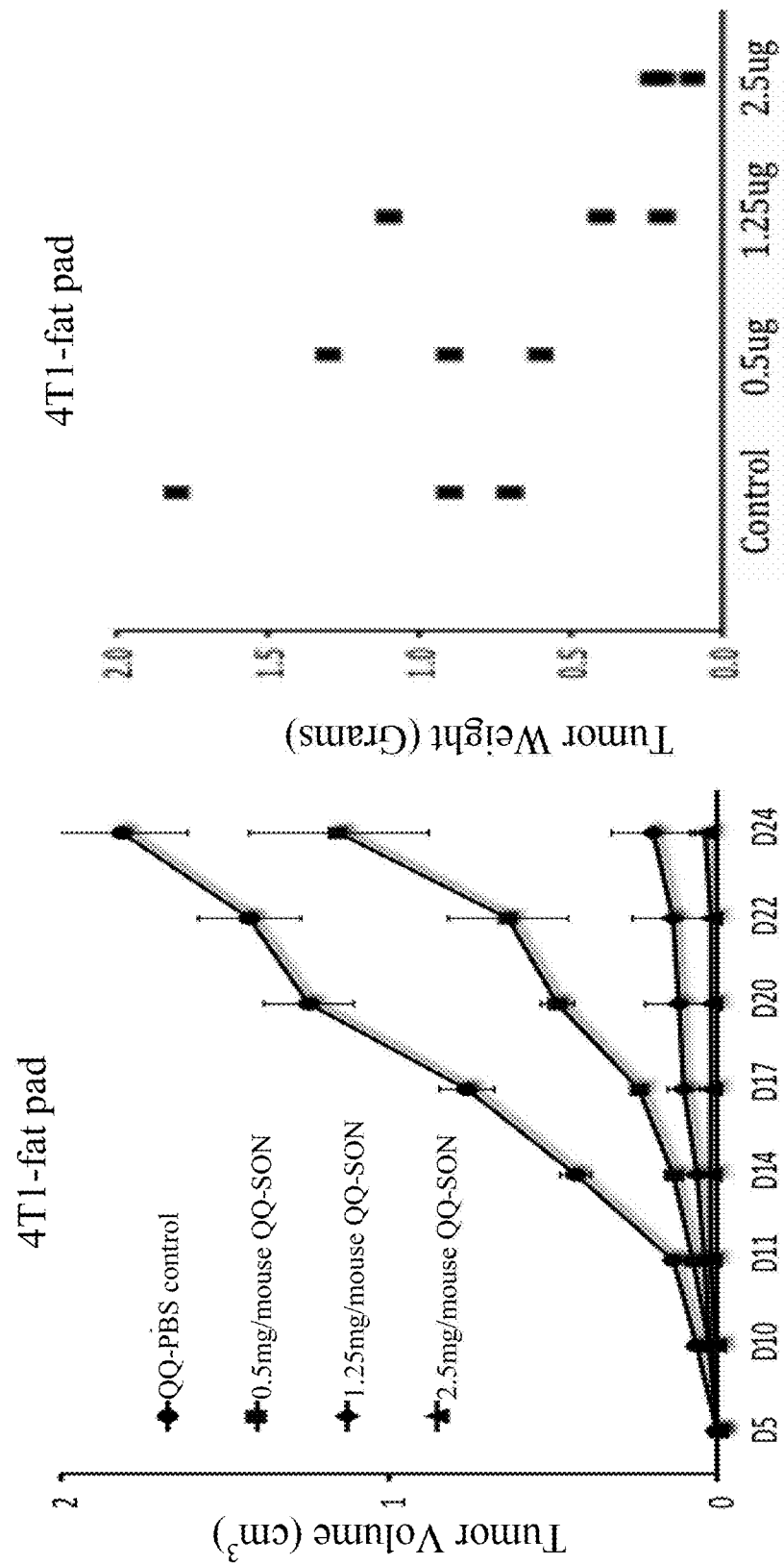
FIG. 7D is a graph showing effects of various QQ-SON protein dosages on 4T1-tumor growth monitored by tumor volume in the breast over a 25-day time course.
FIG. 7E is a graph showing effects of various QQ-SON protein dosages on 4T1-tumor weight in the breast at day 25.

Various dosages of QQ-SON proteins were administered, 0.5 µg QQ-modified SON proteins/mouse, 1.25 µg QQ-modified SON proteins/mouse, or 2.5 µg QQ-modified SON proteins/mouse, and compared with QQ-PBS control. Efficacy was determined by measurement of tumor volume over a 25-day time course, FIG. 7D, and measurement of tumor weight in grams, FIG. 7E, at day 25.

Figures 7F, 7G:
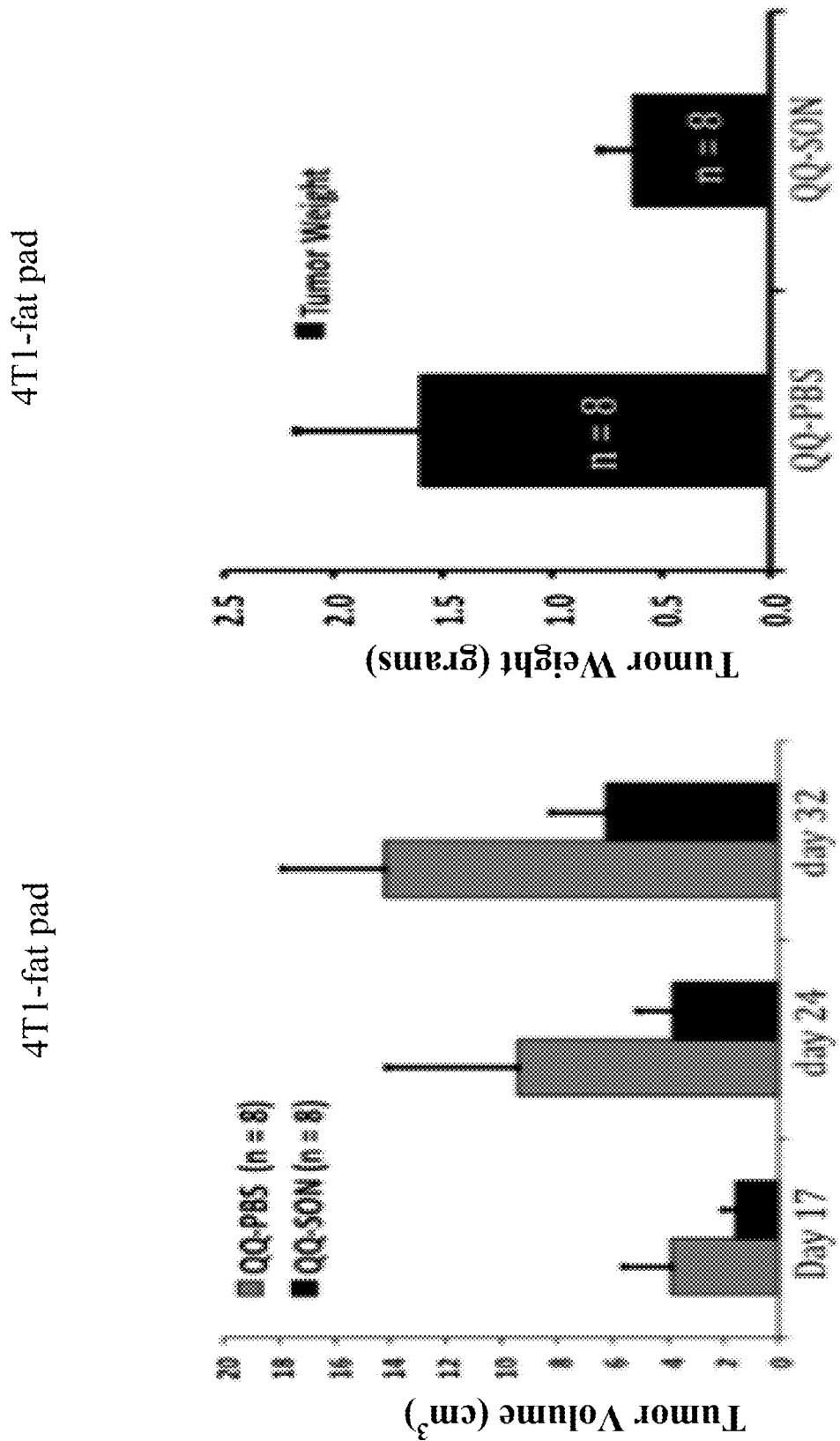
FIG. 7F is a graph showing changes of tumor volumes at different time points, determined by MRI imaging, of 4T1-tumor bearing mice treated either with QQ-SON proteins (n=8) or QQ-PBS as a control (n=8), showing major tumor stasis without primary tumor removal.
FIG. 7G is a graph showing tumor weight of 4T1-tumor bearing mice treated either with QQ-SON proteins (n=8) or QQ-PBS as the control (n=8) at day 35, showing major tumor stasis without primary tumor removal.
Figure 7H:
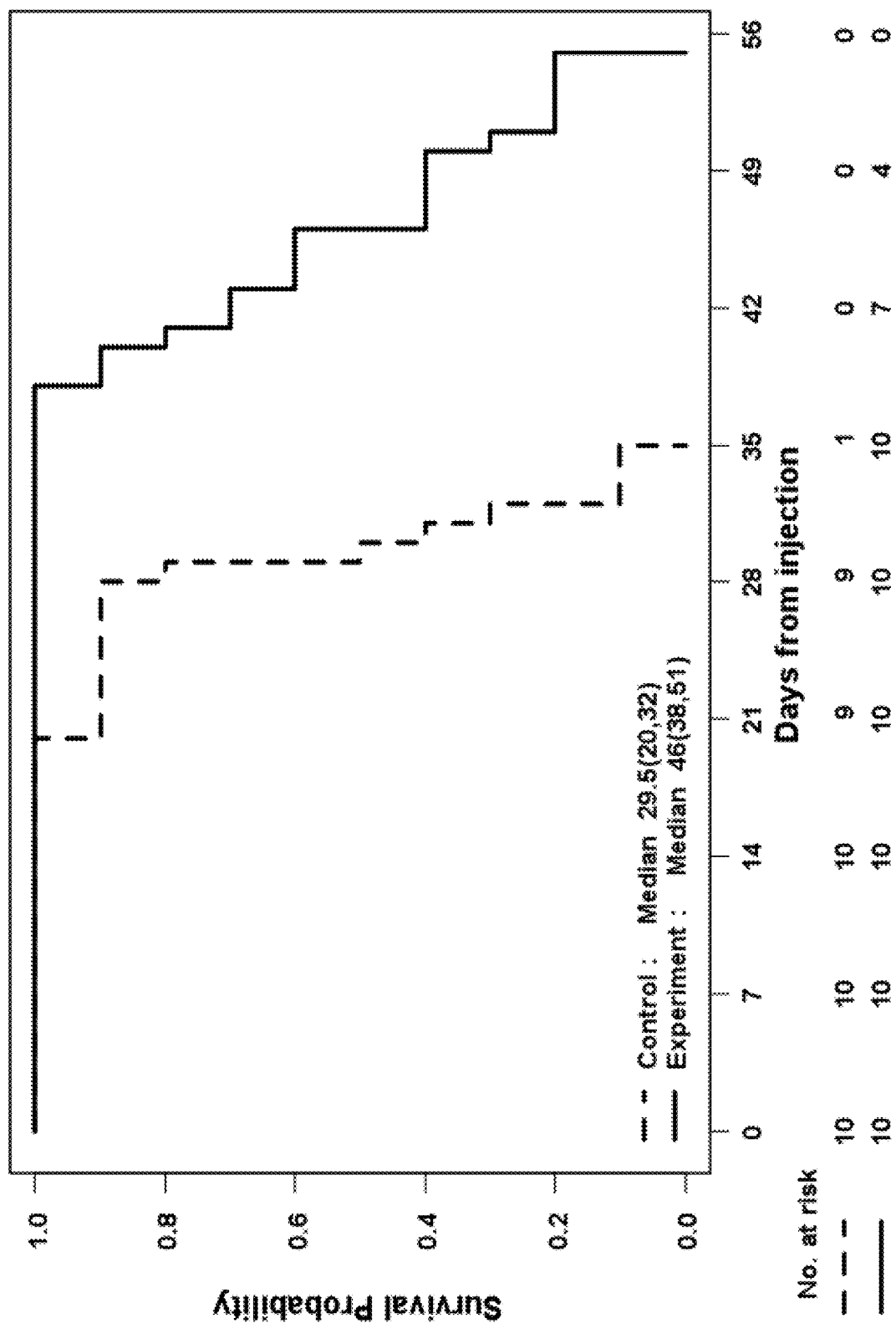
FIG. 7H is a Kaplan-Meier survival curve of 4T1-breast cancer bearing mice treated with QQ-PBS (Control, dotted line) and QQ-SON proteins (Treatment, solid line) during a 60-day survival experiment without primary 4T1 breast cancer removed as shown in FIG. 7H. The treatment started at day 5 after 4T1-cell implantation. Mice that met the endpoint, including tumor size burden, labored breath, uncontrollable pain, etc. were sacrificed.

In a further experiment, tumor volume of the mice treated either with QQ-SON proteins (n=8) or QQ-PBS as the control (n=8) during a 35-day time course was determined by MRI, see FIG. 7F, and tumor weights of both groups were determined by weighing at day 35, see FIG. 7G. QQ-SON protein treatment caused major tumor stasis without primary tumor removal.

Figure 7I:
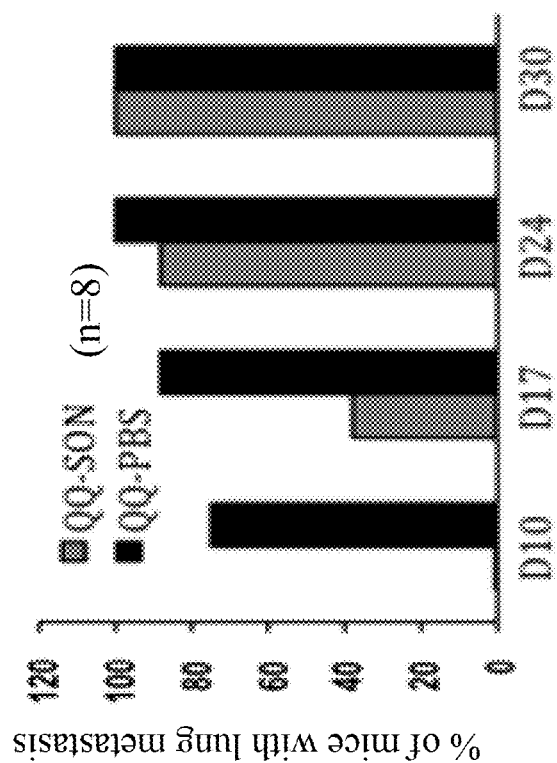
FIG. 7I is a graph showing the percentage of QQ-SON or QQ-PBS treated 4T1 tumor-bearing mice having metastatic lesions in the lung, without primary tumor removal, as observed by MRI at indicated days, indicating a major metastasis inhibition in the 4T1-bearing mice caused by QQ-SON protein treatment without primary tumor removal.
Figure 7J:
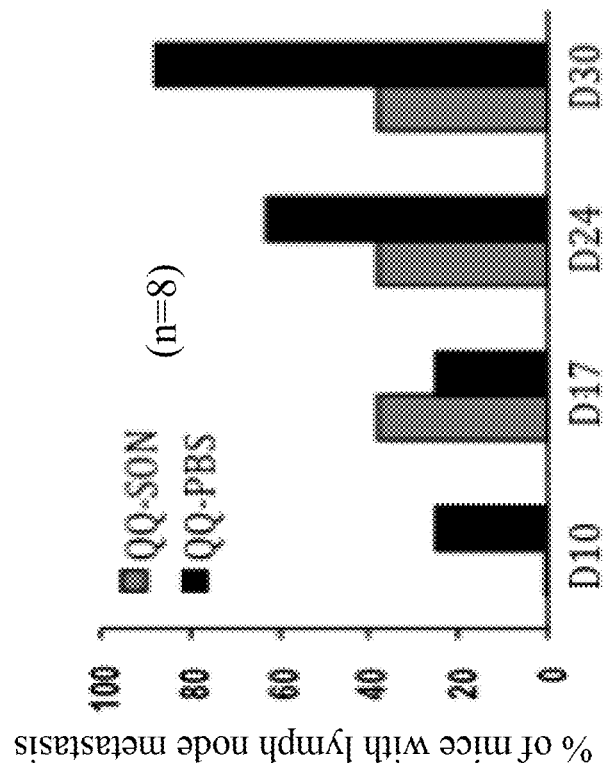
FIG. 7J is a graph showing the percentage of QQ-SON or QQ-PBS treated 4T1 tumor-bearing mice having metastatic lesions in lymph nodes, without primary tumor removal, as observed by MRI at indicated days, indicating a major metastasis inhibition in the 4T1-bearing mice caused by QQ-SON protein treatment without primary tumor removal.
Figure 7K:
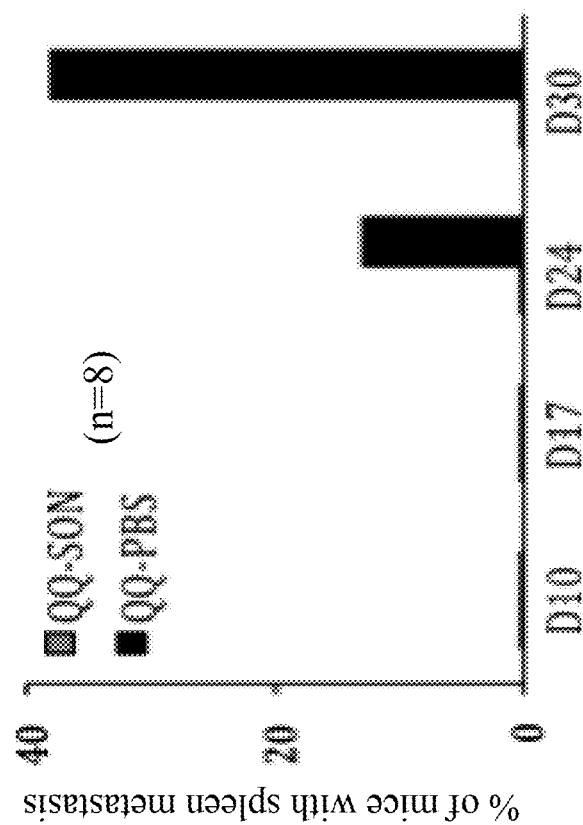
FIG. 7K is a graph showing the percentage of QQ-SON or QQ-PBS treated 4T1 tumor-bearing mice having metastatic lesions in the liver, without primary tumor removal, as observed by MRI at indicated days, indicating a major metastasis inhibition in the 4T1-bearing mice caused by QQ-SON protein treatment without primary tumor removal.
Figure 7L:
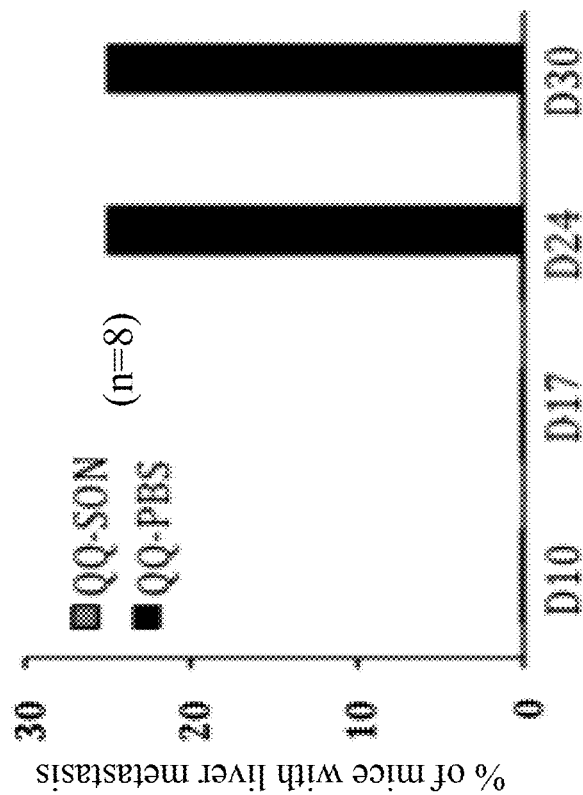
FIG. 7L is a graph showing the percentage of QQ-SON or QQ-PBS treated 4T1 tumor-bearing mice having metastatic lesions in the spleen, without primary tumor removal, as observed by MRI at indicated days, indicating a major metastasis inhibition in the 4T1-bearing mice caused by QQ-SON protein treatment without primary tumor removal.
Figure 7N:
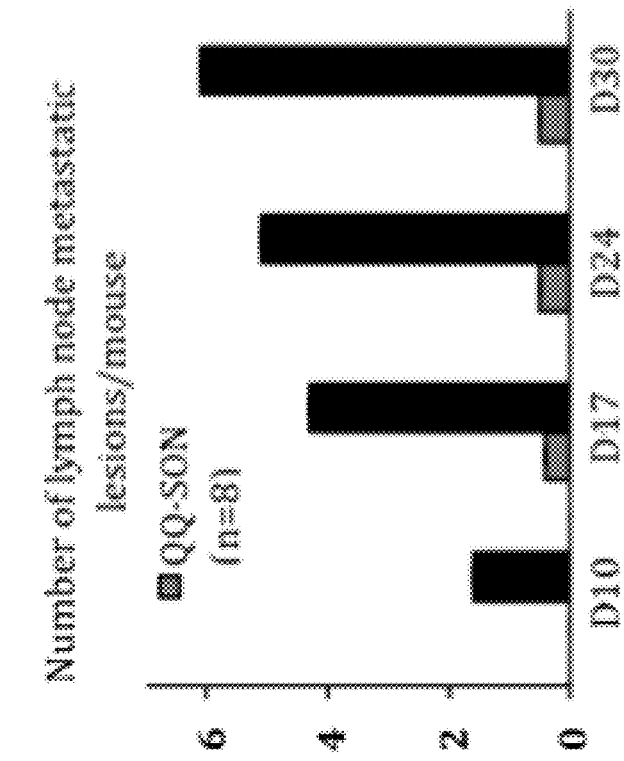
FIG. 7N is a graph showing the average number per mouse of QQ-SON or QQ-PBS treated 4T1 tumor-bearing mice having metastatic lesions in the lymph nodes, without primary tumor removal, as observed by MRI at indicated days, indicating a major metastasis inhibition in the 4T1-bearing mice caused by QQ-SON protein treatment without primary tumor removal.
Figure 7M:
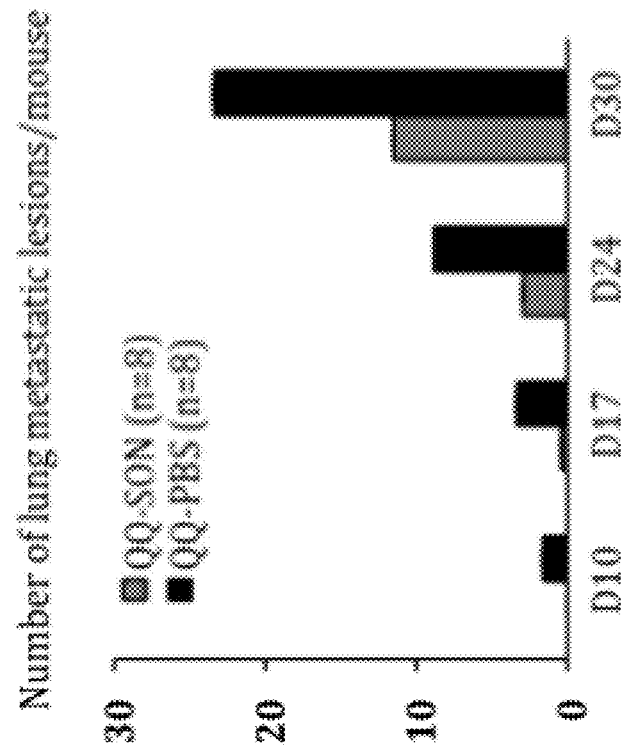
FIG. 7M is a graph showing the average number per mouse of QQ-SON or QQ-PBS treated 4T1 tumor-bearing mice having metastatic lesions in the lung, without primary tumor removal, as observed by MRI at indicated days, indicating a major metastasis inhibition in the 4T1-bearing mice caused by QQ-SON protein treatment without primary tumor removal.
Figure 7O:
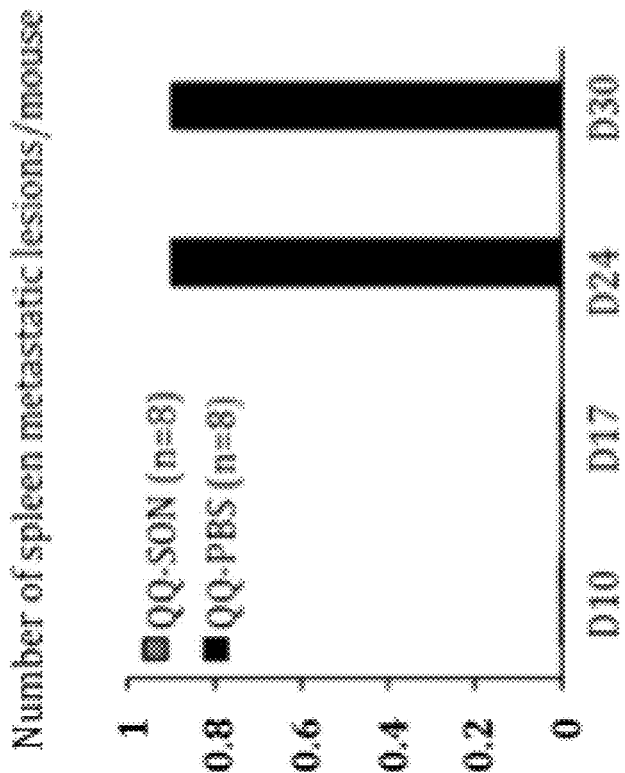
FIG. 7O is a graph showing the average number per mouse of QQ-SON or QQ-PBS treated 4T1 tumor-bearing mice having metastatic lesions in the liver, without primary tumor removal, as observed by MRI at indicated days, indicating a major metastasis inhibition in the 4T1-bearing mice caused by QQ-SON protein treatment without primary tumor removal.
Figure 7P:
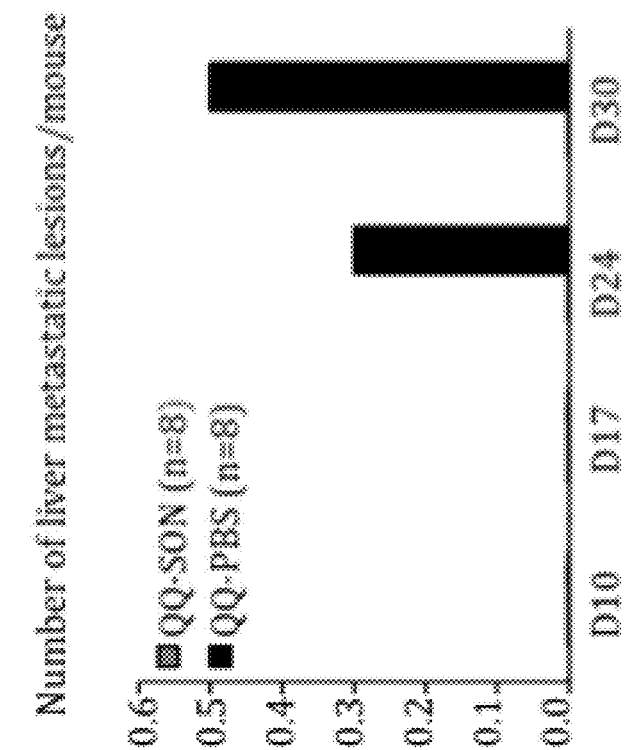
FIG. 7P is a graph showing the average number per mouse of QQ-SON or QQ-PBS treated 4T1 tumor-bearing mice having metastatic lesions in the spleen, without primary tumor removal, as observed by MRI at indicated days, indicating a major metastasis inhibition in the 4T1-bearing mice caused by QQ-SON protein treatment without primary tumor removal.

Mice were analyzed to determine number and percentage of metastases in the lung, FIGS. 7I and 7M, lymph nodes, FIGS. 7J and 7N, liver, FIGS. 7K and 7O, and spleen, FIGS. 7L and 7P, of the QQ-SON and QQ-PBS treated 4T1-bearing mice without primary tumor removal as observed by MRI at indicated days. These results demonstrate that, as compared to QQ-PBS treated mice, QQ-SON treated mice displayed metastasis at much later dates after 4T1-cell implantation and much less metastatic lesions in the lung, lymph nodes and no metastasis lesion was observed in the liver and spleen. This data indicates a major metastasis inhibition in the 4T1-bearing mice caused by QQ-SON protein treatment without primary tumor removal.

Example 23

Histological Analysis of the Tumor Tissue Sections Treated with QQ-PBS and QQ-SON Proteins without Primary Tumor Removed.

H&E stains of a 9L-tumor tissue slides of a rat treated with QQ-reagents in PBS buffer for 18 daily treatments, showing uniform tumor cells with extensive angiogenesis. Immunostains of a nearby tissue slide with anti-VE-cadherin antibody confirmed angiogenesis. This rat was sacrificed at day 26 after subcutaneous 9L cell implantation with a tumor of 13.5 cm$^3$ (around 15.5 g). In contrast. H&E stains of a tumor tissue slide of a rat treated with QQ-SON protein for 18 daily treatments showed different cell zones including tumor cell zone, connective tissue zone and fibroblast zone. This rat was sacrificed at day 49 after subcutaneous 9L cell implantation and its tumor was significantly reduced in size to 0.2 cm$^3$ (around 0.6 g). Immunostain of the fibroblast zone of a nearby tumor tissue slide of the same rat using an anti-a-procollagen, a fibroblast marker, antibody, confirmed the fibroblast zoon (positively stained) and tumor cell zone (negatively stained). Immunostains of the tumor tissue slides of the same rat treated with QQ-SON proteins for 18 daily treatments using anti-GFAP and anti-Tuj1 antibodies showed positive stains of both markers with neuronal cell morphology and neural rosette formation. This data indicates that the injected QQ-SON proteins induced in situ generation of transient 9L-piPSCs that differentiate into non-cancerous cells including neuronal lineage cells.

Similarly, H&E stains of 4T1-tumor tissue slides of the mice treated with QQ-SON protein also showed adipocytes and mammary duct, which were immunostained positive with adiponectin and cytokaratin 5/8/14, indicating that the injected QQ-SON protein also induced in situ 4T1-tumor cell reprogramming inside the primary tumor into 4T1-piPSCs that differentiate into breast tissue.

Example 24

QQ-SON Treatment Significantly Enhances the Genome Stability of the Treated 9L-Cells In Vivo.

SKY genome analysis of explanted cells of two subcutaneous 9L-tumor-bearing rats, both treated with QQ-SON protein for 18-days was performed. One rat (#12) displayed major response to the QQ-SON treatment and tumor started to shrink. Before the tumor disappeared, this rat was sacrificed and the tumor collected for both explants and tumor tissue slides. Another rat (#15) displayed no response to the QQ-SON protein treatment and tumor continued to grow to reach the ending point (>12 cm$^3$). This rat was also sacrificed and explants and tumor tissue slides were prepared.

The cells from the explant of #15 rat grew rapidly and reached confluency in 3-days. The cells displayed typical 9L-cell spindle morphology. However, the cells from the explant of #12 rat grew very slowly and only two-weeks later some cells with neural morphology with some colonies were observed. Immunostains of the tumor tissue slides with GFAP and Tuj I showed positive stains for both markers for those cells that displayed neural morphology in #12 rat, but negative stains for these two markers for #15 rat. Additional immunostains with β-catenin, CK5/6, E-cadherin, Lefty, Nodal and Cripto-1 showed opposite results for #12 and #15 rats. While the tumor tissue slides of #12 rat showed positive stains of CK5/6, E-cadherin, Lefty and β-catenin, a negative stain was observed in the tumor tissue slides of #15 rat. Interestingly, Lefty and E-cadherin co-stained in the same areas of the tumor tissue sections as well as CK5/6 and E-cadherin. In contrast, the tumor tissue slides of #15 rat showed positive stains for Nodal and Cripto-1, but those tissue sections of #12 showed negative stains for these two markers. These results indicate tumor cell conversion into non-cancerous cells in the tissue section of #12 rat, whereas the tissue sections of #15 rat remained 9L-tumor cells.

To assess genome stability of the explant cells, molecular cytogenetic analyses were performed. 20 mitotic images were collected for each explant of rat #15 and rat #12 and the average number of chromosomes for rat #15 and for rat #12 were analyzed. Table 4 shows a comparison of chromosomal aberrations of rat #15 and rat #12. Molecular cytogenetic analyses indicated 35% non-clonal chromosomal aberrations (NCCAs) and 20% of clonal chromosomal aberrations (CCAs) for rat #12 and 70% NCCAs and 15% CCAs for rat #15 (Table 4). Since the frequencies of NCCAs represent the level of genome instability while CCAs represent relative stability, these data suggest that the tumor that did not respond to QQ-SON protein treatment (rat #15) displayed higher levels of genome heterogeneity than those of the tumor (rat #12) that showed a good response to the QQ-SON treatment. This result indicates that the protein-induced in situ cell reprogramming significantly enhances genome stability of the treated cancer cells, indicating cell conversion of malignant cancer cells into non-cancerous cells.

TABLE 4 tumors that respond to the QQ-SON protein treatment (#12) display higher genome stability than a tumor that did not respond (#15); NCCA: non-clonal chromosomal aberrations; CCA: clonal chromosomal aberrations

| Rat | #mitotic images | # chromosomes | # NCCAs | % NCCAs | # CCAs | % CCAs |
|---|---|---|---|---|---|---|
| #12 | 20 | 64 | 7 | 35 | 4 | 20 |
| #15 | 20 | 60 | 14 | 70 | 3 | 15 |

Example 25

QQ-SON induced cell-converting cancer therapy mediated by protein-induced in situ cell reprogramming caused cancer cure of subcutaneous 9L-tumor bearing rats and late stage 4T1-bearing mice after surgical removal of primary tumors.

Subcutaneous implantation of 9L-cells into Fisher rats was performed to generate tumor-bearing rats. Five days after tumor cell implantation, daily intratumor injections of QQ-modified SON (QQ-SON) proteins were performed. A proper control of QQ-reagents in PBS (QQ-PBS) was also performed. A 90-day survival experiment was performed following a 18 daily intratumoral treatment regimen using QQ-SON proteins at 10 μg/mouse/day. During treatments, significantly reduced tumor growth in all treated rats was observed. After 18 daily treatments, 50% of the treated rats displayed diminished tumor volume over time, and no palpable tumor was present in these animals. The remaining treated rats displayed significantly slower tumor growth. The median survival of the treated group was 49±20 days (n=8) whereas survival in the control group was 21±4 days (n=6). Tumor recurrence was observed in three treated rats at day 32, 43 and 62, with a median recurrence of 45±13 days. The recurrent tumors grew very aggressively and reached a volume of >12 cm³ in 5-7 days (Table 5, Treatment 1). The fourth glioma-cured rat remained tumor-free for more than 30 months without evidence of teratoma formation.

When the daily intratumor treatment regimen was expanded to 30 days, 100% glioma-cured rats within the first 73 days during a 400-day survival experiment (n=8) were obtained. Again, tumor recurrence for three treated rats at day 73, 78, and 92 (median recurrence: 81±8 days) was observed, which was much later than the tumor recurrence observed in rats treated for only 18 days. The remaining 5 rats remained tumor-free for 400-days. The three rats with recurrent tumors were treated for an additional 30 days (daily intra-tumor injection, 10 μg/day QQ-SON). Of the three rats, two had very slow progression and survived for an additional 66 days (tumor occurrence on day 78) or 68 days (tumor reoccurrence on day 92). Only one rat displayed slow tumor growth and was sacrificed at day 109 (36 days after tumor recurrence was identified) when the tumor reached 12 cm³ in volume. The median survival of the treated rats was 280±155 days (n=8) compared to 21±4 days for the control group (n=6) (Table 5, Treatment 2).

To ensure that this result was reproducible, the above 30 daily treatment experiment was repeated and achieved 80% glioma-cured rats within the first 79-days. Two rats displayed slow tumor growth but had reached a tumor volume of 12 cm³ at day 29 and 48, respectively (Table 5, Treatment 3). However, two glioma-cured rats displayed tumor recurrence at day 79 and 111 (median recurrence: 95±16 days). These two rats were treated with the QQ-SON proteins (10 mg/day) for an additional 30 days. One of the two rats displayed a slow tumor growth and reached a volume of 12 cm³ in 30 days after the tumor recurred on day 79. The other rat survived for an additional 69-days. The median survival of the treated rats was 276±156 days (n=10), whereas the control rats treated with QQ-PBS only survived for 23±3 days after tumor implantation (n=6). The tumor-cured rats from both treatments 2 and 3 survived for more than 15-months so far without tumor recurrence and without teratoma formation.

TABLE 5

| Group | # of Rats | # injections | 9L-Glioma Cured (%) | Mean Survival (Day) | Mean Recurrence (day/Recurrence %) | Recurrence day |
|---|---|---|---|---|---|---|
| Control | 6 | 18 or 30 (QQ-PBS) | 0 | 21 ± 4 | — | — |
| Treatment 1 | 8 | 18 (QQ-SON) | 13 (90 day survival) | 49 ± 20 | 45 ± 13/37.5 | 32/42/62 |
| Treatment 2 | 8 | 30 (QQ-SON) | 70 (400 day survival) | 280 ± 155 | 81 ± 8/30 | 72/78/92 |
| Treatment 3 | 10 | 30 (QQ-SON) | 60 (400 day survival) | 276 ± 156 | 95 ± 16/20 | 79/111 |

A similar result was observed for late stage of 4T1-breast cancer bearing mice after surgical removal of the primary tumors at day 18 after 4T1-cell implantation for both QQ-PBS and QQ-SON treated mice. The daily intra-tumor QQ-SON protein treatment was performed at day 5 and continued for 40-days. Previously, it was shown that lung metastasis started at day 7. At day 18, MRI observable lung metastatic lesions for every mouse were observed. A 250-day survival experiment was performed. The resultant data, Table 6, indicated that while the QQ-PBS control mice died between days 25-47, the QQ-SON treated mice survived much longer and 61% (n=11) of QQ-SON treated mice survived entire 250-days without tumor recurrence and teratoma formation (n=18), see FIG. 8. MRI results showed disappearance of lung metastatic lesions. These data demonstrate high treatment efficacy of this QQ-SON-induced cell-converting cancer therapy.

TABLE 6

| Mice | Group | Tumor size at surgery (mm³) | Primary Tumor Recurrence | Day detecting lung lesion | Day of lung lesions disappeared or cause of death | Survival Day | Alive Oct. 23, 2014) |
|---|---|---|---|---|---|---|---|
| Red 1 | Control | 114 | No | 16 | Metastasis | 46 | |
| Red 2 | Control | 125 | No | 16 | Metastasis | 46 | |
| Red 3 | Control | 60.5 | No | 16 | Metastasis | 44 | |
| Red 4 | Control | 25.5 | No | 16 | Metastasis | 44 | |
| Blue 1 | Treatment | 6.5 | No | 16 | Inflammation | 47 | |
| Blue 2 | Treatment | 20.5 | No | 16 | Stasis | | 110 |
| Blue 3 | Treatment | 3.5 | No | 16 | 74 | | 267 |
| Blue 4 | Treatment | 60.5 | No | 16 | Metastasis | 49 | |
| Blue 5 | Treatment | 33.5 | No | 16 | 59 | | 267 |
| Green 1 | Treatment | 20 | No | 16 | 60 | | 267 |
| Green 2 | Treatment | 18.5 | No | 16 | Inflammation | 75 | |
| Green 3 | Treatment | 15.5 | No | 16 | 60 | | 267 |
| Green 4 | Treatment | 54 | No | 16 | Metastasis position | 45 | |
| Green 5 | Treatment | 53 | No | 16 | Inflammation | 54 | |

Figure 8:
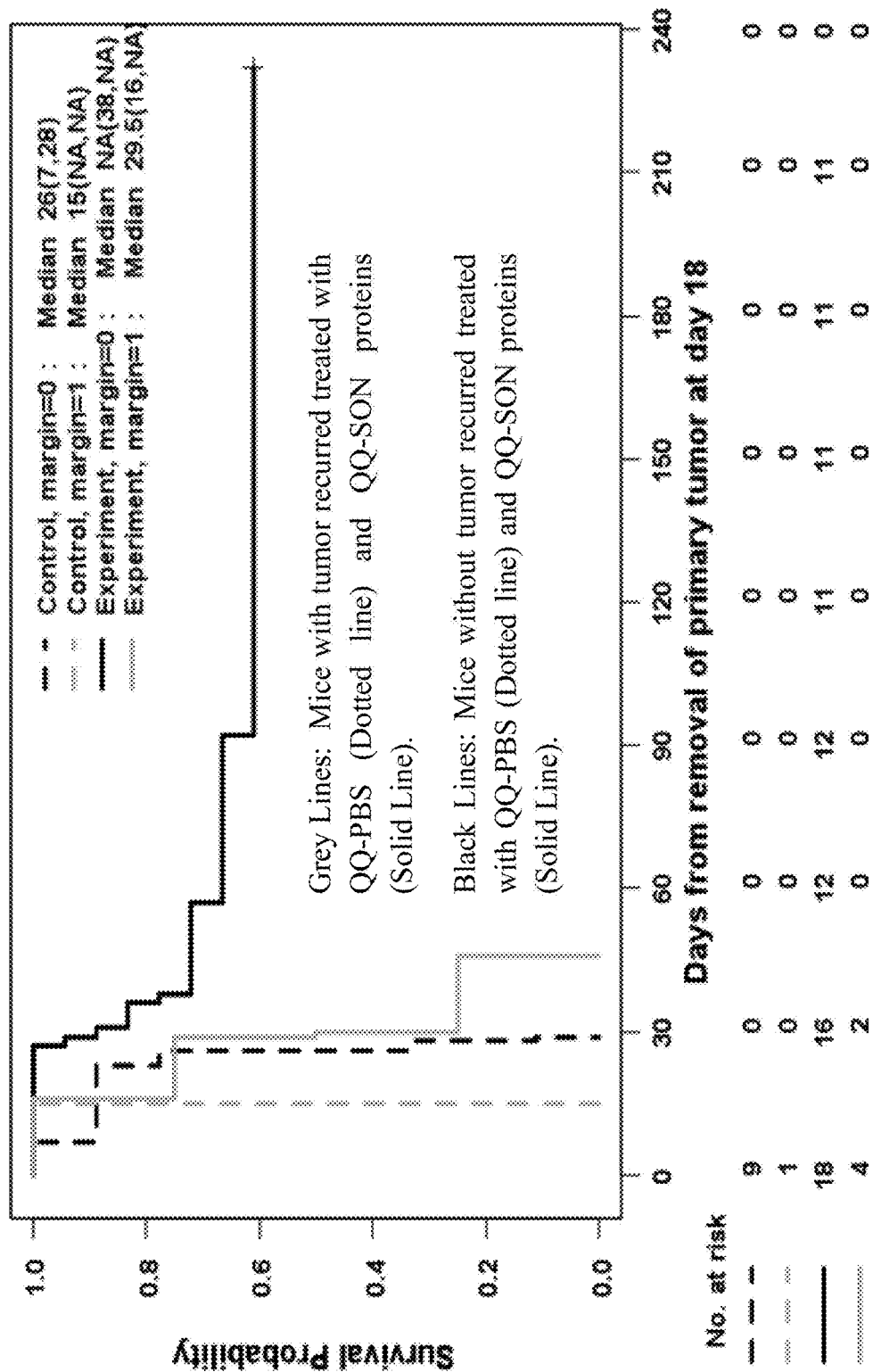
FIG. 8 is a Kaplan-Meier survival curve (250-day survival) of 4T1-breast cancer bearing mice after surgical removal of the primary 4T1-breast cancer at day 18 and QQ-SON protein treatment started at day 6.

FIG. 8 is a Kaplan-Meier survival curve (250-day survival) of 4T1-breast cancer bearing mice after surgical removal of the primary 4T1-breast cancer at day 18. These 4T1 breast cancer bearing mice were treated with QQ-PBS (Control) and QQ-SON proteins (Treatment) at day 6 after 4T1-cell implantation into the 1 fat pad of female BALB/c mice. The primary tumors were palpable around day 5 and surgically removed at day 18. The QQ-PBS/QQ-SON treatment was performed daily by both intra-tumoral (5 μg/mouse/day) and intraperitoneal injections (25 μg/mouse/day).

Day 0 in the Kaplan-Meier survival curve of FIG. 8 is the day when the surgery was performed at day 18. A small population of mice displayed tumor recurrence due to incomplete tumor removal. These mice were treated with QQ-SON protein or QQ-PBS via intra-tumoral injections and their survival were also compared (dotted survival curves). For those mice without tumor recurrence, their survival curves are shown in solid lines. Mice that survived for this entire 250-day survival experiment without tumor recurrence are considered tumor-cured mice. Tumor-cure has been achieved in 61% of population of treated mice.

Thus, QQ-SON-induced in situ cell reprogramming of the cancer cells inside the tumor to generate transient piPSCs that differentiate into different non-cancerous cells within that tissue is demonstrated. The types of the differentiated non-cancerous cells depend on specific tissue environment. This inter-play between QQ-SON-induced in situ cell reprogramming and tissue environment induced differentiation precisely regulates generation of transient piPSCs inside tumor and induced differentiation, preventing tumor and teratoma formation. This safe protein-induced in situ cell reprogramming technology in situ generates stem cells and which then differentiate into normal cells induced by tissue environment to replace diseased cells for treatment of many diseases and injuries.

```
Sequences
Homo sapiens SRY (sex determining region Y)-box 2 (SOX2)
(NM_00106) SEQ ID NO: 1 (protein) and SEQ ID NO: 65 (DNA)
                                                           (SEQ ID NO: 1)
MYNMMETELKPPGPQQTSGGGGGNSTAAAAGGNQKNSPDRVKRPMNAFMVWSRGQRRKMAQENPK

MHNSEISKRLGAEWKLLSETEKRPFIDEAKRLRALHMKEHPDYKYRPRRKTKTLMKKDKYTLPGG

LLAPGGNSMASGVGVGAGLGAGVNQRMDSYAHMNGWSNGSYSMMQDQLGYPQHPGLNAHGAAQMQ

PMHRYDVSALQYNSMTSSQTYMNGSPTYSMSYSQQGTPGMALGSMGSVVKSEASSSPPVVTSSSH

SRAPCQAGDLRDMISMYLPGAEVPEPAAPSRLHMSQHYQSGPVPGTAINGTLPLSHM (SEQ ID NO: 65)
                   atgtacaacatgatggagacggagctgaagccgccgggcccgcagcaaacttcggggggcggcgg cggcaactccaccgcggcggcggccggcggcaaccagaaaaacagcccggaccgcgtcaagcggc ccatgaatgccttcatggtgtggtcccgcgggcagcggcgcaagatggcccaggagaacccaag atgcacaactcggagatcagcaagcgcctgggcgccgagtggaaacttttgtcggagacggagaa gcggccgttcatcgacgaggctaagcggctgcgagcgctgcacatgaaggagcacccggattata
```

-continued

```
aataccggccccggcggaaaaccaagacgctcatgaagaaggataagtacacgctgcccggcggg ctgctggccccggcggcaatagcatggcgagcgggtcggggtgggcgccggcctgggcgcggg cgtgaaccagcgcatggacagttacgcgcacatgaacggctggagcaacggcagctacagcatga tgcaggaccagctgggctaccgcagcacccgggcctcaatgcgcacggcgcagcgcagatgcag cccatgcaccgctacgacgtgagcgccctgcagtacaactccatgaccagctcgcagacctacat gaacggctcgcccacctacagcatgtcctactcgcagcagggcacccctggcatggctcttggct ccatgggttcggtggtcaagtccgaggccagctccagccccctgtggttacctcttcctcccac tccagggcgccctgccaggccggggacctccgggacatgatcagcatgtatctccccggcgccga ggtgccggaacccgccgccccagcagacttcacatgtcccagcactaccagagcggcccggtgc ccggcacggccattaacggcacactgcccctctcacacatgtga
```

*Homo sapiens* POU class 5 homeobox 1 (POU5F1) also known as Oct4
(NM_002701) SEQ ID NO: 2 (protein) and SEQ ID NO: 66 (DNA)

(SEQ ID NO: 2)
MAGHLASDFAFSPPPGGGGDGPGGPEPGWVDPRTWLSFQGPPGGPGIGPGVGPGSEVWGIPPCPP

PYEFCGGMAYCGPQVGVGLVPQGGLETSQPEGEAGVGVESNSDGASPEPCTVTPGAVKLEKEKLE

QNPEESQDIKALQKELEQFAKLLKQKRITLGYTQADVGLTLGVLFGKVFSQTTICRFEALQLSFK

NMCKLRPLLQKWVEEADNNENLQEICKAETLVQARKRKRTSIENRVRGNLENLFLQCPKPTLQQI

SHIAQQLGLEKDVVRVWFCNRRQKGKRSSSDYAQREDFEAAGSPFSGGPVSFPLAPGPHFGTPGY

GSPHFTALYSSVPFPEGEAFPPVSVTTLGSPMHSN (SEQ ID NO: 66)
```
atggcgggacacctggcttcggatttcgccttctcgccccctccaggtggtggaggtgatgggcc agggggggccggagccgggctggttgatcctcggacctggctaagcttccaaggccctcctggag ggccaggaatcgggccgggggttgggccaggctctgaggtgtgggggattcccccatgccccccg ccgtatgagttctgtggggggatggcgtactgtgggcccaggttggagtggggctagtgcccca aggcggcttggagacctctcagcctgagggcgaagcaggagtcggggtggagagcaactccgatg gggcctccccggagccctgcaccgtcacccctggtgccgtgaagctggagaaggagaagctggag caaaacccggaggagtcccaggacatcaaagctctgcagaaagaactcgagcaatttgccaagct cctgaagcagaagaggatcaccctgggatatacacaggccgatgtggggctcaccctgggggttc tatttgggaaggtattcagccaaacgaccatctgccgctttgaggctctgcagcttagcttcaag aacatgtgtaagctgcggcccttgctgcagaagtgggtggaggaagctgacaacaatgaaaatct tcaggagatatgcaaagcagaaaccctcgtgcaggcccgaaagagaaagcgaaccagtatcgaga accgagtgagaggcaacctggagaatttgttcctgcagtgcccgaaacccacactgcagcagatc agccacatcgcccagcagcttgggctcgagaaggatgtggtccgagtgtggttctgtaaccggcg ccagaagggcaagcgatcaagcagcgactatgcacaacgagaggattttgaggctgctgggtctc ctttctcaggggggaccagtgtcctttcctctggccccagggcccattttggtaccccaggctat gggagccctcacttcactgcactgtactcctcggtccctttccctgaggggaagcctttccccc tgtctccgtcaccactctgggctctcccatgcattcaaactga
```

*Homo sapiens* Nanog homeobox (NANOG) (NM_024865) SEQ ID NO: 3
(protein) and SEQ ID NO: 67 (DNA)

(SEQ ID NO: 3)
MSVDPACPQSLPCFEASDCKESSPMPVICGPEENYPSLQMSSAEMPHTETVSPLPSSMDLLIQDS

PDSSTSPKGKQPTSAEKSVAKKEDKVPVKKQKTRTVFSSTQLCVLNDRFQRQKYLSLQQMQELSN

ILNLSYKQVKTWFQNQRMKSKRWQKNNWPKNSNGVTQKASAPTYPSLYSSYHQGCLVNPTGNLPM

WSNQTWNNSTWSNQTQNIQSWSNHSWNTQTWCTQSWNNQAWNSPFYNCGEESLQSCMQFQPNSPA

-continued

SDLEAALEAAGEGLNVIQQTTRYFSTPQTMDLFLNYSMNMQPEDV (SEQ ID NO: 67)
atgagtgtggatccagcttgtccccaaagcttgccttgctttgaagcatccgactgtaaagaatc
ttcacctatgcctgtgatttgtgggcctgaagaaaactatccatccttgcaaatgtcttctgctg
agatgcctcacacggagactgtctctcctcttccttcctccatggatctgcttattcaggacagc
cctgattcttccaccagtcccaaaggcaaacaacccacttctgcagagaagagtgtcgcaaaaaa
ggaagacaaggtcccggtcaagaaacagaagaccagaactgtgttctcttccacccagctgtgtg
tactcaatgatagatttcagagacagaaatacctcagcctccagcagatgcaagaactctccaac
atcctgaacctcagctacaaacaggtgaagacctggttccagaaccagagaatgaaatctaagag
gtggcagaaaaacaactggccgaagaatagcaatggtgtgacgcagaaggcctcagcacctacct
accccagcctttactcttcctaccaccagggatgcctggtgaacccgactgggaaccttccaatg
tggagcaaccagacctggaacaattcaacctggagcaaccagacccagaacatccagtcctggag
caaccactcctggaacactcagacctggtgcacccaatcctggaacaatcaggcctggaacagtc
ccttctataactgtggagaggaatctctgcagtcctgcatgcagttccagccaaattctcctgcc
agtgacttggaggctgccttggaagctgctggggaaggccttaatgtaatacagcagaccactag
gtatttagtactccacaaaccatggatttattcctaaactactccatgaacatgcaacctgaag
acgtgtga Homo sapiens lin-28 homolog A (C. elegans) (LIN28A)
(NM_024674) SEQ ID NO: 4 (protein) and SEQ ID NO: 68 (DNA)

(SEQ ID NO: 4)
MGSVSNQQFAGGCAKAAEEAPEEAPEDAARAADEPQLLHGAGICKWFNVRMGFGFLSMTARAGVA

LDPPVDVFVHQSKLHMEGFRSLKEGEAVEFTFKKSAKGLESIRVTGPGGVFCIGSERRPKGKSMQ

KRRSKGDRCYNCGGLDHHAKECKLPPQPKKCHFCQSISHMVASCPLKAQQGPSAQGKPTYFREEE

EEIHSPTLLPEAQN (SEQ ID NO: 68)
atgggctccgtgtccaaccagcagtttgcaggtggctgcgccaaggcggcagaagaggcgccga
ggaggcgccggaggacgcggcccgggcggcggacgagcctcagctgctgcacggtgcgggcatct
gtaagtggttcaacgtgcgcatggggttcggcttcctgtccatgaccgcccgcgccggggtcgcg
ctcgaccccccagtggatgtctttgtgcaccagagtaagctgcacatggaagggttccggagctt
gaaggagggtgaggcagtggagttcacctttaagaagtcagccaagggtctggaatccatccgtg
tcaccggacctggtggagtattctgtattgggagtgagaggcggccaaaaggaaagagcatgcag
aagcgcagatcaaaggagacaggtgctacaactgtggaggtctagatcatcatgccaaggaatg
caagctgccaccccagcccaagaagtgccacttctgccagagcatcagccatatggtagcctcat
gtccgctgaaggcccagcagggccctagtgcacagggaaagccaacctactttcgagaggaagaa
gaagaaatccacagccctaccctgctcccggaggcacagaattga Homo sapiens Krueppel-like factor 4 (Klf4) (NP_004226)
SEQ ID NO: 5 (protein) and SEQ ID NO: 69 (DNA)

(SEQ ID NO: 5)
MRQPPGESDMAVSDALLPSFSTFASGPAGREKTLRQAGAPNNRWREELSHMKRLPPVLPGRPYDL

AAATVATDLESGGAGAACGGSNLAPLPRRETEEFNDLLDLDFILSNSLTHPPESVAATVSSSASA

SSSSSPSSSGPASAPSTCSFTYPIRAGNDPGVAPGGTGGGLLYGRESAPPPTAPFNLADINDVSP

SGGFVAELLRPELDPVYIPPQQPQPPGGGLMGKFVLKASLSAPGSEYGSPSVISVSKGSPDGSHP

VVVAPYNGGPPRTCPKIKQEAVSSCTHLGAGPPLSNGHRPAAHDFPLGRQLPSRTTPTLGLEEVL

SSRDCHPALPLPPGFHPHPGPNYPSFLPDQMPQPVPPLHYQELMPPGSCMPEEPKPKRGRRSWPR

-continued

KRTATHTCDYAGCGKTYTKSSHLKAHLRTHTGEKPYHCDWDGCGWKFARSDELTRHYRKHTGHRP

FQCQKCDRAFSRSDHLALHMKRHF (SEQ ID NO: 69)
atgaggcagccacctggcgagtctgacatggctgtcagcgacgcgctgctcccatctttctccac gttcgcgtctggcccggcgggaagggagaagacactgcgtcaagcaggtgccccgaataaccgct ggcgggaggagctctcccacatgaagcgacttcccccagtgcttccggccgcccctatgacctg gcggcggcgaccgtggccacagacctggagagcggcggagccggtgcggcttgcggcggtagcaa cctggcgcccctacctcggagagagaccgaggagttcaacgatctcctggacctggactttattc tctccaattcgctgacccatcctccggagtcagtggccgccaccgtgtcctcgtcagcgtcagcc tcctcttcgtcgtcgccgtcgagcagcggccctgccagcgcgccctccacctgcagcttaccta tccgatccgggccgggaacgacccgggcgtggcgccgggcggcacgggcggaggcctcctctatg gcagggagtccgctccccctccgacggctcccttcaacctggcggacatcaacgacgtgagcccc tcgggcggcttcgtggccgagctcctgcggccagaattggaccggtgtacattccgccgcagca gccgcagccgccaggtggcgggctgatgggcaagttcgtgctgaaggcgtcgctgagcgccctg gcagcgagtacggcagcccgtcggtcatcagcgtcagcaaaggcagccctgacggcagccacccg gtggtggtggcgccctacaacggcgggccgccgcgcacgtgccccaagatcaagcaggaggcggt ctcttcgtgcacccacttgggcgctggaccccctctcagcaatggccaccggccggctgcacacg acttcccctggggcggcagctcccagcaggactaccccgaccctgggtcttgaggaagtgctg agcagcagggactgtcaccctgccctgccgcttcctcccggcttccatcccacccggggcccaa ttacccatccttcctgcccgatcagatgcagccgcaagtccgccgctccattaccaagagctca tgccacccggttcctgcatgccagaggagcccaagccaaagaggggaagacgatcgtggccccgg aaaaggaccgccacccacacttgtgattacgcgggctgcggcaaaacctacacaaagagttccca tctcaaggcacacctgcgaacccacacaggtgagaaaccttaccactgtgactgggacggctgtg gatggaaattcgcccgctcagatgaactgaccaggcactaccgtaaacacacggggcaccgcccg ttccagtgccaaaaatgcgaccgagcattttccaggtcggaccacctcgccttacacatgaagag gcattttttaa Homo sapiens c-MYC (NP_002458) SEQ ID NO: 6 (protein) and
SEQ ID NO: 70 (DNA)

(SEQ ID NO: 6)
MDFFRVVENQQPPATMPLNVSFTNRNYDLDYDSVQPYFYCDEEENFYQQQQQSELQPPAPSEDIW

KKFELLPTPPLSPSRRSGLCSPSYVAVTPFSLRGDNDGGGGSFSTADQLEMVTELLGGDMVNQSF

ICDPDDETFIKNIIIQDCMWSGFSAAAKLVSEKLASYQAARKDSGSPNPARGHSVCSTSSLYLQD

LSAAASECIDPSVVFPYPLNDSSSPKSCASQDSSAFSPSSDSLLSSTESSPQGSPEPLVLHEETP

PTTSSDSEEEQEDEEEIDVVSVEKRQAPGKRSESGSPSAGGHSKPPHSPLVLKRCHVSTHQHNYA

APPSTRKDYPAAKRVKLDSVRVLRQISNNRKCTSPRSSDTEENVKRRTHNVLERQRRNELKRSFF

ALRDQIPELENNEKAPKVVILKKATAYILSVQAEEQKLISEEDLLRKRREQLKHKLEQLRNSCA (SEQ ID NO: 70)
atggatttttttcgggtagtggaaaaccagcagcctcccgcgacgatgcccctcaacgttagctt caccaacaggaactatgacctcgactacgactcggtgcagccgtatttctactgcgacgaggagg agaacttctaccagcagcagcagcagagcgagctgcagcccccggcgcccagcgaggatatctgg aagaaattcgagctgctgcccaccccgcccctgtccctagccgccgctccgggctctgctcgcc ctcctacgttgcggtcacacccttctcccttcggggagacaacgacggcggtggcgggagcttct ccacggccgaccagctggagatggtgaccgagctgctgggaggagacatggtgaaccagagtttc -continued

```
atctgcgacccggacgacgagaccttcatcaaaaacatcatcatccaggactgtatgtggagcgg cttctcggccgccgccaagctcgtctcagagaagctggcctcctaccaggctgcgcgcaaagaca gcggcagcccgaaccccgcccgcggccacagcgtctgctccacctccagcttgtacctgcaggat ctgagcgccgccgcctcagagtgcatcgacccctcggtggtcttcccctaccctctcaacgacag cagctcgcccaagtcctgcgcctcgcaagactccagcgccttctctccgtcctcggattctctgc tctcctcgacggagtcctccccgcagggcagcccgagcccctggtgctccatgaggagacaccg cccaccaccagcagcgactctgaggaggaacaagaagatgaggaagaaatcgatgttgtttctgt ggaaaagaggcaggctcctggcaaaaggtcagagtctggatcaccttctgctggaggccacagca aacctcctcacagcccactggtcctcaagaggtgccacgtctccacacatcagcacaactacgca gcgcctccctccactcggaaggactatcctgctgccaagagggtcaagttggacagtgtcagagt cctgagacagatcagcaacaaccgaaaatgcaccagccccaggtcctcggacaccgaggagaatg tcaagaggcgaacacacaacgtcttggagcgccagaggaggaacgagctaaaacggagctttttt gccctgcgtgaccagatcccggagttggaaaacaatgaaaaggcccccaaggtagttatccttaa aaaagccacagcatacatcctgtccgtccaagcagaggagcaaaagctcatttctgaagaggact tgttgcggaaacgacgagaacagttgaaacacaaacttgaacagctacggaactcttgtgcgtaa
```

*Homo sapiens* GATA binding protein 4 (GATA4) (NM_002052)
SEQ ID NO: 7 (protein) and SEQ ID NO: 71 (DNA)

(SEQ ID NO: 7)

```
MYQSLAMAANHGPPPGAYEAGGPGAFMHGAGAASSPVYVPTPRVPSSVLGLSYLQGGGAGSASGG

ASGGSSGGAASGAGPGTQQGSPGWSQAGADGAAYTPPPVSPRFSFPGTTGSLAAAAAAAAAREAA

AYSSGGGAAGAGLAGREQYGRAGFAGSYSSPYPAYMADVGASWAAAAAASAGPFDSPVLHSLPGR

ANPAARHPNLDMFDDFSEGRECVNCGAMSTPLWRRDGTGHYLCNACGLYHKMNGINRPLIKPQRR

LSASRRVGLSCANCQTTTTTLWRRNAEGEPVCNACGLYMKLHGVPRPLAMRKEGIQTRKRKPKNL

NKSKTPAAPSGSESLPPASGASSNSSNATTSSSEEMRPIKTEPGLSSHYGHSSSVSQTFSVSAMS

GHGPSIHPVLSALKLSPQGYASPVSQSPQTSSKQDSWNSLVLADSHGDIITA
```

(SEQ ID NO: 71)

```
atgtatcagagcttggccatggccgccaaccacgggccgccccccggtgcctacgaggcgggcgg ccccggcgcccttcatgcacggcgcgggcgccgcgtcctcgccagtctacgtgcccacaccgcggg tgccctcctccgtgctgggcctgtcctacctccagggcggaggcgcgggctctgcgtccggaggc gcctcgggcggcagctccggtggggccgcgtctggtgcggggcccgggacccagcagggcagccc gggatggagccaggcggagccgacggagccgcttacacccccgccgccggtgtcgccgcgcttct ccttcccggggaccaccgggtccctggcggccgccgccgccgctgccgcggcccgggaagctgcg gcctacagcagtggcggcggagcggcgggtgcgggcctggcggggccgcgagcagtacggggcgcgc cggcttcgcgggctcctactccagcccctaccggcttacatggccgacgtgggcgcgtcctggg ccgcagccgccgccgcctccgccggcccttcgacagcccggtcctgcacagcctgccccggccgg gccaacccggccgcccgacaccccaatctcgatatgtttgacgacttctcagaaggcagagagtg tgtcaactgtggggctatgtccaccccgctctggaggcgagatgggacgggtcactatctgtgca acgcctgcgcctctaccacaagatgaacggcatcaaccggccgctcatcaagcctcagcgccgg ctgtccgcctcccgccgagtgggcctctcctgtgccaactgccagaccaccaccaccacgctgtg gcgccgcaatgcggagggcgagcctgtgtgcaatgcctgcggcctctacatgaagctccacgggg tcccccaggcctcttgcaatgcggaaagaggggatccaaaccagaaaacggaagcccaagaacctg aataaatctaagacaccagcagctccttcaggcagtgagagccttcctcccgccagcggtgcttc cagcaactccagcaacgccaccaccagcagcagcgaggagatgcgtcccatcaagacggagcctg
```

```
gcctgtcatctcactacgggcacagcagctccgtgtcccagacgttctcagtcagtgcgatgtct ggccatgggccctccatccaccctgtcctctcggccctgaagctctccccacaaggctatgcgtc tcccgtcagccagtctccacagaccagctccaagcaggactcttggaacagcctggtcttggccg acagtcacggggacataatcactgcgtaa
```

*Homo sapiens* heart and neural crest derivatives expressed 2
(HAND2) (NM_021973) SEQ ID NO: 8 (protein) and SEQ ID NO: 72
(DNA)

(SEQ ID NO: 8)
MSLVGGFPHHPVVHHEGYPFAAAAAAAAAAAAASRCSHEENPYFHGWLIGHPEMSPPDYSMALSYS

PEYASGAAGLDHSHYGGVPPGAGPPGLGGPRPVKRRGTANRKERRRTQSINSAFAELRECIPNVP

ADTKLSKIKTLRLATSYIAYLMDLLAKDDQNGEAEAFKAEIKKTDVKEEKRKKELNEILKSTVSS

NDKKTKGRTGWPQHVWALELKQ

```
                                                        (SEQ ID NO: 72)
atgagtctggtaggtggttttccccaccaccggtggtgcaccacgagggctacccgtttgccgc cgccgccgccgcagctgccgccgccgccgccagccgctgcagccatgaggagaacccctacttcc atggctggctcatcggccaccccgagatgtcgccccccgactacagcatggccctgtcctacagc cccgagtatgccagcggcgccgccggcctggaccactcccattacgggggggtgccgccgggcgc cgggccccgggcctggggggccgcgcccggtgaagcgccgaggcaccgccaaccgcaaggagc ggcgcaggactcagagcatcaacagcgccttcgccgaactgcgcgagtgcatccccaacgtaccc gccgacaccaaactctccaaaatcaagaccctgcgcctggccaccagctacatcgcctacctcat ggacctgctggccaaggacgaccagaatggcgaggcggaggccttcaaggcagagatcaagaaga ccgacgtgaaagaggagaagaggaagaaggagctgaacgaaatcttgaaaagcacagtgagcagc aacgacaagaaaaccaaggccggacgggctggccgcagcacgtctgggccctggagctcaagca gtga
```

*Homo sapiens* myocyte enhancer factor 2C (MEF2C) NM_001193350)
SEQ ID NO: 9 (protein) and SEQ ID NO: 73 (DNA)

(SEQ ID NO: 9)
MGRKKIQITRIMDERNRQVTFTKRKFGLMKKAYELSVLCDCEIALIIFNSTNKLFQYASTDMDKV

LLKYTEYNEPHESRTNSDIVETLRKKGLNGCDSPDPDADDSVGHSPESEDKYRKINEDIDLMISR

QRLCAVPPPNFEMPVSIPVSSHNSLVYSNPVSSLGNPNLLPAHPSLQRNSMSPGVTHRPPSAGN

TGGLMGGDLTSGAGTSAGNGYGNPRNSPGLLVSPGNLNKNMQAKSPPPMNLGMNNRKPDLRVLIP

PGSKNTMPSVSEDVDLLLNQRINNSQSAQSLATPVVSVATPTLPGQGMGGYPSAISTTYGTEYSL

SSADLSSLSGFNTASALHLGSVTGWQQQHLHNMPPSALSQLGACTSTHLSQSSNLSLPSTQSLNI

KSEPVSPPRDRTTTPSRYPQHTRHEAGRSPVDSLSSCSSSYDGSDREDHRNEFHSPIGLTRPSPD

ERESPSVKRMRLSEGWAT

```
                                                        (SEQ ID NO: 73)
atggggagaaaaaagattcagattacgaggattatggatgaacgtaacagacaggtgacatttac aaagaggaaatttgggttgatgaagaaggcttatgagctgagcgtgctgtgtgactgtgagattg cgctgatcatcttcaacagcaccaacaagctgttccagtatgccagcaccgacatggacaaagtg cttctcaagtacacggagtacaacgagccgcatgagagccggacaaactcagacatcgtggagac gttgagaaagaaggggccttaatggctgtgacagcccagaccccgatgcggacgattccgtaggtc acagccctgagtctgaggacaagtacaggaaaattaacgaagatattgatctaatgatcagcagg caaagattgtgtgctgttccacctcccaacttcgagatgccagtctccatcccagtgtccagcca caacagtttggtgtacagcaaccctgtcagctcactgggaaaccccaacctattgccactggctc acccttctctgcagaggaatagtatgtctcctggtgtaacacatcgacctccaagtgcaggtaac
```

-continued

```
acaggtggtctgatgggtggagacctcacgtctggtgcaggcaccagtgcagggaacgggtatgg
caatccccgaaactcaccaggtctgctggtctcacctggtaacttgaacaagaatatgcaagcaa
aatctcctcccccaatgaatttaggaatgaataaccgtaaaccagatctccgagttcttattcca
ccaggcagcaagaatacgatgccatcagtgtctgaggatgtcgacctgcttttgaatcaaaggat
aaataactcccagtcggctcagtcattggctaccccagtggtttccgtagcaactcctactttac
caggacaaggaatggaggatatccatcagccatttcaacaacatatggtaccgagtactctctg
agtagtgcagacctgtcatctctgtctgggtttaacaccgccagcgctcttcaccttggttcagt
aactggctggcaacagcaacacctacataacatgccaccatctgccctcagtcagttgggagctt
gcactagcactcatttatctcagagttcaaatctctccctgccttctactcaaagcctcaacatc
aagtcagaacctgtttctcctcctagagaccgtaccaccaccccttcgagatacccacaacacac
gcgccacgaggcggggagatctcctgttgacagcttgagcagctgtagcagttcgtacgacggga
gcgaccgagaggatcaccggaacgaattccactcccccattggactcaccagaccttcgccggac
gaaagggaaagtccctcagtcaagcgcatgcgactttctgaaggatgggcaacatga
```

Human transcription factor TBX5 (U80987) SEQ ID NO: 10
(protein) and SEQ ID ID NO: 74 (DNA)

(SEQ ID NO: 10)
MADADEGFGLAHTPLEPDAKDLPCDSKPESALGAPSKSPSSPQAAFTQQGMEGIKVFLHERELWL
KFHEVGTEMIITKAGRRMFPSYKVKVTGLNPKTKYILLMDIVPADDHRYKFADNKWSVTGKAEPA
MPGRLYVHPDSPATGAHWMRQLVSFQKLKLTNNHLDPFGHIILNSMHKYQPRLHIVKADENNGFG
SKNTAFCTHVFPETAFIAVTSYQNHKITQLKIENNPFAKGFRGSDDMELHRMSRMQSKEYPVVPR
STVRQKVASNHSPFSSESRALSTSSNLGSQYQCENGVSGPSQDLLPPPNPYPLPQEHSQIYHCTK
RKGECDHPWSICFLSYLFLSLGWG (SEQ ID NO: 74)
```
atggccgacgcagacgagggctttggcctggcgcacacgcctctggagcctgacgcaaaagacct
gccctgcgattcgaaacccgagagcgcgctcggggcccccagcaagtccccgtcgtccccgcagg
ccgccttcacccagcagggcatggagggaatcaaagtgtttctccatgaaagagaactgtggcta
aaattccacgaagtgggcacggaaatgatcataaccaaggctggaaggcggatgtttcccagtta
caaagtgaaggtgacgggccttaatcccaaaacgaagtacattcttctcatggacattgtacctg
ccgacgatcacagatacaaattcgcagataataaatggtctgtgacgggcaaagctgagcccgcc
atgcctggccgcctgtacgtgcacccagactcccccgccaccggggcgcattggatgaggcagct
cgtctccttccagaaactcaagctcaccaacaaccacctggacccatttgggcatattattctaa
attccatgcacaaataccagcctagattacacatcgtgaaagcggatgaaaataatggatttggc
tcaaaaaatacagcgttctgcactcacgtctttcctgagactgcgtttatagcagtgacttccta
ccagaaccacaagatcacgcaattaaagattgagaataatccctttgccaaaggatttcggggca
gtgatgacatggagctgcacagaatgtcaagaatgcaaagtaaagaatatcccgtggtccccagg
agcaccgtgaggcaaaaagtggcctccaaccacagtccttttcagcagcgagtctcgagctctctc
cacctcatccaatttggggtcccaataccagtgtgagaatggtgtttccggcccctcccaggacc
tcctgcctccacccaacccatacccactgcccaggagcatagccaaatttaccattgtaccaag
aggaaaggtgagtgtgatcacccctggtcaatttgctttctttcttacctttttccttttccttggg
ttgggggtga
```

Homo sapiens neurogenin 3 (NEUROG3) (NM_020999.3)
SEQ ID NO: 11 (protein) and SEQ ID NO: 75 (DNA)

(SEQ ID NO: 11)
MTPQPSGAPTVQVTRETERSFPRASEDEVTCPTSAPPSPTRTRGNCAEAEEGGCRGAPRKLRARR

-continued

GGRSRPKSELALSKQRRSRRKKANDRERNRMHNLNSALDALRGVLPTFPDDAKLTKIETLRFAHN

YIWALTQTLRIADHSLYALEPPAPHCGELGSPGGSPGDWGSLYSPVSQAGSLSPAASLEERPGLL

GATFSACLSPGSLAFSDFL (SEQ ID NO: 75)
atgacgcctcaaccctcgggtgcgcccactgtccaagtgacccgtgagacggagcggtccttccc cagagcctcggaagacgaagtgacctgccccacgtccgccccgcccagccccactcgcacacggg ggaactgcgcagaggcggaagagggaggctgccgaggggccccgaggaagctccgggcacggcgc gggggacgcagccggcctaagagcgagttggcactgagcaagcagcgacggagtcggcgaaagaa ggccaacgaccgcgagcgcaatcgaatgcacaacctcaactcggcactggacgccctgcgcggtg tcctgcccaccttcccagacgacgcgaagctcaccaagatcgagacgctgcgcttcgcccacaac tacatctgggcgctgactcaaacgctgcgcatagcggaccacagcttgtacgcgctggagccgcc ggcgccgcactgcggggagctgggcagcccaggcggttcccccggggactgggggtccctctact ccccagtctcccaggctggcagcctgagtcccgccgcgtcgctggaggagcgacccgggctgctg ggggccaccttttccgcctgcttgagcccaggcagtctggctttctcagattttctgtga Homo sapiens paired box 4 (PAX4) (NM_006193.2) SEQ ID NO: 12
(protein) and SEQ ID NO: 76 (DNA)
(SEQ ID NO: 12)
MNQLGGLFVNGRPLPLDTRQQIVRLAVSGMRPCDISRILKVSNGCVSKILGRYYRTGVLEPKGIG

GSKPRLATPPVVARIAQLKGECPALFAWEIQRQLCAEGLCTQDKTPSVSSINRVLRALQEDQGLP

CTRLRSPAVLAPAVLTPHSGSETPRGTHPGTGHRNRTIFSPSQAEALEKEFQRGQYPDSVARGKL

ATATSLPEDTVRVWFSNRRAKWRRQEKLKWEMQLPGASQGLTVPRVAPGIISAQQSPGSVPTAAL

PALEPLGPSCYQLCWATAPERCLSDTPPKACLKPCWGHLPPQPNSLDSGLLCLPCPSSHCHLASL

SGSQALLWPGCPLLYGLE (SEQ ID NO: 76)
atgaaccagcttgggggctctttgtgaatggccggcccctgcctctggatacccggcagcagat tgtgcggctagcagtcagtggaatgcggccctgtgacatctcacggatccttaaggtatctaatg gctgtgtgagcaagatcctagggcgttactaccgcacaggtgtcttggagccaaagggcattggg ggaagcaagccacggctggctacacccctgtggtggctcgaattgcccagctgaagggtgagtg tccagccctcttttgcctgggaaatccaacgccagctttgtgctgaagggctttgcacccaggaca agactcccagtgtctcctccatcaaccgagtcctgcgggcattacaggaggaccagggactaccg tgcacacggctcaggtcaccagctgttttggctccagctgtcctcactcccatagtggctctga gactccccggggtacccacccagggaccggccaccggaatcggactatcttctccccaagccaag cagaggcactggagaaagagttccagcgtgggcagtatcctgattcagtggcccgtggaaagctg gctactgccacctctctgcctgaggacacggtgagggtctggttttccaacagaagagccaaatg gcgtcggcaagagaagctcaagtgggaaatgcagctgccaggtgcttcccaggggctgactgtac caagggttgccccaggaatcatctctgcacagcagtcccctggcagtgtgcccacagcagccctg cctgccctggaaccactgggtcctcctgctatcagctgtgctgggcaacagcaccagaaaggtg tctgagtgacacccccacctaaagcctgtctcaagccctgctggggccacttgccccacagccga attccctggactcaggactgctttgccttccttgcccttcctcccactgtcacctggccagtctt agtggctctcaggccctgctctggcctggctgcccactactgtatggcttggaatga Homo sapiens pancreatic and duodenal homeobox 1 (PDX1)
(NM_000209.3) SEQ ID NO: 13 (protein) and SEQ ID NO: 77 (DNA)
(SEQ ID NO: 13)
MNGEEQYYAATQLYKDPCAFQRGPAPEFSASPPACLYMGRQPPPPPPHPFPGALGALEQGSPPDI -continued

SPYEVPPLADDPAVAHLHHHLPAQLALPHPPAGPFPEGAEPGVLEEPNRVQLPFPWMKSTKAHAW

KGQWAGGAYAAEPEENKRTRTAYTRAQLLELEKEFLFNKYISRPRRVELAVMLNLTERHIKIWFQ

NRRMKWKKEEDKKRGGGTAVGGGGVAEPEQDCAVTSGEELLALPPPPPPGGAVPPAAPVAAREGR

LPPGLSASPQPSSVAPRRPQEPR (SEQ ID NO: 77)
atgaacggcgaggagcagtactacgcggccacgcagctttacaaggacccatgcgcgttccagcg aggcccggcgccggagttcagcgccagccccctgcgtgcctgtacatgggccgccagccccgc cgccgccgccacccgttccctggcgccctgggcgcgctggagcagggcagcccccggacatc tccccgtacgaggtgccccccctcgccgacgaccccgcggtggcgcaccttcaccaccacctccc ggctcagctcgcgctccccacccgcccgccgggcccttccggagggagccgagccgggcgtcc tggaggagcccaaccgcgtccagctgccttccccatggatgaagtctaccaaagctcacgcgtgg aaaggccagtgggcaggcggcgcctacgctgcggagccggaggagaacaagcggacgcgcacggc ctacacgcgcgcacagctgctagagctggagaaggagttcctattcaacaagtacatctcacggc cgcgccgggtggagctggctgtcatgttgaacttgaccgagagacacatcaagatctggttccaa aaccgccgcatgaagtggaaaaaggaggaggacaagaagcgcggcggcgggacagctgtcggggg tggcggggtcgcggagcctgagcaggactgcgccgtgacctccggcgaggagcttctggcgctgc cgccgccgccgcccccggaggtgctgtgccgcccgctgccccgttgccgcccgagagggccgc ctgccgcctggccttagcgcgtcgccacagccctccagcgtcgcgcctcggcggccgcaggaacc acgatga Human SOX9 protein (1-509) (Z46629.1) SEQ ID NO: 14 (protein)
and SEQ ID NO: 78 (DNA)

(SEQ ID NO: 14)
MNLLDPFMKMTDEQEKGLSGAPSPTMSEDSAGSPCPSGSGSDTENTRPQENTFPKGEPDLKKESE

EDKFPVCIREAVSQVLKGYDWTLVPMPVRVNGSSKNKPHVKRPMNAFMVWAQAARRKLADQYPHL

HNAELSKTLGKLWRLLNESEKRPFVEEAERLRVQHKKDHPDYKYQPRRRKSVKNGQAEAEEATEQ

THISPNAIFKALQADSPHSSSGMSEVHSPGEHSGQSQGPPTPPTTPKTDVQPGKADLKREGRPLP

EGGRQPPIDFRDVDIGELSSDVISNIETFDVNEFDQYLPPNGHPGVPATHGQVTYTGSYGISSTA

ATPASAGHVWMSKQQAPPPPPQQPPQAPPAPQAPPQPQAAPPQQPAAPPQQPQAHTLTTLSSEPG

QSQRTHIKTEQLSPSHYSEQQQHSPQQIAYSPFNLPHYSPSYPPITRSQYDYTDHQNSSSYYSHA

AGQGTGLYSTFTYMNPAQRPMYTPIADTSGVPSIPQTHSPQHWEQPVYTQLTRP (SEQ ID NO: 78)
atgaatctcctggaccccttcatgaagatgaccgacgagcaggagaagggcctgtccggcgcccc cagccccaccatgtccgaggactccgcgggctcgccctgccgtcgggctcggctcggacaccg agaacacgcggccccaggagaacacgttccccaagggcgagcccgatctgaagaaggagagcgag gaggacaagttccccgtgtgcatccgcgaggcggtcagccaggtgctcaaaggctacgactggac gctggtgcccatgccggtgcgcgtcaacggctccagcaagaacaagccgcacgtcaagcggcca tgaacgccttcatggtgtgggcgcaggcggcgcgcaggaagctcgcggaccagtacccgcacttg cacaacgccgagctcagcaagacgctgggcaagctctggagacttctgaacgagagcgagaagcg gcccttcgtggaggaggcggagcggctgcgcgtgcagcacaagaaggaccacccggattacaagt accagccgcggcggaggaagtcggtgaagaacgggcaggcggaggcagaggaggccacggagcag acgcacatctccccaacgccatcttcaaggcgctgcaggccgactcgccacactcctcctccgg catgagcgaggtgcactcccccggcgagcactcggggcaatcccagggcccaccgaccccaccca ccaccccaaaaccgacgtgcagccgggcaaggctgacctgaagcgagaggggcgccccttgcca -continued gagggggggcagacagcccctatcgacttccgcgacgtggacatcggcgagctgagcagcgacgt catctccaacatcgagaccttcgatgtcaacgagtttgaccagtacctgccgcccaacggccacc cggggggtgccggccacgcacggccaggtcacctacacgggcagctacggcatcagcagcaccgcg gccaccccggcgagcgcgggccacgtgtggatgtccaagcagcaggcgccgccgccaccccgca gcagccccacaggcccgccggccccgcaggcgccccgcagccgcaggcggcgcccccacagc agccggcggcaccccgcagcagccacaggcgcacacgctgaccacgctgagcagcgagccgggc cagtcccagcgaacgcacatcaagacggagcagctgagcccagccactacagcgagcagcagca gcactcgccccaacagatcgcctacgcccttcaacctcccacactacagcccctcctacccgc ccatcacccgctcacagtacgactacaccgaccaccagaactccagctcctactacagccacgcg gcaggccagggcaccggcctctactccaccttcacctacatgaaccccgctcagcgccccatgta cacccccatcgccgacacctctggggtccctccatcccgcagacccacagcccccagcactggg aacaacccgtctacacacagctcactcgaccttga Homo sapiens zinc finger protein SLUG (SLUG) gene (AF084243.1)
SEQ ID NO: 15 (protein) and SEQ ID NO: 79 (DNA)

(SEQ ID NO: 15)
MPRSFLVKKHFNASKKPNYSELDTHTVIISPYLYESYSMPVIPQPEILSSGAYSPITVWTTAAPF

HAQLPNGLSPLSGYSSSLGRVSPPPPSDTSSKDHSGSESPISDEEERLQSKLSDPHAIEAEKFQC

NLCNKTYSTFSGLAKHKQLHCDAQSRKSFSCKYCDKEYVSLGALKMHIRTHTLPCVCKICGKAFS

RPWLLQGHIRTHTGEKPFSCPHCNRAFADRSNLRAHLQTHSDVKKYQCKNCSKTFSRMSLLHKHE

ESGCCVAH (SEQ ID NO: 79)
atgccgcgctccttcctggtcaagaagcatttcaacgcctccaaaaagccaaactacagcgaact ggacacacatacagtgattatttccccgtatctctatgagagttactccatgcctgtcataccac aaccagagatcctcagctcaggagcatacagccccatcactgtgtggactaccgctgctccattc cacgcccagctacccaatggcctctctcctctttccggatactcctcatctttggggcgagtgag tccccctcctccatctgacacctcctccaaggaccacagtggctcagaaagccccattagtgatg aagaggaaagactacagtccaagctttcagacccccatgccattgaagctgaaaagtttcagtgc aatttatgcaataagacctattcaacttttctgggctggccaaacataagcagctgcactgcga tgcccagtctagaaaatcttttcagctgtaaatactgtgacaaggaatatgtgagcctgggcgccc tgaagatgcatattcggacccacacattaccttgtgtttgcaagatctgcggcaaggcgttttcc agaccctggttgcttcaaggacacattagaactcacacggggagaagccttttctcttgccctca ctgcaacagagcatttgcagacaggtcaaatctgagggctcatctgcagacccattctgatgtaa agaaataccagtgcaaaaactgctccaaaaccttctccagaatgtctctcctgcacaaacatgag gaatctggctgctgtgtagcacactga Homo sapiens v-maf avian musculoaponeurotic fibrosarcoma
oncogene homolog A (MafA) (NM_201589.3) SEQ ID NO: 16
(protein) and SEQ ID NO: 80 (DNA)

(SEQ ID NO: 16)
MAAELAMGAELPSSPLAIEYVNDFDLMKFEVKKEPPEAERFCHRLPPGSLSSTPLSTPCSSVPSS

PSFCAPSPGTGGGGAGGGGSSQAGGAPGPPSGGPGAVGGTSGKPALEDLYWMSGYQHMLNPEA

LNLTPEDAVEALIGSGHHGAHHGAHHPAAAAAYEAFRGPGFAGGGGADDMGAGHHHGAHHAAHHH

HAAHHHHHHHHHGGAGHGGGAGHHVRLEERFSDDQLVSMSVRELNRQLRGFSKEEVIRLKQKRR

TLKNRGYAQSCRFKRVQQRHILESEKCQLSQVEQLKLEVGRLAKERDLYKEKYEKLAGRGGPGS

AGGAGFPREPSPPQAGPGGAKGTADFFL (SEQ ID NO: 80)

-continued

```
atggccgcggagctggcgatgggcgccgagctgcccagcagcccgctggccatcgagtacgtcaa cgacttcgacctgatgaagttcgaggtgaagaaggagcctcccgaggccgagcgcttctgccacc gcctgccgccaggctcgctgtcctcgacgccgctcagcacgccctgctcctccgtgccctcctcg cccagcttctgcgcgcccagcccgggcaccgcggcggcggcggcgcggggggcggcggcggctc gtctcaggccggggcgccccgggccgccgagcgggggccccggcgccgtcggggcacctcgg ggaagccggcgctggaggatctgtactggatgagcggctaccagcatcacctcaaccccgaggcg ctcaacctgacgcccgaggacgcggtggaggcgctcatcggcagcggccaccacggcgcgcacca cggcgcgcaccaccggcggccgccgcagcctacgaggctttccgcggcccgggcttcgcgggcg gcggcggagcggacgacatgggcgccggccaccaccacggcgcgcaccacgccgcccaccatcac cacgccgcccaccaccaccaccaccaccaccaccatggcggcgcgggacacggcggtggcgc gggccaccacgtgcgcctggaggagcgcttctccgacgaccagctggtgtccatgtcggtgcgcg agctgaaccggcagctccgcggcttcagcaaggaggaggtcatccggctcaagcagaagcggcgc acgctcaagaaccgcggctacgcgcagtcctgccgcttcaagcgggtgcagcagcggcacattct ggagagcgagaagtgccaactccagagccaggtggagcagctgaagctggaggtggggcgcctgg ccaaagagcgggacctgtacaaggagaaatacgagaagctggcgggccggggcggccccgggagc gcgggcggggccggtttcccgcgggagccttcgccgccgcaggccggtcccggcggggccaaggg cacggccgacttcttcctgtag
```

Homo sapiens neuronal differentiation 1 (NEUROD1) (NM_002500.4)
SEQ ID NO: 17 (protein) and SEQ ID NO: 81 (DNA)

(SEQ ID NO: 17)
MTKSYSESGLMGEPQPQGPPSWTDECLSSQDEEHEADKKEDDLEAMNAEEDSLRNGGEEEDEDED

LEEEEEEEEDDDQKPKRRGPKKKKMTKARLERFKLRRMKANARERNRMHGLNAALDNLRKVVPC

YSKTQKLSKIETLRLAKNYIWALSEILRSGKSPDLVSFVQTLCKGLSQPTTNLVAGCLQLNPRTF

LPEQNQDMPPHLPTASASFPVHPSYQSPGLPSPPYGTMDSSHVFHVKPPPHAYSAALEPFFESP

LTDCTSPSFDGPLSPPLSINGNFSFKHEPSAEFEKNYAFTMHYPAATLAGAQSHGSIFSGTAAPR

CEIPIDNIMSFDSHSHHERVMSAQLNAIFHD (SEQ ID NO: 81)
```
atgaccaaatcgtacagcgagagtgggctgatgggcgagcctcagccccaaggtcctccaagctg gacagacgagtgtctcagttctcaggacgaggagcacgaggcagacaagaaggaggacgacctcg aagccatgaacgcagaggaggactcactgaggaacggggagaggaggaggacgaagatgaggac ctggaagaggaggaagaagaggaagaggaggatgacgatcaaaagcccaagagacgcggccccaa aaagaagaagatgactaaggctcgcctggagcgttttaaattgagacgcatgaaggctaacgccc gggagcggaaccgcatgcacggactgaacgcggcgctagacaacctgcgcaaggtggtgccttgc tattctaagacgcagaagctgtccaaaatcgagactctgcgcttggccaagaactacatctgggc tctgtcggagatcctgcgctcaggcaaaagcccagacctggtctccttcgttcagacgctttgca agggcttatcccaacccaccaccaacctggttgcgggctgcctgcaactcaatcctcggactttt ctgcctgagcagaaccaggacatgcccccccacctgccgacggccagcgcttccttccctgtaca cccctactcctaccagtcgcctgggctgcccagtccgccttacggtaccatggacagctcccatg tcttccacgttaagcctccgccgcacgcctacagcgcagcgctggagcccttctttgaaagccct ctgactgattgcaccagcccttcctttgatggaccctcagcccgccgctcagcatcaatggcaa cttctctcttcaaacacgaaccgtccgccgagtttgagaaaaattatgcctttaccatgcactatc ctgcagcgacactggcaggggcccaaagccacggatcaatcttctcaggcaccgctgcccctcgc tgcgagatccccatagacaatattatgtccttcgatagccattcacatcatgagcgagtcatgag
```

-continued tgcccagctcaatgccatatttcatgattag

Homo sapiens myogenic factor 5 (MYF5) (NM_005593.2)
SEQ ID NO: 18 (protein) and SEQ ID NO: 82 (DNA)

(SEQ ID NO: 18)
MDVMDGCQFSPSEYFYDGSCIPSPEGEFGDEFVPRVAAFGAHKAELQGSDEDEHVRAPTGHHQAG

HCLMWACKACKRKSTTMDRRKAATMRERRRLKKVNQAFETLKRCTTTNPNQRLPKVEILRNAIRY

IESLQELLREQVENYYSLPGQSCSEPTSPTSNCSDGMPECNSPVWSRKSSTFDSIYCPDVSNVYA

TDKNSLSSLDCLSNIVDRITSSEQPGLPLQDLASLSPVASTDSQPATPGASSSRLIYHVL (SEQ ID NO: 82)
atggacgtgatggatggctgccagttctcaccttctgagtacttctacgacggctcctgcatacc gtcccccgagggtgaatttggggacgagtttgtgccgcgagtggctgccttcggagcgcacaaag cagagctgcagggctcagatgaggacgagcacgtgcgagcgcctaccggccaccaccaggctggt cactgcctcatgtgggcctgcaaagcctgcaagaggaagtccaccaccatggatcggcggaaggc agccactatgcgcgagcggaggcgcctgaagaaggtcaaccaggctttcgaaaccctcaagaggt gtaccacgaccaaccccaaccagaggctgcccaaggtggagatcctcaggaatgccatccgctac atcgagagcctgcaggagttgctgagagagcaggtggagaactactatagcctgccgggacagag ctgctcggagcccaccagcccacctccaactgctctgatggcatgcccgaatgtaacagtcctg tctggtccagaaagagcagtacttttgacagcatctactgtcctgatgtatcaaatgtatatgcc acagataaaaactccttatccagcttggattgcttatccaacatagtggaccggatcacctcctc agagcaacctgggttgcctctccaggatctggcttctctctctccagttgccagcaccgattcac agcctgcaactccaggggcttctagttccaggcttatctatcatgtgctatga Homo sapiens PR-domain-containing protein 16 (PRDM16)
(AF294278.1) SEQ ID NO: 19 (protein) and SEQ ID NO: 83 (DNA)

(SEQ ID NO: 19)
MRSKARARKLAKSDGDVVNNMYEPNRDLLASHSAEDEAEDSAMSPIPVGSPPPFPTSEDFTPKEG

SPYEAPVYIPEDIPIPADFELRESSIPGAGLGVWAKRKMEAGERLGPCVVVPRAAAKETDFGWEQ

ILTDVEVSPQEGCITKISEDLGSEKFCVDANQAGAGSWLKYIRVACSCDDQNLTMCQISEQVIYY

KVIKDIEPGEELLVHVKEGVYPLGTVPPGLDEEPTFRCDECDELFQSKLDLRRHKKYTCGSVGAA

LYEGLAEELKPEGLGGGSGQAHECKDCERMFPNKYSLEQHMVIHTEEREYKCDQCPKAFNWKSNF

IRHQMSHDSGKRFECENCVKVFTDPSNLQRHIRSQHVGARAHACPDCGKTFATSSGLKQHKIHS

TVKPFICEVCHKSYTQFSNLCRHKRMHADCRTQIKCKDCGQMFSTTSSLNKHRRFCEGKNHYTPG

GIFAPGLPLTPSPMMDKAKPSPSLNHASLGFNEYFPYRPHPGSLPFSTAPPTFPALTPGFPGIFP

PSLYPRPPLLPPTSLLKSPLNHTQDAKLPSPLGNPALPLVSAVSNSSQGTTAAAGPEEKFESRLE

DSCVEKLKTRSSDMSDGSDFEDVNTTTGTDLDTTTGTGSDLDSDVDSDPDKDKGKGKSAEGQPKF

GGGLAPPGAPNSVAEVPVFYSQHSFFPPPDEQLLTATGAAGDSIKAIASIAEKYFGPGFMGMQEK

KLGSLPYHSAFPFQFLPNFPHSLYPFTDRALAHNLLVKAEPKSPRDALKVGGPSAECPFDLTTKP

KDVKPILPMPKGPSAPASGEEQPLDLSIGSRARASQNGGGREPRKNHVYGERKLGAGEGLPQVCP

ARMPQQPPLHYAKPSPFFMDPIYRVEKRKVTDPVGALKEKYLRPSPLLFHPQMSAIETMTEKLES

FAAMKADSGSSLQPLPHHPFNFRSPPPTLSDPILRKGKERYTCRYCGKIFPRSANLTRHLRTHTG

EQPYRCKYCDRSFSISSNLQRHVRNIHNKEKPFKCHLCNRCFGQQTNLDRHLKKHEHENAPVSQH

PGVLTNHLGTSASSPTSESDNHALLDEKEDSYFSEIRNFIANSEMNQASTRTEKRADMQIVDGSA

QCPGLASEKQEDVEEEDDDDLEEDDEDSLAGKSQDDTVSPAPEPQAAYEDEEDEEPAASLAVGFD

HTRRCAEDHEGGLLALEPMPTFGKGLDLRRAAEEEAFEVKDVLNSTLDSEALKHTLCRQAKNQAYA

MMLSLSEDTPLHTPSQGSLDAWLKVTGATSESGAFHPINHL (SEQ ID NO: 83)

```
atgcgatccaaggcgagggcgaggaagctagccaaaagtgacggtgacgttgtaaataatatgta
tgagcccaaccgggacctgctggccagccacagcgcggaggacgaggccgaggacagtgccatgt
cgcccatccccgtggggtcaccgccccccttccccaccagcgaggacttcacccccaaggagggc
tcgccgtacgaggcccctgtctacattcctgaagacattccgatcccagcagacttcgagctccg
agagtcctccatcccaggggctggcctgggggtctgggccaagaggaagatggaagccggggaga
ggctgggcccctgcgtggtggtgccccgggcggcggcaaaggagacagacttcggatgggagcaa
atactgacggacgtggaagtgtcgccccaggaaggctgcatcacaaagatctccgaagacctggg
cagtgagaagttctgcgtggatgcaaatcaggcggggctggcagctggctcaagtacatccgtg
tggcgtgctcctgcgatgaccagaacctcaccatgtgtcagatcagtgagcaggtaatttactat
aaagtcattaaggacattgagccaggtgaggagctgctggtgcacgtgaaggaaggcgtctaccc
cctgggcacagtgccgcccggcctggacgaggagcccacgttccgctgtgacgagtgtgacgaac
tcttccagtccaagctggacctgcggcgccataagaagtacacgtgtggctcagtggggctgcg
ctctacgagggcctggctgaggagctcaagcccagggccttggcggtggcagcggccaagccca
cgagtgcaaggactgcgagcggatgttccccaacaagtacagcctggagcagcacatggtcatcc
acacggaggagcgcgagtacaaatgcgaccagtgtcccaaggccttcaactggaagtccaacttc
atccgccaccagatgtcccacgacagcggcaaacgcttcgaatgtgaaaactgcgtgaaggtgtt
cacggaccccagcaaccttcagcggcacatccgctcgcagcacgtgggcgctcgggcccacgcct
gccccgactgcgggaagaccttcgccacgtcctccggcctcaagcagcacaagcatatccacagc
acggtgaagcctttcatatgtgaggtctgccacaagtcctacacgcagttctccaacctgtgccg
gcacaagcggatgcacgccgactgccgcacgcagatcaagtgcaaggactgtggccagatgttca
gcactacctcctccctcaacaagcaccggcgcttctgcgagggcaagaaccattacacgccgggc
ggcatctttgccccgggcctgcccttgaccccagcccatgatggacaaggcaaaaccctcccc
cagcctcaatcacgccagcctgggcttcaacgagtactttccctacaggccgcacccggggagcc
tgcccttctccacggcgcctcccacgttccccgcactcaccccggcttcccgggcatcttccct
ccatccttgtaccccggccgcctctgctacctcccacatcgctgctcaagagcccctgaacca
cacccaggacgccaagctccccagtcccctggggaacccagccctgcccctggtctccgccgtca
gcaacagcagccagggcacgacggcagctgcggggcccgaggagaagttcgagagccgcctggag
gactcctgtgtggagaagctgaagaccaggagcagcgacatgtcggacggcagtgactttgagga
cgtcaacaccaccacggggaccgacctggacacgaccacggggacgggctcggacctggacagcg
acgtggacagcgaccctgacaaggacaagggcaagggcaagtccgccgagggccagcccaagttt
gggggcggcttggcgccccgggggccccgaacagcgtggccgaggtgcctgtcttctattccca
gcactcattcttcccgccaccgacgagcagctgctgactgcaacgggcgccgccggggactcca
tcaaggccatcgcatccattgccgagaagtactttggccccggcttcatggggatgcaggagaag
aagctgggctcgctcccctaccactcggcgttcccttccagttcctgcccaacttcccccactc
cctttaccccttcacggaccgagccctcgcccacaacttgctggtcaaggccgagccaaagtcac
cccgggacgccctcaaggtgggcggccccagtgccgagtgccccttgatctcaccaccaagccc
aaagacgtgaagcccatcctgcccatgcccaagggccctcggccccgcatccggcgaggagca
gccgctggacctgagcatcggcagccgggcccgtgccagccaaaacggcggcgggcgggagcccc
gcaagaaccacgtctatggggaacgcaagctgggcgccggcgaggggctgccccaggtgcccg
gcgcggatgccccagcagcccccgctccactacgccaagccctcgcccttcttcatggaccccat
```

-continued

```
ctacagggtagaaaagcggaaggtcacagaccccgtgggagccctgaaggagaagtacctgcggc cgtccccgctgctcttccaccccagatgtcagccatagagaccatgacagagaagctggagagc tttgcagccatgaaggcggactcgggcagctccctgcagcccctcccccaccaccccttcaactt ccggtccccaccccaacgctctccgaccccatcctcaggaagggcaaggagcgatacacgtgca ggtactgtgggaagatcttccccagatcagccaatctcaccagacacctgaggacgcacactggg gagcagccgtacaggtgtaagtactgcgaccgctccttcagcatctcttcgaacctccagcggca cgtccggaacatccacaacaaggagaagccttttcaagtgccacctgtgcaaccgctgcttcgggc agcagaccaacctggaccggcacctcaagaagcacgagcacgagaacgcaccagtgagccagcac cccggggtcctcacgaaccacctggggaccagcgcgtcctctcccacctcagagtcggacaacca cgcacttttagacgagaaagaagactcttatttctcggaaatcagaaactttattgccaatagtg agatgaaccaagcatcaacgcgaacagagaaacgggcggacatgcagatcgtggacggcagtgcc cagtgtccaggcctagccagtgagaagcaggaggacgtggaggaggaggacgacgatgacctgga ggaggacgatgaggacagcctggccgggaagtcgcaggatgacaccgtgtccccgcacccgagc cccaggccgcctacgaggatgaggaggatgaggagccagccgcctccctggccgtgggctttgac cacacccgaaggtgtgctgaggaccacgaaggcggtctgttagctttggagccgatgccgacttt tgggaaggggctggacctccgcagagcagctgaggaagcatttgaagttaaagatgtgcttaatt ccaccttagattctgaggctttaaaacatacactgtgcaggcaggctaagaaccaggcatatgca atgatgctgtccctttccgaagacactcctctccacacccctcccagggttctctggacgcttg gttgaaggtcactggagccacgtcggagtctggagcatttcaccccatcaaccacctctga
```

*Homo sapiens* paired box 6 (PAX6) (NM_001604.5) SEQ ID NO: 20
(protein) and SEQ ID NO: 84 (DNA)

(SEQ ID NO: 20)
MQNSHSGVNQLGGVFVNGRPLPDSTRQKIVELAHSGARPCDISRILQTHADAKVQVLDNQNVSNG

CVSKILGRYYETGSIRPRAIGGSKPRVATPEVVSKIAQYKRECPSIFAWEIRDRLLSEGVCTNDN

IPSVSSINRVLRNLASEKQQMGADGMYDKLRMLNGQTGSWGTRPGWYPGTSVPGQPTQDGCQQQE

GGGENTNSISSNGEDSDEAQMRLQLKRKLQRNRTSFTQEQIEALEKEFERTHYPDVFARERLAAK

IDLPEARIQVWFSNRRAKWRREEKLRNQRRQASNTPSHIPISSSFSTSVYQPIPQPTTPVSSFTS

GSMLGRTDTALTNTYSALPPMPSFTMANNLPMQPPVPSQTSSYSCMLPTSPSVNGRSYDTYTPTH

MQTHMNSQPMGTSGTTSTGLISPGVSVPVQVPGSEPDMSQYWPRLQ (SEQ ID NO: 84)
```
atgcagaacagtcacagcggagtgaatcagctcggtggtgtctttgtcaacgggcggccactgcc ggactccacccggcagaagattgtagagctagctcacagcggggcccggccgtgcgacatttccc gaattctgcagacccatgcagatgcaaaagtccaagtgctggacaatcaaaacgtgtccaacgga tgtgtgagtaaaattctgggcaggtattacgagactggctccatcagacccagggcaatcggtgg tagtaaaccgagagtagcgactccagaagttgtaagcaaaatagcccagtataagcgggagtgcc cgtccatctttgcttgggaaatccgagacagattactgtccgaggggtctgtaccaacgataac ataccaagcgtgtcatcaataaacagagttcttcgcaacctggctagcgaaaagcaacagatggg cgcagacggcatgtatgataaactaaggatgttgaacgggcagaccggaagctggggcacccgcc ctggttggtatccggggacttcggtgccagggcaacctacgcaagatggctgccagcaacaggaa ggaggggagagaataccaactccatcagttccaacggagaagattcagatgaggctcaaatgcg acttcagctgaagcggaagctgcaaagaaatagaacatccttttacccaagagcaaattgaggccc tggagaaagagtttgagagaacccattatccagatgtgtttgcccgagaaagactagcagccaaa
```

-continued atagatctacctgaagcaagaatacaggtatggttttctaatcgaagggccaaatggagaagaga agaaaaactgaggaatcagagaagacaggccagcaacacacctagtcatattcctatcagcagta gtttcagcaccagtgtctaccaaccaattccacaacccaccacaccggtttcctccttcacatct ggctccatgttgggccgaacagacacagccctcacaaacacctacagcgctctgccgcctatgcc cagcttcaccatggcaaataacctgcctatgcaaccccagtccccagccagacctcctcatact cctgcatgctgcccaccagcccttcggtgaatgggcggagttatgatacctacaccccccacat atgcagacacacatgaacagtcagccaatgggcacctcgggcaccacttcaacaggactcatttc ccctggtgtgtcagttccagttcaagttcccggaagtgaacctgatatgtctcaatactggccaa gattacagtaa SEQ ID NO: 21: *Homo sapiens* HNF1 homeobox A (HNF1A)
(NM_000545.5) SEQ ID NO: 21 (protein) and SEQ ID NO: 85 (DNA)

(SEQ ID NO: 21)
MVSKLSQLQTELLAALLESGLSKEALIQALGEPGPYLLAGEGPLDKGESCGGGRGELAELPNGLG

ETRGSEDETDDDGEDFTPPILKELENLSPEEAAHQKAVVETLLQEDPWRVAKMVKSYLQQHNIPQ

REVVDTTGLNQSHLSQHLNKGTPMKTQKRAALYTWYVRKQREVAQQFTHAGQGGLIEEPTGDELP

TKKGRRNRFKWGPASQQILFQAYERQKNPSKEERETLVEECNRAECIQRGVSPSQAQGLGSNLVT

EVRVYNWFANRRKEEAFRHKLAMDTYSGPPPGPGPGPALPAHSSPGLPPPALSPSKVHGVRYGQP

ATSETAEVPSSSGGPLVTVSTPLHQVSPTGLEPSHSLLSTEAKLVSAAGGPLPPVSTLTALHSLE

QTSPGLNQQPQNLIMASLPGVMTIGPGEPASLGPTFTNTGASTLVIGLASTQAQSVPVINSMGSS

LTTLQPVQFSQPLHPSYQQPLMPPVQSHVTQSPFMATMAQLQSPHALYSHKPEVAQYTHTGLLPQ

TMLITDTTNLSALASLTPTKQVFTSDTEASSESGLHTPASQATTLHVPSQDPAGIQHLQPAHRLS

ASPTVSSSSLVLYQSSDSSNGQSHLLPSNHSVIETFISTQMASSSQ (SEQ ID NO: 85)
atggtttctaaaactgagccagctgcagacggagctcctggcggccctgctcgagtcagggctgag caaagaggcactgatccaggcactgggtgagccggggccctacctcctggctggagaaggccccc tggacaaggggagtcctgcggcggcggtcgaggggagctggctgagctgcccaatgggctgggg gagactcggggctccgaggacgagacggacgacgatggggaagacttcacgccacccatcctcaa agagctggagaacctcagccctgaggaggcggccaccagaaagccgtggtggagacccttctgc aggaggacccgtggcgtgtggcgaagatggtcaagtcctacctgcagcagcacaacatcccacag cgggaggtggtcgataccactggcctcaaccagtcccacctgtcccaacacctcaacaagggcac tcccatgaagacgcagaagcgggccgccctgtacacctggtacgtccgcaagcagcgagaggtgg cgcagcagttcacccatgcagggcaggagggctgattgaagagcccacaggtgatgagctacca accaagaaggggcggaggaaccgtttcaagtggggcccagcatcccagcagatcctgttccaggc ctatgagaggcagaagaaccctagcaaggaggagcgagagacgctagtggaggagtgcaataggg cggaatgcatccagagaggggtgtccccatcacaggcacaggggctgggctccaacctcgtcacg gaggtgcgtgtctacaactggtttgccaaccggcgcaaagaagaagccttccggcacaagctggc catggacacgtacagcgggccccccccagggccaggccccgggacctgcgctgcccgctcacagct cccctggcctgcctccacctgccctctccccagtaaggtccacggtgtgcgctatggacagcct gcgaccagtgagactgcagaagtaccctcaagcagcggcggtcccttagtgacagtgtctacacc cctccaccaagtgtcccccacgggcctggagcccagccacagcctgctgagtacagaagccaagc tggtctcagcagctgggggccccctcccccctgtcagcaccctgacagcactgcacagcttggag cagacatccccaggcctcaaccagcagccccagaacctcatcatggcctcacttcctggggtcat gaccatcgggcctggtgagcctgcctccctgggtcctacgttcaccaacacaggtgcctccaccc -continued tggtcatcggcctggcctccacgcaggcacagagtgtgccggtcatcaacagcatgggcagcagc ctgaccaccctgcagcccgtccagttctcccagccgctgcacccctcctaccagcagccgctcat gccacctgtgcagagccatgtgacccagagccccttcatggccaccatggctcagctgcagagcc cccacgccctctacagccacaagcccgaggtggcccagtacacccacacgggcctgctcccgcag actatgctcatcaccgacaccaccaacctgagcgccctggccagcctcacgcccaccaagcaggt cttcacctcagacactgaggcctccagtgagtccgggcttcacacgccggcatctcaggccacca ccctccacgtccccagccaggaccctgccggcatccagcacctgcagccggcccaccggctcagc gccagccccacagtgtcctccagcagcctggtgctgtaccagagctcagactccagcaatggcca gagccacctgctgccatccaaccacagcgtcatcgagaccttcatctccacccagatggcctctt cctcccagtaa

*Homo sapiens* forkhead box A3 (FOXA3) (NM_004497.2)
SEQ ID NO: 22 (protein) and SEQ ID NO: 86 (DNA)

(SEQ ID NO: 22)

MLGSVKMEAHDLAEWSYYPEAGEVYSPVTPVPTMAPLNSYMTLNPLSSPYPPGGLPASPLPSGPL

APPAPAAPLGPTFPGLGVSGGSSSSGYGAPGPGLVHGKEMPKGYRRPLAHAKPPYSYISLITMAI

QQAPGKMLTLSEIYQWIMDLFPYYRENQQRWQNSIRHSLSFNDCFVKVARSPDKPGKGSYWALHP

SSGNMFENGCYLRRQKRFKLEEKVKKGGSGAATTTRNGTGSAASTTTPAATVTSPPQPPPPAPEP

EAQGGEDVGALDCGSPASSTPYFTGLELPGELKLDAPYNFNHPFSINNLMSEQTPAPPKLDVGFG

GYGAEGGEPGVYYQGLYSRSLLNAS (SEQ ID NO: 86)

atgctgggctcagtgaagatggaggcccatgacctggccgagtggagctactacccggaggcggg cgaggtctactcgccggtgaccccagtgcccaccatggccccctcaactcctacatgaccctga atcctctaagctctccctatccccctgggggctccctgcctccccactgccctcaggacccctg gcaccccagcacctgcagccccctggggcccactttccaggcctgggtgtcagcggtggcag cagcagctccgggtacggggcccccgggtcctgggctggtgcacgggaaggagatgccgaagggt atcggcggcccctggcacacgccaagccaccgtattcctatatctcactcatcaccatggccatc cagcaggcgccgggcaagatgctgaccttgagtgaaatctaccagtggatcatggacctcttccc ttactacgggagaatcagcagcgctggcagaactccattcgccactcgctgtctttcaacgact gcttcgtcaaggtggcgcgttccccagacaagcctggcaagggtcctactgggccctacacccc agctcagggaacatgtttgagaatggctgctacctgcgccgccagaaacgcttcaagctggagga gaaggtgaaaaaaggggggcagcggggctgccaccaccaccaggaacgggacagggtctgctgcct cgaccaccaccccgcggccacagtcacctccccgcccagccccgcctcagcccctgagcct gaggcccagggcgggaagatgtgggggctctggactgtggctcaccgcttcctccacacccta tttcactggcctggagctcccaggggagctgaagctggacgcgccctacaacttcaaccaccctt tctccatcaacaacctaatgtcagaacagacaccagcacctcccaaactggacgtggggtttggg ggctacggggctgaaggtggggagcctggagtctactaccagggcctctattcccgctcttgct taatgcatcctag

*Homo sapiens* forkhead box A1 (FOXA1) (NM_004496.3)
SEQ ID NO: 23 (protein) and SEQ ID NO: 87 (DNA)

(SEQ ID NO: 23)

MLGTVKMEGHETSDWNSYYADTQEAYSSVPVSNMNSGLGSMNSMNTYMTMNTMTTSGNMTPASFN

MSYANPGLGAGLSPGAVAGMPGGSAGAMNSMTAAGVTAMGTALSPSGMGAMGAQQAASMNGLGPY

AAAMNPCMSPMAYAPSNLGRSRAGGGGDAKTFKRSYPHAKPPYSYISLITMAIQQAPSKMLTLSE

IYQWIMDLFPYYRQNQQRWQNSIRHSLSFNDCFVKVARSPDKPGKGSYWTLHPDSGNMFENGCYL

-continued

RRQKRFKCEKQPGAGGGGGSGSGGSGAKGGPESRKDPSGASNPSADSPLHRGVHGKTGQLEGAPA

PGPAASPQTLDHSGATATGGASELKTPASSTAPPISSGPGALASVPASHPAHGLAPHESQLHLKG

DPHYSFNHPFSINNLMSSSEQQHKLDFKAYEQALQYSPYGSTLPASLPLGSASVTTRSPIEPSAL

EPAYYQGVYSRPVLNTS (SEQ ID NO: 87)
atgctgggctcagtgaagatggaggcccatgacctggccgagtggagctactacccggaggcggg cgaggtctactcgccggtgaccccagtgcccaccatggccccctcaactcctacatgaccctga atcctctaagctctccctatcccctgggggctccctgcctccccactgccctcaggaccctg gcaccccagcacctgcagccccctggggcccactttcccaggcctgggtgtcagcggtggcag cagcagctccgggtacggggcccgggtcctgggctggtgcacgggaaggagatgccgaaggggt atcggcggccctggcacacgccaagccaccgtattcctatatctcactcatcaccatggccatc cagcaggcgccgggcaagatgctgaccttgagtgaaatctaccagtggatcatggacctcttccc ttactacgggagaatcagcagcgctggcagaactccattcgccactcgctgtctttcaacgact gcttcgtcaaggtggcgcgttccccagacaagcctggcaagggctcctactgggccctacacccc agctcagggaacatgtttgagaatggctgctacctgcgccgccagaaacgcttcaagctggagga gaaggtgaaaaaggggggcagcggggctgccaccaccaccaggaacgggacagggtctgctgcct cgaccaccaccccgcggccacagtcacctccccgccccagccccgcctccagccctgagcct gaggcccagggcggggaagatgtgggggctctggactgtggctcacccgcttcctccacacccta tttcactggcctggagctcccaggggagctgaagctggacgcgccctacaacttcaaccaccctt tctccatcaacaacctaatgtcagaacagacaccagcacctcccaaactggacgtggggtttggg ggctacggggctgaaggtggggagcctggagtctactaccagggcctctattcccgctctttgct taatgcatcctag

*Homo sapiens* forkhead box A2 (FOXA2) (NM_021784.4) SEQ ID
NO: 24 (protein) and SEQ ID NO: 88 (DNA)

(SEQ ID NO: 24)
MHSASSMLGAVKMEGHEPSDWSSYYAEPEGYSSVSNMNAGLGMNGMNTYMSMSAAAMGSGSNMS

AGSMNMSSYVGAGMSPSLAGMSPGAGAMAGMGGSAGAAGVAGMGPHLSPSLSPLGGQAAGAMGGL

APYANMNSMSPMYGQAGLSRARDPKTYRRSYTHAKPPYSYISLITMAIQQSPNKMLTLSEIYQWI

MDLFPFYRQNQQRWQNSIRHSLSFNDCFLKVPRSPDKPGKGSFWTLHPDSGNMFENGCYLRRQKR

FKCEKQLALKEAAGAAGSGKKAAAGAQASQAQLGEAAGPASETPAGTESPHSSASPCQEHKRGGL

GELKGTPAAALSPPEPAPSPGQQQQAAAHLLGPPHHPGLPPEAHLKPEHHYAFNHPFSINNLMSS

EQQHHHSHHHHQPHKMDLKAYEQVMHYPGYGSPMPGSLAMGPVTNKTGLDASPLAADTSYYQGVY

SRPIMNSS (SEQ ID NO: 88)
atgcactcggcttccagtatgctgggagcggtgaagatggaagggcacgagccgtccgactggag cagctactatgcagagcccgagggctactcctccgtgagcaacatgaacgccggcctggggatga acggcatgaacacgtacatgagcatgtcggcggccgccatgggcagcggctcgggcaacatgagc gcgggctccatgaacatgtcgtcgtacgtgggcgctggcatgagcccgtccctggcggggatgtc ccccggcgcggggcgccatggcgggcatgggcggctcggccggggcggccggcgtggcgggcatgg ggccgcacttgagtcccagcctgagcccgctcgggggcaggcggccggggccatgggcggcctg gcccctacgccaacatgaactccatgagccccatgtacgggcaggcgggcctgagccgcgcccg cgaccccaagacctacaggcgcagctacacgcacgcaaagccgccctactcgtacatctcgctca tcaccatggccatccagcagagccccaacaagatgctgacgctgagcgagatctaccagtggatc -continued

```
atggacctcttccccttctaccggcagaaccagcagcgctggcagaactccatccgccactcgct ctccttcaacgactgtttcctgaaggtgccccgctcgcccgacaagcccggcaagggctccttct ggaccctgcaccctgactcgggcaacatgttcgagaacggctgctacctgcgccgccagaagcgc ttcaagtgcgagaagcagctggcgctgaaggaggccgcaggcgccgccggcagcggcaagaaggc ggccgccggagcccaggcctcacaggctcaactcggggaggccgccgggccggcctccgagactc cggcgggcaccgagtcgcctcactcgagcgcctcccgtgccaggagcacaagcgaggggcctg ggagagctgaaggggacgccggctgcggcgctgagccccagagccggcgccctctcccgggca gcagcaggccgcggcccacctgctgggccgccccaccaccgggcctgccgcctgaggccc acctgaagccggaacaccactacgccttcaaccacccgttctccatcaacaacctcatgtcctcg gagcagcagcaccaccacagccaccaccaccaaccccacaaaatggacctcaaggcctacga acaggtgatgcactaccccggctacggttcccccatgcctggcagcttggccatgggcccggtca cgaacaaaacgggcctggacgcctcgcccctggccgcagatacctcctactaccaggggggtgtac tcccggcccattatgaactcctcttaa
```

SEQ ID NO: 25: *Homo sapiens* CCAAT/enhancer binding protein (C/EBP), alpha (CEBPA) (NM_001287435.1) SEQ ID NO: 25 (protein) and SEQ ID NO: 89 (DNA)

(SEQ ID NO: 25)
MSSHLQSPPHAPSSAAFGFPRGAGPAQPPAPPAAPEPLGGICEHETSIDISAYIDPAAFNDEFLA

DLFQHSRQQEKAKAAVGPTGGGGGDFDYPGAPAGPGGAVMPGGAHGPPPGYGCAAAGYLDGRLE

PLYERVGAPALRPLVIKQEPREEDEAKQLALAGLFPYQPPPPPPPSHPHPHPPPAHLAAPHLQFQ

IAHCGQTTMHLQPGHPTPPPTPVPSPHPAPALGAAGLPGPGSALKGLGAAHPDLRASGGSGAGKA

KKSVDKNSNEYRVRRERNNIAVRKSRDKAKQRNVETQQKVLELTSDNDRLRKRVEQLSRELDTLR

GIFRQLPESSLVKAMGNCA (SEQ ID NO: 89)
```
atgagcagccacctgcagagccccccgcacgcgcccagcagcgccgccttcggcttccccgggg cgcgggccccgcgcagcctcccgccccacctgccgccccggagccgctgggcggcatctgcgagc acgagacgtccatcgacatcagcgcctacatcgacccggccgccttcaacgacgagttcctggcc gacctgttccagcacagccggcagcaggagaaggccaaggcggccgtgggccccacgggcggcgg cggcggcggcgactttgactaccccggcgcgcccgcgggccccggcggcgccgtcatgcccgggg gagcgcacgggccccgcccggctacggctgcgcggccgccggctacctggacggcaggctggag cccctgtacgagcgcgtcggggcgccggcgctgcggccgctggtgatcaagcaggagccccgcga ggaggatgaagccaagcagctggcgctggccggcctcttcccttaccagccgccgccgccgccgc cgccctcgcacccgcacccgccgcccgcgcacctggccgccccgcacctgcagttccag atcgcgcactgcggccagaccaccatgcacctgcagcccggtcaccccacgccgccgcccacgcc cgtgcccagcccgcaccccgcgccccgcgctcggtgccgccggcctgccgggccctggcagcgcgc tcaaggggctgggcgccgcgcaccccgacctccgcgcgagtggcggcagcggcgcgggcaaggcc aagaagtcggtggacaagaacagcaacgagtaccgggtgcgcgcgagcgcaacaacatcgcggt gcgcaagagccgcgacaaggccaagcagcgcaacgtggagacgcagcagaaggtgctggagctga ccagtgacaatgaccgcctgcgcaagcgggtggaacagctgagccgcgaactggacacgctgcgg ggcatcttccgccagctgccagagagctccttggtcaaggccatgggcaactgcgcgtga
```

*Homo sapiens* Spi-1 proto-oncogene (SPI1) (PU.1) (NM_001080547.1) SEQ ID NO: 26 (protein) and SEQ ID NO: 90 (DNA)

(SEQ ID NO: 26)
MLQACKMEGFPLVPPQPSEDLVPYDTDLYQRQTHEYYPYLSSDGESHSDHYWDFHPHHVHSEFES

-continued

FAENNFTELQSVQPPQLQQLYRHMELEQMHVLDTPMVPPHPSLGHQVSYLPRMCLQYPSLSPAQP

SSDEEEGERQSPPLEVSDGEADGLEPGPGLLPGETGSKKKIRLYQFLLDLLRSGDMKDSIWWVDK

DKGTFQFSSKHKEALAHRWGIQKGNRKKMTYQKMARALRNYGKTGEVKKVKKKLTYQFSGEVLGR

GGLAERRHPPH (SEQ ID NO: 90)
atgttacaggcgtgcaaaatggaagggtttcccctcgtccccccctcagccatcagaagacctggt gccctatgacacggatctataccaacgccaaacgcacgagtattaccccctatctcagcagtgatg gggagagccatagcgaccattactgggacttccaccccaccacgtgcacagcgagttcgagagc ttcgccgagaacaacttcacggagctccagagcgtgcagccccgcagctgcagcagctctaccg ccacatggagctggagcagatgcacgtcctcgataccccatggtgccaccccatcccagtcttg gccaccaggtctcctacctgccccggatgtgcctccagtacccatccctgtcccagcccagccc agctcagatgaggaggagggcgagcggcagagccccccactggaggtgtctgacggcgaggcgga tggcctggagcccgggcctgggctcctgcctggggagacaggcagcaagaagaagatccgcctgt accagttcctgttggacctgctccgcagcggcgacatgaaggacagcatctggtgggtggacaag gacaagggcaccttccagttctcgtccaagcacaaggaggcgctggcgcaccgctggggcatcca gaagggcaaccgcaagaagatgacctaccagaagatggcgcgcgcgctgcgcaactacggcaaga cgggcgaggtcaagaaggtgaagaagaagctcacctaccagttcagcggcgaagtgctgggccgc gggggcctggccgagcggcgccacccgccccactga

*Homo sapiens* POU class 3 homeobox 2 (POU3F2) (Brn2)
(NM_005604.3) SEQ ID NO: 27 (protein) and SEQ ID NO: 91 (DNA)

(SEQ ID NO: 27)
MATAASNHYSLLTSSASIVHAEPPGGMQQGAGGYREAQSLVQGDYGALQSNGHPLSHAHQWITAL

SHGGGGGGGGGGGGGGGGGGGGDGSPWSTSPLGQPDIKPSVVVQQGGRGDELHGPGALQQQHQQ

QQQQQQQQQQQQQQQQQQQRPPHLVHHAANHHPGPGAWRSAAAAAHLPPSMGASNGGLLYSQPSF

TVNGMLGAGGQPAGLHHHGLRDAHDEPHHADHHPHPHSHPHQQPPPPPPQGPPGHPGAHHDPHS

DEDTPTSDDLEQFAKQFKQRRIKLGFTQADVGLALGTLYGNVFSQTTICRFEALQLSFKNMCKLK

PLLNKWLEEADSSSGSPTSIDKIAAQGRKRKKRTSIEVSVKGALESHFLKCPKPSAQEITSLADS

LQLEKEVVRVWFCNRRQKEKRMTPPGGTLPGAEDVYGGSRDTPPHHGVQTPVQ (SEQ ID NO: 91)
atggcgaccgcagcgtctaaccactacagcctgctcacctccagcgcctccatcgtgcacgccga gccgcccggcggcatgcagcagggcgcgggggggctaccgcgaagcgcagagcctggtgcagggcg actacggcgctctgcagagcaacggacacccgctcagccacgctcaccagtggatcaccgcgctg tcccacggcggcggcggcggggggcggtggcggcggcgggggggcggggcggcggcgggggcgg cggcgacggctccccgtggtccaccagccccctgggccagcggacatcaagccctcggtggtgg tgcagcagggcggccgcggagacgagctgcacgggccaggcgccctgcagcagcagcatcagcag cagcaacagcaacagcagcagcaacagcagcaacagcagcagcagcagcaacagcggccgcc gcatctggtgcaccacgccgctaaccaccacccgggacccggggcatggcggagcgcggcggctg cagcgcacctcccaccctccatgggagcgtccaacgcggcttgctctactcgcagcccagcttc acggtgaacggcatgctgggcgccggcgggcagccggccggtctgcaccaccacggcctgcggga cgcgcacgacgagccacaccatgccgaccaccacccgcacccgcactcgcacccacaccagcagc cgccgccccgccgcccccgcagggtccgcctggccacccaggcgcgcaccacgacccgcactcg gacgaggacacgccgacctcggacgacctggagcagttcgccaagcagttcaagcagcggcggat caaactgggatttacccaagcggacgtggggctggctctgggcaccctgtatggcaacgtgttct -continued

```
cgcagaccaccatctgcaggtttgaggccctgcagctgagcttcaagaacatgtgcaagctgaag cctttgttgaacaagtggttggaggaggcggactcgtcctcgggcagccccacgagcatagacaa gatcgcagcgcaagggcgcaagcggaaaaagcggacctccatcgaggtgagcgtcaaggggctc tggagagccatttcctcaaatgccccaagccctcggcccaggagatcacctccctcgcggacagc ttacagctggagaaggaggtggtgagagtttggttttgtaacaggagacagaaagagaaaggat gaccctcccggagggactctgccgggcgccgaggatgtgtacgggggagtagggacactccac cacaccacggggtgcagacgcccgtccagtga
```

Homo sapiens forkhead box G1 (FOXG1) (NM_005249.4)
SEQ ID NO: 28 (protein) and SEQ ID NO: 92 (DNA)

(SEQ ID NO: 28)

```
MLDMGDRKEVKMIPKSSFSINSLVPEAVQNDNHHASHGHHNSHHPQHHHHHHHHHHPPPPAPQP

PPPPQQQQPPPPPPPAPQPPQTRGAPAADDDKGPQQLLLPPPPPPPPAAALDGAKADGLGGKGEP

GGGPGELAPVGPDEKEKGAGAGGEEKKGAGEGGKDGEGGKEGEKKNGKYEKPPFSYNALIMMAIR

QSPEKRLTLNGIYEFIMKNFPYYRENKQGWQNSIRHNLSLNKCFVKVPRHYDDPGKGNYWMLDPS

SDDVFIGGTTGKLRRRSTTSRAKLAFKRGARLTSTGLTFMDRAGSLYWPMSPFLSLHHPRASSTL

SYNGTTSAYPSHPMPYSSVLTQNSLGNNHSFSTANGLSVDRLVNGEIPYATHHLTAAALAASVPC

GLSVPCSGTYSLNPCSVNLLAGQTSYFFPHVPHPSMTSQSSTSMSARAASSSTSPQAPSTLPCES

LRPSLPSFTTGLSGGLSDYFTHQNQGSSSNPLIH
```

(SEQ ID NO: 92)

```
atgctggacatgggagataggaaagaggtgaaaatgatccccaagtcctcgttcagcatcaacag cctggtgcccgaggcggtccagaacgacaaccaccacgcgagccacggccaccacaacagccacc acccccagcaccaccaccaccaccaccatcaccaccaccccgccgccgcccgccccgcaaccg ccgccgccgccgcagcagcagcagccgccgccgccgccgcccccggcaccgcagcccccccagac gcggggcgccccggccgccgacgacgacaagggccccagcagctgctgctcccgccgccgccac cgccaccaccggccgccgccctggacggggctaaagcggacgggctgggcggcaaggggcgagccg ggcggcgggccgggggagctggcgcccgtcgggccggacgagaaggagaagggcgccggcgccgg ggggaggagaagaaggggcgggcgagggcggcaaggacggggaggggggcaaggagggcgaga agaagaacggcaagtacgagaagccgccgttcagctacaacgcgctcatcatgatggccatccgg cagagccccgagaagcggctcacgctcaacggcatctacgagttcatcatgaagaacttcccctta ctaccgcgagaacaagcagggctggcagaactccatccgccacaatctgtccctcaacaagtgct tcgtgaaggtgccgcgccactacgacgacccgggcaagggcaactactggatgctggacccgtcg agcgacgacgtgttcatcggcggcaccacgggcaagctgcggcgccgctccaccacctcgcgggc caagctggccttcaagcgcggtgcgcgcctcacctccaccggcctcaccttcatggaccgcgccg gctccctctactggcccatgtcgcccttcctgtccctgcaccaccccgcgccagcagcactttg agttacaacggcaccacgtcggcctaccccagccaccccatgccctacagctccgtgttgactca gaactcgctgggcaacaaccactccttctccaccgccaacggcctgagcgtggaccggctggtca acggggagatcccgtacgccacgcaccacctcacggccgccgcgctagccgcctcggtgccctgc ggcctgtcggtgccctgctctgggacctactccctcaacccctgctccgtcaacctgctcgcggg ccagaccagttactttttcccccacgtcccgcacccgtcaatgacttcgcagagcagcacgtcca tgagcgccagggccgcgtcctcctccacgtcgccgcaggcccctcgaccctgccctgtgagtct ttaagaccctctttgccaagttttacgacgggactgtctgggggactgtctgattatttcacaca tcaaaatcaggggtcttcttccaacccttaatacattaa
```

Homo sapiens mRNA for ASC1 protein (SLC7A10 gene) (AJ277731.1)

-continued

SEQ ID NO: 29 (protein) and SEQ ID NO: 93 (DNA)

(SEQ ID NO: 29)
MAGHTQQPSGRGNPRPAPSPSPVPGTVPGASERVALKKEIGLLSACTIIIGNIIGSGIFISPKGV
LEHSGSVGLALFVWVLGGGVTALGSLCYAELGVAIPKSGGDYAYVTEIFGGLAGFLLLWSAVLIM
YPTSLAVISMTFSNYVLQPVFPNCIPPTTASRVLSMACLMLLTWVNSSSVRWATRIQDMFTGGKL
LALSLIIGVGLLQIFQGHFEELRPSNAFAFWMTPSVGHLALAFLQGSFAFSGWNFLNYVTEEMVD
ARKNLPRAIFISIPLVTFVYTFTNIAYFTAMSPQELLSSNAVAVTFGEKLLGYFSWVMPVSVALS
TFGGINGYLFTYSRLCFSGAREGHLPSLLAMIHVRHCTPIPALLVCCGATAVIMLVGDTYTLINY
VSFINYLCYGVTILGLLLLRWRRPALHRPIKVNLLIPVAYLVFWAFLLVFSFISEPMVCGVGVII
ILTGVPIFFLGVFWRSKPKCVHRLTESMTHWGQELCFVVYPQDAPEEEENGPCPPSLLPATDKPS
KPQ (SEQ ID NO: 93)
atggccggccacacgcagcagccgagcgggcgcgggaaccccaggcctgcgccctcgccctccc
agtcccaggaccgtccccggcgcctcggagcgggtggcgctcaagaaggagatcgggctgctga
gcgcctgcaccatcatcatcgggaacatcatcggctcgggcatcttcatctcgcccaagggggtc
ctggagcactcaggctccgtgggtctggccctgttcgtctgggtcctgggtgggggcgtgacggc
tctgggctccctctgctatgcagagctgggagtcgccatccccaagtctggcggggactacgcct
acgtcacagagatcttcggggggcctggctggctttctgctgctctggagcgccgtcctcatcatg
taccccaccagccttgctgtcatctccatgaccttctccaactacgtgctgcagcccgtgttccc
caactgcatccccccaccacagcctcccgggtgctgtccatggcctgcctgatgctcctgacat
gggtgaacagctccagtgtgcgctgggccacgcgcatccaggacatgttcacaggcgggaagctg
ctggccttgtccctcatcatcggcgtgggccttctccagatcttccaaggacacttcgaggagct
gaggcccagcaatgcctttgctttctggatgacgccctccgtgggacacctggccctggccttcc
tccagggctccttcgccttcagtggctggaacttcctcaactatgtcaccgaggagatggttgac
gcccgaaagaacctacctcgcgccatcttcatctccatcccactggtgaccttcgtgtacacgtt
caccaacattgcctacttcacggccatgtcccccaggagctgctcctccaatgcggtggctg
tgaccttcggggagaagctgctgggctacttttcttgggtcatgcctgtctccgtggctctgtca
accttcggagggatcaatggttacctgttcacctactccaggctgtgcttctctggagcccgcga
ggggcacctgcccagcctgctggccatgatccacgtcagacactgcaccccatccccgccctcc
tcgtctgttgcggggccacagccgtcatcatgctcgtgggcgacacgtacacgctcatcaactat
gtgtccttcatcaactacctctgctacggcgtcaccatcctgggcctgctgctgctgcgctggag
gcggcctgcactccacaggcccatcaaggtgaaccttctcatcccgtggcgtacttggtcttct
gggccttcctgctggtcttcagcttcatctcagagcctatggtctgtggggtcggcgtcatcatc
atccttacgggggtgcccattttctttctgggagtgttctggagaagcaaaccaaagtgtgtgca
cagactcacagagtccatgacacactgggccaggagctgtgtttcgtggtctaccccagga cg
cccccgaagaggaggagaatggcccctgcccaccctccctgctgcctgccacagacaagccctcg
aagccacaatga

*Homo sapiens* achaete-scute family bHLH transcription factor 1
(ASCL1) (NM_004316.3) SEQ ID NO: 30 (protein) and SEQ ID NO: 94
(DNA)

(SEQ ID NO: 30)
MESSAKMESGGAGQQPQPQPQQPFLPPAACFFATAAAAAAAAAAAAAAQSAQQQQQQQQQQAPQ
LRPAADGQPSGGGHKSAPKQVKRQRSSSPELMRCKRRLNFSGFGYSLPQQQPAAVARRNERERNR
VKLVNLGFATLREHVPNGAANKKMSKVETLRSAVEYIRALQQLLDEHDAVSAAFQAGVLSPTISP

-continued

NYSNDLNSMAGSPVSSYSSDEGSYDPLSPEEQELLDFTNWF (SEQ ID NO: 94)
atggaaagctctgccaagatggagagcggcggcgccggccagcagccccagccgcagccccagca gcccttcctgccgcccgcagcctgtttctttgccacggccgcagccgcggcggccgcagccgccg cagcggcagcgcagagcgcgcagcagcagcagcagcagcagcagcagcagcagcaggcgccgcag ctgagaccggcggccgacggccagccctcaggggcggtcacaagtcagcgcccaagcaagtcaa gcgacagcgctcgtcttcgcccgaactgatgcgctgcaaacgccggctcaacttcagcggctttg gctacagcctgccgcagcagcagccggccgccgtggcgcgccgcaacgagcgcgagcgcaaccgc gtcaagttggtcaacctgggctttgccacccttcgggagcacgtccccaacggcgcggccaacaa gaagatgagtaaggtggagacactgcgctcggcggtcgagtacatccgcgcgctgcagcagctgc tggacgagcatgacgcggtgagcgccgccttccaggcaggcgtcctgtcgcccaccatctccccc aactactccaacgacttgaactccatggccggctcgccggtctcatcctactcgtcggacgaggg ctcttacgacccgctcagccccgaggagcaggagcttctcgacttcaccaactggttctga

*Homo sapiens* Nurr1 gene (AB017586) SEQ ID NO: 31 (protein) and
SEQ ID NO: 95 (DNA)

(SEQ ID NO: 31)
MPCVQAQYGSSPQGASPASQSYSYHSSGEYSSDFLTPEFVKFSMDLTNTEITATTSLPSFSTFMD

NYSTGYDVKPPCLYQMPLSGQQSSIKVEDIQMHNYQQHSHLPPQSEEMMPHSGSVYYKPSSPPTP

TTPGFQVQHSPMWDDPGSLHNFHQNYVATTHMIEQRKTPVSRLSLFSFKQSPPGTPVSSCQMRFD

GPLHVPMNPEPAGSHHVVDGQTFAVPNPIRKPASMGFPGLQIGHASQLLDTQVPSPPSRGSPSNE

GLCAVCGDNAACQHYGVRTCEGCKGFFKRTVQKNAKYVCLANKNCPVDKRRRNRCQYCRFQKCLA

VGMVKEVVRTDSLKGRRGRLPSKPKSPQEPSPPSPPVSLISALVRAHVDSNPAMTSLDYSRFQAN

PDYQMSGDDTQHIQQFYDLLTGSMEIIRGWAEKIPGFADLPKADQDLLFESAFLELFVLRLAYRS

NPVEGKLIFCNGVVLHRLQCVRGFGEWIDSIVEFSSNLQNMNIDISAFSCIAALAMVTERHGLKE

PKRVEELQNKIVNCLKDHVTFNNGGLNRPNYLSKLLGKLPELRTLCTQGLQRIFYLKLEDLVPPP

AIIDKLFLDTLPF (SEQ ID NO: 95)
atgccttgtgttcaggcgcagtatgggtcctcgcctcaaggagccagccccgcttctcagagcta cagttaccactcttcgggagaatacagctccgatttcttaactccagagtttgtcaagtttagca tggacctcaccaacactgaaatcactgccaccacttctctcccagcttcagtacctttatggac aactacagcacaggctacgacgtcaagccaccttgcttgtaccaaatgcccctgtccggacagca gtcctccattaaggtagaagacattcagatgcacaactaccagcaacacagccacctgccccccc agtctgaggagatgatgccgcactccgggtcggtttactacaagccctcctcgcccccgacgccc accacccgggcttccaggtgcagcacagccccatgtgggacgacccgggatctctccacaactt ccaccagaactacgtggccactacgcacatgatcgagcagaggaaaacgccagtctcccgcctct ccctcttctcctttaagcaatcgcccctggcaccccggtgtctagttgccagatgcgcttcgac gggcccctgcacgtccccatgaacccggagccgccggcagccaccacgtggtggacgggcagac cttcgctgtgcccaaccccattcgcaagcccgcgtccatgggcttcccgggcctgcagatcggcc acgcgtctcagctgctcgacacgcaggtgccctcaccgccgtcgcggggctccccctccaacgag gggctgtgcgctgtgtgtgggacaacgcggcctgccaacactacggcgtgcgcacctgtgaggg ctgcaaaggcttctttaagcgcacagtgcaaaaaaatgcaaaatacgtgtgtttagcaaataaaa actgcccagtggacaagcgtcgccggaatcgctgtcagtactgccgatttcagaagtgcctggct gttgggatggtcaaagaagtggttcgcacagacagtttaaaaggccggagaggtcgtttgccctc -continued

```
gaaaccgaagagcccacaggagccctctcccccttcgccccggtgagtctgatcagtgccctcg tcagggcccatgtcgactccaacccggctatgaccagcctggactattccaggttccaggcgaac cctgactatcaaatgagtggagatgacacccagcatatccagcaattctatgatctcctgactgg ctccatggagatcatccggggctgggcagagaagatccctggcttcgcagacctgcccaaagccg accaagacctgcttttgaatcagctttcttagaactgtttgtccttcgattagcatacaggtcc aacccagtggagggtaaactcatcttttgcaatgggtggtcttgcacaggttgcaatgcgttcg tggctttggggaatggattgattccattgttgaattctcctccaacttgcagaatatgaacatcg acatttctgccttctcctgcattgctgccctggctatggtcacagagagacacgggctcaaggaa cccaagagagtggaagaactgcaaaacaagattgtaaattgtctcaaagaccacgtgactttcaa caatggggggttgaaccgccccaattatttgtccaaactgttggggaagctcccagaacttcgta cccttttgcacacaggggctacagcgcattttctacctgaaattgaagacttggtgccaccgcca gcaataattgacaaacttttcctggacactttacctttctaa
```

SEQ ID NO: 32: *Homo sapiens* neurogenin 2 (NEUROG2) (NM_024019)
SEQ ID NO: 32 (protein) and SEQ ID NO: 96 (DNA)

(SEQ ID NO: 32)
MFVKSETLELKEEEDVLVLLGSASPALAALTPLSSSADEEEEEEPGASGGARRQRGAEAGQGARG
GVAAGAEGCRPARLLGLVHDCKRRPSRARAVSRGAKTAETVQRIKKTRRLKANNRERNRMHNLNA
ALDALREVLPTFPEDAKLTKIETLRFAHNYIWALTETLRLADHCGGGGGGLPGALFSEAVLLSPG
GASAALSSSGDSPSPASTWSCTNSPAPSSSVSSNSTSPYSCTLSPASPAGSDMDYWQPPPPDKHR
YAPHLPIARDCI (SEQ ID NO: 96)
```
atgttcgtcaaatccgagaccttggagttgaaggaggaagaggacgtgttagtgctgctcggatc ggcctcccccgccttggcggccctgaccccgctgtcatccagcgccgacgaagaagaggaggagg agccgggcgcgtcaggcggggcgcgtcggcagcgcggggctgaggccgggcaggggcgcgggc ggcgtggctgcgggtgcggagggctgccggcccgcacggctgctgggtctggtacacgattgcaa acggcgcccttccagggcgcgggccgtctcccgaggcgccaagacggccgagacggtgcagcgca tcaagaagacccgtagactgaaggccaacaaccgcgagcgaaaccgcatgcacaacctcaacgcg gcactggacgcgctgcgcgaggtgctccccacgttccccgaggacgccaagctcaccaagatcga gaccctgcgcttcgcccacaactacatctgggcactcaccgagaccctgcgcctggcggatcact gcgggggcggcggcggggcctgccggggcgctcttctccgaggcagtgttgctgagcccggga ggagccagcgccgccctgagcagcagcggagacagcccctcgcccgcctccacgtggagttgcac caacagccccgcgccgtcctcctccgtgtcctccaattccacctcccctacagctgcactttat cgcccgccagcccggccgggtcagacatggactattggcagcccccacctcccgacaagcaccgc tatgcacctcacctccccatagccagggattgtatctag
```

*Homo sapiens* LIM homeobox transcription factor 1, alpha (LMX1A)
(NM_177398) SEQ ID NO: 33 (protein) and SEQ ID NO: 97 (DNA)

(SEQ ID NO: 33)
MLDGLKMEENFQSAIDTSASFSSLLGRAVSPKSVCEGCQRVILDRFLLRLNDSFWHEQCVQCASC
KEPLETTCFYRDKKLYCKYDYEKLFAVKCGGCFEAIAPNEFVMRAQKSVYHLSCFCCCVCERQLQ
KGDEFVLKEGQLLCKGDYEKERELLSLVSPAASDSGKSDDEESLCKSAHGAGKGTAEEGKDHKRP
KRPRTILTTQQRRAFKASFEVSSKPCRKVRETLAAETGLSVRVVQVWFQNQRAKMKKLARRQQQQ
QQDQQNTQRLSSAQTNGGGSAGMEGIMNPYTALPTPQQLLAIEQSVYSSDPFRQGLTPPQMPGDH
MHPYGAEPLFHDLDSDDTSLSNLGDCFLATSEAGPLQSRVGNPIDHLYSMQNSYFTS (SEQ ID NO: 97)
atgctggacggcctaaagatggaggagaacttccaaagcgcgatcgacacctcggcctccttctc -continued

```
ctcgctgctgggcagagcggtgagccccaagtctgtctgcgagggctgtcagcgggtcatcttgg acaggtttctgctgcggctcaacgacagcttctggcatgagcagtgcgtgcagtgcgcctcctgc aaagagcccctggagaccacctgcttctaccgggacaagaagctgtactgcaagtatgactacga gaagctgtttgctgttaaatgtgggggctgcttcgaggccatcgctcccaatgagtttgttatgc gggcccagaagagtgtataccacctgagctgcttctgctgctgtgtctgcgagcgacagcttcag aagggtgatgagtttgtcctgaaggaggggcagctgctctgcaaaggggactatgagaaggagcg ggagctgctcagcctggtgagcccagcagcctcagactcaggtaaaagtgatgatgaagaaagtc tctgcaagtcagcccatggggcagggaaaggaactgctgaggaaggcaaggaccataagcgcccc aaacgtccgagaaccatcttgacaactcaacagaggcgagcattcaaggcctcatttgaagtatc ctccaagccctgcaggaaggtgagagagactctggctgcagagacagggctgagtgtccgtgtcg tccaggtgtggttccaaaaccagagagcgaagatgaagaagctggccaggcgacagcagcagcag cagcaagatcagcagaacacccagaggctgagctctgctcagacaaacggtggtgggagtgctgg gatggaaggaatcatgaaccccctacacggctctgcccaccccacagcagctcctggccatcgagc agagtgtctacagctcagatcccttccgacagggtctcaccccaccccagatgcctggagaccac atgcacccttatggtgccgagccccttttccatgacctggatagcgacgacacctccctcagtaa cctgggtgattgtttcctagcaacctcagaagctgggcctctgcagtccagagtgggaaacccca ttgaccatctgtactccatgcagaattcttacttcacatcttga
```

Homo sapiens HB9 homeobox gene, (U07663) SEQ ID NO: 34
(protein) and SEQ ID NO: 98 (DNA)

(SEQ ID NO: 34)
MEKSKNFRIEPCWRWTPHEPPLAERALAKVTSPPVPASGTGGGGGGGASGGTSGSCSPASSEPP

AAPADRLRAESPSPPRLLAAHCALLPKPGFLGAGGGGGTGGGHGGPHHHAHPGAAAAAAAAAA

AAAAAGGLALGLHPGGAQGGAGLPAQAALYGHPVYGYSAAAAAAALAGQHPALSYSYPQVQGAHP

AHPPADPIKLGAGTFQLDQWLRATAGMILPKMPDFNSQAQSNLLGKCRRPRTAFTSQQLLELEHQF

KFNKYLSRPKRFEVATSLMLTETQVKIWFQNRRMKWKRSKKAKEQAAQEAEKQKGGGGGAGKGGA

EEPGAEELLGPPAPRDKGSGPPADLRDSDPEEDEDEDDEDHFPYSNGASVHAASSDCSSEDDSPP

PRPSHQPAPQ (SEQ ID NO: 98)
```
atggaaaaatccaaaaatttccgcatcgagccctgctggcggtggacccccacgagccgcctct cgcagagcgcgcgctggccaaggtcacgtcgccgcccgtgcccgcatctggcaccggaggtggcg gcggcggcggcggggcgagcggcgggactagcggcagctgcagccccgcgtcctcggagccgccg gctgcgcccgccgaccgcctgcgcgccgagagcccgtcgccgccgcgcctgctggccgcgcactg cgcgctgctgcccaagccgggcttcctgggcgcgggcggcggcggcggcggcacgggcggcgggc acggggggcccaccaccacgcgcatccgggcgcagcggccgctgccgccgccgccgccgccgcc gccgccgccgccgctggggcctggcgctgggctgcaccctggggcgcgcagggcggcgcggg cctcccggcgcaggcggcgctctacggccacccggtctacggctactccgcggcggcggcggcgg ctgcgctggcgggccagcacccggcgctctcctactcgtacccgcaggtgcaaggcgcgcacccc gcgcaccccgccgacccatcaagctgggcgccggcaccttccagctggaccagtggctgcgcgc gtccaccgcgggcatgatcctgcctaagatgcccgacttcaact
```

Homo sapiens LIM homeobox 3 (LHX3) (NM_178138) SEQ ID NO: 35
(protein) and SEQ ID NO: 99 (DNA)

(SEQ ID NO: 35)
MLLETGLERDRARPGAAAVCTLGGTREIPLCAGCDQHILDRFILKALDRHWHSKCLKCSDCHTPL

AERCFSRGESVYCKDDFFKRFGTKCAACQLGIPPTQVVRRAQDFVYHLHCFACVVCKRQLATGDE

-continued

FYLMEDSRLVCKADYETAKQREAEATAKRPRTTITAKQLETLKSAYNTSPKPARHVREQLSSETG
LDMRVVQVWFQNRRAKEKRLKKDAGRQRWGQYFRNMKRSRGGSKSDKDSVQEGQDSDAEVSFPDE
PSLAEMGPANGLYGSLGEPTQALGRPSGALGNFSLEHGGLAGPEQYRELRPGSPYGVPPSPAAPQ
SLPGPQPLLSSLVYPDTSLGLVPSGAPGGPPPMRVLAGNGPSSDLSTGSSGGYPDFPASPASWLD
EVDHAQF (SEQ ID NO: 99)
atgctgctggaaacgggctcgagcgcgaccgagcgaggcccggggccgccgccgtctgcacctt
gggcggga ctcgggagatcccgctgtgcgctggctgtgaccagcacatcctggaccgcttcatcc
tcaaggctctggaccgccactggcacagcaagtgtctcaagtgcagcgactgccacacgccactg
gccgagcgctgcttcagccgaggggagagcgtttactgcaaggacgactttttcaagcgcttcgg
gaccaagtgcgccgcgtgccagctgggcatcccgcccacgcaggtggtgcgccgcgcccaggact
tcgtgtaccacctgcactgctttgcctgcgtcgtgtgcaagcggcagctggccacgggcgacgag
ttctacctcatggaggacagccggctcgtgtgcaaggcggactacgaaaccgccaagcagcgaga
ggccgaggccacggccaagcggccgcgcacgaccatcaccgccaagcagctggagacgctgaaga
gcgcttacaacacctcgcccaagccggcgcgcacgtgcgcgagcagctctcgtccgagacgggc
ctggacatgcgcgtggtgcaggtttggttccagaaccgccgggccaaggagaagaggctgaagaa
ggacgccggccggcagcgctggggcagtatttccgcaacatgaagcgctcccgcggcggctcca
agtcggacaaggacagcgttcaggaggggcaggacagcgacgctgaggtctccttccccgatgag
ccttccttggcggaaatgggcccggccaatggcctctacgggagcttgggggaacccacccaggc
cttgggccggccctcgggagccctgggcaacttctccctggagcatggaggcctggcaggcccag
agcagtaccgagagctgcgtcccggcagccctacggtgtcccccatccccgccgcccgcag
agcctccctggccccagcccctcctctccagcctggtgtacccagacaccagcttgggccttgt
gccctcgggagccccggcgggccccacccatgagggtgctggcagggaacggacccagttctg
acctatccacggggagcagcggggttaccccgacttccctgccagccccgcctctggctggat
gaggtagaccacgctcagttctga

*Homo sapiens* distal-less homeobox 2 (DLX2) (NM_004405)
SEQ ID NO: 36 (protein) and SEQ ID NO: 100 (DNA)

(SEQ ID NO: 36)
MTGVFDSLVADMHSTQIAASSTYHQHQQPPSGGGAGPGGNSSSSSLHKPQESPTLPVSTATDSS
YYTNQQHPAGGGGGGGSPYAHNGSYQYQASGLNNVPYSAKSSYDLGYTAAYTSYAPYGTSSSPAN
NEPEKEDLEPEIRIVNGKPKKVRKPRTIYSSFQLAALQRRFQKTQYLALPERAELAASLGLTQTQ
VKIWFQNRRSKFKKMWKSGEIPSEQHPGASASPPCASPPVSAPASWDFGVPQRMAGGGGPGSGGS
GAGSSGSSPSSAASAFLGNYPWYHQTSGSASHLQATAPLLHPTQTPQPHHHHHHGGGGAPVSAG
TIF (SEQ ID NO: 100)
atgactggagtctttgacagtctagtggctgatatgcactcgacccagatcgccgcctccagcac
gtaccaccagcaccagcagcccccgagcggcggcggcgccgccgggtggcaacagcagcagca
gcagcagcctccacaagccccaggagtcgcccaccttccggtgtccaccgccaccgacagcagc
tactacaccaaccagcagcacccggcgggcggcggcggcggcggggggctcgccctacgcgcacat
gggttcctaccagtaccaagccagcggcctcaacaacgtcccttactccgccaagagcagctatg
acctgggctacaccgccgcctacacctcctacgctcctatggaaccagttcgtccccagccaac
aacgagcctgagaaggaggaccttgagcctgaaattcggatagtgaacgggaagccaaagaaagt
ccggaaaccccgcaccatctactccagtttccagctggcggctcttcagcggcgtttccaaaaga -continued

```
ctcaatacttggccttgccggagcgagccgagctggcggcctctctgggcctcacccagactcag gtcaaaatctggttccagaaccgccggtccaagttcaagaagatgtggaaaagtggtgagatccc ctcggagcagcaccctggggccagcgcttctccaccttgtgcttcgccgccagtctcagcgccgg cctcctgggactttggtgtgccgcagcggatggcgggcggcggtggtccgggcagtggcggcagc ggcgccggcagctagggctccagcccgagcagcgcggcctcggcttttctgggcaactacccctg gtaccaccagacctcgggatccgcctcacacctgcaggccacggcgccgctgctgcaccccactc agaccccgcagccgcatcaccaccaccaccatcacggcggcgggggcgcccggtgagcgcgggg acgattttctaa
```

Homo sapiens runt-related transcription factor 2 (RUNX2) (NM_001024630) SEQ ID NO: 37 (protein) and SEQ ID NO: 101 (DNA)

(SEQ ID NO: 37)
```
MASNSLFSTVTPCQQNFFWDPSTSRRFSPPSSSLQPGKMSDVSPVVAAQQQQQQQQQQQQQQQQQ
QQQQQQEAAAAAAAAAAAAAAAAAAAVPRLRPPHDNRTMVEIIADHPAELVRTDSPNFLCSVLPSHW
RCNKTLPVAFKVVALGEVPDGTVVTVMAGNDENYSAELRNASAVMKNQVARFNDLRFVGRSGRGK
SFTLTITVFTNPPQVATYHRAIKVTVDGPREPRRHRQKLDDSKPSLFSDRLSDLGRIPHPSMRVG
VPPQNPRPSLNSAPSPFNPQGQSQITDPRQAQSSPPWSYDQSYPSYLSQMTSPSIHSTTPLSSTR
GTGLPAITDVPRRISDDDTATSDFCLWPSTLSKKSQAGASELGPFSDPRQFPSISSLTESRFSNP
RMHYPATFTYTPPVTSGMSLGMSATTHYHTYLPPPYPGSSQSQSGPFQTSSTPYLYYGTSSGSYQ
FPMVPGGDRSPSRMLPPCTTTSNGSTLLNPNLPNQNDGVDADGSHSSSPTVLNSSGRMDESVWRP
Y
```

(SEQ ID NO: 101)
```
atggcatcaaacagcctcttcagcacagtgacaccatgtcagcaaaacttcttttgggatccgag caccagccggcgcttcagccccccctccagcagcctgcagcccggcaaaatgagcgacgtgagcc cggtggtggctgcgcaacagcagcagcaacagcagcagcagcaacagcagcagcagcagcaa cagcagcagcagcaggaggcggcggcggcggctgcggcggcggcggcggctgcggcggcggc agctgcagtgccccggttgcggccgccccacgacaaccgcaccatggtggagatcatcgccgacc accaggccgaactcgtccgcaccgacagccccaacttcctgtgctcggtgctgccctcgcactgg cgctgcaacaagaccctgcccgtggccttcaaggtggtagccctcggagaggtaccagatgggac tgtggttactgtcatggcgggtaacgatgaaaattattctgctgagctccggaatgcctctgctg ttatgaaaaaccaagtagcaaggttcaacgatctgagatttgtgggccggagtggacgaggcaag agtttcaccttgaccataaccgtcttcacaaatcctccccaagtagctacctatcacagagcaat taaagttacagtagatggacctcgggaacccagaaggcacagacagaagcttgatgactctaaac ctagtttgttctctgaccgcctcagtgatttagggcgcattcctcatcccagtatgagagtaggt gtcccgcctcagaacccacggccctccctgaactctgcaccaagtccttttaatccacaaggaca gagtcagattacagaccccaggcaggcacagtcttccccgccgtggtcctatgaccagtcttacc cctcctacctgagccagatgacgtccccgtccatccactctaccacccgctgtcttccacacgg ggcactgggcttcctgccatcaccgatgtgcctaggcgcatttcagatgatgacactgccacctc tgacttctgcctctggccttccactctcagtaagaagagccaggcaggtgcttcagaactgggcc cttttttcagaccccaggcagttcccaagcatttcatccctcactgagagccgcttctccaaccca cgaatgcactatccagccaccttacttacaccccgccagtcacctcaggcatgtccctcggtat gtccgccaccactcactaccacacctacctgccaccaccctaccccggctcttcccaaagccaga gtggacccttccagaccagcagcactccatatctctactatggcacttcgtcaggatcctatcag
```

-continued tttcccatggtgccgggggagaccggtctccttccagaatgcttccgccatgcaccaccacctc gaatggcagcacgctattaaatccaaatttgcctaaccagaatgatggtgttgacgctgatggaa gccacagcagttccccaactgttttgaattctagtggcagaatggatgaatctgtttggcgacca tattga

*Homo sapiens* SRY (sex determining region Y)-box 5 (SOX5)
(NM_006940) SEQ ID NO: 38 (protein) and SEQ ID NO: 102 (DNA)

(SEQ ID NO: 38)
MLTDPDLPQEFERMSSKRPASPYGEADGEVAMVTSRQKVEEEESDGLPAFHLPLHVSFPNKPHSE

EFQPVSLLTQETCGHRTPTSQHNTMEVDGNKVMSSFAPHNSSTSPQKAEEGGRQSGESLSSTALG

TPERRKGSLADVVDTLKQRKMEELIKNEPEETPSIEKLLSKDWKDKLLAMGSGNFGEIKGTPESL

AEKERQLMGMINQLTSLREQLLAAHDEQKKLAASQIEKQRQQMELAKQQQEQIARQQQQLLQQQH

KINLLQQQIQVQGQLPPLMIPVFPPDQRTLAAAAQQGFLLPPGFSYKAGCSDPYPVQLIPTTMAA

AAAATPGLGPLQLQQLYAAQLAAMQVSPGGKLPGIPQGNLGAAVSPTSIHTDKSTNSPPPKSKDE

VAQPLNLSAKPKTSDGKSPTSPTSPHMPALRINSGAGPLKASVPAALASPSARVSTIGYLNDHDA

VTKAIQEARQMKEQLRREQQVLDGKVAVVNSLGLNNCRTEKEKTTLESLTQQLAVKQNEEGKFSH

AMMDFNLSGDSDGSAGVSESRIYRESRGRGSNEPHIKRPMNAFMVWAKDERRKILQAFPDMHNSN

ISKILGSRWKAMTNLEKQPYYEEQARLSKQHLEKYPDYKYKPRPKRTCLVDGKKLRIGEYKAIMR

NRRQEMRQYFNVGQQAQIPIATAGVVYPGAIAMAGMPSPHLPSEHSSVSSSPEPGMPVIQSTYGV

KGEEPHIKEEIQAEDINGEIYDEYDEEEDDPDVDYGSDSENHIAGQAN (SEQ ID NO: 102)
atgcttactgaccctgatttacctcaggagtttgaaaggatgtcttccaagcgaccagcctctcc gtatggggaagcagatggagaggtagccatggtgacaagcagacagaaagtggaagaagaggaga gtgacgggctcccagccttcaccttcccttgcatgtgagttttcccaacaagcctcactctgag gaatttcagccagtttctctgctgacgcaagagacttgtggccataggactcccacttctcagca caatacaatggaagttgatggcaataaagttatgtcttcatttgccccacacaactcatctacct cacctcagaaggcagaagaaggtgggcgacagagtggcgagtccttgtctagtacagccctggga actcctgaacggcgcaagggcagtttagctgatgttgttgacaccttgaagcagaggaaaatgga agagctcatcaaaaacgagccggaagaaaccccagtattgaaaaactactctcaaaggactgga aagacaagcttcttgcaatgggatcggggaactttggcgaaataaaagggactcccgagagctta gctgagaagaaaggcaactcatgggtatgatcaaccagctgaccagcctccgagagcagctgtt ggctgcccacgatgagcagaagaaactagctgcctctcagattgagaaacagcgtcagcaaatgg agctggccaagcagcaacaagaacaaattgcaagacagcagcagcagcttctacagcaacaacac aaaatcaatttgctccagcaacagatccaggttcaaggtcagctgccgccattaatgattcccgt attccctcctgatcaacggacactggctgcagctgcccagcaaggattcctcctccctccaggct tcagctataaggctggatgtagtgaccccttaccctgttcagctgatcccaactaccatggcagct gctgccgcagcaacaccaggcttaggcccactccaactgcagcagttatatgctgcccagctagc tgcaatgcaggtatctccaggagggaagctgccaggcatacccaaggcaaccttggtgctgctg tatctcctaccagcattcacacagacaagagcacaaacagcccaccacccaaaagcaaggatgaa gtggcacagccactgaacctatcagctaaacccaagacctctgatggcaaatcacccacatcacc cacctctccccatatgccagctctgagaataaacagtggggcaggccccctcaaagcctctgtcc cagcagcgttagctagtccttcagccagagttagcacaataggttacttaaatgaccatgatgct gtcaccaaggcaatccaagaagctcggcaaatgaaggagcaactccgacgggaacaacaggtgct tgatgggaaggtggctgttgtgaatagtctgggtctcaataactgccgaacagaaaaggaaaaaa -continued

```
caacactggagagtctgactcagcaactggcagttaaacagaatgaagaaggaaaatttagccat gcaatgatggatttcaatctgagtggagattctgatggaagtgctggagtctcagagtcaagaat ttatagggaatcccgagggcgtggtagcaatgaaccccacataaagcgtccaatgaatgccttca tggtgtgggctaaagatgaacggagaaagatccttcaagcctttcctgacatgcacaactccaac atcagcaagatatttgggatctcgctggaaagctatgacaaacctagagaaacagccatattatga ggagcaagcccgtctcagcaagcagcacctggagaagtaccctgactataagtacaagcccaggc caaagcgcacctgcctggtggatggcaaaaagctgcgcattggtgaatacaaggcaatcatgcgc aacaggcggcaggaaatgcggcagtacttcaatgtgggcaacaagcacagatccccattgccac tgctggtgttgtgtaccctggagccatcgccatggctgggatgccctcccctcacctgccctcgg agcactcaagcgtgtctagcagcccagagcctgggatgcctgttatccagagcacttacggtgtg aaaggagaggagccacatatcaaagaagagatacaggccgaggacatcaatggagaaatttatga tgagtacgacgaggaagaggatgatccagatgtagattatgggagtgacagtgaaaaccatattg caggacaagccaactga
```

*Homo sapiens* SOX6 mRNA (AF309034) SEQ ID NO: 39 (protein) and SEQ ID NO: 103 (DNA)

(SEQ ID NO: 39)
MSSKQATSPPFACAADGEDAMTQDLTSREKEEGSDQHVASHLPLHPIMHNKPHSEELPTLVSTIQQ
DADWDSVLSSQQRMESENNKLCSLYSFRNTSTSPHKPDEGSRDREIMTSVTFGTPERRKGSLADV
VDTLKQKKLEEMTRTEQEDSSCMEKLLSKDWKEKMERLNTSELLGEIKGTPESLAEKERQLSTMI
TQLISLREQLLAAHDEQKKLAASQIEKQRQQMDLARQQQEQIARQQQQLLQQQHKINLLQQQIQV
QGHMPPLMIPIFPHDQRTLAAAAAAQQGFLFPPGITYKPGDNYPVQFIPSTMAAAAASGLSPLQL
QKGHASHPQINQRLKGLSDRFGRNLDTFEHGGGHSYNHKQIEQLYAAQLASMQVSPGAKMPSTPQ
PPNTAGTVSPTGIKNEKRGTSPVTQVKDEAAAQPLNLSSRPKTAEPVKSPTSPTQNLFPASKTSP
VNLPNKSSIPSPIGGSLGRGSSLDILSSLNSPALFGDQDTVMKAIQEARKMREQIQREQQQQQPH
GVDGKLSSINNMGLNSCRNEKERTRFENLGPQLTGKSNEDGKLGPGVIDLTRPEDAEGGATVAEA
RVYRDARGRASSEPHIKRPMNAFMVWAKDERRKILQAFPDMHNSNISKILGSRWKSMSNQEKQPY
YEEQARLSKIHLEKYPNYKYKPRPKRTCIVDGKKLRIGEYKQLMRSRRQEMRQFFTVGQQPQIPI
TTGTGVVYPGAITMATTTPSPQMTSDCSSTSASPEPSLPVIQSTYGMKTDGGSLAGNEMINGEDE
MEMYDDYEDDPKSDYSSENEAPEAVSAN (SEQ ID NO: 103)
```
atgtcttccaagcaagccacctctccatttgcctgtgcagctgatggagaggatgcaatgaccca ggatttaacctcaagggaaaaggaagagggcagtgatcaacatgtggcctcccatctgcctctgc accccataatgcacaacaaacctcactctgaggagctaccaacacttgtcagtaccattcaacaa gatgctgactgggacagcgttctgtcatctcagcaaagaatggaatcagagaataataagttatg ttccctatattccttccgaaatacctctacctcaccacataagcctgacgaagggagtcgggacc gtgagataatgaccagtgttactttttggaaccccagagcgccgcaaagggagtcttgccgatgtg gtggacacactgaaacagaagaagcttgaggaaatgactcggactgaacaagaggattcctcctg catggaaaaactactttcaaaagattggaaggaaaaaatggaaagactaaataccagtgaacttc ttggagaaattaaaggtacacctgagagcctggcagaaaaagaacggcagctctccaccatgatt acccagctgatcagtttacgggagcagctactggcagcgcatgatgaacagaaaaaactggcagc gtcacaaattgagaaacaacggcagcaaatggaccttgctcgccaacagcaagaacagattgcga gacaacagcagcaacttctgcaacagcagcacaaaattaatctcctgcagcaacagatccaggtt
```

-continued

```
cagggtcacatgcctccgctcatgatcccaattttccacatgaccagcggactctggcagcagc
tgctgctgcccaacagggattcctcttcccccctggaataacatacaaaccaggtgataactacc
ccgtacagttcattccatcaacaatggcagctgctgctgcttctggactcagcccttacagctc
cagaagggtcatgcctcccacccacaaattaaccaaaggctaaagggcctaagtgaccgttttgg
caggaatttggacaccttgaacatggtggtggccactcttacaaccacaaacagattgagcagc
tctatgccgctcagctggccagcatgcaggtgtcacctggagcaaagatgccatcaactccacag
ccaccaaacacagcagggacggtctcacctactgggataaaaaatgaaaagagagggaccagccc
tgtaactcaagttaaggatgaagcagcagcacagcctctgaatctctcatcccgacccaagacag
cagagcctgtaaagtccccaacgtctcccacccagaacctcttcccagccagcaaaaccagccct
gtcaatctgccaaacaaaagcagcatccctagccccattggaggaagcctgggaagaggatcctc
tttagatatcctatctagtctcaactcccctgccttttgggggatcaggatacagtgatgaaag
ccattcaggaggcgcggaagatgcgagagcagatccagcgggagcaacagcagcaacagccacat
ggtgttgacgggaaactgtcctccataaataatatggggctgaacagctgcaggaatgaaaagga
aagaacgcgctttgagaatttggggccccagttaacgggaaagtcaaatgaagatggaaaactgg
gcccaggtgtcatcgaccttactcggccagaagatgcagagggaggtgccactgtggctgaagca
cgagtctacagggacgcccgcggccgtgccagcagcgagccacacattaagcgaccaatgaatgc
attcatggtttgggcaaaggatgagaggagaaaaatccttcaggccttccccgacatgcataact
ccaacattagcaaaatcttaggatctcgctggaaatcaatgtccaaccaggagaagcaaccttat
tatgaagagcaggcccggctaagcaagatccacttagagaagtacccaaactataaatacaaacc
ccgaccgaaacgcacctgcattgttgatggcaaaaagcttcggattggggagtataagcaactga
tgaggtctcggagacaggagtgaggcagttctttactgtggggcaacagcctcagattccaatc
accacaggaacaggtgttgtgtatcctggtgctatcactatggcaactaccacaccatcgcctca
gatgacatctgactgctctagcacctcggccagcccggagcccagcctcccggtcatccagagca
cttatggtatgaagacagatggcggaagcctagctggaaatgaaatgatcaatggagaggatgaa
atggaaatgtatgatgactatgaagatgaccccaaatcagactatagcagtgaaaatgaagcccc
ggaggctgtcagtgccaactga
```

*Homo sapiens* GATA binding protein 6 (GATA6) (NM_005257)
SEQ ID NO: 40 (protein) and SEQ ID NO: 104 (DNA)

(SEQ ID NO: 40)
MALTDGGWCLPKRFGAAGADASDSRAFPAREPSTPPSPISSSSSSCSRGGERGPGGASNCGTPQL

DTEAAAGPPARSLLLSSYASHPFGAPHGPSAPGVAGPGGNLSSWEDLLLFTDLDQAATASKLLWS

SRGAKLSPFAPEQPEEMYQTLAALSSQGPAAYDGAPGGFVHSAAAAAAAAAAAASSPVYVPTTRVG

SMLPGLPYHLQGSGSGPANHAGGAGAHPGWPQASADSPPYGSGGGAAGGGAAGPGGAGSAAAHVS

ARFPYSPSPPMANGAAREPGGYAAAGSGGAGGVSGGGSSLAAMGGREPQYSSLSAARPLNGTYHH

HHHHHHHPSPYSPYVGAPLTPAWPAGPFETPVLHSLQSRAGAPLPVPRGPSADLLEDLSESREC

VNCGSIQTPLWRRDGTGHYLCNACGLYSKMNGLSRPLIKPQKRVPSSRRLGLSCANCHTTTTTLW

RRNAEGEPVCNACGLYMKLHGVPRPLAMKKEGIQTRKRKPKNINKSKTCSGNSNNSIPMTPTSTS

SNSDDCSKNTSPTTQPTASGAGAPVMTGAGESTNPENSELKYSGQDGLYIGVSLASPAEVTSSVR

PDSWCALALA (SEQ ID NO: 104)
```
atggcctttgactgacggcggctggtgcttgccgaagcgcttcggggccgcgggtgcggacgccag
cgactccagagcctttccagcgcgggagccctccacgccgccttcccccatctcttcctcgtcct
cctcctgctcccggggcggagagcggggccccggcggcgccagcaactgcgggacgcctcagctc
```

-continued

```
gacacggaggcggcggccggaccccggcccgctcgctgctgctcagttcctacgcttcgcatcc
cttaggggctccccacggaccttcggcgcctggggtcgcgggccccgggggcaacctgtcgagct
gggaggacttgctgctgttcactgacctcgaccaagccgcgaccgccagcaagctgctgtggtcc
agccgcggcgccaagctgagccccttcgcacccgagcagccggaggagatgtaccagaccctcgc
cgctctctccagccagggtccggccgcctacgacggcgcgcccggcggcttcgtgcactctgcgg
ccgcggcggcagcagccgcggcggcggccagctccccggtctacgtgcccaccacccgcgtgggt
tccatgctgcccggcctaccgtaccacctgcagggtcgggcagtgggccagccaaccacgcggg
cggcgcgggcgcgcaccccggctggcctcaggcctcggccgacagccctccatacggcagcggag
gcggcgcggctggcggcggggccgcggggcctggcggcgctggctcagccgcggcgcacgtctcg
gcgcgcttcccctactctcccagcccgcccatggccaacggcgccgcgcgggagccgggaggcta
cgcggcggcgggcagtgggggcgcgggaggcgtgagcggcggcggcagtagcctggcggccatgg
gcggccgcgagcccagtacagctcgctgtcggccgcgcggccgctgaacgggacgtaccaccac
caccaccaccaccaccaccatccgagcccctactcgccctacgtggggcgccactgacgcc
tgcctggcccgccgaccttcgagaccccggtgctgcacagcctgcagagccgcgccggagccc
cgctcccggtgccccggggtcccagtgcagacctgctggaggacctgtccgagagccgcgagtgc
gtgaactgcggctccatccagacgccgctgtggcggcgggacggcaccggccactacctgtgcaa
cgcctgcgggctctacagcaagatgaacggcctcagccggcccctcatcaagccgcagaagcgcg
tgccttcatcacggcggcttggattgtcctgtgccaactgtcacaccacaactaccaccttatgg
cgcagaaacgccgagggtgaacccgtgtgcaatgcttgtggactctacatgaaactccatgggt
gcccagaccacttgctatgaaaaagagggaattcaaaccaggaaacgaaaacctaagaacataa
ataaatcaaagacttgctctggtaatagcaataattccattcccatgactccaacttccacctct
tctaactcagatgattgcagcaaaaatacttccccacaacacaacctacagcctcaggggcggg
tgccccggtgatgactggtgcgggagagagcaccaatcccgagaacagcgagctcaagtattcgg
gtcaagatgggctctacataggcgtcagtctcgcctcgccggccgaagtcacgtcctccgtgcga
ccggattcctggtgcgccctggccctggcctga
```

Homo sapiens GATA binding protein 1 (GATA1) (NM_002049)
SEQ ID NO: 41 (protein) and SEQ ID NO: 105 (DNA)

(SEQ ID NO: 41)
MEFPGLGSLGTSEPLPQFVDPALVSSTPESGVFFPSGPEGLDAAASSTAPSTATAAAAALAYYRD

AEAYRHSPVFQVYPLLNCMEGIPGGSPYAGWAYGKTGLYPASTVCPTREDSPPQAVEDLDGKGST

SFLETLKTERLSPDLLTLGPALPSSLPVPNSAYGGPDFSSTFFSPTGSPLNSAAYSSPKLRGTLP

LPPCEARECVNCGATATPLWRRDRTGHYLCNACGLYHKMNGQNRPLIRPKKRLIVSKRAGTQCTN

CQTTTTTLWRRNASGDPVCNACGLYYKLHQVNRPLTMRKDGIQTRNRKASGKGKKKRGSSLGGTG

AAEGPAGGFMVVAGGSGSGNCGEVASGLTLGPPGTAHLYQGLGPVVLSGPVSHLMPFPGPLLGSP

TGSFPTGPMPPTTSTTVVAPLSS (SEQ ID NO: 105)
```
atggagttccctggcctggggtccctggggacctcagagcccctcccccagtttgtggatcctgc
tctggtgtcctccacaccagaatcaggggttttcttcccctctgggcctgagggcttggatgcag
cagcttcctccactgccccgagcacagccaccgctgcagctgcggcactggcctactacagggac
gctgaggcctacagacactccccagtctttcaggtgtacccattgctcaactgtatggagggat
cccaggggctcaccatatgccggctgggcctacggcaagacggggctctaccctgcctcaactg
tgtgtcccaccgcgaggactctcctccccaggccgtggaagatctggatggaaaaggcagcacc
```

-continued

```
agcttcctggagactttgaagacagagcggctgagcccagacctcctgaccctgggacctgcact gccttcatcactccctgtccccaatagtgcttatgggggccctgacttttccagtaccttctttt ctcccaccgggagccccctcaattcagcagcctattcctctcccaagcttcgtggaactctcccc ctgcctccctgtgaggccagggagtgtgtgaactgcggagcaacagccactccactgtggcggag ggacaggacaggccactacctatgcaacgcctgcggcctctatcacaagatgaatgggcagaaca ggcccctcatccggcccaagaagcgcctgattgtcagtaaacgggcaggtactcagtgcaccaac tgccagacgaccaccacgacactgtggcggagaaatgccagtgggatcccgtgtgcaatgcctg cggcctctactacaagctacaccaggtgaaccggccactgaccatgcggaaggatggtattcaga ctcgaaaccgcaaggcatctggaaaagggaaaaagaaacggggctccagtctgggaggcacagga gcagccgaaggaccagctggtggctttatggtggtggctgggggcagcggtagcgggaattgtgg ggaggtggcttcaggcctgacactgggcccccaggtactgcccatctctaccaaggcctgggcc ctgtggtgctgtcagggcctgttagccacctcatgcctttcctggaccctactgggctcaccc acgggctccttccccacaggccccatgcccccaccaccagcactactgtggtggctccgctcag ctcatga
```

Homo sapiens Fli-1 proto-oncogene, ETS transcription factor (FLI1) (NM_002017) SEQ ID NO: 42 (protein) and SEQ ID NO: 106 (DNA)

(SEQ ID NO: 42)
MDGTIKEALSVVSDDQSLFDSAYGAAAHLPKADMTASGSPDYGQPHKINPLPPQQEWINQPVRVN

VKREYDHMNGSRESPVDCSVSKCSKLVGGGESNPMNYNSYMDEKNGPPPPNMTTNERRVIVPADP

TLWTQEHVRQWLEWAIKEYSLMEIDTSFFQNMDGKELCKMNKEDFLRATTLYNTEVLLSHLSYLR

ESSLLAYNTTSHTDQSSRLSVKEDPSYDSVRRGAWGNNMNSGLNKSPPLGGAQTISKNTEQRPQP

DPYQILGPTSSRLANPGSGQIQLWQFLLELLSDSANASCITWEGTNGEFKMTDPDEVARRWGERK

SKPNMNYDKLSRALRYYYDKNIMTKVHGKRYAYKFDFHGIAQALQPHPTESSMYKYPSDISYMPS

YHAHQQKVNFVPPHPSSMPVTSSSFFGAASQYWTSPTGGIYPNPNVPRHPNTHVPSHLGSYY (SEQ ID NO: 106)
```
atggacgggactattaaggaggctctgtcggtggtgagcgacgaccagtccctctttgactcagc gtacggagcggcagcccatctccccaaggccgacatgactgcctcggggagtcctgactacgggc agccccacaagatcaaccccctcccaccacagcaggagtggatcaatcagccagtgagggtcaac gtcaagcggagtatgaccacatgaatggatccagggagtctccggtggactgcagcgttagcaa atgcagcaagctggtgggcggaggcgagtccaacccatgaactacaacagctatatggacgaga agaatggcccccctcctcccaacatgaccaccaacgagaggagagtcatcgtccccgcagacccc acactgtggacacaggagcatgtgaggcaatggctggagtgggccataaaggagtacagcttgat ggagatcgacacatcctttttccagaacatggatggcaaggaactgtgtaaaatgaacaaggagg acttcctccgcgccaccaccctctacaacacggaagtgctgttgtcacacctcagttacctcagg gaaagttcactgctggcctataatacaacctcccacaccgaccaatcctcacgattgagtgtcaa agaagacccttcttatgactcagtcagaagaggagcttgggcaataacatgaattctggcctca acaaaagtcctccccttggaggggcacaaacgatcagtaagaatacagagcaacggccccagcca gatccgtatcagatcctgggcccgaccagcagtcgcctagccaaccctggaagcgggcagatcca gctgtggcaattcctcctggagctgctctccgacagcgccaacgccagctgtatcacctgggagg ggaccaacggggagttcaaaatgacggaccccgatgaggtggccaggcgctggggcgagcggaaa agcaagcccaacatgaattacgacaagctgagccgggccctccgttattactatgataaaaacat tatgaccaaagtgcacggcaaaagatatgcttacaaatttgacttccacggcattgcccaggctc
```

-continued
```
tgcagccacatccgaccgagtcgtccatgtacaagtacccttctgacatctcctacatgccttcc taccatgcccaccagcagaaggtgaactttgtcccctcccatccatcctccatgcctgtcacttc ctccagcttctttggagccgcatcacaatactggacctccccacggggggaatctaccccaacc ccaacgtccccgccatcctaacacccacgtgccttcacacttaggcagctactactag
```

Human erythroid Kruppel-like factor EKLF gene (U37106)
SEQ ID NO: 43 (protein) and SEQ ID NO: 107 (DNA)

(SEQ ID NO: 43)
```
MATAETALPSISTLTALGPFPDTQDDFLKWWRSEEAQDMGPGPPDPTEPPLHVKSEDQPGEEEDD

ERGADATWDLDLLLTNFSGPEPGGAPQTCALAPSEASGAQYPPPPETLGAYAGGPGLVAGLLGSE

DHSGWVRPALRARAPDAFVGPALAPAPAPEPKALALQPVYPGPGAGSSGGYFPRTGLSVPAASGA

PYGLLSGYPAMYPAPQYQGHFQLFRGLQGPAPGPATSPSFLSCLGPGTVGTGLGGTAEDPGVIAE

TAPSKRGRRSWARKRQAAHTCARPGCGKSYTKSSHLKAHLRTHTGEKPYACTWEGCGWRFARSDE

LTRHYRKHTGQRPFRCQLCPRAFSRSDHLALHMKRHL
```

(SEQ ID NO: 107)
```
atggccacagccgagaccgccttgccctccatcagcacactgaccgccctgggccccttccgga cacacaggatgacttcctcaagtggtggcgctccgaagaggcgcaggacatgggcccgggtcctc ctgaccccacggagccgccctccacgtgaagtctgaggaccagcccggggaggaagaggacgat gagaggggcgcggacgccacctgggacctggatctcctcctcaccaacttctcgggcccggagcc cggtggcgcgccccagacctgcgctctggcgcccagcgaggcctccggggcgcaatatccgccgc cgcccgagactctgggcgcatatgctggcggcccggggctggtggctggcttttgggttcggag gatcactcggggtggtgcgccctgccctgcgagcccgggctcccgacgccttcgtgggcccagc cctggctccagccccggccccgagcccaaggcgctggcgctgcaaccggtgtaccggggcccg gcgccggctcctcgggtggctacttcccgcggaccgggctttcagtgcctgcggcgtcgggcgcc ccctacgggctactgtccgggtaccccgcgatgtacccggcgcctcagtaccaagggcacttcca gctcttccgcgggctccagggacccgcgcccggtcccgccacgtccccctccttcctgagttgtt tgggacccgggacggtgggcactggactcggggggactgcagaggatccaggtgtgatagccgag accgcgccatccaagcgaggccgacgttcgtgggcgcgcaagaggcaggcagcgcacacgtgcgc gcacccggggttgcggcaagagctacaccaagagctcccacctgaaggcgcatctgcgcacgcaca caggggagaagccatacgcctgcacgtgggaaggctgcggctggagattcgcgcgctcggacgag ctgacccgccactaccggaaacacacggggcagcgccccttccgctgccagctctgcccacgtgc ttttcgcgctctgaccacctggccttgcacatgaagcgccacctttga
```

Human MyoD (X56677) SEQ ID NO: 44 (protein) and SEQ ID NO: 108 (DNA)

(SEQ ID NO: 44)
```
MELLSPPLRDVDLTAPDGSLCSFATTDDFYDDPCFDSPDLRFFEDLDPRLMHVGALLKPEEHSHF

PAAVHPAPGAREDEHVRAPSGHHQAGRCLLWACKACKRKTTNADRRKAATMRERRRLSKVNEAFE

TLKRCTSSNPNQRLPKVEILRNAIRYIEGLQALLRDQDAAPPGAAAFYAPGPLPPGRGGEHYSGD

SDASSPRSNCSDGMMDYSGPPSGARRRNCYEGAYYNEAPSEPRPGKSAAVSSLDYLSSIVERIST

ESPAAPALLLADVPSESPPRRQEAAAPSEGESSGDPTQSPDAAPQCPAGANPNPIYQVL
```

(SEQ ID NO: 108)
```
atggagctactgtcgccaccgctccgcgacgtagacctgacggcccccgacggctctctctgctc ctttgccacaacggacgacttctatgacgacccgtgtttcgactcccggacctgcgcttcttcg aagacctggacccgcgcctgatgcacgtgggcgcgctcctgaaacccgaagagcactcgcacttc cccgcggcggtgcaccggccccgggcgcacgtgaggacgagcatgtgcgcgcgcccagcgggca ccaccaggcgggccgctgcctactgtgggcctgcaaggcgtgcaagcgcaagaccaccaacgccg
```

```
accgccgcaaggccgccaccatgcgcgagcggcgccgcctgagcaaagtaaatgaggcctttgag acactcaagcgctgcacgtcgagcaatccaaaccagcggttgcccaaggtggagatcctgcgcaa cgccatccgctatatcgagggcctgcaggctctgctgcgcgaccaggacgccgcgcccctggcg cagccgccttctatgcgccgggcccgctgccccgggccgcggcggcgagcactacagcggcgac tccgacgcgtccagcccgcgctccaactgctccgacggcatgatggactacagcggcccccgag cggcgcccggcggcggaactgctacgaaggcgcctactacaacgaggcgcccagcgaacccaggc ccgggaagagtgcggcggtgtcgagcctagactacctgtccagcatcgtggagcgcatctccacc gagagccctgcggcgcccgccctcctgctggcggacgtgccttctgagtcgcctccgcgcaggca agaggctgccgcccccagcgagggagagagcagcggcgaccccacccagtcaccggacgccgccc cgcagtgccctgcgggtgcgaaccccaacccgatataccaggtgctctga
```

*Homo sapiens* NGFI-A binding protein 2 (EGR1 binding protein 2) (NAB2) NM_005967) SEQ ID NO: 45 (protein) and SEQ ID NO: 109 (DNA)

(SEQ ID NO: 45)
MHRAPSPTAEQPPGGGDSARRTLQPRLKPSARAMALPRTLGELQLYRVLQRANLLSYYETFIQQG

GDDVQQLCEAGEEEFLEIMALVGMATKPLHVRRLQKALREWATNPGLFSQPVPAVPVSSIPLFKI

SETAGTRKGSMSNGHGSPGEKAGSARSFSPKSPLELGEKLSPLPGGPGAGDPRIWPGRSTPESDV

GAGGEEEAGSPPFSPPAGGGVPEGTGAGGLAAGGTGGGPDRLEPEMVRMVVESVERIFRSFPRGD

AGEVTSLLKLNKKLARSVGHIFEMDDNDSQKEEEIRKYSIIYGRFDSKRREGKQLSLHELTINEA

AAQFCMRDNTLLLRRVELFSLSRQVARESTYLSSLKGSRLHPEELGGPPLKKLKQEVGEQSHPEI

QQPPPGPESYVPPYRPSLEEDSASLSGESLDGHLQAVGSCPRLTPPPADLPLALPAHGLWSRHIL

QQTLMDEGLRLARLVSHDRVGRLSPCVPAKPPLAEFEEGLLDRCPAPGPHPALVEGRRSSVKVEA

EASRQ (SEQ ID NO: 109)
```
atgcacagagcgcctttcccccacagccgagcagccgccgggcggaggggacagcgcccgccggac cctgcagcccagactcaagcccagtgcccgagccatggcactgcctcggacgctgggggagctgc agctgtaccgggtcctgcagcgcgccaacctcctttcctactatgagaccttcatccagcaggga ggggacgacgtgcagcagctgtgtgaggcgggtgaggaggagtttctggagatcatggcacttgt gggcatggccaccaagcccctccatgtccggcgcctgcagaaggcactgagagagtgggccacca atccagggctcttcagtcaaccagtgcctgctgttcccgtctccagcatcccgctcttcaagatc tctgagactgcgggtacccggaaagggagcatgagcaatgggcatggcagcccaggggaaaaggc aggcagtgcccgcagttttagccccaagagccccttgaacttggagagaagctatcaccactgc ctggggacctgggcaggggaccccggatctggccaggccggagcactccagagtcggacgtt ggggcaggaggagaagaggaggctggctcgccccccttctccccccctgcaggggaggagtccc tgaggggactggggctgggggggctggcagcaggtgggactggggggtggtccagaccgactggagc cagagatggtacgcatggtggtggaaagtgtggagaggatcttccggagcttcccaaggggggat gctgggggaggtcacatccctgctaaagctgaataagaagctggcacggagcgttgggcacatctt tgagatggatgataatgacagccagaaggaagaggagatccgcaaatacagcatcatctatggcc gtttcgactctaagcggcgggagggcaagcagctcagcctgcacgagctcaccatcaacgaggct gctgcccagttctgcatgagggacaacacgctcttattacggagagtggagctcttctctttgtc ccgccaagtagcccgagagagcacctacttgtcctccttgaagggctccaggcttcaccctgaag aactgggaggccctccactgaagaagctgaaacaagaggttggagaacagagtcaccctgaaatc cagcagcctcccccaggccctgagtcctatgtacccccataccgccccagcctggaggaggacag
```

-continued

```
cgccagcctgtctggggagagtctggatggacatttgcaggctgtggggtcatgtccaaggctga
cgccgcccctgctgacctgcctctggcattgccagcccatgggctatggagccgacacatcctg
cagcagacactgatggacgaggggctgcggctcgcccgcctcgtctcccacgaccgcgtgggccg
cctcagccctgtgtgcctgcgaagccacctctcgcagagttcgaggaagggctgctggacagat
gtcctgccccaggaccccatcccgcgctggtggagggtcgcaggagcagcgtgaaagtggaggct
gaggccagccggcagtga
```

*Homo sapiens* early growth response 1 (EGR1) (NM_001964)
SEQ ID NO: 46 (protein) and SEQ ID NO: 110 (DNA)

(SEQ ID NO: 46)

MAAAKAEMQLMSPLQISDPFGSFPHSPTMDNYPKLEEMMLLSNGAPQFLGAAGAPEGSGSNSSSS

SSGGGGGGGGGSNSSSSSSTFNPQADTGEQPYEHLTAESFPDISLNNEKVLVETSYPSQTTRLPP

ITYTGRFSLEPAPNSGNTLWPEPLFSLVSGLVSMTNPPASSSSAPSPAASSASASQSPPLSCAVP

SNDSSPIYSAAPTFPTPNTDIFPEPQSQAFPGSAGTALQYPPPAYPAAKGGFQVPMIPDYLFPQQ

QGDLGLGTPDQKPFQGLESRTQQPSLTPLSTIKAFATQSGSQDLKALNTSYQSQLIKPSRMRKYP

NRPSKTPPHERPYACPVESCDRRFSRSDELTRHIRIHTGQKPFQCRICMRNFSRSDHLTTHIRTH

TGEKPFACDICGRKFARSDERKRHTKIHLRQKDKKADKSVVASSATSSLSSYPSPVATSYPSPVT

TSYPSPATTSYPSPVPTSFSSPGSSTYPSPVHSGFPSPSVATTYSSVPPAFPAQVSSFPSSAVTN

SFSASTGLSDMTATFSPRTIEIC (SEQ ID NO: 110)

```
atggccgcggccaaggccgagatgcagctgatgtccccgctgcagatctctgacccgttcggatc
ctttcctcactcgcccaccatggacaactaccctaagctggaggagatgatgctgctgagcaacg
gggctccccagttcctcggcgccgccgggccccagaggggcagcggcagcaacagcagcagcagc
agcagcggggcggtggaggcggcggggcggcagcaacagcagcagcagcagcagcaccttcaa
ccctcaggcggacacgggcgagcagccctacgagcacctgaccgcagagtcttttcctgacatct
ctctgaacaacgagaaggtgctggtggagaccagttaccccagccaaaccactcgactgcccccc
atcacctatactggccgcttttccctggagcctgcacccaacagtggcaacaccttgtggcccga
gcccctcttcagcttggtcagtggcctagtgagcatgaccaacccaccgcctcctcgtcctcag
caccatctccagcggcctcctccgcctccgcctcccagagcccacccctgagctgcgcagtgcca
tccaacgacagcagtcccatttactcagcggcacccaccttccccacgccgaacactgacatttt
ccctgagccacaaagccaggccttccgggctcggcagggacagcgctccagtacccgcctcctg
cctaccctgccgccaagggtggcttccaggttcccatgatccccgactacctgtttccacagcag
caggggggatctgggcctgggcaccccagaccagaagcccttccagggcctggagagccgcccca
gcagccttcgctaacccctctgtctactattaaggcctttgccactcagtcgggctcccaggacc
tgaaggccctcaataccagctaccagtcccagctcatcaaacccagccgcatgcgcaagtacccc
aaccggcccagcaagacgcccccccacgaacgcccttacgcttgcccagtggagtcctgtgatcg
ccgcttctcccgctccgacgagctcacccgccacatccgcatccacacaggccagaagcccttcc
agtgccgcatctgcatgcgcaacttcagccgcagcgaccacctcaccacccacatccgcacccac
acaggcgaaaagcccttcgcctgcgacatctgtggaagaaagtttgccaggagcgatgaacgcaa
gaggcataccaagatccacttgcggcagaaggacaagaaagcagacaaaagtgttgtggcctctt
cggccacctcctctctctcttcctacccgtccccggttgctacctcttacccgtccccggttact
acctcttatccatcccggccaccacctcataccccatcccctgtgcccacctcctttctcctctcc
cggctcctcgacctaccccatcccctgtgcacagtggcttcccctcccgtcggtggccaccacgt
```

-continued

```
actcctctgttcccctgctttcccggccaggtcagcagcttccttcctcagctgtcaccaac tccttcagcgcctccacagggctttcggacatgacagcaaccttttctcccaggacaattgaaat ttgctaa
```

*Homo sapiens* growth factor independent 1 transcription repressor(GFI1) NM_005263) SEQ ID NO: 47 (protein) and SEQ ID NO: 111 (DNA)

(SEQ ID NO: 47)
MPRSFLVKSKKAHSYHQPRSPGPDYSLRLENVPAPSRADSTSNAGGAKAEPRDRLSPESQLTEAP

DRASASPDSCEGSVCERSSEFEDFWRPPSPSASPASEKSMCPSLDEAQPFPLPFKPYSWSGLAGS

DLRHLVQSYRPCGALERGAGLGLFCEPAPEPGHPAALYGPKRAAGGAGAGAPGSCSAGAGATAGP

GLGLYGDFGSAAAGLYERPTAAAGLLYPERGHGLHADKGAGVKVESELLCTRLLLGGGSYKCIKC

SKVFSTPHGLEVHVRRSHSGTRPFACEMCGKTFGHAVSLEQHKAVHSQERSFDCKICGKSFKRSS

TLSTHLLIHSDTRPYPCQYCGKRFHQKSDMKKHTFIHTGEKPHKCQVCGKAFSQSSNLITHSRKH

TGFKPFGCDLCGKGFQRKVDLRRHRETQHGLK (SEQ ID NO: 111)
```
atgccgcgctcatttctcgtcaaaagcaagaaggctcacagctaccaccagccgcgctcccagg accagactattccctccgtttagagaatgtaccggcgcctagccgagcagacagcacttcaaatg caggcggggcgaaggcggagcccggaccgtttgtcccccgaatcgcagctgaccgaagcccca gacagagcctccgcatcccagacagctgcgaaggcagcgtctgcgaacggagctcggagtttga ggacttctggaggccccgtcaccctccgcgtctccagcctcggagaagtcaatgtgcccatcgc tggacgaagcccagcccttccccctgcctttcaaaccgtactcatggagcggcctggcgggttct gacctgcggcacctggtgcagagctaccgaccgtgtggggccctggagcgtggcgctggcctggg cctcttctgcgaacccgccccggagcctggccacccggccgcgctgtacggcccgaagcgggctg ccggcggcgcggggccggggcgccagggagctgcagcgcaggggccggtgccaccgctggccct ggcctagggctctacggcgacttcgggtctgcggcagccgggctgtatgagaggcccacggcagc ggcgggcttgctgtaccccgagcgtggccacgggctgcacgcagacaagggcgctggcgtcaagg tggagtcggagctgctgtgcacccgcctgctgctgggcggcggctcctacaagtgcatcaagtgc agcaaggtgttctccacgccgcacgggctcgaggtgcacgtgcgcaggtcccacagcggtaccag acccttgcctgcgagatgtgcggcaagaccttcgggcacgcggtgagcctggagcagcacaaag ccgtgcactcgcaggaacggagctttgactgtaagatctgtgggaagagcttcaagaggtcatcc acactgtccacacacctgcttatccactcagacactcggccctacccctgtcagtactgtggcaa gaggttccaccagaagtcagacatgaagaaacacactttcatccacactggtgagaagcctcaca agtgccaggtgtgcggcaaggcattcagccagagctccaacctcatcacccacagccgcaaacac acaggcttcaagcccttcggctgcgacctctgtgggaagggtttccagaggaaggtggacctccg aaggcaccgggagacgcagcatgggctcaaatga
```

*Homo sapiens* paired box 5 (PAX5) (NM_016734) SEQ ID NO: 48 (protein) and SEQ ID NO: 112 (DNA)

(SEQ ID NO: 48)
MDLEKNYPTPRTSRTGHGGVNQLGGVFVNGRPLPDVVRQRIVELAHQGVRPCDISRQLRVSHGCV

SKILGRYYETGSIKPGVIGGSKPKVATPKVVEKIAEYKRQNPTMFAWEIRDRLLAERVCDNDTVP

SVSSINRIIRTKVQQPPNQPVPASSHSIVSTGSVTQVSSVSTDSAGSSYSISGILGITSPSADTN

KRKRDEGIQESPVPNGHSLPGRDFLRKQMRGDLFTQQQLEVLDRVFERQHYSDIFTTTEPIKPEQ

TTEYSAMASLAGGLDDMKANLASPTPADIGSSVPGPQSYPIVTGRDLASTTLPGYPPHVPPAGQG

SYSAPTLTGMVPGSEFSGSPYSHPQYSSYNDSWRFPNPGLLGSPYYYSAAARGAAPPAAATAYDR

H

-continued (SEQ ID NO: 112)
atggatttagagaaaaattatccgactcctcggaccagcaggacaggacatggaggagtgaatca gcttggggggttttttgtgaatggacggccactcccggatgtagtccgccagaggatagtggaac ttgctcatcaaggtgtcaggccctgcgacatctccaggcagcttcgggtcagccatggttgtgtc agcaaaattcttggcaggtattatgagacaggaagcatcaagcctggggtaattggaggatccaa accaaaggtcgccacacccaaagtggtggaaaaaatcgctgaatatataaacgccaaaatcccacca tgtttgcctgggagatcagggaccggctgctggcagagcgggtgtgtgacaatgacaccgtgcct agcgtcagttccatcaacaggatcatccggacaaaagtacagcagccacccaaccaaccagtccc agcttccagtcacagcatagtgtccactggctccgtgacgcaggtgtcctcggtgagcacggatt cggccggctcgtcgtactccatcagcggcatcctgggcatcacgtccccagcgccgacaccaac aagcgcaagagagacgaaggtattcaggagtctccggtgccgaacggccactcgcttccgggcag agacttcctccggaagcagatgcggggagacttgttcacacagcagcagctggaggtgctggacc gcgtgtttgagaggcagcactactcagacatcttcaccaccacagagcccatcaagcccgagcag accacagagtattcagccatggcctcgctggctggtgggctggacgacatgaaggccaatctggc cagccccaccctgctgacatcgggagcagtgtgccaggcccgcagtcctacccccattgtgacag gccgtgacttggcgagcacgaccctccccgggtaccctccacacgtcccccgctggacagggc agctactcagcaccgacgctgacagggatggtgcctgggagtgagttttccgggagtccctacag ccaccctcagtattcctcgtacaacgactcctggaggttccccaacccggggctgcttggctccc cctactattatagcgctgccgcccgaggagccgccccacctgcagccgccactgcctatgaccgt cactga

*Homo sapiens* T-cell-specific T-box transcription factor T-bet
mRNA (AF241243) SEQ ID NO: 49 (protein) and SEQ ID NO: 113 (DNA)

(SEQ ID NO: 49)
MGIVEPGCGDMLTGTEPMPGSDEGRAPGADPQHRYFYPEPGAQDADERRGGGSLGSPYPGGALVP

APPSRFLGAYAYPPRPQAAGFPGAGESFPPPADAEGYQPGEGYAAPDPRAGLYPGPREDYALPAG

LEVSGKLRVALNNHLLWSKFNQHQTEMIITKQGRRMFPFLSFTVAGLEPTSHYRMFVDVVLVDQH

HWRYQSGKWVQCGKAEGSMPGNRLYVHPDSPNTGAHWMRQEVSFGKLKLTNNKGASNNVTQMIVL

QSLHKYQPRLHIVEVNDGEPEAACNASNTHIFTFQETQFIAVTAYQNAEITQLKIDNNPFAKGFR

ENFESMYTSVDTSIPSPPGPNCQFLGGDHYSPLLPNQYPVPSRFYPDLPGQAKDVVPQAYWLGAP

RDHSYEAEFRAVSMKPAFLPSAPGPTMSYYRGQEVLAPGAGWPVAPQYPPKMGPASWFRPMRTLP

MEPGPGGSEGRGPEDQGPPLVWTEIAPIRPESSDSGLGEGDSKRRRVSPYPSSGDSSSPAGAPSP

FDKEAEGQFYNYFPN (SEQ ID NO: 113)
atgggcatcgtggagccgggttgcggagacatgctgacgggcaccgagccgatgccggggagcga cgagggccgggcgcctggcgcgccgacccgcagcaccgctacttctacccggagccgggcgcgcagg acgcggacgagcgtcgcggggggcggcagcctgggtctccctacccggggggcgccttggtgccc gccccgccagccgcttccttggagcctacgcctacccgccgcgaccccaggcggccggcttccc cggcgcgggcgagtcctttcccgccgcccgcggacgccgagggctaccagccgggcgagggctacg ccgccccggaccccgcgcgccgggctctacccggggccgcgtgaggactacgcgctacccgcggga ctggaggtgtcggggaaactgagggtcgcgctcaacaaccacctgttgtggtccaagtttaatca gcaccagacagagatgatcatcaccaagcagggacggcggatgttcccattcctgtcatttactg tggccggctggagcccaccagccactacaggatgtttgtggacgtggtcttggtggaccagcac cactggcggtaccagagcggcaagtgggtgcagtgtggaaaggccgagggcagcatgccaggaaa -continued

```
ccgcctgtacgtccacccggactcccccaacacaggagcgcactggatgcgccaggaagtttcat
ttgggaaactaaagctcacaaacaacaaggggggcgtccaacaatgtgacccagatgattgtgctc
cagtccctccataagtaccagccccggctgcatatcgttgaggtgaacgacggagagccagaggc
agcctgcaacgcttccaacacgcatatctttactttccaagaaacccagttcattgccgtgactg
cctaccagaatgccgagattactcagctgaaaattgataataaccccttttgccaaaggattccgg
gagaactttgagtccatgtacacatctgttgacaccagcatcccctccccgcctggacccaactg
tcaattccttgggggagatcactactctcctctcctacccaaccagtatcctgttcccagccgct
tctaccccgaccttcctggccaggcgaaggatgtggttcccaggcttactggctggggggccccc
cgggaccacagctatgaggctgagtttcgagcagtcagcatgaagcctgcattcttgccctctgc
ccctgggccaccatgtcctactaccgaggccaggaggtcctggcacctggagctggctggcctg
tggcacccagtaccctcccaagatgggcccggccagctggttccgccctatgcggactctgccc
atggaacccggccctggaggctcagagggacggggaccagaggaccagggtccccccttggtgtg
gactgagattgccccatccggccggaatccagtgattcaggactgggcgaaggagactctaaga
ggaggcgcgtgtccccctatccttccagtggtgacagctcctcccctgctggggcccttctcct
tttgataaggaagctgaaggacagttttataactatttttcccaactga
```

*Homo sapiens* GATA binding protein 3 (GATA3) (NM_001002295)
SEQ ID NO: 50 (protein) and SEQ ID NO: 114 (DNA)

(SEQ ID NO: 50)
MEVTADQPRWVSHHHPAVLNGQHPDTHHPGLSHSYMDAAQYPLPEEVDVLFNIDGQGNEVPPYYG
NSVRATVQRYPPTHHGSQVCRPPLLHGSLPWLDGGKALGSHHTASPWNLSPFSKTSIHHGSPGPL
SVYPPASSSSLSGGHASPHLFTFPPTPPKDVSPDPSLSTPGSAGSARQDEKECLKYQVPLPDSMK
LESSHSRGSMTALGGASSSTHHPITTYPPYVPEYSSGLFPPSSLLGGSPTGFGCKSRPKARSSTE
GRECVNCGATSTPLWRRDGTGHYLCNACGLYHKMNGQNRPLIKPKRRLSAARRAGTSCANCQTTT
TTLWRRNANGDPVCNACGLYYKLHNINRPLTMKKEGIQTRNRKMSSKSKKCKKVHDSLEDFPKNS
SFNPAALSRHMSSLSHISPFSHSSHMLTTPTPMHPPSSLSFGPHHPSSMVTAMG (SEQ ID NO: 114)
```
atggaggtgacggcggaccagccgcgctgggtgagccaccaccaccccgccgtgctcaacgggca
gcacccggacacgcaccacccgggcctcagccactcctacatggacgcggcgcagtacccgctgc
cggaggaggtggatgtgctttttaacatcgacggtcaaggcaaccacgtcccgccctactacgga
aactcggtcagggccacggtgcagaggtaccctccgacccaccacgggagccaggtgtgccgccc
gcctctgcttcatggatccctaccctggctggacggcggaaagccctgggcagccaccacaccg
cctcccctggaatctcagccccttctccaagacgtccatccaccacggctccccggggccccctc
tccgtctaccccccggcctcgtcctcctccttgtcggggggccacgccagcccgcacctcttcac
cttcccgcccacccgccgaaggacgtctccccggacccatcgctgtccaccccaggctcggccg
gctcggcccggcaggacgagaaagagtgcctcaagtaccaggtgcccctgcccgacagcatgaag
ctggagtcgtcccactccgtggcagcatgaccgccctgggtggagcctcctcgtcgacccacca
ccccatcaccacctacccgccctacgtgcccgagtacagctccggactcttccccccagcagcc
tgctgggcggctcccccaccggcttcggatgcaagtccaggcccaaggcccggtccagcacagaa
ggcagggagtgtgtgaactgtggggcaacctcgaccccactgtggcggcgagatggcacgggaca
ctacctgtgcaacgcctgcgggctctatcacaaaatgaacggacagaaccggcccctcattaagc
ccaagcgaaggctgtctgcagccaggagagcagggacgtcctgtgcgaactgtcagaccaccaca
accacactctggaggaggaatgccaatggggaccctgtctgcaatgcctgtgggctctactacaa
```

-continued

```
gcttcacaatattaacagacccctgactatgaagaaggaaggcatccagaccagaaaccgaaaaa tgtctagcaaatccaaaaagtgcaaaaaagtgcatgactcactggaggacttccccaagaacagc tcgtttaacccggccgccctctccagacacatgtcctccctgagccacatctcgcccttcagcca ctccagccacatgctgaccacgccacgccgatgcacccgccatccagcctgtcctttggaccac accacccctccagcatggtcaccgccatgggttag
```

Homo sapiens FOXP3 (EF534714) SEQ ID NO: 51 (protein) and
SEQ ID NO: 115 (DNA)

(SEQ ID NO: 51)
MPNPRPGKPSAPSLALGPSPGASPSWRAAPKASDLLGARGPGGTFQGRDLRGGAHASSSSLNPMP
PSQLQLPTLPLVMVAPSGARLGPLPHLQALLQDRPHFMHQLSTVDAHARTPVLQVHPLESPAMIS
LTPPTTATGVFSLKARPGLPPGINVASLEWVSREPALLCTFPNPSAPRKDSTLSAVPQSSYPLLA
NGVCKWPGCEKVFEEPEDFLKHCQADHLLDEKGRAQCLLQREMVQSLEQQLVLEKEKLSAMQAHL
AGKMALTKASSVASSDKGSCCIVAAGSQGPVVPAWSGPREAPDSLFAVRRHLWGSHGNSTFPEFL
HNMDYFKFHNMRPPFTYATLIRWAILEAPEKQRTLNEIYHWFTRMFAFFRNHPATWKNAIRHNLS
LHKCFVRVESEKGAVWTVDELEFRKKRSQRPSRCSNPTPGP (SEQ ID NO: 115)
```
atgcccaaccccaggcctggcaagccctcggccccttccttggcccttggcccatcccaggagc ctcgcccagctggagggctgcacccaaagcctcagacctgctgggggcccggggcccagggggaa ccttccagggccgagatcttcgaggcggggccatgcctcctcttcttccttgaacccatgcca ccatcgcagctgcagctgcccacactgcccctagtcatggtggcaccctccggggcacggctggg ccccttgccccacttacaggcactcctccaggacaggccacatttcatgcaccagctctcaacgg tggatgcccacgcccggacccctgtgctgcaggtgcacccctggagagcccagccatgatcagc ctcacaccacccaccaccgccactgggtcttctccctcaaggcccggcctggcctcccacctgg gatcaacgtggccagcctggaatgggtgtccagggagccggcactgctctgcaccttcccaaatc ccagtgcacccaggaaggacagcacccttcggctgtgccccagagctcctacccactgctggca aatggtgtctgcaagtggcccggatgtgagaaggtcttcgaagagccagaggacttcctcaagca ctgccaggcggaccatcttctggatgagaagggcagggcacaatgtctcctccagagagagatgg tacagtctctggagcagcagctggtgctggagaaggagaagctgagtgccatgcaggcccacctg gctgggaaaatggcactgaccaaggcttcatctgtggcatcatccgacaagggctcctgctgcat cgtagctgctggcagccaaggccctgtcgtcccagcctggtctggccccgggaggcccctgaca gcctgtttgctgtccggaggcacctgtggggtagccatggaaacagcacattcccagagttcctc cacaacatggactacttcaagttccacaacatgcgacccccctttcacctacgccacgctcatccg ctgggccatcctggaggctccagagaagcagcggacactcaatgagatctaccactggttcacac gcatgtttgccttcttcagaaaccatcctgccacctggaagaacgccatccgccacaacctgagt ctgcacaagtgctttgtgcgggtggagagcgagaaggggctgtgtggaccgtggatgagctgga gttccgcaagaaacggagccagaggcccagcaggtgttccaaccctacacctggcccctga
```

Human orphan receptor ROR gamma (U16997) SEQ ID NO: 52
(protein) and SEQ ID NO: 116 (DNA)

(SEQ ID NO: 52)
MDRAPQRQHRASRELLAAKKTHTSQIEVIPCKICGDKSSGIHYGVITCEGCKGFFRRSQRCNAAY
SCTRQQNCPIDRTSRNRCQHCRLQKCLALGMSRDAVKFGRMSKKQRDSLHAEVQKQLQQRQQQQ
EPVVKTPPAGAQGADTLTYTLGLPDGQLPLGSSPDLPEASACPPGLLKASGSGPSYSNNLAKAGL
NGASCHLEYSPERGKAEGRESFYSTGSQLTPDRCGLRFEEHRHPGLELGQGPDSYGSPSFRSTP
EAPYASLTEIEHLVQSVCKSYRETCQLRLEDLLRQRSNIFSREEVTGYQRKSMWEMWERCAHHLT

-continued

EAIQYVVEFAKRLSGFMELCQNDQIVLLKAGAMEVVLVRMCRAYNADNRTVFFEGKYGGMELFRA

LGCSELISSIFDFSHSLSALHFSEDEIALYTALVLINAHRPGLQEKRKVEQLQYNLELAFHHHLC

KTHRQSILAKLPPKGKLRSLCSQHVERLQIFQHLHPIVVQAAFPPLYKELFSTETESPVGCPSDL

EEGLLASPYGLLATSLDPVPPSPFSFPMNPGGWSPPALWK (SEQ ID NO: 116)
atggacagggccccacagagacagcaccgagcctcacgggagctgctggctgcaaagaagaccca cacctcacaaattgaagtgatcccttgcaaaatctgtggggacaagtcgtctgggatccactacg gggttatcacctgtgaggggtgcaagggcttcttccgccggagccagcgctgtaacgcggcctac tcctgcacccgtcagcagaactgccccatcgaccgcaccagccgaaaccgatgccagcactgccg cctgcagaaatgcctggcgctgggatgtcccgagatgctgtcaagttcggccgcatgtccaaga agcagagggacagcctgcatgcagaagtgcagaaacagctgcagcagcggcaacagcagcaacag gaaccagtggtcaagacccctccagcaggggcccaaggagcagatacccctcacctacaccttggg gctcccagacgggcagctgcccctgggctcctcgcctgacctgcctgaggcttctgcctgtcccc ctggcctcctgaaagcctcaggctctgggccctcatattccaacaacttggccaaggcagggctc aatgggcctcatgccacctttgaatacagccctgagcggggcaaggctgagggcagagagagctt ctatagcacaggcagccagctgacccctgaccgatgtggacttcgttttgaggaacacaggcatc ctgggcttggggaactgggacagggcccagacagctacggcagcccagtttccgcagcacaccg gaggcaccctatgcctccctgacagagatagagcaccctggtgcagagcgtctgcaagtcctacag ggagacatgccagctgcggctggaggacctgctgcggcagcgctccaacatcttctcccgggagg aagtgactggctaccagaggaagtccatgtgggagatgtgggaacggtgtgcccaccacctcacc gaggccattcagtacgtggtggagttcgccaagaggctctcaggctttatggagctctgccagaa tgaccagattgtgcttctcaaagcaggagcaatggaagtggtgctggttaggatgtgccgggcct acaatgctgacaaccgcacggtctttttgaaggcaaatacggtggcatggagctgttccgagcc ttgggctgcagcgagctcatcagctccatctttgacttctcccactccctaagtgccttgcactt ttccgaggatgagattgccctctacacagcccttgttctcatcaatgcccatcggccagggctcc aagagaaaggaaagtagaacagctgcagtacaatctggagctggccttcatcatcatctctgc aagactcatcgccaaagcatcctggcaaagctgccacccaaggggaagcttcggagcctgtgtag ccagcatgtggaaaggctgcagatcttccagcacctccaccccatcgtggtccaagccgctttcc ctccactctacaaggagctcttcagcactgaaaccgagtcacctgtgggctgtccaagtgacctg gaagagggactccttgcctctccctatggcctgctggccacctccctggaccccgttccaccctc acccttttcctttcccatgaaccctggagggtggtccccaccagctctttggaagtga

*Homo sapiens* hepatocyte nuclear factor 4 alpha (HNF4A),
(NM_178849) SEQ ID NO: 53 (protein) and SEQ ID NO: 117 (DNA)

(SEQ ID NO: 53)
MRLSKTLVDMDMADYSAALDPAYTTLEFENVQVLTMGNDTSPSEGTNLNAPNSLGVSALCAICGD

RATGKHYGASSCDGCKGFFRRSVRKNHMYSCRFSRQCVVDKDKRNQCRYCRLKKCFRAGMKKEAV

QNERDRISTRRSSYEDSSLPSINALLQAEVLSRQITSPVSGINGDIRAKKIASIADVCESMKEQL

LVLVEWAKYIPAFCELPLDDQVALLRAHAGEHLLLGATKRSMVFKDVLLLGNDYIVPRHCPELAE

MSRVSIRILDELVLPFQELQIDDNEYAYLKAIIFFDPDAKGLSDPGKIKRLRSQVQVSLEDYIND

RQYDSRGRFGELLLLLPTLQSITWQMIEQIQFIKLFGMAKIDNLLQEMLLGGSPSDAPHAHHPLH

PHLMQEHMGTNVIVANTMPTHLSNGQMSTPETPQPSPPGGSGSEPYKLLPGAVATIVKPLSAIPQ

PTITKQEVI (SEQ ID NO: 117)

-continued

```
atgcgactctccaaaaccctcgtcgacatggacatggccgactacagtgctgcactggacccagc
ctacaccacctggaatttgagaatgtgcaggtgttgacgatgggcaatgacacgtccccatcag
aaggcaccaacctcaacgcgcccaacagcctgggtgtcagcgccctgtgtgccatctgcgggac
cgggccacgggcaaacactacggtgcctcgagctgtgacggctgcaagggcttcttccggaggag
cgtgcggaagaaccacatgtactcctgcagatttagccggcagtgcgtggtggacaaagacaaga
ggaaccagtgccgctactgcaggctcaagaaatgcttccgggctggcatgaagaaggaagccgtc
cagaatgagcgggaccggatcagcactcgaaggtcaagctatgaggacagcagcctgccctccat
caatgcgctcctgcaggcggaggtcctgtcccgacagatcacctcccccgtctccgggatcaacg
gcgacattcgggcgaagaagattgccagcatcgcagatgtgtgtgagtccatgaaggagcagctg
ctggttctcgttgagtgggccaagtacatcccagctttctgcgagctcccctggacgaccaggt
ggccctgctcagagccatgctggcgagcacctgctgctcggagccaccaagagatccatggtgt
tcaaggacgtgctgctcctaggcaatgactacattgtccctcggcactgcccggagctggcggag
atgagccgggtgtccatacgcatccttgacgagctggtgctgccttccaggagctgcagatcga
tgacaatgagtatgcctacctcaaagccatcatcttctttgacccagatgccaaggggctgagcg
atccaggaagatcaagcggctgcgttcccaggtgcaggtgagcttggaggactacatcaacgac
cgccagtatgactcgcgtggccgctttggagagctgctgctgctgcccaccttgcagagcat
cacctggcagatgatcgagcagatccagttcatcaagctcttcggcatggccaagattgacaacc
tgttgcaggagatgctgctgggagggtccccagcgatgcaccccatgcccaccacccctgcac
cctcacctgatgcaggaacatatgggaaccaacgtcatcgttgccaacacaatgcccactcacct
cagcaacggacagatgtccacccctgagacccacagccctcaccgccaggtggctcagggtctg
agccctataagctcctgccgggagccgtcgccacaatcgtcaagcccctctctgccatcccccag
ccgaccatcaccaagcaggaagttatctag
```

Human signal transducer and activator of transcription Stat5A (U43185) SEQ ID NO: 54 (protein) and SEQ ID NO: 118 (DNA)

(SEQ ID NO: 54)

MAGWIQAQQLQGDALRQMQVLYGQHFPIEVRHYLAQWIESQPWDAIDLDNPQDRAQATQLLEGLV

QELQKKAEHQVGEDGFLLKIKLRHYATQLQKTYDRCPLELVRCIRHILYNEQRLVREANNCSSPA

GILVDAMSQKHLQINQTFEELRLVTQDTENELKKLQQTQEYFIIQYQESLRIQAQFAQLAQLSPQ

ERLSRETALQQKQVSLEAWLQREAQTLQQYRVELAEKHQKTLQLLRKQQTIILDDELIQWKRRQQ

LAGNGGPPEGSLDVLQSWCEKLAEIIWQNRQQIRRAEHLCQQLPIPGPVEEMLAEVNATITDIIS

ALVTSTFIIEKQPPQVLKTQTKFAATVRLLVGGKLNVHMNPPQVKATIISEQQAKSLLKNENTRN

ECSGEILNNCCVMEYHQATGTLSARFRNMSLKRIKRADRRGAESVTEEKFTVLFESQFSVGSNEL

VFQVKTLSLPVVVIVHGSQDHNATATVLWDNAFAEPGRVPFAVPDKVLWPQLCEALNMKFKAEVQ

SNRGLTKENLVFLAQKLFMNSSSHLEDYSGLSVSWSQFNRENLPGWNYTFWQWFDGVMEVLKKHH

KPHWNDGAILGFVNKQQAHDLLINKPDGTFLLRFSDSEIGGITIAWKFDSPERNLWNLKPFTTRD

FSIRSLADRLGDLSYLIYVFPDRPKDEVFSKYYTPVLAKAVDGYVKPQIKQVVPEFVNASADAGG

SSATYMDQAPSPAVCPQAPYNMYPQNPDHVLDQDGEFDLDETMDVARHVEELLRRPMDSLDSRLS

PPAGLFTSARGSLS (SEQ ID NO: 118)
```
atggcgggctggatccaggcccagcagctgcagggagacgcgctgcgccagatgcaggtgctgta
cggccagcacttccccatcgaggtccggcactacttggcccagtggattgagagccagccatggg
atgccattgacttggacaatccccaggacagagcccaagccacccagctcctggagggcctggtg
caggagctgcagaagaaggcggagcaccaggtgggggaagatgggttttttactgaagatcaagct
```

```
gaggcactacgccacgcagctccagaaaacatatgaccgctgcccctggagctggtccgctgca tccggcacattctgtacaatgaacagaggctggtccgagaagccaacaattgcagctctccggct gggatcctggttgacgccatgtcccagaagcaccttcagatcaaccagacatttgaggagctgcg actggtcacgcaggacacagagaatgagctgaagaaactgcagcagactcaggagtacttcatca tccagtaccaggagagcctgaggatccaagctcagtttgcccagctggcccagctgagcccccag gagcgtctgagccgggagacggccctccagcagaagcaggtgtctctggaggcctggttgcagcg tgaggcacagacactgcagcagtaccgcgtggagctggccgagaagcaccagaagaccctgcagc tgctgcggaagcagcagaccatcatcctggatgacgagctgatccagtggaagcggcggcagcag ctggccgggaacggcgggccccccgagggcagcctggacgtgctacagtcctggtgtgagaagtt ggccgagatcatctggcagaaccggcagcagatccgcagggctgagcacctctgccagcagctgc ccatccccggcccagtggaggagatgctggccgaggtcaacgccaccatcacggacattatctca gccctggtgaccagcacattcatcattgagaagcagcctcctcaggtcctgaagacccagaccaa gtttgcagccaccgtacgcctgctggtgggcgggaagctgaacgtgcacatgaatccccccagg tgaaggccaccatcatcagtgagcagcaggccaagtctctgcttaaaaatgagaacacccgcaac gagtgcagtggtgagatcctgaacaactgctgcgtgatggagtaccaccaagccacgggcaccct cagtgcccacttcaggaacatgtcactgaagaggatcaagcgtgctgaccggcggggtgcagagt ccgtgacagaggagaagttcacagtcctgtttgagtctcagttcagtgttggcagcaatgagctt gtgttccaggtgaagactctgtccctacctgtggttgtcatcgtccacggcagccaggaccacaa tgccacggctactgtgctgtgggacaatgcctttgctgagccgggcagggtgccatttgccgtgc ctgacaaagtgctgtggccgcagctgtgtgaggcgctcaacatgaaattcaaggccgaagtgcag agcaaccggggcctgaccaaggagaacctcgtgttcctggcgcagaaactgttcaacaacagcag cagccacctggaggactacagtggcctgtccgtgtcctggtcccagttcaacagggagaacttgc cgggctggaactacaccttctggcagtggtttgacggggtgatggaggtgttgaagaagcaccac aagcccactggaatgatggggccatcctaggttttgtgaataagcaacaggcccacgacctgct catcaacaagcccgacgggaccttcttgttgcgcttttagtgactcagaaatcgggggcatcacca tcgcctggaagtttgattccccggaacgcaacctgtggaacctgaaaccattcaccacgcgggat ttctccatcaggtccctggctgaccggctgggggacctgagctatctcatctatgtgtttcctga ccgccccaaggatgaggtcttctccaagtactacactcctgtgctggctaaagctgttgatggat atgtgaaaccacagatcaagcaagtggtccctgagtttgtgaatgcatctgcagatgctgggggc agcagcgccacgtacatggaccaggcccctccccagctgtgtgccccaggctccctataacat gtacccacagaaccctgaccatgtactcgatcaggatggagaattcgacctggatgagaccatgg atgtggccaggcacgtggaggaactcttacgccgaccaatggacagtcttgactccgcctctcg cccccctgccggtcttttcacctctgccagaggctccctctcatga
```

*Homo sapiens* squalene epoxidase (ERG1) mRNA, (AF098865)
SEQ ID NO: 55 (protein) and SEQ ID NO: 119 (DNA)

(SEQ ID NO: 55)
MWTFLGIATFTYFYKKFGDFITLANREVLLCVLVFLSLGLVLSYRCRHRNGGLLGRQQSGSQFAL

FSDILSGLPFIGFFWAKSPPESENKEQLEARRRRKGTNISETSLIGTAACTSTSSQNDPEVIIVG

AGVLGSALAAVLSRDGRKVTVIERDLKEPDRIVGEFLQPGGYHVLKDLGLGDTVEGLDAQVVNGY

MIHDQESKSEVQIPYPLSENNQVQSGRAFHHGRFIMSLRKAAMAEPNAKFIEGVVLQLLEEDDVV

MGVQYKDKETGDIKELHAPLTVVADGLFSKFRKSLVSNKVSVSSHFVGFLMKNAPQFKANHAELI

LANPSPVLIYQISSSETRVLVDIRGEMPRNLREYMVEKIYPQIPDHLKEPFLEATDNSHLRSMPA

-continued

SFLPPSSVKKRGVLLLGDAYNMRHPLTGGGMTVAFKDIKLWRKLLKGIPDLYDDAAIFEAKKSFY
WARKTSHSFVVNILAQALYELFSATDDSLHQLRKACFLYFKLGGECVAGPVGLLSVLSPNPLVLI
GHFFAVAIYAVYFCFKSEPWITKPRALLSSGAVLYKACSVIFPLIYSEMKYMVH (SEQ ID NO: 119)
```
atgtggactttctgggcattgccactttcacctattttataagaagttcggggacttcatcac
tttggccaacagggaggtcctgttgtgcgtgctggtgttcctctcgctgggcctggtgctctcct
accgctgtcgccaccgaaacgggggtctcctcgggcgccagcagagcggctcccagttcgccctc
ttctcggatattctctcaggcctgcctttcattggcttcttctgggccaaatccccccctgaatc
agaaaataaggagcagctcgaggccaggaggcgcagaaaaggaaccaatatttcagaaacaagct
taataggaacagctgcctgtacatcaacatcttctcagaatgacccagaagttatcatcgtggga
gctggcgtgcttggctctgctttggcagctgtgctttccagagatggaagaaaggtgacagtcat
tgagagagacttaaaagagcctgacagaatagttggagaattcctgcagccgggtggttatcatg
ttctcaaagaccttggtcttggagatacagtggaaggtcttgatgcccaggttgtaaatggttac
atgattcatgatcaggaaagcaaatcagaggttcagattccttaccctctgtcagaaacaatca
agtgcagagtggaagagctttccatcacggaagattcatcatgagtctccggaaagcagctatgg
cagagcccaatgcaaagtttattgaaggtgttgtgttacagttattagaggaagatgatgttgtg
atgggagttcagtacaaggataaagagactggagatatcaaggaactccatgctccactgactgt
tgttgcagatgggcttttctccaagttcaggaaaagcctggtctccaataaagtttctgtatcat
ctcattttgttggctttcttatgaagaatgcaccacagtttaaagcaaatcatgctgaacttatt
ttagctaacccgagtccagttctcatctaccagatttcatccagtgaaactcgagtacttgttga
cattagaggagaaatgccaaggaatttaagagaatacatggttgaaaaaatttacccacaaatac
ctgatcacctgaaagaaccattcttagaagccactgacaattctcatctgaggtccatgccagca
agcttccttcctccttcatcagtgaagaaacgaggtgttcttcttttgggagacgcatataatat
gaggcatccacttactggtggaggaatgactgttgcttttaaagatataaaactatggagaaaac
tgctaaagggtatccctgacctttatgatgatgcagctattttcgaggccaaaaaatcattttac
tgggcaagaaaaacatctcattcctttgtcgtgaatatccttgctcaggctctttatgaattatt
ttctgccacagatgattccctgcatcaactaagaaaagcctgttttctttatttcaaacttggtg
gcgaatgtgttgcgggtcctgttgggctgctttctgtattgtctcctaaccctctagttttaatt
ggacacttcttttgctgttgcaatctatgccgtgtattttttgctttaagtcagaaccttggattac
aaaacctcgagcccttctcagtagtggtgctgtattgtacaaagcgtgttctgtaatatttcctc
taatttactcagaaatgaagtatatggttcattaa
```

*Homo sapiens* ets variant 2 (ETV2/ER71), (NM_014209)
SEQ ID NO: 56 (protein) and SEQ ID NO: 120 (DNA)

(SEQ ID NO: 56)
MDLWNWDEASPQEVPPGNKLAGLEGAKLGFCFPDLALQGDTPTATAETCWKGTSSSLASFPQLDW
GSALLHPEVPWGAEPDSQALPWSGDWTDMACTAWDSWSGASQTLGPAPLGPGPIPAAGSEGAAGQ
NCVPVAGEATSWSRAQAAGSNTSWDCSVGPDGDTYWGSLGGEPRTDCTISWGGPAGPDCTTSWN
PGLHAGGTTSLKRYQSSALTVCSEPSPQSDRASLARCPKTNHRGPIQLWQFLLELLHDGARSSCI
RWTGNSREFQLCDPKEVARLWGERKRKPGMNYEKLSRGLRYYYRRDIVRKSGGRKYTYRFGGRVP
SLAYPDCAGGGRGAETQ (SEQ ID NO: 120)
```
atggacctgtggaactgggatgaggcatccccacaggaagtgcctccagggaacaagctggcagg
gcttgaaggagccaaattaggcttctgtttccctgatctggcactccaaggggacacgccgacag
```

-continued

```
cgacagcagagacatgctggaaaggtacaagctcatccctggcaagcttcccacagctggactgg ggctccgcgttactgcacccagaagttccatggggggcggagcccgactctcaggctcttccgtg gtccggggactggacagacatggcgtgcacagcctgggactcttggagcggcgcctcgcagaccc tgggccccgcccctctcggcccgggccccatccccgccgccggctccgaaggcgccgcgggccag aactgcgtccccgtggcgggagaggccacctcgtggtcgcgcgcccaggccgccgggagcaacac cagctgggactgttctgtggggcccgacggcgatacctactggggcagtggcctgggcggggagc cgcgcacggactgtaccatttcgtggggcgggcccgcgggcccggactgtaccacctcctggaac ccgggggctgcatgcgggtggcaccacctctttgaagcggtaccagagctcagctctcaccgtttg ctccgaaccgagcccgcagtcggaccgtgccagtttggctcgatgccccaaaactaaccaccgag gtcccattcagctgtggcagttcctcctggagctgctccacgacggggcgcgtagcagctgcatc cgttggactggcaacagccgcgagttccagctgtgcgaccccaaagaggtggctcggctgtgggg cgagcgcaagagaaagccgggcatgaattacgagaagctgagccggggccttcgctactactatc gccgcgacatcgtgcgcaagagcgggggcgaaagtacacgtaccgcttcggggccgcgtgccc agcctagcctatccggactgtgcgggaggcggacggggagcagagacacaataa
```

*Homo sapiens* GATA binding protein 2 (GATA2) (NM_001145661)
SEQ ID NO: 57 (protein) and SEQ ID NO: 121 (DNA)

(SEQ ID NO: 57)
MEVAPEQPRWMAHPAVLNAQHPDSHHPGLAHNYMEPAQLLPPDEVDVFFNHLDSQGNPYYANPAH

ARARVSYSPAHARLTGGQMCRPHLLHSPGLPWLDGGKAALSAAAAHHHNPWTVSPFSKTPLHPSA

AGGPGGPLSVYPGAGGGSGGGSGSSVASLTPTAAHSGSHLFGFPPTPPKEVSPDPSTTGAASPAS

SSAGGSAARGEDKDGVKYQVSLTESMKMESGSPLRPGLATMGTQPATHHPIPTYPSYVPAAAHDY

SSGLFHPGGFLGGPASSFTPKQRSKARSCSEGRECVNCGATATPLWRRDGTGHYLCNACGLYHKM

NGQNRPLIKPKRRLSAARRAGTCCANCQTTTTTLWRRNANGDPVCNACGLYYKLHNVNRPLTMKK

EGIQTRNRKMSNKSKKSKKGAECFEELSKCMQEKSSPFSAAALAGHMAPVGHLPPFSHSGHILPT

PTPIHPSSSLSFGHPHPSSMVTAMG (SEQ ID NO: 121)
```
atggaggtggcgcccgagcagccgcgctggatggcgcacccggccgtgctgaatgcgcagcaccc cgactcacaccacccgggcctggcgcacaactacatggaacccgcgcagctgctgcctccagacg aggtggacgtcttcttcaatcacctcgactcgcagggcaaccctactatgccaaccccgctcac gcgcgggcgcgcgtctcctacagccccgcgcacgcccgcctgaccggaggccagatgtgccgccc acacttgttgcacagcccgggtttgccctggctggacgggggcaaagcagccctctctgccgctg cggcccaccaccacaaaccctggaccgtgagccccttctccaagacgccactgcacccctcagct gctggaggcctggaggccactctctgtgtacccaggggctgggggtgggagcggggggaggcag cgggagctcagtggcctccctcacccctacagcagcccactctggctcccacctttcggcttcc cacccacgccacccaaagaagtgtctcctgacctagcaccacggggctgcgtctccagcctca tcttccgcggggggtagtgcagcccgaggagaggacaaggacggcgtcaagtaccaggtgtcact gacgagagcatgaagatgaaagtggcagtcccctgcgcccaggcctagctactatgggcaccc agcctgctacacaccaccccatccccacctaccccctcctatgtgccggcggctgcccacgactac agcagcggactcttccaccccggaggcttcctgggggggaccggcctccagcttcaccccctaagca gcgcagcaaggctcgttcctgttcagaaggccgggagtgtgtcaactgtggggccacagccaccc ctctctggcggcgggacggcaccggccactacctgtgcaatgcctgtggcctctaccacaagatg aatgggcagaaccgaccactcatcaagcccaagcgaagactgtcggccgccagaagagccggcac
```

```
ctgttgtgcaaattgtcagacgacaaccaccaccttatggcgccgaaacgccaacggggaccctg tctgcaacgcctgtggcctctactacaagctgcacaatgttaacaggccactgaccatgaagaag gaagggatccagactcggaaccggaagatgtccaacaagtccaagaagagcaagaaggggcgga gtgcttcgaggagctgtcaaagtgcatgcaggagaagtcatccccttcagtgcagctgccctgg ctggacacatggcacctgtgggccacctcccgcccttcagccactccggacacatcctgcccact ccgacgccatccacccctcctccagcctctccttcggccacccccacccgtccagcatggtgac cgccatgggctag
```

*Homo sapiens* hes-related family bHLH transcription factor with
YRPW motif 1 (HEY1) (NM_012258) SEQ ID NO: 58 (protein) and
SEQ ID NO: 122 (DNA)

(SEQ ID NO: 58)
```
MKRAEPEYSSSDSELDETIEVEKESADENGNLSSALGSMSPTTSSQILARKRRRGIIEKRRRDRI

NNSLSELRRLVPSAFEKQGSAKLEKAEILQMTVDHLKMLHTAGGKGYFDAHALAMDYRSLGFREC

LAEVARYLSIIEGLDASDPLRVRLVSHLNNYASQREAASGAHAGLGHIPWGTVFGHHPHIAHPLL

LPQNGHGNAGTTASPTEPHHQGRLGSAHPEAPALRAPPSGSLGPVLPVVTSASKLSPPLLSSVAS

LSAFPFSFGSFHLLSPNALSPSAPTQAANLGKPYRPWGTEIGAF
```

(SEQ ID NO: 122)
```
atgaagcgagctcaccccgagtacagctcctcggacagcgagctggacgagaccatcgaggtgga gaaggagagtgcggacgagaatggaaacttgagttcggctctaggttccatgtccccaactacat cttcccagattttggccagaaaaagacggagaggaataattgagaagcgccgacgagaccggatc aataacagtttgtctgagctgagaaggctggtacccagtgcttttgagaagcagggatctgctaa gctagaaaaagccgagatcctgcagatgaccgtggatcacctgaaaatgctgcatacggcaggag ggaaaggttactttgacgcgcacgccttgctatggactatcggagtttgggatttcgggaatgc ctggcagaagttgcgcgttatctgagcatcattgaaggactagatgcctctgacccgcttcgagt tcgactggtttcgcatctcaacaactacgcttcccagcgggaagccgcgagcggcgcccacgcgg gcctcggacacattccctgggggaccgtcttcggacatcacccgcacatcgcgcacccgctgttg ctgccccagaacggccacgggaacgcgggcaccacggcctcacccacggaaccgcaccaccaggg caggctgggctcggacatccggaggcgcctgctttgcgagcgccccctagcggcagcctcggac cggtgctccctgtggtcacctccgcctccaaactgtcgccgcctctgctctcctcagtggcctcc ctgtcggccttccccttctctttcggctccttccacttactgtctcccaatgcactgagcccttc agcacccacgcaggctgcaaaccttggcaagccctatagaccttgggggacggagatcggagctt tttaa
```

*Homo sapiens* Hey2 (AB044755) SEQ ID NO: 59 (protein) and
SEQ ID NO: 123 (DNA)

(SEQ ID NO: 59)
```
MKRPCEETTSESDMDETIDVGSENNYSGQSTSSVIRLNSPTTTSQIMARKKRRGIIEKRRRDRIN

NSLSELRRLVPTAFEKQGSAKLEKAEILQMTVDHLKMLQATGGKGYFDAHALAMDFMSIGFRECL

TEVARYLSSVEGLDSSDPLRVRLVSHLSTCATQREAAAMTSSMAHHHHPLHPHHWAAAFHHLPAA

LLQPNGLHASESTPCRLSTTSEVPPAHGSALLTATFAHADSALRMPSTGSVAPCVPPLSTSLLSL

SATVHAAAAATAAAHSFPLSFAGAFPMLPPNAAAAVAAATAISPPLSVSATSSPQQTSSGTNNK

PYRPWGTEVGAF
```

(SEQ ID NO: 123)
```
atgaagcgcccctgcgaggagacgacctccgagagcgacatggacgagaccatcgacgtggggag cgagaacaattactcggggcaaagtactagctctgtgattagattgaattctccaacaacaacat ctcagattatggcaagaaagaaaaggagagggattatagagaaaaggcgtcgggatcggataaat
```

```
aacagtttatctgagttgagaagacttgtgccaactgcttttgaaaaacaaggatctgcaaagtt agaaaaagctgaaatattgcaaatgacagtggatcatttgaagatgcttcaggcaacaggggta aaggctactttgacgcacacgctcttgccatggacttcatgagcataggattccgagagtgccta acagaagttgcgcggtacctgagctccgtggaaggcctggactcctcggatccgctgcgggtgcg gcttgtgtctcatctcagcacttgcgccacccagcgggaggcggcggccatgacatcctccatgg cccaccaccatcatccgctccacccgcatcactgggccgccgccttccaccacctgcccgcagcc ctgctccagcccaacggcctccatgcctcagagtcaacccctttgtcgcctctccacaacttcaga agtgcctcctgcccacggctctgctctcctcacggccacgtttgcccatgcggattcagccctcc gaatgccatccacgggcagcgtcgcccctgcgtgccacctctctccacctctctcttgtccctc tctgccaccgtccacgccgcagccgcagcagccaccgcggctgcacacagcttccctctgtcctt cgcgggggcattccccatgcttccccaaacgcagcagcagcagtggccgcggccacagccatca gcccgcccttgtcagtatcagccacgtccagtcctcagcagaccagcagtggaacaaacaataaa ccttaccgaccctgggggacagaagttggagcttttaa
```

*Homo sapiens* forkhead box C1 (FOXC1) (NM_001453) SEQ ID NO: 60 (protein) and SEQ ID NO: 124 (DNA)

(SEQ ID NO: 60)
MQARYSVSSPNSLGVVPYLGGEQSYYRAAAAAGGGYTAMPAPMSVYSHPAHAEQYPGGMARAYG

PYTPQPQPKDMVKPPYSYIALITMAIQNAPDKKITLNGIYQFIMDRFPFYRDNKQGWQNSIRHNL

SLNECFVKVPRDDKKPGKGSYWTLDPDSYNMFENGSFLRRRRRFKKKDAVKDKEEKDRLHLKEPP

PPGRQPPPAPPEQADGNAPGPQPPPVRIQDIKTENGTCPSPPQPLSPAAALGSGSAAAVPKIESP

DSSSSSLSSGSSPPGSLPSARPLSLDGADSAPPPPAPSAPPPHHSQGFSVDNIMTSLRGSPQSAA

AELSSGLLASAAASSRAGIAPPLALGAYSPGQSSLYSSPCSQTSSAGSSGGGGGGAGAAGGAGGA

GTYHCNLQAMSLYAAGERGGHLQGAPGGAGGSAVDDPLPDYSLPPVTSSSSSSLSHGGGGGGGGG

GQEAGHHPAAHQGRLTSWYLNQAGGDLGHLASAAAAAAAAGYPGQQQNFHSVREMFESQRIGLNN

SPVNGNSSCQMAFPSSQSLYRTSGAFVYDCSKF (SEQ ID NO: 124)
```
atgcaggcgcgctactccgtgtccagccccaactccctgggagtggtgccctacctcggcggcga gcagagctactaccgcgcggcggccgcggcggccgggggcggctacaccgccatgccggccccca tgagcgtgtactcgcaccctgcgcacgccgagcagtaccgggcggcatggcccgcgcctacggg ccctacacgccgcagccgcagcccaaggacatggtgaagccgccctatagctacatcgcgctcat caccatggccatccagaacgccccggacaagaagatcaccctgaacggcatctaccagttcatca tggaccgcttccccttctaccgggacaacaagcagggctggcagaacagcatccgccacaacctc tcgctcaacgagtgcttcgtcaaggtgccgcgcgacgacaagaagccgggcaagggcagctactg gacgctggacccggactcctacaacatgttcgagaacggcagcttcctgcggcggcggcggcgct tcaagaagaaggacgcggtgaaggacaaggaggagaaggacaggctgcacctcaaggagccgcc ccgcccggccgccagccccgcccgcgccgccggagcaggccgacggcaacgcgcccggtccgca gccgccgcccgtgcgcatccaggacatcaagaccgagaacggtacgtgcccctcgccgccccagc ccctgtcccggccgccgccctgggcagcggcagcgccgccgcggtgcccaagatcgagagcccc gacagcagcagcagcagcctgtccagcgggagcagcccccgggcagcctgccgtcggcgcggcc gctcagcctggacggtgcggattccgcgccgccgccgcccgccctccgccccgccgccgcacc atagccagggcttcagcgtggacaacatcatgacgtcgctgcgggggtcgccgcagagcgcggcc gcggagctcagctccggccttctggcctcggcggccgcgtcctcgcgcgcggggatcgcaccccc gctggcgctcggcgcctactcgcccggccagagctccctctacagctccccctgcagccagacct
```

-continued

```
ccagcgcgggcagctcggggcggcggcggcggcgcgggggccgcggggggcgcgggcggcgcc gggacctaccactgcaacctgcaagccatgagcctgtacgcggccggcgagcgcgggggccactt gcagggcgcgcccggggcgcgggcggctcggccgtggacgaccccctgcccgactactctctgc ctccggtcaccagcagcagctcgtcgtccctgagtcacggcggcggcggcggcggcggcgggga ggccaggaggccggccaccaccctgcggcccaccaaggccgcctcacctcgtggtacctgaacca ggcggggcggagacctgggccacttggcgagcgcggcggcggcggcggccgcaggctacccgg gccagcagcagaacttccactcggtgcgggagatgttcgagtcacagaggatcggcttgaacaac tctccagtgaacgggaatagtagctgtcaaatggccttcccttccagccagtctctgtaccgcac gtccggagctttcgtctacgactgtagcaagttttga
```

*Homo sapiens* forkhead box C2 (MFH-1, mesenchyme forkhead 1) (FOXC2) (NM_005251) SEQ ID NO: 61 (protein) and SEQ ID NO: 125 (DNA)

(SEQ ID NO: 61)

```
MQARYSVSDPNALGVVPYLSEQNYYRAAGSYGGMASPMGVYSGHPEQYSAGMGRSYAPYHHHQPA

APKDLVKPPYSYIALITMAIQNAPEKKITLNGIYQFIMDRFPFYRENKQGWQNSIRHNLSLNECF

VKVPRDDKKPGKGSYWTLDPDSYNMFENGSFLRRRRRFKKKDVSKEKEERAHLKEPPPAASKGAP

ATPHLADAPKEAEKKVVIKSEAASPALPVITKVETLSPESALQGSPRSAASTPAGSPDGSLPEHH

AAPNGLPGFSVENIMTLRTSPPGGELSPGAGRAGLVVPPLALPYAAAPPAAYGQPCAQGLEAGA

AGGYQCSMRAMSLYTGAERPAHMCVPPALDEALSDHPSGPTSPLSALNLAAGQEGALAATGHHHQ

HHGHHHPQAPPPPPAPQPQPTPQPGAAAAQAASWYLNHSGDLNHLPGHTFAAQQQTFPNVREMFN

SHRLGIENSTLGESQVSGNASCQLPYRSTPPLYRHAAPYSYDCTKY
```

(SEQ ID NO: 125)

```
atgcaggcgcgctactccgtgtccgaccccaacgccctgggagtggtgccctacctgagcgagca gaattactaccgggctgcgggcagctacggcggcatggccagcccatgggcgtctattccggcc acccggagcagtacagcgcggggatgggccgctcctacgcgccctaccaccaccaccagcccgcg gcgcctaaggacctggtgaagccgccctacagctacatcgcgctcatcaccatggccatccagaa cgcgcccgagaagaagatcaccttgaacggcatctaccagttcatcatggaccgcttcccccttct accgggagaacaagcagggctggcagaacagcatccgccacaacctctcgctcaacgagtgcttc gtcaaggtgccccgcgacgacaagaagcccggcaagggcagttactggaccctggacccggactc ctacaacatgttcgagaacggcagcttcctgcggcgccggcggcgcttcaaaaagaaggacgtgt ccaaggagaaggaggagcgggcccacctcaaggagccgccccggcggcgtccaagggcgccccg gccacccccacctagcggacgccccaaggaggccgagaagaaggtggtgatcaagagcgaggc ggcgtcccggcgctgccggtcatcaccaaggtggagacgctgagccccgagagcgcgctgcagg gcagcccgcgcagcgcggcctccacgcccgccggctcccccgacggctcgctgccggagcaccac gccgcggcgcccaacgggctgcctggcttcagcgtggagaacatcatgaccctgcgaacgtcgcc gccggcggagagctgagcccggggccggacgcgcgggcctggtggtgccgccgctggcgctgc cctacgccgccgcgccgccgccgcctacggccagccgtgcgctcagggcctggaggccggggcc gccggggctaccagtgcagcatgcgagcgatgagcctgtacaccggggccgagcggccggcgca catgtgcgtcccgcccgccctggacgaggccctctcggaccacccgagcggccccacgtcgcccc tgagcgctctcaacctcgccgccggcaggagggcgcgctcgccgccacgggccaccaccaccag caccacggccaccaccaccgcaggcgccgccgccccgccggctcccagcccagccgacgcc gcagcccggggccgccgcggcgcaggcggcctcctggtatctcaaccacagcggggacctgaacc acctccccggccacacgttcgcggcccagcagcaaactttcccccaacgtgcgggagatgttcaac
```

-continued

```
tcccaccggctggggattgagaactcgaccctcggggagtcccaggtgagtggcaatgccagctg ccagctgccctacagatccacgccgcctctctatcgccacgcagcccctactcctacgactgca cgaaatactga
```

SEQ ID NO: 62: *Homo sapiens* SRY (sex determining region Y)-
box 7 (SOX7) NM_031439 SEQ ID NO: 62 (protein) and SEQ ID
NO: 126 (DNA)

(SEQ ID NO: 62)

```
MASLLGAYPWPEGLECPALDAELSDGQSPPAVPRPPGDKGSESRIRRPMNAFMVWAKDERKRLAV

QNPDLHNAELSKMLGKSWKALTLSQKRPYVDEAERLRLQHMQDYPNYKYRPRRKKQAKRLCKRVD

PGFLLSSLSRDQNALPEKRSGSRGALGEKEDRGEYSPGTALPSLRGCYHEGPAGGGGGGTPSSVD

TYPYGLPTPPEMSPLDVLEPEQTFFSSPCQEEHGHPRRIPHLPGHPYSPEYAPSPLHCSHPLGSL

ALGQSPGVSMMSPVPGCPPSPAYYSPATYHPLHSNLQAHLGQLSPPPEHPGFDALDQLSQVELLG

DMDRNEFDQYLNTPGHPDSATGAMALSGHVPVSQVTPTGPTETSLISVLADATATYYNSYSVS
```

(SEQ ID NO: 126)

```
atggcttcgctgctgggagcctacccttggcccgagggtctcgagtgcccggccctggacgccga gctgtcggatggacaatcgccgccggccgtccccggccccgggggacaagggctccgagagcc gtatccggcggcccatgaacgccttcatggtttgggccaaggacgagaggaaacggctggcagtg cagaacccggacctgcacaacgccgagctcagcaagatgctgggaaagtcgtggaaggcgctgac gctgtcccagaagaggccgtacgtggacgaggcggagcggctgcgcctgcagcacatgcaggact accccaactacaagtaccggccgcgcaggaagaagcaggccaagcggctgtgcaagcgcgtggac ccgggcttccttctgagctccctctcccgggaccagaacgccctgccggagaagagaagcggcag ccgggggggcgctgggggagaaggaggacaggggtgagtactccccggcactgccctgcccagcc tccggggctgctaccacgaggggccggctggtggtggcggcggcggcaccccgagcagtgtggac acgtacccgtacgggctgcccacacctcctgaaatgtctcccctggacgtgctggagccggagca gacctcttctcctcccccctgccaggaggagcatggccatcccgccgcatcccccacctgccag ggcacccgtactcaccggagtacgccccaagccctctccactgtagccacccctgggctccctg gcccttggccagtccccgccgtctccatgatgtcccctgtaccggctgtcccccatctcctgc ctattactccccggccacctaccacccactccactccaacctccaagcccacctgggccagcttt ccccgcctcctgagcacccctggcttcgacgccctggatcaactgagccaggtggaactcctgggg gacatggatcgcaatgaattcgaccagtatttgaacactcctggccacccagactccgccacagg ggccatggccctcagtgggcatgttccggtctcccaggtgacaccaacgggtcccacagagacca gcctcatctccgtcctggctgatgccacggccacgtactacaacagctacagtgtgtcatag
```

*Homo sapiens* SOX18 (AB033888) SEQ ID NO: 63 (protein) and
SEQ ID NO: 127 (DNA)

(SEQ ID NO: 63)

```
MQRSPPGYGAQDDPPARRDCAWAPGHGAAADTRGLAAGPAALAAPAAPASPPSPQRSPPRSPEPG

RYGLSPAGRGERQAADESRIRRPMNAFMVWAKDERKRLAQQNPDLHNAVLSKMLGKAWKELNAAE

KRPFVEEAERLRVQHLRDHPNYKYRPRRKKQARKARRLEPGLLLPGLAPPQPPPEPFPAASGSAR

AFRELPPLGAEFDGLGLPTPERSPLDGLEPGEAAFFPPPAAPEDCALRPFRAPYAPTELSRDPGG

CYGAPLAEALRTAPPAAPLAGLYYGTLGTPGPYPGPLSPPPEAPPLESAEPLGPAADLWADVDLT

EFDQYLNCSRTRPDAPGLPYHVALAKLGPRAMSCPEESSLISALSDASSAVYYSACISG
```

(SEQ ID NO: 127)

```
atgcagagatcgccgccggctacggcgcacaggacgacccgccgcccgccgcgactgtgcatg ggccccgggacacggggccgccgctgacacgcgcggcctcgccgccggccccgccgcccgtccg cgcccgccgcgcccgcctcgccgcccagcccgcagcgcagtccccgcgcagcccgagccgggg
```

-continued

```
cgctatggcctcagcccggccggccgcggggaacgccaggcggcagacgagtcgcgcatccggcg gcccatgaacgccttcatggtgtgggcaaaggacgagcgcaagcggctggctcagcagaacccgg acctgcacaacgcggtgctcagcaagatgctgggcaaagcgtggaaggagctgaacgcggcggag aagcggcccttcgtggaggaagccaacggctgcgcgtgcagcacttgcgcgaccaccccaacta caagtaccggccgccgccgcaagaagcaggcgcgcaaggcccggcggctggagcccggcctcctgc tcccgggattagcgcccccgcagccaccgcccgagcctttcccgcggcgtctggctcggctcgc gccttccgcgagctgccccgctgggcgccgagttcgacggcctggggctgcccacgcccgagcg ctcgcctctggacggcctggagcccggcgaggctgccttcttcccaccgcccgcggcgcccgagg actgcgcgctgcggcccttccgcgcgcccctacgcgcccaccgagttgtcgcgggaccccggcggt tgctacggggctcccctggcggaggcgctcaggaccgcgcccccgcgggcgccgctcgctggcct gtactacggcaccctgggcacgcccggcccgtaccccggcccgctgtcgccgccgcccgaggccc cgccgctggagagcgccgagccgctggggcccgccgccgatctgtgggccgacgtggacctcacc gagttcgaccagtacctcaactgcagccggactcggcccgacgccccgggctcccgtaccacgt ggcactggccaaactgggcccgcgcgccatgtcctgcccagaggagagcagcctgatctccgcgc tgtcggacgccagcagcgcggtctattacagcgcgtgcatctccggctag
```

Any patents or publications mentioned in this specification are incorporated herein by reference to the same extent as if each individual publication is specifically and individually indicated to be incorporated by reference. U.S. provisional patent application Ser. No. 61/895,562, filed Oct. 25, 2013 is incorporated herein by reference.

The compositions and methods described herein are presently representative of preferred embodiments, exemplary, and not intended as limitations on the scope of the invention. Changes therein and other uses will occur to those skilled in the art. Such changes and other uses can be made without departing from the scope of the invention as set forth in the claims.

---

The invention claimed is:

1. A method of treating a subject having a heart disease or heart damage, comprising:

administering a pharmaceutical composition comprising at least one of a protein transduction reagent-modified Gata4, Hand2, MEF2c or Tbox5 to the subject, wherein the protein transduction reagent is non-covalently bound to the Gata4, Hand2, MEF2c or Tbox5 and wherein the protein transduction reagent comprises a cation reagent and a lipid.

2. The method of claim 1, wherein the cation reagent comprises polyethylenimine.

3. The method of claim 1, wherein the wherein the lipid is selected from the group consisting of DOTMA (N—I(-(2,3-dioleyloxy)propyl-N,N,N,-trimethyl-ammonium chloride, DOGS, dioctadecylamido-glycylspermine; DOTAP, 1,2-dioleoyl-3-trimethylammonium-propane; DOPE, 1,2-dioleoyl-sn-glycero-3-phosphoethanolamine; POPC, 1-palmitoyl-2-oleoyl-sn-glycero-3-phosphocholine; and DMPTE 1,2-dimyristoyl-sn-glycero-3-phosphocholine.

4. The method of claim 1, wherein the pharmaceutical composition comprises a protein transduction reagent-modified Gata4, protein transduction reagent-modified Hand2, protein transduction reagent-modified MEF2c and protein transduction reagent-modified Tbox5.

5. The method of claim 1, wherein the heart disease or heart damage is selected from the group consisting of: acute myocardial infarction, chronic myocardial infarction and heart failure.

6. The method of claim 1, wherein the protein transduction reagent is selected from the group consisting of: QQ1a, QQ2a, QQ3a, QQ4a, QQ5a, QQ6a, QQ7a, QQ8a and QQ9a.

7. The method of claim 1, wherein the administration of the pharmaceutical composition is a systemic administration.

8. The method of claim 7, wherein the systemic administration is by intravenous injection.

9. The method of claim 1, wherein the administration of the pharmaceutical composition is a local administration.

10. The method of claim 9, wherein the local administration is intracardiac administration.

11. The method of claim 1, further comprising administration of an additional therapeutic agent.

12. The method of claim 11, wherein the additional therapeutic agent is a chemical compound, a biological molecule, an antibody, or a combination thereof.

13. A pharmaceutical composition, comprising at least one of: protein transduction reagent-modified Gata4, protein transduction reagent-modified Hand2, protein transduction reagent-modified MEF2c or protein transduction reagent-modified Tbox5, wherein the protein transduction reagent is non-covalently bound to the Gata4, Hand2, MEF2c or Tbox5 and wherein the protein transduction reagent comprises a cation reagent and a lipid.

14. The pharmaceutical composition of claim 13, wherein the cation reagent comprises polyethylenimine.

15. The pharmaceutical composition of claim 13, wherein the wherein the lipid is selected from the group consisting of DOTMA (N—I(-(2,3-dioleyloxy)propyl-N,N,N,-trimethylammonium chloride, DOGS, dioctadecylamido-glycylspermine; DOTAP, 1,2-dioleoyl-3-trimethylammonium-propane; DOPE, 1,2-dioleoyl-sn-glycero-3-phosphoethanolamine; POPC, 1-palmitoyl-2-oleoyl-sn-glycero-3-phosphocholine; and DMPTE 1,2-dimyristoyl-sn-glycero-3-phosphocholine.

16. The pharmaceutical composition of claim 13, wherein the protein transduction reagent is selected from the group consisting of: QQ1a, QQ2a, QQ3a, QQ4a, QQ5a, QQ6a, QQ7a, QQ8a and QQ9a.

* * * * *